US012583836B2

(12) United States Patent
Garnier et al.

(10) Patent No.: US 12,583,836 B2
(45) Date of Patent: Mar. 24, 2026

(54) SULPHONAMIDE COMPOUNDS

(71) Applicant: Anaxis Pharma Pty Ltd, Parkville (AU)

(72) Inventors: Jean-Marc Daniel Garnier, Parkville (AU); Martin Brzozowski, Parkville (AU); John Thomas Feutrill, Parkville (AU); Guillaume Laurent Lessene, Parkville (AU); Christopher Gardner, Parkville (AU); Peter Edward Czabotar, Parkville (AU); Angus Cowan, Parkville (AU); Katherine Davies, Parkville (AU); Pooja Sharma, Parkville (AU); Carole Annie Schuster-Klein, Parkville (AU); Christophe Poitevin, Parkville (AU)

(73) Assignee: Anaxis Pharma Pty Ltd, Parkville (AU)

( * ) Notice: Subject to any disclaimer, the term of this patent is extended or adjusted under 35 U.S.C. 154(b) by 277 days.

(21) Appl. No.: 18/011,410

(22) PCT Filed: Jun. 18, 2021

(86) PCT No.: PCT/AU2021/050638
§ 371 (c)(1),
(2) Date: Dec. 19, 2022

(87) PCT Pub. No.: WO2021/253095
PCT Pub. Date: Dec. 23, 2021

(65) Prior Publication Data

US 2023/0227429 A1 Jul. 20, 2023

(30) Foreign Application Priority Data

Jun. 19, 2020 (AU) ................................ 2020902035

(51) Int. Cl.
*C07D 401/12* (2006.01)
*C07D 231/38* (2006.01)
*C07D 401/14* (2006.01)
*C07D 403/12* (2006.01)
*C07D 413/14* (2006.01)
*C07D 417/14* (2006.01)

(52) U.S. Cl.
CPC ......... *C07D 401/12* (2013.01); *C07D 231/38* (2013.01); *C07D 401/14* (2013.01); *C07D 403/12* (2013.01); *C07D 413/14* (2013.01); *C07D 417/14* (2013.01)

(58) Field of Classification Search
None
See application file for complete search history.

(56) References Cited

U.S. PATENT DOCUMENTS

2005/0085637 A1 4/2005 Cheung et al.
2023/0227428 A1 7/2023 Garnier et al.

FOREIGN PATENT DOCUMENTS

WO WO-2003/072541 A2 9/2003
WO WO-2014/025976 A1 2/2014
WO WO-2015/172203 A1 11/2015
WO WO-2016/127213 A1 8/2016

OTHER PUBLICATIONS

International Search Report and Written Opinion for Application No. PCT/AU2021/050638 dated Jul. 26, 2021.
Database Registry CAS, Accession No. 1027541-96-3, Entered STN: Jun. 12, 2008.
Database Registry CAS, Accession No. 1348030-53-4, Entered STN: Dec. 4, 2011.
International Search Report and Written Opinion for International Application No. PCT/AU21/50644 dated Jul. 22, 2021.

*Primary Examiner* — Sarah Pihonak
*Assistant Examiner* — Donna M Nestor
(74) *Attorney, Agent, or Firm* — Foley Hoag LLP; Brendan T. Jones; Dana M. Gordon

(57) ABSTRACT

This invention relates to compounds of formula (I) and salts, solvates, tautomers, N-oxides, stereoisomers, polymorphs and/or prodrugs thereof. Also disclosed is the use of the compounds of formula (I) to treat necroptosis and/or inhibit MLKL.

22 Claims, No Drawings

SULPHONAMIDE COMPOUNDS

This application is a U.S. National Stage Application of International Application No. PCT/AU2021/050638, filed Jun. 18, 2021; which claims priority to Australian provisional patent application no. 2020902035 (filed on 19 Jun. 2020), the entire contents of each of which is hereby incorporated by reference.

FIELD

The present disclosure relates to sulphonamide compounds which treat necroptosis and/or inhibit MLKL, and methods for their use.

BACKGROUND

In many diseases, cell death is mediated through apoptotic and/or necrotic pathways. While much is known about the mechanisms of action that control apoptosis, control of necrosis is not as well understood. Understanding the mechanisms in respect of both necrosis and apoptosis in cells is essential to being able to treat conditions, such as neurodegenerative diseases, stroke, coronary heart disease, kidney disease, liver disease, AIDS and the conditions associated with AIDS.

Cell death has traditionally been categorized as either apoptotic or necrotic based on morphological characteristics (Wyllie et al., *Int. Rev. Cytol.* 68:251, 1980). These two modes of cell death were also initially thought to occur via regulated (caspase-dependent) and non-regulated processes, respectively. More recent studies, however, demonstrate that the underlying cell death mechanisms resulting in these two phenotypes are much more complicated and under some circumstances interrelated. Furthermore, conditions that lead to necrosis can occur by either regulated caspase-independent or non-regulated processes.

One regulated caspase-independent cell death pathway with morphological features resembling necrosis, called necroptosis, has been described (Degterev et al., *Nat. Chem. Biol.* 1:112, 2005). This cell death modality can be initiated with various stimuli (e.g., TNF-[alpha] and Fas ligand) and in an array of cell types (e.g., monocytes, fibroblasts, lymphocytes, macrophages, epithelial cells and neurons). Necroptosis may represent a significant contributor to and in some cases predominant mode of cellular demise under pathological conditions involving excessive cell stress, rapid energy loss and massive oxidative species generation, where the highly energy-dependent apoptosis process is not operative.

In WO2015/172203, we reported that particular compounds described in US2005/0085637 have been found to be suitable for inhibiting necroptosis. We also discussed particularly suitable compounds for inhibiting necroptosis in WO2016/127213.

All publications, patents and patent applications that may be cited herein are hereby incorporated by reference in their entirety.

Any discussion of documents, acts, materials, devices, articles or the like which has been included in the present specification is not to be taken as an admission that any or all of these matters form part of the prior art base or were common general knowledge in the field relevant to the present disclosure as it existed before the priority date of each claim of this application.

SUMMARY

As discussed above, certain compounds described in WO2016/127213, US2005/0085637 and WO2015/172203 have been found to be suitable for treating necroptosis. Surprisingly, the inventors of this invention have now discovered that other types of compounds are also suitable for treating necroptosis. Further, and equally surprising, the compounds described in this invention target a key effector of the necroptotic pathway, namely mixed lineage kinase domain-like protein (MLKL). The inventors have also found that the compounds described in this invention target human MLKL.

In one aspect, there is provided a compound according to Formula (I)

(I)

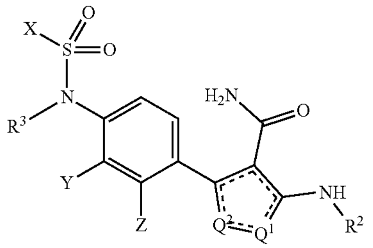

wherein $Q^1$ and $Q^2$ are selected from N and $NR^1$, wherein when $Q^1$ is N, $Q^2$ is $NR^1$ and when $Q^2$ is N, $Q^1$ is $NR^1$;

$R^1$ and $R^3$ are independently selected from H and an optionally substituted $C_{1-6}$-alkyl;

$R^2$ is an optionally substituted $C_1$-$C_6$-alkyl, an optionally substituted aryl or an optionally substituted heterocyclyl;

X is selected from optionally substituted $C_{1-6}$alkyl, optionally substituted halo$C_{1-6}$alkyl, optionally substituted $C_{2-6}$alkynyl, optionally substituted cycloalkyl, optionally substituted halocycloalkyl, optionally substituted aryl, optionally substituted alkylaryl, optionally substituted $C_{1-6}$alkylcycloalkyl and optionally substituted amino;

Y and Z are independently selected from H, $R^4$, —$OR^4$ and —$NR^4R^5$, wherein at least one of Y and Z is H;

$R^4$ is independently selected from optionally substituted $C_{1-6}$alkyl, optionally substituted aryl, optionally substituted $C_{1-6}$alkylaryl, optionally substituted heterocyclyl, $C_{1-6}$alkylheterocyclyl, optionally substituted cycloalkyl, optionally substituted $C_{1-6}$alkyl$C_{3-10}$cycloalkyl, optionally substituted $C_{3-10}$cycloalkylaryl, optionally substituted $C_{3-10}$cycloalkylheterocyclyl, optionally substituted $C_{3-10}$cycloalkyl, optionally substituted 3-6 membered non-aromatic heterocyclyl-aryl, optionally substituted 3-6 membered non-aromatic heterocyclyl$C_{3-10}$cycloalkyl and optionally substituted 3-6 membered non-aromatic heterocyclyl-3-10 membered heterocyclyl; and $R^5$ is H or optionally substituted $C_{1-6}$alkyl.

In any aspect or embodiment described herein, the compound of the invention may be provided in the form of a pharmaceutically acceptable salt, solvate, tautomer, N-oxide, stereoisomer and/or prodrug thereof.

The inventors have found that compounds of Formula (I) are selective inhibitors of MLKL.

In some embodiments, the compound of the invention is selected from any of compounds 1-320 described herein, preferably from any of compounds 9, 14, 21-22, 24-25, 34, 39, 41-43, 53, 62-63, 66, 68, 71, 84, 88, 90, 92-93, 101-102, 108, 113, 115, 123-124, 127-128, 139-140, 143-144, 146, 150, 152-158, 160-166, 169-171, 175-176, 181, 188, 190-191, 194, 196, 198-199, 202, 208, 222-223, 229, 233-235, 238, 242, 245-246, 248-249, 251-253, 256, 259-260, 262, 264-266, 271, 273-279, 281-286, 288-299, 301-312, 314 and 316-320.

In another aspect, there is provided a medicament comprising a compound of the invention.

In another aspect, there is provided a pharmaceutical composition comprising a compound of the invention and a pharmaceutically acceptable excipient.

In another aspect, there is provided a method of treating necroptosis, comprising administering to a subject in need thereof an effective amount of a compound of the invention.

In another aspect, there is provided a method of inhibiting MLKL, comprising contacting a cell with a compound of the invention.

Any embodiment herein shall be taken to apply mutatis mutandis to any other embodiment unless specifically stated otherwise.

The present disclosure is not to be limited in scope by the specific embodiments described herein, which are intended for the purpose of exemplification only.

Functionally-equivalent products, compositions and methods are clearly within the scope of the invention, as described herein.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Definitions

Unless otherwise herein defined, the following terms will be understood to have the general meanings which follow.

The term "$C_{1-6}$alkyl" refers to optionally substituted straight chain or branched chain hydrocarbon groups having from 1 to 6 carbon atoms. Examples include methyl (Me), ethyl (Et), propyl (Pr), isopropyl (i-Pr), butyl (Bu), isobutyl (i-Bu), sec-butyl (s-Bu), tert-butyl (t-Bu), pentyl, neopentyl, hexyl and the like. Unless the context requires otherwise, the term "$C_{1-6}$alkyl" also encompasses alkyl groups containing one less hydrogen atom such that the group is attached via two positions i.e. divalent. "$C_{1-4}$alkyl" and "$C_{1-3}$alkyl" including methyl, ethyl, propyl, isopropyl, n-butyl, isobutyl, sec-butyl and tert-butyl are preferred with methyl being particularly preferred.

The term "$C_{2-6}$alkenyl" refers to optionally substituted straight chain or branched chain hydrocarbon groups having at least one double bond of either E or Z stereochemistry where applicable and 2 to 6 carbon atoms. Examples include vinyl, 1-propenyl, 1- and 2-butenyl and 2-methyl-2-propenyl. Unless the context requires otherwise, the term "$C_{2-6}$ alkenyl" also encompasses alkenyl groups containing one less hydrogen atom such that the group is attached via two positions i.e. divalent. "$C_{2-4}$alkenyl" and "$C_{2-3}$alkenyl" including ethenyl, propenyl and butenyl are preferred with ethenyl being particularly preferred.

The term "$C_{2-6}$alkynyl" refers to optionally substituted straight chain or branched chain hydrocarbon groups having at least one triple bond and 2 to 6 carbon atoms. Examples include ethynyl, 1-propynyl, 1- and 2-butynyl, 2-methyl-2-propynyl, 2-pentynyl, 3-pentynyl, 4-pentynyl, 2-hexynyl, 3-hexynyl, 4-hexynyl and 5-hexynyl and the like. Unless the context indicates otherwise, the term "$C_{2-6}$alkynyl" also encompasses alkynyl groups containing one less hydrogen atom such that the group is attached via two positions i.e. divalent. $C_{2-3}$alkynyl is preferred.

The term "$C_{3-10}$cycloalkyl" refers to non-aromatic cyclic groups having from 3 to 10 carbon atoms, including cyclopropyl, cyclobutyl, cyclopentyl, cyclohexyl, cycloheptyl, cyclooctyl, cyclononyl and cyclodecyl. It will be understood that cycloalkyl groups may be saturated such as cyclohexyl or unsaturated such as cyclohexenyl. $C_{3-6}$cycloalkyl such as cyclopropyl, cyclobutyl, cyclopentyl and cyclohexyl are preferred. Cycloalkyl groups also include polycyclic carbocycles and include fused, bridged and spirocyclic systems.

The terms "hydroxy" and "hydroxyl" refer to the group —OH.

The term "oxo" refers to the group ═O.

The term "$C_{1-6}$alkoxy" refers to an alkyl group as defined above covalently bound via an 0 linkage containing 1 to 6 carbon atoms, such as methoxy, ethoxy, propoxy, isoproxy, butoxy, tert-butoxy and pentoxy. "$C_{1-4}$alkoxy" and "$C_{1-3}$alkoxy" including methoxy, ethoxy, propoxy and butoxy are preferred with methoxy being particularly preferred.

The terms "halo$C_{1-6}$alkyl" and "$C_{1-6}$alkylhalo" refer to a $C_{1-6}$alkyl which is substituted with one or more halogens. Halo$C_{1-3}$alkyl groups are preferred, such as for example, —$CH_2CF_3$, and —$CF_3$.

The terms "halo$C_{1-6}$alkoxy" and "$C_{1-6}$alkoxyhalo" refer to a $C_{1-6}$alkoxy which is substituted with one or more halogens. $C_{1-3}$alkoxyhalo groups are preferred, such as for example, —$OCF_3$.

The term "carboxylate" or "carboxyl" refers to the group —COO— or —COOH.

The term "ester" refers to a carboxyl group having the hydrogen replaced with, for example a $C_{1-6}$alkyl group ("carboxyl$C_{1-6}$alkyl" or "alkylester"), an aryl or aralkyl group ("arylester" or "aralkylester") and so on. $CO_2C_{1-3}$ alkyl groups are preferred, such as for example, methylester ($CO_2Me$), ethylester ($CO_2Et$) and propylester ($CO_2Pr$) and includes reverse esters thereof (e.g. —OC(O)Me, —OC(O)Et and —OC(O)Pr).

The terms "cyano" and "nitrile" refer to the group —CN.

The term "nitro" refers to the group —$NO_2$.

The term "amino" refers to the group —$NH_2$.

The term "substituted amino" refers to an amino group having at least one hydrogen replaced with, for example a $C_{1-6}$alkyl group ("$C_{1-6}$alkylamino"), an aryl or aralkyl group ("arylamino", "aralkylamino") and so on. Substituted amino groups include "monosubstituted amino" (or "secondary amino") groups, which refer to an amino group having a single hydrogen replaced with, for example a $C_{1-6}$alkyl group, an aryl or aralkyl group and so on. Preferred secondary amino groups include $C_{1-3}$alkylamino groups, such as for example, methylamino (NHMe), ethylamino (NHEt) and propylamino (NHPr). Substituted amino groups also include "disubstituted amino" (or "tertiary amino") groups, which refer to amino groups having both hydrogens replaced with, for example $C_{1-6}$alkyl groups, which may be the same or different ("dialkylamino"), aryl and alkyl groups ("aryl (alkyl)amino") and so on. Preferred tertiary amino groups include di($C_{1-3}$alkyl)amino groups, such as for example, dimethylamino ($NMe_2$), diethylamino ($NEt_2$), dipropylamino ($NPr_2$) and variations thereof (e.g. N(Me)(Et) and so on).

The term "aldehyde" refers to the group —C(═O)H.

The terms "acyl" and "acetyl" refers to the group —C(O) $CH_3$.

The term "ketone" refers to a carbonyl group which may be represented by —C(O)—.

The term "substituted ketone" refers to a ketone group covalently linked to at least one further group, for example, a $C_{1-6}$alkyl group ("$C_{1-6}$alkylacyl" or "alkylketone" or "ketoalkyl"), an aryl group ("arylketone"), an aralkyl group ("aralkylketone) and so on. $C_{1-3}$alkylacyl groups are preferred.

The term "amido" or "amide" refers to the group —C(O)$NH_2$.

The term "substituted amido" or "substituted amide" refers to an amido group having a hydrogen replaced with, for example a $C_{1-6}$alkyl group ("$C_{1-6}$alkylamido" or "$C_{1-6}$alkylamide"), an aryl ("arylamido"), aralkyl group ("aralkylamido") and so on. $C_{1-3}$alkylamide groups are preferred, such as for example, methylamide (—C(O)NHMe), ethylamide (—C(O)NHEt) and propylamide (—C(O)NHPr) and includes reverse amides thereof (e.g. —NHMeC(O)—, —NHEtC(O)— and —NHPrC(O)—).

The term "disubstituted amido" or "disubstituted amide" refers to an amido group having the two hydrogens replaced with, for example a $C_{1-6}$alkyl group ("di($C_{1-6}$alkyl)amido" or "di($C_{1-6}$alkyl)amide"), an aralkyl and alkyl group ("alkyl (aralkyl)amido") and so on. Di($C_{1-3}$alkyl)amide groups are preferred, such as for example, dimethylamide (—C(O)$NMe_2$), diethylamide (—C(O)$NEt_2$) and dipropylamide ((—C(O)$NPr_2$) and variations thereof (e.g. —C(O)N(Me)Et and so on) and includes reverse amides thereof (e.g. —N(Me)C(O)Me, —N(Et)C(O)Et, —N(Pr)C(O)Pr and —N(Me)C(O)Et).

The term "thiol" refers to the group —SH.

The term "$C_{1-6}$alkylthio" refers to a thiol group having the hydrogen replaced with a $C_{1-6}$alkyl group. $C_{1-3}$alkylthio groups are preferred, such as for example, thiolmethyl, thiolethyl and thiolpropyl.

The terms "thioxo" refer to the group =S.

The term "sulfinyl" refers to the group —S(=O)H.

The term "substituted sulfinyl" or "sulfoxide" refers to a sulfinyl group having the hydrogen replaced with, for example a $C_{1-6}$alkyl group ("$C_{1-6}$alkylsulfinyl" or "$C_{1-6}$alkylsulfoxide"), an aryl ("arylsulfinyl"), an aralkyl ("aralkyl sulfinyl") and so on.

$C_{1-3}$alkylsulfinyl groups are preferred, such as for example, —SOmethyl, —SOethyl and —SOpropyl.

The term "sulfonyl" refers to the group —$SO_2H$.

The term "substituted sulfonyl" refers to a sulfonyl group having the hydrogen replaced with, for example a $C_{1-6}$alkyl group ("sulfonyl$C_{1-6}$alkyl"), an aryl ("arylsulfonyl"), an aralkyl ("aralkylsulfonyl") and so on. Sulfonyl$C_{1-3}$alkyl groups are preferred, such as for example, —$SO_2$Me, —$SO_2$Et and —$SO_2$Pr.

The terms "sulfonylamido", "sulfonamido", "sulfonamide", "sulphonylamido", "sulphonamido", "sulphonylamide" or "sulphonamide" refer to the group —$SO_2NH_2$.

The terms "substituted sulfonamido", "substituted sulfonamide", "substituted sulphonamido" or "substituted sulphonamide" refer to an sulfonylamido group having a hydrogen replaced with, for example a $C_{1-6}$alkyl group (e.g. "sulfonylamido$C_{1-6}$alkyl"), an aryl ("arylsulfonamide"), aralkyl ("aralkylsulfonamide") and so on. Sulfonylamido-$C_{1-3}$alkyl groups are preferred, such as for example, —$SO_2$NHMe, —$SO_2$NHEt and —$SO_2$NHPr and includes reverse sulfonamides thereof (e.g. —$NHSO_2$Me, —$NHSO_2$Et and —$NHSO_2$Pr). In some embodiments, the alkylsulfonamides may be optionally substituted, for example with a halo group.

The terms "disubstituted sulfonamido", "disubstituted sulfonamide", "disubstituted sulphonamido" or "disubstituted sulphonamide" refers to an sulfonylamido group having the two hydrogens replaced with, for example a $C_{1-6}$alkyl group, which may be the same or different ("sulfonylamidodi($C_{1-6}$alkyl)"), an aralkyl and alkyl group ("sulfonamido(aralkyl)alkyl") and so on. Sulfonylamidodi ($C_{1-3}$alkyl) groups are preferred, such as for example, —$SO_2NMe_2$, —$SO_2NEt_2$ and —$SO_2NPr_2$ and variations thereof (e.g. —$SO_2$N(Me)Et and so on) and includes reserve sulfonamides thereof (e.g. —N(Me)$SO_2$Me and so on).

The term "sulfate" refers to the group $OS(O)_2OH$ and includes groups having the hydrogen replaced with, for example a $C_{1-6}$alkyl group ("alkylsulfates"), an aryl ("arylsulfate"), an aralkyl ("aralkylsulfate") and so on. $C_{1-3}$sulfates are preferred, such as for example, $OS(O)_2OMe$, $OS(O)_2OEt$ and $OS(O)_2OPr$.

The term "sulfonate" refers to the group $SO_3H$ and includes groups having the hydrogen replaced with, for example a $C_{1-6}$alkyl group ("alkylsulfonate"), an aryl ("arylsulfonate"), an aralkyl ("aralkylsulfonate") and so on. $C_{1-3}$sulfonates are preferred, such as for example, $SO_3Me$, $SO_3Et$ and $SO_3Pr$.

The term "aryl" refers to a carbocyclic (non-heterocyclic) aromatic ring or mono-, bi- or tri-cyclic ring system. Polycyclic ring systems may be referred to as "aryl" provided at least 1 of the rings within the system is aromatic. The aromatic ring or ring system is generally composed of 6 to 10 carbon atoms. Examples of aryl groups include but are not limited to phenyl, biphenyl, naphthyl and tetrahydronaphthyl. 6-membered aryls such as phenyl are preferred. The term "alkylaryl" refers to $C_{1-6}$alkylaryl such as benzyl.

The term "alkoxyaryl" refers to $C_{1-6}$alkyloxyaryl such as benzyloxy.

The term "heterocyclyl" refers to a moiety obtained by removing a hydrogen atom from a ring atom of a heterocyclic compound which moiety has from 3 to 10 ring atoms (unless otherwise specified), of which 1, 2, 3 or 4 are ring heteroatoms with each heteroatom being independently selected from O, S and N. Heterocyclyl groups include monocyclic and polycyclic (such as bicyclic) ring systems, such as fused, bridged and spirocyclic systems, provided at least one of the rings of the ring system contains at least one heteroatom.

In this context, the prefixes 3-, 4-, 5-, 6-, 7-, 8-, 9- and 10-membered denote the number of ring atoms, or range of ring atoms, whether carbon atoms or heteroatoms. For example, the term "3-10 membered heterocylyl", as used herein, pertains to a heterocyclyl group having 3, 4, 5, 6, 7, 8, 9 or 10 ring atoms. Examples of heterocylyl groups include 5-6-membered monocyclic heterocyclyls and 9-10 membered fused bicyclic heterocyclyls.

Examples of monocyclic heterocyclyl groups include, but are not limited to, those containing one nitrogen atom such as aziridine (3-membered ring), azetidine (4-membered ring), pyrrolidine (tetrahydropyrrole), pyrroline (e.g., 3-pyrroline, 2,5-dihydropyrrole), 2H-pyrrole or 3H-pyrrole (isopyrrole, isoazole) or pyrrolidinone (5-membered rings), piperidine, dihydropyridine, tetrahydropyridine (6-membered rings), and azepine (7-membered ring); those containing two nitrogen atoms such as imidazoline, pyrazolidine (diazolidine), imidazoline, pyrazoline (dihydropyrazole) (5-membered rings), piperazine (6-membered ring); those containing one oxygen atom such as oxirane (3-membered ring), oxetane (4-membered ring), oxolane (tetrahydrofuran), oxole (dihydrofuran) (5-membered rings), oxane (tetrahydropyran), dihydropyran, pyran (6-membered rings), oxepin (7-membered ring); those containing two oxygen atoms such as dioxolane (5-membered ring), dioxane (6-membered ring), and dioxepane (7-membered ring); those containing three oxygen atoms such as trioxane (6-membered ring); those containing one sulfur atom such as thiirane (3-membered ring), thietane (4-membered ring), thiolane (tetrahydrothiophene) (5-membered ring), thiane (tetrahydrothiopyran) (6-membered ring), thiepane (7-membered ring); those containing one nitrogen and one oxygen atom such as tetrahydrooxazole, dihydrooxazole, tetrahydroisoxazole, dihydroisoxazole (5-membered rings), morpholine, tetrahydrooxazine, dihydrooxazine, oxazine (6-membered rings); those containing one nitrogen and one sulfur atom such as thiazoline, thiazolidine (5-membered rings), thiomorpholine (6-membered ring); those containing two nitrogen and one oxygen atom such as oxadiazine (6-membered ring); those containing one oxygen and one sulfur such as: oxathiole (5-membered ring) and oxathiane (thioxane) (6-membered ring); and those containing one nitrogen, one oxygen and one sulfur atom such as oxathiazine (6-membered ring).

Heterocyclyls encompass aromatic heterocyclyls and non-aromatic heterocyclyls. Such groups may be substituted or unsubstituted.

The term "aromatic heterocyclyl" may be used interchangeably with the term "heteroaromatic" or the term "heteroaryl" or "hetaryl". The heteroatoms in the aromatic heterocyclyl group may be independently selected from N, S and O. The aromatic heterocyclyl groups may comprise 1, 2, 3, 4 or more ring heteroatoms. In the case of fused aromatic heterocyclyl groups, only one of the rings must contain a heteroatom and not all rings must be aromatic.

"Heteroaryl" is used herein to denote a heterocyclic group having aromatic character and embraces aromatic monocyclic ring systems and polycyclic (e.g. bicyclic) ring systems containing one or more aromatic rings. The term aromatic heterocyclyl also encompasses pseudoaromatic heterocyclyls. The term "pseudoaromatic" refers to a ring system which is not strictly aromatic, but which is stabilized by means of delocalization of electrons and behaves in a similar manner to aromatic rings. The term aromatic heterocyclyl therefore covers polycyclic ring systems in which all of the fused rings are aromatic as well as ring systems where one or more rings are non-aromatic, provided that at least one ring is aromatic. In polycyclic systems containing both aromatic and non-aromatic rings fused together, the group may be attached to another moiety by the aromatic ring or by a non-aromatic ring.

Examples of heteroaryl groups are monocyclic and bicyclic groups containing from five to ten ring members. The heteroaryl group can be, for example, a five membered or six membered monocyclic ring or a bicyclic structure formed from fused five and six membered rings or two fused six membered rings or two fused five membered rings. Each ring may contain up to about four heteroatoms typically selected from nitrogen, sulphur and oxygen. The heteroaryl ring will contain up to 4 heteroatoms, more typically up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Aromatic heterocyclyl groups may be 5-membered or 6-membered mono-cyclic aromatic ring systems.

Examples of 5-membered monocyclic heteroaryl groups include but are not limited to furanyl, thienyl, pyrrolyl, oxazolyl, oxadiazolyl (including 1,2,3 and 1,2,4 oxadiazolyls and furazanyl i.e. 1,2,5-oxadiazolyl), thiazolyl, isoxazolyl, isothiazolyl, pyrazolyl, imidazolyl, triazolyl (including 1,2,3, 1,2,4 and 1,3,4 triazolyls), oxatriazolyl, tetrazolyl, thiadiazolyl (including 1,2,3 and 1,3,4 thiadiazolyls) and the like.

Examples of 6-membered monocyclic heteroaryl groups include but are not limited to pyridinyl, pyrimidinyl, pyridazinyl, pyrazinyl, triazinyl, pyranyl, oxazinyl, dioxinyl, thiazinyl, thiadiazinyl and the like. Examples of 6-membered aromatic heterocyclyls containing nitrogen include pyridyl (1 nitrogen), pyrazinyl, pyrimidinyl and pyridazinyl (2 nitrogens).

Aromatic heterocyclyl groups may also be bicyclic or polycyclic heteroaromatic ring systems such as fused ring systems (including purine, pteridinyl, napthyridinyl, 1H thieno[2,3-c]pyrazolyl, thieno[2,3-b]furyl and the like) or linked ring systems (such as oligothiophene, polypyrrole and the like). Fused ring systems may also include aromatic 5-membered or 6-membered heterocyclyls fused to carbocyclic aromatic rings such as phenyl, naphtyl, indenyl, azulenyl, fluorenyl, anthracenyl and the like, such as 5-membered aromatic heterocyclyls containing nitrogen fused to phenyl rings, 5-membered aromatic heterocyclyls containing 1 or 2 nitrogens fused to phenyl ring.

A bicyclic heteroaryl group may be, for example, a group selected from: a) a benzene ring fused to a 5- or 6-membered ring containing 1, 2 or 3 ring heteroatoms; b) a pyridine ring fused to a 5- or 6-membered ring containing 1, 2 or 3 ring heteroatoms; c) a pyrimidine ring fused to a 5- or 6-membered ring containing 1 or 2 ring heteroatoms; d) a pyrrole ring fused to a 5- or 6-membered ring containing 1, 2 or 3 ring heteroatoms; e) a pyrazole ring fused to a 5- or 6-membered ring containing 1 or 2 ring heteroatoms; f) an imidazole ring fused to a 5- or 6-membered ring containing 1 or 2 ring heteroatoms; g) an oxazole ring fused to a 5- or 6-membered ring containing 1 or 2 ring heteroatoms; h) an isoxazole ring fused to a 5- or 6-membered ring containing 1 or 2 ring heteroatoms; i) a thiazole ring fused to a 5- or 6-membered ring containing 1 or 2 ring heteroatoms; j) an isothiazole ring fused to a 5- or 6-membered ring containing 1 or 2 ring heteroatoms; k) a thiophene ring fused to a 5- or 6-membered ring containing 1, 2 or 3 ring heteroatoms; l) a furan ring fused to a 5- or 6-membered ring containing 1, 2 or 3 ring heteroatoms; m) a cyclohexyl ring fused to a 5- or 6-membered ring containing 1, 2 or 3 ring heteroatoms; and n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo [1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), benzodioxole and pyrazolopyridine (e.g. pyrazolo[1,5-a]pyridine) groups. A further example of a six membered ring fused to a five membered ring is a pyrrolopyridine group such as a pyrrolo[2,3-b]pyridine group.

Particular examples of bicyclic heteroaryl groups containing two fused six membered rings include but are not limited to quinoline, isoquinoline, chroman, thiochroman, chromene, isochromene, isochroman, benzodioxan, quinolizine, benzoxazine, benzodiazine, pyridopyridine, quinoxaline, quinazoline, cinnoline, phthalazine, naphthyridine and pteridine groups.

Examples of heteroaryl groups containing an aromatic ring and a non-aromatic ring include tetrahydronaphthalene, tetrahydroisoquinoline, tetrahydroquinoline, dihydrobenzothiophene, dihydrobenzofuran, 2,3-dihydro-benzo[1,4]dioxine, benzo[1,3]dioxole, 4,5,6,7-tetrahydrobenzofuran, indoline, isoindoline and indane groups.

Examples of aromatic heterocyclyls fused to carbocyclic aromatic rings may therefore include but are not limited to benzothiophenyl, indolyl, isoindolyl, benzofuranyl, isobenzofuranyl, benzimidazolyl, indazolyl, benzoxazolyl, benzisoxazolyl, isobenzoxazoyl, benzothiazolyl, benzisothiazolyl, quinolinyl, isoquinolinyl, quinoxalinyl, quinazolinyl, cinnolinyl, benzotriazinyl, phthalazinyl, carbolinyl and the like.

The term "non-aromatic heterocyclyl" encompasses optionally substituted saturated and unsaturated rings which contain at least one heteroatom selected from the group consisting of N, S and O. The ring may contain 1, 2 or 3 heteroatoms. The ring may be a monocyclic ring or part of a polycyclic ring system. Polycyclic ring systems include fused rings and spirocycles. Not every ring in a non-aromatic heterocyclic polycyclic ring system must contain a heteroatom, provided at least one ring contains one or more heteroatoms.

Non-aromatic heterocyclyls may be 3-7 membered monocyclic rings.

Examples of 5-membered non-aromatic heterocyclyl rings include 2H-pyrrolyl, 1-pyrrolinyl, 2-pyrrolinyl, 3-pyrrolinyl, pyrrolidinyl, 1-pyrrolidinyl, 2-pyrrolidinyl, 3-pyrrolidinyl, tetrahydrofuranyl, tetrahydrothiophenyl, pyrazolinyl, 2-pyrazolinyl, 3-pyrazolinyl, pyrazolidinyl, 2-pyrazolidinyl, 3-pyrazolidinyl, imidazolidinyl, 3-dioxalanyl, thiazolidinyl, isoxazolidinyl, 2-imidazolinyl and the like.

Examples of 6-membered non-aromatic heterocyclyls include piperidinyl, piperidinonyl, pyranyl, dihyrdopyranyl, tetrahydropyranyl, 2H pyranyl, 4H pyranyl, thianyl, thianyl oxide, thianyl dioxide, piperazinyl, diozanyl, 1,4-dioxinyl, 1,4-dithianyl, 1,3,5-triozalanyl, 1,3,5-trithianyl, 1,4-morpholinyl, thiomorpholinyl, 1,4-oxathianyl, triazinyl, 1,4-thiazinyl and the like.

Examples of 7-membered non-aromatic heterocyclyls include azepanyl, oxepanyl, thiepanyl and the like.

Non-aromatic heterocyclyl rings may also be bicyclic heterocyclyl rings such as linked ring systems (for example uridinyl and the like) or fused ring systems. Fused ring systems include non-aromatic 5-membered, 6-membered or 7-membered heterocyclyls fused to carbocyclic aromatic rings such as phenyl, napthyl, indenyl, azulenyl, fluorenyl, anthracenyl and the like. Examples of non-aromatic 5-membered, 6-membered or 7-membered heterocyclyls fused to carbocyclic aromatic rings include indolinyl, benzodiazepinyl, benzazepinyl, dihydrobenzofuranyl and the like.

The term "halo" refers to fluoro, chloro, bromo or iodo.

Unless otherwise defined, the term "optionally substituted" or "optional substituent" as used herein refers to a group which may or may not be further substituted with 1, 2, 3, 4 or more groups, preferably 1, 2 or 3, more preferably 1 or 2 groups selected from the group consisting of $C_{1-6}$alkyl, $C_{2-6}$alkenyl, $C_{2-6}$alkynyl, $C_{3-8}$cycloalkyl, hydroxyl, oxo, $C_{1-6}$alkoxy, aryloxy, $C_{1-6}$alkoxyaryl, halo, $C_{1-6}$alkylhalo (such as $CF_3$), $C_{1-6}$alkoxyhalo (such as $OCF_3$), carboxyl, esters, cyano, nitro, amino, substituted amino, disubstituted amino, acyl, ketones, substituted ketones, amides, aminoacyl, substituted amides, disubstituted amides, thiol, alkylthio, thioxo, sulfates, sulfonates, sulfinyl, substituted sulfinyl, sulfonyl, substituted sulfonyl, sulfonylamides, substituted sulfonamides, disubstituted sulfonamides, aryl, ar$C_{1-6}$alkyl, heterocyclyl and heteroaryl wherein each alkyl, alkenyl, alkynyl, cycloalkyl, aryl and heterocyclyl and groups containing them may be further optionally substituted. Optional substituents in the case of heterocycles containing N may also include but are not limited to $C_{1-6}$alkyl i.e. N—$C_{1-3}$alkyl, more preferably methyl particularly N-methyl.

For optionally substituted "$C_{1-6}$alkyl", "$C_{2-6}$alkenyl" and "$C_{2-6}$alkynyl", the optional substituent or substituents are preferably selected from halo, aryl, heterocyclyl, $C_{3-8}$cycloalkyl, $C_{1-6}$alkoxy, hydroxyl, oxo, aryloxy, halo$C_{1-6}$alkyl, halo$C_{1-6}$alkoxyl and carboxyl. Each of these optional substituents may also be optionally substituted with any of the optional substituents referred to above, where nitro, amino, substituted amino, cyano, heterocyclyl (including non-aromatic heterocyclyl and heteroaryl), $C_{1-6}$alkyl, $C_{2-6}$akenyl, $C_{2-6}$alkynyl, $C_{1-6}$alkoxyl, halo$C_{1-6}$alkyl, halo$C_{1-6}$alkoxy, halo, hydroxyl and carboxyl are preferred.

It will be understood that suitable derivatives of aromatic heterocyclyls containing nitrogen include N-oxides thereof.

In the case of hybrid naming of substituent radicals describing two moieties that may both form a bond attaching the radical to the rest of the compound, such as alkylamino and alkylaryl, no direction in the order of groups is intended, so the point of attachment may be to any of the moieties included in the hybrid radical. For example, the terms "alkylaryl" and "arylalkyl", are intended to refer to the same group and the point of attachment may be via the alkyl or the aryl moiety (or both in the case of diradical species). The direction of attachment of such a hybrid radical may be denoted by inclusion of a bond, for example, "-alkylaryl" or "arylalkyl-" denotes that the point of attachment of the radical to the rest of the compound is via the alkyl moiety, and "alkylaryl-" or "-arylalkyl" denotes that the point of attachment is via the aryl moiety.

As used herein, except where the context requires otherwise, the term "comprise" and variations of the term, such as "comprising", "comprises" and "comprised", are not intended to exclude further additives, components, integers or steps.

It must be noted that as used herein and in the appended claims, the singular forms "a", "an" and "the" include plural reference unless the context clearly dictates otherwise. Thus, for example, a reference to "a salt" may include a plurality of salts and a reference to "at least one heteroatom" may include one or more heteroatoms, and so forth.

The term "and/or" can mean "and" or "or".

The term "(s)" following a noun contemplates the singular or plural form, or both.

Various features of the invention are described with reference to a certain value, or range of values. These values are intended to relate to the results of the various appropriate measurement techniques, and therefore should be interpreted as including a margin of error inherent in any particular measurement technique. Some of the values referred to herein are denoted by the term "about" to at least in part account for this variability. The term "about", when used to describe a value, may mean an amount within ±25%, ±10%, ±5%, ±1% or ±0.1% of that value.

Further aspects of the present invention and further embodiments of the aspects described in the preceding paragraphs will become apparent from the following description, given by way of example and with reference to the accompanying drawings.

DETAILED DESCRIPTION OF EMBODIMENTS

The invention provides a compound of Formula (I)

(I)

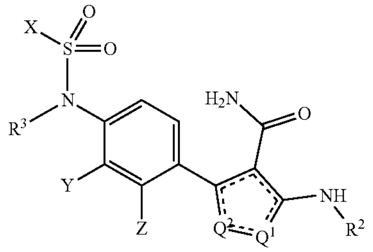

wherein

- $Q^1$ and $Q^2$ are selected from N and $NR^1$, wherein when $Q^1$ is N, $Q^2$ is $NR^1$ and when $Q^2$ is N, $Q^1$ is $NR^1$;
- $R^1$ and $R^3$ are independently selected from H and an optionally substituted $C_{1-6}$-alkyl;
- $R^2$ is an optionally substituted $C_1$-$C_6$-alkyl, an optionally substituted aryl or an optionally substituted heterocyclyl;
- X is selected from optionally substituted $C_{1-6}$alkyl, optionally substituted halo$C_{1-6}$alkyl, optionally substituted $C_{2-6}$alkynyl, optionally substituted cycloalkyl, optionally substituted halocycloalkyl, optionally substituted aryl, optionally substituted alkylaryl, optionally substituted $C_{1-6}$alkylcycloalkyl and optionally substituted amino;
- Y and Z are independently selected from H, $R^4$, —$OR^4$, —$NR^4R^5$, wherein at least one of Y and Z is H;

- $R^4$ is independently selected from optionally substituted $C_{1-6}$alkyl, optionally substituted aryl, optionally substituted $C_{1-6}$alkylaryl, optionally substituted heterocyclyl, optionally substituted $C_{1-6}$alkylheterocyclyl, optionally substituted cycloalkyl, optionally substituted $C_{1-6}$alkyl$C_{3-10}$cycloalkyl, optionally substituted $C_{3-10}$cycloalkylaryl, optionally substituted $C_{3-10}$cycloalkylheterocyclyl, optionally substituted $C_{3-10}$cycloalkyl$C_{3-10}$cycloalkyl, optionally substituted 3-6 membered non-aromatic heterocyclyl-aryl, optionally substituted 3-6 membered non-aromatic heterocyclyl$C_{3-10}$cycloalkyl and optionally substituted 3-6 membered non-aromatic heterocyclyl-3-10 membered heterocyclyl; and
- $R^5$ is H or optionally substituted $C_{1-6}$alkyl.

In some embodiments, X is selected from $C_{1-6}$alkyl, $C_{2-6}$alkynyl, $C_{3-6}$cycloalkyl, aryl, —$(CH_2)_n$aryl, —$(CH_2)_n$cycloalkyl, and —$N(C_{1-4}alkyl)_2$;

wherein n is 1 or 2, and each alkyl and alkynyl is optionally substituted with one or more groups selected from halo, nitrile, —$OR^6$, —$N(R^7)R^8$;

$R^6$, $R^7$ and $R^8$ are independently selected from H, $C_{1-6}$alkyl and halo$C_{1-6}$alkyl, and wherein each aryl and cycloalkyl is optionally substituted with one or more groups that are independently selected from halo, nitrile, $C_{1-4}$alkoxy, halo$C_{1-4}$alkyl and halo$C_{1-4}$alkoxy.

It will be appreciated that ⎓ denotes a single or a double bond. For example, the 5-membered heterocyclyl depicted in formula (I) with ⎓ is a pyrazole that may adopt one of two isomeric forms.

In some embodiments, $Q^2$ is N and $Q^1$ is $NR^1$. In these embodiments, the compound of formula (I) may be a compound of formula (1A):

(1A)

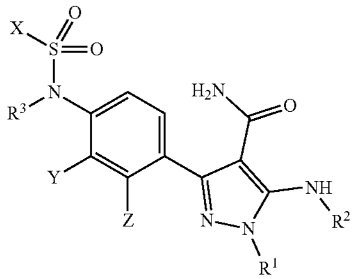

In some embodiments, $Q^2$ is $NR^1$ and $Q^1$ is N. In these embodiments, the compound of formula (I) may be a compound of formula (1B):

(1B)

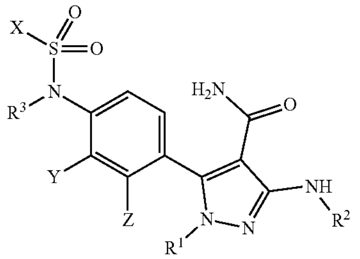

In the compounds of formula (1A) and/or (1B), $R^1$, $R^2$, $R^3$, X, Y and Z are as defined in formula (I) or any embodiment thereof as described herein.

In some embodiments, X is selected from optionally substituted $C_{1-4}$alkyl, optionally substituted $C_{2-4}$alkynyl, optionally substituted $C_{1-4}$alkylnitrile, optionally substituted halo$C_{1-4}$alkyl, optionally substituted $C_{3-6}$cycloalkyl, optionally substituted $C_1$alkyl$C_{3-6}$cycloalkyl, optionally substituted aryl, optionally substituted haloaryl, optionally substituted $C_1$alkylaryl, optionally substituted halo$C_1$alkylaryl, optionally substituted halo$C_1$alkoxyaryl, optionally substituted benzyl, optionally substituted halobenzyl, optionally substituted $C_1$alkylbenzyl, optionally substituted $C_1$alkoybenzyl and optionally substituted halo$C_1$alkoybenzyl.

In some embodiments, X is selected from an optionally substituted $C_{1-4}$alkyl, an optionally substituted halo$C_{1-4}$alkyl and a $C_{3-6}$cycloalkyl.

In some embodiments, X is selected from an optionally substituted $C_{1-2}$alkyl, an optionally substituted halo$C_{1-2}$alkyl and a $C_3$cycloalkyl.

In some embodiments, X is an optionally substituted halo$C_{1-4}$alkyl selected from —$CHF_2$, —$CF_3$, —$CH_2CF_3$, —$CH_2CHF_2$ and —$CH_2CH_2CF_3$.

In some embodiments, X is an optionally substituted amino preferably disubstituted amino, such as —N$(C_{1-4}alkyl)_2$. In some embodiments, X is —$N(CH_3)_2$.

In some embodiments, X is selected from any one of the following groups:

methyl, ethyl, isopropyl, tert-butyl, —$CHF_2$, —$CF_3$, —$CH_2CF_3$, —$CH_2CHF_2$, —$CH_2CH_2CF_3$, —$CH_2CH_2OCH_3$, —$CH_2CH_2NH_2$, —$CH_2CH_2N(CH_3)_2$, cyclohexyl, cyclopropyl, —$N(CH_3)_2$

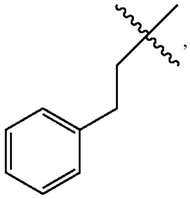, 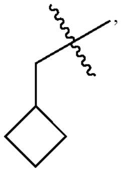,

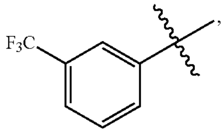, 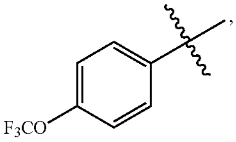,

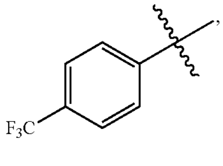, 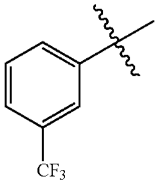

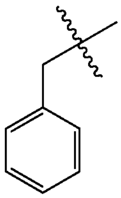, 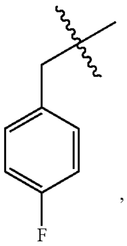, 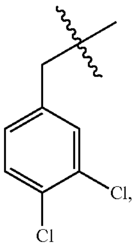

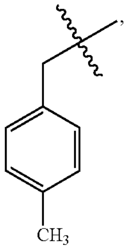, 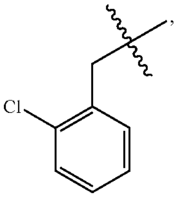, 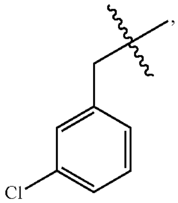,

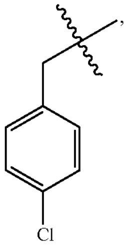, 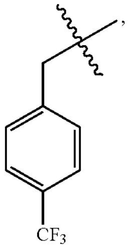, 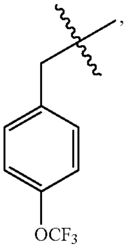,

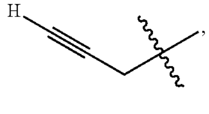, and 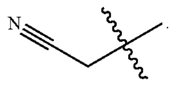.

In some embodiments, X is selected from any one of the following groups: ethyl, difluoromethyl, trifluoroethyl and cyclopropyl.

In some embodiments, X is selected from $C_{1-4}$alkyl and $C_{1-4}$fluroalkyl, preferably —$CHF_2$, —$CH_2CF_3$ and —$CH_2CH_3$.

In some embodiments, X is difluoromethyl.

In some embodiments, X is a group that has a longest linear chain extending from the sulfur atom depicted in formula (I) by not more than 6, 5, 4, 3 or 2 atoms, preferably 3-6 atoms. By "longest linear chain" it is meant the number of atoms from the point of attachment not including any branching or rings. For example, when X is benzyl, the longest linear chain is 6 atoms which includes the methylene carbon atom, four ring atoms and the hydrogen atom attached to the carbon at the 4-position of the benzyl, and when X is —$CH_2CF_3$, the longest linear chain is 3. The longest linear chain in each of these exemplary X-substituents is numbered in the partial formulas shown below:

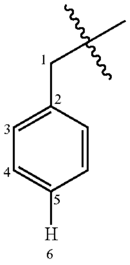 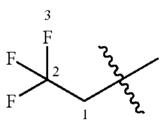

In some embodiments, Y and Z are independently selected from H, $R^4$, —$OR^4$, —$NR^4R^5$, wherein at least one of Y and Z is H; and $R^4$ is selected from optionally substituted $C_{1-6}$alkyl, optionally substituted aryl, optionally substituted $C_{1-6}$alkylaryl, optionally substituted heterocyclyl, optionally substituted $C_{1-6}$alkylheterocyclyl, optionally substituted cycloalkyl, optionally substituted $C_{1-6}$alkyl$C_{3-10}$cycloalkyl.

In some embodiments, Y and Z are independently selected from H, $R^4$, —$OR^4$, —$NR^4R^5$, wherein at least one of Y and Z is H; and $R^4$ is selected from $C_{1-6}$alkyl, aryl, cycloalkyl, heterocyclyl, $C_{1-6}$alkylcycloalkyl, $C_{1-6}$alkylaryl and $C_{1-6}$alkylheterocyclyl, wherein each alkyl (including when present as an optional substituent) is optionally substituted with one or more groups independently selected from halo, $C_{1-4}$alkoxy, hydroxy, nitrile, amino, $C_{1-4}$alkylamino, $(C_{1-4}alkyl)_2$ amino, aryl, cycloalkyl and heterocyclyl;

wherein each aryl (including when present as an optional substituent) is optionally substituted with one or more groups independently selected from halo, hydroxy, nitrile, amino, $C_{1-4}$alkylamino and $(C_{1-4}alkyl)_2$amino, $C_{1-4}$alkoxy, halo$C_{1-4}$alkoxy, aryl, cycloalkyl and heterocyclyl;

wherein each cycloalkyl (including when present as an optional substituent) is optionally substituted with one or more groups independently selected from halo, hydroxy, nitrile, amino, $C_{1-4}$alkylamino and $(C_{1-4}alkyl)_2$ amino, $C_{1-4}$alkyl, $C_{1-4}$alkoxy, halo$C_{1-4}$alkyl, halo$C_{1-4}$alkoxy, aryl, cycloalkyl and heterocyclyl; and wherein each heterocyclyl (including when present as an optional substituent) is optionally substituted with one or more groups independently selected from halo, hydroxy, nitrile, amino, $C_{1-4}$alkylamino and $(C_{1-4}alkyl)_2$ amino, $C_{1-4}$alkoxy, halo$C_{1-4}$alkoxy, cycloalkyl, heterocyclyl and aryl.

In some embodiments, $R^4$ is selected from $C_{1-6}$alkyl, aryl, cycloalkyl, heterocyclyl, $C_{1-6}$alkylcycloalkyl, $C_{1-6}$alkylaryl, $C_{1-6}$alkylheterocyclyl, $C_{3-10}$cycloalkylaryl, $C_{3-10}$cycloalkyl-heterocyclyl, $C_{3-10}$cycloalkyl$C_{3-10}$cycloalkyl, 3-6 membered non-aromatic heterocyclyl-aryl, 3-6 membered non-aromatic heterocyclyl-$C_{3-10}$cycloalkyl and 3-6 membered non-aromatic heterocyclyl-3-10 membered heterocyclyl and wherein each cycloalkyl, aryl and heterocyclyl are optionally substituted with one or more groups independently selected from halo, hydroxy, nitrile, amino, $C_{1-4}$alkylamino and $(C_{1-4}alkyl)_2$amino, $C_{1-4}$alkoxy, halo$C_{1-4}$alkyl and halo$C_{1-4}$alkoxy.

In some embodiments, Y and Z are independently selected from H, $R^4$, —$OR^4$, —$NR^4R^5$, wherein at least one of Y and Z is H; and $R^4$ is selected from $C_{1-6}$alkyl, aryl, cycloalkyl, heterocyclyl and —$(CH_2)_mR^9$, $R^9$ is selected from $C_{3-10}$cycloalkyl, aryl, heterocyclyl, and m is an integer selected from 1 to 6;

wherein each cycloalkyl, aryl and heterocyclyl are optionally substituted with one or more groups independently selected from halo, $C_{1-4}$alkyl, $C_{1-4}$alkoxy, halo$C_{1-4}$alkyl and halo$C_{1-4}$alkoxy.

In some embodiments, Y and Z are independently selected from H, $R^4$, —$OR^4$, —$NR^4R^5$, wherein at least one of Y and Z is H; and $R^4$ is selected from $C_{1-4}$alkyl, cycloalkyl, haloaryl, —$C_{1-2}$ alkylaryl, —$C_{1-2}$alkylarylhalo, —$C_{1-2}$alkyl$C_{3-6}$cycloalkyl, —$C_{1-2}$alkylheterocyclyl, —$C_{1-2}$ alkylaryl$C_1$alkylhalo, —$C_{1-2}$alkylarylhalo$C_1$alkyl, —$C_{1-2}$alkylarylhaloalkoxy, cycloalkylaryl, cycloalkyl-heterocyclyl, cycloalkylcycloalkyl, 3-6 membered non-aromatic heterocyclyl-aryl, 3-6 membered non-aromatic heterocyclylcycloalkyl, 3-6 membered non-aromatic heterocyclyl-3-10 membered heterocyclyl, 3-6 membered heteroaryl-aryl, 3-6 membered heteroarylcycloalkyl, 3-6 membered heteroaryl-3-10 membered heteroaryl, $C_{1-2}$alkyl-3-6 membered non-aromatic hereocyclyl and $C_{1-2}$alkyl-3-6 membered heteroaryl;

wherein each alkyl, cycloalkyl, aryl, aralkyl, non-aromatic heterocyclyl, heteroaryl and alkoxy is optionally substituted with a group selected from halo, hydroxy, nitrile, amino, $C_{1-4}$alkylamino and $(C_{1-4}alkyl)_2$amino, $C_{1-4}$alkoxy, halo$C_{1-4}$alkoxy and acyl.

In some embodiments, Y and Z are independently selected from H and —$OR^4$.

In some embodiments, Z is H.

In some embodiments, Y is selected from H, $R^4$, —$OR^4$, —$NR^4R^5$.

In some embodiments, Z is H and Y is selected from $R^4$, —$OR^4$, —$NR^4R^5$.

In some embodiments, Z is H and Y is —$OR^4$.

In some embodiments, $R^4$ is an optionally substituted $C_1$alkyl$C_6$aryl or an optionally substituted $C_1$alkylheteroaryl. In some embodiments, the $C_1$alkyl moiety is substituted. In some embodiments, the aryl or heteroaryl moiety is substituted.

In some embodiments, $R^4$ is an optionally substituted $C_1$alkyl$C_6$aryl moiety represented by the following partial formula:

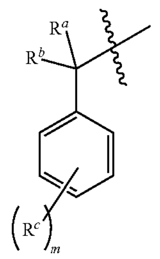

wherein $R^a$ and $R^b$ are independently selected from H, optionally substituted $C_{1-4}$alkyl, optionally substituted $C_{1-4}$alkoxy, optionally substituted $C_{1-4}$alkylhydroxy, optionally substituted $C_{1-4}$alkylnitrile, optionally substituted amino, optionally substituted $C_{1-4}$alkylamino and optionally substituted $(C_{1-4}alkyl)_2$amino, or $R^a$ and $R^b$ together with the carbon atom to which they are attached form an optionally substituted $C_{3-6}$cycloalkyl or a 3-6 membered non-aromatic heterocyclyl;

$R^c$ is selected from halo and an optionally substituted $C_{1-4}$alkyl; and m is 0, 1 or 2.

In some embodiments, $R^a$ and $R^b$ are independently selected from H, optionally substituted $C_{1-4}$alkyl, optionally substituted $C_{1-4}$alkoxy, optionally substituted $C_{1-4}$alkoxy$C_{1-2}$alkyl, optionally substituted $C_{1-4}$alkylhydroxy, optionally substituted $C_{1-4}$alkylnitrile, optionally substituted $C_{1-4}$alkylamino and optionally substituted $(C_{1-4}alkyl)_2$amino. When $R^a$ and/or $R^b$ are an optionally substituted $C_{1-4}$alkylamino, either the $C_{1-4}$alkyl or amino moiety may be optionally substituted.

In some embodiments, $R^a$ and $R^b$ together with the carbon atom to which they are attached form an optionally substituted $C_{3-6}$cycloalkyl or a 3-6 membered non-aromatic heterocyclyl selected from an optionally substituted cyclopropyl, an optionally substituted cyclobutyl, an optionally substituted cyclopentyl, an optionally substituted cyclohexyl, an optionally substituted oxetane and an optionally substituted azetidine.

In some embodiments, $R^a$ and $R^b$ together with the carbon atom to which they are attached form a 3-6 membered non-aromatic heterocyclyl comprising 1 or 2, preferably 1 heteroatom, preferably selected from O and N.

In some embodiments, m is 0 or 1.

In some embodiments, m is 1 or 2.

In some embodiments, at least one $R^c$ is in the para position relative to the benzyl carbon atom.

In some embodiments, $R^c$ is selected from methyl, fluoro and chloro.

In some embodiments, $R^a$ is selected from H and methyl, and $R^b$ is H.

In some embodiments, $R^a$ and $R^b$ together with the carbon atom to which they are attached are cyclopropyl.

In some embodiments, $R^4$ is —$CR^aR^b$heteroaryl, wherein the heteroaryl moiety is optionally substituted by 1 or 2 $R^c$ groups. $R^a$, $R^b$ and $R^c$ may be as defined for any embodiment described herein. In some embodiments, the heteroaryl moiety of the —$CR^aR^b$heteroaryl group is a 5- or 6-membered heteroaryl comprising 1 or 2 heteroatoms selected from N, S and O. In some embodiments, the heteroaryl moiety is selected from an optionally substituted oxazolyl and an optionally substituted thiazolyl.

In some embodiments, Y is selected from —$OR^4$, —$NR^4R^5$.

In some embodiments, wherein Y is selected from —$OR^4$, —$NR^4R^5$, $R^4$ has partial structure (A):

(A)

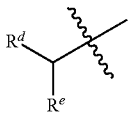

wherein $R^d$ is selected from H, optionally substituted $C_{1-4}$alkyl, optionally substituted $C_{1-4}$alkoxy, optionally substituted $C_{1-4}$alkoxy$C_{1-4}$alkyl, optionally substituted $C_{1-4}$alkylhydroxy, optionally substituted $C_{1-4}$alkylnitrile, optionally substituted $C_{1-4}$alkylamino and optionally substituted $(C_{1-4}alkyl)_2$amino, optionally substituted cycloalkyl and optionally substituted $C_{1-4}$alkylcycloalkyl; and $R^e$ is selected from optionally substituted aryl, optionally substituted $C_{1-5}$alkylaryl, optionally substituted heterocyclyl, optionally substituted $C_{1-5}$alkylheterocyclyl, optionally substituted cycloalkyl, and optionally substituted $C_{1-5}$alkyl$C_{3-10}$cycloalkyl.

In some embodiments, $R^d$ is methyl.

In some embodiments, $R^e$ is selected from optionally substituted aryl, optionally substituted $C_{1-5}$alkylaryl, optionally substituted heterocyclyl, optionally substituted $C_{1-4}$alkylheterocyclyl, optionally substituted cycloalkyl, and optionally substituted $C_{1-4}$alkyl$C_{3-10}$cycloalkyl.

In some embodiments, $R^e$ is selected from optionally substituted aryl, optionally substituted cycloalkyl and optionally substituted heterocyclyl.

In some embodiments, $R^e$ is selected from optionally substituted aryl and optionally substituted heteroaryl.

In some embodiments, $R^d$ is selected from optionally substituted $C_{1-4}$alkyl, optionally substituted $C_{1-4}$alkoxy, optionally substituted $C_{1-4}$alkoxy$C_{1-4}$alkyl, optionally substituted cycloalkyl and optionally substituted $C_{1-4}$alkylcycloalkyl. In these embodiments, where $R^d$ and $R^e$ are not the same group, the partial structure (A) may contain a chiral centre at the carbon to which $R^d$ and $R^e$ are attached. Therefore, the carbon atom to which $R^d$ and $R^e$ are attached may be enantiomerically enriched. In some embodiments, the carbon atom to which $R^d$ and $R^e$ is attached is enriched as the (S) stereoisomer, for example when $R^e$ has a higher ranking than $R^d$ in the Cahn-Ingold-Prelog rules for stereochemical assignment. In some embodiments, the carbon atom to which $R^d$ and $R^e$ is attached is enriched as the (R) stereoisomer, for example when $R^e$ has a lower ranking than $R^d$ the Cahn-Ingold-Prelog rules for stereochemical assignment. In some embodiments, $R^d$ is selected from optionally substituted $C_{1-4}$alkyl, and the carbon atom to which $R^d$ and $R^e$ are attached is enriched in the (S) stereoisomer. The inventors have surprisingly found that compounds with the (S) configuration at this position possess greater MLKL activity than those with the (R) configuration at the same position. In some cases, the S-stereoisomer is greater than 2-fold more active than the corresponding R-stereoisomer, and in some embodiments, the S-stereoisomer may be at least about 5-fold or about 10-fold more active than the corresponding R-stereoisomer for MLKL inhibition.

In some embodiments, partial structure (A) may have the stereochemical configuration shown in by partial structure (A1):

(A1)

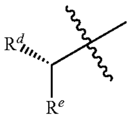

wherein $R^e$ has a higher ranking than $R^d$ in the Cahn-Ingold-Prelog rules for stereochemical assignment.

In some embodiments, the compound is provided as a compound of formula (S):

(S)

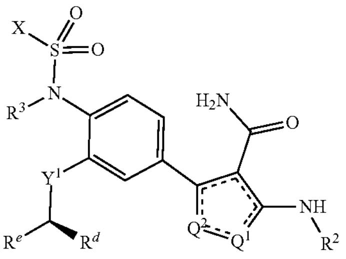

wherein X, $Q^1$, $Q^2$, $R^2$ and $R^3$ are as defined for formula (I), $R^e$ and $R^d$ are as defined for partial formula (A) and $Y^1$ is selected from O and $NR^5$.

In some embodiments, $R^4$ is selected from any one of the following groups:

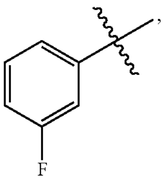
,
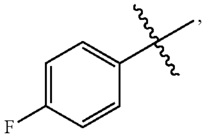
,
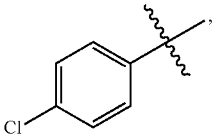
,
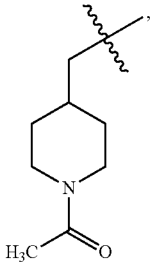
,
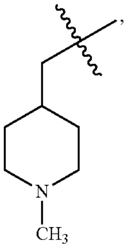
,
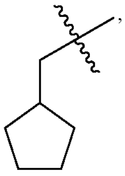
,
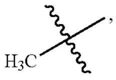
, -continued
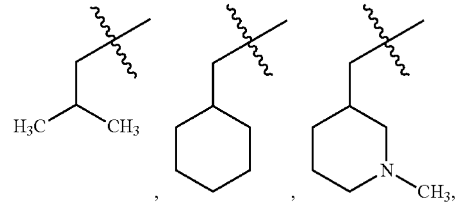
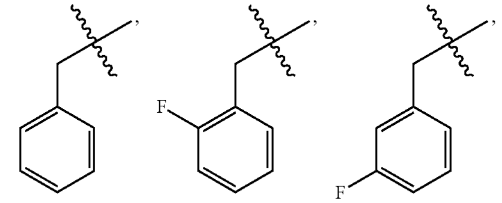
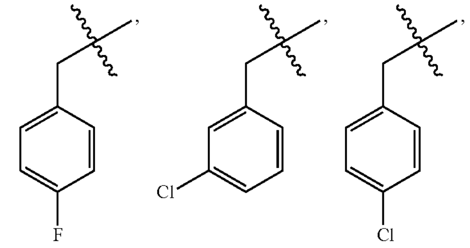
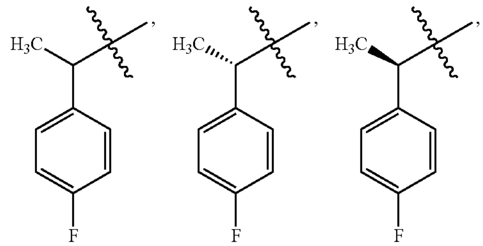
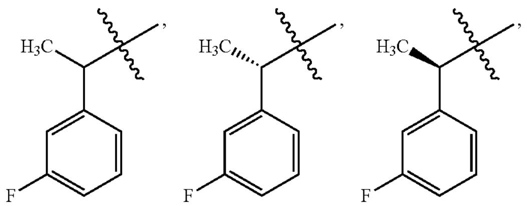
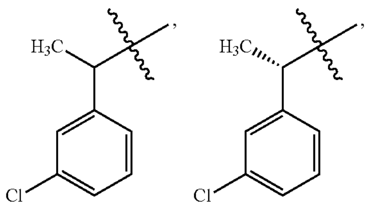
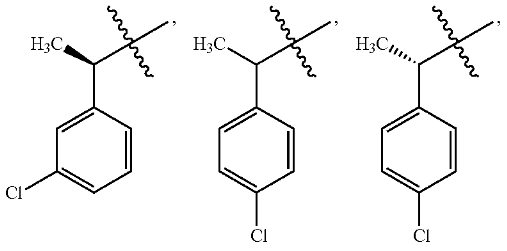
-continued
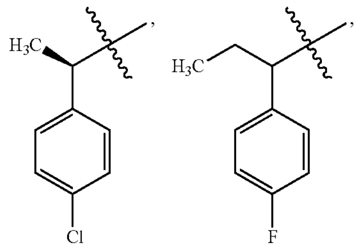
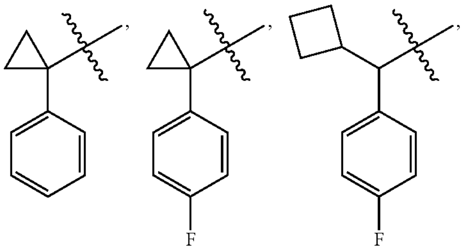
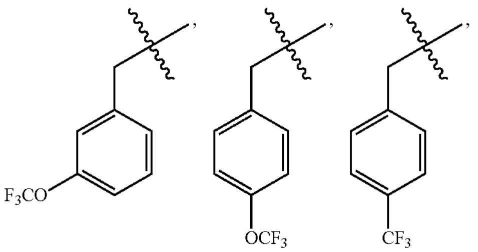
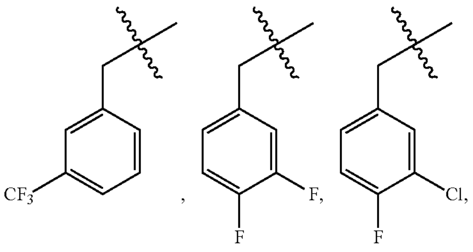
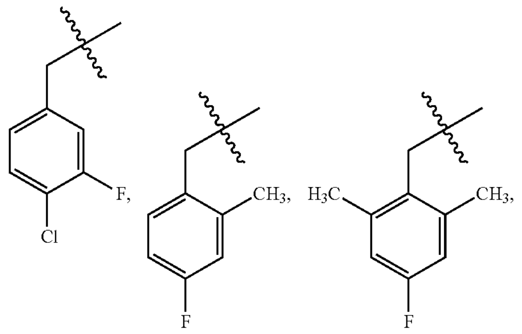
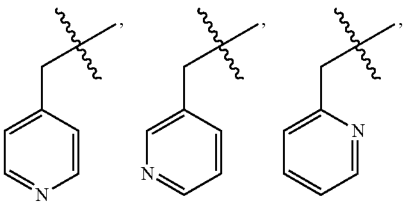

-continued

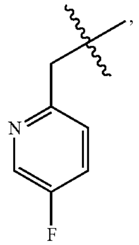
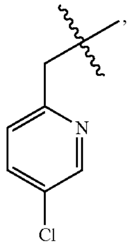
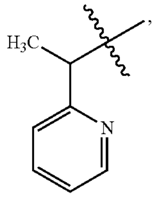
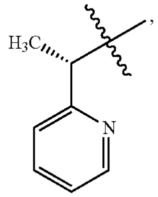
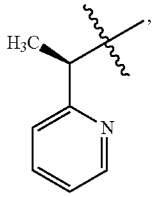
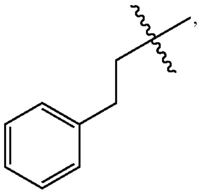
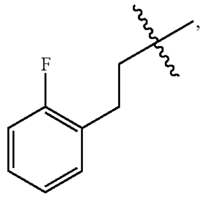
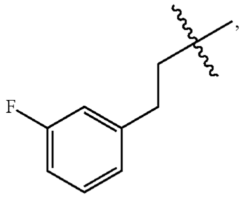
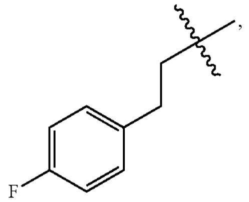
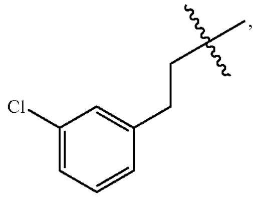
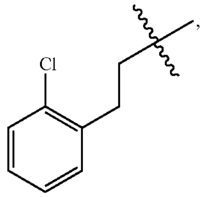
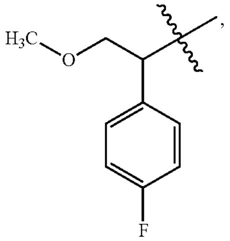
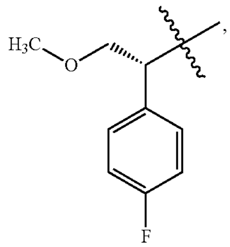
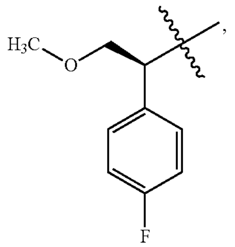
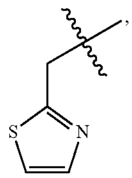
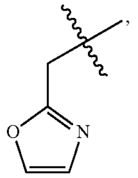
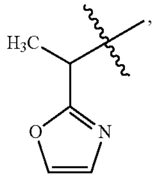
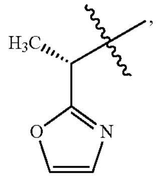 and 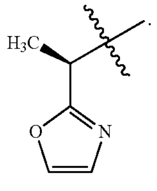

In some embodiments, $R^4$ is

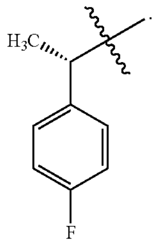 [SMILES: *[C@@H](C)c1ccc(F)cc1]

In some embodiments, $R^5$ is selected from H and methyl.

In some embodiments, $R^5$ is H.

In some embodiments, Y is H.

In some embodiments, Z is H.

In some embodiments, both Y and Z are H.

In some embodiments, $R^1$ and $R^3$ are H.

In some embodiments, $R^2$ is selected from an optionally substituted phenyl, an optionally substituted 5-membered heteroaryl, an optionally substituted 6-membered heteroaryl, an optionally substituted 8-membered heteroaryl, an optionally substituted 9-membered heteroaryl and an optionally substituted 10-membered heteroaryl.

In some embodiments, $R^2$ is selected from an optionally substituted phenyl, an optionally substituted 5-membered monocyclic heteroaryl, an optionally substituted 6-membered monocyclic heteroaryl and an optionally substituted 10-membered bicyclic heteroaryl.

In some embodiments, $R^2$ is represented by any one of partial formulas Ar1-Ar3:

Ar1

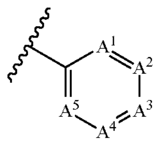

Ar2

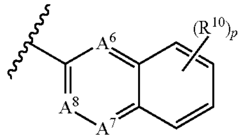

Ar3

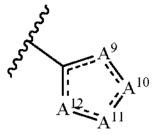

wherein $A^1$, $A^2$, $A^3$, $A^4$, $A^5$, $A^6$, $A^7$, and $A^8$ are independently selected from $CR^{11}$ and N;

$A^9$, $A^{10}$, $A^{11}$ and $A^{12}$ are independently selected from $C(R^{11})_q$, O, S, N and $NR^{12}$;

wherein not more than 2 of $A^1$, $A^2$, $A^3$, $A^4$ and $A^5$ are N wherein not more than 2 of $A^6$, $A^7$ and $A^8$ are N wherein at least 1 of $A^9$, $A^{10}$, $A^{11}$ and $A^{12}$ is selected from $C(R^{11})_q$, O, S and $NR^{12}$;

each $R^{11}$ is independently selected from H and $R^{10}$;

each $R^{10}$ is independently selected from halo, $C_{1-6}$alkyl, $C_{1-6}$alkoxy, $C_{3-10}$cycloalkyl, —$OC_{1-6}$alkyl$C_{1-4}$alkoxy, halo$C_{1-6}$alkyl, halo$C_{1-6}$alkoxy, nitrile, amido, $C_{1-6}$alkylamido, $(C_{1-6}alkyl)_2$amido, halo$C_{1-6}$alkylamido, (halo$C_{1-6}$alkyl)$_2$amido, acyl, $C_{1-6}$alkylacyl, halo$C_{1-6}$alkylacyl, arylacyl, heterocyclylacyl, $C_{3-10}$cycloalkylacyl, heterocyclyl, halo$C_{1-6}$alkoxy, $C_{3-10}$cycloalkyl, $C_{1-6}$alkyl$C_{3-10}$cycloalkyl, $C_{1-6}$alkoxy$C_{3-10}$cycloalkyl, halo$C_{1-6}$alkyl$C_{3-10}$cycloalkyl, halo$C_{1-6}$alkoxy$C_{3-10}$cycloalkyl, $C_{1-6}$alkylheterocyclyl, $C_{1-6}$alkoxyheterocyclyl, halo$C_{1-6}$alkylheterocyclyl, halo$C_{1-6}$alkoxyheterocyclyl, $C_{1-6}$alkyl$C_{1-6}$alkoxy, and —COOH;

each $R^{12}$ is independently selected from H, $C_{1-6}$alkyl, $C_{1-6}$alkylacyl and halo$C_{1-6}$alkylacyl;

or when two adjacent groups selected from $A^1$, $A^2$, $A^3$, $A^4$, $A^5$, $A^7$, $A^8$ $A^9$, $A^{10}$, $A^{11}$ and $A^{12}$ (e.g., $A^1$ and $A^2$, $A^2$ and $A^3$, $A^3$ and $A^4$, $A^4$ and $A^5$, $A^8$ and $A^7$, $A^9$ and $A^{10}$, $A^{10}$ and $A^{11}$, $A^{11}$ and $A^{12}$) are selected from $CR^{11}$ and $NR^{12}$, two $R^{11}$, two $R^{12}$ or one $R^{11}$ and one $R^{12}$ may together form an optionally substituted 5-10 membered ring selected from cycloalkyl, aryl and heterocyclyl;

p is an integer from 0 to 4; and q is 1 or 2.

In some embodiments, 0, 1 or 2 of $A^1$, $A^2$, $A^3$, $A^4$ and $A^5$ are N.

In some embodiments, 0, 1 or 2 of $A^6$, $A^7$ and $A^8$ are N.

In some embodiments, $R^{10}$ is selected from fluoro, chloro, methyl, isopropyl, tert-butyl, difluoromethyl, trifluoromethyl, methoxy, ethoxy, difluoroethoxy, nitrile, amido, trifluoromethoxy, —$OCH_2CH_2OCH_3$, cyclopropyl and morpholino.

In some embodiments, the compound comprises not more than 1, 2, 3 or 4 instances if $R^{10}$.

In some embodiments, $R^2$ is represented by partial formula Ar1.

In some embodiments, $R^2$ is represented by partial formula Ar3.

In some embodiments, $A^{10}$ is $NR^{12}$ and $A^{12}$ is $CR^{11}$.

In some embodiments, $A^9$ and $A^{11}$ may be independently selected from $CR^{11}$, N, O and S. In some embodiments, when $A^9$ is $CR^{11}$, $A^{11}$ is N, O or S and when $A^9$ is N, O or S, $A^{11}$ is $CR^{11}$.

In some embodiments, $A^9$ and $A^{11}$ are each $CR^{11}$.

In some embodiments, $A^{10}$ and $A^{12}$ are each $CR^{11}$.

In some embodiments, at least one of $A^9$, $A^{10}$, $A^{11}$ and $A^{12}$ is selected from O, S, N and $NR^{12}$.

In some embodiments, one of $A^9$, $A^{10}$, $A^{11}$ and $A^{12}$ is selected from O, S and $NR^{12}$.

In some embodiments, partial formula Ar3 is provided by any one of the partial formulas Ar3-I, Ar3-II, Ar3-III and Ar3-IV Ar3-I

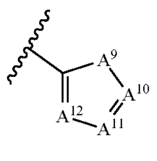

Ar3-II

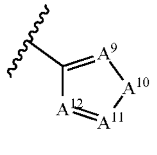

Ar3-III

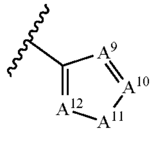

-continued

Ar3-IV

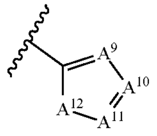

wherein in Ar3-I, $A^9$ is selected from $C(R^{11})_2$, O, S and $NR^{12}$, preferably O, S and $NR^{12}$;

in Ar3-II, $A^{10}$ is selected from $C(R^{11})_2$, O, S and $NR^{12}$, preferably O, S and $NR^{12}$;

in Ar3-III, $A^{11}$ is selected from $C(R^{11})_2$, O, S and $NR^{12}$, preferably O, S and $NR^{12}$; and in Ar3-IV, $A^{12}$ is selected from $C(R^{11})_2$, O, S and $NR^{12}$, preferably O, S and $NR^{12}$.

In some embodiments, $A^{10}$ and $A^{11}$ are independently selected from $CR^{11}$ and $NR^{12}$ such that two $R^{11}$, two $R^{12}$ or $R^{11}$ and $R^{12}$ together form a 5-10 membered cycloalkyl, aryl or heterocyclyl ring.

In some embodiments, $A^{10}$ is $CR^{11}$ and $A^{11}$ is $NR^{12}$, and $R^{11}$ and $R^{12}$ together form a 5-10 membered cycloalkyl, aryl or heterocyclyl ring. In these embodiments, $A^{12}$ may be N and/or $A^9$ may be $CR^{11}$. In some embodiments, when $A^{10}$ is $CR^{11}$ and $A^{11}$ is $NR^{12}$, and $R^{11}$ and $R^{12}$ together form a 5-10 membered heterocyclyl ring, preferably a non-aromatic heterocyclyl ring. In some embodiments, when $A^{10}$ is $CR^{11}$ and $A^{11}$ is $NR^{12}$, $R^{11}$ and $R^{12}$ together form a 5-8 membered cycloalkyl, aryl or heterocyclyl ring, preferably a 6 or 7 membered ring, more preferably a 6 or 7 membered heterocyclyl ring.

When two $R^{11}$, two $R^{12}$ or one $R^{11}$ and $R^{12}$ on adjacent ring atoms form a fused ring, the fused ring may be optionally substituted by 1-3 $R^{10}$ groups. Any $R^{10}$ group described herein may be suitable.

In some embodiments, $R^{12}$ is methyl.

In some embodiments, the compound of formula (I) is a compound of formula (II)

(II)

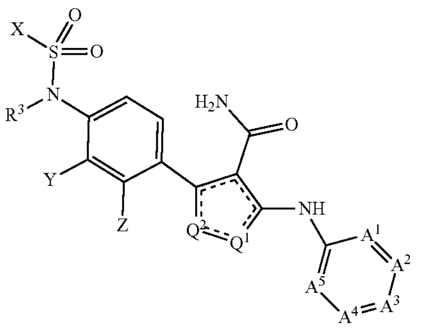

wherein $Q^1$, $Q^2$, X, Y, Z and $R^3$ are as defined in formula (I) and $A^1$-$A^5$ are as defined for partial formula Ar1.

In some embodiments, $A^1$ is N.

In some embodiments, $A^4$ is N.

In some embodiments, $A^1$ and $A^4$ are N.

In some embodiments, $A^2$ is N.

In some embodiments, $A^1$ and $A^3$ are N.

In some embodiments, $A^2$ is $CR^{10}$.

In some embodiments, $A^6$ is N.

In some embodiments, $A^7$ is N.

In some embodiments, $A^6$ and $A^7$ are N.

In some embodiments, $R^2$ is a 5-, 6- or 10-membered heteroaryl comprising 0, 1 or 2 substituents selected from fluoro, chloro, methyl, isopropyl, tert-butyl, difluoromethyl, trifluoromethyl, methoxy, ethoxy, difluoroethoxy, trifluoromethoxy, $—OCH_2CH_2OCH_3$, cyclopropyl, nitrile, amido and morpholino. Preferably, the substituents are selected from methyl, trifluoromethyl and methoxy. Preferably, when $R^2$ is a 10-membered heteroaryl, it is a fused bicyclic ring system.

In some embodiments, $R^2$ is a 5-, 6- or 10-membered heteroaryl comprising 1 or 2 nitrogen atoms, which is substituted by 0, 1 or 2 substituents.

In some embodiments, $R^2$ is a 6-membered heteroaryl comprising 1 or 2 nitrogen atoms, which is substituted by 0 or 1 substituents selected from methyl, trifluoromethyl and methoxy. Typically, if present, the substituent is in the meta or para position relative to the nitrogen atom to which $R^2$ is attached (eg corresponding to positions shown for $A^2$ or $A^3$ in partial formula Ar1).

In some embodiments, $R^2$ is selected from any one of the following radicals:

methyl,

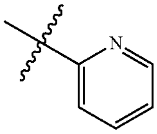
,
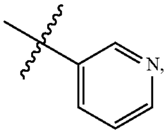

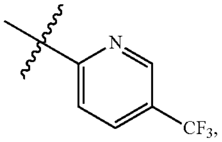
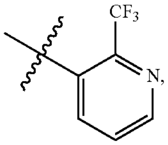

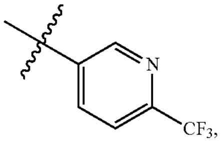
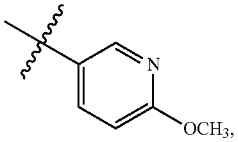

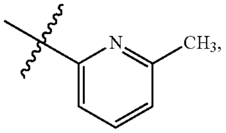
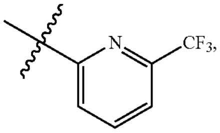

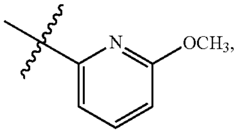

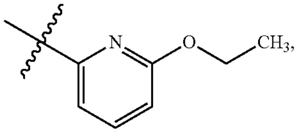

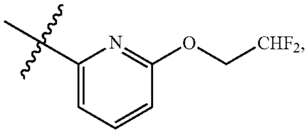

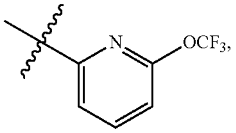

-continued

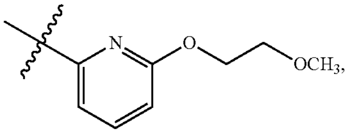

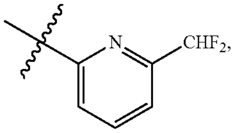
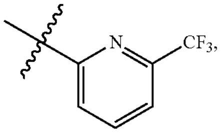

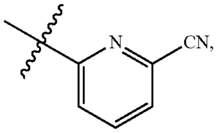
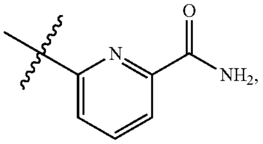

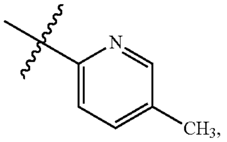
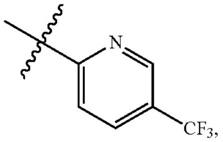

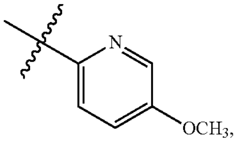

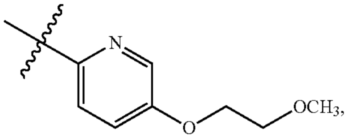

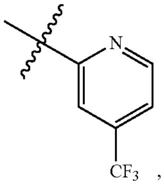
,
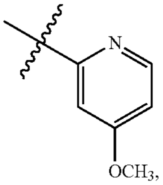

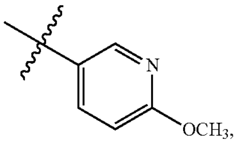
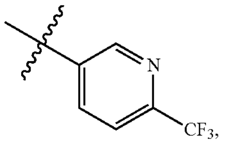

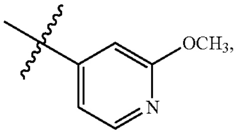
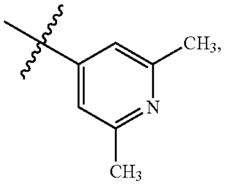

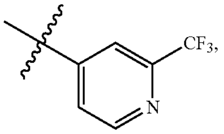

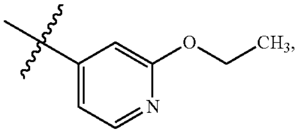

-continued
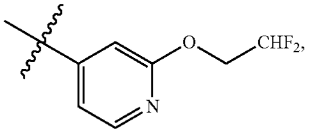
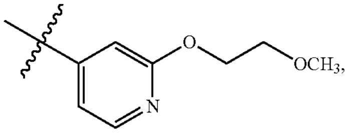
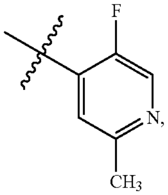
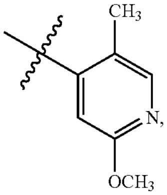
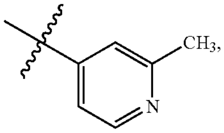
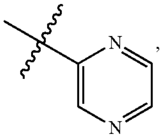
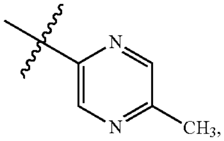
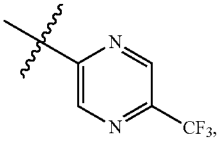
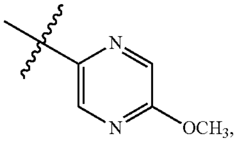
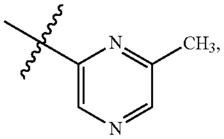
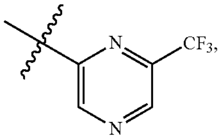
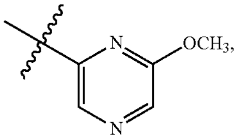
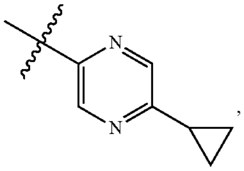
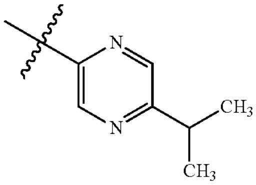
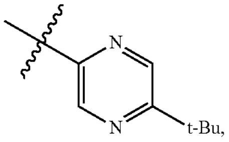
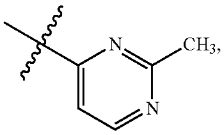
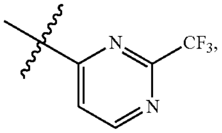
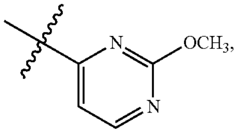
-continued
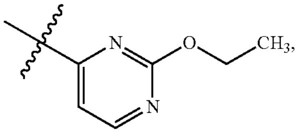
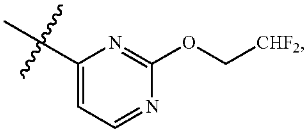
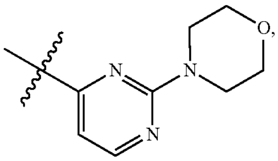
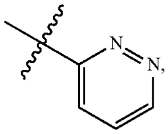
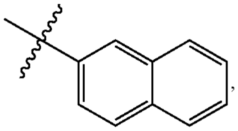
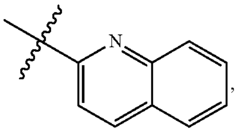
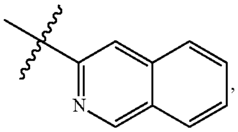
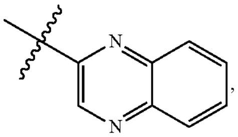
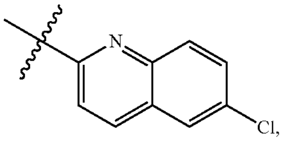
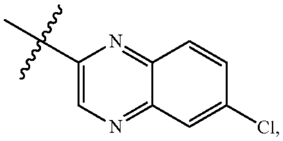
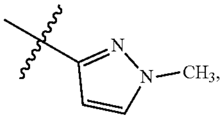
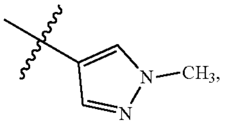
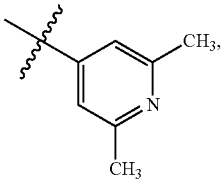
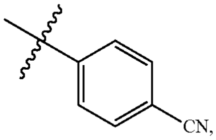
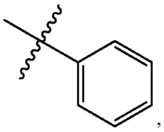
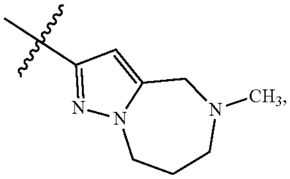

-continued
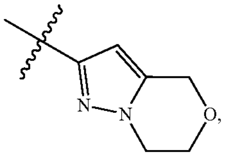
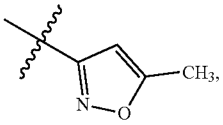
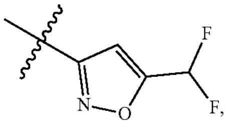
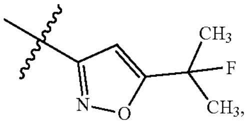
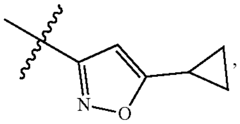
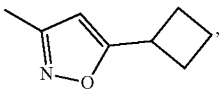
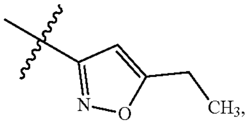
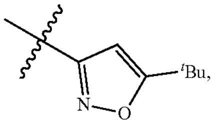
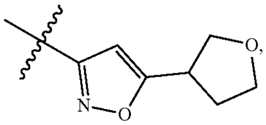
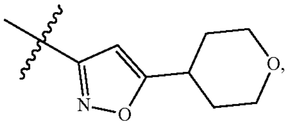
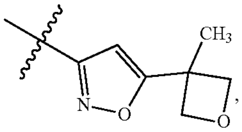
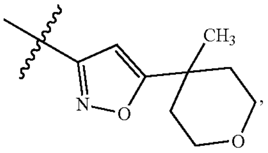
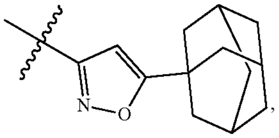
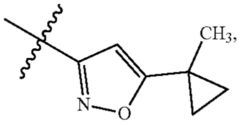
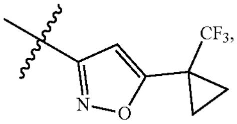
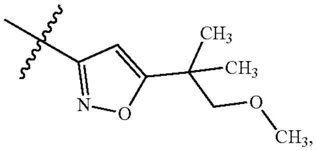
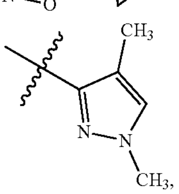
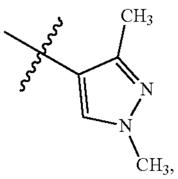
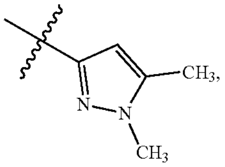
-continued
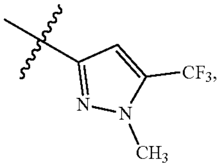
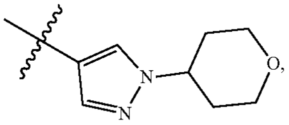
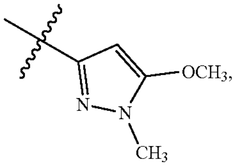
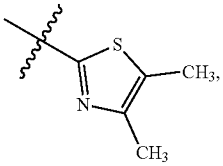
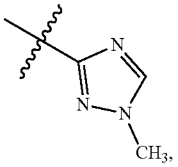
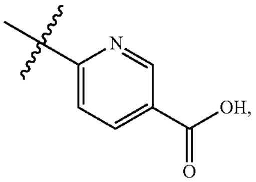
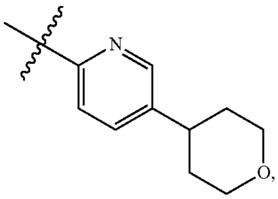
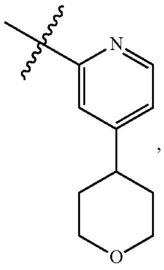
, and
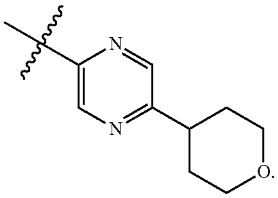
In some embodiments, $R^2$ is selected from any one of the following radicals:
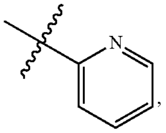
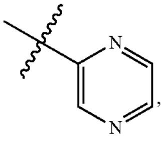
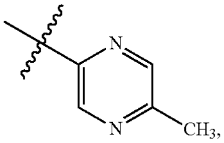
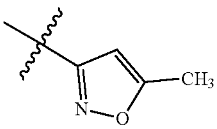
and
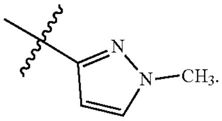

In some embodiments of the compound of formula (I)

X is selected from an optionally substituted $C_{1-4}$alkyl, an optionally substituted halo$C_{1-4}$alkyl and an optionally substituted $C_{3-6}$cycloalkyl;

Y and Z are independently selected from H and —$OC_1$alkylaryl, $R^1$ and $R^3$ are H; and $R^2$ is 6-membered heteroaryl comprising 1 or 2 nitrogen atoms, which is substituted by 0 or 1 substituents selected from methyl, trifluoromethyl and methoxy.

In some embodiments of the compound of formula (I)

X is selected from an optionally substituted halo$C_{1-4}$alkyl, preferably an optionally substituted halo$C_{1-2}$alkyl, more preferably difluoromethyl;

Y is —$OR^4$, preferably optionally substituted —$OC_{1-4}$alkylaryl, more preferably (S)-1-(4-fluorophenyl)-1-methyl-methoxy;

Z is H $R^1$ and $R^3$ are H; and $R^2$ is 5- or 6-membered heteroaryl comprising 1 or 2 heteroatoms selected from N and O substituted by 0 or 1 substituents selected from methyl, trifluoromethyl and methoxy, preferably substituted by 0 or 1 methyl substituents.

In some embodiments, the compound is selected from compounds 1-320 described herein, preferably 9, 14, 21-22, 24-25, 34, 39, 41-43, 53, 62-63, 66, 68, 71, 84, 88, 90, 92-93, 101-102, 108, 113, 115, 123-124, 127-128, 139-140, 143-144, 146, 150, 152-158, 160-166, 169-171, 175-176, 181, 188, 190-191, 194, 196, 198-199, 202, 208, 222-223, 229, 233-235, 238, 242, 245-246, 248-249, 251-253, 256, 259-260, 262, 264-266, 271, 273-279, 281-286,288-299, 301-312, 314 and 316-320.

Typically, the compounds of the invention may be prepared by techniques known in the art.

In another aspect, there is also provided a process for preparing a compound of formula (I) or a salt, solvate, tautomer, N-oxide, stereoisomer and/or prodrug thereof.

In some embodiments, the process comprises any of the following 4 steps:

reacting a compound of formula (III) with a compound of formula (IV)

III

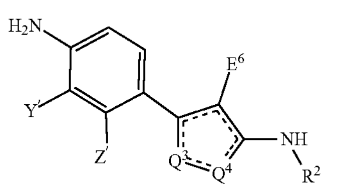

IV

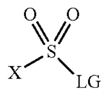

wherein X and $R^2$ are as defined for formula (I)

$Q^3$ and $Q^4$ are selected from N and N-$PG^1$, wherein when $Q^3$ is N, $Q^4$ is N-$PG^1$ and when $Q^4$ is N, $Q^3$ is N-$PG^1$;

Y' is selected from halo and Y, wherein Y is as defined for formula (I);

Z' is selected from halo and Z, wherein Z is as defined for formula (I);

$PG^1$ is $R^1$ or an amino protecting group, such as tert-butyl, benzyl, BOC and the like, wherein $R^1$ is as defined for formula (I); and LG is a leaving group, such as halo. The leaving group may be any that is capable of activating the sulphonyl moiety of the compound of formula (IV) as an electrophile capable of reacting under appropriate conditions with the free aniline nitrogen of the compound of formula (III); and $E^6$ is selected from —CN and —C(O)$NH_2$.

reacting a compound of formula (V) with a compound of formula (VI)

V

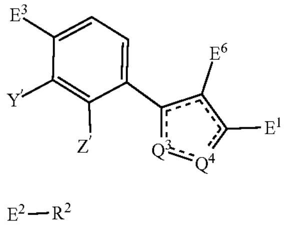

VI $E^2$—$R^2$ wherein $Q^3$, $Q^4$, $E^6$, Y' and Z' are as defined for formula (III) and $R^2$ is as defined for formula (I)

$E^3$ is selected from —$NO_2$, —$NHR^3$, —$NR^3PG^2$ and —$NHSO_2X$, wherein X an $R^3$ are as defined in formula (I) and $PG^2$ is an amino protecting group E' is selected from $NH_2$ or halo $E^2$ is selected from $NH_2$ or halo with the proviso that one of $E^1$ and $E^2$ is $NH_2$ and the other is halo;

reacting a compound of formula (VII) with a compound of formula (VIII)

VII

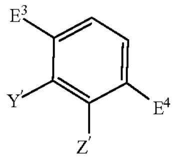

VIII

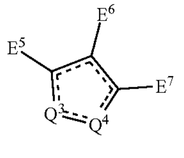

wherein $E^3$ is as defined for formula (V) and $Q^3$, $Q^4$, $E^6$, Y' and Z' are as defined for formula (III), $E^4$ is selected from halo, a boronic acid and a boronic ester, $E^5$ is selected from halo, a boronic acid and a boronic ester, with the proviso that one of $E^4$ and $E^5$ is halo and the other is a boronic acid or a boronic ester, $E^7$ is selected from halo, —$NH_2$ and —$NHR^2$, wherein $R^2$ is as defined for formula (I);

converting a compound of formula (I) into one of its salts.

In some embodiments, $Q^3$ is N and $Q^4$ is N-$PG^1$.

In some embodiments, $Q^3$ is N-$PG^1$ and $Q^4$ is N.

In some embodiments of the above process, wherein $PG^1$ is an amino protecting group, the process further comprises a deprotection step.

In some embodiments, wherein Y' is halo, the process comprises reacting the compound of formula (III), (V) or (VII) with Y-$LG^2$, wherein $LG^2$ is a leaving group and Y is as defined in formula (I). Typically, this reaction is a palladium mediated cross-couling reaction. In some embodiments, this reaction takes place on the reaction product of the compound of formula (III) and (IV), (V) and (VI) or (VII) and (VIII).

In some embodiments, wherein Z' is halo, the process comprises reacting the compound of formula (III), (V) or (VII) with Z-$LG^3$, wherein $LG^3$ is a leaving group and Z is as defined in formula (I). Typically, this reaction is a palladium mediated cross-couling reaction. In some embodiments, this reaction takes place on the reaction product of the compound of formula (III) and (IV), (V) and (VI) or (VII) and (VIII).

In some embodiments, wherein $E^6$ is —CN, the process further comprises conversion of the —CN into —C(O)$NH_2$.

Embodiments of these steps are shown in Schemes 1-7 below with reference to compounds wherein $R^2$ is represented by partial formula Ar1.

The specific reagents and conditions for effecting each of these steps will depend on the specific substituents selected for each reaction partner. The skilled person would readily appreciate how to determine and/or optimise these reagents and conditions. Similarly, where a starting material is not commercially available, the skilled person would be able to design and implement its preparation based on techniques and reactions previously described. Embodiments of these steps are provided in the Examples with reference to specific compounds described herein.

Methods

In another aspect, there is provided a method for inhibiting necroptosis in a subject in need thereof, the method comprising administering a therapeutically effective amount of a compound according to Formula (I) or a pharmaceutically acceptable salt, solvate, tautomer, N-oxide, stereoisomer and/or prodrug thereof.

Without wishing to be bound by theory, it is believed that the compounds of the invention treat necroptosis by binding to the ATP-binding site of the pseudokinase domain of Mixed Lineage Kinase Domain-like (MLKL) protein.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

In one embodiment of the present disclosure, administration of a compound according to Formula (I) inhibits a conformational change of MLKL. In another embodiment, the conformational change of MLKL involves release of the four-helix bundle (4HB) domain of MLKL. In another embodiment, administration of the compound inhibits oligomerisation of MLKL. In yet another embodiment, administration of the compound inhibits translocation of MLKL to the cell membrane.

In a further embodiment, administration of the compound inhibits a conformational change of MLKL, inhibits oligomerisation of MLKL and inhibits translocation of MLKL to the cell membrane.

It is envisaged that some compounds of the present disclosure can bind to MLKL in various species and inhibit necroptosis.

As used herein, the term "pseudokinase domain" as understood by a person skilled in the art, means a protein containing a catalytically-inactive or catalytically-defective kinase domain. "Pseudokinase domains" are often referred to as "protein kinase-like domains" as these domains lack conserved residues known to catalyse phosphoryl transfer. It would be understood by a person skilled in the art that although pseudokinase domains are predicted to function principally as catalysis independent protein-interaction modules, several pseudokinase domains have been attributed unexpected catalytic functions. Accordingly, in the present disclosure the term "pseudokinase domain" includes "pseudokinase domains" which lack kinase activity and "pseudokinase domains" which possess weak kinase activity.

As used herein, the term "ATP-binding site" as understood by a person skilled in the art, means a specific sequence of protein subunits that promotes the attachment of ATP to a target protein. An ATP binding site is a protein micro-environment where ATP is captured and hydrolyzed to ADP, thereby releasing energy that is utilized by the protein to work by changing the protein shape and/or making the enzyme catalytically active. In pseudokinase domains, the "ATP-binding site" is often referred to as the "pseudoactive site". The term "ATP-binding site" may also be referred to as a "nucleotide-binding site" as binding at this site includes the binding of nucleotides other than ATP. It would be understood by a person skilled in the art that the term "nucleotide" includes any nucleotide. Exemplary nucleotides include, but are not limited to, AMP, ADP, ATP, AMPPNP, GTP, CTP and UTP.

As described herein, treatment and/or inhibition of necroptosis includes both complete and partial inhibition of necroptosis. In one embodiment, inhibition of necroptosis is complete inhibition. In another embodiment, inhibition of necroptosis is partial inhibition.

Binding of the compound to the ATP-binding site of the pseudokinase domain of MLKL may inhibit phosphorylation of MLKL by an effector kinase or binding of the compound to the ATP-binding site of the pseudokinase domain of MLKL may not inhibit phosphorylation of MLKL by an effector kinase. The present disclosure demonstrates that compounds that bind to the ATP-binding site of the pseudokinase domain of the MLKL protein, as described herein, can inhibit necroptosis without inhibiting phosphorylation of MLKL by an effector kinase. In one embodiment, binding of the compound to the ATP-binding site of the pseudokinase domain of MLKL does not inhibit phosphorylation of MLKL by an effector kinase. In another embodiment, binding of the compound to the ATP-binding site of the pseudokinase domain of MLKL inhibits phosphorylation of MLKL by an effector kinase.

RIP1, RIP3 and MLKL are three proteins implicated in the necroptotic pathway. Upon necroptotic stimulus (e.g. using the combination of TNF, SMAC mimetic and QVD-OPh on suitable cell lines), RIP1 is auto-phosphorylated leading to association with RIP3, which in turn auto-phosphorylates itself. Activated RIP3 phosphorylates MLKL leading to a putative conformational change that triggers its necroptotic activity (Murphy, *Immunity,* 39, pp 443-453, 2013). MLKL acts downstream of RIP1 and RIP3, and is therefore understood to be a key effector of necroptosis. Compounds of this invention may bind to MLKL and block this conformational change or any other key event in its activation.

The compounds of the invention may be selective for MLKL. In some embodiments, the compounds of the invention are selective for MLKL over RIP1. In some embodiments, the compounds of the invention are selective for MLKL over RIP3. In some embodiments, the compounds of the invention are selective for MLKL over RIP1 and RIP3. A selective compound may have 5-fold, 10-fold, 50-fold, 100-fold, 500-fold, 1000-fold or greater selectivity for MLKL compared to RIP1 and/or RIP3. Typically, the relative selectivity may be assessed by comparing $K_D$ values for each respective compound binding to the relevant protein (ie MLKL and either or both of RIP1 and RIP3). Suitable assay conditions are described in the Examples below. Compounds selective for MLKL may avoid undesired side-effects associated with RIP1 and/or RIP3 loss of function.

In another aspect, there is provided a compound of Formula (I) or a pharmaceutically acceptable salt, solvate, tautomer, stereoisomer, N-oxide and/or prodrug thereof for use as a medicament.

In another aspect, there is provided use of a compound of Formula (I) a pharmaceutically acceptable salt, solvate, tautomer, N-oxide, stereoisomer and/or prodrug thereof in the preparation of a medicament for the inhibition of necroptosis in a subject.

In another aspect, there is provided use of a composition comprising a compound of Formula (I) or a pharmaceutically acceptable salt, solvate, tautomer, N-oxide, stereoisomer and/or prodrug thereof for the inhibition of necroptosis in a subject.

In another aspect, there is provided use of a compound of Formula (I) or a pharmaceutically acceptable salt, solvate, tautomer, N-oxide, stereoisomer and/or prodrug thereof for inhibiting necroptosis.

In another aspect, there is provided use of a composition comprising a compound of Formula (I) or a salt, solvate, tautomer, N-oxide, stereoisomer and/or prodrug thereof for inhibiting necroptosis.

In yet another aspect, there is provided a compound according to Formula (I) or a salt, solvate, tautomer, N-oxide, stereoisomer and/or prodrug thereof for use in inhibiting necroptosis.

In yet another aspect, there is provided a composition comprising a compound according to Formula (I) or a pharmaceutically acceptable salt, solvate, tautomer, N-oxide, stereoisomer and/or prodrug thereof for use in inhibiting necroptosis. In some embodiments, the composition is a pharmaceutical composition.

In yet another aspect, there is provided a compound according to Formula (I) or a pharmaceutically acceptable salt, solvate, tautomer, N-oxide, stereoisomer and/or prodrug thereof when used for inhibiting necroptosis.

In yet another aspect, there is provided a composition comprising a compound according to Formula (I) or a pharmaceutically acceptable salt, solvate, tautomer, N-oxide, stereoisomer and/or prodrug thereof when used for inhibiting necroptosis.

In another aspect, there is provided a method of inhibiting MLKL, comprising contacting a cell with an effective amount of a compound of formula (I) or a salt, solvate, tautomer, N-oxide, stereoisomer and/or prodrug thereof.

The salts of the compounds of Formula (I) are preferably pharmaceutically acceptable, but it will be appreciated that non-pharmaceutically acceptable salts also fall within the scope of the present disclosure, for example, as these may be useful as intermediates in the preparation of pharmaceutically acceptable salts or in methods not requiring administration to a subject.

The term "pharmaceutically acceptable" may be used to describe any salt, solvate, tautomer, N-oxide, stereoisomer and/or prodrug thereof, or any other compound which upon administration to a subject, is capable of providing (directly or indirectly) a compound of Formula (I) or an active metabolite or residue thereof and typically that is not deleterious to the subject.

Suitable pharmaceutically acceptable salts include, but are not limited to, salts of pharmaceutically acceptable inorganic acids such as hydrochloric, sulphuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine. General information on types of pharmaceutically acceptable salts and their formation is known to those skilled in the art and is as described in general texts such as "Handbook of Pharmaceutical salts" P. H. Stahl, C. G. Wermuth, 1st edition, 2002, Wiley-VCH.

In the case of compounds that are solids, it will be understood by those skilled in the art that the inventive compounds, agents and salts may exist in different crystalline or polymorphic forms, all of which are intended to be within the scope of the present invention and specified formulae.

The invention includes all crystalline forms of a compound of Formula (I) including anhydrous crystalline forms, hydrates, solvates and mixed solvates. If any of these crystalline forms demonstrates polymorphism, all polymorphs are within the scope of this invention.

Formula (I) is intended to cover, where applicable, solvated as well as unsolvated forms of the compounds. Thus, Formula (I) includes compounds having the indicated structures, including the hydrated or solvated forms, as well as the non-hydrated and non-solvated forms.

The compounds of Formula (I) or salts, tautomers, N-oxides, polymorphs or prodrugs thereof may be provided in the form of solvates. Solvates contain either stoichiometric or non-stoichiometric amounts of a solvent, and may be formed during the process of crystallization with pharmaceutically acceptable solvents such as water, alcohols such as methanol, ethanol or isopropyl alcohol, DMSO, acetonitrile, dimethyl formamide (DMF), acetic acid, and the like with the solvate forming part of the crystal lattice by either non-covalent binding or by occupying a hole in the crystal lattice. Hydrates are formed when the solvent is water, alcoholates are formed when the solvent is alcohol. Solvates of the compounds of the present invention can be conveniently prepared or formed during the processes described herein. In general, the solvated forms are considered equivalent to the unsolvated forms for the purposes of the invention.

Basic nitrogen-containing groups may be quarternised with such agents as $C_{1-6}$alkyl halide, such as methyl, ethyl, propyl, and butyl chlorides, bromides and iodides; dialkyl sulfates like dimethyl and diethyl sulfate; and others.

Nitrogen containing groups may also be oxidised to form an N-oxide.

The compound of Formula (I) or salts, tautomers, N-oxides, solvates and/or prodrugs thereof that form crystalline solids may demonstrate polymorphism. All polymorphic forms of the compounds, salts, tautomers, N-oxides, solvates and/or prodrugs are within the scope of the invention.

The compound of Formula (I) may demonstrate tautomerism. Tautomers are two interchangeable forms of a molecule that typically exist within an equilibrium. Any tautomers of the compounds of Formula (I) are to be understood as being within the scope of the invention. For example, when $R^1$ is H the compounds of formula (1A) and (1B) may exist as tautomers, eg in equilibrium with each other. The compounds of formula (1A) and (1B) wherein $R^1$ is H are depicted below as compounds of formulas (1A) and (1B). The proportion of compounds of formula (1A') to (1B) in equilibrium may depend on the specific compound and conditions, such as solvent, temperature, concentration, etc. This equilibrium may be described as follows:

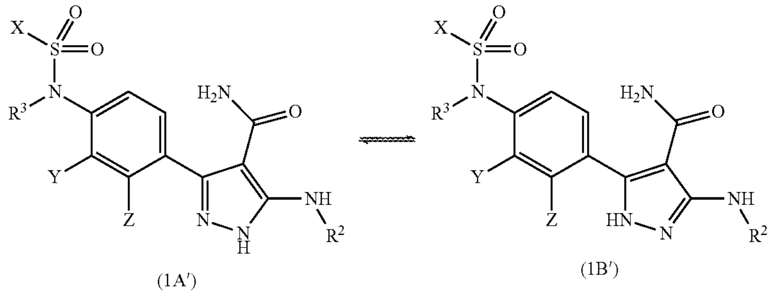

(1A′) (1B′)

Similar tautomerism may occur for any pyrazole-containing compound described herein, including compounds of formula (II), (III), (V), (VIII) and (SI) and compounds 1-320. All tautomers of these compounds are contemplated and considered within the scope of the present invention. In addition, further tautomeric forms may exist for the compounds described herein for example depending on various substituents selected.

The compound of Formula (I) may contain one or more stereocentres. All stereoisomers of the compounds of formula (I) are within the scope of the invention. Stereoisomers include enantiomers, diastereomers, geometric isomers (E and Z olephinic forms and cis and trans substitution patterns) and atropisomers. In some embodiments, the compound is a stereoisomerically enriched form of the compound of formula (I) at any stereocentre. The compound may be enriched in one stereoisomer over another by at least about 60, 70, 80, 90, 95, 98 or 99%.

The compound of Formula (I) or its salts, tautomers, solvates, N-oxides, and/or stereoisomers, may be isotopically enriched with one or more of the isotopes of the atoms present in the compound. For example, the compound may be enriched with one or more of the following minor isotopes: $^{2}H$, $^{3}H$, $^{13}C$, $^{14}C$, $^{15}N$ and/or $^{17}O$. An isotope may be considered enriched when its abundance is greater than its natural abundance.

A "prodrug" is a compound that may not fully satisfy the structural requirements of the compounds provided herein, but is modified in vivo, following administration to a subject or patient, to produce a compound of formula (I) provided herein. For example, a prodrug may be an acylated derivative of a compound as provided herein. Prodrugs include compounds wherein hydroxy, carboxy, amine or sulfhydryl groups are bonded to any group that, when administered to a mammalian subject, cleaves to form a free hydroxy, carboxy, amino, or sulfhydryl group, respectively. Examples of prodrugs include, but are not limited to, acetate, formate, phosphate and benzoate derivatives of alcohol and amine functional groups within the compounds provided herein. Prodrugs of the compounds provided herein may be prepared by modifying functional groups present in the compounds in such a way that the modifications are cleaved in vivo to generate the parent compounds.

Prodrugs include compounds wherein an amino acid residue, or a polypeptide chain of two or more (eg, two, three or four) amino acid residues which are covalently joined to free amino, and amido groups of compounds of Formula (I). The amino acid residues include the 20 naturally occurring amino acids commonly designated by three letter symbols and also include, 4-hydroxyproline, hydroxylysine, demosine, isodemosine, 3-methylhistidine, norvlin, beta-alanine, gamma-aminobutyric acid, citrulline, homocysteine, homoserine, ornithine and methionine sulfone. Prodrugs also include compounds wherein carbonates, carbamates, amides and alkyl esters which are covalently bonded to the above substituents of Formula (I) through the carbonyl carbon prodrug sidechain.

Pharmaceutical compositions may be formulated from compounds according to Formula (I) for any appropriate route of administration including, for example, oral, rectal, nasal, vaginal, topical (including transdermal, buccal, ocular and sublingual), parenteral (including subcutaneous, intraperitoneal, intradermal, intravascular (for example, intravenous), intramuscular, spinal, intracranial, intrathecal, intraocular, periocular, intraorbital, intrasynovial and intraperitoneal injection, intracisternal injection as well as any other similar injection or infusion techniques), inhalation, insufflation, infusion or implantation techniques (e.g., as sterile injectable aqueous or non-aqueous solutions or suspensions).

In certain embodiments, compositions in a form suitable for oral use or parenteral use are preferred. Suitable oral forms include, for example, tablets, troches, lozenges, aqueous or oily suspensions, dispersible powders or granules, emulsions, hard or soft capsules, or syrups or elixirs. For intravenous, intramuscular, subcutaneous, or intraperitoneal administration, one or more compounds may be combined with a sterile aqueous solution which is preferably isotonic with the blood of the recipient. Such formulations may be prepared by dissolving solid active ingredient in water containing physiologically compatible substances such as sodium chloride or glycine, and having a buffered pH compatible with physiological conditions to produce an aqueous solution, and rendering said solution sterile. The formulations may be present in unit or multi-dose containers such as sealed ampoules or vials. Examples of components are described in Martindale—The Extra Pharmacopoeia (Pharmaceutical Press, London 1993), and Remington: *The Science and Practice of Pharmacy,* 21st Ed., 2005, Lippincott Williams & Wilkins. All methods include the step of bringing the active ingredient, for example a compound defined by Formula (I), or a pharmaceutically acceptable salt, solvate, tautomer, stereoisomer, N-oxide and/or prodrug thereof, into association with the carrier which constitutes one or more accessory ingredients. In general, the pharmaceutical compositions are prepared by uniformly and intimately bringing the active ingredient, for example a compound defined by Formula (I), or a pharmaceutically acceptable salt, solvate, tautomer, stereoisomer, N-oxide and/or prodrug thereof, into association with a liquid carrier or a finely divided solid carrier or both, and then, if necessary, shaping the product into the desired formulation. In the pharmaceutical composition the active object compound is included in an amount sufficient to produce the desired effect. In some embodiments, the method of the invention comprises administering a pharmaceutical comprising a compound of Formula (I) or a pharmaceutically acceptable salt, solvate, tautomer, stereoisomer, N-oxide and/or prodrug thereof and a pharmaceutically acceptable carrier, diluent and/or excipient.

In the context of this specification the term "administering" and variations of that term including "administer" and "administration", includes contacting, applying, delivering or providing a compound or composition of the invention to an organism, or a surface by any appropriate means.

For the inhibition of necroptosis, the dose of the biologically active compound according to the invention may vary within wide limits and may be adjusted to individual requirements. Active compounds according to the present invention are generally administered in a therapeutically effective amount. The daily dose may be administered as a single dose or in a plurality of doses. The amount of active ingredient that may be combined with the carrier materials to produce a single dosage form will vary depending upon the subject treated and the particular mode of administration.

It will be understood, however, that the specific dose level for any particular subject will depend upon a variety of factors including the activity of the specific compound employed, the age, body weight, general health, sex and diet of the subject, time of administration, route of administration, and rate of excretion, drug combination (i.e. other drugs being used to treat the subject), and the severity of the particular disorder undergoing therapy. Such treatments may be administered as often as necessary and for the period of time judged necessary by the treating physician. A person skilled in the art will appreciate that the dosage regime or therapeutically effective amount of the compound of formula (I) to be administered may need to be optimized for each individual.

It will also be appreciated that different dosages may be required for treating different disorders. An effective amount of an agent is that amount which causes a statistically significant decrease in necroptosis.

For in vitro analysis, the necroptosis inhibition may be determined by assays used to measure TSQ-induced necroptosis, as described in the biological tests defined herein.

The terms "treating", "treatment" and "therapy" are used herein to refer to curative therapy, prophylactic therapy and preventative therapy. Thus, in the context of the present disclosure the term "treating" encompasses curing, ameliorating or tempering the severity of necroptosis and/or associated diseases or their symptoms.

"Preventing" or "prevention" means preventing the occurrence of the necroptosis or tempering the severity of the necroptosis if it develops subsequent to the administration of the compounds or pharmaceutical compositions of the present invention.

"Subject" includes any human or non-human animal. Thus, in addition to being useful for human treatment, the compounds of the present invention may also be useful for veterinary treatment of mammals, including companion animals and farm animals, such as, but not limited to dogs, cats, horses, cows, sheep, and pigs.

The term "inhibit" is used to describe any form of inhibition that results in prevention, reduction or otherwise amelioration of necroptosis and/or MLKL function, including complete and partial inhibition.

The compounds of the present invention may be administered along with a pharmaceutical carrier, diluent and/or excipient as described above.

The methods of the present disclosure can be used to prevent or treat the following disease(s), condition(s) and/or disorder(s) in a subject:

- diseases of the bones, joints, connective tissue and of cartilage, such as osteoporosis, osteomyelitis including chronic recurrent multifocal osteomyelitis, arthritises including for example osteoarthritis, rheumatoid arthritis and psoriatic arthritis, avascular necrosis, progressive fibrodysplasia ossificans, rickets, Cushing's syndrome;
- muscular diseases such as muscular dystrophy, such as for example Duchenne's muscular dystrophy, myotonic dystrophies, myopathies and myasthenias;
- diseases of the skin, such as dermatitis, eczema, psoriasis, aging or even alterations of scarring;
- cardiovascular diseases such as cardiac and/or vascular ischemia, myocardial infarction, ischemic cardiopathy, chronic or acute congestive heart failure, cardiac dysrythmia, atrial fibrillation, ventricular fibrillation, paroxystic tachycardia, congestive heart failure, hypertrophic cardiopathy, anoxia, hypoxia, secondary effects due to therapies with anti-cancer agents;
- circulatory diseases such as atherosclerosis, arterial scleroses and peripheral vascular diseases, strokes including cerebrovascular strokes, aneurisms;
- haematological and vascular diseases such as: anemia, aplastic anemia, vascular amyloidosis, haemorrhages, drepanocytosis, red cell fragmentation syndrome, neutropenia, leukopenia, medullar aplasia, pantocytopenia, thrombocytopenia, haemophilia;
- lung diseases including pneumonia, asthma; obstructive chronic diseases of the lungs such as for example chronic obstructive pulmonary disease (COPD), chronic bronchitis and emphysema;
- diseases of the gastro-intestinal tract, such as ulcers; inflammatory bowel diseases (IBD), including Crohn's disease, ulcerative colitis;
- diseases of the liver such as for example hepatitis particularly hepatitis of viral origin or having as causative agent other infectious agents, auto-immune hepatitis, fulminating hepatitis, inflammatory hepatitis, certain hereditary metabolic disorders, Wilson's disease, cirrhoses, non-alcoholic fatty liver disease (NAFLD) including non-alcoholic hepatic steatosis and/or non-alcoholic steatohepatitis (NASH), diseases of the liver due to toxins and to drugs such as drug-induced liver injury, ethanol (or alcohol)-induced liver disease;
- diseases of the pancreas such as for example acute or chronic pancreatitis;

metabolic diseases such as diabetes, including diabetes mellitus, pre-diabetes and insipid diabetes; thyroiditis;

diseases of the kidneys such as acute renal disorders (such as acute kidney injury (AKI), including ischaemic reperfusion injury (IRI)) or glomerulonephritis;

viral and bacterial infections such as septicemia;

severe intoxications by chemicals, toxins or drugs;

degenerative diseases associated with the Acquired Immune Deficiency Syndrome (AIDS);

disorders associated with aging such as the syndrome of accelerated aging;

inflammatory diseases such as Terminal ileitis including Crohn's disease, rheumatoid polyarthritis, TNF-induced systemic inflammatory syndrome;

auto-immune diseases such as erythematous lupus (including systemic lupus erythematosus), cleavage-resistant RIPK1-induced autoinflammatory (CRIA) syndrome;

dental disorders such as those resulting in degradation of tissues such as for example periodontitis;

ophthalmic diseases or disorders including diabetic retinopathies, glaucoma, macular degenerations, retinal degeneration, retinitis pigmentosa, retinal holes or tears, retinal detachment, retinal ischemia, acute retinopathies associated with trauma, inflammatory degenerations, post-surgical complications, medicinal retinopathies, cataract, cone cell degeneration;

disorders of the audition tracts, such as otosclerosis and deafness induced by antibiotics;

Ischemic reperfusion injury, including retinal ischaemic reperfusion injury;

Neuronal loss, including Alzheimer's disease and neurodegenerative diseases such as amyotrophic lateral sclerosis (ALS; also referred to as motor neuron disease (MND) and Charcot disease);

diseases associated with mitochondria (mitochondrial pathologies), such as Friedrich's ataxia, congenital muscular dystrophy with structural mitochondrial abnormality, certain myopathies (MELAS syndrome, MERFF syndrome, Pearson's syndrome), MIDD (mitochondrial diabetes and deafness) syndrome, Wolfram's syndrome, dystonia;

cancer and metastasis including but not limited to cancers of the lung and bronchus, including non-small cell lung cancer (NSCLC), squamous lung cancer, brochioloalveolar carcinoma (BAC), adenocarcinoma of the lung, and small cell lung cancer (SCLC); prostate cancer, including androgen-dependent and androgen-independent prostate cancer; breast cancer, including metastatic breast cancer; pancreatic cancer; cancers of the colon and rectum; thyroid cancer; cancers of the liver and intrahepatic bile duct; hepatocellular cancer; gastric cancer; endometrial cancer; melanoma; cancers of the kidney, renal pelvis, urinary bladder, uterine corpus and uterine cervix; ovarian cancer, including progressive epithelial or primary peritoneal cancer; multiple myeloma; oesophageal cancer, including squamous cell carcinoma and adenocarcinoma of the oesophagus; acute myelogenous leukemia (AML); chronic myelogenous leukemia (CML), including accelerated CML and CML blast phase (CML-BP); lymphocytic leukemia; myeloid leukemia; acute lymphoblastic leukemia (ALL); chronic lymphocytic leukemia (CLL); Hodgkin's disease (HD); non-Hodgkin's lymphoma (NHL), including follicular lymphoma and mantle cell lymphoma; B-cell lymphoma, including diffuse large B-cell lymphoma (DLBCL); T-cell lymphoma; multiple myeloma (MM); amyloidosis; Waldenstrom's macroglobulinemia; myelodysplastic syndromes (MDS), including refractory anemia (RA), refractory anemia with ringed siderblasts (RARS), (refractory anemia with excess blasts (RAEB), and RAEB in transformation (RAEB-T); and myeloproliferative syndromes; cancers of the brain, including glioma/glioblastoma, anaplastic oligodendroglioma, and adult anaplastic astrocytoma; neuroendocrine cancers, including metastatic neuroendocrine tumors; cancers of the head and neck, including, e.g., squamous cell carcinoma of the head and neck, and nasopharyngeal cancer; cancers of the oral cavity, pharynx and small intestine; bone cancer; soft tissue sarcoma; and villous colon adenoma; and diseases of the central nervous system (CNS), such as multiple sclerosis (MS).

In some embodiments, the methods of the present disclosure may be for treating and/or preventing any one or more of the diseases, conditions and/or disorders disclosed herein. For example, in some embodiments, there is provided a method for treating and/or preventing any one or more of: retinal ischaemic reperfusion injury, chronic recurrent multifocal osteomyelitis, aplastic anaemia, CRIA, ethanol-induced liver disease, NASH, inflammatory hepatitis, acute kidney injury, IRI, multiple sclerosis, amyotrophic lateral sclerosis, Alzheimer's disease, stroke, systemic lupus erythematosus, myocardial infarction, diabetes, Crohn's disease, inflammatory bowel disease and COPD, comprising administering to a subject in need thereof an effective amount of a compound of the invention or a pharmaceutically acceptable salt, solvate, tautomer, N-oxide, stereoisomer and/or prodrug thereof.

The methods can also be used for protecting cells, tissues and/or transplanted organs, whether before, during (removal, transport and/or re-implantation) or after transplantation.

In some embodiments, the compound of the invention may be administered in combination with a further active pharmaceutical ingredient (API). The API may be any that is suitable for treating any of the diseases, conditions and/or disorders associated with necroptosis, such as those described herein. The compound of the invention may be co-formulated with the further API in any of the pharmaceutical compositions described herein, or the compound of the invention may be administered in a concurrent, sequential or separate manner. Concurrent administration includes administering the compound of the invention at the same time as the other API, whether coformulated or in separate dosage forms administered through the same or different route. Sequential administration includes administering, by the same or different route, the compound of the invention and the other API according to a resolved dosage regimen, such as within about 0.5, 1, 2, 3, 4, 5, or 6 hours of the other. When sequentially administered, the compound of the invention may be administered before or after administration of the other API. Separate administration includes administering the compound of the invention and the other API according to regimens that are independent of each other and by any route suitable for either active, which may be the same or different.

The methods may comprise administering the compound of Formula (I) in any pharmaceutically acceptable form. In some embodiments, the compound of Formula (I) is provided in the form of a pharmaceutically acceptable salt, solvate, N-oxide, polymorph, tautomer or prodrug thereof, or a combination of these forms in any ratio.

The methods may also comprise administering a pharmaceutical composition comprising the compound of formula (I) or a pharmaceutically acceptable salt, solvate, N-oxide, polymorph, tautomer or prodrug thereof to the subject in need thereof. The pharmaceutical composition may comprise any pharmaceutically acceptable carrier, diluent and/or excipient described herein.

The compounds of Formula (I), or a pharmaceutically acceptable salt or prodrug thereof, as defined herein, may be administered by any suitable means, for example, orally, rectally, nasally, vaginally, topically (including buccal and sub-lingual), parenterally, such as by subcutaneous, intraperitoneal, intravenous, intramuscular, or intracisternal injection, inhalation, insufflation, infusion or implantation techniques (e.g., as sterile injectable aqueous or non-aqueous solutions or suspensions).

The compounds of the invention may be provided as pharmaceutical compositions including those for oral, rectal, nasal, topical (including buccal and sub-lingual), parenteral administration (including intramuscular, intraperitoneal, sub-cutaneous and intravenous), or in a form suitable for administration by inhalation or insufflation. The compounds of Formula (I), or a pharmaceutically acceptable salt or prodrug thereof, together with a conventional adjuvant, carrier or diluent, may thus be placed into the form of pharmaceutical compositions and unit dosages thereof, and in such form may be employed as solids, such as tablets or filled capsules, or liquids as solutions, suspensions, emulsions, elixirs or capsules filled with the same, all for oral use, or in the form of sterile injectable solutions for parenteral (including subcutaneous) use.

Also provided is a kit of parts, comprising in separate parts:

a compound of Formula (I) or a pharmaceutically acceptable salt, solvate, N-oxide, polymorph, tautomer or prodrug thereof; and instructions for its use in any of the methods of the invention.

The compounds, compositions, kits and methods described herein are described by the following illustrative and non-limiting examples.

EXAMPLES

Chemistry

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents, which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., 1H or 13C), infrared spectroscopy, spectrophotometry (e.g., UV-visible), or mass spectrometry, or by chromatography such as high-performance liquid chromatography (HPLC) or thin layer chromatography.

The expressions, "ambient temperature," "room temperature," "RT" and "r.t.", as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared according to numerous preparatory routes known in the literature. Example synthetic methods for preparing compounds of the invention are provided in the Schemes below.

General Description of Chemistry

Scheme 1 shows a general synthesis of aminopyrazolocarboxamide compounds of the invention. Aminopyrazolonitrile (F1), which can be prepared via routes known to one skilled in the art, can be converted to N-heteroaryl aminopyrazolonitrile F2 (step 1) by treatment with a haloheteroarene in the presence of palladium such as tris(dibenzylideneacetone)dipalladium(0) or palladium(II) acetate and a ligand such as Xantphos with a base such as cesium carbonate in a solvent such as 1,4-dioxane or diglyme at elevated temperature such as 65° C. or under microwave reaction such as 150° C. The nitrile group can be converted to a primary amide in a presence of a reagent such as Ghaffar-Parkins catalyst in a solvent such as 1,4-dioxane and water at elevated temperature such as 100° C., or with 30% hydrogen peroxide in water with an aqueous sodium hydroxide solution in a polar solvent such as dimethyl sulfoxide and a protic solvent such as ethanol at elevated temperature such as 100° C. (step 2). The nitro substituent can be reduced to the aniline in the presence of an aqueous solution of ammonium chloride in a protic solvent such as methanol in a presence of zinc dust at room temperature (step 3). The aniline can subsequently be converted to the sulfonamide with the appropriate sulfonyl chloride in the presence of an amine base such as pyridine or triethylamine in a chlorinated solvent such as dichloromethane or chloroform or neat at room temperature (step 4). The compounds of invention can be obtained via an acidic deprotection with an acid such as trifluoroacetic acid in a solvent such as dichloromethane at room temperature.

Scheme 1

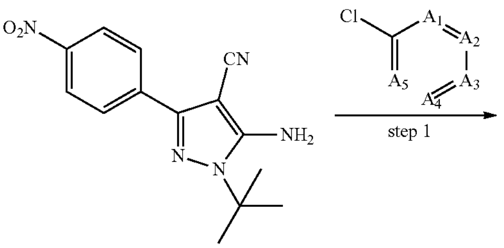

F1

-continued

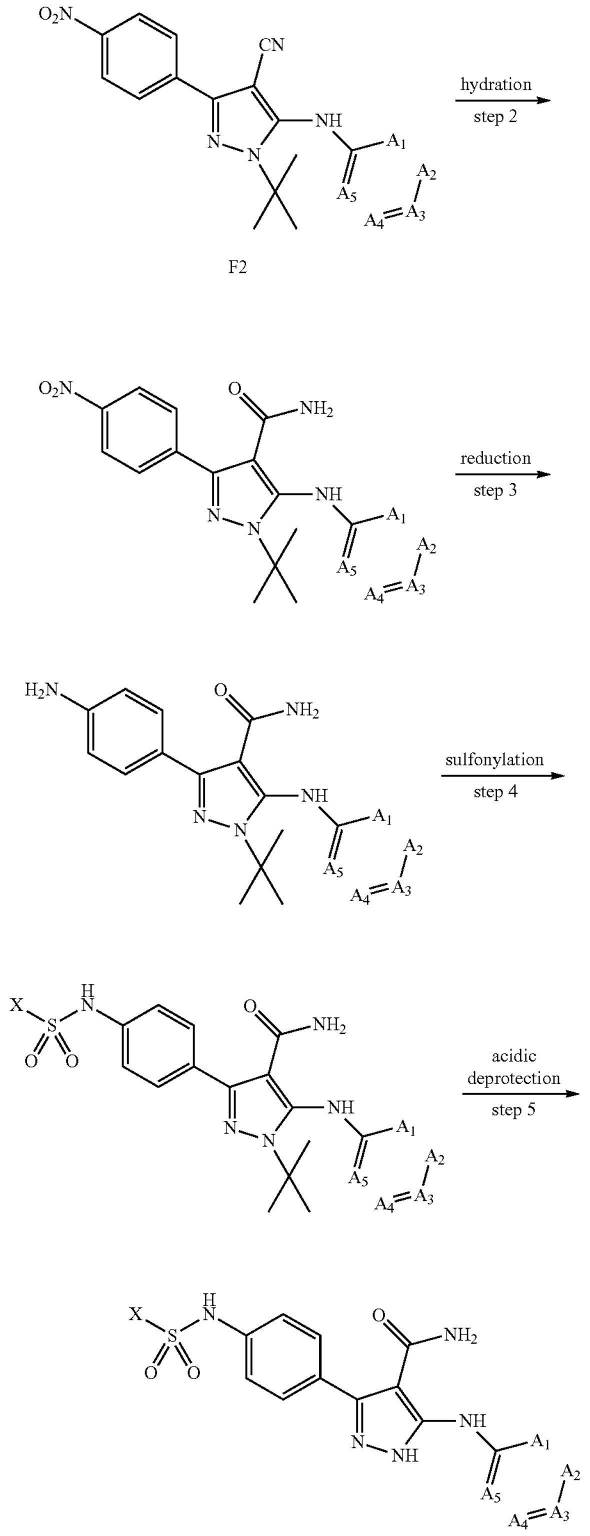

F2

Alternatively, compound F2 can be prepared from the iodoheteroarenes (examples where A1 and A5 are CH) by treatment with palladium species such as palladium acetate in the presence of a ligand such as Xantphos with a base such as cesium carbonate in a solvent such as 1,4-dioxane at elevated temperature such as 65° C.

Scheme 2

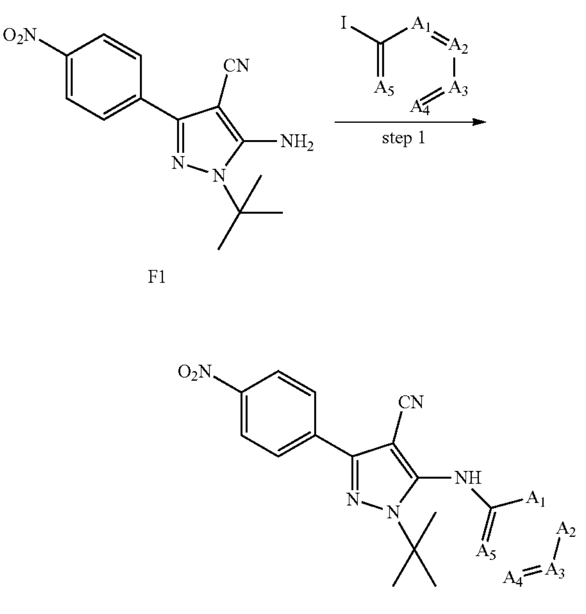

F1

F2

Alternatively, compound F2 can be prepared from F1 by treatment with a reagent such as isoamyl nitrite in the presence of a copper species such as copper(II) bromide in a polar solvent such as acetonitrile at room temperature (step 1). The bromopyrazole can be converted to F2 with arylamines by treatment with a palladium species such as tris (dibenzylideneacetone)dipalladium(0) in the presence of a ligand such as Xantphos with a base such as cesium carbonate in a solvent such as 1,4-dioxane at elevated temperature such as 65° C.

Scheme 3

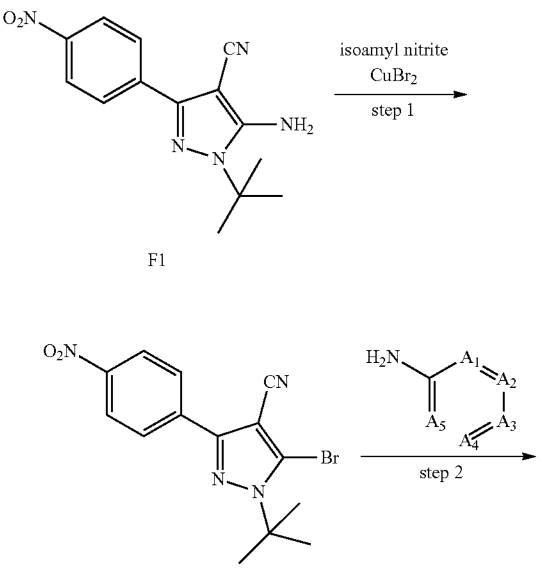

F1

-continued

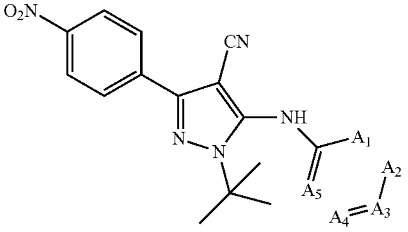

F2

Scheme 4 shows an alternative general synthesis of aminopyrazolocarboxamide compounds of the invention. Dibromopyrazole (F3), which can be prepared via routes known to one skilled in the art, can be converted to N-heteroaryl bromopyrazolonitrile F4 in the presence of a palladium catalyst such as tris(dibenzylideneacetone)dipalladium (0), a phosphine ligand such as Xantphos, a base such as cesium carbonate, in a non-polar solvent such as 1,4-dioxane at an elevated temperature such as 65° C. (Step 1). Conversion of the nitrile group to a primary amide can be performed in the presence of a reagent such as Ghaffar-Parkins catalyst in a solvent such as 1,4-dioxane and water at elevated temperature such as 100° C., or with 30% hydrogen peroxide in water with an aqueous sodium hydroxide solution in a polar solvent such as dimethyl sulfoxide and protic solvent such as ethanol at elevated temperature such as 100° C. (step 2). The subsequent coupling reaction can be performed in the presence of a palladium catalyst such as [1,1'-bis(diphenylphosphino)ferrocene]dichloropalladium(II) or palladium (II) acetate with a ligand such as SPhos and a base such as sodium carbonate or potassium carbonate in a solvent such as a mixture 1,4-dioxane and water or acetonitrile and water at elevated temperature such as 100° C. or under microwave irradiation at elevated temperature such as 100° C. to provide F5 (step 3). The SEM protecting group can be removed to provide compounds of the invention under acidic conditions such as trifluoroacetic acid in a solvent such as dichloromethane or using an aqueous hydrogen chloride solution at room temperature.

Scheme 4

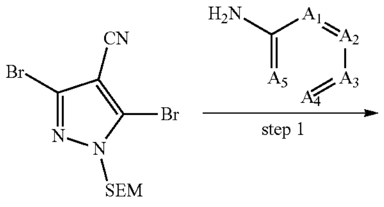

F3

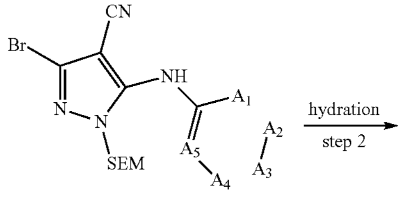

F4

-continued

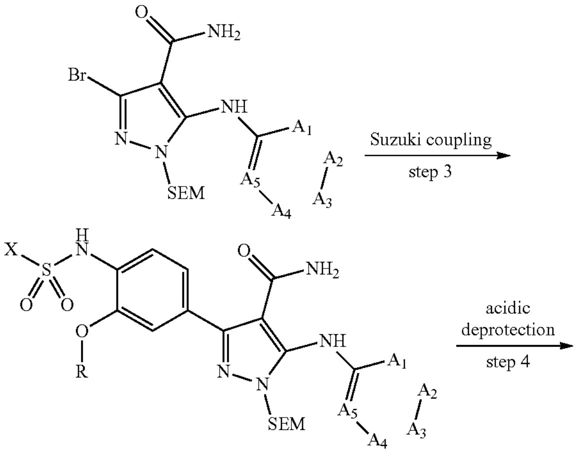

F5

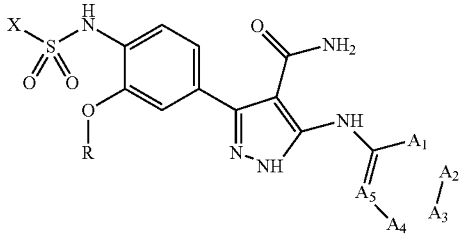

Alternatively (scheme 5), step 2 and step 3 from scheme 4 can be interconverted to provide F5 from F4 following the same description as depicted in scheme 4.

Scheme 5

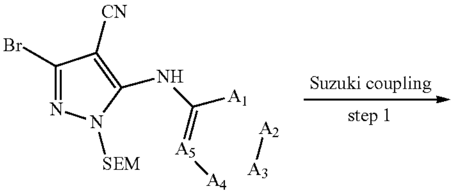

F4

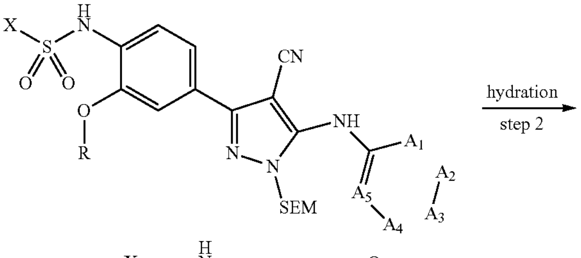

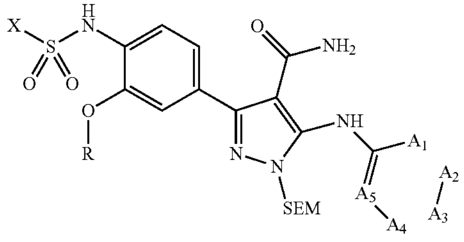

F5

Alternatively, the Suzuki cross coupling reaction can be performed with boronate ester F8, F9 or F11 following the previously described reactions (scheme 6).

F11 can be obtained from F10 via a borylation reaction previously described and F10 can be obtained from a phenol and the desired alcohol via a Mitsunobu reaction with $PPh_3$, Scheme 6

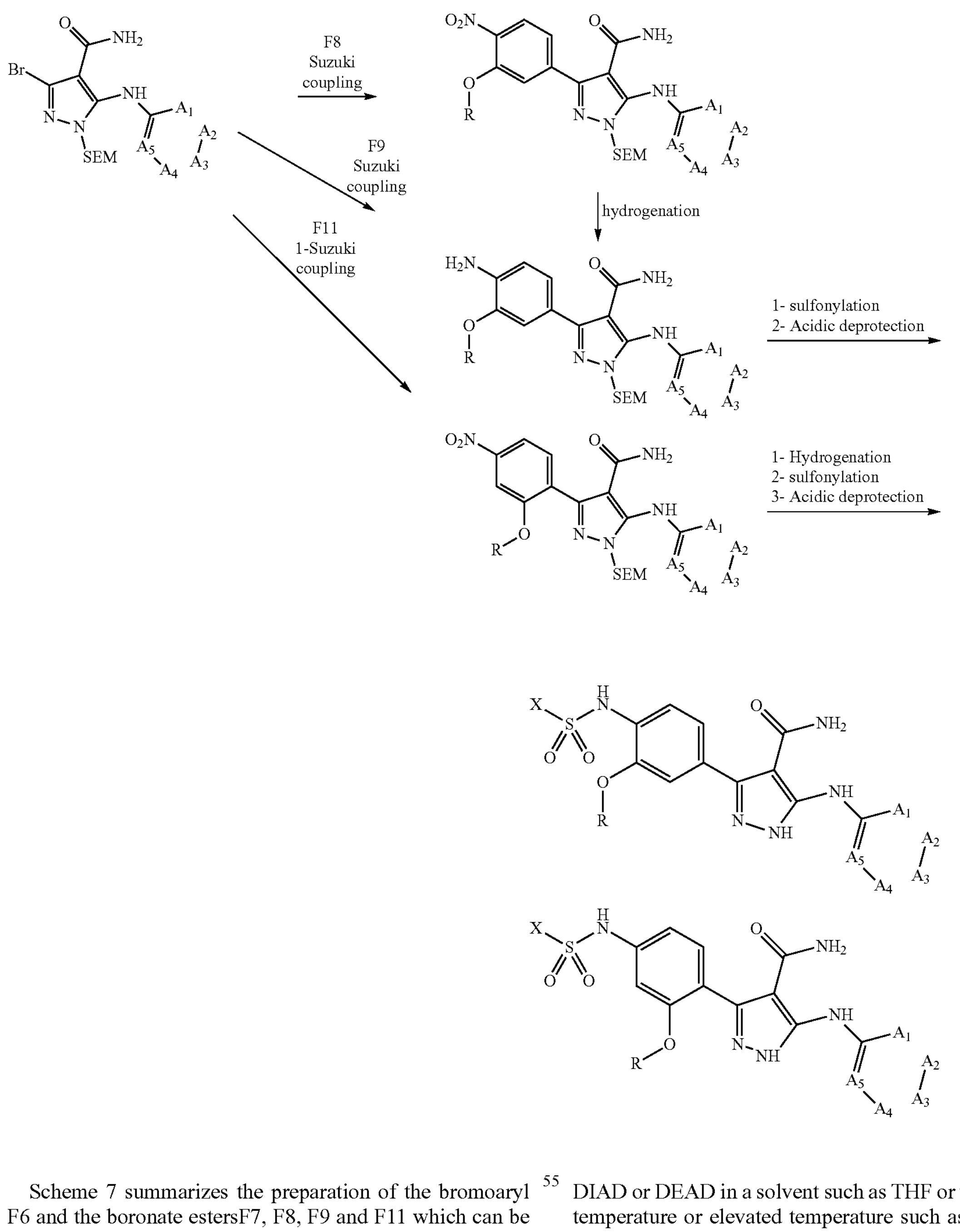

DIAD or DEAD in a solvent such as THF or toluene at room temperature or elevated temperature such as 70° C.

F6 can be obtained via either alkylation of the substituted phenol F8 with the corresponding halogenoalkyl or halogenomethyl(hetero)aryl in the presence of a base such as potassium carbonate in a solvent such as acetonitrile, or via the nucleophilic substitution of the fluoronitroarene F9 with the corresponding alcohol/(hetero)arylalcohol in the presence of a strong base such as sodium hydride in a polar solvent such as N,N-dimethylformamide or tetrahydrofuran.

Scheme 7 summarizes the preparation of the bromoaryl F6 and the boronate estersF7, F8, F9 and F11 which can be obtained from F6 or F10.

F7 can be obtained following a nitro reduction and sulfonylation reaction previously described above and a borylation reaction in the presence of bis(pinacolato)diboron and palladium species such as [1,1'-bis(diphenylphosphino) ferrocene]-dichloropalladium(II) and a base such as potassium acetate in a solvent such as 1,4-dioxane at elevated temperature such as 100° C. F8 can be obtained from F6 via a borylation reaction previously described and F9 can be prepared from F8 via a nitro reduction previously described.

Scheme 7

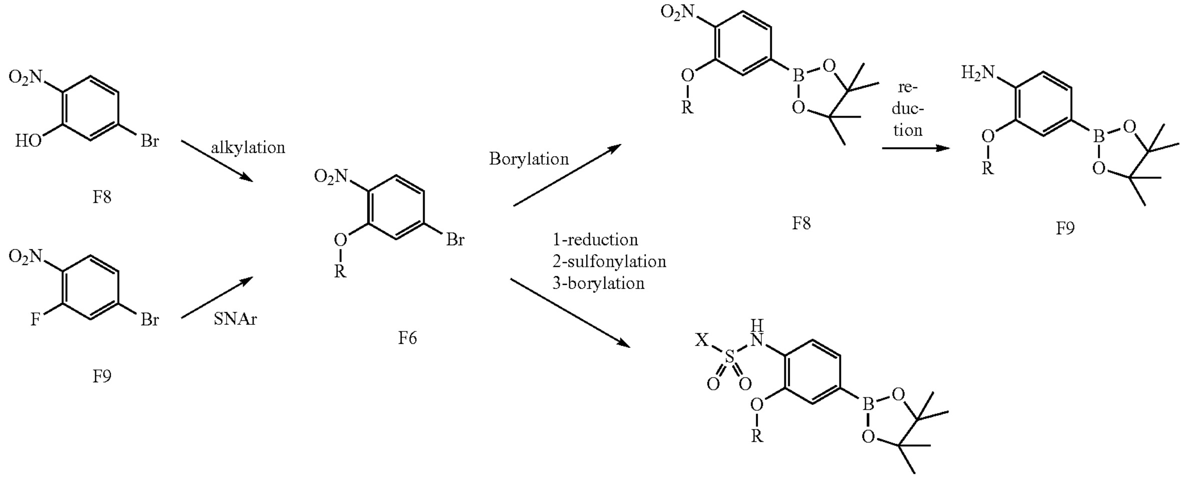

F8

F9

F6

F8

F9

F7

Scheme 8 summarize the synthesis of F10 and F11. F10 can be obtained via alkylation of the substituted phenol F12 with the corresponding halogenoalkyl or halogenomethyl (hetero)aryl in the presence of a base such as potassium carbonate in a solvent such as acetonitrile and F11 can be obtain via a borylation reaction of F10 already described.

Scheme 8

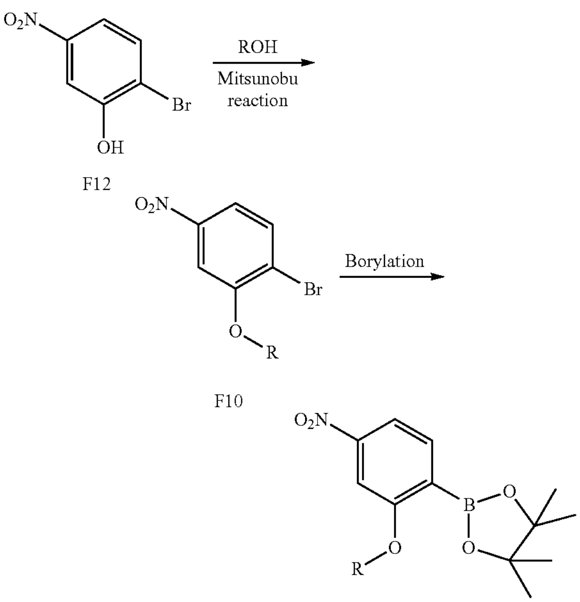

F12

F10

F11

Scheme 9 shows an alternative route for the trisubstituted phenyl derivatives synthesis. Compound F13, which can be prepared via routes known to one skilled in the art, can be converted to N-(hetero)aryl pyrazolonitrile F14 as described above (step 1). Displacement of the fluoroaryl F14 in the presence of alcohols/(hetero)arylalcohols with strong base such as sodium hydride in a polar solvent such as N,N-dimethylformamide or tetrahydrofuran can provide F15, which can then be substituted to the compound of the invention following route described below (steps Scheme 9

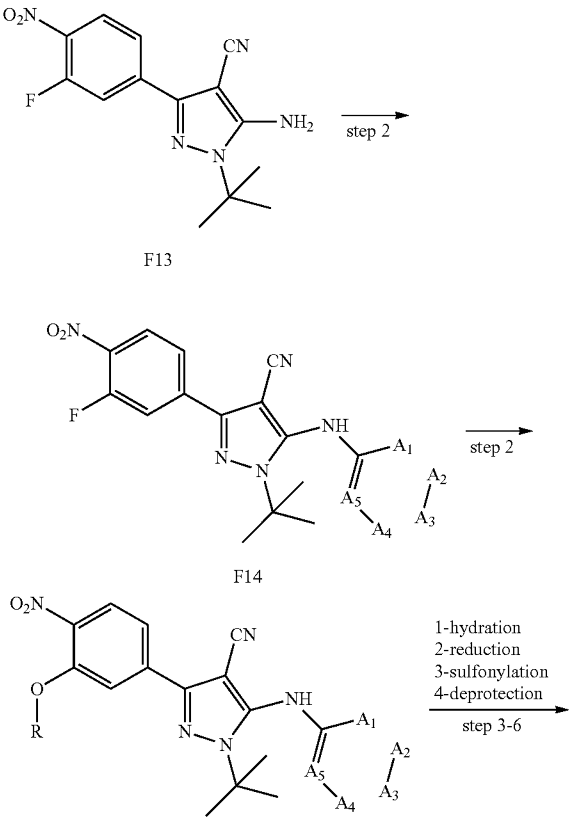

F13

F14

F15

-continued

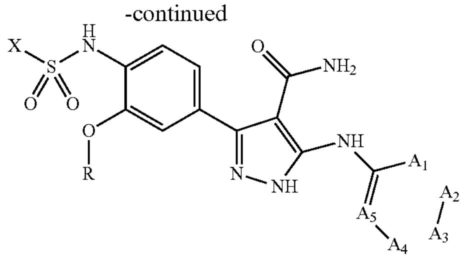

General Chemistry Methods

Definitions

AcCl (acetyl chloride);
$Ac_2O$ (acetic anhydride);
AcOH (acetic acid);
atm (atmosphere);
$B_2pin_2$ (bis(pinacolato)diboron);
BINAP (2,2'-bis(diphenylphosphino)-1,1'-binaphthyl);
BnBr (benzyl bromide);
$Boc_2O$ (di-tert-butyl dicarbonate);
c-Hex (cyclohexane);
$C_6H_{19}O_3P_3Pt$ (dimethylphosphinite; dimethylphosphinous acid; platinum(2+) -Ghaffar-Parkins catalyst);
$CDCl_3$ (deuterated chloroform);
$CD_3OD$ (deuterated methanol);
$CHCl_3$ (chloroform);
$Cs_2CO_3$ (cesium carbonate);
CsF (cesium fluoride);
conc. (concentrated);
d (day);
DAST (diethylaminosulphur trifluoride);
dba (dibenzylideneacetone);
DCM (dichloromethane);
DEAD (diethyl azodicarboxylate);
DIAD (diisopropyl azodicarboxylate);
DIPEA (N,N-d iisopropylethylamine);
DMAP (4-dimethylaminopyridine);
DME (1,2-dimethwryethane);
DMF (N,N-dimethylformamide);
DMSO (dimethyl sulfoxide);
DMSO-$d_6$ (deuterated dimethyl sulfoxide);
EDCl (1-ethyl-3-(3-dimethylaminopropyl)carbodiimide);
eq (equivalent);
ES-API (electrospray atmospheric pressure ionization);
$Et_3N$ (triethylamine);
$Et_2O$ (diethyl ether);
EtOAc (ethyl acetate);
EtOH (ethanol);
$EtSO_2Cl$ (ethanesulfonyl chloride);
g (gram);
h (hour);
$H_2$ (hydrogen);
$H_2O_2$ (hydrogen peroxide);
HATU (1-[bis(dimethylamino)methylene]-1H-1,2,3-triazolo[4,5-b]pyridinium 3-oxide hexafluorophosphate);
HCl (hydrochloric acid/hydrogen chloride);
HOBt (hydroxybenzotriazole);
$^1H$ NMR (proton nuclear magnetic resonance);
Hz (hertz);
i-PrOH (iso-propanol);
KI (potassium iodide);
L (litre);
LCMS (liquid chromatography-mass spectrometry);
LiHMDS (lithium bis(trimethylsilyl)amide);
M (molar);
MeCN (acetonitrile);
$Me_2NH$ (dimethylamine);
MeOH (methanol);
MeOD-$d_4$ (deuterated methanol);
mg (milligrams);
MHz (megahertz);
min (minutes);
mL (millilitres);
mmol (millimoles);
MsCl (methanesulfonyl chloride);
n-BuLi (n-butyllithium);
NaH (sodium hydride);
$NaHCO_3$ (sodium bicarbonate);
NaOEt (sodium ethoxide);
NaOH (sodium hydroxide);
NaOMe (sodium methoxide); $Na_2SO_4$ (sodium sulphate);
NBS (N-bromosuccinimide);
$NH_4Cl$ (ammonium chloride);
NMP (N-methyl-2-pyrrolidone);
Pd/C (palladium on activated charcoal);
$Pd_2(dba)_3$ (tris(dibenzylideneacetone)dipalladium(0));
$Pd(dppf)Cl_2$ ([1,1'-Bis(diphenylphosphino)ferrocene]dichloropalladium(II), complex with DCM);
$Pd(OH)_2$ (palladium(II) hydroxide on carbon—Pearlman's catalyst);
PE (Petroleum Ether);
prep-HPLC (preparative high-performance liquid chromatography);
prep-TLC (preparative thin layer chromatography);
ppm (parts per million);
psi (pounds per square inch);
p-TSA (p-toluenesulfonic acid);
quant. (quantitative yield)
RT (room temperature);
SEMCl (2-(trimethylsilyl)ethoxymethyl chloride);
SPhos (2-Dicyclohexylphosphino-2',6'-dimethoxybiphenyl);
TBAF (tetra-n-butylammonium fluoride);
t-$BuNHNH_2$·HCl (tert-butylhydrazine hydrochloride);
TFA (trifluoroacetic acid);
THF (tetrahydrofuran);
TLC (thin layer chromatography);
v/v (volume/volume);
Xantphos (9,9-Dimethyl-4,5-bis(di-tert-butylphosphino) xanthene);

LCMS Methodology

Electrospray mass spectroscopy (MS) was carried out using the following method;

Method A (5 minutes): LC model: Agilent 1200 (Pump type: Binary Pump, Detector type: DAD) MS model: Agilent G6110A Quadrupole. Column: Xbridge-C18, 2.5 μm, 2.1×30 mm. Column temperature: 30° C. Acquisition of wavelength: 214 nm, 254 nm. Mobile phase: A: 0.07% HCOOH aqueous solution, B: MeOH. Run time: 5 min. MS: Ion source: ES+(or ES−). MS range: 50-900 m/z. Fragmentor: 60. Drying gas flow: 10 L/min. Nebulizer pressure: 35 psi. Drying gas temperature: 350° C. Vcap: 3.5 kV.

Method B (3.5 minutes): LC model: Agilent 1200 (Pump type: Binary Pump, Detector type: DAD) MS model: Agilent G6110A Quadrupole. Column: Xbridge-C18, 2.5 μm, 2.1×30 mm. Column temperature: 30° C. Acquisition of wavelength: 214 nm, 254 nm. Mobile phase: A: 0.07% HCOOH aqueous solution, B: MeOH. Run time: 5 min. MS: Ion source: ES+ (or ES−). MS range: 50-900 m/z. Fragmentor: 60. Drying gas flow: 10 L/min. Nebulizer pressure: 35 psi. Drying gas temperature: 350° C. Vcap: 3.5 kV.

Method C (4 minutes): Agilent LCMS system composed of an Agilent G6120B Mass Detector, 1260 Infinity G1312B Binary pump, 1260 Infinity G1367E HiPALS autosampler, and 1260 Infinity G4212B Diode Array Detector. Conditions for LCMS were as follows: column, Poroshell 120 EC-C18, 2.1×50 mm, 2.7 μm at 30° C.; injection volume, 2 μL; gradient, 5-100% B over 3 min (solvent A: water/0.1% formic acid; solvent B: AcCN/0.1% formic acid); flow rate, 1.0 mL/min; detection, 214 and 254 nm; acquisition time, 4.1 min; ion source: single quadrupole; ion mode: API-ES; drying gas temperature: 350° C.; capillary voltage: 4.0 kV; scan range 100-1000; step size: 0.1.

Method D: (8 minutes) LC model: Waters 2695 alliance, Pump: Quaternary Pump, Detector: 2996 Photodiode Array Detector, MS model: Micromass ZQ, LC: Column: Xbridge-C18, 3.5 μm, 2.1×50 mm, Column temperature: 20° C. Acquisition of wavelength: 214 nm, 254 nm. Mobile phase: A: 0.05% HCOOH aqueous solution, B: CAN Run time: 8 min MS: Ion source: ES+ (or ES−) MS range: 100~1000 m/z Capillary: 3 kv Cone: 40 V Extractor: 3 V Drying gas flow: 800 L/hr cone: 50 L/hr Desolvation temperature: 500° C. Source temperature: 120° C.

Preparative HPLC

Instrument type: VARIAN 940 LC. Pump type: Binary Pump. Detector type: PDA. LC conditions: Column: Waters SunFire prep C18 OBD, 5 μm, 19×100 mm. Acquisition wavelength: 214 nm, 254 nm. Mobile Phase: A: 0.07% TFA aqueous solution, B: MeOH.

NMR

Nuclear magnetic resonance spectra were recorded on a Bruker Avance DRX 300 instrument at 300.13 MHz or Bruker 400 MHz for 1H nuclei as specified. Samples were recorded in deuterated solvent as specified, and data acquired at 25° C. Chemical shifts are reported in ppm on the δ scale and referenced to the appropriate solvent peak. In reporting spectral data, the following abbreviations have been used: s, singlet; br s, broad singlet; d, doublet; t, triplet; q, quartet; m, multiplet.

Synthesis of Common Intermediates

Intermediate A1: 3-(4-aminophenyl)-1-(tert-butyl)-5-(pyridin-2-ylamino)-1H-pyrazole-4-carboxamide

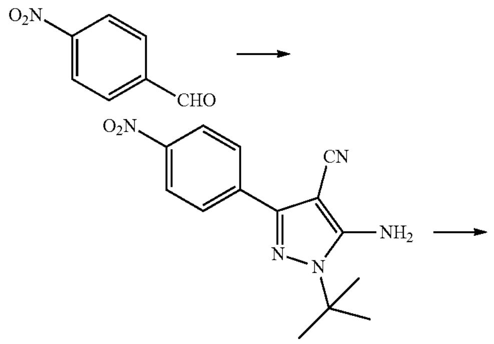

-continued

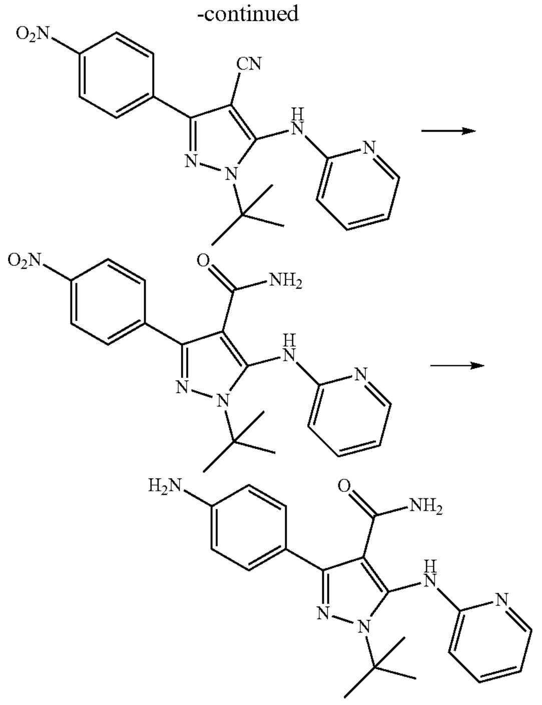

Intermediate A1

Step 1: 5-amino-1-(tert-butyl)-3-(4-nitrophenyl)-1H-pyrazole-4-carbonitrile

A mixture of 4-nitrobenzaldehyde (100 g, 0.66 mol) and t-$BuNHNH_2$·HCl (90.7 g, 0.73 mol) in DMF (500 mL) was stirred at RT overnight. The reaction mixture was cooled to 0° C. and NBS (129.6 g, 0.73 mol) was added slowly. The resultant mixture was stirred at 0° C. for 5 h and then a solution of malononitrile (52.5 g, 0.79 mol) and NaOEt (112.7 g, 1.66 mol) in EtOH (300 mL) was slowly added over a 30 min period at 0° C. The mixture was stirred at RT for 16 h, then partitioned between $H_2O$ (3 L) and EtOAc (3 L). The aqueous layer was extracted with EtOAc (2×3 L), and the combined organic layers were washed with brine, dried ($Na_2SO_4$) and concentrated under reduced pressure. The crude residue was purified by silica gel column chromatography (PE:EtOAc, 5:1) to afford the title product (58 g, 31%) as a yellow solid. LCMS (Method A): 1.93 min; m/z: 286.1 $[M+H]^+$.

Step 2: 1-(tert-butyl)-3-(4-nitrophenyl)-5-(pyridin-2-ylamino)-1H-pyrazole-4-carbonitrile To a solution of 5-amino-1-(tert-butyl)-3-(4-nitrophenyl)-1H-pyrazole-4-carbonitrile (13 g, 45.6 mmol) in diglyme (200 mL) was added 2-bromopyridine (7.6 g, 47.8 mmol), $Pd(OAc)_2$ (614 mg, 2.73 mmol), Xantphos (1.6 g, 2.73 mmol) and $Cs_2CO_3$ (37.1 g, 114 mmol) and the mixture was stirred at 150° C. under $N_2$ for 8 h. The reaction mixture was filtered through Celite and the filter cake was washed with MeOH. The filtrate was concentrated under reduced pressure and the crude residue was purified by silica gel column chromatography (PE:EtOAc, 5:1) to afford the title product (7.0 g, 42%) as a yellow solid. LCMS (Method A): 2.91 min; m/z: 363.2 $[M+H]^+$.

Step 3: 1-(tert-butyl)-3-(4-nitrophenyl)-5-(pyridin-2-ylamino)-1H-pyrazole-4-carboxamide To a solution of 1-(tert-butyl)-3-(4-nitrophenyl)-5-(pyridin-2-ylamino)-1H-pyrazole-4-carbonitrile (11 g, 30.3 mmol) in DMSO (35 mL) and EtOH (130 mL), was added 30% aq. $H_2O_2$ (35 mL) and 5% aq. NaOH (0.3 mL), and the mixture was stirred at 80° C. for 2 h. The reaction mixture was concentrated under reduced pressure and the residue was diluted with water to form a yellow suspension. The solids were collected by filtration and dried under reduced pressure to afford the title product (10.5 g, 90%) as a yellow solid. LCMS (Method A): 2.65 min; m/z: 381.1 $[M+H]^+$.

Step 4: 3-(4-aminophenyl)-1-(tert-butyl)-5-(pyridin-2-ylamino)-1H-pyrazole-4-carboxamide To a solution of 1-(tert-butyl)-3-(4-nitrophenyl)-5-(pyridin-2-ylamino)-1H-pyrazole carboxamide (10 g, 26.3 mmol) in MeOH (200 mL), was added sat. aq. $NH_4Cl$ (100 mL) and Zn dust (8.6 g, 131.5 mmol) and the mixture was stirred at 40° C. for 2 h. The reaction mixture was filtered through Celite, and the filter cake was washed with MeOH. The filtrate was concentrated under reduced pressure and diluted with $H_2O$, then basified to pH 10 with sat. aq. $Na_2CO_3$. The mixture was extracted with DCM (3×100 mL) and the combined organics were washed with brine, dried ($Na_2SO_4$) and concentrated under reduced pressure to afford the title product (8.0 g, 75%) as a yellow solid. LCMS (Method A): 0.53 min; m/z: 351.1 $[M+H]^+$.

The following intermediates (Table 1) were similarly prepared from 5-amino-1-(tert-butyl)-3-(4-nitrophenyl)-1H-pyrazole-4-carbonitrile according to the escribed for the synthesis of 3-(4-aminophenyl)-1-(tert-butyl)-5-(pyridin-2-ylamino)-1H-pyrazole-4-carboxamide (intermediate A1)

TABLE 1

| Compound No. | Name | Structure | LCMS data | $^1H$ NMR data | Starting material |
|---|---|---|---|---|---|
| Intermediate A2 | 3-(4-aminophenyl)-1-(tert-butyl)-5-((6-(trifluoromethyl)pyridin-2-yl)amino)-1H-pyrazole-4-carboxamide | 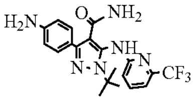 | LCMS (Method A): 3.44 min; m/z: 419.1 [M + H]+. | $^1H$ NMR (400 MHz, DMSO-$d_6$): 8.84 (s, 1H), 7.75 (d, J = 16.0 Hz, 1H), 7.41 (t, J = 8.4 Hz, 1H), 7.15 (br s, 2H), 6.83 (s, 1H), 6.67 (s, 1H), 6.56 (t, J = 8.4 Hz, 2H), 5.28 (s, 2H), 1.54 (s, 9H). | 2-chloro-6-(trifluoromethyl) pyridine |
| Intermediate A3 | 3-(4-aminophenyl)-1-(tert-butyl)-5-(pyrazin-2-ylamino)-1H-pyrazole-4-carboxamide | 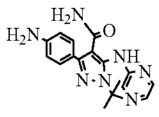 | LCMS (Method A): 1.53 min; m/z: 352.4 $[M + H]^+$. | $^1H$ NMR (400 MHz, DMSO-$d_6$): 8.72 (s, 1H), 8.02 (d, J = 8.4 Hz, 2H), 7.92 (d, J = 2.4 Hz, 1H), 7.37 (d, J = 8.4 Hz, 2H), 7.05 (s, 1H), 6.73 (s, 1H), 6.55 (d, J = 8.4 Hz, 2H), 5.16 (s, 2H), 1.54 (s, 9H). | 2-chloropyrazine |

Intermediate B1: 3-bromo-5-((2-methoxypyridin-4-yl)amino)-1-((2-(trimethylsilyl)methyl)-1H-pyrazole-4-carbonitrile

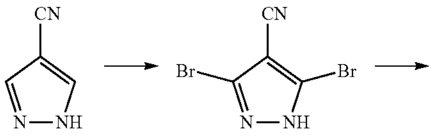

-continued

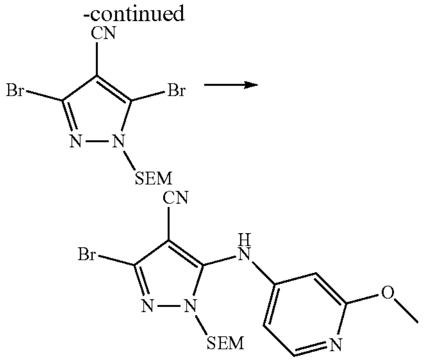

Step 1: 3,5-dibromo-1H-pyrazole-4-carbonitrile

To a stirred solution of 1H-pyrazole-4-carbonitrile (15.0 g, 161 mmol) and NaOAc (89.3 g, 1.09 mol) in 40% aq. EtOH (550 mL), was added $Br_2$ (24 mL, 644 mmol) slowly at RT. The mixture was stirred at 30° C. for 3.5 h, then diluted with $H_2O$ (600 mL) and extracted with DCM (3×300 mL). The combined organic layers were washed with brine, dried ($Na_2SO_4$) and concentrated under reduced pressure to afford the title product (25 g, 62%) as a yellow solid. LCMS (Method B): 0.87 min; m/z: 249.7 $[M+H]^+$.

Step 2: 3,5-dibromo-1-((2-(trimethylsilyl)ethoxy) methyl)-1H-pyrazole-4-carbonitrile To a solution of 3,5-dibromo-1H-pyrazole-4-carbonitrile (25 g, 99.6 mmol) in DMF (150 mL), was added NaH (60% in oil, 2.85 g, 119 mmol) at RT and the mixture was stirred for 0.5 h. SEM-Cl (24.8 g, 149 mmol) was added and the mixture was stirred at RT for 4 h, then diluted with $H_2O$ (200 mL) and extracted with $Et_2O$ (3×150 mL). The combined organics were washed with brine, dried ($Na_2SO_4$), and concentrated under reduced pressure. The crude residue was purified by silica gel column chromatography (PE:EtOAc, 20:1) to afford the title product (16.0 g, 42%) as a clear oil. LCMS (Method B): 0.43 min; m/z: 380.0, 382.0 $[M+H]^+$.

Step 3: 3-bromo-5-[(2-methoxypyridin-4-yl)amino]-1-{[2-(trimethylsilyl)ethoxy]methyl}-1H-pyrazole-4-carbonitrile A mixture of 3,5-dibromo-1-{[2-(trimethylsilyl)ethoxy] methyl}-1H-pyrazole-4-carbonitrile (13.8 g, 36.2 mmol), 2-methoxypyridin-4-amine (4.9 g, 39.8 mmol), $Pd(OAc)_2$ (812 mg, 3.62 mmol), Xantphos (4.18 g, 7.24 mmol) and $Cs_2CO_3$ (17.6 g, 54.3 mmol) in degassed 1,4-dioxane (200 mL) was heated to 110° C. under $N_2$ for 12 h. The mixture was concentrated under reduced pressure and the residue was purified by silica gel column chromatography (PE: EtOAc, 12:1) to afford the title product (7.5 g, 49%) as a white solid. LCMS (Method B): 2.56 min; m/z: 424.1, 426.1 $[M+H]^+$.

Intermediate B2: 3-bromo-5-(pyridin-2-ylamino)-1-((2-(trimethylsilyl)ethoxy)methyl)-1H-pyrazole-4-carboxamide

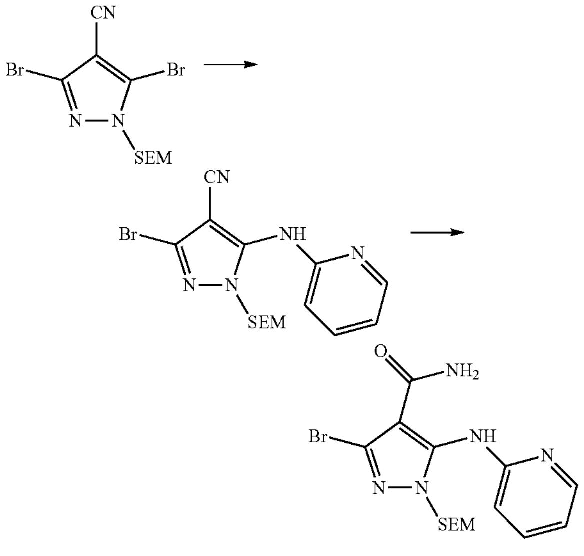

Intermediate B2

Step 1: 3-bromo-5-[(pyridin-2-yl)amino]-1-{[2-(trimethylsilyl)ethoxy]methyl}-1H-pyrazole-4-carbonitrile A mixture of 3,5-dibromo-1-{[2-(trimethylsilyl)ethoxy]methyl}-1H-pyrazole-4-carbonitrile (10 g, 26.2 mmol), pyridin-2-amine (2.46 g, 26.2 mmol), $Pd_2(dba)_3$ (2.39 g, 2.62 mmol), Xantphos (3.03 g, 5.24 mmol) and $Cs_2CO_3$ (25.6 g, 78.6 mmol) in degassed 1,4-dioxane (150 mL) was stirred at 100° C. under $N_2$ for 16 h. The reaction mixture was filtered, concentrated under reduced pressure and the residue was purified by silica gel column chromatography (PE:EtOAc, 5:1) to afford the title product (5.0 g, 49%) as a yellow solid. LCMS (Method A: 3.79 min; m/z: 394.0, 396.0 $[M+H]^+$.

Step 2: 3-bromo-5-(pyridin-2-ylamino)-1-((2-(trimethylsilyl)ethoxy)methyl)-1H-pyrazole-4-carboxamide (Intermediate B2)

A mixture of 3-bromo-5-[(pyridin-2-yl)amino]-1-{[2-(trimethylsilyl)ethoxy]methyl}-1H-pyrazole-4-carbonitrile (4.3 g, 10.9 mmol) and Ghaffar-Parkins catalyst (50.0 mg, 0.1170 mmol) in 50% aq. 1,4-dioxane (200 mL) was stirred at 100° C. for 16 h. The reaction mixture was extracted with EtOAc (2×200 mL), and the combined organics were washed with water and brine, dried ($Na_2SO_4$) and concentrated under reduced pressure. The crude residue was purified by silica gel column chromatography (PE:EtOAc, 3:1) to afford the title product (2.5 g, 56%) as a yellow solid. LCMS (Method A): 3.77 min; m/z: 412.1, 414.1 $[M+H]^+$. $^1H$ NMR (400 MHz, MeOD-$d_4$): 8.84 (s, 1H), 8.24 (s, 1H), 9.01 (d, J=4.0 Hz, 1H), 7.79 (t, J=7.6 Hz, 1H), 7.29 (s, 1H), 6.79 (t, J=6.0 Hz, 1H), 6.74 (d, J=8.4 Hz, 1H), 5.27 (s, 2H), 3.44 (t, J=8.4 Hz, 2H), 0.74 (t, J=8.0 Hz, 2H), 0.11 (s, 9H).

Intermediate B3 (3-bromo-5-(pyrazin-2-ylamino)-1-((2-(trimethylsilyl)ethoxy)methyl)-1H-pyrazole-4-carbonitrile) and Intermediate B4 (3-bromo-5-(pyrazin-2-ylamino)-1-((2-(trimethylsilyl)ethoxy)methyl)-1H-pyrazole-4-carboxamide)

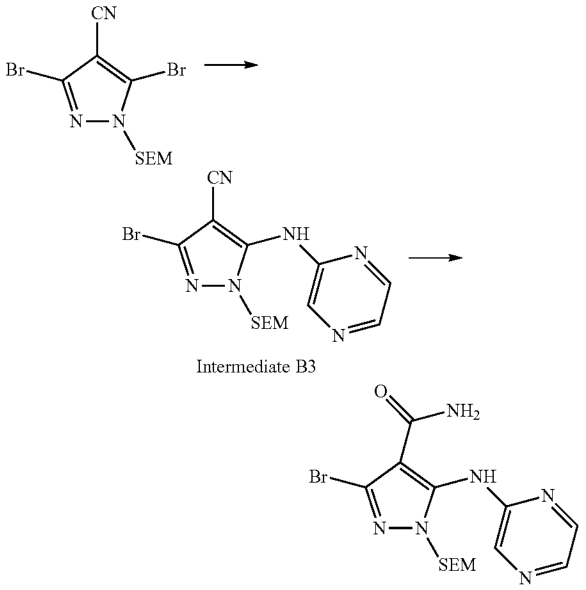

Intermediate B3

Intermediate B4

Step 1: 3-bromo-5-(pyrazin-2-ylamino)-1-((2-(trimethylsilyl)ethoxy)methyl)-1H-pyrazole-4-carbonitrile (Intermediate B3)

A mixture of 3,5-dibromo-1-{[2-(trimethylsilyl)ethoxy]methyl}-1H-pyrazole-4-carbonitrile (4 g, 10.4 mmol), pyrazin-2-amine (989 mg, 10.4 mmol), $Pd_2(dba)_3$ (952 mg, 1.04 mm 1), Xantphos (1.20 g, 2.08 mmol) and $Cs_2CO_3$ (10.1 g, 31.2 mmol) in degassed 1,4-dioxane (50 mL) was stirred at 100° C. under $N_2$ for 16 h. The reaction mixture was filtered, and the liter cake was rinsed with EtOAc (3×20 mL). The combined filtrates were concentrated under reduced pressure and the crude residue was purified by silica gel column chromatography (PE:EtOAc, 10:1 to 8:1) to afford the title compound (2.5 g, 61%) as a yellow solid. LCMS (Method A): 4.14 min; m/z: 395.0, 397.0 $[M+H]^+$.

Step 2: 3-bromo-5-(pyrazin-2-ylamino)-1-((2-(trimethylsilyl)ethoxy)methyl)-1H-pyrazole-4-carboxamide (Intermediate B4)

A mixture of 3-bromo-5-[(pyrazin-2-yl)amino]-1-{[2-(trimethylsilyl)ethoxy]methyl}-1H-pyrazole-4-carbonitrile (6 g, 15.1 mmol), Ghaffar-Parkins catalyst (100 mg, 0.2340 mmol) and 50% aq. 1,4-dioxane (120 mL) was stirred at 100° C. under $N_2$ for 16 h. The mixture was concentrated and the crude residue was purified by silica gel column chromatography (DCM:MeOH, 200:1 to 10:1) to afford the title product (2.1 g, 34%) as a brown solid. LCMS (Method A): 3.59 min; m/z: 415.1 $[M+H]^+$. $^1H$ NMR (400 MHz, DMSO-$d_6$): 9.34 (s, 1H), 8.19 (d, J=1.2 Hz, 1H), 8.05-8.03 (m, 1H), 8.02-8.00 (m, 1H), 7.31 (s, 1H), 7.04 (s, 1H). 5.31 (s, 2H), 8.46 (t, J=8.4 Hz, 2H), 0.75 (t, J=7.6 Hz, 2H), –0.11 (s, 9H).

Intermediate B5 3-bromo-5-[(5-methylpyrazin-2-yl)amino]-1-{[2-(trimethylsilyl)ethoxy]methyl}-1H-pyrazole-4-carbonitrile and Intermediate B6 3-bromo-5-[(5-methylpyrazin-2-yl)amino]-1-{[2-(trimethylsilyl)ethoxy]methyl}-1H-pyrazole-4-carboxamide

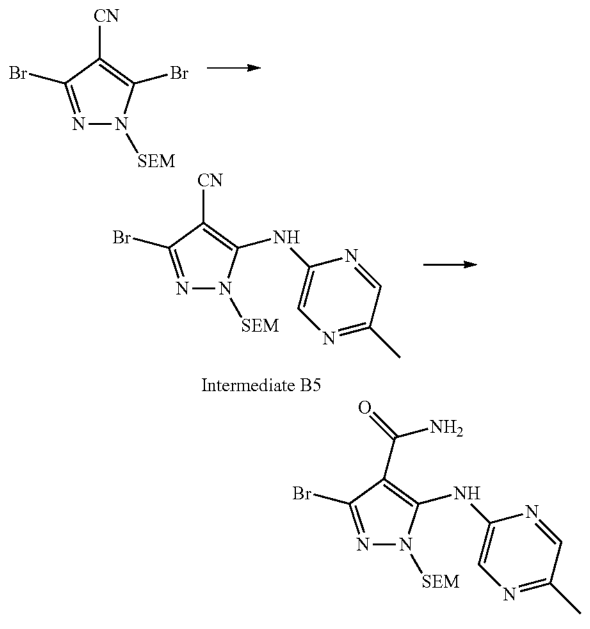

Intermediate B5

Intermediate B6

Step 1: 3-bromo-5-[(5-methylpyrazin-2-yl)amino]-1-{[2-(trimethylsilyl)ethoxy)]methyl}-1H-pyrazole-4-carbonitrile (Intermediate B5)

To a solution of 3,5-dibromo-1-{[2-(trimethylsilyl)ethoxy]methyl}-1H-pyrazole-4-carbonitrile (2 g, 5.24 mmol) in 1,4-dioxane (100 mL), was added 5-methylpyrazin-2-amine (571 mg, 5.24 mmol), Xantphos (302 mg, 0.524 mmol), $Cs_2CO_3$ (3.38 g, 10.4 mmol) and $Pd_2(dba)_3$ (239 mg, 0.262 mmol). The mixture was evacuated and back-filled with $N_2$ three times and then stirred at 100° C. overnight. The mixture was concentrated and the residue purified by prep-TLC (PE:EtOAc, 20:1) to afford the title product (1.03 g, 48%) as a yellow solid. LCMS (Method A): 4.10 min; m/z: 409.1, 411.1 $[M+H]^+$.

Step 2: 3-bromo-5-[(5-methylpyrazin-2-yl)amino]-1-{[2-(trimethylsilyl)ethoxy]methyl}-1H-pyrazole-4-carboxamide (Intermediate B6)

A mixture of 3-bromo-5-[(5-methylpyrazin-2-yl)amino]-1-{[2-(trimethylsilyl)ethoxy]methyl}-1H-pyrazole-4-carbonitrile (1.05 g, 2.56 mmol), Ghaffar-Parkin's catalyst (150 mg, 0.35 mmol) and 75% aq. 1,4-dioxane (55 mL) was stirred at 100° C. under $N_2$. After 16 h, the reaction mixture was concentrated and the crude residue was purified by prep-TLC (DCM:MeOH, 60:1) to afford the title product (490 mg, 45%) as a yellow solid. LCMS (Method A): 3.58 min; m/z: 427.1, 429.1 $[M+H]^+$.

The following intermediates B (see Table 2, below) were similarly prepared from the appropriate amino aryl/alkyl (step 1) according to the method described for the synthesis of intermediate B5.

TABLE 2

| Compound No | Name | Structure | LCMS data | SM |
|---|---|---|---|---|
| Intermediate B7 | 3-bromo-5-{[6-(trifluoromethyl)pyridin-2-yl]amino}-1-{[2-(trimethylsilyl)ethoxy]methyl}-1H-pyrazole-4-carbonitrile | 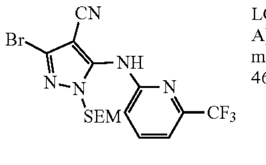 | LCMS (Method A): 4.51 min; m/z: 462.1, 464.1 $[M + H]^+$. | 6-(trifluoromethyl)pyridin-2-amine |
| Intermediate B8 | 3-bromo-5-{[6-(trifluoromethyl)pyridin-2-yl]amino}-1-{[2-(trimethylsilyl)ethoxy]methyl}-1H-pyrazole-4-carboxamide | 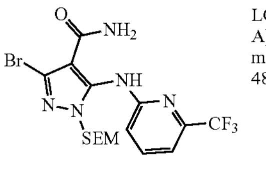 | LCMS (Method A): 4.11 min; m/z: 480.1, 482.1 $[M + H]^+$. | n/a |

Intermediate C1: N-(2-((4-fluorobenzyl)oxy)-4-(4,4,5,5-tetramethyl-1,3,2-dioxaborolan-2-yl)phenyl)ethanesulfonamide

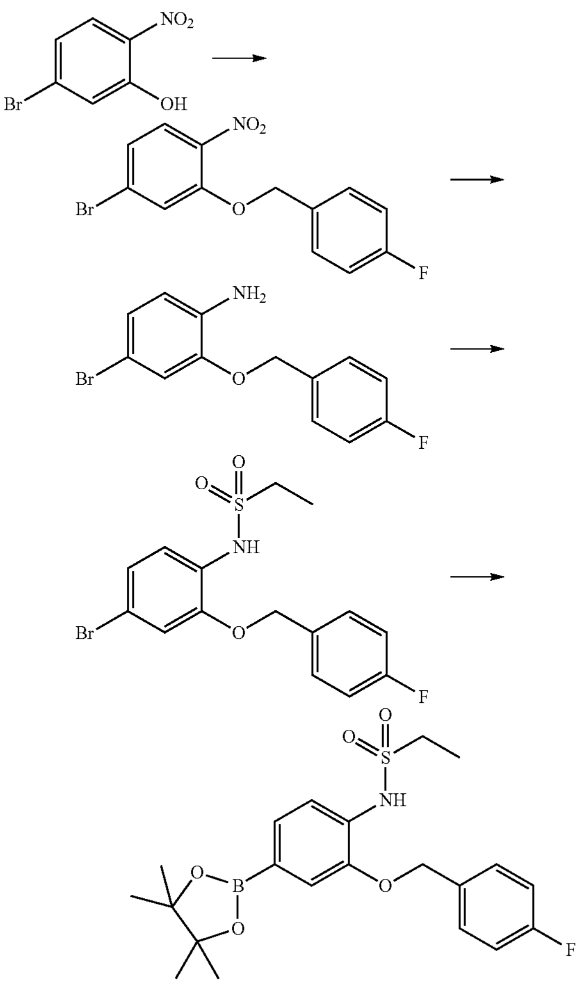

intermediate C1

Step 1: 4-bromo-2-((4-fluorobenzyl)oxy)-1-nitrobenzene

A mixture of 5-bromo-2-nitrophenol (10 g, 45.8 mmol), $K_2CO_3$ (12.6 g, 91.6 mmol) and 1-(bromomethyl)-4-fluorobenzene (8.65 g, 45.8 mmol) in MeCN (100 mL) was stirred at 70° C. under $N_2$ for 16 h. The mixture was diluted with $H_2O$ (100 mL) extracted with EtOAc (3×200 mL). The combined organic layers were dried ($Na_2SO_4$) and then concentrated under reduced pressure to afford the title product (15.0 g, 100%) as a white solid.

Step 2: 4-bromo-2-((4-fluorobenzyl)oxy)aniline

To a solution of 4-bromo-2-((4-fluorobenzyl)oxy)-1-nitrobenzene (15 g, 45.9 mmol) in MeOH (300 mL) and sat. aq. $NH_4Cl$ (100 mL) was added Zn dust (14.9 g, 229 mmol) and the reaction mixture was stirred at 60° C. for 4 h. The mixture was filtered, and the filtrate was concentrated under reduced pressure. The residue was partitioned between $H_2O$ (250 mL) and EtOAc (300 mL), and the organic layer was separated, dried ($Na_2SO_4$) and then concentrated under reduced pressure to afford the title product (13.0 g, 96%) as a black oil. LCMS (Method A): 4.24 min; m/z: 296.0 $[M+H]^+$.

Step 3: N-(4-bromo-2-((4-fluorobenzyl)oxy)phenyl)ethanesulfonamide

A mixture of 4-bromo-2-((4-fluorobenzyl)oxy)aniline (13 g, 43.8 mmol), $EtSO_2Cl$ (8.43 g, 65.6 mmol) and pyridine (50 mL) in $CHCl_3$ (50 mL) was stirred at RT for 3 h. The mixture was concentrated under reduced pressure and the crude residue was purified by silica gel column chromatography (PE:EtOAc, 1:1) to afford the title product (12.5 g, 73%) as a yellow solid. LCMS (Method A): 4.24 min; m/z: 410.0 $[M+H]^+$.

Step 4: N-(2-((4-fluorobenzyl)oxy)-4-(4,4,5,5-tetramethyl-1,3,2-dioxaborolan-2-yl)phenyl)ethanesulfonamide A mixture of N-(4-bromo-2-((4-fluorobenzyl)oxy)phenyl)ethanesulfonamide (12.5 g, 32.1 mmol) $Pd(dppf)Cl_2$ (1.46 g, 1.60 mmol), KOAc (6.29 g, 64.2 mmol) and $B_2pin_2$ (8.96 g, 35.2 mmol) in degassed 1,4-dioxane (200 mL) was stirred at 100° C. under $N_2$ for 16 h. The mixture was concentrated under reduced pressure and the crude residue was purified by silica gel column chromatography (PE: EtOAc, 2:1) to afford the title product (14.8 g, >100%) as a brown solid. LCMS (Method A): 4.51 min; m/z: 453.2 $[M+H]^+$. $^1H$ NMR (400 MHz, DMSO-$d_6$): 8.99 (s, 1H), 7.63-7.60 (m, 2H), 7.38-7.32 (m, 2H), 7.28-7.21 (m, 3H), 5.15 (s, 2H), 3.03 (q, J=14.8, 7.2 Hz, 2H), 1.29 (s, 12H), 1.11 (t, J=7.2 Hz, 3H).

The following intermediates C (Table 3) were similarly prepared from the appropriate bromo aryl/alkyl (step 1) according to the method described for the synthesis of N-(2-((4-fluorobenzyl)oxy)-4-(4,4,5,5-tetramethyl-1,3,2-dioxaborolan-2-yl)phenyl)ethanesulfonamide (intermediate C1).

TABLE 3

| Compound No | Name | Structure | LCMS data | SM |
|---|---|---|---|---|
| Intermediate C2 | N-(2-(benzyloxy)-4-(4,4,5,5-tetramethyl-1,3,2-dioxaborolan-2-yl)phenyl)ethanesulfonamide | 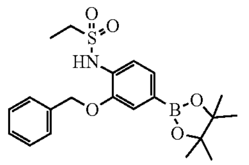 [SMILES: CCS(=O)(=O)Nc1ccc(B2OC(C)(C)C(C)(C)O2)cc1OCc1ccccc1] | LCMS (Method A): 4.51 min; m/z: 440.1 $[M + Na]^+$. | (bromomethyl) benzene |

TABLE 3-continued

| Compound No | Name | Structure | LCMS data | SM |
|---|---|---|---|---|
| Intermediate C3 | N-(2-(cyclohexylmethoxy)-4-(4,4,5,5-tetramethyl-1,3,2-dioxaborolan-2-yl)phenyl) ethanesulfonamide | 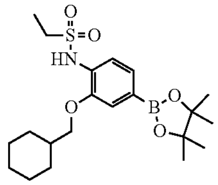 [SMILES: CCS(=O)(=O)Nc1ccc(B2OC(C)(C)C(C)(C)O2)cc1OCC1CCCCC1] | LCMS (Method A): 3.85 min; m/z: 424.0 $[M + H]^+$. | (bromomethyl) cyclohexane |
| Intermediate C4 | N-(2-((4-chlorobenzyl)oxy)-4-(4,4,5,5-tetramethyl-1,3,2-dioxaborolan-2-yl)phenyl) ethanesulfonamide | 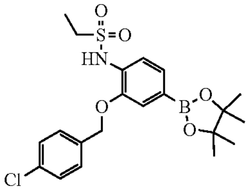 [SMILES: CCS(=O)(=O)Nc1ccc(B2OC(C)(C)C(C)(C)O2)cc1OCc1ccc(Cl)cc1] | LCMS (Method A): 4.65 min; m/z: 474.1 $[M + Na]^+$. | 4-chlorobenzene |
| intermediate C5 | N-(2-((3-chlorobenzyl)oxy)-4-(4,4,5,5-tetramethyl-1,3,2-dioxaborolan-2-yl)phenyl) ethanesulfonamide | 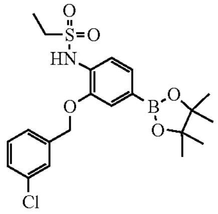 [SMILES: CCS(=O)(=O)Nc1ccc(B2OC(C)(C)C(C)(C)O2)cc1OCc1cccc(Cl)c1] | LCMS (Method A): 4.65 min; m/z: 474.1 $[M + Na]^+$ | 1-(bromomethyl)-3-chlorobenzene |
| Intermediate C6 | N-(2-(pyridin-4-ylmethoxy)-4-(4,4,5,5-tetramethyl-1,3,2-dioxaborolan-2-yl)phenyl) ethanesulfonamide | 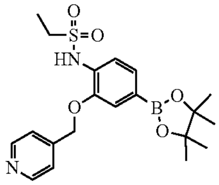 [SMILES: CCS(=O)(=O)Nc1ccc(B2OC(C)(C)C(C)(C)O2)cc1OCc1ccncc1] | LCMS (Method A): 3.29 min; m/z: 419.1 $[M + H]^+$. | 4-(bromomethyl) pyridine |
| Intermediate C7 | N-(2-(pyridin-3-ylmethoxy)-4-(4,4,5,5-tetramethyl-1,3,2-dioxaborolan-2-yl)phenyl) ethanesulfonamide | 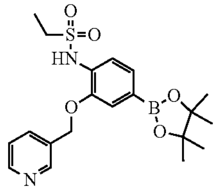 [SMILES: CCS(=O)(=O)Nc1ccc(B2OC(C)(C)C(C)(C)O2)cc1OCc1cccnc1] | LCMS (Method A): 3.55 min; m/z: 419.2 $[M + H]^+$. | 3-(bromomethyl) pyridine |
| Intermediate C8 | N-(2-(cyclopentylmethoxy)-4-(4,4,5,5-tetramethyl-1,3,2-dioxaborolan-2-yl)phenyl) ethanesulfonamide | 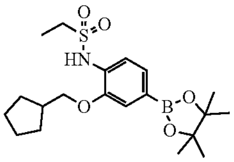 [SMILES: CCS(=O)(=O)Nc1ccc(B2OC(C)(C)C(C)(C)O2)cc1OCC1CCCC1] | LCMS (Method A): 4.79 min; m/z: 410.2 $[M + H]^+$. | (bromomethyl) cyclopentane |
| intermediate C9 | N-(2-isobutoxy-4-(4,4,5,5-tetramethyl-1,3,2-dioxaborolan-2-yl)phenyl) ethanesulfonamide | 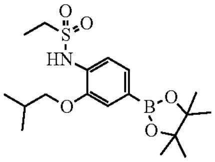 [SMILES: CCS(=O)(=O)Nc1ccc(B2OC(C)(C)C(C)(C)O2)cc1OCC(C)C] | LCMS (Method A): 4.61 min; m/z: 384.2 $[M + H]^+$. | 1-bromo-2-methylpropane |
| Intermediate C10 | N-(2-methoxy-4-(4,4,5,5-tetramethyl-1,3,2-dioxaborolan-2-yl)phenyl) ethanesulfonamide | 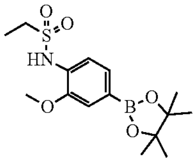 [SMILES: CCS(=O)(=O)Nc1ccc(B2OC(C)(C)C(C)(C)O2)cc1OC] | LCMS (Method A): 4.02 min; m/z: 364.1 $[M + Na]^+$. | methyliodide |

Intermediate C11

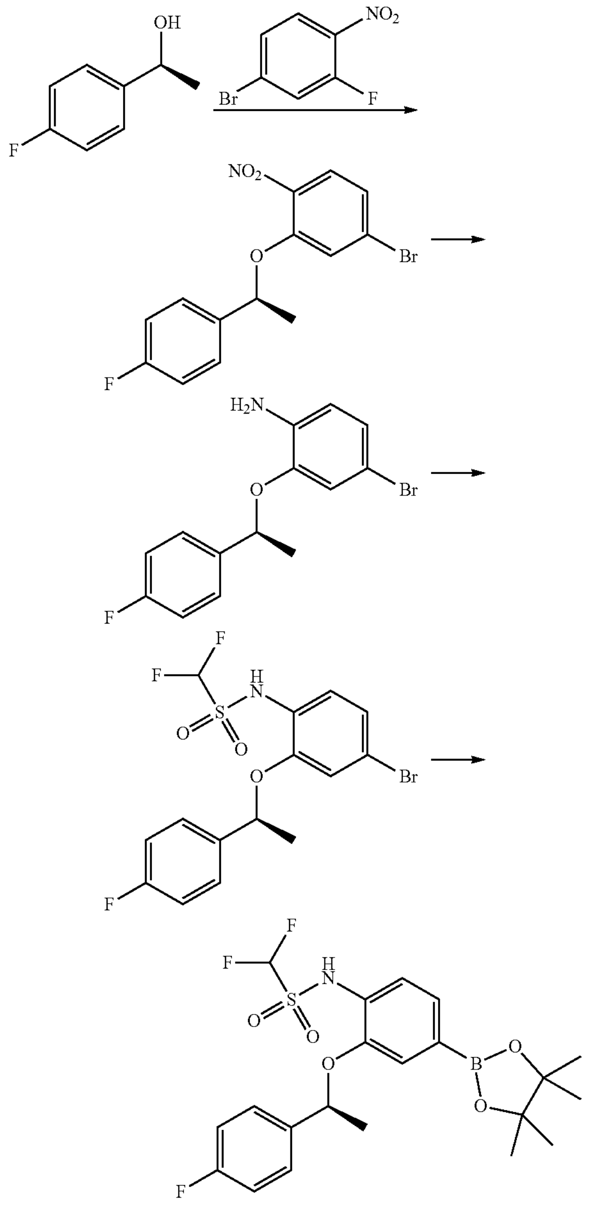

Step 1: (S)-4-bromo-2-(1-(4-fluorophenyl)ethoxy)-1-nitrobenzene

To a solution of (1S)-1-(4-fluorophenyl)ethan-1-ol (40 g, 285 mmol) in THF (600 mL) was added NaH (57.1 g, 1425 mmol). The mixture was stirred at 0° C. under $N_2$ for 30 min. Then 4-bromo-2-fluoro-1-nitrobenzene (62.6 g, 285 mmol) was added to the mixture and stirred at RT overnight. The reaction mixture was diluted with water (500 mL) and extracted with EtOAc (500 mL×3). The combined organic phases were washed with water and brine, dried ($Na_2SO_4$) and concentrated under reduced pressure to give the crude product (70 g, 72%) as a yellow oil. $^1$H NMR (400 MHz, DMSO-$d_6$): 7.80 (d, J=8.4 Hz, 1H), 7.54 (d, J=2.0 Hz, 1H), 7.48 (q, J=4.8 Hz, 2H), 7.26 (dd, J=8.8, 2.0 Hz, 1H), 7.20 (t, J=8.8 Hz, 1H), 5.89 (q, J=6.4 Hz, 1H), 1.54 (d, J=6.0 Hz, 3H).

Step 2: 4-bromo-2-[(1S)-1-(4-fluorophenyl)ethoxy]aniline

To a solution of 4-bromo-2-[(1S)-1-(4-fluorophenyl)ethoxy]-1-nitrobenzene (70 g, 205 mmol) in MeOH (500 mL), was added Zn dust (67.0 g, 1025 mmol) followed by sat. aq. $NH_4Cl$ (170 mL). The mixture was stirred at 60° C. for 6 h, then diluted with water (500 mL) and extracted with EtOAc (3×500 mL). The combined organic phases were washed with water and brine, dried ($Na_2SO_4$) and concentrated in vacuo. The crude residue was purified by silica gel column chromatography (PE:EtOAc, 100:1) to afford the title product (40 g, 63%) as a brown oil. LCMS (Method A): 4.13 min; m/z: 311.0, 311.9 $[M+H]^+$.

Step 3: N-{4-bromo-2-[(1S)-1-(4-fluorophenyl)ethoxy]phenyl}-1,1-difluoromethanesulfonamide To a solution of 4-bromo-2-[(1S)-1-(4-fluorophenyl)ethoxy]aniline (40 g, 128 mmol) in DCM (200 mL) and pyridine (40.5 g, 512 mmol) was added difluoromethanesulfonyl chloride (24.9 g, 166 mmol). After stirring at RT overnight, the residue was diluted with water (500 mL) and extracted with DCM (3×500 mL). The combined organic layers were washed (brine), dried ($Na_2SO_4$) and concentrated under reduced pressure. The residue was purified by silica gel column chromatography (PE:EtOAc, 100:1) to give the title product (39 g, 72%) as a brown oil. $^1$H NMR (400 MHz, DMSO-$d_6$): 10.43 (s, 1H), 7.57 (q, J=4.8 Hz, 2H), 7.21-7.15 (m, 3H), 7.07-7.04 (m, 2H), 6.98 (t, J=52.4 Hz, 1H), 5.65 (q, J=6.4 Hz, 1H), 1.54 (d, J=6.0 Hz, 3H).

Step 4: (S)-1,1-difluoro-N-(2-(1-(4-fluorophenyl)ethoxy)-4-(4,4,5,5-tetramethyl-1,3,2-dioxaborolan-2-yl)phenyl)methanesulfonamide To a solution of N-{4-bromo-2-[(1S)-1-(4-fluorophenyl)ethoxy]phenyl}-1,1-difluoromethanesulfonamide (39 g, 91.9 mmol) in dioxane (300 mL), was added KOAc (26.9 g, 275 mmol), $B_2pin_2$ (34.7 g, 137 mmol) and Pd(dppf)$Cl_2$ (2.01 g, 2.75 mmol). The mixture was stirred at 100° C. under $N_2$ overnight, then concentrated in vacuo. The residue was diluted with water (500 mL) and extracted with EtOAc (3×500 mL). The combined organic phases were washed with water and brine, dried ($Na_2SO_4$) and concentrated under reduced pressure. The residue was purified by silica gel column chromatography (PE:EtOAc, 50:1) to give the title product (41 g, 94%) as a yellow oil. $^1$H NMR (400 MHz, DMSO-$d_6$): 10.41 (s, 1H), 7.58 (q, J=4.8 Hz, 2H), 7.27 (d, J=7.6 Hz, 1H), 7.20-7.16 (m, 3H), 7.12 (s, 1H), 6.98 (t, J=52.4 Hz, 1H), 5.63 (q, J=6.4 Hz, 1H), 1.54 (d, J=6.4 Hz, 3H), 1.25 (d, J=4.8 Hz, 12H).

The following intermediates C12-C15 (Table 4) were similarly prepared according to the method described for the synthesis of (S)-1,1-difluoro-N-(2-(1-(4-fluorophenyl)ethoxy)-4-(4,4,5,5-tetramethyl-1,3,2-dioxaborolan-2-yl)phenyl)methanesulfonamide (intermediate C11).

TABLE 4

| Compound No | Name | Structure | $^1$H NMR data | SM |
|---|---|---|---|---|
| Intermediate C12 | N-{2-[(3,4-difluorophenyl) methoxy]-4-(4,4,5,5-tetramethyl-1,3,2-dioxaborolan-2-yl)phenyl}-1,1-difluoromethanesulfonamide | 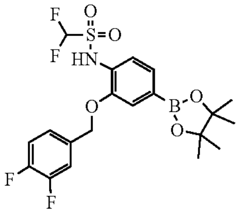 [SMILES: CC1(C)OB(c2ccc(NS(=O)(=O)C(F)F)c(OCc3ccc(F)c(F)c3)c2)OC1(C)C] | $^1$H NMR (400 MHz, DMSO-$d_6$): 10.48 (br s, 1H), 7.72-7.67 (m, 1H), 7.50-7.39 (m, 2H), 7.33-7.25 (m, 3H), 6.91 (t, J = 52.5 Hz, 1H), 5.18 (s, 2H), 1.29 (s, 12H). | (3,4-difluorophenyl) methanol |
| Intermediate C13 | (R)-1,1-difluoro-N-(2-(1-(4-fluorophenyl)ethoxy)-4-(4,4,5,5-tetramethyl-1,3,2-dioxaborolan-2-yl)phenyl) methanesulfonamide | 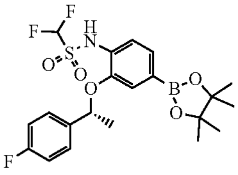 [SMILES: C[C@@H](Oc1cc(B2OC(C)(C)C(C)(C)O2)ccc1NS(=O)(=O)C(F)F)c1ccc(F)cc1] | $^1$H NMR (400 MHz, DMSO-$d_6$): 10.41 (s, 1H), 7.58 (q, J = 4.8 Hz, 2H), 7.27 (d, J = 7.6 Hz, 1H), 7.20-7.16 (m, 3H), 7.12 (s, 1H), 6.98 (t, J = 52.4 Hz, 1H), 5.63 (q, J = 6.4 Hz, 1H), 1.54 (d, J = 6.4 Hz, 3H), 1.25 (d, J = 4.8 Hz, 12H). | (1R)-1-(4-fluorophenyl) ethan-1-ol |
| Intermediate C14 | 1,1-difluoro-N-(4-(4,4,5,5-tetramethyl-1,3,2-dioxaborolan-2-yl)-2-(thiazol-2-ylmethoxy)phenyl) methanesulfonamide | 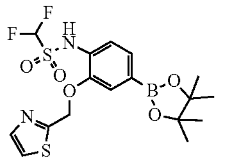 [SMILES: CC1(C)OB(c2ccc(NS(=O)(=O)C(F)F)c(OCc3nccs3)c2)OC1(C)C] | LCMS (Method A): 4.1 min, $[M + H]^+$ = 447.2 | thiazol-2-ylmethanol |
| intermediate C15 | 1,1-difluoro-N-{2-[1-(1,3-oxazol-2-yl)ethoxy]-4-(4,4,5,5-tetramethyl-1,3,2-dioxaborolan-2-yl)phenyl} methanesulfonamide | 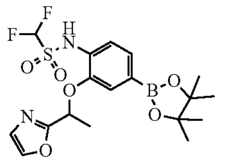 [SMILES: CC(Oc1cc(B2OC(C)(C)C(C)(C)O2)ccc1NS(=O)(=O)C(F)F)c1ncco1] | LCMS (Method A): 4.00 min, $[M + H]^+$ = 445.2 | 1-(oxazol-2-yl)ethan-1-ol |

Intermediate C16: N-(4-(4,4,5,5-tetramethyl-1,3,2-dioxaborolan-2-yl)phenyl)ethane sulfonamide

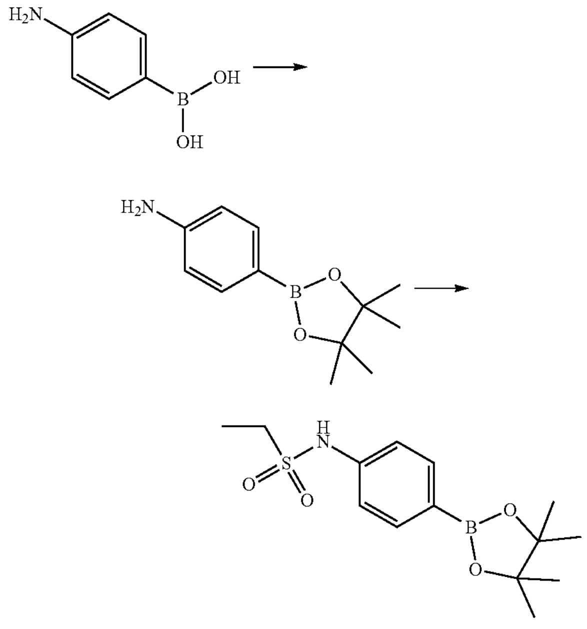

Step 1: 4-(4,4,5,5-tetramethyl-1,3,2-dioxaborolan-2-yl)analine

A mixture of (4-aminophenyl)boronic acid hydrochloride (4.0 g, 23.0 mmol), $NaHCO_3$ (3.86 g, 46.0 mmol), $MgSO_4$ (8.30 g, 69.0 mmol) and pinacol (2.98 g, 25.3 mmol) in THF (23 mL) was stirred at RT for 22 h. The reaction mixture was diluted with EtOAc (50 mL), filtered through Celite and then concentrated under reduced pressure. The residue was triturated ($Et_2O$) to afford the title compound (1.33 g, 26%) as an off-white solid. LCMS (Method C): 1.40 min; m/z: 220.2 $[M+H]^+$. $^1$H NMR (300 MHz, $CDCl_3$): 7.65-7.61 (m, 2H), 6.70-6.66 (m, 2H), 1.32 (s, 12H).

Step 2: N-(4-(4,4,5,5-tetramethyl-1,3,2-dioxaborolan-2-yl)phenyl)ethane sulfonamide A mixture of 4-(4,4,5,5-tetramethyl-1,3,2-dioxaborolan-2-yl)aniline (1.6 g, 7.30 mmol), $EtSO_2Cl$ (1.37 mL, 14.6 mmol), pyridine (2.94 mL, 36.5 mmol) and DCM (15 mL) was stirred at RT for 3 h. The reaction mixture was concentrated under reduced pressure, azeotroped with toluene, then diluted with $H_2O$ (50 mL) and extracted with EtOAc (3×30 mL). The combined organic layers were dried ($MgSO_4$), concentrated under reduced pressure and the crude residue purified by silica gel column chromatography (PE:EtOAc, 1:0 to 1:1) to afford the title compound (1.37 g, 60%) as a beige solid. LCMS (Method A): 1.92 min; m/z: 312.2 $[M+H]^+$. $^1$H NMR (300 MHz, $CDCl_3$): 7.80-7.76 (m, 2H), 7.21-7.17 (m, 2H), 6.63 (br s, 1H), 3.15 (q, J=7.4 Hz, 2H), 1.34 (t, J=7.4 Hz, 3H), 1.33 (s, 9H).

Intermediate D1: 5-((6-(difluoromethyl)pyridin-2-yl)amino)-3-(4-(ethylsulfonamido)phenyl)-1H-pyrazole-4-carboxamide

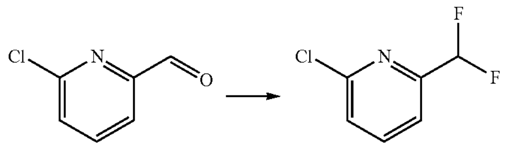 [SMILES: O=Cc1cccc(Cl)n1 ; FC(F)c1cccc(Cl)n1]

Step 1: 5-((6-(difluoromethyl)pyridin-2-yl)amino)-3-(4-(ethylsulfonamido)phenyl)-1H-pyrazole-4-carboxamide A solution of 6-chloropyridine-2-carbaldehyde (5 g, 35.3 mmol) in DCM (50 mL) was stirred at −20° C. for 1 h. DAST (9.65 ml, 60.0 mmol) was then added, and the mixture was stirred at RT for 16 h. The mixture was neutralized to pH 7-8 with sat. aq. $NaHCO_3$ and extracted with DCM (3x20 mL). The combined organic layers were washed with $H_2O$, dried ($Na_2SO_4$) and concentrated under reduced pressure to afford the title product (1.65 g, 29%) as a black liquid. LCMS (Method A): 0.92 min; m/z: 164.0 $[M+H]^+$.

Intermediate E1: 5-(1-(trifluoromethyl)cyclopropyl)isoxazol-3-amine

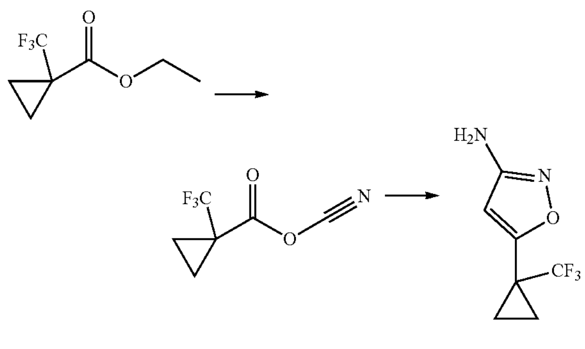

Step 1: 3-oxo-3-(1-(trifluoromethyl)cyclopropyl) propanenitrile

To a solution of NaH (60% in oil, 2.18 g, 54.8 mmol) in THF (70 mL) was added ethyl 1-(trifluoromethyl)cyclopropane-1-carboxylate (5 g, 27.4 mmol), followed by the dropwise addition of acetonitrile (1.68 g, 41.0 mmol) over 45 min. The suspension was heated at 70° C. overnight. Once cooled, the reaction mixture was poured into water (150 mL) and the organics were extracted with EtOAc (2×100 mL). The combined organics were dried ($Na_2SO_4$) and concentrated under reduced pressure to afford the title compound (4.60 g, 95%) as a yellow oil. $^1H$ NMR (400 MHz, $CDCl_3$): 3.95 (s, 2H), 1.60 (dtd, J=5.4, 3.8, 1.5 Hz, 2H), 1.49 (t, J=3.6 Hz, 2H).

Step 2: 5-(1-(trifluoromethyl)cyclopropyl)isoxazol-3-amine

A mixture of 3-oxo-3-[1-(trifluoromethyl)cyclopropyl] propanenitrile (460 mg, 2.59 mmol), $NH_2OH{\cdot}HCl$ (0.215 mg, 3.10 mmol), and $NaHCO_3$ (435 mg, 5.2 mmol) in MeOH (1 mL) and water (9 mL) was heated at 140° C. under microwave irradiation for 5 min. The reaction mixture was concentrated under reduced pressure, and the residue was poured into water (10 mL) and extracted with EtOAc (5 mL×2). The combined organics were dried ($Na_2SO_4$) and concentrated under reduced pressure to give the title product (330 mg, 66%) as a pale yellow solid. LCMS (Method A): 3.00 min; m/z: 193.1 $[M+H]^+$.

Intermediate E2: 5-(1-methoxy-2-methylpropan-2-yl)isoxazol-3-amine

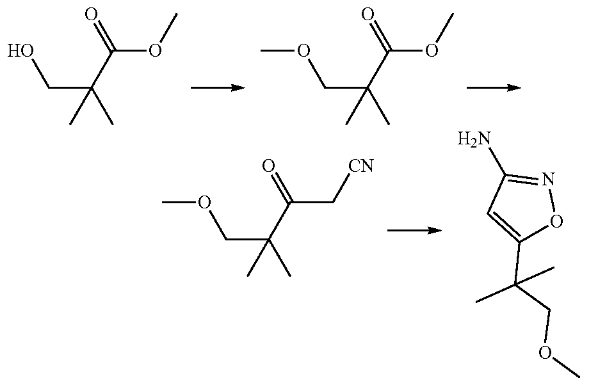

Step 1: methyl 3-methoxy-2,2-dimethylpropanoate

A mixture of methyl 3-hydroxy-2,2-dimethylpropanoate (5 g, 37.8 mmol), KOH (8.47 g, 151 mmol) and MeI (21.4 g, 151 mmol) in DMSO (150 mL) was stirred at RT overnight. The reaction mixture was concentrated under reduced pressure, and the residue was poured into water (500 mL) and extracted with EtOAc (300 mL×5). The combined organic phases were dried ($Na_2SO_4$) and concentrated under reduced pressure to give the title product (3 g, 54%) as a yellow oil. $^1H$ NMR (400 MHz, DMSO-$d_6$): 3.59 (s, 3H), 3.32 (s, 2H), 3.22 (s, 3H), 1.10 (s, 6H).

Step 2: 5-methoxy-4,4-dimethyl-3-oxopentanenitrile

Acetonitrile (1.68 g, 41.0 mmol) was added dropwise to a solution of LDA (4.39 g, 41.0 mmol) in THF (60 mL) and the solution was stirred at −78° C. for 30 minutes. Methyl 3-methoxy-2,2-dimethylpropanoate (3 g, 20.5 mmol) was then added dropwise at −78° C. and the reaction mixture was stirred at RT overnight. The reaction mixture was concentrated under reduced pressure, and the residue was poured into water (100 mL) and extracted with EtOAc (50 mL×2). The combined organics were dried ($Na_2SO_4$) and concentrated under reduced pressure to give the title product (2.3 g, 72%) as a yellow oil. $^1H$ NMR (400 MHz, DMSO-$d_6$): 4.18 (s, 2H), 3.36 (s, 3H), 3.34 (s, 2H), 1.06 (s, 6H).

Step 3: 5-(1-methoxy-2-methylpropan-2-yl)isoxazol-3-amine

A mixture of 5-methoxy-4,4-dimethyl-3-oxopentanenitrile (2.3 g, 14.8 mmol), $NH_2OH{\cdot}HCl$ (1.12 g, 16.2 mmol) and NaOH (647 mg, 16.2 mmol) in water (20 mL) and EtOH (20 mL) was stirred at 80° C. overnight. The reaction mixture was concentrated under reduced pressure, and the residue was poured into water (100 mL) and extracted with EtOAc (50 mL×2). The combined organics were dried ($Na_2SO_4$) and concentrated under reduced pressure to give the title product (960 mg, 38%) as a yellow oil. LCMS (Method A): 0.9 min; m/z: 171.1 $[M+H]^+$.

Intermediate E3: 5-(4-methyltetrahydro-2H-pyran-4-yl)isoxazol-3-amine

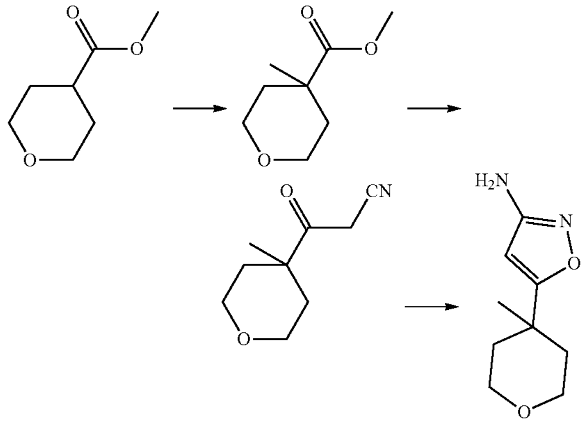

Step 1: methyl 4-methyltetrahydro-2H-pyran-4-carboxylate

To a solution of methyl oxane-4-carboxylate (5 g, 34.6 mmol) in dry THF (15 mL) was added LDA (2M in THF, 34.6 mL, 69.2 mmol) and the mixture was stirred at −78° C. for 30 min. MeI (5.89 g, 41.5 mmol) was then added dropwise and the mixture was stirred at RT overnight. The mixture was adjusted to pH=3 with aq. HCl (0.5 M) and the organics were extracted with EtOAc (50 mL×3). The combined organic layers were washed with brine, dried over $Na_2SO_4$ and concentrated under reduced pressure. The residue was purified by column chromatography on silica gel (PE/EtOAc=100/1, V/V) to give the title product (5.40 g, 34.1 mmol, 98.7%) as a yellow oil.

$^1H$ NMR (400 MHz, $CDCl_3$): 3.78 (dt, J=11.8, 4.1 Hz, 2H), 3.70 (s, 3H), 3.50-3.42 (m, 2H), 2.10-2.01 (m, 2H), 1.53-1.43 (m, 2H), 1.21 (s, 3H).

Step 2: 3-(4-methyltetrahydro-2H-pyran-4-yl)-3-oxopropanenitrile

Acetonitrile (4.31 g, 105 mmol) was slowly added to a solution of lithium diisopropylamide (2M/THF, 10.9 g, 102 mmol) in dry THF (50 mL), and the mixture was stirred at −78° C. for 1 h followed by the addition of methyl 4-methyloxane-4-carboxylate (5.4 g, 34.1 mmol) in dry THF (40 mL) over 10 min. The mixture was stirred at −78° C. for 1 h and at RT overnight. The mixture was diluted with water (100 mL) and the pH was adjusted to pH=3 with HCl (2M). The organics were extracted with EtOAc (3×50 mL) and the combined organics were dried ($Na_2SO_4$) and concentrated under reduced pressure to give the title product (4.20 g, 74%) as a yellow oil. $^1H$ NMR (400 MHz, $CDCl_3$): 3.74 (ddd, J=12.0, 6.4, 3.7 Hz, 2H), 3.55 (ddd, J=11.7, 8.1, 3.3 Hz, 2H), 2.02-1.95 (m, 2H), 1.90 (d, J=0.7 Hz, 2H), 1.59-1.51 (m, 2H), 1.24 (s, 3H).

Step 3: 5-(4-methyltetrahydro-2H-pyran-4-yl)isoxazol-3-amine

A mixture of 3-(4-methyltetrahydro-2H-pyran-4-yl)-3-oxopropanenitrile (7 g, 41.8 mmol), $NH_2OH·HCl$ (3.30 g, 50.1 mmol) and $NaHCO_3$ (8.73 g, 104 mmol) in water (63 mL) and MeOH (7 mL) was stirred at 65° C. overnight under $N_2$. The reaction mixture was concentrated under reduced pressure, and the residue was poured into water (40 mL) and extracted with EtOAc (100 mL×3). The combined organic phases were dried ($Na_2SO_4$) and concentrated under reduced pressure. The residue was purified by column chromatography on silica gel (PE:EtOAc, 9:1 to 1:9) to give the title product (1.20 g, 16%) as a red oil. $^1H$ NMR (400 MHz, $CDCl_3$): 4.96 (s, 1H), 4.52 (br s, 2H), 3.82-3.71 (m, 2H), 3.64-3.57 (m, 2H), 2.03-1.97 (m, 2H), 1.63 (ddd, J=13.6, 9.5, 4.0 Hz, 2H), 1.26 (s, 3H).

Intermediate E4: 5-(2-fluoropropan-2-yl)isoxazol-3-amine

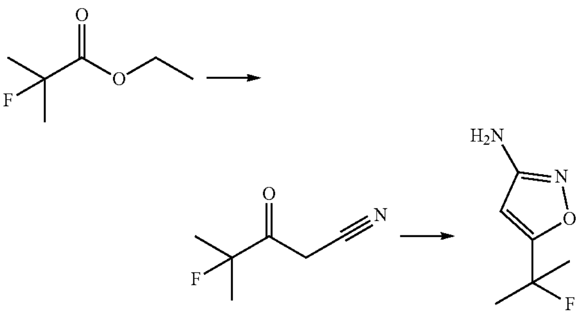

Step 1: 4-fluoro-4-methyl-3-oxopentanenitrile

To a suspension of NaH (60% in oil, 2.49 g, 104 mmol) in THF (30 mL) was added ethyl 2-fluoro-2-methylpropanoate (3.5 g, 26.0 mmol), followed by the dropwise addition of acetonitrile (1.66 g, 40.5 mmol). The resulting mixture was heated at 70° C. for 3 h. The mixture was poured into water (50 mL) and extracted with EtOAc (50 mL×2). The combined organic phases were dried ($Na_2SO_4$) and concentrated under reduced pressure to afford the title product (3.10 g, 92%) as a yellow oil.

Step 2: 5-(2-fluoropropan-2-yl)isoxazol-3-amine

A mixture of 4-fluoro-4-methyl-3-oxopentanenitrile (2.3 g, 17.8 mmol), $NaHCO_3$ (3.73 g, 44.5 mmol) and $NH_2OH·HCl$ (703 mg, 21.3 mmol) in $H_2O$ (27 mL) and MeOH (3 mL) was stirred at 65° C. overnight. The reaction mixture was concentrated under reduced pressure and the residue was poured into water (50 mL) and extracted with EtOAc (50 mL×2). The combined organic phases were dried ($Na_2SO_4$) and concentrated under reduced pressure. The residue was purified by column chromatography on silica gel (PE:EA, 5:1) to afford the title product (450 mg, 18%) as a yellow oil. LCMS (Method A): 2.496 min; m/z: 145.1 $[M+H]^+$.

Intermediate E5: 5-(3-methyloxetan-3-yl)isoxazol-3-amine

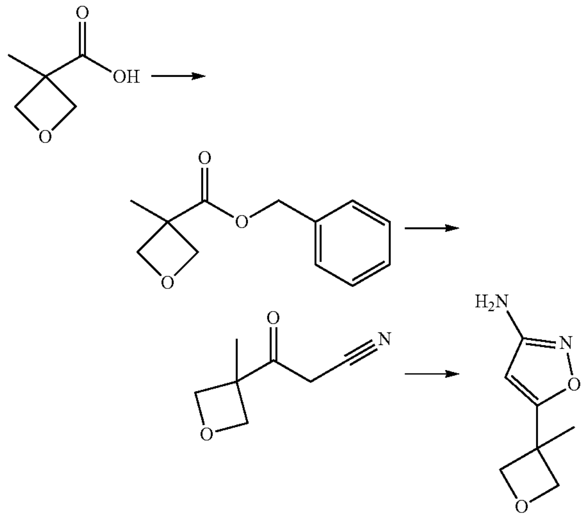

Step 1: benzyl 3-methyloxetane-3-carboxylate

A mixture of 3-methyloxetane-3-carboxylic acid (4 g, 34.4 mmol), $K_2CO_3$ (14.2 g, 103 mmol) and benzyl bromide (5.88 g, 34.4 mmol) in acetonitrile (50 mL) was stirred at 70° C. under $N_2$ overnight. The reaction mixture was concentrated under reduced pressure, and the residue was poured into water (100 mL) and extracted with EtOAc (50 mL×2). The combined organic phases were dried ($Na_2SO_4$) and concentrated under reduced pressure. The residue was purified by column chromatography on silica gel (PE:EtOAc, 10:1) to give the title product (6.9 g, 97%) as a colorless oil. $^1$H NMR (400 MHz, DMSO-$d_6$): 7.41-7.31 (m, 5H), 5.18 (s, 2H), 4.77 (d, J=5.9 Hz, 2H), 4.34 (d, J=5.9 Hz, 2H), 1.53 (s, 3H).

Step 2: 3-(3-methyloxetan-3-yl)-3-oxopropanenitrile

Acetonitrile (2.04 g, 49.7 mmol) was added to a solution of LDA (2 M in THF, 25 mL, 49.7 mmol) in dry THF (100 mL) and the solution was stirred at −78° C. under $N_2$ for 1 hour. Benzyl 3-methyloxetane-3-carboxylate (7.9 g, 38.3 mmol) was then added at −78° C. and the reaction mixture was stirred at RT overnight. The reaction mixture was concentrated under reduced pressure, and the residue was poured into water (100 mL) and extracted with EtOAc (100 mL×2). The combined organic phases were dried ($Na_2SO_4$) and concentrated under reduced pressure to give the title product (3 g, 56%) as a colorless oil. $^1$H NMR (400 MHz, DMSO-$d_6$): 4.74 (d, J=6.2 Hz, 2H), 4.28 (t, J=3.1 Hz, 4H), 1.49 (s, 3H).

Step 3: 5-(3-methyloxetan-3-yl)isoxazol-3-amine

A mixture of 3-(3-methyloxetan-3-yl)-3-oxopropanenitrile (3 g, 21.5 mmol), $NH_2OH{\cdot}HCl$ (1.63 g, 23.6 mmol) and NaOH (943 mg, 23.6 mmol) in water (40 mL) and EtOH (40 mL) was stirred at 80° C. under $N_2$ overnight. The reaction mixture was concentrated under reduced pressure and the residue was poured into water (100 mL). The mixture was extracted with EtOAc (50 mL×2), and the combined organics were dried ($Na_2SO_4$) and concentrated under reduced pressure to give the title product (1.9 g, 57%) as a yellow solid. LCMS (Method A): 3.22 min; m/z: 155.1 $[M+H]^+$.

Intermediate E6: 5-(adamantan-1-yl)isoxazol-3-amine

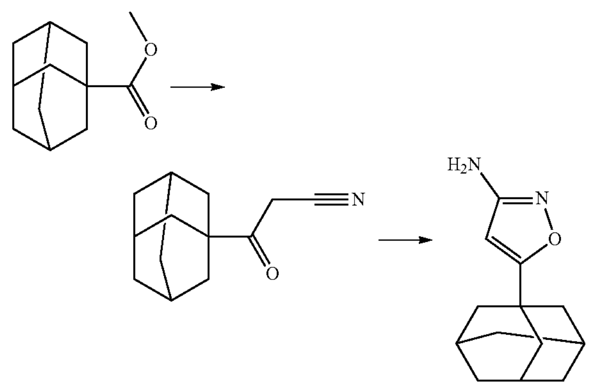

Step 1: 3-(adamantan-1-yl)-3-oxopropanenitrile

A solution of LDA (2 M in THF, 23.1 mL, 46.2 mmol) was slowly added to a pre-cooled solution of acetonitrile (1.26 g, 30.8 mmol) in dry THF (25 mL) at −78° C., and the mixture was stirred at −78° C. for 1 h. A solution of methyl adamantane-1-carboxylate (3 g, 15.4 mmol) in dry THF (15 mL) was then added dropwise at −78° C. and the mixture was stirred at RT overnight. A sat. aq. Solution of $NH_4Cl$ (50 mL) was added and the organics were extracted with EtOAc (3×50 mL). The combined organics were dried ($Na_2SO_4$) and concentrated under reduced pressure to afford the title product (3.5 g, 99%) as a yellow liquid.

Step 2: 5-(adamantan-1-yl)isoxazol-3-amine

A mixture of 3-(adamantan-1-yl)-3-oxopropanenitrile (3.5 g, 17.2 mmol), $NH_2OH{\cdot}HCl$ (1.36 g, 20.6 mmol) and $NaHCO_3$ (3.60 g, 42.9 mmol) in water (54 mL) and MeOH (6 mL) was stirred under $N_2$ at 65° C. overnight. The reaction mixture was concentrated under reduced pressure, and the residue was poured into water (50 mL) and extracted with EtOAc (50 mL×2). The combined organic phases were dried ($Na_2SO_4$) and concentrated under reduced pressure. The residue was purified by column chromatography on silica gel (PE:EA, 5:1) to give the title product (0.8 g, 21%) as a yellow solid. LCMS (Method A): 4.74 min, m/z: 292.2 $[M+H]^+$.

Intermediate E7: 5-(tetrahydrofuran-3-yl)isoxazol-3-amine

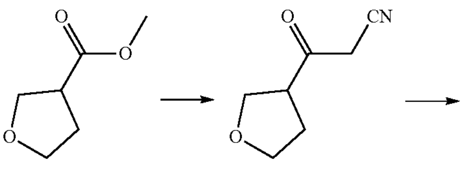

-continued

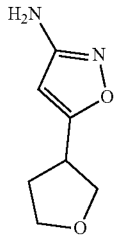

Step 1: 3-oxo-3-(tetrahydrofuran-3-yl)propanenitrile

Acetonitrile (4.14 mL) was added to a solution of LDA (2 M in THF, 12.5 mL, 24.9 mmol) in dry THF (50 mL) and the mixture was stirred at −78° C. for 1 hour under $N_2$. Methyl tetrahydrofuran-3-carboxylate (2.5 g 19.2 mmol) was then added at −78° C. and the reaction mixture was stirred at RT overnight. The reaction mixture was concentrated under reduced pressure, and the residue was poured into water (100 mL) and extracted with EtOAc (100 mL×2). The combined organic phases were dried ($Na_2SO_4$) and concentrated under reduced pressure to give the title product (2 g, 75%) as a yellow oil.

Step 2: 5-(tetrahydrofuran-3-yl)isoxazol-3-amine

To a solution of 3-oxo-3-(tetrahydrofuran-3-yl)propanenitrile (2 g, 14.3 mmol) in $H_2O$ (10 mL) and EtOH (10 mL) were added $NH_2OH·HCl$ (1.09 g, 15.7 mmol) and NaOH (627 mg, 15.7 mmol), and the reaction mixture was stirred at 80° C. overnight. The mixture was diluted with water (50 mL) and the organics were extracted with EtOAc (50 mL×3). The combined organic phases were washed with water and brine, dried ($Na_2SO_4$) and concentrated under reduced pressure to give the title product (1.9 g, 86%) as a yellow solid. LCMS (Method A): 1.08 min; m/z: 155.1 $[M+H]^+$.

Intermediate E8: 5-(difluoromethyl)isoxazol-3-amine

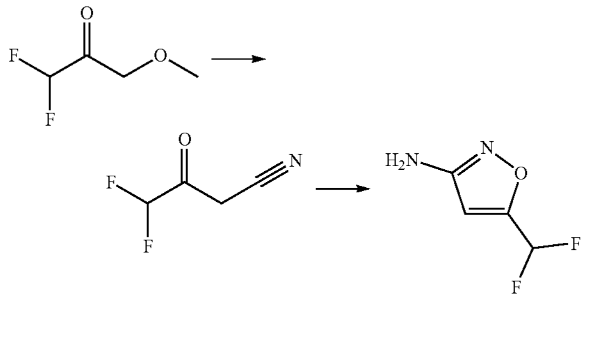

Step 1: 4,4-difluoro-3-oxobutanenitrile

To a solution of diisopropylamine (5.28 g, 52.2 mmol) in dry THF (100 ml), cooled to −78° C. under $N_2$, was added a solution of n-BuLi (1.6 M in hexanes, 52.2 mmol) dropwise, and the mixture was stirred at −78° C. for 1 h. A solution of MeCN (2.14 g, 52.2 mmol) in dry THF (20 ml) was then added dropwise and the resulting mixture was stirred at −78° C. for 30 min. A solution of ethyl 2,2-difluoroacetate (5 g, 40.2 mmol) in dry THF (10 ml) was then added and the reaction mixture was stirred at RT overnight. Water (100 mL) was then added, and the mixture was concentrated under reduced pressure. The aqueous residue was extracted with EtOAc (200 mL×3) and the combined organics were washed with brine, dried ($Na_2SO_4$) and concentrated under reduced pressure to give the title product (5 g, >100%) as a brown oil.

Step 2: 5-(difluoromethyl)isoxazol-3-amine

To a mixture of 4,4-difluoro-3-oxobutanenitrile (5 g, 41.9 mmol) and NaOH (1.83 g, 46.0 mmol) in EtOH (100 mL) and $H_2O$ (100 mL) was added $NH_2OH·HCl$ (3.19 g, 46.0 mmol), and the mixture was stirred at 80° C. overnight. Water (30 mL) was added and the organics were extracted with EtOAc (300 mL×3). The combined organics were washed with brine, dried ($Na_2SO_4$) and concentrated under reduced pressure. The residue was purified by column chromatography on silica gel (PE:EA, 10:1) to give the title product (876 mg, 16%) as a yellow oil.

Intermediate E9: 5-cyclopropyl-1,2-oxazol-3-amine

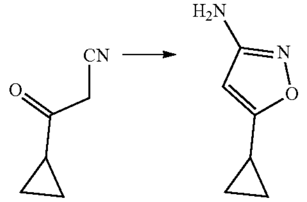 [SMILES: N#CCC(=O)C1CC1 ; Nc1cc(C2CC2)on1]

Step 1: 5-cyclopropyl-1,2-oxazol-3-amine

A mixture of 3-cyclopropyl-3-oxopropanenitrile (1 g, 9.16 mmol), $NH_2OH·HCl$ (359 mg, 10.9 mmol) and $NaHCO_3$ (1.92 g, 22.9 mmol) in MeOH (2 mL) and $H_2O$ (18 mL) was stirred at 65° C. for 15 h under $N_2$. The reaction mixture was concentrated under reduced pressure, and the residue was poured into water (50 mL) and extracted with EtOAc (50 mL×2). The combined organic phases were dried ($Na_2SO_4$) and concentrated under reduced pressure. The residue was purified by column chromatography on silica gel (PE:EA, 5:1) to afford the title product (320 mg, 28%) as a brown oil. LCMS (Method A): 0.78 min; m/z: 145.1 $[M+H]^+$.

Intermediate F1: 5-(tert-butyl)pyrazin-2-amine

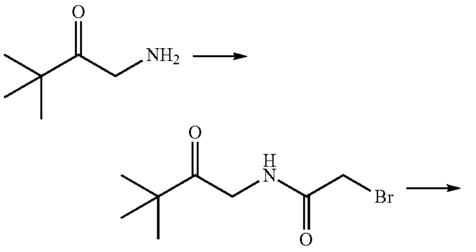

-continued

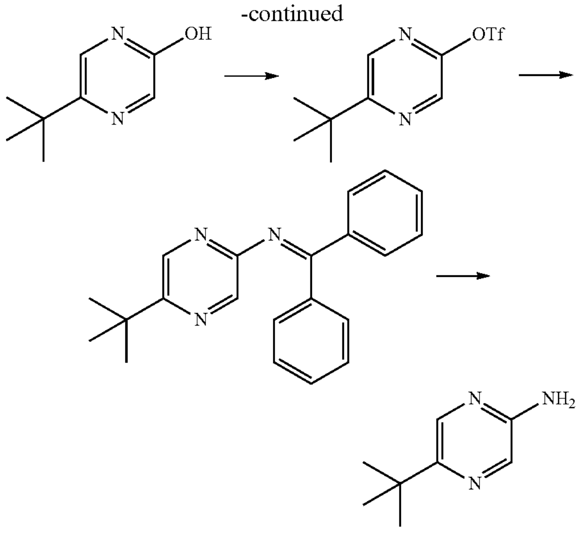

Step 1: 2-bromo-N-(3,3-dimethyl-2-oxobutyl)acetamide

To a solution of 2-bromoacetyl bromide (17.5 g, 86.8 mmol) in DCM (120 mL) was added sat. aq. $Na_2CO_3$ (60 mL) followed by 1-amino-3,3-dimethylbutan-2-one (10 g, 86.8 mmol) at 0° C. The solution was stirred at RT for 4 h. Water (100 mL) was then added and the organics were extracted with DCM (200 mL×3). The combined organics were washed with water and brine, dried ($Na_2SO_4$) and concentrated under reduced pressure to give the title product (6.76 g, 33%) as a white solid. LCMS (Method A): 2.80 min; m/z: 236.1 $[M+H]^+$.

Step 2: 5-(tert-butyl)pyrazin-2-ol

To a solution of 2-bromo-N-(3,3-dimethyl-2-oxobutyl) acetamide (6.76 g, 28.6 mmol) in $EtOH{\cdot}NH_3$ (20 mL) was added KI (949 mg, 5.72 mmol), and the reaction was stirred at 60° C. overnight. The mixture was poured into water (200 mL) and the organics were extracted with DCM (120 mL×4). The combined organic phases were washed with brine, dried ($Na_2SO_4$) and concentrated under reduced pressure. The residue was purified by column chromatography on silica gel (DCM:MeOH, 30:1) to give the title product (2.6 g, 50%) as a yellow oil. LCMS (Method B): 1.90 min; m/z: 152.9 $[M+H]^+$.

Step 3: 5-(tert-butyl)pyrazin-2-yl trifluoromethanesulfonate

To a mixture of 5-tert-butylpyrazin-2-ol (2.6 g, 17.0 mmol) and $Et_3N$ (3.44 g, 34.0 mmol) in DCM (70 mL) at 0° C. was added $Tf_2O$ (7.19 g, 25.5 mmol), and the reaction was stirred at RT overnight. The mixture was poured into water (60 mL) and the organics were extracted with EtOAc (150 mL×2). The combined organic phases were washed with brine, dried ($Na_2SO_4$) and concentrated under reduced pressure. The residue was purified by column chromatography on silica gel (PE:EtOAc, 20:1) to give the title product (2.72 g, 56%) as a yellow oil. LCMS (Method B): 5.30 min; m/z: 284.9 $[M+H]^+$.

Step 4: N-(5-(tert-butyl)pyrazin-2-yl)-1,1-diphenylmethanimine

A mixture of 5-tert-butylpyrazin-2-yl trifluoromethanesulfonate (2.72 g, 9.56 mmol), Xantphos (1.10 g, 1.91 mmol), $Pd_2(dba)_3$ (875 mg, 956 μmol), $Cs_2CO_3$ (6.22 g, 19.1 mmol) and diphenylmethanimine (2.06 g, 11.4 mmol) in degassed 1,4-dioxane (80 mL) was stirred at 100° C. overnight. The reaction mixture was concentrated under reduced pressure and the residue was purified by column chromatography on silica gel (PE:EtOAc, 10:1) to give the title product (2 g, 66%) as a white solid. LCMS (Method B): 5.42 min; m/z: 316.1 $[M+H]^+$.

Step 5: 5-(tert-butyl)pyrazin-2-amine

A mixture of N-(5-tert-butylpyrazin-2-yl)-1,1-diphenylmethanimine (150 mg, 475 μmol) in aq. HCl (2 M, 6 mL) and MeOH (6 mL) was stirred at RT overnight. The reaction mixture was concentrated under reduced pressure and the residue was purified by prep-TLC (PE:EtOAc, 2:1) to give the title product (47 mg, 65%) as a white solid. LCMS (Method B): 4.33 min; m/z 152.1 $[M+H]^+$.

Intermediate F2: 5-(tetrahydro-2H-pyran-4-yl)pyrazin-2-amine

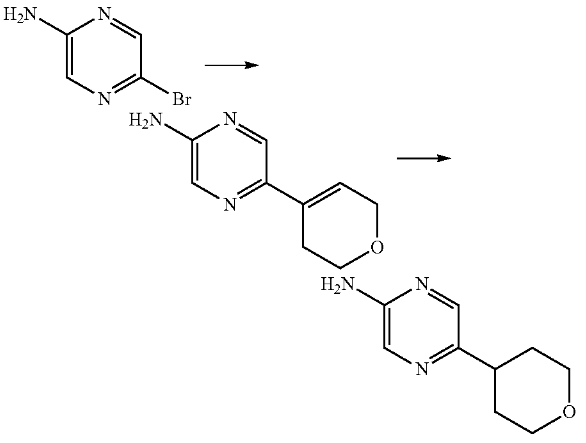

Step 1: 5-(3,6-dihydro-2H-pyran-4-yl)pyrazin-2-amine

To a mixture of 5-bromopyrazin-2-amine (828 mg, 4.76 mmol), 2-(3,6-dihydro-2H-pyran-4-yl)-4,4,5,5-tetramethyl-1,3,2-dioxaborolane (1 g, 4.76 mmol) and $Na_2CO_3$ (1.50 g, 14.2 mmol) in degassed 1,4-dioxane (30 mL) and $H_2O$ (7.5 mL) was added $Pd(dppf)Cl_2$ (217 mg, 238 μmol), and the reaction mixture was stirred at 100° C. under $N_2$ overnight. The reaction mixture was concentrated under reduced pressure and the residue was purified by column chromatography on silica gel (PE:EtOAc, 1:1 to 0:1) to give the title product (700 mg, 83%) as a brown solid.

Step 2: 5-(tetrahydro-2H-pyran-4-yl)pyrazin-2-amine

A mixture of 5-(3,6-dihydro-2H-pyran-4-yl)pyrazin-2-amine (700 mg, 3.95 mmol) and 10% Pd/C (70 mg, 0.658 mmol) in MeOH (30 mL) was stirred at 50° C. under $H_2$ overnight. The reaction mixture was filtered over Celite, and the filtrate was concentrated under reduced pressure. The residue was purified by column chromatography on silica gel (PE:EtOAc, 4:1 to 1:4) to give the title product (520 mg, 74%) as a brown oil. LCMS (Method A): 0.85 min, m/z: 180.0 $[M+H]^+$.

Intermediate F3: 5-(tetrahydro-2H-pyran-4-yl)pyridin-2-amine

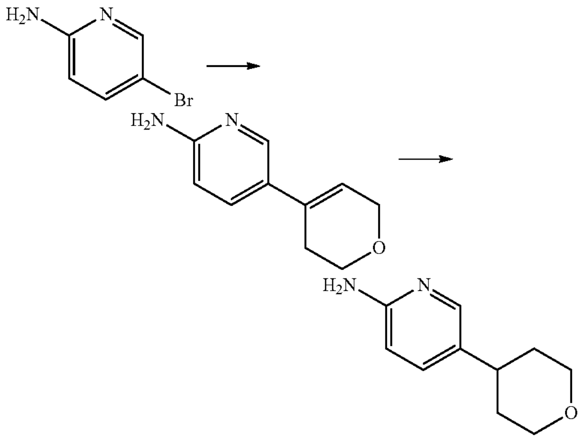

Step 1: 5-(3,6-dihydro-2H-pyran-4-yl)pyridin-2-amine

A mixture of 5-bromopyridin-2-amine (2 g, 11.5 mmol), 2-(3,6-dihydro-2H-pyran-4-yl)-4,4,5,5-tetramethyl-1,3,2-dioxaborolane (2.41 g, 11.5 mmol), $Na_2CO_3$ (4.87 g, 46.0 mmol) and $Pd(dppf)Cl_2$ (516 mg, 2.30 mmol) in degassed 1,4-dioxane (100 mL) and $H_2O$ (20 mL) was heated at 100° C. for 12 h under $N_2$. The mixture was cooled to RT and the organics were extracted with EtOAc (2×10 mL). The combined organics were washed with brine, dried ($Na_2SO_4$) and concentrated. The residue was purified by column chromatography on silica gel (PE:EtOAc, 10:1) to give the title product (800 mg, 4.53 mmol) as a yellow oil. LCMS (Method A): 3.02 min; m/z: 177.1 $[M+H]^+$.

Step 2: 5-(tetrahydro-2H-pyran-4-yl)pyridin-2-amine

A mixture of 5-(3,6-dihydro-2H-pyran-4-yl)pyridin-2-amine (3 g, 17 mmol) and 10% Pd/C (361 mg, 3.40 mmol) in MeOH (20 mL) was stirred at RT for 6 h under $H_2$. The solvent was removed under reduced pressure and the residue was purified by column chromatography on silica gel (PE:EtOAc, 5:1 to 1:5) to give the title product (2.0 g, 11.2 mmol) as a yellow oil. LCMS (Method A): 0.72 min, m/z: 179.2 $[M+H]^+$.

Intermediate F4: 5-cyclopropylpyrazin-2-amine

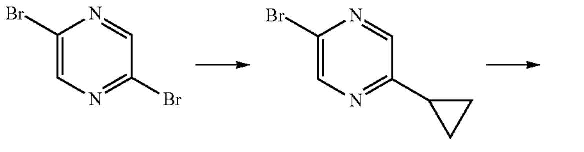

-continued

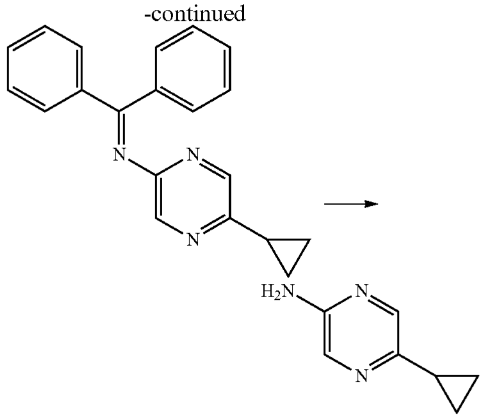

Step 1: 2-bromo-5-cyclopropylpyrazine

To a solution of 2,5-dibromopyrazine (4.0 g, 16.8 mmol) in degassed 1,4-dioxane (80 mL) was added a solution of $K_2CO_3$ (5.80 g, 42.0 mmol) in water (20 mL), followed by cyclopropylboronic acid (1.72 g, 20.1 mmol), $Pd(OAc)_2$ (188 mg, 840 μmol) and $Pd(dppf)Cl_2$ (685 mg, 840 μmol). The reaction mixture was stirred at 120° C. for 16 h before being filtered through Celite. The filtrate was diluted with EtOAc (200 mL) and the organics were separated, washed with water (100 mL) and brine (100 mL), dried ($Na_2SO_4$) and concentrated under reduced pressure. The residue was purified by column chromatography on silica gel (PE:EA, 100:1) to afford the title product (1.6 g, 43%) as a yellow solid. LCMS (Method A): 3.83 min, m/z: 200.9 $[M+H]^+$.

Step 2: N-(5-cyclopropylpyrazin-2-yl)-1,1-diphenylmethanimine

A mixture of 2-bromo-5-cyclopropylpyrazine (700 mg, 3.51 mmol), $Pd_2(dba)_3$ (160 mg, 175 μmol), Xantphos (203 mg, 351 μmol), $Cs_2CO_3$ (2.28 g, 7.02 mmol) and diphenylmethanimine (699 mg, 3.86 mmol) in degassed 1,4-dioxane (5 mL) was stirred overnight at 100° C. under $N_2$. The mixture was poured into water (10 mL) and the organics were extracted with EtOAc (50 mL×2). The combined organics were dried ($Na_2SO_4$) and concentrated under reduced pressure. The residue was purified by column chromatography on silica gel (PE:EtOAc, 5:1) to give the title product (1.3 g, 62%) as a yellow solid. LCMS (Method A): 4.27 min, m/z 300.2 $[M+H]^+$.

Step 3: 5-cyclopropylpyrazin-2-amine

To a solution of N-(5-cyclopropylpyrazin-2-yl)-1,1-diphenylmethanimine (1.3 g, 4.34 mmol) in MeOH (40 mL) was added aq. HCl (2 M, 10 mL), and the mixture was stirred at 30° C. overnight. Most of the MeOH was removed under reduced pressure and the remaining mixture was adjusted to pH=8 with sat. aq. $Na_2CO_3$. The aqueous mixture was extracted with EtOAc (50 mL×2) and the combined organics were washed with water and brine, dried ($Na_2SO_4$) and concentrated under reduced pressure. The residue was purified by column chromatography on silica gel (PE:EtOAc; 1:1) to give the title product (100 mg, 17%) as a brown solid. LCMS (Method A): 4.45 min, m/z: 136.0 $[M+H]^+$.

Intermediate G1: 5-methyl-2-nitro-4H,5H,6H,7H,8H-pyrazolo[1,5-a][1,4]diazepine

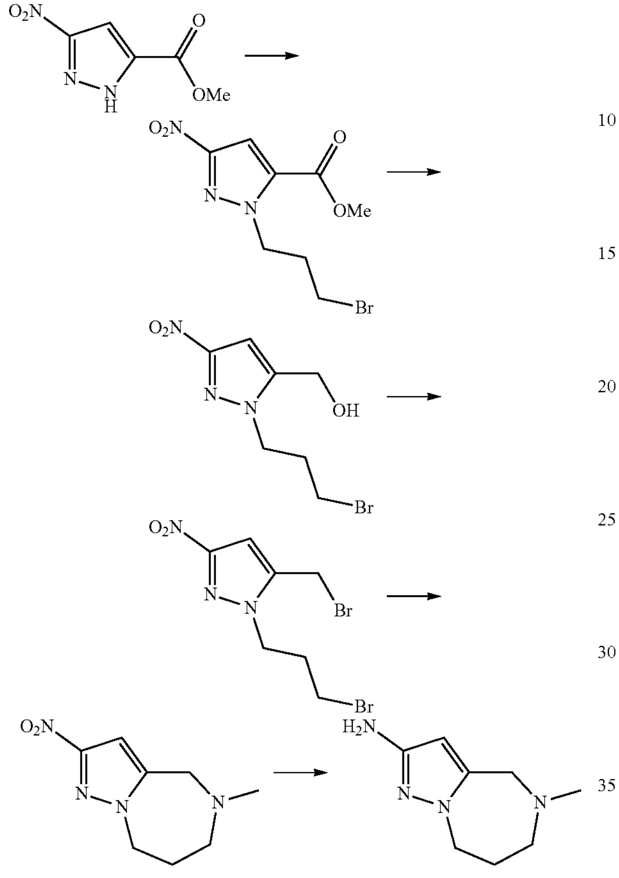

Step 1: methyl 1-(3-bromopropyl)-3-nitro-1H-pyrazole-5-carboxylate

To a solution of methyl 3-nitro-1H-pyrazole-5-carboxylate (1.0 g, 5.84 mmol) in acetone (30 mL) were added $K_2CO_3$ (4.02 g, 29.1 mmol) and 1,3-dibromopropane (2.10 mL, 17.5 mmol), and the reaction was then heated at reflux for 2 h. The mixture was then cooled to 0° C., filtered and concentrated. The residue was purified by flash chromatography (EtOAc:n-Hep 0-50%) to give the title compound (1.22 g, 72%) as a colourless oil. LCMS (Method D): 1.90 min, m/z 291.8/293.8 $[M+H]^+$.

Step 2: [1-(3-bromopropyl)-3-nitro-1H-pyrazol-5-yl]methanol

To a 0° C. solution of methyl 1-(3-bromopropyl)-3-nitro-1H-pyrazole-5-carboxylate (1.22 g, 4.17 mmol) in THF (40 mL) was added $LiBH_4$ (2.08 mL, 4.17 mmol) in portions. The reaction was stirred at 0° C. for 4 h, then quenched with sat. $NH_4Cl$ (20 mL) and extracted with EtOAc (3×30 mL). The combined organics were dried ($MgSO_4$) and concentrated to give the title compound (882 mg, 80%) as a colourless oil. LCMS (Method D): 1.17 min, m/z 263.8/265.8 $[M+H]^+$.

Step 3: 5-(bromomethyl)-1-(3-bromopropyl)-3-nitro-1H-pyrazole

To a suspension of [1-(3-bromopropyl)-3-nitro-1H-pyrazol-5-yl]methanol (880 mg, 3.33 mmol) in $CHCl_3$ (30 mL) was added $PBr_3$ (468 µL, 4.99 mmol) and the reaction was heated at reflux for 2 h. Once cooled, the mixture was basified to pH 9 with sat. $NaHCO_3$. The mixture was extracted with $CHCl_3$ (3×25 mL), and the combined organics were washed with water (25 mL), dried ($MgSO_4$) and concentrated to give the title compound (1.09 g, Quant.) as a white solid. LCMS (Method D): 1.98 min, m/z 327.8 $[M+H]^+$.

Step 4: 5-methyl-2-nitro-4H,5H,6H,7H,8H-pyrazolo[1,5-a][1,4]diazepine

To a solution of 5-(bromomethyl)-1-(3-bromopropyl)-3-nitro-1H-pyrazole (1.09 g, 3.33 mmol) in THF (33.3 mL) was added $MeNH_2$ (2.0 M in THF, 9.95 mL, 19.9 mmol) and the reaction was stirred at RT overnight. The mixture was concentrated and the residue was diluted with sat. $NaHCO_3$ (15 mL). The aqueous mixture was extracted with DCM (2×20 mL), and the combined organics were washed with water (15 mL) and brine (10 mL), dried ($MgSO_4$) and concentrated. The residue was purified by flash chromatography (0-20% MeOH:DCM) to give the title compound (468 mg, 72%) as a yellow oil. LCMS (Method D): 0.14 min, m/z 197.0 $[M+H]^+$.

Step 5: 5-methyl-4H,5H,6H,7H,8H-pyrazolo[1,5-a][1,4]diazepin-2-amine

A mixture of 5-methyl-2-nitro-4H,5H,6H,7H,8H-pyrazolo[1,5-a][1,4]diazepine (465 mg, 2.36 mmol) and 10% Pd/C (251 mg, 236 µmol) in MeOH (11.7 mL) was stirred under $H_2$ overnight. The reaction was filtered over Celite and concentrated to give the title compound (387 mg, 99%) as a yellow oil. LCMS (Method D): rt 0.10 min, m/z 167.0 $[M+H]^+$.

Compound 131

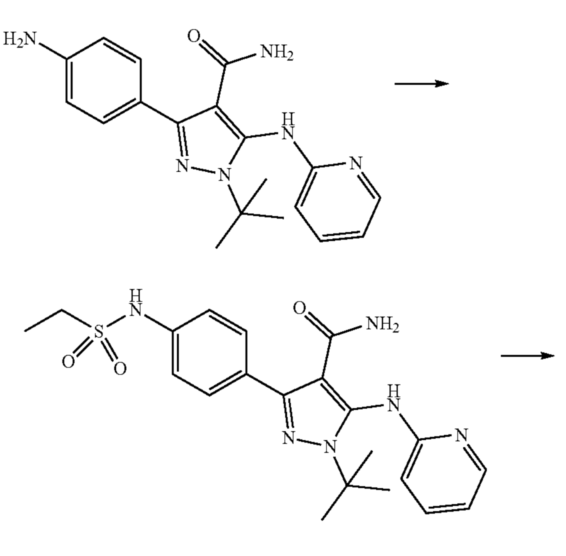

-continued

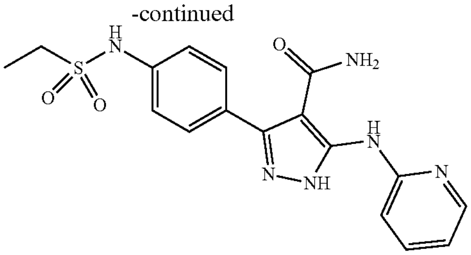

Step 1: 1-(tert-butyl)-3-(4-(ethylsulfonamido)phenyl)-5-(pyridin-2-ylamino)-1H-pyrazole-4-carboxamide A mixture of 3-(4-aminophenyl)-1-(tert-butyl)-5-(pyridin-2-ylamino)-1H-pyrazole-4-carboxamide (Intermediate A, 200 mg, 0.57 mmol), $EtSO_2Cl$ (88 mg, 0.69 mmol) and pyridine (90 mg, 1.14 mmol) in $CHCl_3$ (5 mL) was stirred at RT for 16 h. The mixture was diluted with $H_2O$ (5 mL) and then extracted with DCM (3x30 mL). The combined organic layers were dried ($Na_2SO_4$), concentrated under reduced pressure and the crude residue was purified by prep-TLC (DCM:MeOH, 10:1) to afford the title product (100 mg, 40%) as a yellow solid. LCMS (Method A): 2.12 min; m/z: 443.2 $[M+H]^+$.

Step 2: 3-(4-(ethylsulfonamido)phenyl)-5-(pyridin-2-ylamino)-1H-pyrazole-4-carboxamide (compound 131)

A solution of 1-(tert-butyl)-3-(4-(ethylsulfonamido)phenyl)-5-(pyridin-2-ylamino)-1H-pyrazole-4-carboxamide (50 mg, 0.11 mmol) in TFA (4 mL) was stirred at 60° C. for 2 h. The mixture was concentrated under reduced pressure, basified with $NH_4OH$ (1 mL) and extracted with DCM (3x5 mL). The combined organic layers were dried ($Na_2SO_4$), concentrated under reduced pressure and the crude residue was purified by prep-TLC (DCM:MeOH:$NH_4OH$, 10:1:0.1) to afford the title product (40 mg, 94%) as a yellow solid. LCMS (Method A): 0.29 min; m/z: 387.1 $[M+H]^+$. $^1H$ NMR (400 MHz, DMSO-$d_6$): 12.83 (s, 1H), 10.26 (br s, 1H), 9.48 (s, 1H), 8.17 (d, J=2.4 Hz, 1H), 7.99 (d, J=8.0 Hz, 1H), 7.80-7.60 (m, 1H), 7.56 (d, J=8.0 Hz, 2H), 7.13-7.12 (m, 3H), 6.85-6.84 (m, 1H), 6.05 (br s, 1H), 3.17 (q, J=7.2 Hz, 2H), 1.23 (t, J=7.2 Hz, 3H).

The following compounds (Table 5) were similarly prepared from the appropriate sulfonyl chloride and Intermediate A1 according to the method described for the synthesis of 3-(4-(ethylsulfonamido)phenyl)-5-(pyridin-2-ylamino)-1H-pyrazole-4-carboxamide.

TABLE 5

| Compound No | Name | Structure | LCMS data | $^1H$ NMR data | SM |
|---|---|---|---|---|---|
| 135 | 5-(pyridin-2-ylamino)-3-(4-(((4-(trifluoromethoxy)phenyl)methyl)sulfonamido)phenyl)-1H-pyrazole-4-carboxamide | 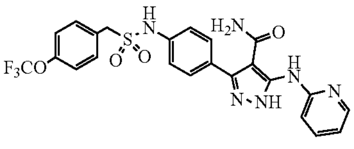 [SMILES: NC(=O)c1c(-c2ccc(NS(=O)(=O)Cc3ccc(OC(F)(F)F)cc3)cc2)n[nH]c1Nc1ccccn1] | LCMS (Method A: 2.37 min; m/z: 533.2 [M + H]$^+$. | $^1H$ NMR (400 MHz, MeOD-$d_4$): 8.31-8.30 (m, 1H), 7.76 (t, J = 6.4 Hz, 1H), 7.59 (d, J = 6.8 Hz, 2H), 7.45-7.43 (m, 3H), 7.37 (d, J = 8.8 Hz, 2H), 7.29 (d, J = 8.4 Hz, 2H), 7.00 (t, J = 6.8 Hz, 1H), 4.56 (s, 2H). | (4-(trifluoromethoxy)phenyl) methanesulfonyl chloride |
| 136 | 3-(4-(phenylmethyl-sulfonamido)phenyl)-5-(pyridin-2-ylamino)-1H-pyrazole-4-carboxamide | 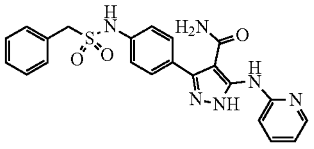 [SMILES: NC(=O)c1c(-c2ccc(NS(=O)(=O)Cc3ccccc3)cc2)n[nH]c1Nc1ccccn1] | LCMS (Method A): 1.95 min; m/z: 449.1 [M + H]$^+$. | $^1H$ NMR (400 MHz, DMSO-$d_6$): 12.80 (s, 1H), 10.17 (s, 1H), 9.54 (s, 1H), 8.18 (d, J = 2.8 Hz, 1H), 8.00 (d, J = 8.2 Hz, 1H), 7.73-7.68 (m, 1H), 7.53 (d, J = 8.8 Hz, 1H), 7.37-7.28 (m, 9H), 6.85 (s, 1H), 5.98 (br s, 1H), 4.57 (s, 2H). | phenylmethane-sulfonyl chloride |
| 132 | 5-(pyridin-2-ylamino)-3-(4-((p-tolylmethyl)sulfonamido)phenyl)-1H-pyrazole-4-carboxamide | 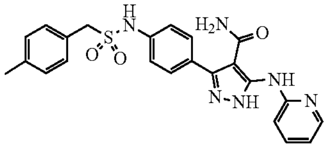 [SMILES: Cc1ccc(CS(=O)(=O)Nc2ccc(-c3n[nH]c(Nc4ccccn4)c3C(N)=O)cc2)cc1] | LCMS (Method A): 2.22 min; m/z: 463.1 [M + H]$^+$. | $^1H$ NMR (400 MHz, DMSO-$d_6$): 13.7 (br s, 1H), 10.0-9.98 (m, 1H), 9.67(br s, 1H), 8.99 (d, 1H, J = 7.2 Hz), 8.36-8.21 (m, 2H), 7.85-7.71 (m, 1H), 7.55 (d, J = 8.4 Hz, 1H), 7.33-7.29 (m, 3H), 7.18-7.16 (m, 5H), 7.03-6.89 (m, 1H), 4.49 (d, J = 5.2 Hz, 2H), 2.30 (s, 3H). | P-tolylmethanesulfonyl chloride |

TABLE 5-continued

| Compound No | Name | Structure | LCMS data | $^1$H NMR data | SM |
|---|---|---|---|---|---|
| 129 | 3-(4-(((3-chlorophenyl) methyl) sulfonamido) phenyl)-5-(pyridin-2-ylamino)-1H-pyrazole-4-carboxamide | 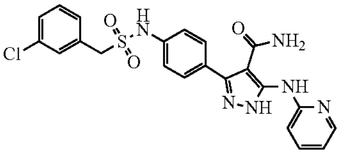 [SMILES: NC(=O)c1c(-c2ccc(NS(=O)(=O)Cc3cccc(Cl)c3)cc2)n[nH]c1Nc1ccccn1] | LCMS (Method A): 2.21 min; m/z: 483.0 [M + H]$^+$. | $^1$H NMR (400 MHz, DMSO-$d_6$): 12.55(br s, 1H), 9.71 (s, 1H), 8.30-8.20 (m, 1H), 8.03 (s, 1H), 7.70 (t, J = 7.6 Hz, 1H), 7.32-7.27 (m, 4H), 7.20-7.17 (m, 4H), 6.98 (d, J = 8.4 Hz, 2H), 6.83 (t, J = 6.4 Hz, 1H), 5.73 (s, 1H), 3.98 (s, 2H). | (3-chlorophenyl) methanesulfonyl chloride |
| 134 | 3-(4-((cyclobutylmethyl) sulfonamido)phenyl-5-(pyridin-2-ylamino)-1H-pyrazole-4-carboxamide | 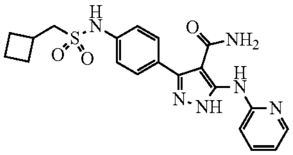 [SMILES: NC(=O)c1c(-c2ccc(NS(=O)(=O)CC3CCC3)cc2)n[nH]c1Nc1ccccn1] | LCMS (Method A: 2.54 min; m/z: 426.9 [M + H]$^+$. | $^1$H NMR (400 MHz, MeOD-$d_4$): 8.28 (br s, 1H), 7.71-7.36 (m, 6H), 6.95 (t, J = 6.0 Hz, 1H), 3.30 (s, 2H), 2.85-2.81 (m, 1H), 2.18-2.16 (m, 2H), 1.95-1.62 (m, 4H). | cyclobutylmethane sulfonyl chioride |
| 133 | 3-(4-(phenylsulfonamido) phenyl)-5-(pyridin-2-ylamino)-1H-pyrazole-4-carboxamide | 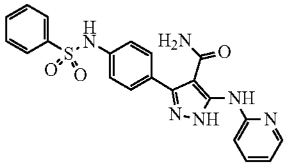 [SMILES: NC(=O)c1c(-c2ccc(NS(=O)(=O)c3ccccc3)cc2)n[nH]c1Nc1ccccn1] | LCMS (Method A): 1.98 min; m/z: 434.9 [M + H]$^+$. | $^1$H NMR (400 MHz, DMSO-$d_6$): 12.83 (br s, 1H), 9.53 (br s, 1H), 8.18 (d, J = 4.4 Hz, 1H), 7.85-7.80 (m, 3H),7.68 (t, J = 6.8 Hz, 1H), 7.60-7.45 (m, 4H), 7.42 (d, J = 8.4 Hz, 2H), 7.23-7.10 (m, 3H), 6.84 (t, J = 6.0 Hz, 1H), 5.87 (s, 1H). | benzenesulfonyl chloride |
| 130 | 3-(4-((2-phenylethyl) sulfonamido) phenyl)-5-(pyridin-2-ylamino)-1H-pyrazole-4-carboxamide | 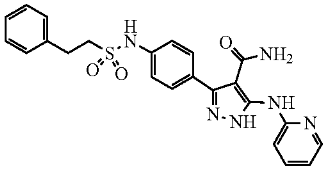 [SMILES: NC(=O)c1c(-c2ccc(NS(=O)(=O)CCc3ccccc3)cc2)n[nH]c1Nc1ccccn1] | LCMS (Method A): 2.61 min; m/z: 463.1 [M + H]$^+$. | $^1$H NMR (400 MHz, DMSO-$d_6$): 12.77 (br s, 1H), 10.18 (br s, 1H), 9.50 (s, 1H), 8.18 (s, 1H), 7.98 (s, 1H), 7.50 (t, J = 6.8 Hz, 1H), 7.55 (d, J = 8.4 Hz, 2H), 7.37-7.20 (m, 8H), 6.85 (br s, 1H), 6.00 (br s, 1H), 3.46 (t, J = 8.0 Hz, 2H), 3.03 (t, J = 6.8 Hz, 2H). | 2-phenylethanesulfonyl chloride |
| 48 | 3-(4-((difluoro-methyl) sulfonamido) phenyl)-5-(pyridin-2-ylamino)-1H-pyrazole-4-carboxamide | 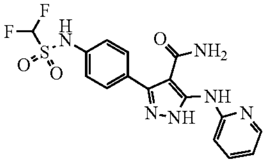 [SMILES: NC(=O)c1c(-c2ccc(NS(=O)(=O)C(F)F)cc2)n[nH]c1Nc1ccccn1] | LCMS (Method A): 2.70 min; m/z: 409.0 [M + H]$^+$. | $^1$H NMR (400 MHz, DMSO-$d_6$): 12.81 (s, 1H), 9.47 (s, 1H), 8.18 (s, 1H), 7.97 (s, 1H), 7.72-7.68 (m, 1H), 7.53 (d, J = 8.0 Hz, 2H), 7.33 (d, J = 8.4 Hz, 2H), 7.21-6.95 (m, 1H), 6.85 (br s, 1H). | difluoromethane-sulfonyl chloride |
| 268 | 5-[(pyridin-2-yl)amino]-3-[4-(2,2,2-trifluoroethane-sulfonamido) phenyl]-1H-pyrazole-4-carboxamide | 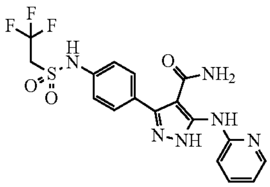 [SMILES: NC(=O)c1c(-c2ccc(NS(=O)(=O)CC(F)(F)F)cc2)n[nH]c1Nc1ccccn1] | LCMS (Method D): 3.29 min; m/z: 440.9 [M + H]$^+$. | $^1$H NMR (400 MHz, DMSO-$d_6$): 12.80 (s, 1H), 10.72 (s, 1H), 9.51 (s, 1H), 8.17 (s, 1H), 7.98 (d, J = 8.0 Hz, 1H), 7.70 (t, J = 7.2 Hz, 1H), 7.57 (d, J = 8.4 Hz, 2H), 7.36 (d, J = 7.6 Hz, 2H), 6.85 (s, 1H), 6.02 (s, 1H), 4.61 (t, J = 9.6 Hz, 2H). | 2,2,2-trifluoroethanesulfonyl chloride |

Compound 81

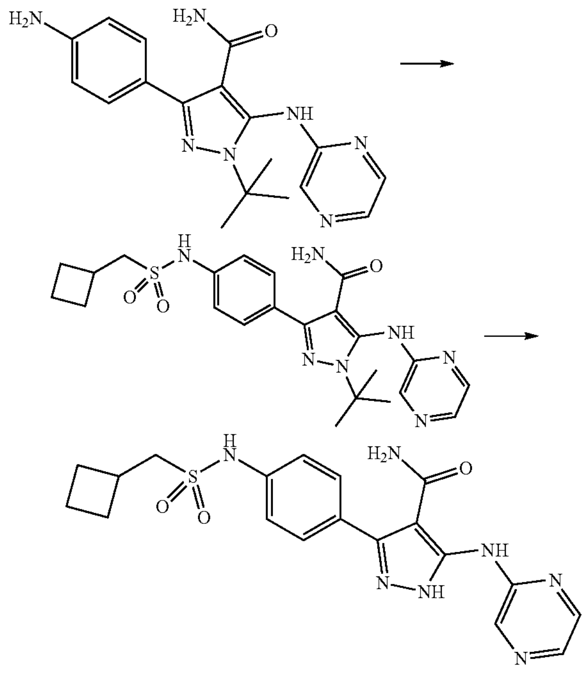

Step 1: 1-(tert-butyl)-3-(4-((cyclobutylmethyl)sulfonamido)phenyl)-5-(pyrazin-2-ylamino)-1H-pyrazole-4-carboxamide A mixture of 3-(4-aminophenyl)-1-(tert-butyl)-5-(pyrazin-2-ylamino)-1H-pyrazole-4-carboxamide (Intermediate A3, 300 mg, 853 μmol), cyclobutylmethanesulfonyl chloride (286 mg, 1.7 mmol) and pyridine (202 mg, 2.56 mmol) in $CHCl_3$ (10 mL) was stirred at RT for 16 h. The reaction mixture was concentrated under reduced pressure and the crude residue was purified by prep-TLC (DCM: MeOH, 12:1) to afford the title product (120 mg, 29%) as a white solid. LCMS (Method A): 3.53 min; m/z: 484.2 $[M+H]^+$.

Step 2: 3-(4-((cyclobutylmethyl)sulfonamido)phenyl)-5-(pyrazin-2-ylamino)-1H-pyrazole-4-carboxamide (compound 81)

A mixture of 1-(tert-butyl)-3-(4-((cyclobutylmethyl)sulfonamido)phenyl)-5-(pyrazin-2-ylamino)-1H-pyrazole-4-carboxamide (60 mg, 124 μmol) in DCM (4 mL) and TFA (4 mL) was stirred at 30° C. for 16 h. The mixture was concentrated under reduced pressure and the residue was neutralized to pH 7-8 with $NH_4OH$, then extracted with DCM (3×40 mL). The combined organic layers were dried ($Na_2SO_4$), concentrated under reduced pressure and the crude residue was purified by prep-TLC (DCM:MeOH, 12:1) to afford the title product (20 mg, 37%) as a white solid. LCMS (Method A): 3.20 min; m/z: 428.1 $[M+H]^+$. $^1H$ NMR (400 MHz, MeOD-$d_4$): 12.94 (s, 1H), 10.10 (s, 1H), 9.64 (s, 1H), 9.26 (s, 1H), 8.22 (t, J=4.0 Hz, 1H), 8.11 (d, J=8.4 Hz, 1H), 7.55 (d, J=8.4 Hz, 2H), 7.32 (d, J=8.0 Hz, 2H), 3.30 (s, 2H), 2.08 (s, 1H), 1.83-1.73 (m, 4H).

The following compounds (Table 6) were similarly prepared from the appropriate sulfonyl chloride and Intermediate A3 according to the method described for the synthesis of 3-(4-((cyclobutylmethyl)sulfonamido)phenyl)-5-(pyrazin-2-ylamino)-1H-pyrazole-4-carboxamide.

TABLE 6

| Compound No | Name | Structure | LCMS data | $^1H$ NMR data | SM |
|---|---|---|---|---|---|
| 72 | 5-(pyrazin-2-ylamino)-3-(4-((3,3,3-trifluoropropyl) sufonamido) phenyl)-1H-pyrazole-4-carboxamide | 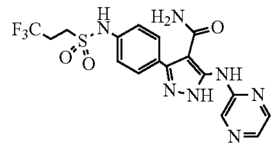 [SMILES: NC(=O)c1c(-c2ccc(NS(=O)(=O)CCC(F)(F)F)cc2)n[nH]c1Nc1cnccn1] | LCMS (Method A): 3.21 min; m/z: 456.1 $[M + H]^+$. | $^1H$ NMR (400 MHz, DMSO-$d_6$): 12.97 (s, 1H), 10.35 (s, 1H), 9.63 (s, 1H), 9.26 (s, 1H), 8.25-8.21 (m, 1H), 8.11 (d, J = 2.4 Hz, 1H), 7.59 (d, J = 8.8 Hz, 2H), 7.38 (d, J = 8 Hz, 2H), 6.15 (s, 1H), 3.45 (t, J = 7.6 Hz, 3H), 2.85-2.72 (m, J = 8.8 Hz, 3H). | 3,3,3-trifluoro-propane-1-sulfonyl chloride |
| 73 | 5-(pyrazin-2-ylamino)-3-(4-((3-(trifluoro-methyl) phenyl) sulfonamido) phenyl)-1H-pyrazole-4-carboxamide | 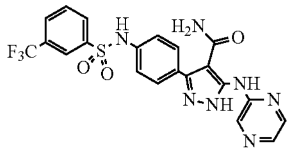 [SMILES: NC(=O)c1c(-c2ccc(NS(=O)(=O)c3cccc(C(F)(F)F)c3)cc2)n[nH]c1Nc1cnccn1] | LCMS (Method A): 3.56 min; m/z: 504.1 $[M + H]^+$. | $^1H$ NMR (400 MHz, DMSO-$d_6$): 12.91 (br s, 1H), 9.59 (br s, 1H), 9.21 (br s, 1H), 8.20-7.80 (m, 7H), 7.44 (d, J = 8.0 Hz, 2H), 7.22 (d, J = 8.0 Hz, 2H). | 4-methyl-3-(trifluoromethyl) benzenesulfonyl chloride |
| 74 | 3-(4-(cyclohexane-sulfonamido) phenyl)-5-(pyrazin-2-ylamino)-1H-pyrazole-4-carboxamide | 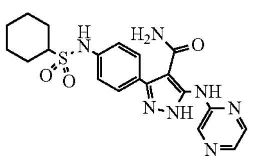 [SMILES: NC(=O)c1c(-c2ccc(NS(=O)(=O)C3CCCCC3)cc2)n[nH]c1Nc1cnccn1] | LCMS (Method A): 3.30 min; m/z: 442.1 $[M + H]^+$. | $^1H$ NMR (400 MHz, DMSO-$d_6$): 12.96 (br s, 1H), 10.09 (br s, 1H), 9.63 (br s, 1H), 9.26 (s, 1H), 8.22 (d, J = 2.4 Hz, 1H), 8.11 (d, J = 2.4 Hz, 1H), 7.56 (d, J = 8.8 Hz, 2H), 7.37 (d, J = 8.8 Hz, 2H), 3.10-3.05 (m, 1H), 2.07-2.04 (m, 2H), 1.79-1.76 (m, 2H), 1.61 -1.27 (m, 4H), 1.33-1.11 (m, 2H). | cyclohexane-sulfonyl chloride |

TABLE 6-continued

| Compound No | Name | Structure | LCMS data | $^1$H NMR data | SM |
|---|---|---|---|---|---|
| 82 | 3-(4-((4-methoxyphenyl) sulfonamido) phenyl)-5-(pyrazin-2-ylamino)-1H-pyrazole-4-carboxamide | 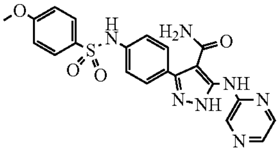 [SMILES: COc1ccc(S(=O)(=O)Nc2ccc(-c3n[nH]c(Nc4cnccn4)c3C(N)=O)cc2)cc1] | LCMS (Method A): 3.24 min; m/z: 466.1 $[M + H]^+$. | $^1$H NMR (400 MHz, DMSO-$d_6$): 12.89 (s, 1H), 10.57 (s, 1H), 9.58 (s, 1H), 9.23 (s, 1H), 8.22 (s, 1H), 8.11 (d, J = 2.8 Hz, 1H), 7.78 (d, J = 8.8 Hz, 2H), 7.48 (d, J = 8.8 Hz, 2H), 7.24 (d, J = 8.4 Hz, 2H), 7.10 (d, J = 8.8 Hz, 2H), 5.98 (s, 1H), 3.81 (s, 3H). | 4-methoxy-benzenesulfonyl chloride |
| 78 | 5-(pyrazin-2-ylamino)-3-(4-((4-(trifluoro-methoxy) phenyl) sulfonamido) phenyl)-1H-pyrazole-4-carboxamide | 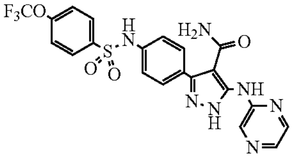 [SMILES: NC(=O)c1c(-c2ccc(NS(=O)(=O)c3ccc(OC(F)(F)F)cc3)cc2)n[nH]c1Nc1cnccn1] | LCMS (Method A): 3.63 min; m/z: 520.1 $[M + H]^+$. | $^1$H NMR (400 MHz, DMSO-$d_6$): 12.90 (s, 1H), 10.83 (s, 1H), 9.54 (s, 1H), 9.20 (s, 1H), 8.20 (s, 1H), 7.97 (d, J = 8.4 Hz, 2H), 7.60 (s, 2H), 7.50 (s, 2H), 7.26 (s, 3H). | 4-(trifluoromethoxy) benzenesulfonyl chloride |
| 79 | 5-(pyrazin-2-ylamino)-3-(4-((4-(trifluoromethyl) phenyl) sulfonamido) phenyl)-1H-pyrazole-4-carboxamide | 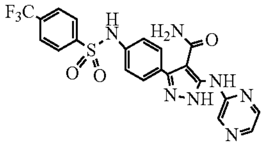 [SMILES: NC(=O)c1c(-c2ccc(NS(=O)(=O)c3ccc(C(F)(F)F)cc3)cc2)n[nH]c1Nc1cnccn1] | LCMS (Method A): 2.42 min; m/z: 503.6 $[M + H]^+$. | $^1$H NMR (400 MHz, DMSO-$d_6$): 12.92 (s, 1H), 11.03 (s, 1H), 9.56 (s, 1H), 8.20 (s, 1H), 8.07 (s, J = 11.6 Hz, 4H), 7.50 (s, 2H), 7.27 (s, 2H), 8.20 (s, 1H). | 4-(trifluoromethyl) benzenesulfonyl chloride |
| 70 | 3-(4-(((4-chlorophenyl) methyl) sulfonamido) phenyl)-5-(pyrazin-2-ylamino)-1H-pyrazole-4-carboxamide | 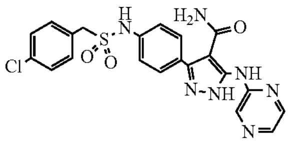 [SMILES: NC(=O)c1c(-c2ccc(NS(=O)(=O)Cc3ccc(Cl)cc3)cc2)n[nH]c1Nc1cnccn1] | LCMS (Method A): 3.48 min; m/z: 484.1 $[M + H]^+$. | $^1$H NMR (400 MHz, DMSO-de): 12.97 (s, 1H), 10.16 (s, 1H), 9.65 (s, 1H), 9.27 (s, 1H), 8.23 (s, 1H), 8.16 (s, 1H), 7.51 (br s, 4H), 7.32 (s, 4H), 4.59 (s, 2H). | (4-chlorophenyl) methanesulfonyl chloride |
| 83 | 5-[(pyrazin-2-yl)amino]-3-(4-{[3-(trifluoromethyl) phenyl] methane-sulfonamido} phenyl)-1H-pyrazole-4-carboxamide | 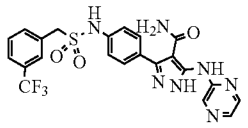 [SMILES: NC(=O)c1c(-c2ccc(NS(=O)(=O)Cc3cccc(C(F)(F)F)c3)cc2)n[nH]c1Nc1cnccn1] | LCMS (Method A): 3.55 min; m/z: 518.1 $[M + H]^+$. | $^1$H NMR (400 MHz, DMSO-$d_6$): 12.98 (s, 1H), 10.25 (s, 1H), 9.66 (s, 1H), 9.27 (s, 1H), 8.22 (s, 1H), 8.11 (s, 1H), 7.73-7.68 (m, 2H), 7.59-7.54 (m, 5H), 7.32 (d, J = 7.2 Hz, 2H), 6.07 (s, 1H), 4.74 (s, 3H). | (3-(trifluoromethyl) phenyl) methanesulfonyl chloride |
| 76 | 5-[(pyrazin-2-yl)amino]-3-(4-{[4-(trifluoromethyl) phenyl] methane-sulfonamido} phenyl)-1H-pyrazole-4-carboxamide | 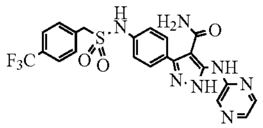 [SMILES: NC(=O)c1c(-c2ccc(NS(=O)(=O)Cc3ccc(C(F)(F)F)cc3)cc2)n[nH]c1Nc1cnccn1] | LCMS (Method A): 3.69 min; m/z: 518.1 $[M + H]^+$ | $^1$H NMR (400 MHz, DMSO-$d_6$): 13.00 (s, 1H), 10.24 (s, 1H), 9.65 (s, 1H), 9.27 (s, 1H), 8.23-8.22 (m, 1H), 8.11 (d, J = 2.4 Hz, 1H), 7.76 (d, J = 8.4 Hz, 2H), 7.58-7.52 (m, 5H), 7.35 (d, J = 8.4 Hz, 3H), 4.71 (s, 2H). | (4-(trifluoromethyl) phenyl) methanesulfonyl chloride |
| 80 | 5-(pyrazin-2-ylamino)-3-(4-(((4-(trifluoro-methoxy) phenyl)methyl) sulfonamido) phenyl)-1H-pyrazole-4-carboxamide | 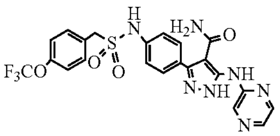 [SMILES: NC(=O)c1c(-c2ccc(NS(=O)(=O)Cc3ccc(OC(F)(F)F)cc3)cc2)n[nH]c1Nc1cnccn1] | LCMS (Method A): 3.63 min; m/z: 534.1 $[M + H]^+$. | $^1$H NMR (400 MHz, DMSO-$d_6$): 13.00 (s, 1H), 10.24 (s, 1H), 9.65 (s, 1H), 9.27 (s, 1H), 8.23-8.22 (m, 1H), 8.11 (d, 1H), 7.56 (d, 2H), 7.46-7.33 (m, 6H), 6.14 (br s, 1H), 4.64 (s, 2H), 2.08 (s, 1H). | (4-(trifluoromethoxy) phenyl) methanesulfonyl chloride |

TABLE 6-continued

| Compound No | Name | Structure | LCMS data | $^1H$ NMR data | SM |
|---|---|---|---|---|---|
| 77 | 3-(4-((phenylmethyl) sulfonamido) phenyl)-5-(pyrazin-2-ylamino)-1H-pyrazole-4-carboxamide | 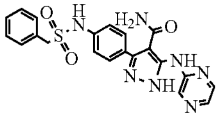 [SMILES: NC(=O)c1c(-c2ccc(NS(=O)(=O)Cc3ccccc3)cc2)n[nH]c1Nc1cnccn1] | LCMS (Method A): 3.22 min; m/z: 450.1 $[M + H]^+$. | $^1H$ NMR (400 MHz, $CDCl_3$): 12.98 (s, 1H), 10.17 (s, 1H), 9.67 (s, 1H), 9.28 (s, 1H), 8.23 (s, 1H), 8.12 (d, J = 2.4 Hz, 1H), 7.54 (d, J = 8.4 Hz, 2H), 7.36 (t, J = 3.6 Hz, 3H), 7.32 (s, 2H), 7.31 (d, J = 2.8 Hz, 2H), 4.56 (s, 2H), 0.87-0.84 (m, 1H). | phenylmethane sulfonyl chloride |
| 71 | 3-(4-((1-methylethyl) sulfonamido) phenyl)-5-(pyrazin-2-ylamino)-1H-pyrazole-4-carboxamide | 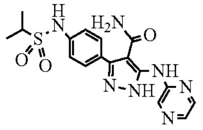 [SMILES: CC(C)S(=O)(=O)Nc1ccc(-c2n[nH]c(Nc3cnccn3)c2C(N)=O)cc1] | LCMS (Method A): 2.92 min; m/z: 402.1 $[M + H]^+$. | $^1H$ NMR (400 MHz, DMSO-$d_6$): 12.93 (s, 1H), 10.09 (s, 1H), 9.63 (s, 1H), 9.26 (s, 1H), 8.22 (s, 1H), 8.11 (s, 1H), 7.55 (t, J = 8.4 Hz, 2H), 7.33 (t, J = 8.4 Hz, 2H), 1.28 (t, J = 6.8 Hz, 6H). | propane-sulfonyl chloride |
| 108 | 3-(4-(ethyl-sulfonamido) phenyl)-5-(pyrazin-2-ylamino)-1H-pyrazole-4-carboxamide | 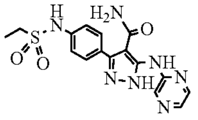 [SMILES: CCS(=O)(=O)Nc1ccc(-c2n[nH]c(Nc3cnccn3)c2C(N)=O)cc1] | LCMS (Method A): 2.78 min; m/z: 388.1 $[M + H]^+$. | $^1H$ NMR (400 MHz, MeOD-$d_4$): 12.94 (s, 1H), 10.13 (s, 1H), 9.64 (s, 1H), 9.26 (s, 1H), 8.22 (t, J = 4.0 Hz, 1H), 8.11 (d, J = 8.4 Hz, 1H), 7.55 (d, J = 8.4 Hz, 2H), 7.32 (d, J = 8.0 Hz, 2H), 3.30 (s, 2H), 2.08 (s, 1H), 1.83-1.73 (m, 4H). | ethanesulfonyl chloride |
| 68 | 3-(4-(cyclopropane-sulfonamido) phenyl)-5-(pyrazin-2-ylamino)-1H-pyrazole-4-carboxamide | 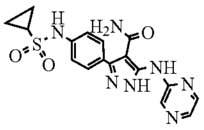 | LCMS (Method A): 3.25 min; m/z: 400.1 $[M + H]^+$. | $^1H$ NMR (400 MHz, $CDCl_3$): 12.99 (s, 1H), 10.11 (s, 1H), 9.60 (s, 1H), 9.26 (s, 1H), 8.22 (s, 1H), 8.12 (s, 1H), 7.45 (dd, J = 7.6, 7.2 Hz, 5H), 6.04 (s, 1H), 2.72 (s, 1H), 0.99 (s, 4H). | cyclopropane-sulfonyl chloride |
| 97 | 3-(4-(propyl-sulfonamido) phenyl)-5-(pyrazin-2-ylamino)-1H-pyrazole-4-carboxamide | 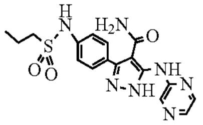 | LCMS (Method A): 4.06 min; m/z: 401.8 $[M + H]^+$. | $^1H$ NMR (400 MHz, DMSO-$d_6$): 12.95 (s, 1H), 10.13 (s, 1H), 9.63 (s, 1H), 9.25 (s, 1H), 8.22 (s, 1H), 8.11 (d, J = 1.6 Hz, 1H), 7.57 (d, J = 8.0 Hz, 2H), 7.35 (d, J = 7.2 Hz, 2H), 3.15 (t, J = 5.6 Hz, 2H), 1.72 (q, J = 14.8 Hz, 2H), 0.45 (t, J = 14.8 Hz, 3H). | propane-1-sulfonyl chloride |
| 63 | 3-(4-((difluoromethyl) sulfonamido) phenyl)-5-(pyrazin-2-ylamino)-1H-pyrazole-4-carboxamide | 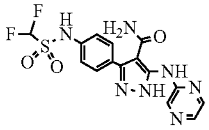 [SMILES: NC(=O)c1c(-c2ccc(NS(=O)(=O)C(F)F)cc2)n[nH]c1Nc1cnccn1] | LCMS (Method A): 3.05 min; m/z: 410.0 $[M + H]^+$. | $^1H$ NMR (400 MHz, DMSO-$d_6$): 12.99 (s, 1H), 11.24 (s, 1H), 9.57 (s, 1H), 9.23 (s, 1H), 8.21 (s, 1H), 8.11 (s, 1H), 7.59 (d, J = 9.4 Hz, 2H), 7.39-7.34 (m, 3H), 7.21-7.08 (m, 1H), 6.17 (s, 1H). | difluoro-methanesulfonyl chloride |
| 69 | 3-(4-((1,1-dimethylethyl) sulfonamido) phenyl)-5-(pyrazin-2-ylamino)-1H-pyrazole-4-carboxamide | 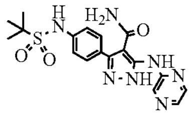 [SMILES: CC(C)(C)S(=O)(=O)Nc1ccc(-c2n[nH]c(Nc3cnccn3)c2C(N)=O)cc1] | LCMS (Method A): 3.15 min; m/z: 416.1 $[M + H]^+$. | $^1H$ NMR (400 MHz, MeOD-$d_4$): 12.96 (br s, 1H), 9.93 (br s, 1H), 9.65 (br s, 1H), 9.26 (s, 1H), 8.23 (s, 1H), 8.11 (s, 1H), 7.51 (d, J = 8.4 Hz, 2H), 7.41 (d, J = 8.0 Hz, 2H), 1.33 (s, 9H). Two active protons not observed. | 2-methylpropane-2-sulfonyl chloride |
| 23 | 3-(4-((3,3-difluoropropyl) sulfonamido) phenyl)-5-(pyrazin-2-ylamino)-1H-pyrazole-4-carboxamide | 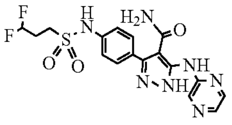 [SMILES: NC(=O)c1c(-c2ccc(NS(=O)(=O)CCC(F)F)cc2)n[nH]c1Nc1cnccn1] | LCMS (Method A): 3.06 min; m/z: 438.1 $[M + H]^+$. | $^1H$ NMR (400 MHz, DMSO-$d_6$): 13.03 (s, 1H), 9.62 (s, 1H), 9.25 (s, 1H), 8.23 (br s, 1H), 8.11 (t, J = 2.8 Hz, 1H), 7.59 (t, J = 8.4 Hz, 2H), 7.37 (t, J = 8.4 Hz, 2H), 6.21 (m, 1H), 2.30 (br s, 2H). | 3,3-difluoropropane-1-sulfonyl chloride |

Compound 60

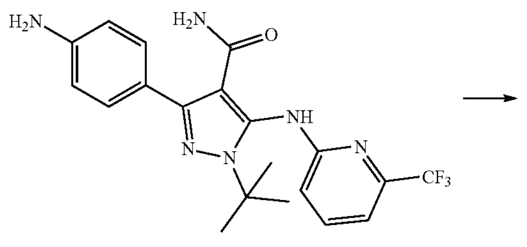

Intermediate A2

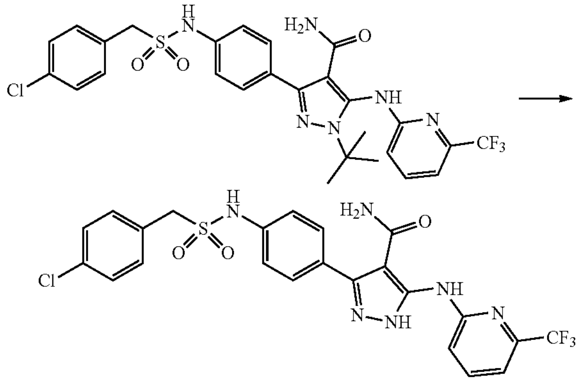

Step 1: 1-tert-butyl-3-{4-[(4-chlorophenyl)methanesulfonamido]phenyl}-5-{[6-(trifluoromethyl)pyridin-2-yl]amino}-1H-pyrazole-4-carboxamide To a solution of 3-(4-aminophenyl)-1-tert-butyl-5-{[6-(trifluoromethyl)pyridin-2-yl]amino}-1H-pyrazole-4-carboxamide (Intermediate A2, 124 mg, 296 μmol) in pyridine (5 mL) at 0° C. was added (4-chlorophenyl)methanesulfonyl chloride (115 mg, 510 μmol) and the resulting mixture was stirred at RT for 16 h. The reaction mixture was concentrated under reduced pressure and the crude residue was purified by prep-TLC (DCM:MeOH, 15:1) to afford the title product (70 mg, 39%) as a yellow solid. LCMS (Method A): 4.32 min; m/z: 607.1 $[M+H]^+$.

Step 2: 3-(4-(((4-chlorophenyl)methyl)sulfonamido)phenyl)-5-((6-(trifluoromethyl)pyridin-2-yl)amino)-1H-pyrazole-4-carboxamide (compound 60)

A solution of 1-tert-butyl-3-{4-[(4-chlorophenyl)methanesulfonamido]phenyl}-5-{[6-(trifluoromethyl)pyridin-2-yl]amino}-1H-pyrazole-4-carboxamide (70 mg, 115 μmol) in DCM (4 mL) and TFA (4 mL) was stirred at 35° C. for 2 h. The reaction mixture was concentrated under reduced pressure and then neutralized to pH 7-8 with sat. aq. $Na_2CO_3$. The mixture was diluted with $H_2O$ (10 mL), and the precipitate was collected via filtration and purified by prep-TLC (DCM:MeOH, 15:1) to afford the title product (18 mg, 28%) as a yellow solid.

The following compounds (Table 7) were similarly prepared from the appropriate sulfonyl chloride starting material (SM) and Intermediate A2 according to the method described for the synthesis of 3-(4-(((4-chlorophenyl)methyl)sulfonamido)phenyl)-5-((6-(trifluoromethyl)pyridin-2-yl)amino)-1H-pyrazole-4-carboxamide.

TABLE 7

| Compound No | Name | Structure | LCMS data | $^1H$ NMR data | SM |
|---|---|---|---|---|---|
| 56 | 3-(4-((3,4-dichlorophenyl)methyl-sulfonamido)phenyl)-5-((6-(trifluoromethyl)pyridin-2-yl)amino)-1H-pyrazole-4-carboxamide | 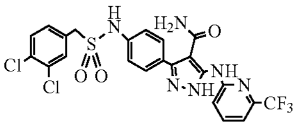 [SMILES: NC(=O)c1c(-c2ccc(NS(=O)(=O)Cc3ccc(Cl)c(Cl)c3)cc2)n[nH]c1Nc1cccc(C(F)(F)F)n1] | LCMS (Method A): 4.23 min; m/z: 585.0 $[M + H]^+$. | $^1H$ NMR (400 MHz, DMSO-$d_6$): 12.97 (s, 1H), 10.22 (s, 1H), 9.79 (s, 1H), 8.24 (d, J = 8.8 Hz, 1H), 7.99 (t, J = 8.0 Hz, 1H), 7.66 (d, J = 8.4 Hz, 1H), 7.60 (s, 1H), 7.57 (d, J = 2.8 Hz, 2H), 7.35-7.26 (m, 5H), 6.13 (br s, 1H), 4.65 (s, 2H). | (3,4-dichlorophenyl)methanesulfonyl chloride |
| 55 | 3-(4-(((4-fluorophenyl)methyl)sulfonamido)phenyl)-5-((6-(trifluoromethyl)pyridin-2-yl)amino)-1H-pyrazole-4-carboxamide | 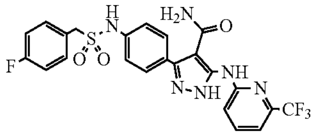 [SMILES: NC(=O)c1c(-c2ccc(NS(=O)(=O)Cc3ccc(F)cc3)cc2)n[nH]c1Nc1cccc(C(F)(F)F)n1] | LCMS (Method A): 4.03 min; m/z: 535.1 $[M + H]^+$. | $^1H$ NMR (400 MHz, DMSO-$d_6$): 12.96 (s, 1H), 10.16 (s, 1H), 9.79 (s, 1H), 8.23 (s, 1H), 7.98 (s, 1H), 7.33 (s, 5H), 7.21 (t, J = 8.4 Hz, 2H), 7.57 (s, 2H). Three active protons not observed. | (4-fluorophenyl)methanesulfonyl chloride |
| 59 | 3-(4-(((3-chlorophenyl)methyl)sulfonamido)phenyl)-5-((6-(trifluoromethyl)pyridin-2-yl)amino)-1H-pyrazole-4-carboxamide | 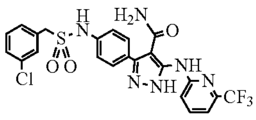 [SMILES: NC(=O)c1c(-c2ccc(NS(=O)(=O)Cc3cccc(Cl)c3)cc2)n[nH]c1Nc1cccc(C(F)(F)F)n1] | LCMS (Method A): 4.10 min; m/z: 551.2 $[M + H]^+$. | $^1H$ NMR (400 MHz, DMSO-$d_6$): 12.96 (s, 1H), 10.23 (s, 1H), 9.80 (s, 1H), 8.24 (d, J = 8.8 Hz, 1H), 7.56 (d, J = 8.4 Hz, 2H), 7.45-7.25 (m, 7H), 4.63 (s, 2H). Three active protons not observed. | (3-chlorophenyl)methanesulfonyl chloride |

TABLE 7-continued

| Compound No | Name | Structure | LCMS data | $^1$H NMR data | SM |
|---|---|---|---|---|---|
| 58 | 3-(4-(((2-chlorophenyl) methyl) sulfonamido) phenyl)-5-((6-(trifluoromethyl) pyridin-2-yl)amino)-1H-pyrazole-4-carboxamide | 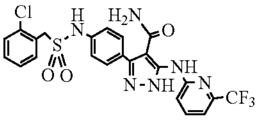 [SMILES: NC(=O)c1c(-c2ccc(NS(=O)(=O)Cc3ccccc3Cl)cc2)n[nH]c1Nc1cccc(C(F)(F)F)n1] | LCMS (Method A): 4.08 min; m/z: 551.2 $[M + H]^+$. | $^1$H NMR (400 MHz, DMSO-$d_6$): 12.73 (s, 1H), 9.92 (s, 1H), 8.29 (d, J = 7.6 Hz, 1H), 7.47 (q, J = 5.6 Hz, 1H), 7.38 (q, J = 5.6 Hz, 1H), 7.30-7.24 (m, 6H), 7.08 (d, J = 8.4 Hz, 1H), 4.28 (s, 2H). Four active protons not observed. | (2-chlorophenyl) methanesulfonyl chloride |
| 126 | 3-(4-(ethylsulfonamido) phenyl)-5-((6-(trifluoromethyl) pyridin-2-yl)amino)-1H-pyrazole-4-carboxamide | 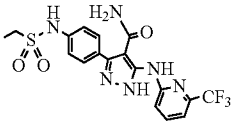 [SMILES: CCS(=O)(=O)Nc1ccc(-c2n[nH]c(Nc3cccc(C(F)(F)F)n3)c2C(N)=O)cc1] | LCMS (Method A): 2.53 min; m/z: 455.1 $[M + H]^+$. | $^1$H NMR (400 MHz, MeOD-$d_4$): 8.20-8.16 (m, 1H), 7.85-7.77 (m, 1H), 7.49-7.46 (m, 2H), 7.32-7.30 (m, 2H), 7.23-7.10 (m, 1H), 3.10 (q, J = 7.2 Hz, 2H), 1.25 (t, J = 7.6 Hz, 3H). | Ethylsulfonyl chloride |
| 57 | 3-(4-((p-tolylmethyl) sulfonamido) phenyl)-5-((6-(trifluoromethyl) pyridin-2-yl)amino)-1H-pyrazole-4-carboxamide | 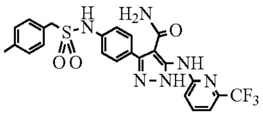 [SMILES: Cc1ccc(CS(=O)(=O)Nc2ccc(-c3n[nH]c(Nc4cccc(C(F)(F)F)n4)c3C(N)=O)cc2)cc1] | LCMS (Method A): 4.12 min; m/z: 531.1 $[M + H]^+$. | $^1$H NMR (400 MHz, DMSO-$d_6$): 12.96 (s, 1H), 10.12 (br s, 1H), 9.80 (s, 1H), 8.23 (d, J = 7.6 Hz, 1H), 7.98 (t, J = 7.6 Hz, 1H), 7.55 (d, J = 8.4 Hz, 2H), 7.34-7.30 (m, 3H), 7.17 (s, 4H), 4.50 (s, 2H), 2.29 (s, 3H). | P-tolylmethane-sulfonyl chloride |
| 54 | 3-(4-((1-methylethyl) sulfonamido) phenyl)-5-((6-(trifluoromethyl) pyridin-2-yl)amino)-1H-pyrazole-4-carboxamide | 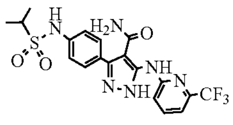 [SMILES: CC(C)S(=O)(=O)Nc1ccc(-c2n[nH]c(Nc3cccc(C(F)(F)F)n3)c2C(N)=O)cc1] | LCMS (Method A): 4.78 min; m/z: 469.1 $[M + H]^+$. | $^1$H NMR (400 MHz, DMSO-$d_6$): 12.93 (s, 1H), 10.09 (s, 1H), 9.76 (s, 1H), 8.22 (d, J = 8.0 Hz, 1H), 9.78 (t, J = 7.6 Hz, 1H), 7.55 (d, J = 8.4 Hz, 2H), 7.37 (d, J = 8.4 Hz, 2H), 7.30 (d, J = 7.2 Hz, 1H),6.11 (s, 1H), 1.28 (d, J = 6.8 Hz, 6H). | propane-2-sulfonyl chloride |
| 53 | 3-(4-((difluoromethyl) sulfonamido) phenyl)-5-((6-(trifluoromethyl) pyridin-2-yl)amino)-1H-pyrazole-4-carboxamide | 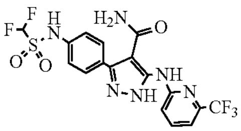 [SMILES: NC(=O)c1c(-c2ccc(NS(=O)(=O)C(F)F)cc2)n[nH]c1Nc1cccc(C(F)(F)F)n1] | LCMS (Method A): 3.85 min; m/z: 477.0 $[M + H]^+$. | $^1$H NMR (400 MHz, DMSO-$d_6$): 12.98 (s, 1H), 11.29 (s, 1H), 9.72 (s, 1H), 8.21 (d, J = 8.8 Hz 1H), 7.98 (t, J = 8 Hz 1H), 7.58 (d, J = 8.4 Hz, 2H), 7.38 (d, J = 8.4 Hz2H), 7.31-7.05 (m, 2H). | difluoro-methanesulfonyl chloride |
| 50 | 3-(4-((2-methoxyethyl) sulfonamido) phenyl)-5-((6-(trifluoromethyl) pyridin-2-yl)amino)-1H-pyrazole-4-carboxamide | 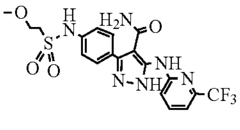 [SMILES: COCCS(=O)(=O)Nc1ccc(-c2n[nH]c(Nc3cccc(C(F)(F)F)n3)c2C(N)=O)cc1] | LCMS (Method A): 3.59 min; m/z: 485.1 $[M + H]^+$. | $^1$H NMR (400 MHz, DMSO-$d_6$): 12.96 (s, 1H), 10.14 (s, 1H), 9.77 (s, 1H), 8.22 (d, J = 8.4 Hz, 1H), 7.98 (t, J = 8.0 Hz, 1H), 7.56 (d, J = 8.4 Hz, 2H), 7.36-7.30 (m, 4H), 6.10 (s, 1H), 3.67 (t, J = 6.0 Hz, 2H), 3.44 (t, J = 6.0 Hz, 2H), 3.19 (s, 3H). | 2-methoxyethane-1-sulfonyl chloride |
| 51 | 3-(4-((2-(dimethylamino) ethyl) sulfonamido) phenyl)-5-((6-(trifluoromethyl) pyridin-2-yl)amino)-1H-pyrazole-4-carboxamide | 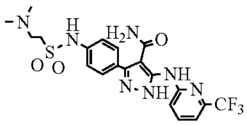 [SMILES: CN(C)CCS(=O)(=O)Nc1ccc(-c2n[nH]c(Nc3cccc(C(F)(F)F)n3)c2C(N)=O)cc1] | LCMS (Method A): 2.83 min; m/z: 498.1 $[M + H]^+$. | $^1$H NMR (400 MHz, DMSO-$d_6$): 12.78 (s, 1H), 9.86 (s, 1H), 8.24 (d, J = 7.2 Hz, 1H), 7.97 (t, J = 8.0 Hz, 1H), 7.36 (d, J = 8.4 Hz, 2H), 7.30 (d, J = 7.2 Hz, 1H), 7.13 (d, J = 8.4 Hz, 2H), 5.93 (s, 1H), 3.09-3.05 (m, 2H), 2.61-2.58 (m, 2H), 2.08 (s, 6H). | 2-chloroethane-1-sulfonyl chloride |

TABLE 7-continued

| Compound No | Name | Structure | LCMS data | $^1H$ NMR data | SM |
|---|---|---|---|---|---|
| 29 | 3-(4-((cyanomethyl) sulfonamido) phenyl)-5-((6-(trifluoromethyl) pyridin-2-yl)amino)-1H-pyrazole-4-carboxamide | 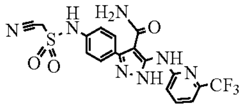 [SMILES: N#CCS(=O)(=O)Nc1ccc(-c2n[nH]c(Nc3cccc(C(F)(F)F)n3)c2C(N)=O)cc1] | LCMS (Method A): 3.59 min; m/z: 466.1 $[M + H]^+$. | $^1H$ NMR (400 MHz, DMSO-$d_6$): 13.12 (s, 1H), 11.06 (s, 1H), 9.97 (s, 1H), 8.52 (s, 1H), 8.07 (s, 1H), 7.61 (d, J = 8.8 Hz, 2H), 7.42-7.39 (m, 4H), 4.99 (s, 2H). | cyanomethane-sulfonyl chloride |
| 52 | 3-(4-(cyclopropane-sulfonamido) phenyl)-5-((6-(trifluoromethyl) pyridin-2-yl)amino)-1H-pyrazole-4-carboxamide | 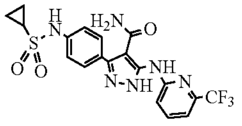 [SMILES: NC(=O)c1c(-c2ccc(NS(=O)(=O)C3CC3)cc2)n[nH]c1Nc1cccc(C(F)(F)F)n1] | LCMS (Method A): 3.68 min; m/z: 467.1 $[M + H]^+$. | $^1H$ NMR (400 MHz, DMSO-$d_6$): 12.96 (s, 1H), 10.10 (br s, 1H), 9.75 (s, 1H), 8.21 (s, 1H), 7.98 (t, J = 8.0 Hz, 1H), 7.58-7.56 (m, 2H), 7.39-7.30 (m, 4H), 6.10 (br s, 1H), 2.76-2.70 (m, 1H), 1.00-0.98 (m, 4H). | cyclopropane-sulfonyl chloride |
| 49 | 3-(4-((2,2-difluoroethyl) sulfonamido) phenyl)-5-((6-(trifluoromethyl) pyridin-2-yl)amino)-1H-pyrazole-4-carboxamide | 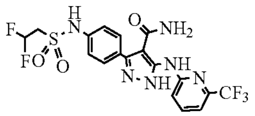 [SMILES: NC(=O)c1c(-c2ccc(NS(=O)(=O)CC(F)F)cc2)n[nH]c1Nc1cccc(C(F)(F)F)n1] | LCMS (Method A): 3.72 min; m/z: 491.1 $[M + H]^+$. | $^1H$ NMR (400 MHz, DMSO-$d_6$): 12.97 (s, 1H), 10.54 (s, 1H), 9.79 (s, 1H), 8.23 (d, J = 8.4 Hz, 1H), 7.99 (t, J = 8.0 Hz, 1H), 7.59 (d, J = 8.0 Hz, 2H), 7.37 (d, J = 8.4 Hz, 2H), 7.31 (d, J = 7.2 Hz, 1H) 6.41 (tt, J = 5.4 Hz, 4.4 Hz, 1H), 4.02 (dt, J = 14.8, 4.0 Hz, 2H). | 2,2-difluoroethane-1-sulfonyl chloride |
| 43 | 3-(4-((2,2,2-trifluoroethyl) sulfonamido) phenyl)-5-((6-(trifluoromethyl) pyridin-2-yl)amino)-1H-pyrazole-4-carboxamide | 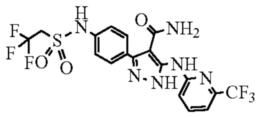 [SMILES: NC(=O)c1c(-c2ccc(NS(=O)(=O)CC(F)(F)F)cc2)n[nH]c1Nc1cccc(C(F)(F)F)n1] | LCMS (Method A): 3.86 min; m/z: 509.1 $[M + H]^+$. | $^1H$ NMR (400 MHz, DMSO-$d_6$): 12.72 (s, 1H), 9.92 (s, 1H), 8.30 (d, J = 8.4 Hz, 1H), 7.98 (d, J = 8.0 Hz, 1H), 7.29 (d, J = 7.2 Hz, 1H), 7.25 (d, J = 8.4 Hz, 2H), 7.02 (d, J = 8.4 Hz, 2H), 5.84 (s, 1H), 3.66 (q, J = 10.4 Hz, 2H). | 2,2,2-trifluoroethane-1-sulfonyl chloride |

Compound 119

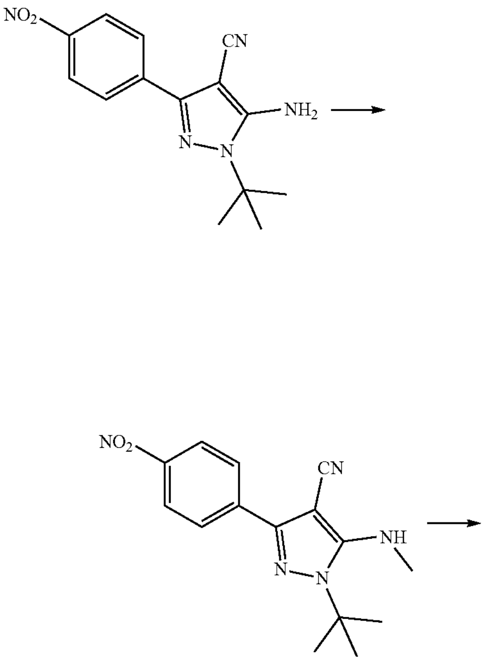

-continued

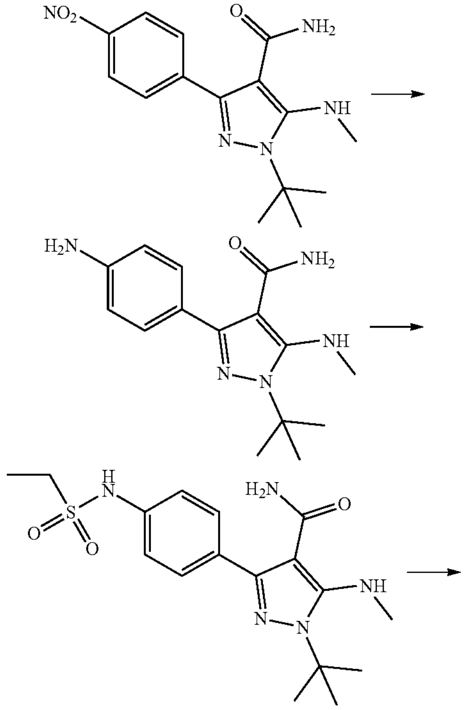

-continued

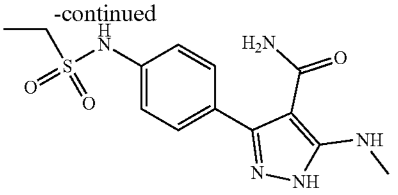

Step 1: 1-(tert-butyl)-5-(methylamino)-3-(4-nitrophenyl)-1H-pyrazole-4-carbonitrile A mixture of 5-amino-1-(tert-butyl)-3-(4-nitrophenyl)-1H-pyrazole-4-carbonitrile (300 mg, 1.05 mmol), paraformaldehyde (315 mg, 10.5 mmol), NaOMe (228 mg, 4.2 mmol), and MeOH (20 mL) was stirred at RT for 16 h. $NaBH_4$ (160 mg, 4.2 mmol) was added and the mixture was stirred for 2 h at RT. The mixture was concentrated under reduced pressure, diluted with $H_2O$ (20 mL) and extracted with EtOAc (3×30 mL). The combined organic layers were dried ($Na_2SO_4$) and then concentrated under reduced pressure to afford the crude product (300 mg, 76%) as a yellow solid. LCMS (Method B): 2.45 min; m/z: 300.0 $[M+H]^+$.

Step 2: 1-tert-butyl-5-(methylamino)-3-(4-nitrophenyl)-1H-pyrazole-4-carboxamide To a solution of 1-tert-butyl-5-(methylamino)-3-(4-nitrophenyl)-1H-pyrazole-4-carbonitrile (270 mg, 0.9 mmol) in DMSO (20 mL) and EtOH (20 mL) were added 30% aq. $H_2O_2$ (20 mL) and 5% aq. NaOH (1 mL). The mixture was stirred at RT for 20 min, and then heated to 80° C. for 16 h. The mixture was concentrated under reduced pressure and then diluted with $H_2O$ (20 mL). The precipitate was collected via filtration, washed with $H_2O$ and dried under reduced pressure to afford the title product (250 mg, 87%) as yellow solid. LCMS (Method B): 1.92 min; m/z: 318.0 $[M+H]^+$.

Step 3: 3-(4-aminophenyl)-1-tert-butyl-5-(methylamino)-1H-pyrazole-4-carboxamide A mixture of 1-tert-butyl-5-(methylamino)-3-(4-nitrophenyl)-1H-pyrazole-4-carboxamide (185 mg, 0.58 mmol), sat. aq. $NH_4Cl$ (5 mL), Zn dust (190 mg, 2.91 mmol) and MeOH (10 mL) was heated to 60° C. for 16 h. The reaction mixture was filtered, concentrated under reduced pressure, and then diluted with $H_2O$. The precipitate was collected by filtration and dried under reduced pressure to afford the title product (150 mg, 90%) as yellow solid. LCMS (Method B): 0.35 min; m/z: 288.1 $[M+H]^+$.

Step 4: 1-tert-butyl-3-(4-ethanesulfonamidophenyl)-5-(methylamino)-1H-pyrazole-4-carboxamide To a solution of 3-(4-aminophenyl)-1-tert-butyl-5-(methylamino)-1H-pyrazole-4-carboxamide (100 mg, 0.35 mmol) and pyridine (55.0 mg, 0.7 mmol) in $CHCl_3$ (5 mL) was added $EtSO_2Cl$ (53.6 mg, 0.42 mmol) and the mixture was stirred at RT overnight. The reaction mixture was concentrated and the crude residue was purified by prep-TLC (DCM:MeOH, 15:1) to afford the title product (35 mg, 27%) as yellow solid. LCMS (Method B): 0.87 min; m/z: 380.0 $[M+H]^+$.

Step 5: 3-(4-(ethylsulfonamido)phenyl)-5-(methylamino)-1H-pyrazole-4-carboxamide (compound 119)

A solution of 1-tert-butyl-3-(4-ethanesulfonamidophenyl)-5-(methylamino)-1H-pyrazole-4-carboxamide (35 mg, 0.09 mmol) in TFA (2 mL) and DCM (2 mL) was stirred at RT overnight. The reaction mixture was concentrated under reduced pressure and the crude residue was purified by prep-TLC (DCM:MeOH:$NH_4OH$, 10:1:0.1) to afford the title product (12 mg, 40%) as a grey solid. LCMS (Method B): 3.50 min; m/z: 324.0 $[M+H]^+$. $^1H$ NMR (400 MHz, MeOD-$d_4$): 7.51 (d, J=8.4 Hz, 2H), 7.38 (d, J=8.4 Hz, 2H), 3.19-3.14 (q, J=7.2 Hz, 2H), 2.94 (s, 3H), 1.34 (t, J=7.2 Hz, 3H).

Compound 64

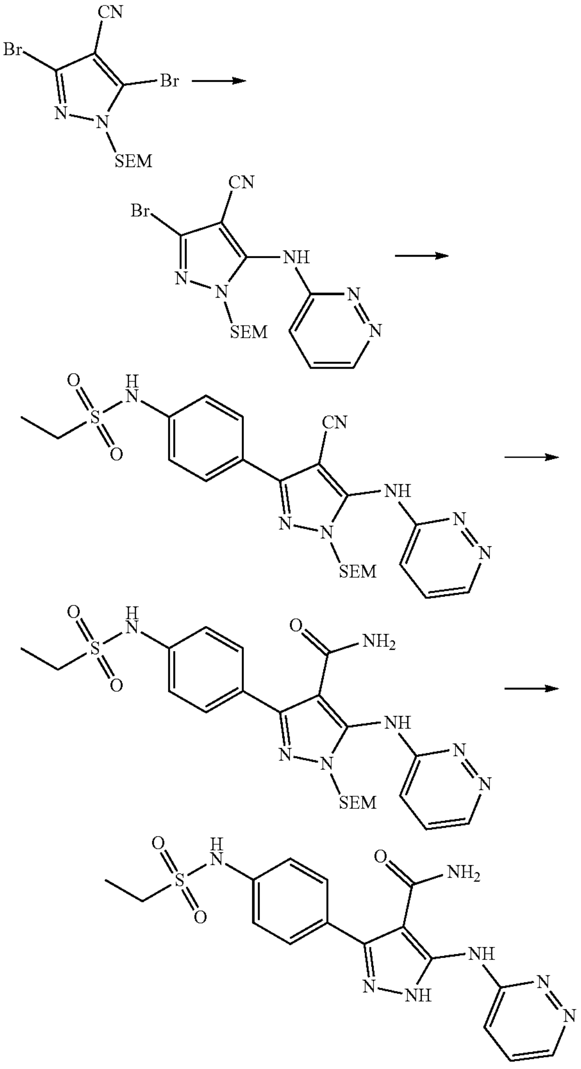

Step 1: 3-bromo-5-[(pyridazin-3-yl)amino]-1-{[2-(trimethylsilyl)ethoxy]methyl}-1H-pyrazole-4-carbonitrile A mixture of 3,5-dibromo-1-{[2-(trimethylsilyl)ethoxy]methyl}-1H-pyrazole-4-carbonitrile (2 g, 5.24 mmol), pyridazin-3-amine (498 mg, 5.24 mmol), $Pd_2(dba)_3$ (479 mg, 524 μmol), Xantphos (599 mg, 1.04 mmol) and $Cs_2CO_3$ (5.11 g, 15.7 mmol) in degassed 1-4-dioxane (150 mL) was stirred at 80° C. under $N_2$ for 16 h. The mixture was concentrated under reduced pressure and the crude residue was purified by silica gel column chromatography (PE:EtOAc, 1:1) to afford title product (380 mg, 18%) as a yellow solid. LCMS (Method A): 3.15 min; m/z: 395.0, 397.1 $[M+H]^+$.

Step 2: N-(4-{4-cyano-5-[(pyridazin-3-yl)amino]-1-{[2-(trimethylsilyl)ethoxy]methyl}-1H-pyrazol-3-yl}phenyl)ethane-1-sulfonamide A mixture of 3-bromo-5-[(pyridazin-3-yl)amino]-1-{[2-(trimethylsilyl) ethoxy]methyl}-1H-pyrazole-4-carbonitrile (300 mg, 758 μmol), N-[4-(4,4,5,5-tetramethyl-1,3,2-dioxaborolan-2-yl)phenyl]ethane-1-sulfonamide (235 mg, 758 μmol), $Pd(dppf)Cl_2$ (69.4 mg, 75.8 μmol), mmol) and $Na_2CO_3$ (3.79 mmol) in degassed 1,4-dioxane (10 mL) was stirred at 100° C. under microwave irradiation for 20 min. The mixture was concentrated under reduced pressure and the crude residue was purified by silica gel column chromatography (PE:EtOAc, 1:0 to 0:1) to afford title product (230 mg, 87%) as a yellow solid. LCMS (Method A): 3.31 min; m/z: 500.0 $[M+H]^+$.

Step 3: 3-(4-ethanesulfonamidophenyl)-5-[(pyridazin-3-yl)amino]-1-{[2-(trimethylsilyl) ethoxy]methyl}-1H-pyrazole-4-carboxamide To a solution of N-(4-{4-cyano-5-[(pyridazin-3-yl) amino]-1-{[2-(trimethylsilyl) ethoxy]methyl}-1H-pyrazol-3-yl}phenyl)ethane-1-sulfonamide (200 mg, 400 μmol) in 50% aq. 1,4-dioxane (20 mL), was added Ghaffar-Parkins catalyst (10 mg, 23.4 μmol) and the mixture was heated to 100° C. under $N_2$ for 16 h. The reaction mixture was then concentrated under reduced pressure and the crude residue was purified by prep-TLC (PE:EtOAc, 10:1) to afford the title product (80 mg, 38%) as a yellow solid. LCMS (Method A): 3.53 min; m/z: 518.2 $[M+H]^+$.

Step 4: 3-(4-ethanesulfonamidophenyl)-5-[(pyridazin-3-yl)amino]-1H-pyrazole-4-carboxamide (compound 64)

A mixture of 3-(4-ethanesulfonamidophenyl)-5-[(pyridazin-3-yl)amino]-1-{[2-(trimethylsilyl)ethoxy] methyl}-1H-pyrazole-4-carboxamide (80 mg, 154 μmol), 12.0 M HCl (0.5 mL) and THF (5 mL) was stirred at 30° C. under $N_2$ overnight. The mixture was concentrated under reduced pressure and the crude residue was purified by prep-TLC (DCM:MeOH:$NH_4OH$, 10:1:0.1) to afford the title product (10 mg, 25%) as a yellow solid. LCMS (Method A): 2.44 min; m/z: 388.0 $[M+H]^+$. $^1H$ NMR (400 MHz, MeOD-$d_4$): 7.67 (d, J=8.4 Hz, 2H), 7.44 (d, J=8.4 Hz, 2H), 7.41-7.37 (m, 1H), 7.30-7.26 (m, 1H), 3.35 (s, 1H), 3.20 (q, J=7.2 Hz, 2H), 1.35 (t, J=7.6 Hz, 3H).

Following the full synthesis of Compound 64, starting from 3,5-dibromo-1-{[2-(trimethylsilyl)ethoxy]methyl}-1H-pyrazole-4-carbonitrile with the mentioned intermediates used as described in step 1, the following compounds (Table 8) were prepared:

TABLE 8

| Compound No | Name | Structure | LCMS data | $^1H$ NMR data | Intermediates |
|---|---|---|---|---|---|
| 44 | 3-(4-(ethylsulfonamido)phenyl)-5-((6-(trifluoromethyl)pyrazin-2-yl)amino)-1H-pyrazole-4-carboxamide | 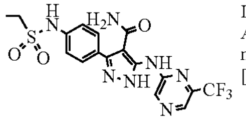 | LCMS (Method A): 3.44 min; m/z: 456.1 $[M + H]^+$. | $^1H$ NMR (400 MHz, MeOD-$d_4$): 13.17 (s, 1H), 9.99 (s, 1H), 9.42 (s, 1H), 8.54 (s, 1H), 7.58 (d, J = 7.6 Hz, 2H), 7.34 (d, J = 7.6 Hz, 2H), 3.18 (q, J = 6.4 Hz, 2H), 1.23 (t, J = 6.4 Hz, 3H). | 6-(trifluoromethyl) pyrazin-2-amine |
| 90 | 3-(4-(ethylsulfonamido)phenyl)-5-((5-methoxypyrazin-2-yl)amino)-1H-pyrazole-4-carboxamide | 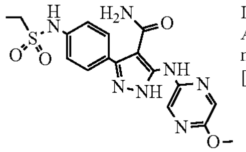 | LCMS (Method A): 3.13 min; m/z: 418.1 $[M + H]^+$. | $^1H$ NMR (400 MHz, MeOD-$d_4$): 12.81 (s, 1H), 10.13 (s, 1H), 9.40 (s, 1H), 8.85 (s, 1H), 7.99 (s, 1H), 7.55 (d, J = 7.6 Hz, 2H), 7.36 (d, J = 8.0 Hz, 2H), 3.87 (s, 3H), 3.19 (q, J = 6.8 Hz, 2H), 1.23 (t, J = 6.8 Hz, 3H). | 5-methoxypyrazin-2-amine |

Compound 89

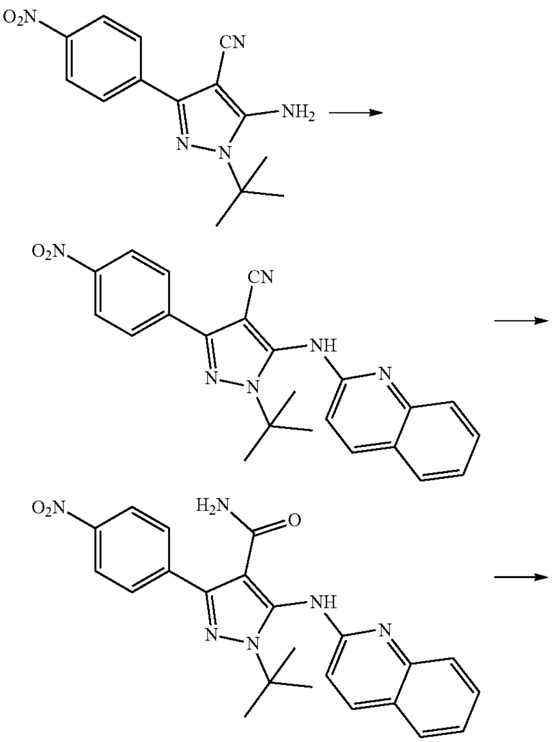

-continued

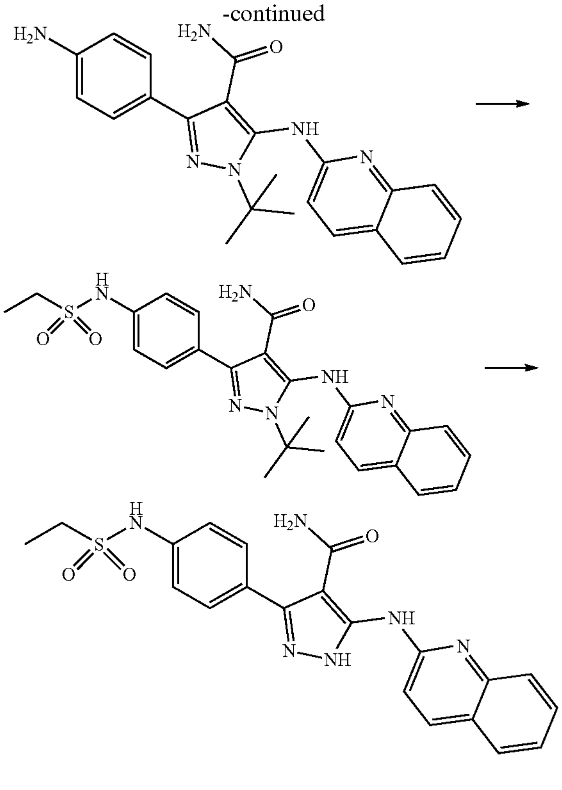

Step 1: 1-tert-butyl-3-(4-nitrophenyl)-5-[(quinolin-2-yl)amino]-1H-pyrazole-4-carbonitrile A mixture of 5-amino-1-tert-butyl-3-(4-nitrophenyl)-1H-pyrazole-4-carbonitrile (2 g, 7.00 mmol), 2-chloroquinoline (1.03 g, 6.30 mmol), $Pd_2(dba)_3$ (641 mg, 0.7 mmol), Xantphos (810 mg, 1.40 mmol) and $Cs_2CO_3$ (6.84 g, 21.0 mmol) in degassed 1,4-dioxane (5 mL) was stirred at 100° C. for 16 h. The mixture was concentrated under reduced pressure and the crude residue was purified by silica gel column chromatography (PE:EtOAc, 2:1) to afford the title product (520 mg, 18% yield) as a yellow oil. LCMS (Method A): 3.54 min; m/z: 413.0 $[M+H]^+$.

Step 2: 1-tert-butyl-3-(4-nitrophenyl)-5-[(quinolin-2-yl)amino]-1H-pyrazole-4-carboxamide To a mixture of 1-tert-butyl-3-(4-nitrophenyl)-5-[(quinolin-2-yl)amino]-1H-pyrazole-4-carbonitrile (520 mg, 1.26 mmol) in EtOH (20 mL) and DMSO (10 mL) were added 30% aq. $H_2O_2$ (10 mL) and 5% aq. NaOH (1.5 mL), and the reaction was stirred at 80° C. overnight. The mixture was concentrated under reduced pressure, then the residue was diluted with $H_2O$ (150 mL) and extracted with EtOAc (3×70 mL). The combined organic layers were dried ($Na_2SO_4$) and concentrated under reduced pressure to afford the title product (1 g, >100%) as a brown solid. LCMS (Method A): 3.80 min; m/z: 431.1 $[M+H]^+$.

Step 3: 3-(4-aminophenyl)-1-tert-butyl-5-[(quinolin-2-yl)amino]-1H-pyrazole-4-carboxamide A mixture of 1-tert-butyl-3-(4-nitrophenyl)-5-[(quinolin-2-yl)amino]-1H-pyrazole-4-carboxamide (500 mg, 1.16 mmol) and 10% Pd/C (50 mg) in MeOH (10 mL) was stirred at RT overnight under $H_2$. The suspension was filtered over Celite and the filtrate was concentrated under reduced pressure to afford the title product (460 mg, 99%) as a yellow solid. LCMS (Method A): 2.60 min; m/z: 401.2 $[M+H]^+$.

Step 4: 1-tert-butyl-3-(4-ethanesulfonamidophenyl)-5-[(quinolin-2-yl)amino]-1H-pyrazole-4-carboxamide A mixture of 3-(4-aminophenyl)-1-tert-butyl-5-[(quinolin-2-yl)amino]-1H-pyrazole-4-carboxamide (460 mg, 1.14 mmol), $EtSO_2Cl$ (174 mg, 1.36 mmol) and pyridine (270 mg, 3.42 mmol) in $CHCl_3$ (5 mL) was stirred at RT overnight. The mixture was concentrated and the crude residue was purified by prep-TLC (DCM:MeOH, 12:1) to afford the title product (120 mg, 21%) as a yellow solid. LCMS (Method A): 2.12 min; m/z: 493.1 $[M+H]^+$.

Step 5: 3-(4-(ethylsulfonamido)phenyl)-5-(quinolin-2-ylamino)-1H-pyrazole-4-carboxamide (compound 89)

A solution of 1-tert-butyl-3-(4-ethanesulfonamidophenyl)-5-[(quinolin-2-yl)amino]-1H-pyrazole-4-carboxamide (120 mg, 0.2436 mmol) in TFA (5 mL) and DCM (5 mL) was stirred at RT overnight. The mixture was concentrated, and the residue was basified to pH 9-10 with 1.0 M $NH_4Cl$. The precipitate was triturated with PE (3×5 mL), collected by filtration and then dried under reduced pressure to afford the title product (80 mg, 75%) as a yellow solid. LCMS (Method A): 2.80 min; m/z: 437.1 $[M+H]^+$. $^1H$ NMR (400 MHz, DMSO-$d_6$): 13.52 (br s, 1H), 12.93 (br s, 1H), 10.31 (br s, 1H), 10.04 (s, 1H), 8.23 (d, J=8.0 Hz, 1H), 7.81 (d, J=8.0 Hz, 1H), 7.33-7.66 (m, 8H), 6.17 (br s, 1H), 3.18 (t, J=7.2 Hz, 2H), 1.24 (t, J=7.2 Hz, 3H).

Compound 84

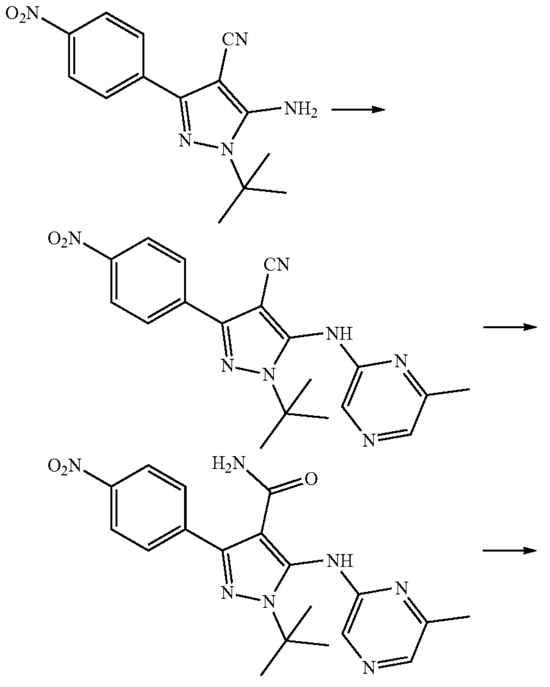

-continued

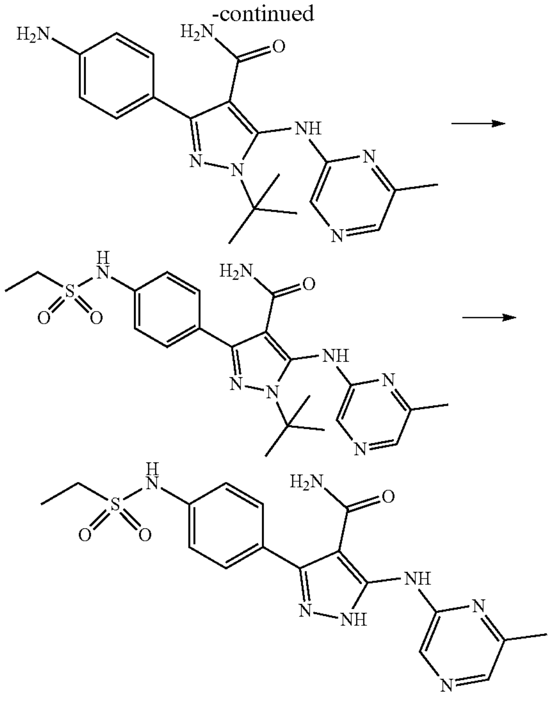

Step 1: 1-tert-butyl-5-[(6-methylpyrazin-2-yl)amino]-3-(4-nitrophenyl)-1H-pyrazole-4-carbonitrile A mixture of 5-amino-1-tert-butyl-3-(4-nitrophenyl)-1H-pyrazole-4-carbonitrile (2 g, 7.00 mmol), 2-chloro-6-methylpyrazine (899 mg, 7.00 mmol), $Pd_2(dba)_3$ (641 mg, 700 μmol), Xantphos (810 mg, 1.40 mmol) and $Cs_2CO_3$ (6.84 g, 21.0 mmol) in degassed 1,4-dioxane (60 mL) was stirred at 100° C. overnight. The reaction mixture was concentrated under reduced pressure and the crude residue was purified by silica gel column chromatography (PE:EtOAc, 2:1) to afford the title product (2.22 g, 84%) as a yellow solid. LCMS (Method A): 3.20 min; m/z: 378.2 $[M+H]^+$.

Step 2: 1-tert-butyl-5-[(6-methylpyrazin-2-yl)amino]-3-(4-nitrophenyl)-1H-pyrazole-4-carboxamide To a solution of 1-tert-butyl-5-[(6-methylpyrazin-2-yl)amino]-3-(4-nitrophenyl)-1H-pyrazole-4-carbonitrile (1 g, 2.64 mmol) in DMSO (15 mL) and EtOH (30 mL), were added 30% aq. $H_2O_2$ (15 mL) and 5% aq. NaOH (0.8 mL). The mixture was heated to 80° C. overnight, then concentrated under reduced pressure and diluted with $H_2O$ (50 mL). The precipitate was collected by filtration and dried under reduced pressure to afford the title product (750 mg, 72%) as a yellow solid. LCMS (Method A): 2.65 min; m/z: 396.2 $[M+H]^+$.

Step 3: 3-(4-aminophenyl)-1-tert-butyl-5-[(6-methylpyrazin-2-yl)amino]-1H-pyrazole-4-carboxamide A mixture of 1-tert-butyl-5-[(6-methylpyrazin-2-yl)amino]-3-(4-nitrophenyl)-1H-pyrazole-4-carboxamide (200 mg, 505 μmol) and 10% Pd/C (20 mg) in MeOH (10 mL) was stirred at RT overnight under $H_2$. The reaction mixture was filtered, concentrated under reduced pressure and the crude residue was purified by prep-TLC (DCM:MeOH, 10:1) to afford the title product (210 mg, >100%) as a yellow solid. LCMS (Method A): 1.02 min; m/z: 366.2 $[M+H]^+$.

Step 4: 1-tert-butyl-3-(4-ethanesulfonamidophenyl)-5-[(6-methylpyrazin-2-yl)amino]-1H-pyrazole-4-carboxamide A mixture of 3-(4-aminophenyl)-1-tert-butyl-5-[(6-methylpyrazin-2-yl)amino]-1H-pyrazole-4-carboxamide (200 mg, 547 μmol), $EtSO_2Cl$ (84.3 mg, 656 μmol) and pyridine (86.2 mg, 1.09 mmol) in $CHCl_3$ (7 mL) was stirred at RT overnight. The mixture was concentrated under reduced pressure and the crude residue was purified by silica gel column chromatography (DCM:MeOH, 10:1) to afford the title product (140 mg, 56%) as a yellow solid. LCMS (Method A): 1.49 min; m/z: 458.2 $[M+H]^+$.

Step 5: 3-(4-(ethylsulfonamido)phenyl)-5-((6-methylpyrazin-2-yl)amino)-1H-pyrazole carboxamide (compound 84)

A solution of 1-tert-butyl-3-(4-ethanesulfonamidophenyl)-5-[(6-methylpyrazin-2-yl)amino]-1H-pyrazole-4-carboxamide (130 mg, 284 μmol) in DCM (4 mL) and TFA (4 mL) was stirred at RT overnight. The reaction mixture was concentrated under reduced pressure and then neutralized to pH=7-8 with $NH_4OH$. The precipitate was collected by filtration, triturated with PE (2×5 mL) and dried under reduced pressure to afford the title product (80 mg, 70%) as a yellow solid. LCMS (Method A): 2.97 min; m/z: 402.1 $[M+H]^+$. $^1H$ NMR (400 MHz, DMSO-$d_6$): 12.91 (s, 1H), 10.13 (s, 1H), 9.55 (s, 1H), 9.09 (s, 1H), 8.01 (s, 1H), 7.56 (d, J=8.4 Hz, 2H), 7.35 (d, J=8.8 Hz, 2H), 6.09 (s, 1H), 3.19 (q, J=7.2 Hz, 2H), 2.38 (s, 3H), 1.23 (t, J=7.2 Hz, 3H).

Following the full synthesis of Compound 84, starting from 5-amino-1-tert-butyl-3-(4-nitrophenyl)-1H-pyrazole-4-carbonitrile with the mentioned starting materials used as described in step 1, the following compounds (Table 9) were prepared:

TABLE 9

| Compound No | Name | Structure | LCMS data | $^1H$ NMR data | Starting material |
|---|---|---|---|---|---|
| 101 | 3-(4-(ethylsulfonamido)phenyl)-5-((5-methylpyrazin-2-yl)amino)-1H-pyrazole-4-carboxamide | 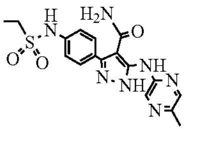 [SMILES: CCS(=O)(=O)Nc1ccc(-c2n[nH]c(Nc3cnc(C)cn3)c2C(N)=O)cc1] | LCMS (Method B): 3.50 min; m/z: 402.0 $[M + H]^+$. | $^1H$ NMR (400 MHz, DMSO-$d_6$): 9.54 (br s, 1H), 9.12 (br s, 1H), 8.11 (s, 1H), 7.53 (d, J = 8.4 Hz, 2H), 7.33 (d, J = 8.4 Hz, 2H), 3.18 (q, J = 6.0 Hz, 2H), 2.39 (s, 3H), 1.23 (t, J = 6.0 Hz, 3H). Five active protons not detected. | 2-chloro-5-methylpyrazine |

TABLE 9-continued

| Compound No | Name | Structure | LCMS data | $^1H$ NMR data | Starting material |
|---|---|---|---|---|---|
| 75 | 3-(4-ethane-sulfonamidophenyl)-5-{[5-(trifluoromethyl)pyrazin-2-yl]amino}-1H-pyrazole-4-carboxamide | 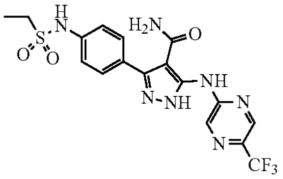 [SMILES: CCS(=O)(=O)Nc1ccc(-c2n[nH]c(Nc3cnc(C(F)(F)F)cn3)c2C(N)=O)cc1] | LCMS (Method A): 3.48 min; m/z: 456.1 [M + H]$^+$. | $^1H$ NMR (400 MHz, DMSO-$d_6$): 13.16 (s, 1H), 10.13 (s, 1H), 9.19 (s, 1H), 8.66 (s, 1H), 7.58 (d, J = 8.8 Hz, 2H), 7.34 (d, J = 8.0 Hz, 2H), 6.36 (s, 1H), 3.18 (q, J = 7.2 Hz, 2H), 1.23 (t, J = 7.2 Hz, 3H). | 2-chloro-5-(trifluoromethyl) pyrazine |
| 99 | 3-(4-(ethylsulfonamido) phenyl)-5-((6-methoxypyrazin-2-yl)amino)-1H-pyrazole-4-carboxamide | 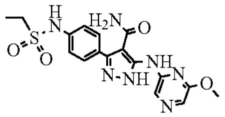 [SMILES: CCS(=O)(=O)Nc1ccc(-c2n[nH]c(Nc3cncc(OC)n3)c2C(N)=O)cc1] | LCMS (Method A): 1.63 min; m/z: 418.0 [M + H]$^+$. | $^1H$ NMR (400 MHz, DMSO-$d_6$): 12.95 (br s, 1H), 10.15 (br s, 1H), 9.47 (br s, 1H), 8.82 (s, 1H), 7.75 (s, 1H), 7.57 (d, J = 8.0 Hz, 2H), 7.36 (d, J = 8.0 Hz, 2H), 6.13 (br s, 1H), 3.88 (s, 3H), 3.20 (q, J = 6.0 Hz, 2H), 1.24 (t, J = 6.8 Hz, 3H). Two active protons not observed. | 2-chloro-6-methoxypyrazine |
| 96 | 5-((6-ethoxypyridin-2yl)amino)-3-(4-(ethylsulfonamido) phenyl)-1H-pyrazole-4-carboxamide | 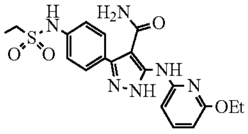 [SMILES: CCOc1cccc(Nc2[nH]nc(-c3ccc(NS(=O)(=O)CC)cc3)c2C(N)=O)n1] | LCMS (Method A): 3.53 min; m/z: 431.5 [M + H]$^+$. | $^1H$ NMR (400 MHz, DMSO-$d_6$): 12.74 (s, 1H), 10.21 (s, 1H), 9.33 (s, 1H), 7.59 (s, 1H), 7.51 (d, J = 8.4 Hz, 2H), 7.32 (d, J = 8.4 Hz, 2H), 6.24 (d, J = 8.0 Hz, 1H), 5.99 (S, 1H), 4.25 (q, J = 6.8 Hz, 2H), 3.14 (q, J = 6.8 Hz, 2H), 1.31 (t, J = 7.2 Hz, 3H), 1.22 (q, J = 7.2 Hz, 3H). | 2-chloro-6-ethoxypyridine |
| 92 | 5-((6-(difluoromethyl) pyridin-2-yl)amino)-3-(4-(ethylsulfonamido) phenyl)-1H-pyrazole-4-carboxamide | 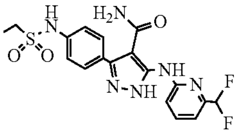 [SMILES: CCS(=O)(=O)Nc1ccc(-c2n[nH]c(Nc3cccc(C(F)F)n3)c2C(N)=O)cc1] | LCMS (Method A): 1.84 min; m/z: 437.8 [M + H]$^+$. | $^1H$ NMR (400 MHz, DMSO-$d_6$): 12.87 (s, 1H), 10.08 (s, 1H), 9.68 (s, 1H), 8.12 (d, J = 8.4 Hz, 1H), 7.90 (t, J = 7.6 Hz, 1H), 7.56 (d, J = 8.4 Hz, 2H), 7.35 (d, J = 7.6 Hz, 2H), 7.13 (d, J = 7.2 Hz, 1H), 6.96 (s, 1H), 6.83 (s, 1H), 6.69 (s, 1H), 3.18 (q, J = 6.8 Hz, 2H), 1.23 (d, J = 7.2 Hz, 3H). | Intermediate D1 |
| 94 | 3-(4-(ethylsulfonamido) phenyl)-5-((6-methylpyridin-2-yl)amino)-1H-pyrazole-4-carboxamide | 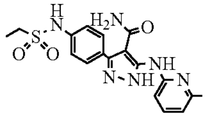 [SMILES: CCS(=O)(=O)Nc1ccc(-c2n[nH]c(Nc3cccc(C)n3)c2C(N)=O)cc1] | LCMS (Method A): 0.95 min; m/z: [M + H]$^+$. | $^1H$ NMR (400 MHz, $CDCl_3$): 12.73 (s, 1H), 10.09 (s, 1H), 9.40 (s, 1H), 7.79 (d, J = 8.0 Hz, 1H), 7.59 (d, J = 7.6 Hz, 1H), 7.54 (d, J = 8.4 Hz, 2H), 7.35 (d, J = 8.0 Hz, 2H), 6.70 (s, 1H), 5.98 (s, 1H), 3.18 (d, J = 7.2 Hz, 2H), 2.35 (s, 3H), 1.23 (t, J = 7.6 Hz, 3H). | 2-chloro-6-methylpyridine |
| 124 | 3-(4-(ethylsulfonamido) phenyl)-5-(phenylamino)-1H-pyrazole-4-carboxamide | 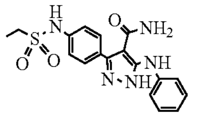 | LCMS (Method A): 1.02 min; m/z: 386.0 [M + H]$^+$. | $^1H$ NMR (400 MHz, MeOD-$d_4$): 7.57 (d, J = 8.8 Hz, 2H), 7.43 (m, 4H), 7.25 (t, J = 7.6 Hz, 2H), 6.87 (t, J = 7.6 Hz, 1H), 3.20 (q, J = 7.2 Hz, 2 H), 1.33 (t, J = 7.2 Hz, 3H). | bromophenyl |
| 123 | 3-(4-(ethylsulfonamido) phenyl)-5-((2-methoxypyrimidin-4-yl)amino)-1H-pyrazole-4-carboxamide | 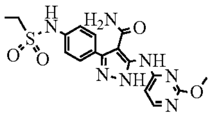 [SMILES: CCS(=O)(=O)Nc1ccc(-c2n[nH]c(Nc3ccnc(OC)n3)c2C(N)=O)cc1] | LCMS (Method A): 0.34 min; m/z: 418.0 [M + H]$^+$. | $^1H$ NMR (400 MHz, MeOD-$d_4$): 8.11(d, J = 4.8 Hz, 1H), 7.48 (m, 3H), 7.31 (d, J = 6.4 Hz, 2H), 4.48 (s, 3H), 3.11 (q, J = 7.6 Hz, 2H), 1.22 (t, J = 7.6 Hz, 3H). | 4-chloro-2-methoxypyrimidine |
| 125 | 3-(4-(ethylsulfonamido) phenyl)-5-((2-methylpyrimidin-4-yl)amino)-1H-pyrazole-4-carboxamide | 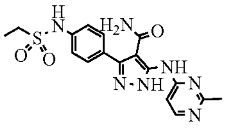 [SMILES: CCS(=O)(=O)Nc1ccc(-c2n[nH]c(Nc3ccnc(C)n3)c2C(N)=O)cc1] | LCMS (Method B): 0.32 min; m/z: 402.0 [M + H]$^+$. | $^1H$ NMR (400 MHz, MeOD-$d_4$): 8.41 (d, J = 5.6 Hz,1H), 8.02 (d, J = 4.2 Hz, 1H), 7.56 (d, J = 8.0 Hz, 2H), 7.43 (d, J = 7.6 Hz, 2H), 3.20 (q, J = 7.2 Hz, 2H), 2.42 (s, 3H), 1.35 (t, J = 7.2 Hz, 3H). | 4-chloro-2-methylpyrimidine |

TABLE 9-continued

| Compound No | Name | Structure | LCMS data | $^1$H NMR data | Starting material |
| --- | --- | --- | --- | --- | --- |
| 111 | 3-(4-(ethylsulfonamido) phenyl)-5-((5-fluoro-2-methylpyridin-4-yl)amino)-1H-pyrazole-4-carboxamide | 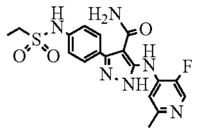 [SMILES: CCS(=O)(=O)Nc1ccc(-c2n[nH]c(Nc3cc(C)ncc3F)c2C(N)=O)cc1] | LCMS (Method A): 0.39 min; m/z: 419.0 [M + H]$^+$. | $^1$H NMR (400 MHz, MeOD-$d_4$): 8.54 (d, J = 7.6 Hz,1H), 8.48 (d, J = 9.2 Hz, 1H), 7.60 (d, J = 8.8 Hz, 2H), 7.46 (d, J = 8.8 Hz, 2H), 3.23 (q, J = 7.2 Hz, 2H), 2.63 (s, 3H), 1.36 (t, J = 7.2 Hz, 3H). | 4-bromo-5-fluoro-2-methylpyridine |
| 104 | 3-(4-(ethylsulfonamido) phenyl)-5-((2-(trifluoromethyl) pyridin-4-yl) amino)-1H-pyrazole-4-carboxamide | 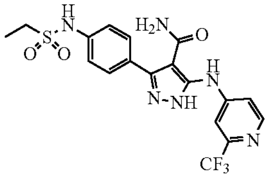 [SMILES: CCS(=O)(=O)Nc1ccc(-c2n[nH]c(Nc3ccnc(C(F)(F)F)c3)c2C(N)=O)cc1] | LCMS (Method A): 1.25 min; m/z: 455.0 [M + H]$^+$. | $^1$H NMR (400 MHz, MeOD-$d_4$): 8.37 (d, J = 6.0 Hz, 1H), 8.11 (s, 1H), 7.67 (d, J = 4.4 Hz, 1H), 7.59 (d, J = 8.8 Hz, 2H), 7.44 (d, J = 8.4 Hz, 2H), 3.21 (q, J = 7.2 Hz, 2H), 1.35 (t, J = 7.2 Hz, 3H). | 4-Chloro-(2-trifluoromethyl) pyridine |
| 88 | 3-(4-(ethylsulfonamido) phenyl)-5-((5-methoxypyridin-2-yl)amino)-1H-pyrazole-4-carboxamide | 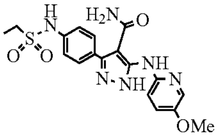 [SMILES: CCS(=O)(=O)Nc1ccc(-c2n[nH]c(Nc3ccc(OC)cn3)c2C(N)=O)cc1] | LCMS (Method A): 3.20 min; m/z: 417.4 [M + H]$^+$. | $^1$H NMR (400 MHz, DMSO-$d_6$): 9.83 (br s, 1H), 8.10 (s, 1H), 7.78 (d, J = 2.8 Hz, 1H), 7.65 (dd, J = 6.8, 2.0 Hz, 2H), 7.26 (dd, J = 9.2, 3.2 Hz, 1H), 7.20 (dd, J = 9.2, 2.0 Hz, 2H), 7.09 (s, 1H), 6.99 (s, 1H),6.52 (d, J = 8.8 Hz, 1H), 3.71 (s, 3H), 3.13 (q, J = 7.6 Hz, 2H), 1.55 (t, J = 7.6 Hz, 3H). | 2-chloro-5-methoxypyridine |
| 85 | 3-(4-(ethylsulfonamido) phenyl)-5-((4-(trifluoromethyl) pyridin-2-yl) amino)-1H-pyrazole-4-carboxamide | 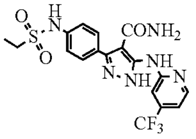 [SMILES: CCS(=O)(=O)Nc1ccc(-c2n[nH]c(Nc3cc(C(F)(F)F)ccn3)c2C(N)=O)cc1] | LCMS (Method A): 3.52 min; m/z: 455.1 [M + H]$^+$. | $^1$H NMR (400 MHz, MeOD-$d_4$): 12.96 (s, 1H), 10.14 (s, 1H), 9.90 (s, 1H), 8.44 (d, J = 4.4 Hz, 1H), 8.34 (s, 1H), 7.55 (d, J = 8.8 Hz, 2H), 7.35 (d, J = 8.0 Hz, 2H), 7.17 (d, J = 4.0 Hz, 1H), 6.12 (s, 1H), 3.18 (d, J = 7.2 Hz, 2H), 1.22 (t, J = 7.2 Hz, 3H). | 2-chloro-4-(trifluoromethyl) pyridine |
| 95 | 3-(4-(ethylsulfonamido) phenyl)-5-((4-methoxypyridin-2-yl)amino)-1H-pyrazole-4-carboxamide | 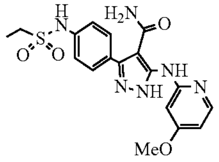 [SMILES: CCS(=O)(=O)Nc1ccc(-c2n[nH]c(Nc3cc(OC)ccn3)c2C(N)=O)cc1] | LCMS (Method A): 1.02 min; m/z: 416.8 [M + H]$^+$. | $^1$H NMR (400 MHz, DMSO-$d_6$): 12.87 (s, 1H), 10.10 (s, 1H), 9.52 (s, 1H), 8.02 (d, J = 5.2 Hz, 1H), 7.54 (d, J = 8.8 Hz, 2H), 7.34 (d, J = 8.4 Hz, 2H), 6.50 (d, J = 4.4 Hz, 1H), 3.83 (s, 3H), 3.18 (q, J = 7.2 Hz, 2H), 1.23 (t, J = 7.2 Hz, 3H). | 2-chloro-4-methoxypyridine |
| 93 | 3-(4-(ethylsulfonamido) phenyl)-5-((5-(trifluoromethyl) pyridin-2-yl)amino)-1H-pyrazole-4-carboxamide | 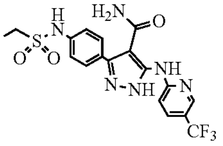 | LCMS (Method A): 2.45 min; m/z: 454.8 [M + H]$^+$. | $^1$H NMR (400 MHz, DMSO-$d_6$): 12.96 (br s, 1H), 10.09 (br s, 1H), 9.94 (s, 1H), 8.53 (s, 1H), 8.07 (s, 2H), 7.56 (d, J = 8.0 Hz, 2H), 7.35 (d, J = 7.6 Hz, 2H), 6.18 (br s, 1H), 3.18 (q, J = 6.8 Hz, 2H), 1.23 (t, J = 6.8 Hz, 3H). | 2-chloro-5-(trifluoromethyl) pyridine |
| 107 | 3-(4-(ethylsulfonamido) phenyl)-5-((6-methoxypyridin-2-yl)amino)-1H-pyrazole-4-carboxamide | 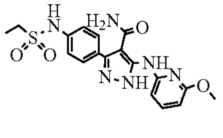 [SMILES: CCS(=O)(=O)Nc1ccc(-c2n[nH]c(Nc3cccc(OC)n3)c2C(N)=O)cc1] | LCMS (Method A): 1.11 min; m/z: 417.0 [M + H]$^+$. | $^1$H NMR (400 MHz, DMSO-$d_6$): 12.76 (s, 1H), 10.10 (s, 1H), 9.32 (s, 1H), 7.60 (t, J = 8.0 Hz, 1H), 7.56-7.53 (m, 3H), 7.36 (d, J = 8.8 Hz, 2H), 6.27 (d, J = 7.6 Hz, 1H), 3.81 (s, 3H), 3.20 (q, J = 7.2 Hz, 2H), 1.24 (t, J = 7.2 Hz, 3H). Two active protons not observed. | 2-chloro-6-methoxypyridine |
| 103 | 3-(4-(ethylsulfonamido) phenyl)-5-((6-(trifluoromethoxy) pyridin-2-yl)amino)-1H-pyrazole-4-carboxamide | 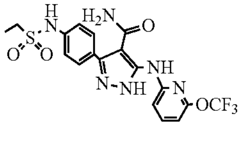 [SMILES: CCS(=O)(=O)Nc1ccc(-c2n[nH]c(Nc3cccc(OC(F)(F)F)n3)c2C(N)=O)cc1] | LCMS (Method A): 2.20 min; m/z: 471.0 [M + H]$^+$. | $^1$H NMR (400 MHz, MeOD-$d_4$): 7.98-7.82 (m, 2H), 7.58 (d, J = 8.4 Hz, 2H), 7.42 (d, J = 8.4 Hz, 2H), 6.72-6.55 (m, 1H), 3.20 (q, J = 7.2 Hz, 2H) 1.33 (t, J = 7.2 Hz, 3H). | 2-Chloro-6-(trifluoromethoxy) pyridine |

TABLE 9-continued

| Compound No | Name | Structure | LCMS data | $^1$H NMR data | Starting material |
|---|---|---|---|---|---|
| 67 | 3-(4-(ethylsulfonamido) phenyl)-5-(quinoxalin-2-ylamino)-1H-pyrazole-4-carboxamide | 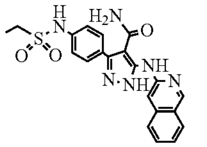 [SMILES: CCS(=O)(=O)Nc1ccc(-c2n[nH]c(Nc3cc4ccccc4cn3)c2C(N)=O)cc1] | LCMS (Method A): 3.29 min; m/z: 438.1 $[M + H]^+$. | $^1$H NMR (400 MHz, DMSO-$d_6$): 13.49 (s, 1), 13.06 (s, 1H), 9.91 (s, 1H), 9.44 (s, 1H), 8.88 (s, 1H), 8.21 (s, 1H), 7.93 (d, J = 8.0 Hz, 1H), 7.71 (d, J = 6.8 Hz, 1H), 7.61 (d, J = 8.4 Hz, 2H), 7.56 (d, J = 6.8 Hz, 1H), 7.34 (d, J = 7.2 Hz, 2H), 6.43 (br s, 1H), 3.18 (q, J = 7.2 Hz, 2H), 1.24 (t, J = 7.2 Hz, 3H). | 2-chloroquinoxaline |
| 65 | 5-((6-chloroquinoxalin-2-yl)amino)-3-(4-(ethylsulfonamido) phenyl)-1H-pyrazole-4-carboxamide | 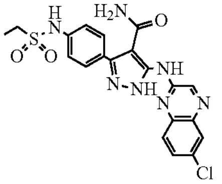 [SMILES: CCS(=O)(=O)Nc1ccc(-c2n[nH]c(Nc3cnc4cc(Cl)ccc4n3)c2C(N)=O)cc1] | LCMS (Method A): 3.48 min; m/z: 472.1 $[M + H]^+$. | $^1$H NMR (400 MHz, DMSO-$d_6$): 9.51 (s, 1H), 8.30 (s, 1H), 7.70 (m. 4H), 7.46 (s, 1H), 7.15 (s, 1H), 6.54 (s, 1H), 4.13 (s, 1H), 3.16 (s, 2H), 1.21 (t, J = 7.2 Hz. 3H). | 2,6-dichloroquinoxaline |
| 87 | 3-(4-(ethylsulfonamido) phenyl)-5-(isoquinolin-3-ylamino)-1H-pyrazole-4-carboxamide | 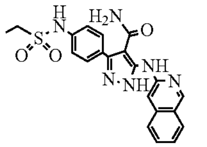 [SMILES: CCS(=O)(=O)Nc1ccc(-c2n[nH]c(Nc3cc4ccccc4cn3)c2C(N)=O)cc1] | LCMS (Method A): 3.38 min; m/z: 437.1 $[M + H]^+$. | $^1$H NMR (400 MHz, DMSO-$d_6$): 12.82 (s, 1H), 9.71 (s, 1H), 9.04 (s, 1H), 8.23 (s, 1H), 7.97 (d, J = 7.2 Hz, 1H), 7.76 (d, J = 8.4 Hz, 1H), 7.64-7.60 (m, 1H), 7.56 (d, J = 8.0 Hz, 2H), 7.39-7.36 (m, 3H), 3.18 (q, J = 7.2 Hz, 2H), 1.23 (t, J = 6.8 Hz, 3H). | 3-chloroisoquinoline |
| 128 | 3-(4-(ethylsulfonamido) phenyl)-5-((6-(2-methoxyethoxy) pyridin-2-yl)amino)-1H-pyrazole-4-carboxamide | 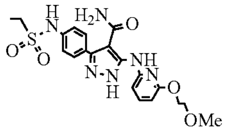 [SMILES: CCS(=O)(=O)Nc1ccc(-c2n[nH]c(Nc3cccc(OCCOC)n3)c2C(N)=O)cc1] | LCMS (Method A): 2.38 min; m/z: 461.2 $[M + H]^+$. | $^1$H NMR (400 MHz, DMSO-$d_6$): 12.77 (s, 1H), 10.12 (s, 1H), 9.32 (s, 1H), 7.61 (t, J = 7.4 Hz, 1H), 7.52-7.57 (m, 4H), 7.35 (d, J = 8.6 Hz, 2H), 7.33 (br s, 1H), 6.05 (br s, 1H), 4.33 (t, J = 5.4 Hz, 2H), 3.65 (t, J = 5.4 Hz,, 2H), 3.31 (s, 3H), 3.18 (q, J = 7.0 Hz, 2H), 1.23 (t, J = 7.5 Hz, 3H). | 2-bromo-6-(2-methoxyethoxy) pyridine |

Compound 98

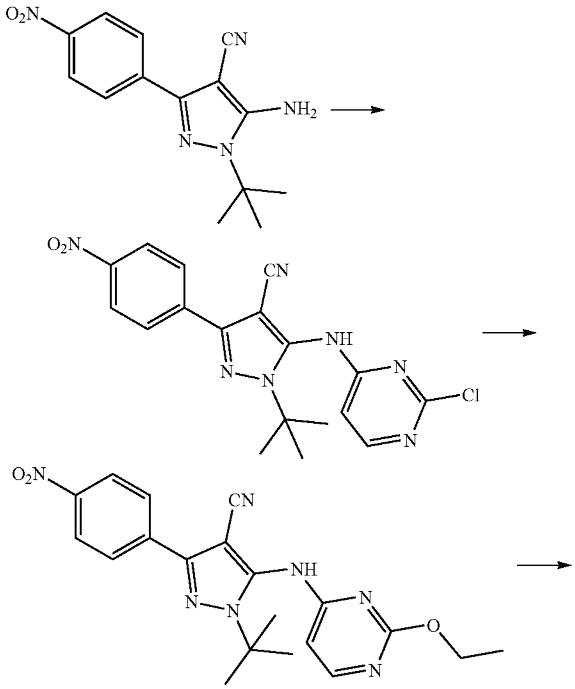

-continued

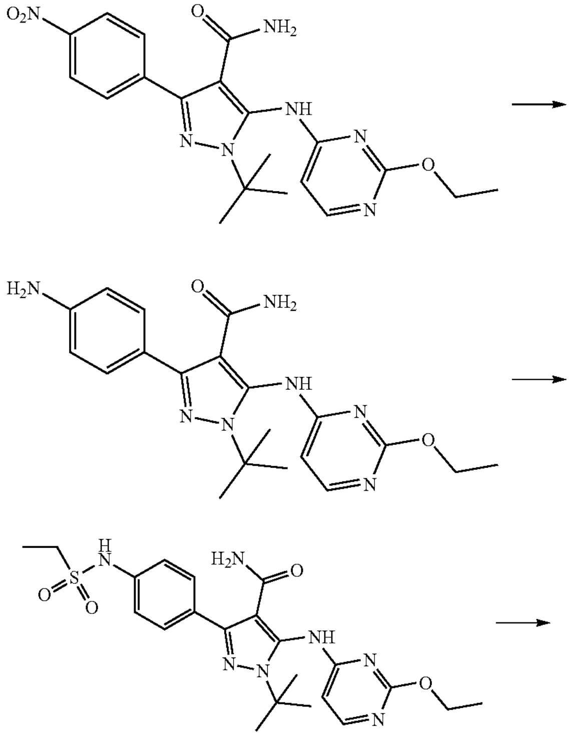

-continued

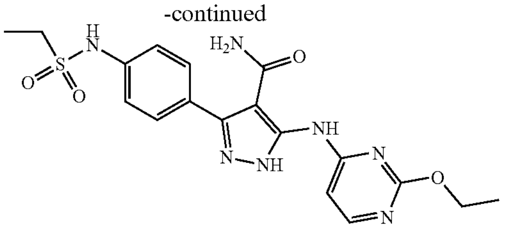

Step 1: 1-tert-butyl-5-[(2-chloropyrimidin-4-yl) amino]-3-(4-nitrophenyl)-1H-pyrazole-4-carbonitrile A mixture of 5-amino-1-(tert-butyl)-3-(4-nitrophenyl)-1H-pyrazole-4-carbonitrile (3 g, 10.5 mmol), 2,4-dichloro-pyrimidine (1.6 g, 11 mmol), $Pd_2(dba)_3$ (960 mg, 1.05 mmol), $Cs_2CO_3$ (10.27 g, 31.5 mmol) and Xantphos (1.2 g, 2.1 mmol) in degassed 1,4-dioxane (100 mL) was stirred at 100° C. under $N_2$ for 16 h. The mixture was concentrated under reduced pressure, diluted with $H_2O$ (20 mL) and extracted with EtOAc (3×20 mL). The combined organic phases were dried ($Na_2SO_4$), concentrated under reduced pressure and the crude residue was purified by silica gel column chromatography (PE:EtOAc, 1:1) to afford the title product (1.2 g, 28%) as a yellow solid. LCMS (Method A): 2.46 min; m/z: 398.0 $[M+H]^+$.

Step 2: 1-tert-butyl-5-[(2-ethoxypyrimidin-4-yl) amino]-3-(4-nitrophenyl)-1H-pyrazole-4-carbonitrile A mixture of 1-tert-butyl-5-[(2-chloropyrimidin-4-yl) amino]-3-(4-nitrophenyl)-1H-pyrazole-4-carbonitrile (700 mg, 1.75 mmol) and NaOEt (595 mg, 8.75 mmol) in THF (30 mL) was stirred at 65° C. under $N_2$ overnight. The reaction mixture was concentrated under reduced pressure and the crude residue was purified by silica gel column chromatography (PE:EtOAc, 15:1) to afford the title product (735 mg, 96%) as a yellow solid. LCMS (Method A): 3.38 min; m/z: 409.1 $[M+H]^+$.

Step 3: 1-tert-butyl-5-[(2-ethoxypyrimidin-4-yl) amino]-3-(4-nitrophenyl)-1H-pyrazole-4-carboxamide To a mixture of 1-tert-butyl-5-[(2-ethoxypyrimidin-4-yl) amino]-3-(4-nitrophenyl)-1H-pyrazole-4-carbonitrile (635 mg, 1.55 mmol) in DMSO (44.5 mL) and EtOH (200 mL) were added 30% aq. $H_2O_2$ (44.5 mL) and aq. NaOH solution (2M, 5 drops), and the resulting mixture was stirred at 100° C. under $N_2$ overnight. The mixture was concentrated under reduced pressure and the residue was diluted with $H_2O$ and EtOAc. The organic phase was separated, dried ($Na_2SO_4$) and concentrated under reduced pressure to afford the title product (675 mg, 88%) as a yellow solid. LCMS (Method A): 2.61 min; m/z: 426.0 $[M+H]^+$.

Step 4: 3-(4-aminophenyl)-1-tert-butyl-5-[(2-ethoxypyrimidin-4-yl)amino]-1H-pyrazole-4-carboxamide A mixture of 1-tert-butyl-5-[(2-ethoxypyrimidin-4-yl) amino]-3-(4-nitrophenyl)-1H-pyrazole-4-carboxamide (625 mg, 1.46 mmol), sat. $NH_4Cl$ (12 mL) and Zn dust (476 mg, 7.29 mmol) in MeOH (50 mL) was stirred at 60° C. under $N_2$ overnight. The reaction mixture was filtered, concentrated under reduced pressure and the residue diluted with $H_2O$ and EtOAc. The organic layer was separated, dried ($Na_2SO_4$) and concentrated under reduced pressure to afford the title product (475 mg, 82%) as a white solid. LCMS (Method A): 3.14 min; m/z: 396.2 $[M+H]^+$.

Step 5: 1-tert-butyl-3-(4-ethanesulfonamidophenyl)-5-[(2-ethoxypyrimidin-4-yl) amino]-1H-pyrazole-4-carboxamide A mixture of 3-(4-aminophenyl)-1-tert-butyl-5-[(2-ethoxypyrimidin-4-yl)amino]-1H-pyrazole-4-carboxamide (271 mg, 0.685 mmol), $EtSO_2Cl$ (131 mg, 1.02 mmol) and pyridine (107 mg, 1.36 mmol) in $CHCl_3$ (25 mL) was stirred at RT overnight, then diluted with $H_2O$ and EtOAc. The organic layer was separated, washed with water, dried ($Na_2SO_4$) and concentrated under reduced pressure. The crude residue was purified by silica gel column chromatography (PE:EtOAc, 50:1) to afford the title product (110 mg, 19%) as a yellow solid. LCMS (Method A): 3.12 min; m/z: 488.2 $[M+H]^+$.

Step 6: 5-((2-ethoxypyrimidin-4-yl)amino)-3-(4-(ethylsulfonamido)phenyl)-1H-pyrazole-4-carboxamide (compound 98)

A solution of 1-tert-butyl-3-(4-ethanesulfonamidophenyl)-5-[(2-ethoxy pyrimidin-4-yl)amino]-1H-pyrazole-4-carboxamide (110 mg, 225 μmol) in TFA (2 mL) was stirred at 60° C. under $N_2$ for 1 h. The reaction mixture was concentrated under reduced pressure and the residue was basified with sat. $NH_4Cl$ (2 mL). The precipitate was filtered, and the filter cake was washed with $Et_2O$ (2×2 mL) followed by n-hexane (2 mL) to afford the title product (71 mg, 73%) as a white solid. LCMS (Method A): 0.96 min; m/z: 433.1 $[M+H]^+$. $^1H$ NMR (400 MHz, DMSO-$d_6$): 13.04 (s, 1H), 10.11 (s, 1H), 9.75 (s, 1H), 8.26 (s, 1H), 7.57 (d, J=8.4 Hz, 2H), 7.45 (s, 1H), 7.35 (d, J=8.4 Hz, 2H), 4.31 (q, J=6.8 Hz, 2H), 3.19 (q, J=7.2 Hz, 2H), 1.31 (t, J=14.0 Hz, 3H), 1.23 (t, J=7.2 Hz, 3H).

Compound 66

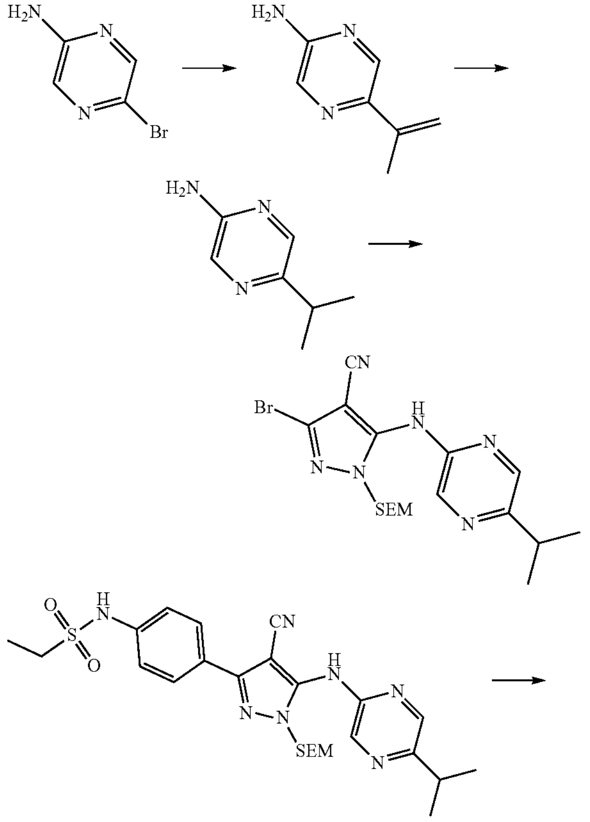

-continued

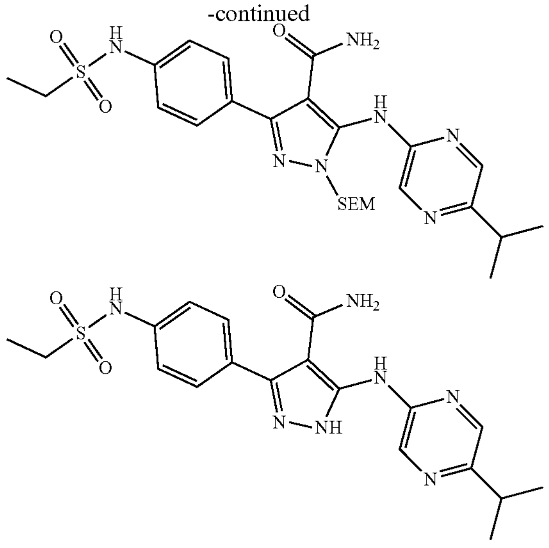

Step 1: 5-(prop-1-en-2-yl)pyrazin-2-amine

A mixture of 5-bromopyrazin-2-amine (5 g, 28.7 mmol), 4,4,5,5-tetramethyl-2-(prop-1-en-2-yl)-1,3,2-dioxaborolane (5.78 g, 34.4 mmol), $K_2CO_3$ (7.93 g, 57.4 mmol) and Pd(dppf)$Cl_2$ (2.34 g, 2.87 mmol) in degassed 80% aq. 1,4-dioxane (300 mL) was heated to 100° C. under $N_2$ overnight. The mixture was diluted with $H_2O$ (300 mL) and extracted with DCM (3×100 mL). The combined organic layers were dried ($Na_2SO_4$), concentrated under reduced pressure and the crude residue was purified by silica gel column chromatography (PE:EtOAc, 4:1) to afford the title product (2.9 g, 75%) as a yellow solid. LCMS (Method A): 1.38 min; m/z: 136.1 $[M+H]^+$.

Step 2: 5-(propan-2-yl)pyrazin-2-amine

A mixture of 5-(prop-1-en-2-yl)pyrazin-2-amine (1 g, 7.39 mmol), $Pd(OH)_2$ (24 mg, 167 μmol) and MeOH (8 mL) was stirred at RT under $H_2$ overnight. The reaction mixture was filtered, and the filtrate concentrated under reduced pressure to afford the title product (850 mg, 84%) as a brown solid. LCMS (Method A): 0.94 min; m/z: 138.0 $[M+H]^+$.

Step 3: 3-bromo-5-{[5-(propan-2-yl)pyrazin-2-yl]amino}-1-{[2-(trimethylsilyl) ethoxy]methyl}-1H-pyrazole-4-carbonitrile A mixture of 3,5-dibromo-1-{[2-(trimethylsilyl)ethoxy]methyl}-1H-pyrazole-4-carbonitrile (2.08 g, 5.46 mmol), 5-(propan-2-yl)pyrazin-2-amine (750 mg, 5.46 mmol), $Pd_2(dba)_3$ (499 mg, 546 μmol), Xantphos (630 mg, 1.09 mmol) and $Cs_2CO_3$ (5.31 g, 16.3 mmol) in degassed 1,4-dioxane (70 mL) was stirred at 100° C. under $N_2$ overnight. The mixture was diluted with $H_2O$ (100 mL) and extracted with EtOAc (3×50 mL). The combined organic layers were dried ($Na_2SO_4$), concentrated under reduced pressure and the crude residue was purified by silica gel column chromatography (PE:EtOAc, 8:1) to afford the title product (1.48 g, 62%) as a yellow solid. LCMS (Method A): 4.64 min; m/z: 438.1 $[M+H]^+$.

Step 4: N-[4-(4-cyano-5-{[5-(propan-2-yl)pyrazin-2-yl]amino}-1-{[2-(trimethyl silyl)ethoxy]methyl}-1H-pyrazol-3-yl)phenyl]ethane-1-sulfonamide A mixture of 3-bromo-5-{[5-(propan-2-yl)pyrazin-2-yl]amino}-1-{[2-(trimethylsilyl)ethoxy]methyl}-1H-pyrazole-4-carbonitrile (1.38 g, 3.15 mmol), N[4-(4,4,5,5-tetramethyl-1,3,2-dioxaborolan-2-yl)phenyl]ethane-1-sulfonamide (980 mg, 3.15 mmol), Pd(dppf)$Cl_2$ (257 mg, 315 μmol) and $K_2CO_3$ (870 mg, 6.30 mmol) in degassed 80% aq. 1,4-dioxane (50 mL) was stirred at 100° C. under $N_2$ overnight. The mixture was diluted with $H_2O$ (100 mL) and extracted with EtOAc (3×100 mL). The combined organic layers were dried ($Na_2SO_4$), concentrated under reduced pressure and the crude residue was purified by silica gel column chromatography (PE:EtOAc, 4:1) to afford the title product (1.2 g, 71%) as a yellow solid. LCMS (Method A): 4.39 min; m/z: 542.2 $[M+H]^+$.

Step 5: 3-(4-ethanesulfonamidophenyl)-5-{[5-(propan-2-yl)pyrazin-2-yl]amino}-1-{[2-(trimethylsilyl) ethoxy]methyl}-1H-pyrazole-4-carboxamide A mixture of N-[4-(4-cyano-5-{[5-(propan-2-yl)pyrazin-2-yl]amino}-1-{[2-(trimethylsilyl)ethoxy]methyl}-1H-pyrazol-3-yl)phenyl]ethane-1-sulfonamide (540 mg, 996 μmol), 30% aq. $H_2O_2$ (60 mL) and 5% aq. NaOH (60 drops) in EtOH (120 mL) and DMSO (60 mL) was stirred at 100° C. under $N_2$ overnight. The mixture was diluted with $H_2O$ (100 mL) and extracted with EtOAc (3×100 mL). The combined organic layers were dried ($Na_2SO_4$), concentrated under reduced pressure and the crude residue was purified by prep-TLC (DCM:MeOH, 15:1) to afford the title product (90 mg, 16%) as a yellow solid. LCMS (Method A): 3.99 min; m/z: 560.2 $[M+H]^+$.

Step 6: 3-(4-(ethylsulfonamido)phenyl)-5-((5-isopropylpyrazin-2-yl)amino)-1H-pyrazole-4-carboxamide (compound 66)

A mixture of 3-(4-ethanesulfonamidophenyl)-5-{[5-(propan-2-yl)pyrazin-2-yl]amino}-1-{[2-(trimethylsilyl)ethoxy]methyl}-1H-pyrazole-4-carboxamide (90 mg, 0.16 mmol) and 2.0 M HCl (0.5 mL) in THF (5 mL) was stirred at RT for 2 h. The reaction mixture was neutralized to pH 7-8 with $NH_4OH$ and then concentrated under reduced pressure. The crude residue was purified by prep-TLC (DCM:MeOH, 10:1) to afford the title product (12 mg, 17%) as a white solid. LCMS (Method A): 3.34 min; m/z: 430.1 $[M+H]^+$. $^1H$ NMR (400 MHz, DMSO-$d_6$): 12.90 (s, 1H), 10.07 (s, 1H), 9.52 (s, 1H), 9.20 (s, 1H), 8.14 (s, 1H), 7.56 (d, J=8.4 Hz, 2H), 7.36 (d, J=8.0 Hz, 2H), 6.10 (br s, 1H), 3.19 (q, J=6.8 Hz, 2H), 3.08-2.99 (m, 1H), 1.24 (t, J=8.0 Hz, 9H).

Compound 121

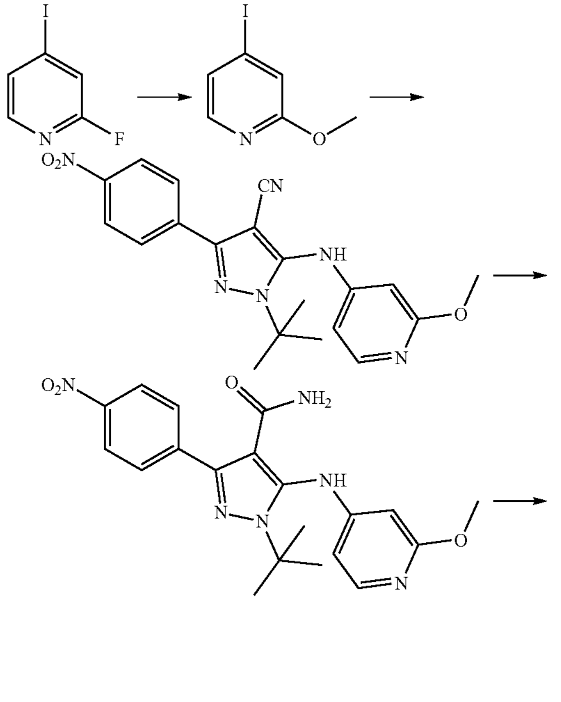

-continued

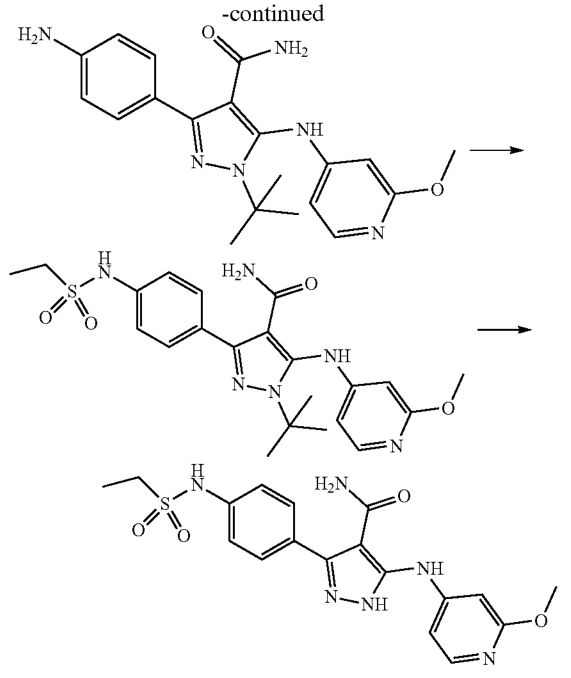

Step 1: 4-iodo-2-methoxypyridine

A mixture of 2-fluoro-4-iodo-pyridine (1.00 g, 4.48 mmol), $Cs_2CO_3$ (4.41 g, 13.5 mmol), DMF (20 mL) and MeOH (0.5 mL) was stirred at 90° C. for 2 h. The reaction mixture was concentrated under reduced pressure, diluted with $H_2O$ (50 mL) and extracted with EtOAc (3×20 mL). The combined organic layers were washed with brine, dried ($MgSO_4$) and then concentrated under reduced pressure to afford the title compound (868 mg, 82%) as a yellow oil. $^1$H NMR (300 MHz, $CDCl_3$): 7.83 (dd, J=5.4, 0.5 Hz, 1H), 7.20 (dd, J=5.4, 1.4 Hz, 1H), 7.17 (dd, J=1.4, 0.5 Hz, 1H), 3.90 (s, 3H).

Step 2: 1-(tert-butyl)-5-((2-methoxypyridin-4-yl) amino)-3-(4-nitrophenyl)-1H-pyrazole-4-carbonitrile A mixture of 5-amino-1-(tert-butyl)-3-(4-nitrophenyl)-1H-pyrazole-4-carbonitrile (1.05 g, 3.68 mmol), 4-iodo-2-methoxy-pyridine (804 mg, 3.42 mmol), $Pd(OAc)_2$ (83.4 mg, 0.368 mmol), Xantphos (426 mg, 0.736 mmol) and $Cs_2CO_3$ (1.81 g, 5.52 mmol) in 1,4-Dioxane (22 mL) was stirred at 110° C. for 3 h. The reaction mixture was diluted with EtOAc (40 mL), filtered through Celite and concentrated under reduced pressure. The residue was diluted with $H_2O$ (50 mL) and the aqueous layer was extracted with EtOAc (3×50 mL).

The combined organic fractions were dried ($MgSO_4$), concentrated under reduced pressure and the crude residue was purified by silica gel column chromatography (PE: EtOAc, 1:0 to 0:1) to afford the title compound (1.04 g, 77%) as an orange foam. LCMS (Method C): 2.31 min; m/z: 393.2 $[M+H]^+$. $^1$H NMR (300 MHz, $CDCl_3$): 8.33-8.28 (m, 2H), 8.19-8.16 (m, 2H), 7.96 (d, J=6.1 Hz, 1H), 6.46 (dd, J=6.0, 2.0 Hz, 1H), 6.19 (br s, 1H), 3.92 (s, 3H), 1.70 (s, 9H).

Step 3: 1-(tert-butyl)-5-((2-methoxypyridin-4-yl) amino)-3-(4-nitrophenyl)-1H-pyrazole-4-carboxamide A mixture of 1-(tert-butyl)-5-((2-methoxypyridin-4-yl) amino)-3-(4-nitrophenyl)-1H-pyrazole-4-carboxamide (500 mg, 1.20 mmol) and Ghaffar-Parkins catalyst (25.7 mg, 59.9 μmol) in 90% aq. EtOH (50 mL) was stirred at 120° C. for 16 h. The mixture was filtered through Celite and concentrated under reduced pressure to give the title compound (530 mg, quant.) as a yellow solid. LCMS (Method C): 1.98 min; m/z: 411.2 $[M+H]^+$. $^1$H NMR (300 MHz, DMSO-$d_6$): 8.51 (s, 1H), 8.30-8.27 (m, 2H), 8.03-8.00 (m, 2H), 7.79 (d, J=5.7 Hz, 1H), 7.41 (br s, 1H), 7.39 (br s, 1H), 6.32 (br s, 1H), 5.82 (br s, 1H), 3.74 (s, 3H), 1.59 (s, 9H).

Step 4: 3-(4-aminophenyl)-1-(tert-butyl)-5-((2-methoxypyridin-4-yl)amino)-1H-pyrazole-4-carboxamide A mixture of 1-(tert-butyl)-5-((2-methoxypyridin-4-yl) amino)-3-(4-nitrophenyl)-1H-pyrazole-4-carboxamide (280 mg, 0.68 mmol) and 5% Pd/C (14 mg) in MeOH (30 mL) was stirred at RT under $H_2$ for 3 d. The reaction mixture was filtered through Celite and concentrated to give the title compound (257 mg, 99%) as a yellow solid. LCMS (Method C): 1.36 min; m/z: 381.2 $[M+H]^+$. $^1$H NMR (300 MHz, MeOD-$d_4$): 7.76 (d, J=5.9 Hz, 1H), 7.46-7.43 (m, 2H), 6.78-6.73 (m, 2H), 6.29 (d, J=4.9 Hz, 1H), 5.93 (s, 1H), 3.80 (s, 3H), 1.63 (m, 9H).

Step 5: 1-(tert-butyl)-3-(4-(ethylsulfonamido)phenyl)-5-((2-methoxypyridin-4-yl)amino)-1H-pyrazole-4-carboxamide A mixture of 3-(4-aminophenyl)-1-(tert-butyl)-5-((2-methoxypyridin-4-yl)amino)-1H-pyrazole-4-carboxamide (50.0 mg, 0.13 mmol) and pyridine (106 μL, 1.31 mmol) in DCM (1 mL) was cooled to 0° C. and $EtSO_2Cl$ (25 μL, 0.26 mmol) was added dropwise. After 1 h, the reaction mixture was diluted with $H_2O$ (10 mL) and extracted with DCM: MeOH (9:1, 5×2 mL). The combined organic extracts were dried ($MgSO_4$), concentrated under reduced pressure and the crude residue was purified by silica gel column chromatography (DCM:MeOH, 1:0 to 9:1) to afford the title compound (28.0 mg, 45%) as a white solid. LCMS (Method C): 1.81 min; m/z: 473.2 $[M+H]^+$. $^1$H NMR (300 MHz, MeOD-$d_4$): 7.77 (d, J=5.9 Hz, 1H), 7.71-7.67 (m, 2H), 7.30-7.26 (m, 2H), 6.31 (d, J=4.8 Hz, 1H), 5.94 (br s, 1H), 3.80 (s, 3H), 3.11 (q, J=7.3 Hz, 2H), 1.65 (s, 9H), 1.30 (t, J=7.3 Hz, 3H).

Step 6: 3-(4-(ethylsulfonamido)phenyl)-5-((2-methoxypyridin-4-yl)amino)-1H-pyrazole-4-carboxamide (compound 121)

A solution of 1-(tert-butyl)-3-(4-(ethylsulfonamido)phenyl)-5-((2-methoxypyridin-4-yl)amino)-1H-pyrazole-4-carboxamide (28.0 mg, 0.059 mmol) in TFA (1 mL) and DCM (1 mL) was stirred at RT for 4 h. The reaction mixture was concentrated under reduced pressure and the crude residue was purified by SCX cartridge (MeOH, then 2.0 M $NH_3$ in MeOH) to afford the title compound (24.2 mg, 98%) as a white solid. LCMS (Method C): 1.58 min; m/z: 417.0 $[M+H]^+$. $^1$H NMR (300 MHz, MeOD-$d_4$): 7.84 (d, J=6.1 Hz, 1H), 7.59-7.55 (m, 2H), 7.45-7.40 (m, 2H), 7.18 (s, 1H), 6.93-6.90 (m, 1H), 3.87 (s, 3H), 3.19 (q, J=7.4 Hz, 2H), 1.33 (t, J=7.4 Hz, 3H).

Following the full synthesis of Compound 121 with the corresponding alcohol in step 1, the following compounds (Table 10) were prepared:

TABLE 10

| Compound No | Name | Structure | LCMS data | $^1$H NMR data | SM |
|---|---|---|---|---|---|
| 105 | 5-((2-ethoxypyridin-4-yl)amino)-3-(4-(ethylsulfonamido)phenyl)-1H-pyrazole-4-carboxamide | 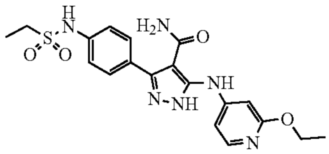 [SMILES: CCOc1cc(Nc2[nH]nc(-c3ccc(NS(=O)(=O)CC)cc3)c2C(N)=O)ccn1] | LCMS (Method A): 0.29 min; m/z: 431.0 [M + H]$^+$. | $^1$H NMR (400 MHz, MeOD-$d_4$): 7.92 (d, J = 7.2 Hz, 1H), 7.60 (d, J = 8.4 Hz, 2H), 7.44 (d, J = 8.4 Hz, 2H), 7.28 (br s, 1H), 5.35 (t, J = 4.8 Hz, 1H), 4.44 (q, J = 7.2 Hz, 2H), 3.23 (q, J = 7.2 Hz, 2H), 1.53 (t, J = 7.2 Hz, 3H), 1.36 (t, J = 7.6 Hz, 3H). | ethanol |
| 106 | 5-((2-(2,2-difluoroethoxy)pyridin-4-yl)amino)-3-(4-(ethylsulfonamido)phenyl)-1H-pyrazole-4-carboxamide | 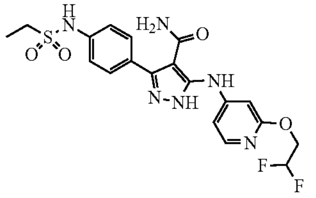 [SMILES: CCS(=O)(=O)Nc1ccc(-c2n[nH]c(Nc3ccnc(OCC(F)F)c3)c2C(N)=O)cc1] | LCMS (Method A): 0.47 min; m/z: 467.0 [M + H]$^+$. | $^1$H NMR (400 MHz, DMSO-$d_6$): 12.90 (s, 1H), 10.14 (s, 1H), 9.33 (s, 1H), 7.89 (d, J = 6.0 Hz, 1H), 7.57 (d, J = 8.4 Hz, 2H), 7.37 (d, J = 8.4 Hz, 2H), 7.19 (s, 1H), 6.97 (dd, J = 7.6, 1.6 Hz, 1H), 6.36 (tt, J = 54.8, 3.6 Hz, 1H), 4.51 (q, J = 7.2 Hz, 2H), 3.18 (q, J = 7.2 Hz, 2H), 1.23 (t, J = 7.2 Hz, 3H). Two active protons not observed. | 2,2-difluoroethan-1-ol |

Compound 118

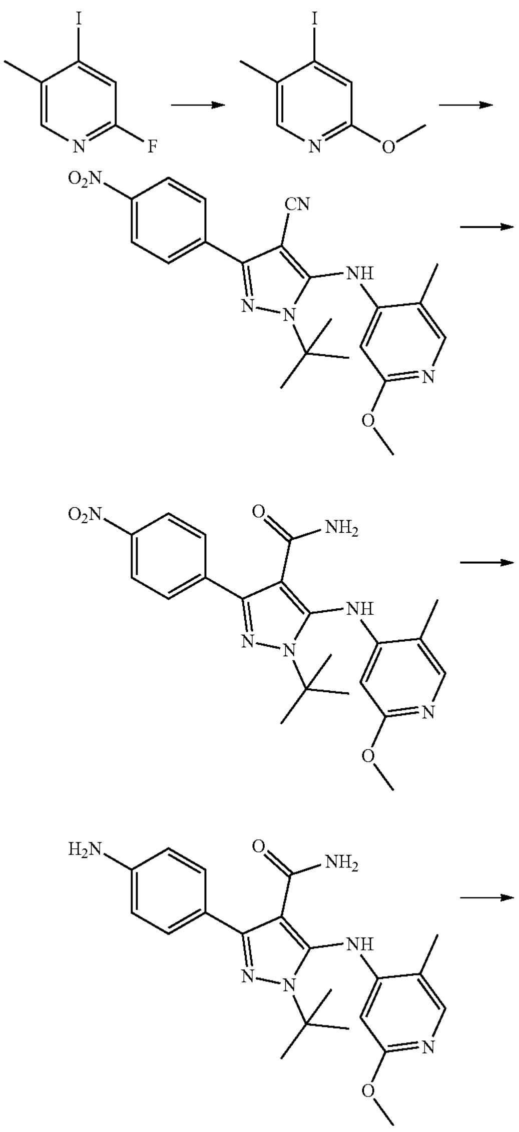

-continued

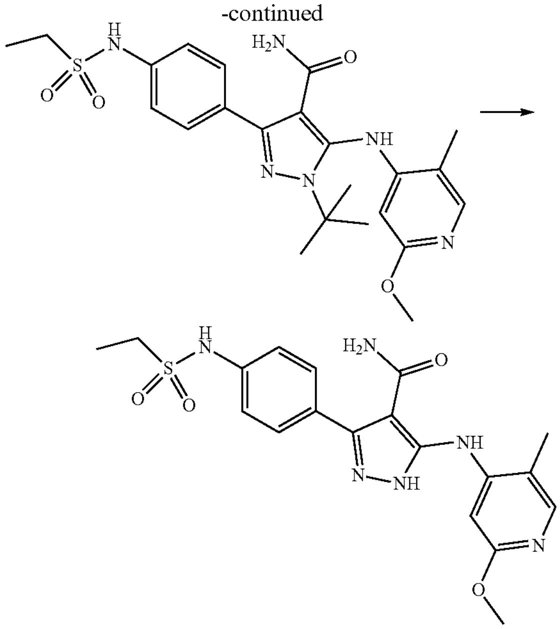

Step 1: 4-iodo-2-methoxy-5-methylpyridine

A mixture of 2-fluoro-4-iodo-5-methylpyridine (1.06 g, 4.47 mmol), $Cs_2CO_3$ (4.36 g, 13.4 mmol), MeOH (542 μL, 13.4 mmol) and DMF (10 mL) was stirred at 90° C. for 3 h. The reaction mixture was diluted with $H_2O$ (100 mL) and extracted with $Et_2O$ (5×50 mL). The combined organic fractions were washed with brine, dried ($MgSO_4$) and concentrated under reduced pressure. The crude residue was purified by silica gel column chromatography (PE:EtOAc, 1:0 to 9:1) to afford the title compound (746 mg, 67%) as a white solid. LCMS (Method C): 2.44 min; m/z: 250.0 [M+H]$^+$. $^1$H NMR (300 MHz, $CDCl_3$): 7.91 (s, 1H), 7.26 (s, 1H), 3.87 (s, 3H), 2.30 (s, 3H).

Step 2: 1-(tert-butyl)-5-((2-methoxy-5-methylpyridin-4-yl)amino)-3-(4-nitrophenyl)-1H-pyrazole-4-carbonitrile A mixture of 5-amino-1-(tert-butyl)-3-(4-nitrophenyl)-1H-pyrazole-4-carbonitrile (696 mg, 2.43 mmol), 4-iodo-2- methoxy-5-methylpyridine (724 mg, 2.91 mmol), $Pd(OAc)_2$ (54.5 mg, 0.24 mmol), Xantphos (281 mg, 0.486 mmol) and $Cs_2CO_3$ (1.18 g, 3.64 mmol) in 1,4-Dioxane (35 mL) was stirred at 110° C. for 21 h. The reaction mixture was diluted with EtOAc (40 mL), filtered through Celite and concentrated under reduced pressure. The crude residue was purified by silica gel column chromatography (PE:EtOAc, 1:0 to 2:3) to afford the title compound (992 mg, 83%) as an orange oil. LCMS (Method C): 2.31 min; m/z: 407.2 $[M+H]^+$. $^1H$ NMR (300 MHz, DMSO-$d_6$): 8.43-8.38 (m, 2H), 8.18-8.13 (m, 3H), 7.80 (s, 1H), 5.62 (s, 2H), 3.71 (s, 3H), 2.18 (s, 3H), 1.62 (s, 9H).

Step 3: 1-(tert-butyl)-5-((2-methoxy-5-methylpyridin-4-yl)amino)-3-(4-nitro phenyl)-1H-pyrazole-4-carboxamide A mixture of 1-(tert-butyl)-5-((2-methoxy-5-methylpyridin-4-yl)amino)-3-(4-nitrophenyl)-1H-pyrazole-4-carbonitrile (443 mg, 1.08 mmol), Ghaffar-Parkins catalyst (23.1 mg, 54.0 μmol) and 90% aq. EtOH (50 mL) was stirred at 110° C. for 16 h. The reaction mixture was concentrated under reduced pressure and the crude residue was purified by recrystallization (EtOH) to afford the title compound (346 mg, 72%) as an off-white solid. LCMS (Method C): 1.95 min; m/z: 425.2 $[M+H]^+$. $^1H$ NMR (300 MHz, DMSO-$d_6$): 8.30-8.25 (m, 2H), 8.06-8.01 (m, 2H), 7.73 (s, 1H), 7.56 (s, 1H), 7.34 (br s, 1H), 7.27 (br s, 1H), 5.43 (s, 1H), 3.67 (s, 3H), 2.17 (s, 3H), 1.59 (s, 9H).

Step 4: 3-(4-aminophenyl)-1-(tert-butyl)-5-((2-methoxy-5-methylpyridin-4-yl)amino)-1H-pyrazole-4-carboxamide A mixture of 1-(tert-butyl)-5-((2-methoxy-5-methylpyridin-4-yl)amino)-3-(4-nitrophenyl)-1H-pyrazole-4-carboxamide (246 mg, 0.553 mmol) and 10% Pd/C (25 mg) in MeOH (30 mL) was stirred at RT under $H_2$ for 16 h. The reaction mixture was filtered through Celite and concentrated under reduced pressure to afford the title compound (215 mg, 96%) as a white solid. LCMS (Method C): 1.44 min; m/z: 395.2 $[M+H]^+$. $^1H$ NMR (300 MHz, DMSO-$d_6$): 7.69 (s, 1H), 7.46 (s, 1H), 7.45-7.41 (m, 2H), 7.07 (br s, 1H), 7.00 (br s, 1H), 6.58-6.51 (m, 2H), 5.41 (s, 1H), 5.16 (br s, 2H), 3.66 (s, 3H), 2.14 (s, 3H), 1.54 (s, 9H).

Step 5: 1-(tert-butyl)-3-(4-(ethylsulfonamido)phenyl)-5-((2-methoxy-5-methylpyridin-4-yl)amino)-1H-pyrazole-4-carboxamide A mixture of 3-(4-aminophenyl)-1-(tert-butyl)-5-((2-methoxy-5-methylpyridin-4-yl)amino)-1H-pyrazole-4-carboxamide (115 mg, 0.291 mmol), $EtSO_2Cl$ (55 μL, 0.583 mmol), pyridine (235 μL, 2.91 mmol) and DCM (5 mL) was stirred at RT for 4 h. The reaction mixture was concentrated under reduced pressure and the crude residue was purified by silica gel column chromatography (DCM:MeOH, 1:0 to 4:1) to give a yellow residue (75.7 mg). Further purification by SCX cartridge (MeOH, then 2 M $NH_3$ in MeOH) afforded the title compound (32.7 mg, 22%) as a white solid. LCMS (Method C): 1.82 min; m/z: 487.2 $[M+H]^+$. $^1H$ NMR (300 MHz, DMSO-$d_6$): 9.84 (br s, 1H), 7.72-7.68 (m, 3H), 7.48 (s, 1H), 7.26-7.21 (m, 2H), 7.18 (br s, 1H), 7.10 (br s, 1H), 5.41 (s, 1H), 3.68 (s, 3H), 3.11 (q, J=7.3 Hz, 2H), 2.16 (s, 3H), 1.56 (s, 9H), 1.21 (t, J=7.3 Hz, 3H).

Step 6: 3-(4-(ethylsulfonamido)phenyl)-5-((2-methoxy-5-methylpyridin-4-yl)amino)-1H-pyrazole-4-carboxamide (compound 118)

A solution of 1-(tert-butyl)-3-(4-(ethylsulfonamido)phenyl)-5-((2-methoxy-5-methylpyridin-4-yl)amino)-1H-pyrazole-4-carboxamide (29.6 mg, 0.0569 mmol) in TFA (0.5 mL) and DCM (0.5 mL) was stirred at RT for 16 h. The reaction mixture was concentrated under reduced pressure and purified by SCX cartridge (MeOH, then 2 M $NH_3$ in MeOH) to afford the title compound (22.0 mg, 90%) as a white solid. LCMS (Method C): 1.66 min; m/z: 431.0 $[M+H]^+$. $^1H$ NMR (300 MHz, DMSO-$d_6$): 12.88 (br, s, 1H), 9.59 (s, 1H), 7.77 (s, 1H), 7.55-7.53 (m, 3H), 7.38-7.34 (m 2H), 3.77 (s, 3H), 3.22-3.14 (m, 2H), 2.14 (s, 3H), 1.22 (t, J=7.3 Hz, 3H).

Following the full synthesis of Compound 118, starting from 5-amino-1-(tert-butyl)-3-(4-nitrophenyl)-1H-pyrazole-4-carbonitrile with the mentioned intermediates as described in step 2, the following compounds (Table 11) were prepared:

TABLE 11

| Compound No | Name | Structure | LCMS data | $^1H$ NMRdata | SM |
|---|---|---|---|---|---|
| 113 | 3-(4-(ethylsulfonamido) phenyl)-5-((2-methylpyridin-4-yl)amino)-1H-pyrazole-4-carboxamide | 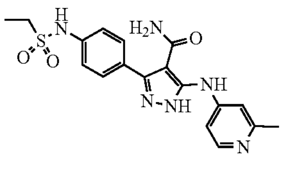 [SMILES: CCS(=O)(=O)Nc1ccc(-c2n[nH]c(Nc3ccnc(C)c3)c2C(N)=O)cc1] | LCMS (Method C): 1.33 min; m/z: 401.0 [M + H]$^+$. | $^1H$ NMR (300 MHz, DMSO-$d_6$): 12.84 (brs, 1H), 9.22 (brs, 1H), 8.14 (d, J = 5.5 Hz, 1H), 7.55 (d, J = 8.6 Hz, 2H), 7.38-7.30 (m, 3H), 7.28-7.24 (m, 1H), 3.21-3.14 (m, 2H), 2.37 (s, 3H), 1.23 (t, J = 7.3 Hz, 3H). | 4-bromo-2-methylpyridine |
| 112 | 5-((2,6-dimethylpyridin-4-yl)amino)-3-(4-(ethylsulfonamido) phenyl)-1H-pyrazole-4-carboxamide | 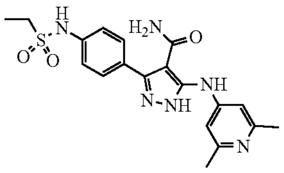 [SMILES: CCS(=O)(=O)Nc1ccc(-c2n[nH]c(Nc3cc(C)nc(C)c3)c2C(N)=O)cc1] | LCMS (Method C): 1.38 min; m/z: 415.0 [M + H]$^+$. | $^1H$ NMR (300 MHz, DMSO-$d_6$): 12.82 (brs, 1H), 9.18 (br s, 1H), 7.56-7.53 (m, 2H), 7.36-7.32 (m, 2H), 7.13 (s. 2H), 3.17 (q, J = 7.3 Hz, 2H), 2.32 (s, 6H), 1.22 (t,J= 7.3 Hz, 3H). | 4-bromo-2,6-dimethylpyridine |

Compound 102

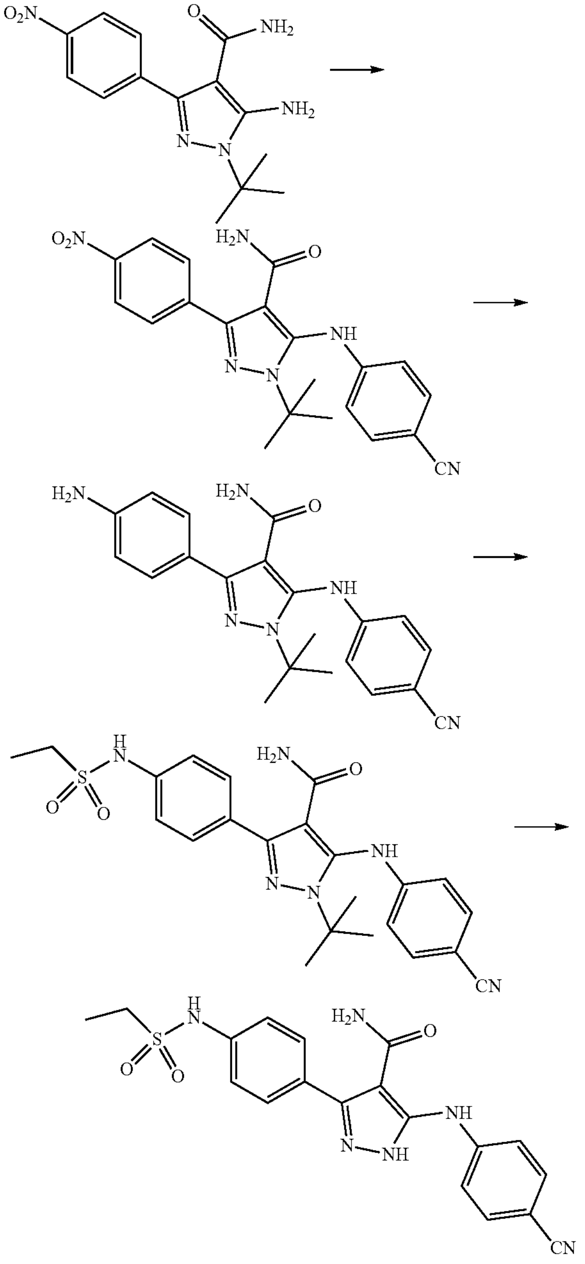

Step 1: 1-(tert-butyl)-5-((4-cyanophenyl)amino)-3-(4-nitrophenyl)-1H-pyrazole-4-carboxamide A mixture of 5-amino-1-tert-butyl-3-(4-nitrophenyl)-1H-pyrazole-4-carboxamide (455 mg, 1.50 mmol), CsF (683 mg, 4.50 mmol) and 4-fluorobenzonitrile (236 mg, 1.95 mmol) in DMSO (10 mL) was stirred at 150° C. under microwave irradiation for 3 h. The mixture was diluted with $H_2O$ (20 mL) and then extracted with EtOAc (20 mL). The organic layer was washed with brine, dried ($Na_2SO_4$), and concentrated under reduced pressure. The crude residue was purified by prep-TLC (DCM:MeOH, 20:1) to afford the title product (304 mg, 23%) as a yellow solid. LCMS (Method B): 2.40 min; m/z: 405.0 $[M+H]^+$.

Step 2: 3-(4-aminophenyl)-1-(tert-butyl)-5-((4-cyanophenyl)amino)-1H-pyrazole-4-carboxamide A mixture of 1-tert-butyl-5-[(4-cyanophenyl)amino]-3-(4-nitrophenyl)-1H-pyrazole-4-carboxamide (304 mg, 0.751 mmol), sat. aq. $NH_4Cl$ (6 mL) and Zn dust (245 mg, 3.75 mmol) in MeOH (18 mL) was stirred at 60° C. overnight. The mixture was filtered, concentrated under reduced pressure and the residue partitioned between water (100 mL) and EtOAc (100 mL). The organic layer was dried ($Na_2SO_4$) and concentrated under reduced pressure to give the title product (255 mg, 90%) as a yellow solid. LCMS (Method B): 0.82 min; m/z: 375.1 $[M+H]^+$.

Step 3: 1-(tert-butyl)-5-((4-cyanophenyl)amino)-3-(4-(ethylsulfonamido) phenyl)-1H-pyrazole-4-carboxamide To a stirred solution of 3-(4-aminophenyl)-1-tert-butyl-5-[(4-cyanophenyl) amino]-1H-pyrazole-4-carboxamide (150 mg, 400 mmol) and pyridine (126 mg, 1.60 mmol) in $CHCl_3$ (10 mL) was added $EtSO_2Cl$ (102 mg, 800 mmol). The mixture was stirred at RT overnight then diluted with $H_2O$ (100 mL) and extracted with EtOAc (100 mL). The organic layer was washed with brine, dried ($Na_2SO_4$) and concentrated under reduced pressure. The crude residue was purified by silica gel column chromatography (DCM:MeOH, 20:1) to afford the title product (27 mg, 14%) as a yellow solid. LCMS (Method A): 2.57 min; m/z: 467.3 $[M+H]^+$.

Step 4: 5-((4-cyanophenyl)amino)-3-(4-(ethylsulfonamido)phenyl)-1H-pyrazole-4-carboxamide (compound 102)

A solution of 1-tert-butyl-5-[(4-cyanophenyl)amino]-3-(4-ethanesulfonamidophenyl)-1H-pyrazole-4-carboxamide (27 mg, 0.0578 mmol) in TFA (1 mL) was stirred at 60° C. for 1 h. The reaction mixture was concentrated under reduced pressure and the residue was triturated with $Et_2O$ (3x3 mL) then dried under reduced pressure to afford the title product as the TFA salt (10 mg, 40%) as a yellow solid. LCMS (Method A): 1.28 min; m/z: 411.2 $[M+H]^+$. $^1$H NMR (400 MHz, MeOD-$d_4$): 7.69 (d, J=8.4 Hz, 2H), 7.62-7.57 (m, 4H), 7.43 (d, J=8.4 Hz, 2H), 3.21 (q, J=7.2 Hz, 2H), 1.34 (t, J=7.2 Hz, 3H).

Compound 237

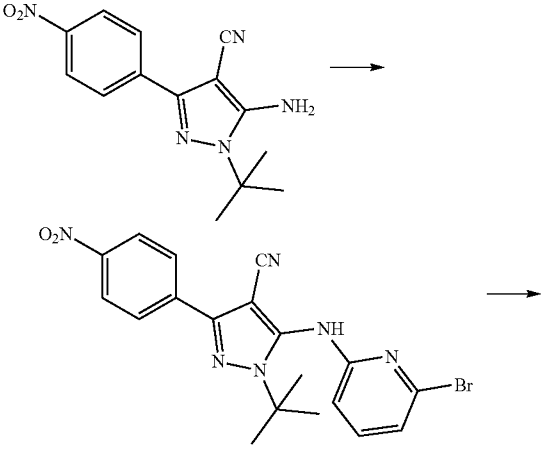

-continued

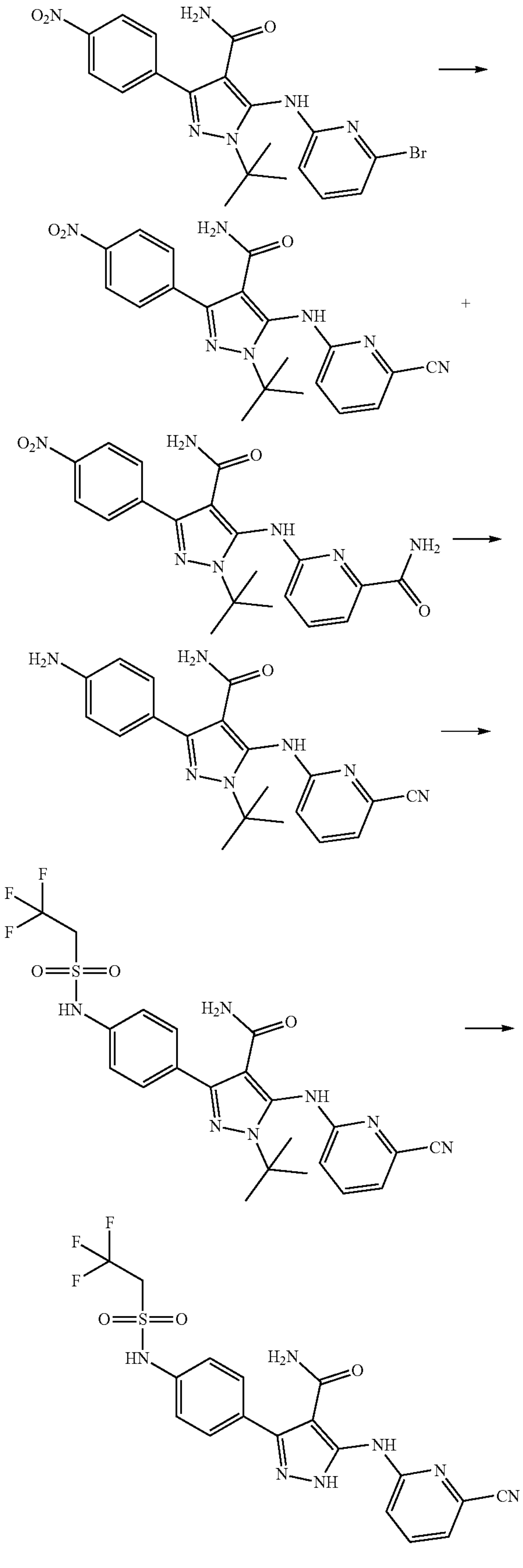

Step 1: 5-[(6-bromopyridin-2-yl)amino]-1-tert-butyl-3-(4-nitrophenyl)-1H-pyrazole-4-carbonitrile A mixture of 5-amino-1-tert-butyl-3-(4-nitrophenyl)-1H-pyrazole-4-carbonitrile (3.0 g, 10.5 mmol), 2,6-dibromopyridine (2.48 g, 10.5 mmol), $Pd_2(dba)_3$ (961 mg, 1.05 mmol), Xantphos (1.21 g, 2.10 mmol) and $Cs_2CO_3$ (6.84 g, 21.0 mmol) in 1,4-dioxane (60 mL) was stirred at 100° C. under $N_2$ for 16 h. The reaction mixture was concentrated and the residue purified by silica gel column chromatography (DCM:MeOH, 30:1) to afford the title product (3.6 g, 77%) as a yellow solid. LCMS (Method A): 4.37 min; m/z: 441.1, 443.1 $[M+H]^+$.

Step 2: 5-((6-bromopyridin-2-yl)amino)-1-(tert-butyl)-3-(4-nitrophenyl)-1H-pyrazole-4-carboxamide A mixture of 5-[(6-bromopyridin-2-yl)amino]-1-tert-butyl-3-(4-nitrophenyl)-1H-pyrazole-4-carbonitrile (2.0 g, 4.53 mmol), Ghaffar-Parkin's catalyst (194 mg, 0.45 mmol) and 90% aq. 1,4-dioxane (110 mL) was stirred at 100° C. under $N_2$. After 16 h, the reaction mixture was concentrated and the crude residue was purified by silica gel column chromatography (DCM:MeOH, 40:1) to afford the title product (630 mg, 30%) as a yellow solid. LCMS (Method A): 3.92 min; m/z: 459.0, 461.0 $[M+H]^+$.

Step 3: 1-tert-butyl-5-[(6-cyanopyridin-2-yl)amino]-3-(4-nitrophenyl)-1H-pyrazole-4-carboxamide and 6-((1-(tert-butyl)-4-carbamoyl-3-(4-nitrophenyl)-1H-pyrazol-5-yl)amino)picolinamide A mixture of 5-[(6-bromopyridin-2-yl)amino]-1-tert-butyl-3-(4-nitrophenyl)-1H-pyrazole-4-carboxamide (10 g, 21.7 mmol), CuI (4.13 g, 21.7 mmol) and CuCN (3.88 g, 43.4 mmol) in NMP (100 mL) was stirred at 150° C. under $N_2$ overnight. The reaction was poured into EtOAc (100 mL) and washed with water (100 mL×3). The organic layer was collected and washed with brine, dried ($Na_2SO_4$) and concentrated. The residue was purified by column chromatography on silica gel (EtOAc:PE, 1:4) to give 1-tert-butyl-5-[(6-cyanopyridin-2-yl)amino]-3-(4-nitrophenyl)-1H-pyrazole-4-carboxamide (2.2 g, 25%) as a yellow solid LCMS (Method A): 3.65 min, m/z: 406.1 $[M+H]^+$, and 6-((1-(tert-butyl)-4-carbamoyl-3-(4-nitrophenyl)-1H-pyrazol-5-yl)amino)picolinamide (390 mg) as a brown solid. LCMS (Method A): 3.25 min, m/z: 424.1 $[M+H]^+$.

Step 4: 3-(4-aminophenyl)-1-tert-butyl-5-[(6-cyanopyridin-2-yl)amino]-1H-pyrazole-4-carboxamide A mixture of 1-tert-butyl-5-[(6-cyanopyridin-2-yl)amino]-3-(4-nitrophenyl)-1H-pyrazole-4-carboxamide (90 mg, 0.22 mmol), Zn powder (71.9 mg, 1.10 mmol), sat. $NH_4Cl$ (2 mL) and MeOH (10 mL) was stirred at 60° C. for 16 h. The reaction mixture was filtered and the filtrate was concentrated, then purified by prep-TLC (DCM:MeOH, 20:1) to afford the title product (50 mg, 60%) as a yellow solid. LCMS (Method A): 2.80 min; m/z: 376.2 $[M+H]^+$.

Step 5: 1-tert-butyl-5-[(6-cyanopyridin-2-yl)amino]-3-[4-(2,2,2-trifluoroethanesulfonamido)phenyl]-1H-pyrazole-4-carboxamide A mixture of 3-(4-aminophenyl)-1-tert-butyl-5-[(6-cyanopyridin-2-yl)amino]-1H-pyrazole-4-carboxamide (50 mg, 0.13 mmol), 2,2,2-trifluoroethane-1-sulfonyl chloride (31.5 mg, 0.17 mmol), pyridine (31.5 mg, 0.39 mmol) and DCM (4 mL) was stirred at RT for 16. The reaction mixture was concentrated and the residue purified by prep-TLC (DCM:MeOH, 20:1) to afford the title product (20 mg, 29%) as a yellow solid. LCMS (Method A): 3.53 min; m/z: 522.2 $[M+H]^+$.

Step 6: 5-[(6-cyanopyridin-2-yl)amino]-3-[4-(2,2,2-trifluoroethanesulfonamido)phenyl]-1H-pyrazole-4-carboxamide (compound 237)

A solution of 1-tert-butyl-5-[(6-cyanopyridin-2-yl)amino]-3-[4-(2,2,2-trifluoroethanesulfonamido)phenyl]-1H-pyrazole-4-carboxamide (20 mg, 0.03 mmol) in DCM (3 mL) and TFA (2 mL) was stirred at RT for 16 h. The reaction mixture was concentrated and the residue was neutralized to pH 7-8 with sat. $Na_2CO_3$. The resulting precipitate was collected by filtration and air dried to afford the title compound (10 mg, 56%) as a white solid. LCMS (Method A): 3.32 min; m/z: 466.1 $[M+H]^+$. $^1H$ NMR (400 MHz, DMSO-$d_6$): 12.99 (br s, 1H), 10.75 (br s, 1H), 9.88 (br s, 1H), 8.21 (d, J=8.4 Hz, 1H), 7.93 (t, J=7.6 Hz, 1H), 7.58 (d, J=8.4 Hz, 2H), 7.45 (d, J=7.2 Hz, 1H), 7.36 (d, J=7.6 Hz, 2H), 4.60 (q, J=10.0 Hz, 2H).

Compound 258

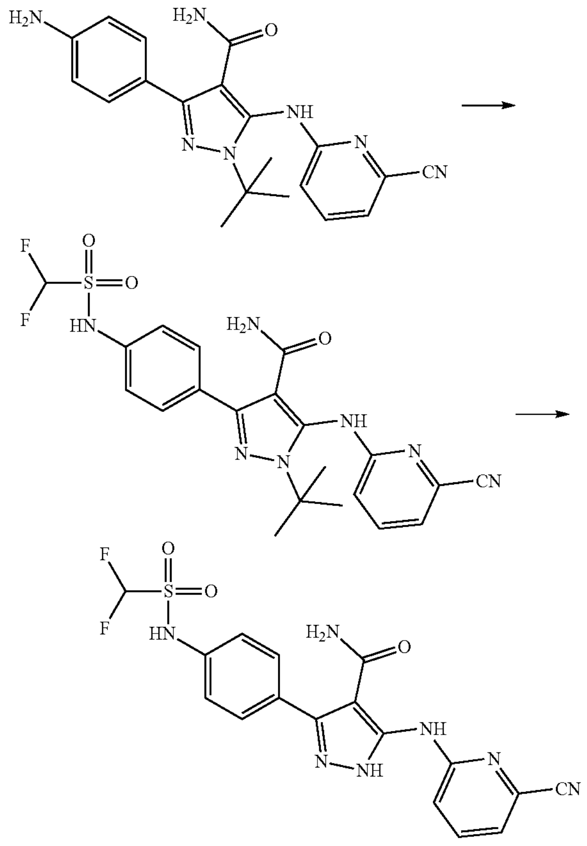

Step 1: 1-tert-butyl-5-[(6-cyanopyridin-2-yl)amino]-3-[4-(difluoromethanesulfonamido)phenyl]-1H-pyrazole-4-carboxamide A mixture of 3-(4-aminophenyl)-1-tert-butyl-5-[(6-cyanopyridin-2-yl)amino]-1H-pyrazole-4-carboxamide (200 mg, 0.53 mmol), $F_2CHSO_2Cl$ (120 mg, 0.79 mmol), pyridine (210 mg, 2.66 mmol) and DCM (10 mL) was stirred at RT for 16 h. The reaction mixture was concentrated and the residue purified by prep-TLC (DCM:MeOH, 20:1) to afford the title product (100 mg, 38%) as a yellow solid. LCMS (Method A): 3.48 min; m/z: 490.2 [M+H]+.

Step 2: 5-[(6-cyanopyridin-2-yl)amino]-3-[4-(difluoromethanesulfonamido)phenyl]-1H-pyrazole-4-carboxamide (compound 258)

A mixture of 1-tert-butyl-5-[(6-cyanopyridin-2-yl)amino]-3-[4-(difluoromethanesulfonamido)phenyl]-1H-pyrazole-4-carboxamide (50 mg, 0.1021 mmol) and 1:1 DCM:TFA (8 mL) was stirred at RT for 16 h. The reaction mixture was concentrated and the residue was neutralized to pH 7-8 with sat. $Na_2CO_3$. The resulting precipitate was collected by filtration and then purified by prep-TLC (DCM:MeOH, 15:1) to afford the title product (20 mg, 45%) as a yellow solid. LCMS (Method A): 3.18 min; m/z: 434.1 $[M+H]^+$. $^1H$ NMR (400 MHz, DMSO-$d_6$): 13.00 (brs, 1H), 9.76 (brs, 1H), 8.19 (d, J=8.4 Hz, 1H), 9.25 (t, J=8.0 Hz, 1H), 7.54 (d, J=8.0 Hz, 2H), 7.44 (d, J=7.2 Hz, 1H), 7.34 (d, J=8.0 Hz, 2H), 7.09 (t, J=12.4 Hz, 1H).

Compound 257

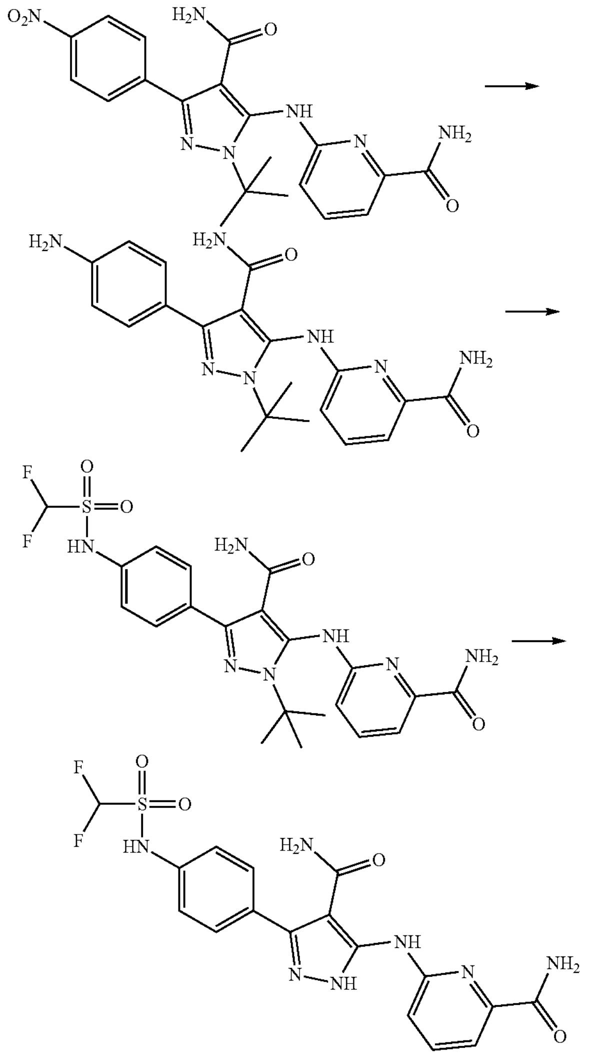

Step 1: 6-((3-(4-aminophenyl)-1-(tert-butyl)-4-carbamoyl-1H-pyrazol-5-yl)amino)picolinamide A mixture of 6-{[1-tert-butyl-4-carbamoyl-3-(4-nitrophenyl)-1H-pyrazol-5-yl]amino}pyridine-2-carboxamide (From Compound 237, 390 mg, 0.9210 mmol) and Zn dust (300 mg, 4.60 mmol) in MeOH (10 mL) and aq. sat. $NH_4Cl$ (2 mL) was stirred at 45° C. overnight. The reaction mixture was filtered and the filtrate was concentrated under reduced pressure. The residue was purified by column chromatography on silica gel (MeOH:DCM, 1:35) to give the title product (320 mg, 88%) as a yellow solid. LCMS (Method A): 2.33 min, m/z: 394.2 $[M+H]^+$.

Step 2: 6-({1-tert-butyl-4-carbamoyl-3-[4-(difluoromethanesulfonamido)phenyl]-1H-pyrazol-5-yl}amino)pyridine-2-carboxamide A mixture of 6-{[3-(4-aminophenyl)-1-tert-butyl-4-carbamoyl-1H-pyrazol yl]amino}pyridine-2-carboxamide (150 mg, 0.38 mmol), $F_2CHSO_2Cl$ (86.0 mg, 0.57 mmol), pyridine (150 mg, 1.90 mmol) and DCM (10 mL) was stirred at RT for 16 h. The reaction mixture was concentrated under reduced pressure and the residue was purified by prep-TLC (DCM:MeOH, 20:1) to afford the title product (75 mg, 39%) as a yellow solid. LCMS (Method A): 3.12 min; m/z: 508.2 $[M+H]^+$.

Step 3: 6-({4-carbamoyl-3-[4-(difluoromethanesulfonamido)phenyl]-1H-pyrazol-5-yl}amino)pyridine-2-carboxamide (compounds 257)

A solution of 6-({1-tert-butyl-4-carbamoyl-3-[4-(difluoromethanesulfonamido)phenyl]-1H-pyrazol-5-yl}amino) pyridine-2-carboxamide (50 mg, 0.09 mmol) in 1:1 DCM:TFA (4 mL) was stirred at RT for 16 h. The reaction mixture was concentrated and the residue was neutralized to pH 7-8 with sat. $Na_2CO_3$. The resulting precipitate was collected by filtration and then dried to afford the title product (30 mg, 68%) as a yellow solid. LCMS (Method A): 2.71 min; m/z: 452.1 $[M+H]^+$. $^1H$ NMR (400 MHz, DMSO-$d_6$): 12.62 (br s, 1H), 9.69 (br s, 1H), 8.16 (br s, 1H), 7.95 (br s, 1H), 7.86 (t, J=7.6 Hz, 1H), 7.52-7.47 (m, 2H), 7.28 s, 1H), 7.22 (d, J=8.8 Hz, 2H), 7.08 (d, J=8.8 Hz, 2H), 6.24 (t, J=54.8 Hz, 1H), 5.82 (br s, 1H).

Compound 115

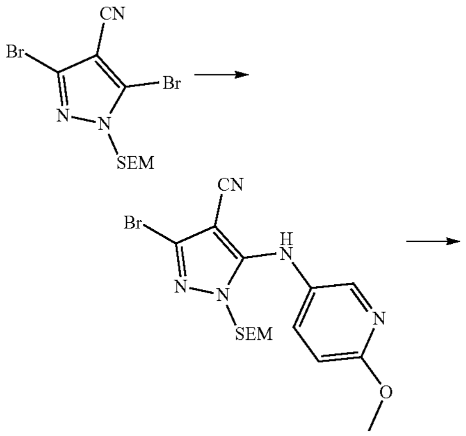

-continued

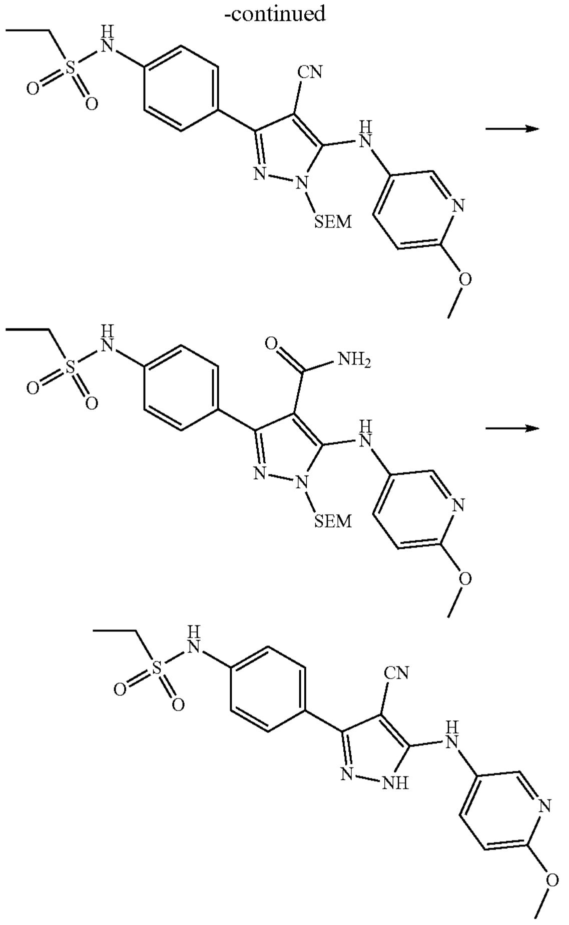

Step 1: 3-bromo-5-((6-methoxypyridin-3-yl)amino)-1-((2-(trimethylsilyl)ethoxy) methyl)-1H-pyrazole-4-carbonitrile A mixture of 3,5-dibromo-1-((2-(trimethylsilyl)ethoxy) methyl)-1H-pyrazole-4-carbonitrile (400 mg, 1.04 mmol), 5-amino-2-methoxypyridine (153 mg, 1.24 mmol), $Pd(OAc)_2$ (23.3 mg, 0.104 mmol), Xantphos (120 mg, 0.208 mmol) and $Cs_2CO_3$ (508 mg, 1.56 mmol) in 1,4-dioxane (20 mL) was stirred at 110° C. for 3 h. The reaction mixture was diluted with EtOAc (25 mL), filtered through Celite and then concentrated under reduced pressure. The crude residue was purified by silica gel column chromatography (PE:EtOAc, 1:0 to 3:2) to afford the title compound (257 mg, 58%) as a white solid. LCMS (Method A): 2.80 min; m/z: 426.0 $[M+H]^+$. $^1H$ NMR (300 MHz, DMSO-$d_6$): 9.23 (br s, 1H), 8.04 (dd, J=2.8, 0.6 Hz, 1H), 7.58 (dd, J=8.8, 2.8 Hz, 1H), 6.84 (dd, J=8.8, 0.6 Hz, 1H), 5.38 (s, 2H), 3.84 (s, 3H), 3.64-3.58 (m, 2H), 0.89-0.84 (m, 2H), −0.04 (s, 9H).

Step 2: N-(4-(4-cyano-5-((6-methoxypyridin-3-yl) amino)-1-((2-(trimethylsilyl) ethoxy)methyl)-1H-pyrazol-3-yl)phenyl)ethanesulfonamide A mixture of 3-bromo-5-((6-methoxypyridin-3-yl) amino)-1-((2-(trimethylsilyl)ethoxy) methyl)-1H-pyrazole-4-carbonitrile (200 mg, 0.471 mmol), N-(4-(4,4,5,5-tetramethyl-1,3,2-dioxaborolan-2-yl)phenyl)ethanesulfonamide (Intermediate C16, 219 mg, 0.706 mmol), $Pd(OAc)_2$ (5.28 mg, 23.5 μmol), SPhos (19.3 mg, 47.1 μmol) and $K_2CO_3$ (194 mg, 1.41 mmol) in 60% aq. MeCN (10 mL) was stirred at 100° C. for 1.5 h. The reaction mixture was concentrated under reduced pressure and the crude residue was purified by silica gel column chromatography (PE:EtOAc, 1:0 to 1:1) to afford the title compound (191 mg, 76%) as a colourless glass. LCMS (Method A): 2.72 min; m/z: 529.2 $[M+H]^+$. $^1H$ NMR (300 MHz, $CDCl_3$): 10.04 (br s, 1H), 8.97 (br s, 1H), 8.02 (dd, J=2.8, 0.6 Hz, 1H), 7.76-7.71 (m, 2H), 7.54 (dd, J=8.8, 2.8 Hz, 1H), 7.32-7.27 (m, 2H), 6.83 (dd, J=8.8, 0.6 Hz, 1H), 5.45 (s, 2H), 3.83 (s, 3H), 3.66-3.61 (m, 2H), 3.14 (q, J=7.3 Hz, 2H), 1.19 (t, J=7.4 Hz, 3H), 0.90-0.84 (m, 2H), −0.061 (s, 9H).

Step 3: 3-(4-(ethylsulfonamido)phenyl)-5-((6-methoxypyridin-3-yl)amino)-1-((2-(trimethylsilyl)ethoxy)methyl)-1H-pyrazole-4-carboxamide A mixture of N-(4-(4-cyano-5-((6-methoxypyridin-3-yl)amino)-1-((2-(trimethylsilyl)ethoxy) methyl)-1H-pyrazol-3-yl)phenyl)ethanesulfonamide (180 mg, 0.340 mmol) and Ghaffar-Parkins catalyst (7.30 mg, 17.0 μmol) in 80% aq. EtOH (10 mL) was stirred at 110° C. for 16 h. The reaction mixture was concentrated under reduced pressure to afford the title compound (181 mg, 97%) a colourless glass. LCMS (Method A): 2.47 min; m/z: 547.2 [M+H]+. $^1H$ NMR (300 MHz, DMSO-$d_6$): 9.93 (br s, 1H), 7.84 (s, 1H), 7.69-7.64 (m, 2H), 7.63 (dd, J=2.9, 0.5 Hz, 1H), 7.25-7.21 (m, 2H), 7.18 (br s, 1H), 7.14 (br s, 1H), 7.12 (dd, J=8.8, 2.9 Hz, 1H), 6.66 (dd, J=8.8, 0.5 Hz, 1H), 5.33 (s, 2H), 3.74 (s, 3H), 3.52-3.46 (m, 2H), 3.12 (q, J=7.4 Hz, 2H), 1.21 (t, J=7.4 Hz, 3H), 0.79-0.74 (m, 2H), −0.10 (s, 9H).

Step 4: 3-(4-(ethylsulfonamido)phenyl)-5-((6-methoxypyridin-3-yl)amino)-1H-pyrazole-4-carboxamide (Compound 115)

A solution of 3-(4-(ethylsulfonamido)phenyl)-5-((6-methoxypyridin-3-yl)amino)-1-((2-(trimethylsilyl)ethoxy) methyl)-1H-pyrazole-4-carboxamide (30 mg, 54.8 μmol) in TFA (0.5 mL) and DCM (0.5 mL) was stirred at RT for 4 h. The reaction mixture was concentrated under reduced pressure and the crude residue was purified by prep-HPLC to afford the title compound as a white solid (6.7 mg, 29%). LCMS (Method A): 1.83 min; m/z: 417.0 $[M+H]^+$. $^1H$ NMR (300 MHz, DMSO-$d_6$): 12.59 (s, 1H), 10.10 (br s, 1H), 8.74 (s, 1H), 8.37 (s, 1H), 7.94 (d, J=6.7 Hz, 2H), 7.52 (d, J=8.2 Hz, 2H), 7.33 (d, J=8.2 Hz, 2H), 6.75 (d, J=8.6 Hz, 1H), 5.75 (s, 1H), 3.79 (s, 3H), 3.21-3.14 (m, 2H), 1.22 (t, J=7.1 Hz, 3H).

Compound 127

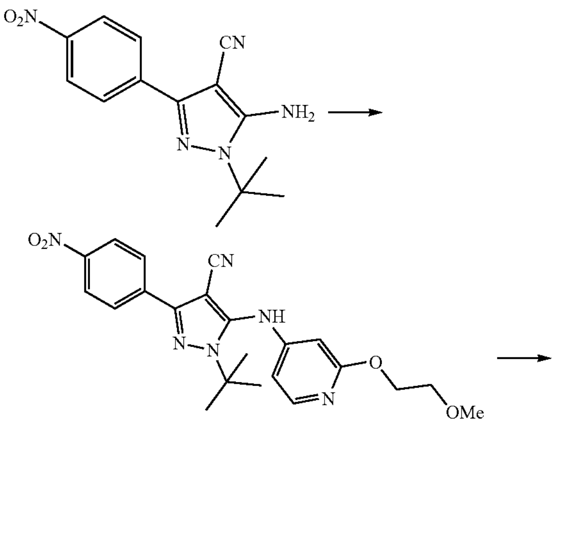

-continued

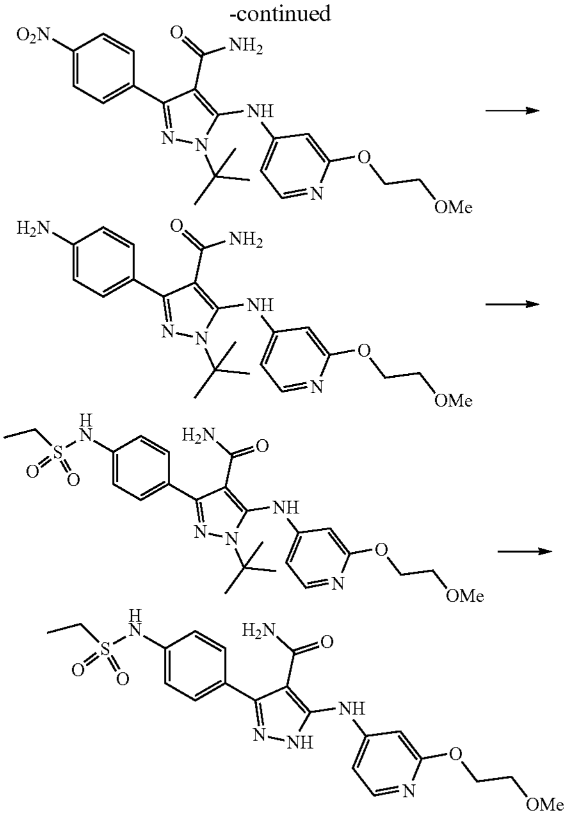

Step 1: 1-(tert-butyl)-3-((2-(2-methoxyethoxy)pyridin-4-yl)amino)-5-(4-nitrophenyl)-1H-pyrazole-4-carbonitrile A mixture of 3-amino-1-(tert-butyl)-5-(4-nitrophenyl)-1H-pyrazole-4-carbonitrile (Intermediate A, 103 mg, 0.360 mmol), 4-bromo-2-(2-methoxyethoxy)pyridine (0.1 g, 0.43 mmol), $Pd(OAc)_2$ (8.11 mg, 0.0400 mmol), Xantphos (36 mg, 0.070 mmol) and $Cs_2CO_3$ (0.18 g, 0.54 mmol) in 1,4-dioxane (3 mL) was stirred at 80° C. under $N_2$ for 0.5 h. The reaction mixture was heated to 100° C. for a further 1.5 h, then diluted with $H_2O$ (50 mL) and extracted with EtOAc (3×40 mL). The combined organic layers were washed with brine, dried ($Na_2SO_4$) and concentrated under reduced pressure. The crude residue was purified by silica gel column chromatography (PE:EtOAc, 1:0 to 1:1) to afford the title compound (105 mg, 67%) as a yellow oil. LCMS (Method A): 2.37 min; m/z: 437.2 $[M+H]^+$.

Step 2: 1-(tert-butyl)-3-((2-(2-methoxyethoxy)pyridin-4-yl)amino)-5-(4-nitrophenyl)-1H-pyrazole-4-carboxamide A mixture of 1-(tert-butyl)-3-((2-(2-methoxyethoxy)pyridin-4-yl)amino)-5-(4-nitrophenyl)-1H-pyrazole-4-carbonitrile (105 mg, 0.240 mmol), $K_2CO_3$ (0.10 g, 0.72 mmol) and 30% aq. $H_2O_2$ (2 mL) in DMSO (5 mL) was stirred at 60° C. for 1 h. An additional charge of $H_2O_2$ was added and the mixture was stirred for a further 2 h. The mixture was diluted with $H_2O$ (150 mL) and extracted with EtOAc (3×100 mL). The combined organic layers were washed with brine, dried ($Na_2SO_4$) and concentrated under reduced pressure. The crude residue was purified by silica gel column chromatography (PE:EtOAc, 1:0 to 1:1) to afford the title product (25 mg, 23%) as a yellow oil. LCMS (Method A): 2.00 min; m/z: 455.2 $[M+H]^+$.

Step 3: 5-(4-aminophenyl)-1-(tert-butyl)-3-((2-(2-methoxyethoxy)pyridin-4-yl)amino)-1H-pyrazole-4-carboxamide A mixture of 1-(tert-butyl)-3-((2-(2-methoxyethoxy)pyridin-4-yl)amino)-5-(4-nitrophenyl)-1H-pyrazole-4-carboxamide (25 mg, 0.05 mmol) 10% Pd/C (5 mg) and MeOH (5 mL) was stirred at RT under $H_2$ overnight. The reaction mixture was filtered over celite and concentrated under reduced pressure to afford the title product (21 mg, 90%) as a yellow oil that solidified upon standing. LCMS (Method A): 1.52 min; m/z: 425.2 $[M+H]^+$.

Step 4: 1-(tert-butyl)-5-(4-(ethylsulfonamido)phenyl)-3-((2-(2-methoxyethoxy)pyridin-4-yl)amino)-1H-pyrazole-4-carboxamide A mixture of 5-(4-aminophenyl)-1-(tert-butyl)-3-((2-(2-methoxyethoxy)pyridin-4-yl)amino)-1H-pyrazole-4-carboxamide (21 mg, 0.050 mmol), $EtSO_2Cl$ (0.01 mL, 0.10 mmol) and pyridine (0.04 mL, 0.49 mmol) in DCM (2 mL) was stirred at RT for 1 h. The reaction mixture was diluted with $H_2O$ (20 mL) and extracted with EtOAc (3×20 mL). The combined organic layers were washed with brine, dried ($Na_2SO_4$) and concentrated under reduced pressure. The crude residue was purified by silica gel column chromatography (DCM:MeOH, 1:0 to 9:1) to afford the title product (12 mg, 47%) as an off white solid. LCMS (Method A): 1.82 min; m/z: 517.2 $[M+H]^+$.

Step 5: 5-(4-(ethylsulfonamido)phenyl)-3-((2-(2-methoxyethoxy)pyridin-4-yl) amino)-1H-pyrazole-4-carboxamide (Compound 127)

A solution of 1-(tert-butyl)-5-(4-(ethylsulfonamido)phenyl)-3-((2-(2-methoxyethoxy)pyridin-4-yl)amino)-1H-pyrazole-4-carboxamide (12 mg, 0.020 mmol) in TFA (1 mL) and DCM (1 mL) was stirred at RT for 5 h. The reaction mixture was concentrated under reduced pressure and the crude residue was purified by SCX cartridge (MeOH, then 2.0 M $NH_3$ in MeOH) to afford the title product (10 mg, 93%) as a cream solid. LCMS (Method A): 1.64 min; m/z: 461.2 $[M+H]^+$. $^1H$ NMR (400 MHz, MeOD-$d_4$): 7.85 (d, J=5.7 Hz, 1H), 7.59 (d, J=8.7 Hz, 2H), 7.43 (d, J=8.7 Hz, 2H), 7.22 (br s, 1H), 6.92 (dd, J=5.9, 1.9 Hz, 1H), 4.35 (m, 2H), 3.76 (m, 2H), 3.43 (s, 3H), 3.21 (q, J=7.3 Hz, 2H), 1.35 (t, J=7.5 Hz, 2H).

Following the full synthesis of compound 127, starting from 5-(4-aminophenyl)-1-(tert-butyl)-3-((2-(2-methoxyethoxy)pyridin-4-yl)amino)-1H-pyrazole-4-carboxamide with the corresponding sulfonyl chloride as described in step 4, the following compounds (Table 12) were prepared:

TABLE 12

| Compound No | Name | Structure | LCMS data | $^1H$ NMR data | SM |
|---|---|---|---|---|---|
| 122 | 5-((2-(2-methoxyethoxy) pyridin-4-yl)amino)-3-(4-(methylsulfonamido) phenyl)-1H-pyrazole-4-carboxamide | 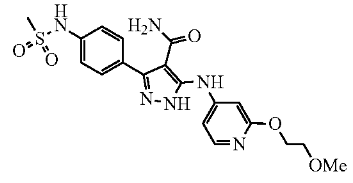 [SMILES: COCCOc1cc(Nc2[nH]nc(-c3ccc(NS(C)(=O)=O)cc3)c2C(N)=O)ccn1] | LCMS (Method A): 2.25 min; m/z: 447.0 $[M + H]^+$. | $^1H$ NMR (400 MHz, MeOD-$d_4$): 7.85 (d, J = 5.2 Hz, 1H), 7.59-7.42 (m, 4H), 7.25 (brs, 1H), 6.95 (d, J = 8.0 Hz, 1H), 4.35 (t, J = 4.4 Hz, 2H), 3.75 (t, J = 4.4 Hz, 2H), 3.44 (s, 3H), 3.06 (s, 3H). | methanesulfonyl chloride |
| 114 | 5-((2-(2-methoxyethoxy) pyridin-4-yl)amino)-3-(4-((trifluoromethyl) sulfonamido) phenyl)-1H-pyrazole-4-carboxamide | 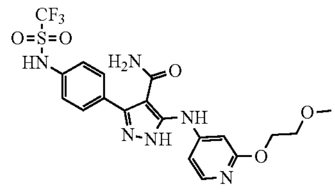 [SMILES: COCCOc1cc(Nc2[nH]nc(-c3ccc(NS(=O)(=O)C(F)(F)F)cc3)c2C(N)=O)ccn1] | LCMS (Method A): 0.62 min; m/z: 501.0 $[M + H]^+$. | $^1H$ NMR (400 MHz, MeOD-$d_4$): 7.94 (d, J = 7.2 Hz, 1H), 7.68-7.62 (m, 3H), 7.49 (d, J = 8.8 Hz, 2H), 7.38 (brs, 1H), 4.5 (t, J = 4.0 Hz, 2H), 3.82 (t, J = 4.0 Hz, 2H), 3.43 (s, 3H). | trifluoro methanesulfonyl chloride |
| 221 | 3-(4-((N,N-dimethylsulfamoyl) amino)phenyl)-5-((2-(2-methoxyethoxy) pyridin-4-yl)amino)-1H-pyrazole-4-carboxamide | 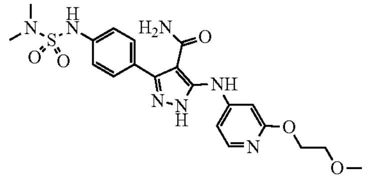 | LCMS (Method A): 2.42 min; m/z: 476.0 $[M + H]^+$. | $^1H$ NMR (400 MHz, MeOD-$d_4$): 7.83 (d, J = 6.0 Hz, 1H), 7.46 (d, J = 8.4 Hz, 2H), 7.34 (d, J = 8.4 Hz, 2H), 7.22 (s, 1H), 6.91 (dd, J = 5.6, 0.8 Hz, 1H), 4.34 (t, J = 4.4 Hz, 2H), 3.75 (t, J = 4.4 Hz, 2H), 3.42 (s, 3H), 2.79 (s, 6H). | dimethylsulfamoyl chloride |

TABLE 12-continued

| Compound No | Name | Structure | LCMS data | $^1$H NMR data | SM |
|---|---|---|---|---|---|
| 120 | 5-((2-(2-methoxyethoxy)pyridin-4-yl)amino)-3-(4-((2-methoxyethyl)sulfonamido)phenyl)-1H-pyrazole-4-carboxamide | 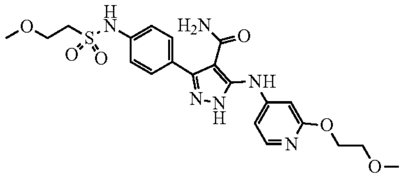 | LCMS (Method A): 0.30 min; m/z: 491.0 [M + H]$^+$. | $^1$H NMR (400 MHz, MeOD-$d_4$): 7.92 (d, J = 6.8 1H), 7.67 (brs, 1H), 7.58 (d, J = 8.4 Hz, 2H), 7.44 (d, J = 8.4 Hz, 2H), 7.36 (d, J = 6.0 Hz, 1H), 4.51 (t, J = 4.4 Hz, 2H), 3.83-3.77 (m, 4H), 3.43-3.40 (m, 5H), 3.30 (m, 3H). | 2-methoxyethyl sulfonylchloride |
| 110 | 3-(4-((cyanomethyl)sulfonamido)phenyl)-5-((2-(2-methoxyethoxy)pyridin-4-yl)amino)-1H-pyrazole-4-carboxamide | 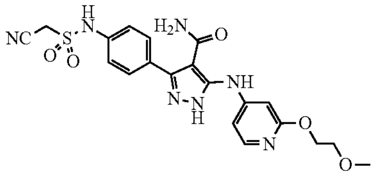 [SMILES: COCCOc1cc(Nc2[nH]nc(-c3ccc(NS(=O)(=O)CC#N)cc3)c2C(N)=O)ccn1] | LCMS (Method A) 2.73 min; m/z: 472.0 [M + H]$^+$. | $^1$H NMR (400 MHz, MeOD-$d_4$): 7.84 (d, J = 6.0 Hz, 1H), 7.62 (d, J = 8.4 Hz, 2H), 7.49 (d, J = 8.4, 2H), 7.23 (s, 1H), 6.93 (dd, J = 5.6, 0.8 Hz, 1H), 4.58 (s, 1H), 4.35 (t, J = 4.4 Hz, 2H), 3.75 (t, J = 4.4, 2H), 3.64 (s, 1H), 3.42 (s, 3H). | cyanomethanesulfonyl chloride |
| 109 | 5-((2-(2-methoxyethoxy)pyridin-4-yl)amino)-3-(4-(prop-2-yn-1-ylsulfonamido)phenyl)-1H-pyrazole-4-carboxamide | 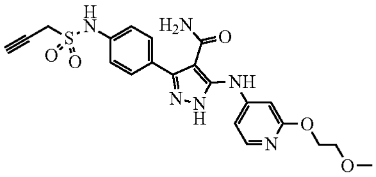 [SMILES: C#CCS(=O)(=O)Nc1ccc(-c2n[nH]c(Nc3ccnc(OCCOC)c3)c2C(N)=O)cc1] | LCMS (Method B) 0.39 min; m/z: 471.0 [M + H]$^+$. | $^1$H NMR (400 MHz, MeOD-$d_4$): 7.94 (d, J = 7.2 Hz, 1H), 7.66 (s, 1H), 7.62-7.59 (m, 2H), 7.50-7.48 (m, 2H), 7.36 (s, 1H), 4.50 (q, J = 2.8 Hz, 2H), 4.14 (d, J = 2.4 Hz, 2H), 3.84-3.81 (m, 2H), 3.43 (s, 3H), 2.90 (t, J = 2.4 Hz, 1H). | prop-2-yne-1-sulfonyl chloride |

Compound 116

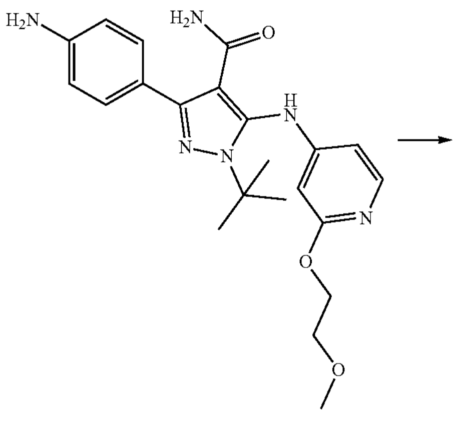

-continued

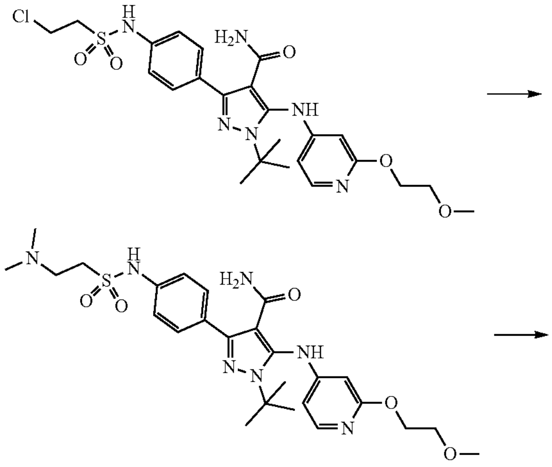

-continued

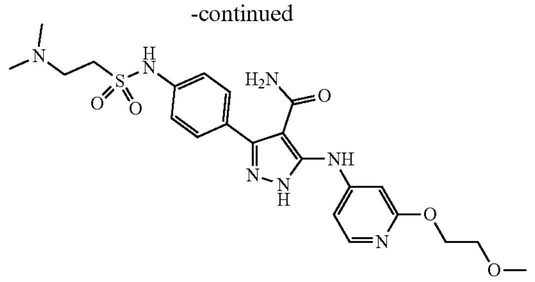

Step 1: 1-(tert-butyl)-3-(4-((2-chloroethyl)sulfonamido)phenyl)-5-((2-(2-methoxyethoxy)pyridin-4-yl)amino)-1H-pyrazole-4-carboxamide A mixture of 3-(4-aminophenyl)-1-tert-butyl-5-{[2-(2-methoxyethoxy) pyridin-4-yl]amino}-1H-pyrazole-4-carboxamide (400 mg, 0.9422 mmol), 2-chloroethane-1-sulfonyl chloride (306 mg, 1.88 mmol) and pyridine (297 mg, 3.76 mmol) in DMF (10 mL) was stirred at RT overnight. The mixture was diluted with $H_2O$ (20 mL) and extracted with DCM (30 mL). The organic layer was dried ($Na_2SO_4$), filtered and concentrated under reduced pressure. The crude residue was purified by silica gel column chromatography (DCM:MeOH, 10:1) to afford a mixture of the title product and the elimination product 1-(tert-butyl)-5-((2-(2-methoxyethoxy)pyridin-4-yl)amino)-3-(4-(vinylsulfonamido)phenyl)-1H-pyrazole-4-carboxamide (100 mg, 19%) as a yellow solid. LCMS (Method B): 0.43 min; m/z: 551.0 $[M+H]^+$.

Step 2: 1-tert-butyl-3-{4-[2-(dimethylamino)ethanesulfonamido]phenyl}-5-{[2-(2-methoxyethoxy)pyridin-4-yl]amino}-1H-pyrazole-4-carboxamide To a solution of 1-tert-butyl-3-[4-(2-chloroethanesulfonamido)phenyl]-5-{[2-(2-methoxyethoxy)pyridin-4-yl]amino}-1H-pyrazole-4-carboxamide (100 mg, 0.18 mmol) in THF (5 mL), was added $Me_2NH$ (905 μL, 1.81 mmol) and the mixture was stirred at 40° C. overnight. Additional $Me_2NH$ (136 μL, 0.27 mmol) was added and the solution was stirred at 60° C. overnight. The reaction mixture was concentrated under reduced pressure and the residue was used directly in the next step without further purification. LCMS (Method B): 0.34 min; m/z: 560.1 $[M+H]^+$.

Step 3: 3-(4-((2-(dimethylamino)ethyl)sulfonamido)phenyl)-5-((2-(2-methoxy ethoxy) pyridin-4-yl)amino)-1H-pyrazole-4-carboxamide A solution of 1-tert-butyl-3-{4-[2-(dimethylamino)ethanesulfonamido]phenyl}-5-{[2-(2-methoxyethoxy)pyridin-4-yl]amino}-1H-pyrazole-4-carboxamide (80 mg, 0.036 mmol) in TFA (1.5 mL) and DCM (1.5 mL) was stirred at RT overnight. The mixture was concentrated under reduced pressure and then triturated with $Et_2O$ (2×5 mL) to afford the title product as the mono TFA salt (28 mg, 38%) as a white solid. LCMS (Method B): 0.33 min; m/z: 505.0 $[M+H]^+$. $^1H$ NMR (400 MHz, MeOD-$d_4$): 7.93 (d, J=5.6 Hz, 1H), 7.63-7.61 (d, 3H), 7.48 (d, J=8.4 Hz, 2H), 7.32 (br s, 1H), 4.49 (t, J=3.6 Hz, 2H), 3.82 (t, J=4.0 Hz, 2H), 3.76 (t, J=7.6 Hz, 2H), 3.63 (t, J=7.6 Hz, 2H), 3.43 (s, 3H), 2.95 (s, 6H). Five active protons not observed.

Compound 117

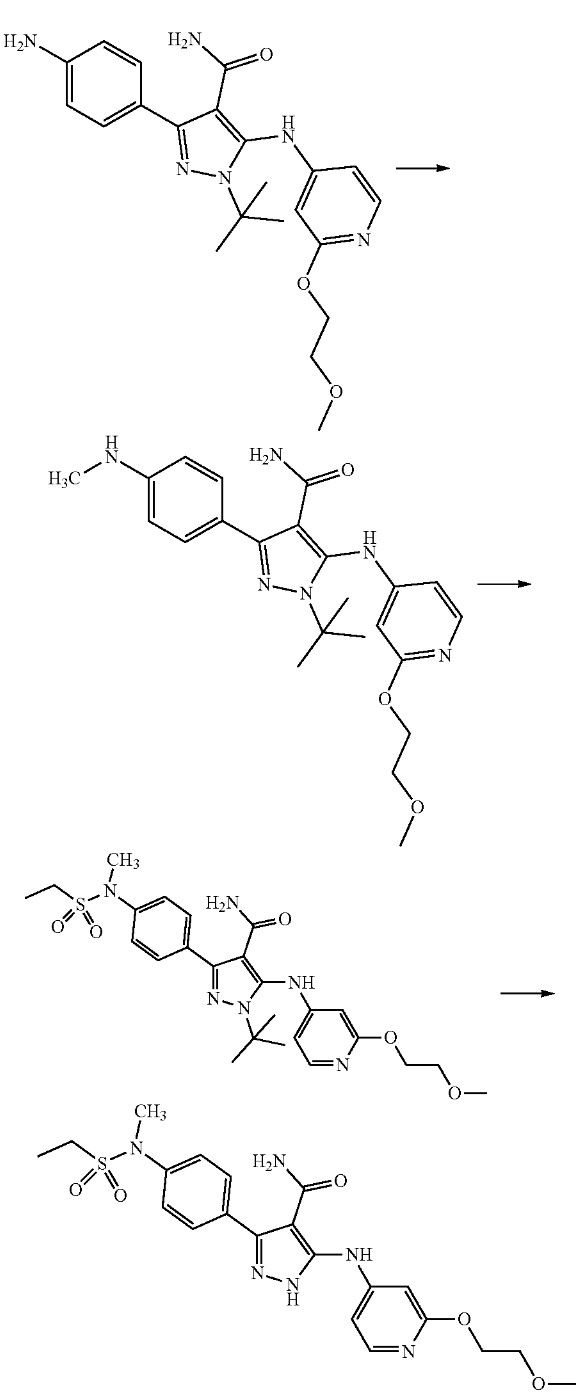

Step 1: 1-(tert-butyl)-5-((2-(2-methoxyethoxy)pyridin-4-yl)amino)-3-(4-(methylamino)phenyl)-1H-pyrazole-4-carboxamide A mixture of 3-(4-aminophenyl)-1-tert-butyl-5-{[2-(2-methoxyethoxy) pyridin-4-yl]amino}-1H-pyrazole-4-carboxamide (100 mg, 0.1177 mmol), NaOMe (25.4 mg, 0.4708 mmol) and paraformaldehyde (35.1 mg, 1.17 mmol) in MeOH (5 mL) was heated to 60° C. under $N_2$ for 3 h. $NaBH_4$ (44.2 mg, 1.17 mmol) was then added and the resulting mixture was stirred at RT overnight. The reaction mixture was concentrated under reduced pressure, diluted with $H_2O$ (20 mL) and extracted with EtOAc (3×20 mL). The combined organic layers were washed with brine, dried ($Na_2SO_4$) and concentrated under reduced pressure. The crude residue was purified by prep-TLC (DCM:MeOH, 12:1) to afford the title compound (45 mg, 44%) as a yellow solid. LCMS (Method B): 0.48 min; m/z: 439.2 $[M+H]^+$.

Step 2: 1-tert-butyl-5-{[2-(2-methoxyethoxy)pyridin-4-yl]amino}-3-[4-(N-methylethanesulfonamido)phenyl]-1H-pyrazole-4-carboxamide To a solution of 1-tert-butyl-5-{[2-(2-methoxyethoxy)pyridin-4-yl]amino}-3-[4-(methylamino)phenyl]-1H-pyrazole-4-carboxamide (40 mg, 0.09121 mmol) in $CHCl_3$ (5 mL), were added $EtSO_2Cl$ (23.4 mg, 0.1824 mmol) and pyridine (28.8 mg, 0.3648 mmol). The mixture was stirred at RT overnight then diluted with $H_2O$ (10 mL) and DCM (20 mL). The organic layer was dried ($Na_2SO_4$) and the crude residue was purified by prep-TLC (DCM:MeOH, 12:1) to afford the title product (13 mg, 27%) as a yellow solid. LCMS (Method B): 1.13 min; m/z: 531.2 $[M+H]^+$.

Step 3: 5-((2-(2-methoxyethoxy)pyridin-4-yl)amino)-3-(4-((2-methoxyethyl) sulfonamido)phenyl)-1H-pyrazole-4-carboxamide (Compound 117)

A solution of 1-tert-butyl-5-{[2-(2-methoxyethoxy)pyridin-4-yl]amino}-3-[4-(N-methylethanesulfonamido)phenyl]-1H-pyrazole-4-carboxamide (13 mg, 0.024 mmol) in TFA (1.5 mL) and DCM (1.5 mL) was stirred at RT overnight. The mixture was then concentrated under reduced pressure to afford the title product as the mono TFA salt (10 mg, 86%) as a brown solid. LCMS (Method B): 2.37 min; m/z: 475.0 $[M+H]^+$. $^1H$ NMR (400 MHz, MeOD-$d_4$): 7.94 (d, J=5.6 Hz, 1H), 7.67-7.62 (m, 5H), 7.36 (s, 1H), 4.50 (t, J=4.0 Hz, 2H), 3.83 (t, J=4.0 Hz, 2H), 3.42 (s, 3H), 3.39 (s, 3H), 3.22 (q, J=7.6 Hz, 2H), 1.35 (t, J=7.6 Hz, 3H).

Compound 86

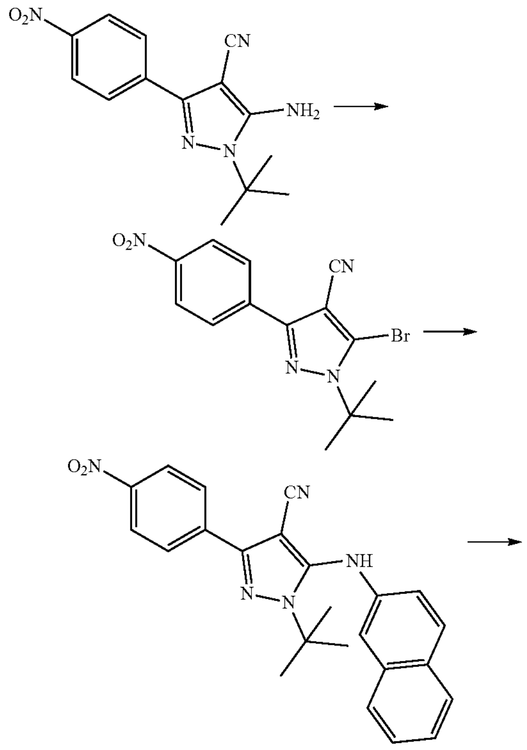

-continued

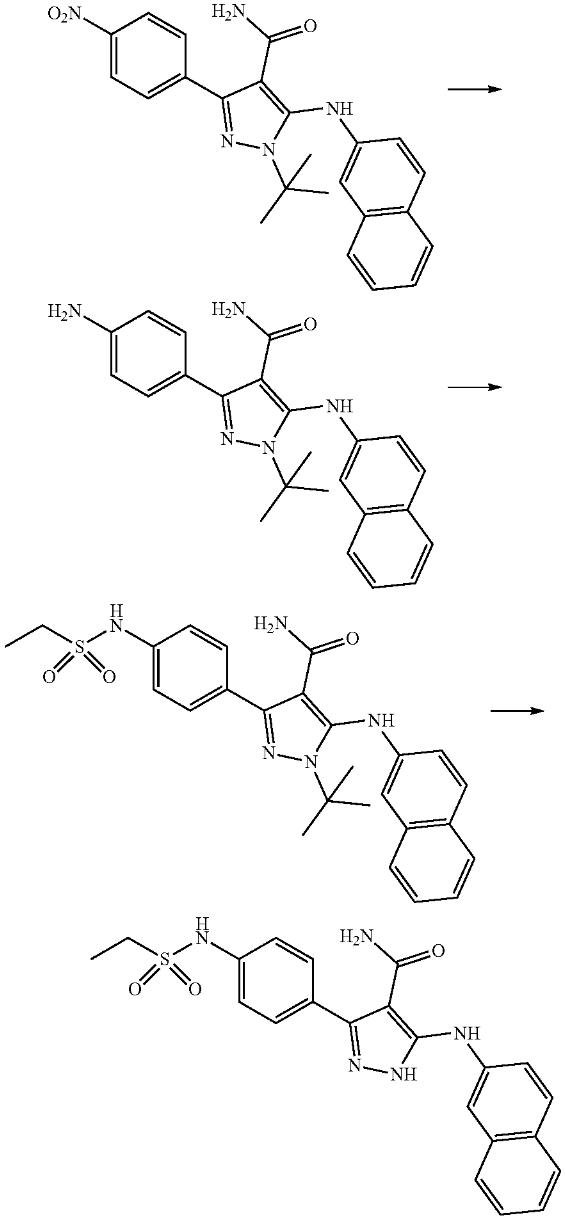

Step 1: 5-bromo-1-(tert-butyl)-3-(4-nitrophenyl)-1H-pyrazole-4-carbonitrile

A mixture of 5-amino-1-tert-butyl-3-(4-nitrophenyl)-1H-pyrazole-4-carbonitrile (500 mg, 1.75 mmol), $CuBr_2$ (448 mg, 2.01 mmol) and isobutyl nitrite (215 mg, 2.09 mmol) in MeCN (60 mL) was stirred at RT under $N_2$ overnight. The reaction mixture was concentrated under reduced pressure and the residue was diluted with EtOAc (100 mL) and sat. aq. $NH_4Cl$ (100 mL). The organic layer was dried ($Na_2SO_4$), concentrated under reduced pressure and the crude residue was purified by silica gel column chromatography (PE:EtOAc, 15:1) to afford the title product (310 mg, 50%) as a yellow solid. LCMS (Method B): 2.13 min; m/z: 349.0, 351.0 $[M+H]^+$. $^1H$ NMR (400 MHz, DMSO-$d_6$): 8.41 (d, J=8.8 Hz, 2H), 8.11 (d, J=9.2 Hz, 2H), 1.77 (s, 1H).

Step 2: 1-tert-butyl-5-[(naphthalen-2-yl)amino]-3-(4-nitrophenyl)-1H-pyrazole-4-carbonitrile A mixture of 5-bromo-1-tert-butyl-3-(4-nitrophenyl)-1H-pyrazole-4-carbonitrile (2 g, 5.72 mmol), naphthalen-2-amine (819 mg, 5.72 mmol), $Pd_2(dba)_3$ (523 mg, 0.5720 mmol), Xantphos (659 mg, 1.14 mmol) and $Cs_2CO_3$ (5.57 g, 17.1 mmol) in degassed 1,4-dioxane (50 mL) was stirred at 100° C. overnight. The reaction mixture was diluted with DCM (150 mL), filtered and concentrated under reduced pressure. The crude residue was purified by silica gel column chromatography (PE:EtOAc, 5:1) to afford the title product (970 mg, 41%) as a yellow solid. LCMS (Method A): 3.92 min; m/z: 412.1 $[M+H]^+$.

Step 3: 1-tert-butyl-5-[(naphthalen-2-yl)amino]-3-(4-nitrophenyl)-1H-pyrazole-4-carboxamide A mixture of 1-tert-butyl-5-[(naphthalen-2-yl)amino]-3-(4-nitrophenyl)-1H-pyrazole-4-carbonitrile (970 mg, 2.35 mmol), 30% aq. $H_2O_2$ (15 mL), 5% aq. NaOH (1.5 mL) and DMSO (15 mL) in EtOH (30 mL) was stirred at 80° C. overnight. The reaction mixture was concentrated under reduced pressure and diluted with $H_2O$. The precipitated solids were collected by filtration and dried under reduced pressure to afford the title product (1.0 g, 100%) as a yellow solid. LCMS (Method A): 2.12 min; m/z: 430.2 $[M+H]^+$.

Step 4: 3-(4-aminophenyl)-1-tert-butyl-5-[(naphthalen-2-yl)amino]-1H-pyrazole-4-carboxamide A mixture of 1-tert-butyl-5-[(naphthalen-2-yl)amino]-3-(4-nitrophenyl)-1H-pyrazole-4-carboxamide (500 mg, 1.16 mmol) and 10% Pd/C (100 mg) in i-PrOH (15 mL) was stirred at RT under $H_2$ overnight. The reaction mixture was filtered, concentrated under reduced pressure and the crude residue was purified by silica gel column chromatography (DCM:MeOH, 15:1) to afford the title product (160 mg, 34%) as a yellow solid. LCMS (Method A): 2.97 min; m/z: 399.9 $[M+H]^+$.

Step 5: 1-tert-butyl-3-(4-ethanesulfonamidophenyl)-5-[(naphthalen-2-yl)amino]-1H-pyrazole-4-carboxamide A mixture of 3-(4-aminophenyl)-1-tert-butyl-5-[(naphthalen-2-yl)amino]-1H-pyrazole-4-carboxamide (160 mg, 0.401 mmol), $EtO_2Cl$ (61.7 mg, 0.48 mmol) and pyridine (76.0 mg, 0.9612 mmol) in $CHCl_3$ (7 mL) was stirred at RT overnight. The reaction mixture was concentrated under reduced pressure and the crude residue was purified by prep-TLC (DCM:MeOH, 12:1) to afford the title product (80 mg, 41%) as a yellow solid. LCMS (Method A): 4.02 min; m/z: 492.2 $[M+H]^+$.

Step 6: 3-(4-(ethylsulfonamido)phenyl)-5-(naphthalen-2-ylamino)-1H-pyrazole-4-carboxamide (compound 86)

A solution of 1-tert-butyl-3-(4-ethanesulfonamidophenyl)-5-[(naphthalen-2-yl)amino]-1H-pyrazole-4-carboxamide (75 mg, 0.1525 mmol) in TFA (3 mL) and DCM (3 mL) was stirred at RT overnight. The reaction mixture was concentrated under reduced pressure and the residue was basified to pH 9-10 with $NH_4OH$. The precipitated solids were collected by filtration, washed ($H_2O$) and dried under reduced pressure to afford the title product (20 mg, 30%) as a yellow solid. LCMS (Method A): 3.70 min; m/z: 436.1 $[M+H]^+$. $^1H$ NMR (400 MHz, DMSO-$d_6$): 12.73 (s, 1H), 10.11 (br s, 1H), 9.23 (s, 1H), 8.23 (s, 1H), 7.78 (m, 2H), 7.70 (d, J=8.0 Hz, 1H), 7.56 (d, J=8.0 Hz, 2H), 7.47-7.35 (m, 4H), 7.27 (t, J=7.2 Hz, 1H), 6.07 (br s, 1H), 3.18 (q, J=6.8 Hz, 2H), 1.23 (t, J=3.2 Hz, 3H).

Compound 100

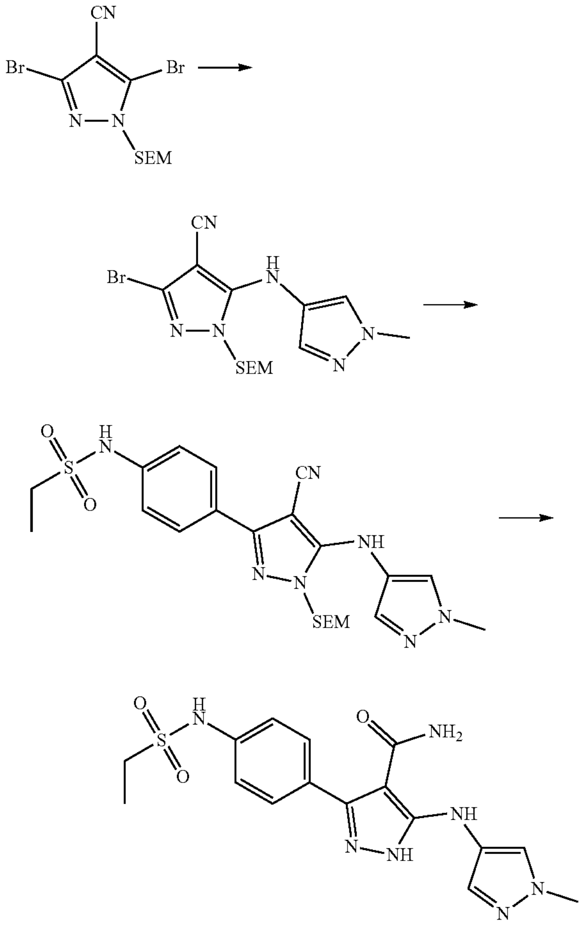

Step 1: 3-bromo-5-[(1-methyl-1H-pyrazol-4-yl)amino]-1-{[2-(trimethylsilyl)ethoxy]methyl}-1H-pyrazole-4-carbonitrile A mixture of 3,5-dibromo-1-{[2-(trimethylsilyl)ethoxy]methyl}-1H-pyrazole-4-carbonitrile (500 mg, 1.31 mmol), 1-methyl-1H-pyrazol-4-amine (127 mg, 1.31 mmol), $Pd_2(dba)_3$ (119 mg, 0.131 mmol), Xantphos (151 mg, 0.262 mmol) and $Cs_2CO_3$ (1.28 g, 3.93 mmol) in 1,4-dioxane (30 mL) was stirred at 100° C. overnight. The mixture was concentrated under reduced pressure and the crude residue was purified by silica gel column chromatography (PE:EtOAc, 1:1) to afford the title product (220 mg, 42%) as a brown oil. LCMS (Method A): 3.05 min; m/z: 396.9, 398.9 [M+H]+. $^1H$ NMR (400 MHz, DMSO-$d_6$): 8.81 (s, 1H), 7.78 (s, 1H), 7.38 (s, 1H), 5.33 (s, 2H), 3.80 (s, 3H), 3.60 (t, J=8.4 Hz, 2H), 0.85 (t, J=8.4 Hz, 2H), 0.00 (s, 9H).

Step 2: N-(4-{4-cyano-5-[(1-methyl-1H-pyrazol-4-yl)amino]-1-{[2-(trimethylsilyl)ethoxy]methyl}-1H-pyrazol-3-yl}phenyl)ethane-1-sulfonamide A mixture of 3-bromo-5-[(1-methyl-1H-pyrazol-4-yl)amino]-1-{[2-(trimethylsilyl)ethoxy]methyl}-1H-pyrazole-4-carbonitrile (210 mg, 0.5284 mmol) and N-[4-(4,4,5,5-tetramethyl-1,3,2-dioxaborolan-2-yl)phenyl]ethane-1-sulfonamide (164 mg, 0.5284 mmol), Pd(dppf)$Cl_2$ (38.6 mg, 0.05 mmol) and $Na_2CO_3$ (111 mg, 1.05 mmol) in 80% aq. 1,4-dioxane (5 mL) was stirred at 120° C. under microwave irradiation for 1 h. The reaction mixture was diluted with EtOAc (5 mL), filtered and the filtrate concentrated under reduced pressure. The crude residue was purified by silica gel column chromatography (PE:EtOAc, 1:1) to afford the title product (170 mg, 64%) as a brown solid. LCMS (Method A): 2.91 min; m/z: 502.1 $[M+H]^+$. $^1H$ NMR (400 MHz, DMSO-$d_6$): 10.00 (s, 1H), 8.55 (s, 1H), 7.76 (s, 1H), 7.69 (d, J=8.4 Hz, 2H), 7.39 (s, 1H), 7.26 (d, J=8.4 Hz, 2H), 5.41 (s, 2H), 3.81 (s, 3H), 3.64 (t, J=7.6 Hz, 2H), 3.13 (q, J=7.2 Hz, 2H), 1.19 (t, J=7.6 Hz, 2H), 0.87 (t, J=8.0 Hz, 2H), −0.04 (s, 9H).

Step 3: 3-(4-(ethylsulfonamido)phenyl)-5-((1-methyl-1H-pyrazol-4-yl)amino)-1H-pyrazole-4-carboxamide (compound 100)

A mixture of N-(4-{4-cyano-5-[(1-methyl-1H-pyrazol-4-yl)amino]-1-{[2-(trimethylsilyl)ethoxy]methyl}-1H-pyrazol-3-yl}phenyl)ethane-1-sulfonamide (20 mg, 0.039 mmol) in conc. $H_2SO_4$ (1 mL) and $H_2O$ (1 mL) was stirred at 60° C. for 2 d. The reaction mixture was basified to pH 9-10 with $NH_4OH$ and then extracted with DCM (3×10 mL). The combined organic layers were dried ($Na_2SO_4$), concentrated under reduced pressure and the crude residue purified by prep-TLC (DCM:MeOH:$NH_4OH$, 8:1:0.1) to afford the title product (4 mg, 25%) as a white solid. LCMS (Method A): 2.57 min; m/z: 390.0 $[M+H]^+$. $^1H$ NMR (400 MHz, DMSO-$d_6$): 12.39 (br s, 1H), 8.26 (s, 1H), 7.76 (s, 1H), 7.50 (d, J=8.4 Hz, 2H), 7.45 (s, 1H), 7.33 (d, J=8.4 Hz, 2H), 7.20 (br s, 1H), 6.64 (br s, 1H), 3.77 (s, 3H), 3.16 (q, J=7.2 Hz, 2H), 1.22 (m, 3H).

Following the synthesis of Compound 100, starting from 3,5-dibromo-1-{[2-(trimethylsilyl)ethoxy]methyl}-1H-pyrazole-4-carbonitrile with the mentioned intermediate as described in step 1, the following compound (Table 13) was prepared:

Compound 22

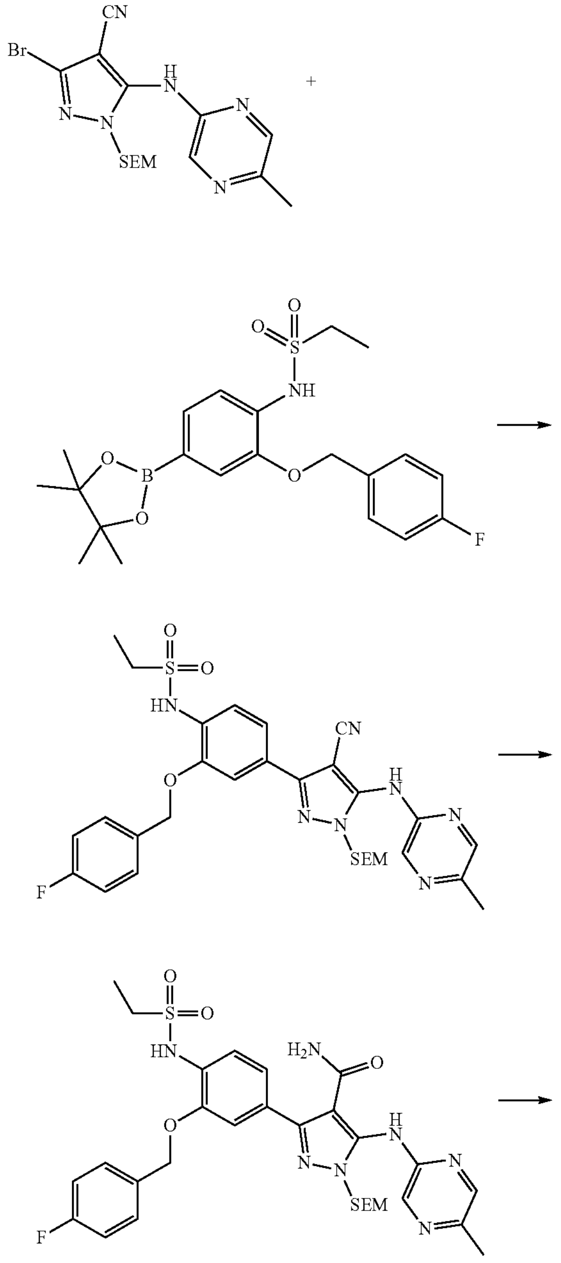

TABLE 13

| Compound No | Name | Structure | LCMS data | $^1H$ NMR data | SM |
|---|---|---|---|---|---|
| 91 | 3-(4-(ethylsulfonamido)phenyl)-5-((1-methyl-1H-pyrazol-3-yl)amino)-1H-pyrazole-4-carboxamide | 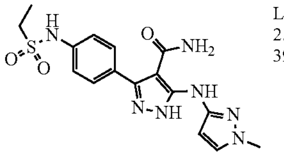 | LCMS (Method A): 2.80 min; m/z: 390.1 $[M + H]^+$. | $^1H$ NMR (400 MHz, MeOD-$d_4$): 12.52 (br s, 1H), 10.00 (brs, 1H), 8.89 (br s, 1H), 7.50 (d, J = 8.0 Hz, 4H), 7.33 (d, J = 8.0 Hz, 2H), 6.39 (brs, 1H), 3.72 (s, 3H), 3.16 (t, J = 7.2 Hz, 2H), 1.22 (t, J = 7.2 Hz, 3H). | 1-methyl-1H-pyrazol-3-amine |

-continued

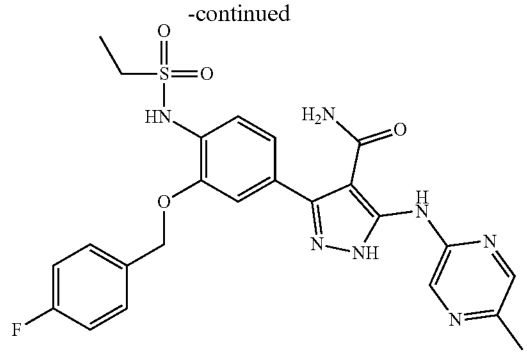

Step 1: N-(4-(4-cyano-5-((5-methylpyrazin-2-yl) amino)-1-((2-(trimethylsilyl) ethoxy)methyl)-1H-pyrazol-3-yl)-2-((4-fluorobenzyl)oxy)phenyl)ethane-sulfonamide A mixture of 3-bromo-5-[(5-methylpyrazin-2-yl)amino]-1-{[2-(trimethylsilyl)ethoxy]methyl}-1H-pyrazole-4-carbonitrile (Intermediate B5, 200 mg, 488 μmol), N-{2-[(4-fluorophenyl)methoxy]-4-(4,4,5,5-tetramethyl-1,3,2-dioxaborolan-2-yl)phenyl}ethane-1-sulfonamide (Intermediate C1, 212 mg, 488 μmol), Pd(dppf)$Cl_2$ (39.8 mg, 48.8 μmol) and $Na_2CO_3$ (103 mg, 976 μmol) in degassed 80% aq. 1,4-dioxane (12.5 mL) was stirred at 100° C. for 1 h under microwave irradiation. The mixture was concentrated under reduced pressure and the crude residue was purified by silica gel column chromatography (PE: EtOAc, 1:1) to afford the title product (200 mg, 64%) as a yellow solid. LCMS (Method A): 4.49 min; m/z: 638.2 $[M+Na]^+$.

Step 2: 3-(4-(ethylsulfonamido)-3-((4-fluorobenzyl) oxy)phenyl)-5-((5-methylpyrazin-2-yl)amino)-1-((2-(trimethylsilyl)ethoxy)methyl)-1H-pyrazole-4-carboxamide A mixture of N-(4-(4-cyano-5-((5-methylpyrazin-2-yl) amino)-1-((2-(trimethylsilyl) ethoxy)methyl)-1H-pyrazol-3-yl)-2-((4-fluorobenzyl)oxy)phenyl)ethanesulfonamide (200 mg, 313 μmol) and Ghaffar-Parkins catalyst in 50% aq. EtOH (20 mL) was stirred at 100° C. overnight. The mixture was concentrated under reduced pressure and the crude residue was purified by prep-TLC (DCM:MeOH, 10:1) to afford the title product (100 mg, 48%) as a yellow solid. LCMS (Method A): 4.14 min; m/z: 656.2 $[M+H]^+$.

Step 3: 3-(4-(ethylsulfonamido)-3-((4-fluorobenzyl) oxy)phenyl)-5-((5-methylpyrazin-2-yl)amino)-1H-pyrazole-4-carboxamide A solution of 3-(4-(ethylsulfonamido)-3-((4-fluorobenzyl)oxy)phenyl)-5-((5-methylpyrazin-2-yl)amino)-1-((2-(trimethylsilyl)ethoxy)methyl)-1H-pyrazole-4-carboxamide (100 mg, 152 μmol) in TFA (2 mL) and DCM (2 mL) was stirred at RT for 1 h. The reaction mixture was neutralized to pH 7-8 with sat. aq. $Na_2CO_3$ and then concentrated under reduced pressure. The crude residue was purified by prep-TLC (DCM:MeOH, 10:1) to afford the title product (40.0 mg, 50%) as a white solid. LCMS (Method A): 3.50 min; m/z: 526.1 $[M+H]^+$. $^1$H NMR (400 MHz, DMSO-$d_6$): 13.05 (s, 1H), 9.51 (s, 1H), 9.17 (s, 1H), 8.11 (s, 1H), 7.62 (dd, J=4.8 Hz, 2H), 7.44 (d, J=9.6 Hz, 2H), 7.24 (t, J=8.8 Hz, 2H), 7.19 (dd, J=1.2 Hz, 8 Hz, 1H), 6.18 (s, 1H), 5.19 (s, 2H), 3.05 (q, J=7.2 Hz, 2H), 2.40 (s, 3H), 1.16 (t, J=7.2 Hz, 3H).

The following compounds (Table 14) were similarly prepared from the appropriate aryl amine starting material according to the method described for the synthesis of 3-(4-(ethylsulfonamido)-3-((4-fluorobenzyl)oxy)phenyl)-5-((5-methylpyrazin-2-yl)amino)-1H-pyrazole-4-carboxamide:

TABLE 14

| Compound No | Name | Structure | LCMS data | $^1$H NMR data | Arylamine |
|---|---|---|---|---|---|
| 34 | 3-(4-(ethylsulfonamido)-3-((4-fluorobenzyl)oxy)phenyl) 5-((5-isopropylpyrazin-2-yl)amino)-1H-pyrazole-4-carboxamide | 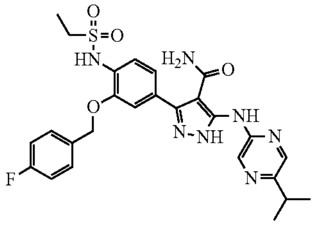 [SMILES: CCS(=O)(=O)Nc1ccc(-c2n[nH]c(Nc3cnc(C(C)C)cn3)c2C(N)=O)cc1OCc1ccc(F)cc1] | LCMS (Method A): 2.93 min; m/z 554.2 [M + H]$^+$. | $^1$H NMR (400 MHz, DMSO-$d_6$): 12.97 (s, 1H), 9.53 (s, 1H), 9.20 (s, 2H), 8.15 (s, 1H), 7.65-7.62 (m, 2H), 7.48-7.41 (m, 2H), 7.28-7.22 (m, 4H), 6.20 (brs, 1H), 5.20 (s, 2H), 3.08-3.03 (m, 3H), 1.25 (d, J = 6.4 Hz, 6H), 1.17 (t, J = 6.8 Hz, 3H). | 5-isopropylpyrazin-2-amine |
| 11 | 3-(4-(ethylsulfonamido)-3-((4-fluorobenzyl)oxy)phenyl) 5-((6-methoxypyridin-2-yl)amino)-1H-pyrazole-4 carboxamide | 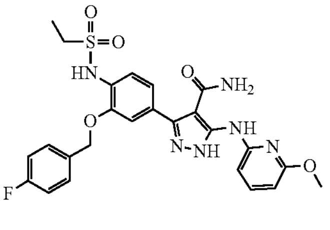 [SMILES: CCS(=O)(=O)Nc1ccc(-c2n[nH]c(Nc3cccc(OC)n3)c2C(N)=O)cc1OCc1ccc(F)cc1] | LCMS (Method A): 3.85 min; m/z 541.1 [M + H]$^+$. | $^1$H NMR (400 MHz, DMSO-$d_6$): 12.83 (s, 1H), 9.33 (s, 1H), 9.12 (s, 1H), 7.62-7.60 (m, 3H), 7.56-7.54 (m, 1H), 7.45 (d, J = 8.0 Hz, 1H), 7.39 (s, 1H), 7.25 (t, J = 8.8 Hz, 2H), 7.18 (d, J = 8.04 Hz, 2H), 6.27 (d, J = 7.6 Hz, 1H), 5.18 (s, 2H), 3.82 (s, 3H), 3.07 (q, J = 7.2 Hz, 2H), 1.16 (t, J = 7.2 Hz, 3H). | 6-methoxypyridin-2-amine |

TABLE 14-continued

| Compound No | Name | Structure | LCMS data | $^1$H NMR data | Arylamine |
|---|---|---|---|---|---|
| 6 | 3-(4-(ethylsulfonamido)-3-((4-fluorobenzyl)oxy)phenyl) 5-(pyridin-3-ylamino)-1H pyrazole-4-carboxamide | 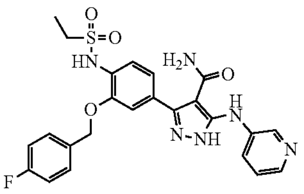 [SMILES: CCS(=O)(=O)Nc1ccc(-c2n[nH]c(Nc3cccnc3)c2C(N)=O)cc1OCc1ccc(F)cc1] | LCMS (Method A): 2.89 min; m/z 511.1 [M + H]$^+$. | $^1$H NMR (400 MHz, MeOD-d$_{64}$): 9.19 (s, 1H), 9.04 (s, 1H), 8.72 (s, 1H), 8.72 (d, J = 5.2 Hz, 2H), 7.63-7.61 (m, 2H), 7.44 (t, J = 8.0 Hz, 2H), 7.29-7.23 (m ,3H), 7.20 (dd, J = 8.4, 1.6 Hz, 1H), 5.20 (s, 2H), 3.05 (t, J = 7.2 Hz, 2H), 1.84 (t, J = 7.6 Hz, 3H). | pyridin-3-amine |
| 18 | 3-(4-(ethylsulfonamido)-3-((4-fluorobenzyl) oxy)phenyl) 5-((2-methoxypyridin-4-yl)amino)-1H-pyrazole-4 carboxamide | 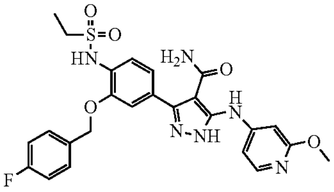 [SMILES: CCS(=O)(=O)Nc1ccc(-c2n[nH]c(Nc3ccnc(OC)c3)c2C(N)=O)cc1OCc1ccc(F)cc1] | LCMS (Method A): 2.90 min; m/z 541.1 [M + H]$^+$. | $^1$H NMR (400 MHz, DMSO-d$_6$): 12.97 (s, 1H), 9.51 (s, 1H), 9.28 (s, 1H), 9.18 (s, 1H), 7.87 (d, J = 5.6 Hz, 1H), 7.62 (q, J = 4.8 Hz, 2H), 7.43 (d, J = 8.4 Hz, 2H), 7.27-7.09 (m, 4H), 5.18 (s, 2H), 3.80 (s, 3H), 3.04 (q, J = 7.2 Hz, 2H), 1.15 (t, J = 7.2 Hz, 3H). | 2-methoxypyridin-4-amine |
| 15 | 3-(4-(ethylsulfonamido)-3-((4-fluorobenzyl) oxy)phenyl) 5-((6-methoxypyrazin-2-yl)amino)-1H-pyrazole-4 carboxamide | 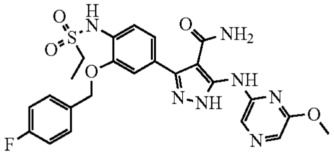 [SMILES: CCS(=O)(=O)Nc1ccc(-c2n[nH]c(Nc3cncc(OC)n3)c2C(N)=O)cc1OCc1ccc(F)cc1] | LCMS (Method A): 3.72 min; m/z 542.1 [M + H]$^+$. | $^1$H NMR (400 MHz, DMSO-d$_6$): 9.51 (brs, 1H). 8.81 (brs. 1H), 7.75 (s, 1H). 7.62-7.59 (m, 2H), 7.44-7.36 (m, 3H), 7.24 (t J = 8.8 Hz, 2H). 7.18 (d, J = 7.8 Hz, 1H). 5.17 (S. 2H), 3.89 (s, 3H), 3.01 (q. J = 7.2 Hz, 2H). 1.15 (t, J = 7.2 Hz, 3H). | 6-methoxypyrazin-2-amine |
| 17 | 3-(4-(ethylsulfonamido)-3-((4-fluorobenzyl) oxy)phenyl) 5-((6-(trifluoromethyl) pyrazin-2 yl)amino)-1H-pyrazole-4 carboxamide | 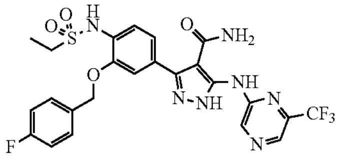 [SMILES: CCS(=O)(=O)Nc1ccc(-c2n[nH]c(Nc3cncc(C(F)(F)F)n3)c2C(N)=O)cc1OCc1ccc(F)cc1] | LCMS (Method A): 3.81 min; m/z 580.1 [M + H]$^+$. | $^1$H NMR (400 MHz, DMSO-d$_6$): 13.21 (s, 1H), 9.99 (s, 1H), 9.41 (s, 1H), 8.55 (s, 1H), 7.62 (d, J = 4.8 Hz, 2H), 7.44 (d, J = 9.6 Hz, 2H), 7.27-7.21 (m, 3H), 5.19 (s, 2H), 3.05 (q, J = 7.2 Hz, 2H), 2.40 (s, 3H), 1.16 (t, J = 7.2 Hz, 3H). | 6-(trifluoromethyl) pyrazin-2-amine |
| 9 | 3-(4-(ethylsulfonamido)-3-((4-fluorobenzyl)oxy) phenyl) 5-((5-(trifluoromethyl) pyrazin-2 yl)amino)-1H-pyrazole-4 carboxamide | 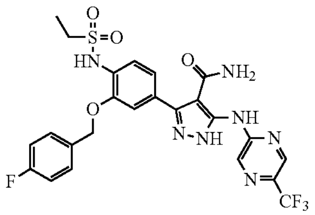 [SMILES: CCS(=O)(=O)Nc1ccc(-c2n[nH]c(Nc3cnc(C(F)(F)F)cn3)c2C(N)=O)cc1OCc1ccc(F)cc1] | LCMS (Method A): 2.88 min; m/z 580.2 [M + H]$^+$. | $^1$H NMR (400 MHz, DMSO-d$_6$): 13.23 (s, 1H), 10.12 (s, 1H), 9.16 (s, 1H), 8.66 (s, 1H), 7.63 (q, J = 6.0 Hz, 2H), 7.44 (d, J = 10.4 Hz, 2H), 7.25 (q, J = 8.8 Hz, 3H), 6.47 (m, 1H), 5.18 (s, 2H), 3.05 (d, J = 7.2 Hz, 2H), 1.15 (t, J = 7.6 Hz, 3H). | 5-(trifluoromethyl) pyrazin-2-amine |
| 14 | 3-(4-(ethylsulfonamido)-3-((4-fluorobenzyl) oxy)phenyl) 5-((5-methoxypyrazin-2-yl)amino)-1H-pyrazole-4 carboxamide | 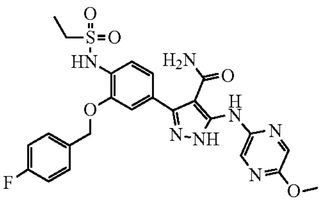 [SMILES: CCS(=O)(=O)Nc1ccc(-c2n[nH]c(Nc3cnc(OC)cn3)c2C(N)=O)cc1OCc1ccc(F)cc1] | LCMS (Method A): 3.60 min; m/z 542.1 [M + H]$^+$. | $^1$H NMR (400 MHz, MeOD-d$_4$): 12.88 (s, 1H), 9.41 (s, 1H), 9.19 (s, 1H), 8.85 (s, 1H), 7.99 (s, 1H), 7.62 (t, J = 5.6 Hz, 2H), 7.45 (d, J = 8.0 Hz, 1H), 7.40 (s, 1H), 7.25 (t, J = 8.8 Hz, 2H), 7.18 (d, J = 8.0 Hz, 1H), 5.19 (s, 2H), 3.87 (s, 3H), 3.05 (q, J = 7.2 Hz, 2H), 1.16 (t, J = 7.2 Hz, 3H). | 5-methoxypyrazin-2-amine |
| 62 | 3-(4-(ethylsulfonamido)-3-((4-fluorobenzyl) oxy)phenyl) 5-(pyrazin-2-ylamino)-1H pyrazole-4-carboxamide | 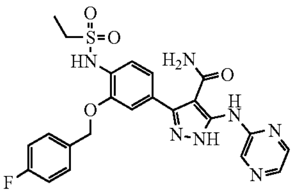 [SMILES: CCS(=O)(=O)Nc1ccc(-c2n[nH]c(Nc3cnccn3)c2C(N)=O)cc1OCc1ccc(F)cc1] | LCMS (Method A): 3.41 min; m/z 512.1 [M + H]$^+$. | $^1$H NMR (400 MHz, MeOD-d$_4$): 8.27 (s, 1H), 8.08 (s, 1H), 7.66 (s, 1H), 7.60 (d, J = 7.2Hz, 1H), 7.47 (s, 2H), 7.26 (s, 1H), 7.19 (d, J = 7.2 Hz, 1H), 7.10 (t, J = 7.2 Hz, 2H), 5.19 (s, 2H), 3.11 (q, J = 4.8 Hz, 2H), 1.29 (t, J = 6.8 Hz, 3H). | pyrazin-2-amine |

Compound 37

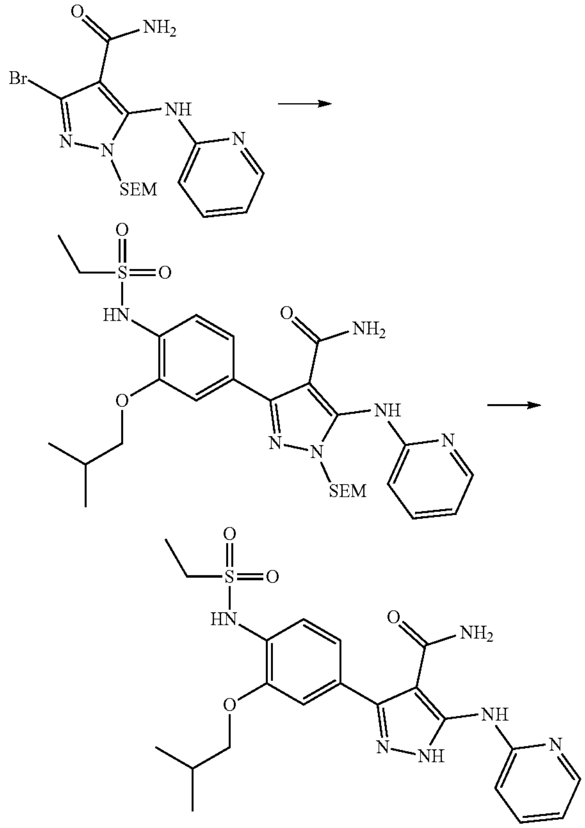

Step 1: 3-[4-ethanesulfonamido-3-(2-methylpropoxy)phenyl]-5-[(pyridin-2-yl)amino]-1-{[2-(trimethylsilyl)ethoxy]methyl}-1H-pyrazole-4-carboxamide A mixture of 3-bromo-5-[(pyridin-2-yl)amino]-1-{[2-(trimethylsilyl)ethoxy]methyl}-1H-pyrazole-4-carboxamide (Intermediate B2, 90 mg, 0.2182 mmol), N-[2-(2-methylpropoxy)-4-(4,4,5,5-tetramethyl-1,3,2-dioxaborolan-2-yl)phenyl]ethane-1-sulfonamide (Intermediate C9, 83.6 mg, 0.218 mmol), Pd(dppf)$Cl_2$ (16.0 mg, 0.022 mmol) and $Na_2CO_3$ (69.3 mg, 0.65 mmol) in 80% aq. 1,4-dioxane (2.5 mL) was stirred at 100° C. for 2 h under microwave irradiation. The mixture was concentrated under reduced pressure, diluted with $H_2O$ (50 mL) and extracted with EtOAc (3×50 mL). The combined organic layers were washed with brine, dried ($Na_2SO_4$) and concentrated under reduced pressure. The crude residue was purified by prep-TLC (DCM:MeOH, 18:1) to afford the title product (110 mg, 86%) as a yellow solid. LCMS (Method A): 4.18 min; m/z: 589.2 $[M+H]^+$.

Step 2: 3-(4-(ethylsulfonamido)-3-isobutoxyphenyl)-5-(pyridin-2-ylamino)-1H-pyrazole-4-carboxamide (compound 37)

A solution of 3-[4-ethanesulfonamido-3-(2-methylpropoxy)phenyl]-5-[(pyridin-2-yl)amino]-1-{[2-(trimethylsilyl)ethoxy]methyl}-1H-pyrazole-4-carboxamide (100 mg, 0.1698 mmol) in TFA (2 mL) and DCM (2 mL) was stirred at RT for 2 h. The mixture was concentrated under reduced pressure and the residue neutralized to pH 7-8 with sat. aq. $Na_2CO_3$. The mixture was diluted with $H_2O$ (30 mL) and the precipitated solids collected by filtration. The crude residue was purified by prep-TLC (DCM:MeOH, 15:1) to afford the title product (20 mg, 25%) as a white solid. LCMS (Method A): 3.06 min; m/z: 459.1 $[M+H]^+$. $^1H$ NMR (400 MHz, MeOD-$d_4$): 12.84 (s, 1H), 9.57 (s, 1H), 9.01 (s, 1H), 8.20 (s, 1H), 7.72 (t, J=8.4 Hz, 1H), 7.43 (d, J=8.0 Hz, 1H), 7.24 (s, 1H), 7.14 (d, J=8.0 Hz, 1H), 6.87 (s, 1H), 6.14 (s, 1H), 3.83 (d, J=6.4 Hz, 2H), 3.11 (q, J=7.2 Hz, 2H), 2.18-2.08 (m, 1H), 1.27 (t, J=7.2 Hz, 3H), 1.02 (d, J=6.8 Hz, 6H).

The following compounds (Table 15) were similarly prepared from Intermediate B1 and the appropriate Intermediate C according to the method described for the synthesis of 3-(4-(ethylsulfonamido)-3-isobutoxyphenyl)-5-(pyridin-2-ylamino)-1H-pyrazole-4-carboxamide:

TABLE 15

| Compound No | Name | Structure | LCMS data | $^1H$ NMR data | SM |
|---|---|---|---|---|---|
| 30 | 3-(4-(ethylsulfonamido)-3-((4-fluorobenzyl)oxy)phenyl)-5-(pyridin-2-ylamino)-1H-pyrazole-4-carboxamide | 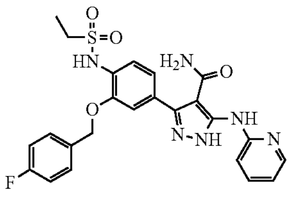 [SMILES: CCS(=O)(=O)Nc1ccc(-c2n[nH]c(Nc3ccccn3)c2C(N)=O)cc1OCc1ccc(F)cc1] | LCMS (Method A): 3.16 min; m/z: 511.1 $[M + H]^+$. | $^1H$ NMR (400 MHz, DMSO-$d_6$): 12.86 (s, 1H), 9.50 (s, 1H), 9.15 (brs, 1H), 8.27-8.18 (m, 1H), 7.97 (d, J = 8.4 Hz, 1H), 7.71 (t, J = 8.0 Hz, 1H), 7.64-7.61 (m, 2H), 7.46-7.40 (m, 2H), 7.25 (t, J = 8.8 Hz, 2H), 7.17 (d, J = 8.0 Hz, 1H), 6.86-6.85 (m, 1H), 5.19 (s, 2H), 3.05 (q, J = 7.2 Hz, 2H), 1.16 (t, J = 7.2 Hz, 3H). | Intermediate C1 |
| 20 | 3-(3-(benzyloxy)-4-(ethylsulfonamido)phenyl)-5-(pyridin-2-ylamino)-1H-pyrazole-4-carboxamide | 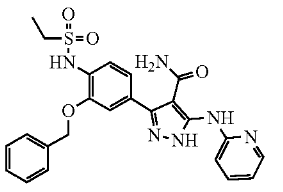 [SMILES: CCS(=O)(=O)Nc1ccc(-c2n[nH]c(Nc3ccccn3)c2C(N)=O)cc1OCc1ccccc1] | LCMS (Method A): 2.96 min; m/z: 493.1 $[M + H]^+$. | $^1H$ NMR (400 MHz, MeOD-$d_4$): 12.87 (s, 1H), 9.44 (s, 1H), 9.11 (s, 1H), 8.17 (s, 1H), 7.95 (d, J = 8.0 Hz, 1H), 7.70 (t, J = 8.0 Hz, 1H), 7.54 (d, J = 7.6 Hz, 2H), 7.41 (d, J = 7.6 Hz, 3H), 7.35 (d, J = 7.2 Hz, 2H), 7.16 (d, J = 7.2 Hz, 1H), 6.85 (s, 1H), 6.12 (s, 1H), 5.19 (s, 2H), 3.04 (q, J = 7.2 Hz, 2H), 1.15 (t, J = 7.2 Hz, 3H). | Intermediate C2 |

TABLE 15-continued

| Compound No | Name | Structure | LCMS data | $^1$H NMR data | SM |
|---|---|---|---|---|---|
| 35 | 3-(3-(cyclohexylmethoxy)-4-(ethylsulfonamido) phenyl)-5-(pyridin-2-ylamino)-1H-pyrazole-4-carboxamide | 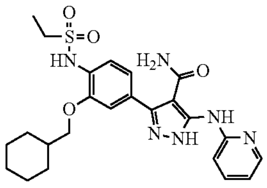 [SMILES: CCS(=O)(=O)Nc1ccc(-c2n[nH]c(Nc3ccccn3)c2C(N)=O)cc1OCC1CCCCC1] | LCMS (Method A): 3.47 min; m/z: 499.2 $[M + H]^+$. | $^1$H NMR (400 MHz, DMSO-$d_6$): 12.82 (s, 1H), 9.50 (s, 1H), 9.23 (s, 1H), 8.18 (s, 1H), 7.97 (d, J = 8.0 Hz, 1H), 7.70 (t, J = 7.6 Hz, 1H), 7.50-7.37 (m, 1H), 7.26- 7.13 (m, 2H), 6.85 (d, J = 5.2 Hz, 1H), 3.86 (d, J = 5.6 Hz, 2H), 3.12 (q, J = 7.2 Hz, 2H), 1.91-1.88 (m, 3H), 1.74-1.65 (m, 3H), 1.28-1.25 (m, 6H), 1.09-1.01 (m, 2H). | Intermediate C3 |
| 39 | 3-(3-((4-chlorobenzyl)oxy)-4-(ethylsulfonamido) phenyl)-5-(pyridin-2-ylamino)-1H-pyrazole-4-carboxamide | 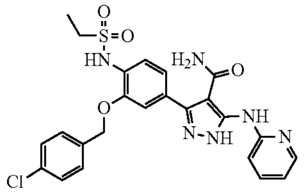 [SMILES: CCS(=O)(=O)Nc1ccc(-c2n[nH]c(Nc3ccccn3)c2C(N)=O)cc1OCc1ccc(Cl)cc1] | LCMS (Method A): 3.33 min; m/z: 527.1 $[M + H]^+$. | $^1$H NMR (400 MHz, DMSO-$d_6$): 12.86 (s, 1H), 9.49 (s, 1H), 9.20 (s, 1H), 8.18 (s, 1H), 7.97 (d, J = 8.0 Hz, 2H), 7.70 (t, J = 8.4 Hz, 1H), 7.48 (d, J = 8.4 Hz, 2H), 7.39 (s, 1H), 7.18 (d, J = 8.0 Hz, 2H), 6.84 (s, 1H), 5.20 (s, 2H), 3.05 (q, J = 7.6 Hz, 2H), 1.16 (t, J = 7.2 Hz, 3H). | Intermediate C4 |
| 38 | 3-(3-((3-chlorobenzyl)oxy)-4-(ethylsulfonamido) phenyl)-5-(pyridin-2-ylamino)-1H-pyrazole-4-carboxamide | 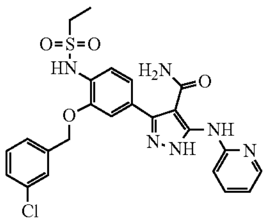 [SMILES: CCS(=O)(=O)Nc1ccc(-c2n[nH]c(Nc3ccccn3)c2C(N)=O)cc1OCc1cccc(Cl)c1] | LCMS (Method A): 3.31 min; m/z: 527.1 $[M + H]^+$. | $^1$H NMR (400 MHz, DMSO-$d_6$): 12.85 (s, 1H), 9.50 (s, 1H), 9.24 (s, 1H), 8.22 (m, 1H), 7.98 (s, 1H), 7.72 (s, 2H), 7.51-7.39 (m, 6H), 7.16 (m, 2H), 6.88 (m, 1H), 5.22 (s, 2H), 3.07 (s, 2H), 1.18 (s, 3H). | Intermediate C5 |
| 27 | 3-(4-(ethylsulfonamido)-3-(pyridin-4-ylmethoxy)phenyl)-5-(pyridin-2-ylamino)-1H-pyrazole-4-carboxamide | 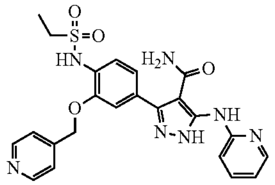 [SMILES: CCS(=O)(=O)Nc1ccc(-c2n[nH]c(Nc3ccccn3)c2C(N)=O)cc1OCc1ccncc1] | LCMS (Method A): 0.35 min; m/z: 494.1 $[M + H]^+$. | $^1$H NMR (400 MHz, DMSO-$d_6$): 13.01 (s, 1H), 9.48 (s, 1H), 9.34 (s, 1H), 8.61 (d, J = 4.8 Hz, 2H), 8.18 (s, 1H), 7.96 (s, 1H), 7.72-7.68 (m, 1H), 7.61 (d, J = 4.8 Hz, 2H), 7.54 (s, 3H), 7.41 (s, 3H), 7.29 (s, 3H), 7.20 (d, J = 7.6 Hz, 1H), 6.85 (s, 1H), 5.30 (s, 2H), 3.09 (q, J = 6.8 Hz, 2H), 1.20 (t, J = 7.2 Hz, 3H). | Intermediate C6 |
| 31 | 3-(4-(ethylsulfonamido)-3-(pyridin-3-ylmethoxy)phenyl)-5-(pyridin-2-ylamino)-1H-pyrazole-4-carboxamide | 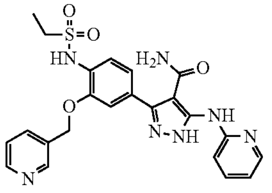 [SMILES: CCS(=O)(=O)Nc1ccc(-c2n[nH]c(Nc3ccccn3)c2C(N)=O)cc1OCc1cccnc1] | LCMS (Method A): 0.38 min; m/z: 494.1 $[M + H]^+$. | $^1$H NMR (400 MHz, DMSO-$d_6$): 9.56 (s, 1H), 8.80 (d, J = 1.6 Hz, 1H), 8.57 (dd, J = 4.8, 1.2 Hz, 1H), 8.20 (s, 1H), 8.02-7.99 (m, 1H), 7.73-7.69 (m, 1H), 7.47-7.43 (m, 3H), 7.20 (dd, J = 8.0, 1.6 Hz, 1H), 6.87 (t, J = 4.2 Hz, 1H), 6.10 (s, 1H), 5.25 (s, 2H), 3.04 (q, J = 7.2 Hz, 2H), 1.15 (t, J = 7.2 Hz, 3H). | Intermediate C7 |
| 36 | 3-(3-(cyclopentylmethoxy)-4-(ethylsulfonamido) phenyl)-5-(pyridin-2-ylamino)-1H-pyrazole-4-carboxamide | 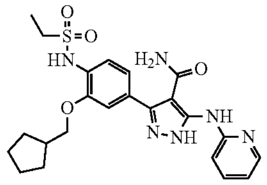 [SMILES: CCS(=O)(=O)Nc1ccc(-c2n[nH]c(Nc3ccccn3)c2C(N)=O)cc1OCC1CCCC1] | LCMS (Method A): 3.31 min; m/z: 485.2 $[M + H]^+$. | $^1$H NMR (400 MHz, MeOD-$d_4$): 9.79 (s, 1H), 8.98 (s, 1H), 8.22 (d, J = 4.8 Hz, 1H), 7.79 (s, 2H), 7.42 (d, J = 8.4 Hz, 1H), 7.26 (s, 1H), 7.15 (d, J = 8.0 Hz, 1H), 6.92 (s, 1H), 6.21 (s, 1H), 3.93 (d, J = 7.2 Hz, 2H), 3.11 (m, 2H), 1.80 (m, 2H), 1.59 (m, 4H), 1.34 (m, 2H), 1.28 (t, J = 7.2 Hz, 3H). | Intermediate C8 |

Compound 223

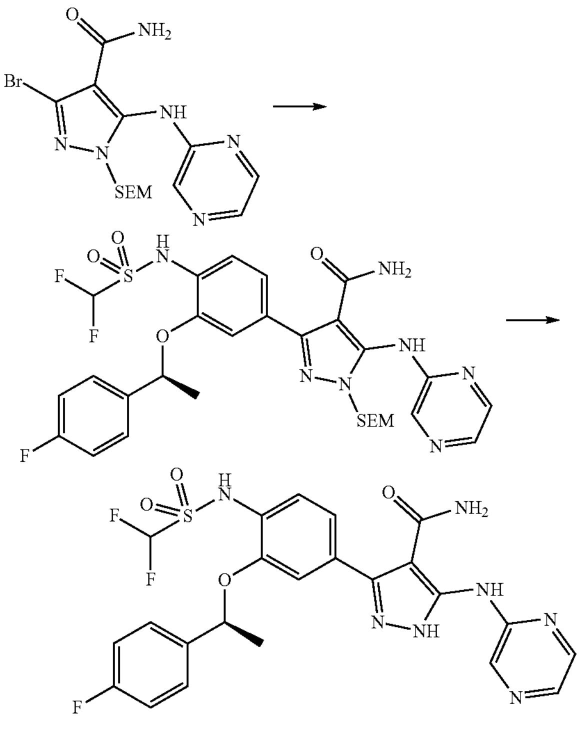

Step 1: 3-[4-(difluoromethanesulfonamido)-3-[(1S)-1-(4-fluorophenyl)ethoxy]phenyl]-5-[(pyrazin-2-yl)amino]-1-{[2-(trimethylsilyl)ethoxy]methyl}-1H-pyrazole-4-carboxamide A mixture of 1,1-difluoro-N-{2-[(1S)-1-(4-fluorophenyl)ethoxy]-4-(4,4,5,5-tetramethyl-1,3,2-dioxaborolan-2-yl)phenyl}methanesulfonamide (Intermediate C11, 23.5 g, 50 mmol), 3-bromo-5-[(pyrazin-2-yl)amino]-1-{[2-(trimethylsilyl)ethoxy]methyl}-1H-pyrazole-4-carboxamide (Intermediate B4, 18.2 g, 44 mmol), $Na_2CO_3$ (10.6 g, 100 mmol) and Pd(dppf)$Cl_2$ (2.5 g, 3 mmol) in degassed 80% aq. 1,4-dioxane (250 mL) was stirred at 100° C. overnight. The mixture was concentrated under reduced pressure and the crude residue was purified by silica gel column chromatography (PE:EtOAc, 1:1) to afford the title compound (23 g, 77%) as a yellow solid. LCMS (Method A): 3.99 min; m/z: 678.2 $[M+H]^+$.

Step 2: 3-[4-(difluoromethanesulfonamido)-3-[(1S)-1-(4-fluorophenyl)ethoxy]phenyl]-5-[(pyrazin-2-yl)amino]-1H-pyrazole-4-carboxamide (compound 223)

A mixture of 3-[4-(difluoromethanesulfonamido)-3-[(1S)-1-(4-fluorophenyl)ethoxy]phenyl]-5-[(pyrazin-2-yl)amino]-1-{[2-(trimethylsilyl)ethoxy]methyl}-1H-pyrazole-4-carboxamide (23 g, 33.9 mmol), DCM (400 mL) and TFA (20 mL) was stirred at RT for 16 h. The mixture was neutralized to pH 7-8 with an sat. $Na_2CO_3$ and the organic phase was washed with water (3×50 mL) and dried ($Na_2SO_4$). The organic layer was concentrated under reduced pressure and the residue purified by silica gel column chromatography (DCM:MeOH, 1:0 to 20:1) to afford the titled product (5.8 g, 31%) as a white solid. LCMS (Method A): 3.45 min; m/z: 548.1 $[M+H]^+$. $^1$H NMR (400 MHz, $CDCl_3$): 12.40 (s, 1H), 10.28 (s, 1H), 8.35 (s, 1H), 8.20-8.15 (m, 2H), 7.61 (d, J=8.0 Hz, 1H), 7.31 (q, J=4.8 Hz, 2H), 7.14 (dd, J=8.0, 1.6 Hz, 1H), 7.04 (t, J=8.4 Hz, 2H), 6.99 (d, J=1.6 Hz, 1H), 6.35 (t, J=53.6 Hz, 1H), 5.40 (q, J=6.4 Hz, 1H), 5.21 (s, 2H), 1.67 (d, J=6.4 Hz, 3H).

The following compounds (Table 16) were similarly prepared from the appropriate Intermediate C and Intermediate B according to the method described for the synthesis of 3-[4-(difluoromethanesulfonamido)-3-[(1S)-1-(4-fluorophenyl)ethoxy]phenyl]-5-[(pyrazin-2-yl)amino]-1H-pyrazole-4-carboxamide:

TABLE 16

| Compound No | Name | Structure | LCMS data | $^1$H NMR data | Intermediates | |
|---|---|---|---|---|---|---|
| 226 | 3-(4-(ethylsulfonamido)-3-((4-fluorobenzyl)oxy)phenyl)-5-(pyridin-2-ylamino)-1H-pyrazole-4-carboxamide | 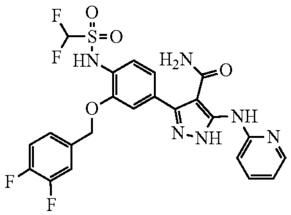 [SMILES: NC(=O)c1c(-c2ccc(NS(=O)(=O)C(F)F)c(OCc3ccc(F)c(F)c3)c2)n[nH]c1Nc1ccccn1] | LCMS (Method D): 4.44 min; m/z: 551.0 [M + H]$^+$. | $^1$H NMR (400 MHz, $CDCl_3$): 12.80 (s, 1H), 10.57 (s, 1H), 9.51 (s, 1H), 8.17 (s, 1H), 7.98 (s, 1H), 7.69 (m, 2H), 7.45 (m, 4H), 7.18 (m, 5H), 5.17 (s, 2H). | B2 | C12 |
| 245 | 3-[4-(difluoromethanesulfonamido)-3-[(1S)-1-(4-fluorophenyl)ethoxy]phenyl]-5-[(5-methylpyrazin-2-yl)amino]-1H-pyrazole-4-carboxamide | 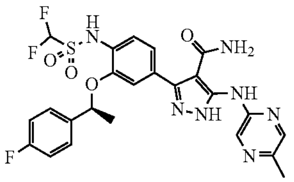 [SMILES: Cc1cnc(Nc2[nH]nc(-c3ccc(NS(=O)(=O)C(F)F)c(O[C@@H](C)c4ccc(F)cc4)c3)c2C(N)=O)cn1] | LCMS (Method A): 3.52 min; m/z: 562.1 [M + H]$^+$. | $^1$H NMR (400 MHz, MeOD-$d_4$): 12.91 (s, 1H), 10.52 (s, 1H), 9.44 (s, 1H), 9.13 (s, 1H), 8.10 (s, 1H), 7.57 (s, 2H), 7.39 (d, J = 7.6 Hz, 1H), 7.20-7.10 (m, 5H), 5.64 (s, 1H), 2.39 (s, 3H), 1.57 (d, J = 5.6 Hz, 3H). | B6 | C11 |

TABLE 16-continued

| Compound No | Name | Structure | LCMS data | $^1$H NMR data | Intermediates | |
|---|---|---|---|---|---|---|
| 271 | (R)-3-(4-((difluoromethyl) sulfonamido)-3-(1-(4-fluorophenyl)ethoxy) phenyl)-5-(pyrazin-2-ylamino)-1H-pyrazole-4-carboxamide | 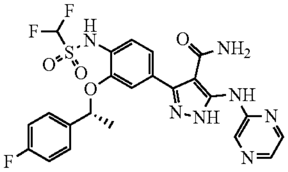 [SMILES: C[C@@H](Oc1cc(-c2n[nH]c(Nc3cnccn3)c2C(N)=O)ccc1NS(=O)(=O)C(F)F)c1ccc(F)cc1] | LCMS (acidic 5 min): 3.67 min; [M + H]$^+$ = 548.2 | $^1$H NMR (400 MHz, DMSO-d$_6$): 12.99 (s, 1H), 10.53 (s, 1H), 9.54 (s, 1H), 9.20 (s, 1H), 8.21 (s, 1H), 8.10 (d, J = 2.5 Hz, 1H), 7.63-7.54 (m, 2H), 7.40 (d, J = 8.1 Hz, 1H), 7.24-6.85 (m, 6H), 5.64 (q, J = 6.1 Hz, 1H), 1.58 (d, J = 6.3 Hz, 3H). | B4 | C13 |
| 291 | 3-(3-((3,4-difluorobenzyl)oxy)-4-((difluoromethyl) sulfonamido)phenyl)-5-((5-methylpyrazin-2-yl)amino)-1H-pyrazole-4-carboxamide | 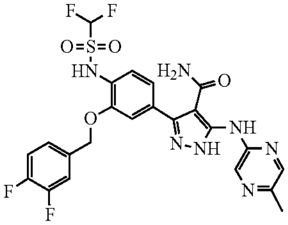 [SMILES: Cc1cnc(Nc2[nH]nc(-c3ccc(NS(=O)(=O)C(F)F)c(OCc4ccc(F)c(F)c4)c3)c2C(N)=O)cn1] | LCMS (Method A): 3.56 min; m/z 566.1 [M + H]$^+$. | $^1$H NMR (400 MHz, DMSO-d$_6$): 12.95 (brs, 1H), 9.51 (brs, 1H), 9.16 (brs, 1H), 8.11 (s, 1H), 7.65 (m, 2H), 7.40 (m, 5H), 7.17 (d, J = 8.0 Hz, 1H), 6.83 (t, J = 51.0 Hz, 1H), 6.11 (brs, 1H), 5.18 (s, 2H), 2.40 (s, 3H). | B6 | C12 |
| 275 | 3-(4-((difluoromethyl) sulfonamido)-3-(thiazol-2-ylmethoxy)phenyl)-5-(pyrazin-2-ylamino)-1H-pyrazole-4-carboxamide | 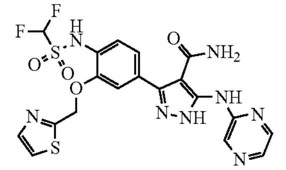 [SMILES: NC(=O)c1c(-c2ccc(NS(=O)(=O)C(F)F)c(OCc3nccs3)c2)n[nH]c1Nc1cnccn1] | LCMS (Method A): 3.25 min, m/z 523.5 [M + H]$^+$. | $^1$H NMR (400 MHz, DMSO-d$_6$): 13.08 (s, 1H), 10.64 (s, 1H), 9.60 (s, 1H), 9.23 (s, 1H), 8.22 (dd, J = 2.6, 1.5 Hz, 1H), 8.11 (d, J = 2.7 Hz, 1H), 7.88 (d, J = 3.2 Hz, 1H), 7.83 (d, J = 3.2 Hz, 1H), 7.55 (s, 1H), 7.43 (d, J = 8.1 Hz, 1H), 7.26 (dd, J = 8.1, 1.8 Hz, 1H), 7.04 (s, 1H), 5.55 (s, 2H). | B4 | C14 |
| 293 | 3-(4-((difluoromethyl) sulfonamido)-3-(1-(oxazol-2-yl)ethoxy)phenyl)-5-(pyrazin-2-ylamino)-1H-pyrazole-4-carboxamide | 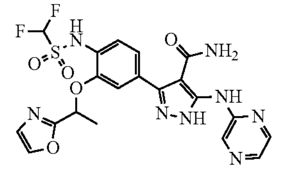 [SMILES: CC(Oc1cc(-c2n[nH]c(Nc3cnccn3)c2C(N)=O)ccc1NS(=O)(=O)C(F)F)c1ncco1] | LCMS (Method A): 3.00 min, m/z 521.1 [M + H]$^+$. | $^1$H NMR (400 MHz, DMSO-d$_6$): 12.84 (s, 1H), 9.89 (s, 1H), 9.35 (s, 1H), 8.28 (s, 1H), 8.17 (s, 1H), 8.13 (s, 1H), 7.48 (d, J = 8.3 Hz, 2H), 7.23 (s, 1H), 7.03 (d, J = 8.4 Hz, 1H), 6.93-6.84 (m, 1H), 6.34 (t, J = 54.8 Hz, 1H), 5.88 (s, 1H), 5.82 (q, J = 6.5 Hz, 1H), 1.68 (d, J = 6.6 Hz, 3H). | B4 | C15 |
| 260 | 3-[4-(difluoromethanesulfonamido)-3-[(1S)-1-(4-fluorophenyl)ethoxy] phenyl]-5-[(pyridin-2-yl)amino]-1H-pyrazole-4-carboxamide | 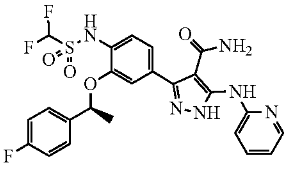 [SMILES: C[C@H](Oc1cc(-c2n[nH]c(Nc3ccccn3)c2C(N)=O)ccc1NS(=O)(=O)C(F)F)c1ccc(F)cc1] | LCMS (Method A): 3.21 min; m/z: 547.1 [M + H]$^+$. | $^1$H NMR (400 MHz, DMSO-d$_6$): 12.77 (s, 1H), 9.46 (s, 1H), 8.17 (s, 1H), 7.95 (d, J = 7.2 Hz, 1H), 7.68 (t, J = 8.4 Hz, 1H), 7.56 (t, J = 6.8 Hz, 2H), 7.39 (d, J = 7.2 Hz, 1H), 7.16 (t, J = 8.4 Hz, 2H), 7.09 (s, 2H), 6.84 (t, J = 52.8 Hz, 1H), 5.64 (q, J = 7.6 Hz, 1H), 1.56 (d, J = 5.6 Hz, 3H). | B2 | C11 |

Compounds 279 and 280

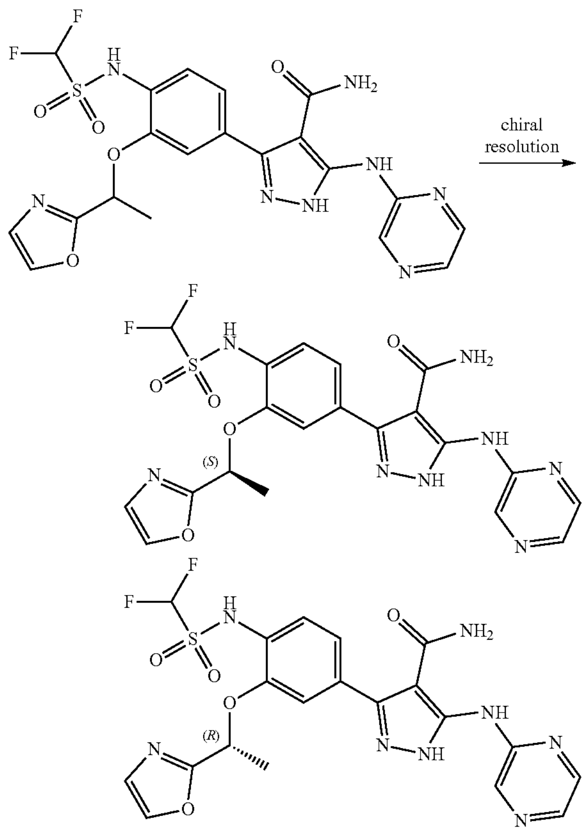

The racemate Compound 293 (500 mg) was subjected to purification by chiral HPLC on a UniChiral CND-5H column, (Column size 50 mm I.D×250 mm L. Mobile phase 60% n-Hexane/40% Ethanol/0.1% TFA (v/v/v), flow rate 90 mL/min, temperature 25° C.). The fractions corresponding to the appropriate peaks were combined and concentrated under reduced pressure. The residue was dissolved in DCM (50 mL), and the mixture was neutralized to pH 7-8 with sat. aq. $Na_2CO_3$. The organic phase was washed with water (3×50 mL), dried ($Na_2SO_4$) and concentrated under reduced pressure. The residue purified by silica gel column chromatography (DCM:MeOH, 1:0 to 20:1) to afford the titled products. The enantiomeric excess was calculated on UniChiral CND-5H, (4.6×250 mm, 50% n-hexanes/50% Ethanol. Flow rate 1 mL/min, injection 5 μL, temperature 30° C.).

Peak 1: (S)-3-(4-((difluoromethyl)sulfonamido)-3-(1-(oxazol-2-yl)ethoxy)phenyl)-5-(pyrazin-2-ylamino)-1H-pyrazole-4-carboxamide (143 mg, retention time 7.49 min, ee >99%). LCMS (Method A): 3.00 min; m/z: 521.1 $[M+H]^+$. $^1H$ NMR (400 MHz, $CDCl_3$): 12.41 (s, 1H), 10.32 (s, 1H), 8.39 (s, 1H), 8.21 (dd, J=2.9, 1.4 Hz, 1H), 8.17 (d, J=2.8 Hz, 1H), 7.66 (dd, J=4.5, 3.7 Hz, 2H), 7.35 (d, J=1.8 Hz, 1H), 7.30 (dd, J=8.2, 1.9 Hz, 1H), 7.12 (d, J=0.8 Hz, 1H), 6.33 (t, J=53.6 Hz, 1H), 5.50 (q, J=6.7 Hz, 1H), 5.44 (s, 2H), 1.84 (d, J=6.7 Hz, 3H).

Peak 2: (R)-3-(4-((difluoromethyl)sulfonamido)-3-(1-(oxazol-2-yl)ethoxy)phenyl)-5-(pyrazin-2-ylamino)-1H-pyrazole-4-carboxamide (147 mg, retention time 9.06 min, ee >99%). LCMS (Method A): 3.00 min; m/z: 521.1 $[M+H]^+$. $^1H$ NMR (400 MHz, $CDCl_3$): 12.41 (s, 1H), 10.32 (s, 1H), 8.39 (s, 1H), 8.21 (dd, J=2.9, 1.4 Hz, 1H), 8.17 (d, J=2.8 Hz, 1H), 7.66 (dd, J=4.5, 3.7 Hz, 2H), 7.35 (d, J=1.8 Hz, 1H), 7.30 (dd, J=8.2, 1.9 Hz, 1H), 7.12 (d, J=0.8 Hz, 1H), 6.33 (t, J=53.6 Hz, 1H), 5.50 (q, J=6.7 Hz, 1H), 5.44 (s, 2H), 1.84 (d, J=6.7 Hz, 3H).

Compound 252

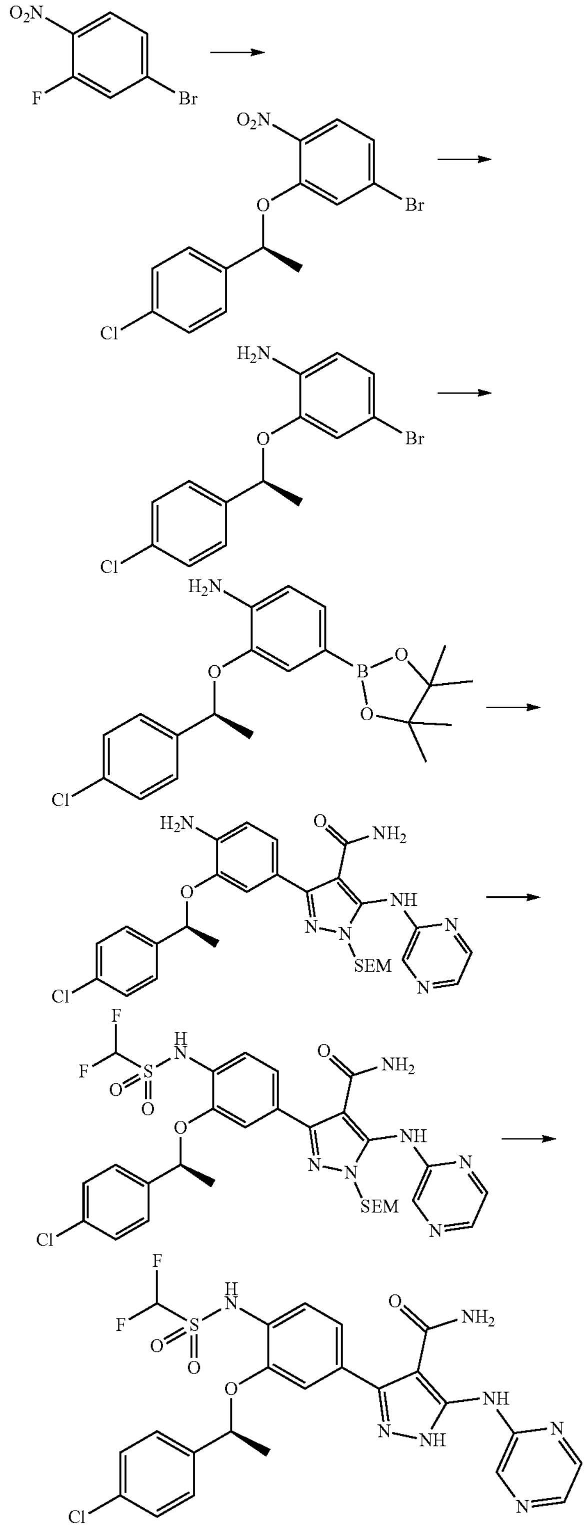

Step 1: 4-bromo-2-[(1S)-1-(4-chlorophenyl)ethoxy]-1-nitrobenzene

To a solution of (1S)-1-(4-chlorophenyl)ethan-1-ol (1.00 g, 6.38 mmol) in THF (20 mL) at 0° C. was added NaH (60% in oil, 763 mg, 19.1 mmol). After 1 h, 4-bromo-2-fluoro-1-nitrobenzene (1.40 g, 6.38 mmol) was added, and the mixture was stirred at RT for 16 h. The reaction mixture was concentrated, diluted with $H_2O$ (50 mL) and extracted with EtOAc (3×30 mL). The combined organic layers were washed (brine), dried ($Na_2SO_4$) and concentrated under reduced pressure. The crude residue was purified by silica gel column chromatography (PE:EtOAc, 10:1) to afford the title product (1.78 g, 78%) as a yellow solid. $^1$H NMR (400 MHz, DMSO-$d_6$): 7.82 (d, J=8.4 Hz, 1H), 7.54 (d, J=2.0 Hz, 1H), 7.46 (s, 4H), 7.29 (dd, J=8.4, 1.6 Hz, 1H), 5.91 (q, J=6.4 Hz, 1H), 1.54 (d, J=6.4 Hz, 3H).

Step 2: 4-bromo-2-[(1S)-1-(4-chlorophenyl)ethoxy]aniline

A mixture of 4-bromo-2-[(1S)-1-(4-chlorophenyl)ethoxy]-1-nitrobenzene (1.78 g, 4.99 mmol), Zn powder (1.62 g, 24.9 mmol), sat. $NH_4Cl$ (3 mL) and MeOH (12 mL) was stirred at 60° C. for 30 min. The reaction mixture was filtered, and the filtrate was concentrated under reduced pressure. The crude residue was purified by silica gel column chromatography (PE:EtOAc, 5:1) to afford the title product (1.40 g, 86%) as a yellow solid. $^1$H NMR (400 MHz, DMSO-$d_6$): 7.48-7.39 (m, 4H), 6.81 (d, J=2 Hz, 1H), 6.75 (dd, J=8.4, 2.4 Hz, 1H), 6.55 (d, J=8.4 Hz, 1H), 5.52 (q, J=6.4 Hz, 1H), 4.99 (s, 2H), 1.52 (d, J=6.4 Hz, 3H).

Step 3: 2-[(1S)-1-(4-chlorophenyl)ethoxy]-4-(4,4,5,5-tetramethyl-1,3,2-dioxaborolan-2-yl)aniline A mixture of 4-bromo-2-[(1S)-1-(4-chlorophenyl)ethoxy]aniline (1.4 g, 4.28 mmol), $B_2pin_2$ (1.19 g, 4.70 mmol), Pd(dppf)$Cl_2$ (174 mg, 214 μmol), KOAc (840 mg, 8.56 mmol) and 1,4-dioxane (20 mL) was stirred at 100° C. for 16 h. The reaction mixture was concentrated, and the residue was diluted with $H_2O$ (200 mL) and extracted with DCM (3×150 mL). The combined organic layers were washed (brine), dried ($Na_2SO_4$) and concentrated under reduced pressure. The crude residue was purified by silica gel column chromatography (PE:EtOAc, 1:1) to afford the title product (1.08 g, 68%) as a yellow oil. $^1$H NMR (400 MHz, DMSO-$d_6$): 7.49-7.38 (m, 4H), 7.00 (dd, J=7.6, 0.8 Hz, 1H), 6.94 (m, 1H), 6.60 (d, J=8.0 Hz, 1H), 5.47 (q, J=6.4 Hz, 1H), 5.24 (s, 2H), 1.50 (d, J=6.4 Hz, 3H), 1.21 (s, 12H).

Step 4: 3-{4-amino-3-[(1S)-1-(4-chlorophenyl)ethoxy]phenyl}-5-[(pyrazin-2-yl)amino]-1-{[2-(trimethylsilyl)ethoxy]methyl}-1H-pyrazole-4-carboxamide A mixture of 2-[(1S)-1-(4-chlorophenyl)ethoxy]-4-(4,4,5,5-tetramethyl-1,3,2-dioxaborolan-2-yl)aniline (945 mg, 2.52 mmol), 3-bromo-5-[(pyrazin-2-yl)amino]-1-{[2-(trimethylsilyl)ethoxy]methyl}-1H-pyrazole-4-carboxamide (Intermediate B4, 987 mg, 2.39 mmol), Pd(dppf)$Cl_2$·DCM (102 mg, 126 μmol), $Na_2CO_3$ (534 mg, 5.04 mmol) and 80% aq. 1,4-dioxane (2.5 mL) was irradiated at 100° C. in a microwave reactor. After 1 h, the reaction mixture was diluted with $H_2O$ (20 mL) and extracted with EtOAc (3×20 mL). The combined organic layers were washed (brine), dried ($Na_2SO_4$) and concentrated under reduced pressure. The crude residue was purified by silica gel column chromatography (DCM:MeOH, 30:1) to afford the title product (561 mg, 38%) as a gray solid. LCMS (Method A): 4.07 min; m/z: 580.2 [M+H]$^+$.

Step 5: 3-{3-[(1S)-1-(4-chlorophenyl)ethoxy]-4-(difluoromethanesulfonamido)phenyl}-5-[(pyrazin-2-yl)amino]-1-{[2-(trimethylsilyl)ethoxy]methyl}-1H-pyrazole-4-carboxamide A mixture of 3-{4-amino-3-[(1S)-1-(4-chlorophenyl)ethoxy]phenyl}-5-[(pyrazin-2-yl)amino]-1-{[2-(trimethylsilyl)ethoxy]methyl}-1H-pyrazole-4-carboxamide (70 mg, 120 μmol) and $F_2CHSO_2Cl$ (27.0 mg, 180 μmol) in 1:1 DCM:pyridine (4 mL) was stirred at RT. After 16 h, the reaction mixture was concentrated and the crude residue was purified by prep-TLC (DCM:MeOH, 15:1) to afford the title product (30 mg, 36%) as a white solid. LCMS (Method D): 5.06 min; m/z: 715.9 [M+Na]$^+$.

Step 6: 3-{3-[(1S)-1-(4-chlorophenyl)ethoxy]-4-(difluoromethanesulfonamido)phenyl}-5-[(pyrazin-2-yl)amino]-1H-pyrazole-4-carboxamide (compound 252)

A solution of 3-{3-[(1S)-1-(4-chlorophenyl)ethoxy]-4-(difluoromethanesulfonamido)phenyl}-5-[(pyrazin-2-yl)amino]-1-{[2-(trimethylsilyl)ethoxy]methyl}-1H-pyrazole-4-carboxamide (40 mg, 57.6 μmol) in 10:1 DCM:TFA (5 mL) was stirred at RT for 16 h. The reaction mixture was neutralized with sat. $Na_2CO_3$ and then concentrated under reduced pressure. The crude residue was purified by prep-TLC (DCM:MeOH, 15:1) to afford the title compound (10.6 mg, 33%) as a white solid. LCMS (Method A): 1.80 min; m/z: 564.1 [M+H]$^+$. $^1$H NMR (400 MHz, DMSO-$d_6$): 10.54 (s, 1H), 9.64 (s, 1H), 9.04 (s, 1H), 8.21-8.20 (m, 1H), 8.10 (d, J=2.8 Hz, 1H), 7.57 (d, J=8.4 Hz, 2H), 7.42 (d, J=8.4 Hz, 2H), 7.39 (d, J=8.0 Hz, 1H), 7.20 (m, 1H), 7.15 (dd, J=8.0, 1.6 Hz, 1H), 7.04 (t, J=52.8 Hz, 1H), 6.20 (br s, 1H), 5.63 (q, J=6.0 Hz, 1H), 1.59 (d, J=6.4 Hz, 3H).

Compound 12

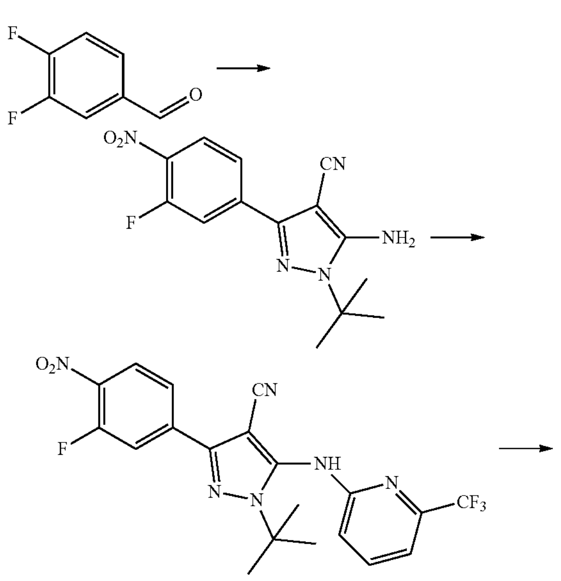

-continued

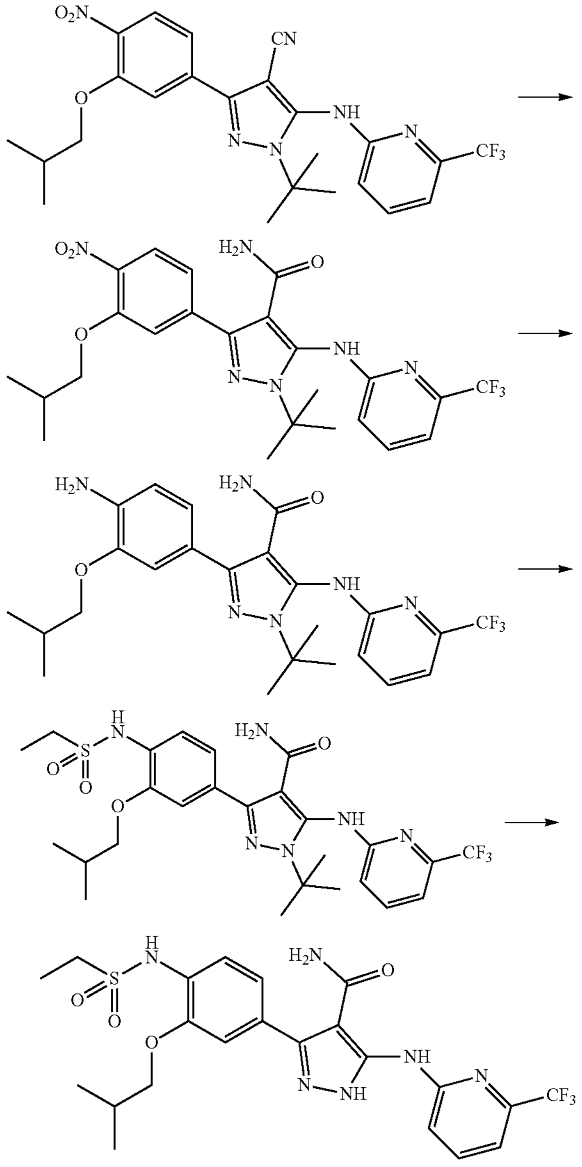

Step 1: 5-amino-1-(tert-butyl)-3-(3-fluoro-4-nitrophenyl)-1H-pyrazole-4-carbonitrile A mixture of 3-fluoro-4-nitrobenzaldehyde (10 g, 59.1 mmol) and t-$BuNHNH_2$·HCl (8.09 g, 65.0 mmol) in DMF (50 mL) was stirred at RT overnight to give a solution of the hydrazone intermediate. LCMS (Method A): 4.38 min; m/z: 240.2 $[M+H]^+$. To this mixture was added NBS (11.4 g, 64.3 mmol) slowly at 0° C. over 5 h, and the mixture was stirred at RT for a further 5 h. The reaction mixture was then cooled to 0° C., and a pre-mixed solution of malonitrile (8.39 g, 127 mmol) and NaOEt (14.4 g, 212 mmol) in EtOH (20 mL) was added. After 2 h at 0° C., the reaction mixture was concentrated under reduced pressure and diluted with $H_2O$ (20 mL). The precipitated solids were collected by filtration, washed with $H_2O$ (2×10 mL) and dried under reduced pressure to afford the title product (15 g, 60%) as a yellow solid. LCMS (Method A): 4.18 min; m/z: 304.1 $[M+H]^+$.

Step 2: 1-tert-butyl-3-(3-fluoro-4-nitrophenyl)-5-{[6-(trifluoromethyl)pyridin-2-yl]amino}-1H-pyrazole-4-carbonitrile A mixture of 5-amino-1-tert-butyl-3-(3-fluoro-4-nitrophenyl)-1H-pyrazole-4-carbonitrile (5 g, 16.4 mmol), 2-chloro-6-(trifluoromethyl)pyridine (3.55 g, 19.6 mmol), $Pd_2(dba)_3$ (1.50 g, 1.64 mmol), Xantphos (1.89 g, 3.28 mmol) and $Cs_2CO_3$ (15.9 g, 49.1 mmol) in degassed 1,4-dioxane (30 mL) was heated at 110° C. overnight. The reaction mixture was concentrated under reduced pressure, diluted with sat. aq. $NaHCO_3$ (20 mL) and extracted with EtOAc (3×20 mL). The combined organics were dried ($Na_2SO_4$), concentrated under reduced pressure and the crude residue purified by silica gel column chromatography (PE:EtOAc, 30:1) to afford the title product (2.5 g, 34%) as a yellow solid. LCMS (Method A): 4.60 min; m/z: 449.1 $[M+H]^+$.

Step 3: 1-tert-butyl-3-[3-(2-methylpropoxy)-4-nitrophenyl]-5-{[6-(trifluoromethyl) pyridin-2-yl]amino}-1H-pyrazole-4-carbonitrile A mixture of 2-methylpropan-1-ol (131 mg, 1.78 mmol), 1-tert-butyl-3-(3-fluoro-4-nitrophenyl)-5-{[6-(trifluoromethyl)pyridin-2-yl]amino}-1H-pyrazole-4-carbonitrile (800 mg, 1.78 mmol) and NaH (876 mg, 7.12 mmol) in THF (12 mL) was stirred at 0° C. overnight. The mixture was concentrated under reduced pressure, diluted with sat. aq. $NaHCO_3$ (20 mL) and extracted with EtOAc (3×20 mL). The combined organic layers were dried ($Na_2SO_4$), concentrated under reduced pressure and the crude residue was purified by silica gel column chromatography (PE:EtOAc, 10:1) to afford the title product (740 mg, 82%) as a yellow solid. LCMS (Method A): 3.55 min; m/z: 503.2 $[M+H]^+$.

Step 4: 1-tert-butyl-3-[3-(2-methylpropoxy)-4-nitrophenyl]-5-{[6-(trifluoromethyl) pyridin-2-yl]amino}-1H-pyrazole-4-carboxamide A mixture of 1-tert-butyl-3-[3-(2-methylpropoxy)-4-nitrophenyl]-5-{[6-(trifluoromethyl)pyridin-2-yl]amino}-1H-pyrazole-4-carbonitrile (680 mg, 1.35 mmol) and Ghaffar-Parkins catalyst (106 mg, 270 μmol) in 50% aq. 1,4-dioxane (22 mL) was stirred at 100° C. overnight. The reaction mixture was concentrated under reduced pressure, diluted with sat. aq. $NaHCO_3$ (20 mL) and extracted with EtOAc (3×20 mL). The combined organics were dried ($Na_2SO_4$) and concentrated under reduced pressure to afford the title product (610 mg, 87%) as a yellow solid. LCMS (Method A): 2.67 min; m/z: 521.2 $[M+H]^+$.

Step 5: 3-[4-amino-3-(2-methylpropoxy)phenyl]-1-tert-butyl-5-{[6-(trifluoromethyl)pyridin-2-yl]amino}-1H-pyrazole-4-carboxamide A mixture of 1-tert-butyl-3-[3-(2-methylpropoxy)-4-nitrophenyl]-5-{[6-(trifluoromethyl)pyridin-2-yl]amino}-1H-pyrazole-4-carboxamide (460 mg, 883 μmol), sat. $NH_4Cl$ (3 mL) and Zn dust (288 mg, 4.41 mmol) in MeOH (12 mL) was stirred at 60° C. overnight. The reaction mixture was concentrated, diluted with sat. $NaHCO_3$ (10 mL) and then extracted with EtOAc (3×10 mL). The combined organic phases were dried ($Na_2SO_4$) and concentrated under reduced pressure to afford the title product (270 mg, 61%) as a yellow solid. LCMS (Method A): 4.08 min; m/z: 491.2 $[M+H]^+$.

Step 6: 1-tert-butyl-3-[4-ethanesulfonamido-3-(2-methylpropoxy)phenyl]-5-{[6-(trifluoromethyl)pyridin-2-yl]amino}-1H-pyrazole-4-carboxamide A mixture of 3-[4-amino-3-(2-methylpropoxy)phenyl]-1-tert-butyl-5-{[6-(trifluoromethyl)pyridin-2-yl]amino}-1H- pyrazole-4-carboxamide (136 mg, 277 μmol), $EtO_2Cl$ (42.6 mg, 332 μmol) and pyridine:$CHCl_3$ (1:1, 6 mL) was stirred at RT overnight. The reaction mixture was concentrated, diluted with sat. $NaHCO_3$ (10 mL) and then extracted with EtOAc (3×10 mL). The combined organic phases were dried ($Na_2SO_4$), concentrated under reduced pressure and the crude residue purified by silica gel column chromatography (DCM:MeOH, 20:1) to afford the title product (79 mg, 49%) as a yellow solid. LCMS (Method A): 4.27 min; m/z: 583.2 $[M+H]^+$.

Step 7: 3-(4-(ethylsulfonamido)-3-isobutoxyphenyl)-5-((6-(trifluoromethyl) pyridin-2-yl)amino)-1H-pyrazole-4-carboxamide (compound 12)

A solution of 1-tert-butyl-3-[4-ethanesulfonamido-3-(2-methylpropoxy)phenyl]-5-{[6-(trifluoromethyl)pyridin-2-yl]amino}-1H-pyrazole-4-carboxamide (100 mg, 171 μmol)

in DCM (4 mL) and TFA (4 mL) was stirred at RT overnight. The reaction mixture was concentrated, neutralized to pH 7-8 with $NH_4OH$, diluted with $H_2O$ (20 mL) and extracted with DCM (3×30 mL). The combined organics were washed with brine, dried ($Na_2SO_4$) and concentrated to afford the title product (30 mg 33%) as a yellow solid. LCMS (Method A): 4.21 min; m/z: 527.1 $[M+H]^+$. $^1H$ NMR (400 MHz, DMSO-$d_6$): 12.97 (s, 1H) 12.97 (s, 1H), 9.77 (s, 1H), 9.02 (s, 1H), 8.22 (d, J=7.6 Hz, 1H), 7.98 (t, J=7.6 Hz, 1H), 7.45 (d, J=8.0 Hz, 1H), 7.23 (t, J=7.6 Hz, 2H), 7.16 (q, J=1.2 Hz, 1H), 3.85 (d, J=6.8 Hz, 2H), 3.14 (q, J=7.5 Hz, 2H), 2.17-2.10 (m, 1H), 1.26 (q, J=7.2 Hz, 3H), 1.03 (d, J=6.4 Hz, 6H).

The following compounds (Table 17) were similarly prepared using the appropriate aryl/alkyl methanol in step 3 according to the method described for the synthesis of 3-(4-(ethylsulfonamido)-3-isobutoxyphenyl)-5-((6-(trifluoromethyl)pyridin-2-yl)amino)-1H-pyrazole-4-carboxamide:

TABLE 17

| Compound No | Name | Structure | LCMS data | $^1H$ NMR data | SM |
|---|---|---|---|---|---|
| 4 | 3-(3-((4-chlorobenzyl)oxy)-4-(ethylsulfonamido)phenyl)-5-((6-(trifluoromethyl)pyridin-2-yl)amino)-1H-pyrazole-4-carboxamide | 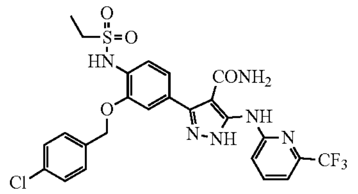 [SMILES: CCS(=O)(=O)Nc1ccc(-c2n[nH]c(Nc3cccc(C(F)(F)F)n3)c2C(N)=O)cc1OCc1ccc(Cl)cc1] | LCMS (Method A): 4.32 min; m/z: 595.1 $[M + H]^+$. | $^1H$ NMR (400 MHz, DMSO-$d_6$): 13.01 (s, 1H), 9.77 (s, 1H), 7.61 (d, J = 8.0 Hz, 2H), 7.49 (q, J = 8.4 Hz, 4H), 7.31 (d, J = 7.6 Hz, 2H), 7.20 (d, J = 8.0 Hz, 2H), 5.21 (s, 2H), 3.07 (q, J = 8.0 Hz, 2H), 1.17 (t, J = 7.2 Hz, 3H). | (4-chlorophenyl) methanol |
| 8 | 3-(4-(ethylsulfonamido)-3-((4-fluorobenzyl)oxy) phenyl)-5-((6-(trifluoromethyl) pyridin-2-yl) amino)-1H-pyrazole-4-carboxamide | 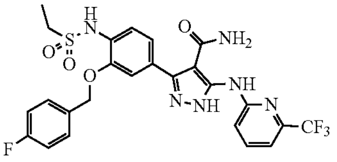 [SMILES: CCS(=O)(=O)Nc1ccc(-c2n[nH]c(Nc3cccc(C(F)(F)F)n3)c2C(N)=O)cc1OCc1ccc(F)cc1] | LCMS (Method A): 3.05 min; m/z: 579.4 [M + H]+. | $^1H$ NMR (400 MHz, DMSO-$d_6$): 13.03 (s, 1H), 9.77 (s, 1H), 9.19 (s, 1H), 8.22 (d, J = 8.4 Hz, 1H), 7.98 (t, J = 8.0 Hz, 1H), 7.62 (t, J = 6.8 Hz, 2H), 7.45 (t, J = 7.2 Hz, 2H), 7.31 (d, J = 7.2 Hz, 1H), 7.27-7.19 (m, 3H), 6.21 (s, 1H), 5.19 (s, 2H), 3.05 (q, J = 6.4 Hz, 2H), 1.16 (t, J = 7.2 Hz, 3H). | (4-fluorophenyl) methanol |
| 3 | 3-(3-((3-chlorobenzyl)oxy)-4-(ethylsulfonamido) phenyl)-5-((6-(trifluoromethyl) pyridin-2-yl) amino)-1H-pyrazole-4-carboxamide | 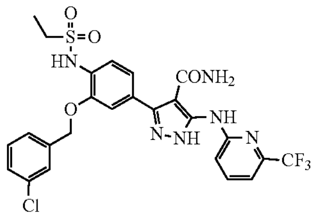 [SMILES: CCS(=O)(=O)Nc1ccc(-c2n[nH]c(Nc3cccc(C(F)(F)F)n3)c2C(N)=O)cc1OCc1cccc(Cl)c1] | LCMS (Method A): 4.31 min; m/z: 595.1 $[M + H]^+$. | $^1H$ NMR (400 MHz, DMSO-$d_6$): 13.04 (s, 1H), 9.76 (s, 1H), 9.30 (s, 1H), 8.21 (d, J = 8.4 Hz, 1H), 7.72 (s, 1H), 7.52 (d, J = 7.2 Hz, 1H), 7.47 (q, J = 7.6 Hz, 4H), 7.30 (d, J = 7.2 Hz, 1H), 7.21 (d, J = 8.0 Hz, 2H), 5.22 (s, 2H), 3.06 (q, J = 8.0 Hz, 2H), 1.18 (t, J = 7.2 Hz, 3H). | (3-chlorophenyl) methanol |
| 16 | 3-(4-(ethylsulfonamido)-3-(pyridin-4-ylmethoxy)phenyl)-5-((6-(trifluoromethyl) pyridin-2-yl) amino)-1H-pyrazole-4-carboxamide | 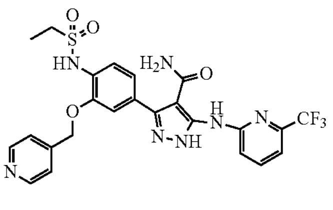 [SMILES: CCS(=O)(=O)Nc1ccc(-c2n[nH]c(Nc3cccc(C(F)(F)F)n3)c2C(N)=O)cc1OCc1ccncc1] | LCMS (Method A): 3.20 min; m/z: 562.1 $[M + H]^+$. | $^1H$ NMR (400 MHz, DMSO-$d_6$): 13.07 (s, 1H), 9.82 (s, 1H), 9.40 (s, 1H), 8.67 (d, J = 4.4 Hz, 1H), 8.27 (d, J = 4.8 Hz, 1H), 8.04 (t, J = 8.0 Hz, 1H), 7.65 (d, J = 5.2 Hz, 2H), 7.55 (d, J = 8.0 Hz, 1H), 7.43 (d, J = 1.2 Hz, 1H), 7.37 (d, J = 7.6 Hz, 1H), 7.29-7.27 (m, 2H) 6.30 (brs, 1H) 5.34 (s, 2H), 3.16 (q, J = 7.2 Hz, 2H), 1.27 (t, J = 7.6 Hz, 3H). | pyridin-4-ylmethanol |

TABLE 17-continued

| Compound No | Name | Structure | LCMS data | $^1$H NMR data | SM |
|---|---|---|---|---|---|
| 33 | 3-(4-(ethylsulfonamido)-3-(pyridin-3-ylmethoxy)phenyl)-5-((6-(trifluoromethyl) pyridin-2-yl) amino)-1H-pyrazole-4-carboxamide | 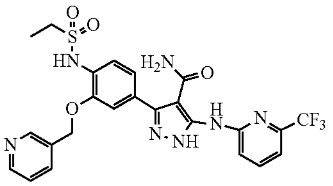 [SMILES: CCS(=O)(=O)Nc1ccc(-c2n[nH]c(Nc3cccc(C(F)(F)F)n3)c2C(N)=O)cc1OCc1cccnc1] | LCMS (Method A): 3.17 min; m/z: 562.1 $[M + H]^+$. | $^1$H NMR (400 MHz, $CDCl_3$): 13.02 (s, 1H), 9.78 (s, 1H), 9.26 (s, 1H), 8.79 (d, J = 1.6 Hz, 1H), 8.57 (dd, J = 4.8, 1.6 Hz, 1H), 8.22 (d, J = 8.4 Hz, 1H), 8.01-7.96 (m, 2H), 7.48-7.44 (m, 3H), 7.31 (d, J = 7.2 Hz, 1H), 7.21 (dd, J = 8.0, 1.2 Hz, 1H), 5.25 (s, 2H), 3.05 (q, J = 7.2 Hz, 2H), 1.15 (t, J = 7.2 Hz, 3H). | pyridin-3-ylmethanol |
| 10 | 3-(3-(cyclopentylmethoxy)-4-(ethylsulfonamido) phenyl)-5-((6-(trifluoromethyl) pyridin-2-yl) amino)-1H-pyrazole-4-carboxamide | 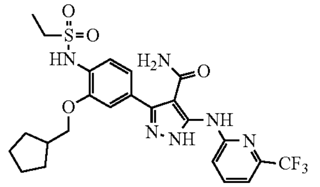 [SMILES: CCS(=O)(=O)Nc1ccc(-c2n[nH]c(Nc3cccc(C(F)(F)F)n3)c2C(N)=O)cc1OCC1CCCC1] | LCMS (Method A): 4.24 min; m/z: 553.2 $[M + H]^+$. | $^1$H NMR (400 MHz, MeOD-$d_4$): 8.30 (d, J = 8.0 Hz, 1H), 7.95 (m, 1H), 7.63-7.56 (m, 1H), 7.40 (m, 1H), 7.26 (d, J = 1.6 Hz, 1H), 7.22-7.19 (m, 1H), 4.02 (d, J = 7.2 Hz, 2H), 3.19-3.13 (m, 2H),2.53-2.46 (m, 1H), 1.94-1.89 (m, 2H),1.71-1.63 (m, 4H), 1.46-1.39 (m, 2H), 1.35 (t, J = 8.0 Hz, 3H). | cyclopentylmethanol |

Compound 5

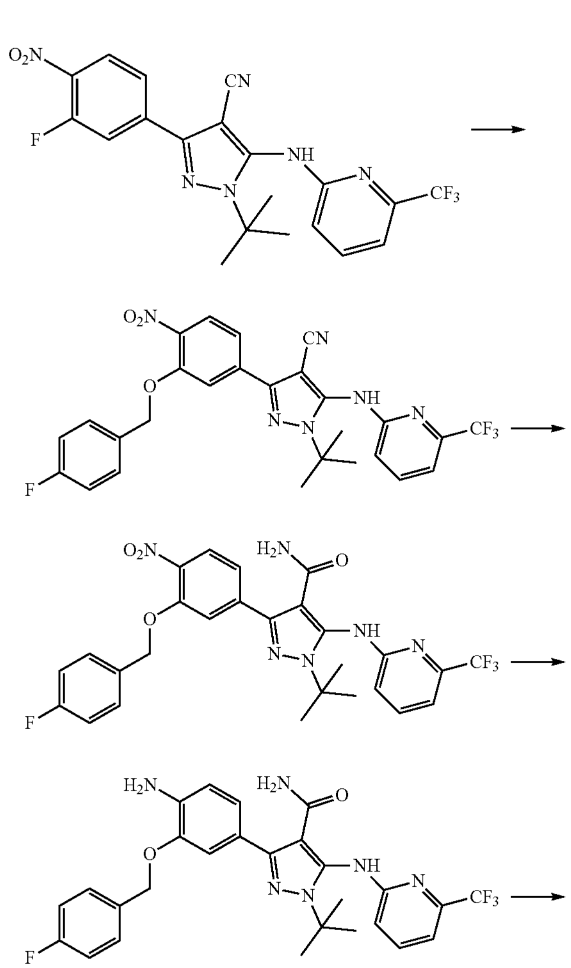

-continued

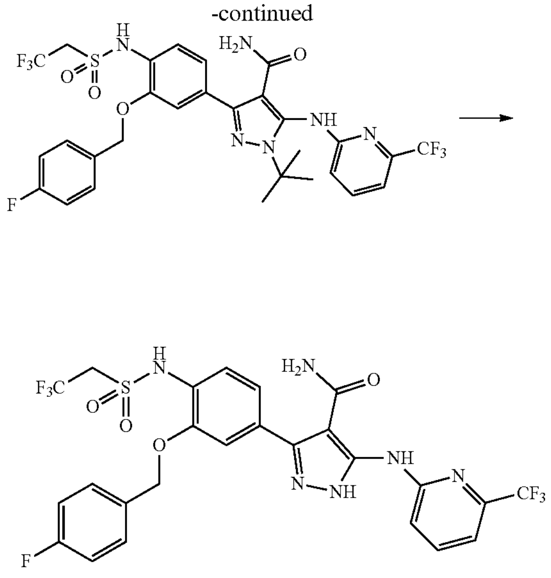

Step 1: 1-(tert-butyl)-3-(3-((4-fluorobenzyl)wry)-4-nitrophenyl)-5-((6-(trifluoromethyl)pyridin-2-yl) amino)-1H-pyrazole-4-carbonitrile To a solution of (4-fluorophenyl)methanol (209 mg, 1.66 mmol) in THF (20 mL) at 0° C., was added NaH (133 mg, 3.33 mmol). After 10 min, 1-tert-butyl-3-(3-fluoro-4-nitro-phenyl)-5-{[6-(trifluoromethyl)pyridin-2-yl]amino}-1H-pyrazole-4-carbonitrile (500 mg, 1.11 mmol) was added and the mixture was stirred at RT overnight. The reaction mixture was concentrated under reduced pressure and the crude residue was purified by silica gel column chromatography (DCM:MeOH, 50:1) to afford the title product (500 mg, 81%) as a yellow solid. LCMS (Method A): 4.87 min; m/z: 555.2 $[M+H]^+$.

Step 2: 1-(tert-butyl)-3-(3-((4-fluorobenzyl)oxy)-4-nitrophenyl)-5-((6-(trifluoromethyl)pyridin-2-yl)amino)-1H-pyrazole-4-carboxamide A mixture of 1-(tert-butyl)-3-(3-((4-fluorobenzyl)oxy)-4-nitrophenyl)-5-((6-(trifluoromethyl)pyridin-2-yl)amino)-1H-pyrazole-4-carbonitrile (500 mg, 0.90 mmol) and Ghaffar-Parkins catalyst (100 mg) in 70% aq. 1,4-dioxane (7 mL) was stirred at 100° C. overnight. The reaction mixture was concentrated under reduced pressure and the crude residue was purified by silica gel column chromatography (DCM) to afford the title product (400 mg, 78%) as yellow solid. LCMS (Method A): 2.66 min; m/z: 573.1 $[M+H]^+$.

Step 3: 3-(4-amino-3-((4-fluorobenzyl)oxy)phenyl)-1-(tert-butyl)-5-((6-(trifluoromethyl)pyridin-2-yl)amino)-1H-pyrazole-4-carboxamide (compound 5)

A mixture of 1-(tert-butyl)-3-(3-((4-fluorobenzyl)oxy)-4-nitrophenyl)-5-((6-(trifluoromethyl)pyridin-2-yl)amino)-1H-pyrazole-4-carboxamide (500 mg, 0.87 mmol), sat. aq. $NH_4Cl$ (2 mL) and Zn dust (285 mg, 4.36 mmol) in MeOH (10 mL) was stirred at 60° C. for 5 h. The reaction mixture was filtered, concentrated under reduced pressure and diluted with $H_2O$. The precipitated solids were collected by filtration and then purified by silica gel column chromatography (DCM:MeOH, 50:1) to afford the title product (230 mg, 49%) as a yellow solid. LCMS (Method A): 4.17 min; m/z: 543.2 $[M+H]^+$.

The compound shown in Table 18 was prepared by a similar synthetic route described for compound 46 (steps 6 and 7).

Compound 46

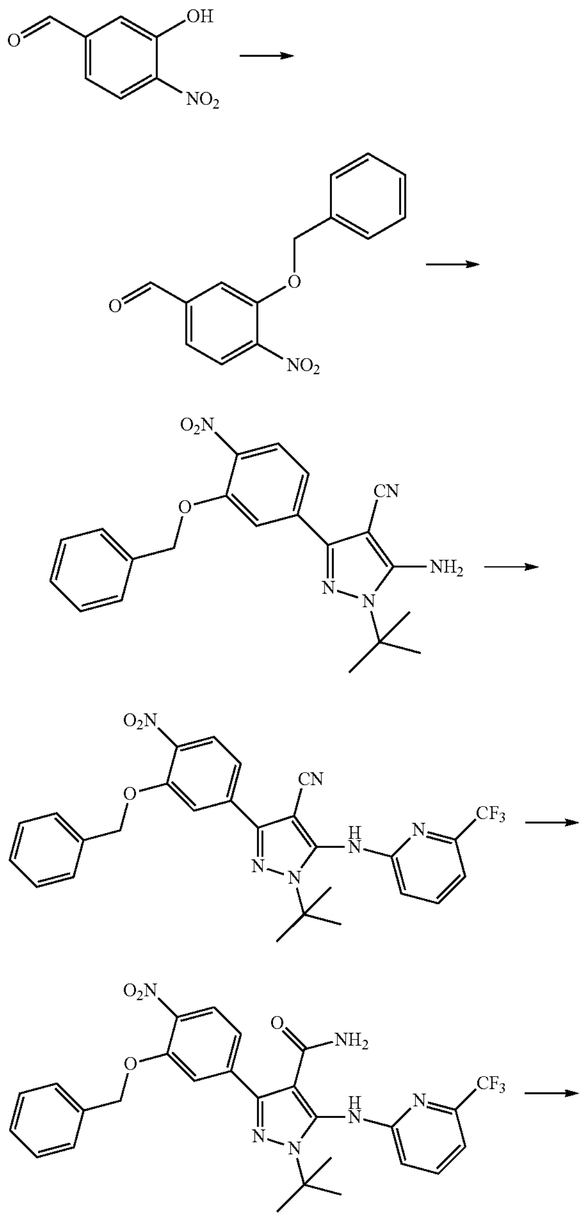

TABLE 18

| Compound No | name | structure | LCMS data | $^1$H NMR data | SM |
|---|---|---|---|---|---|
| 5 | 3-(3-((4-fluorobenzyl)oxy)-4-((2,2,2-trifluoroethyl)sulfonamido)phenyl)-5-((6-(trifluoromethyl)pyridin-2-yl)amino)-1H-pyrazole-4-carboxamide | 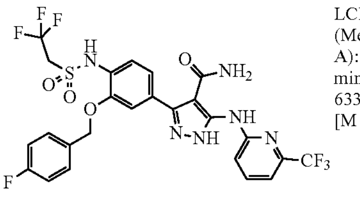 | LCMS (Method A): 4.32 min; m/z: 633.1 $[M + H]^+$. | $^1$H NMR (400 MHz, DMSO-$d_6$): 13.11 (s, 1H), 9.96 (s, 1H), 9.76 (s, 1H), 8.21 (d, J = 8.4 Hz, 1H), 7.98 (t, J = 8.0 Hz, 1H), 7.61 (q, J = 4.8 Hz, 2H), 7.45 (q, J = 5.6 Hz, 2H), 7.30 (d, J = 7.6 Hz, 1H), 7.24 (d, J = 8.8 Hz, 1H), 6.26 (s, 1H), 5.21 (s, 2H), 4.35 (q, J = 9.6 Hz, 2H). | 2,2,2-trifluoroethane-1-sulfonyl chloride |

-continued

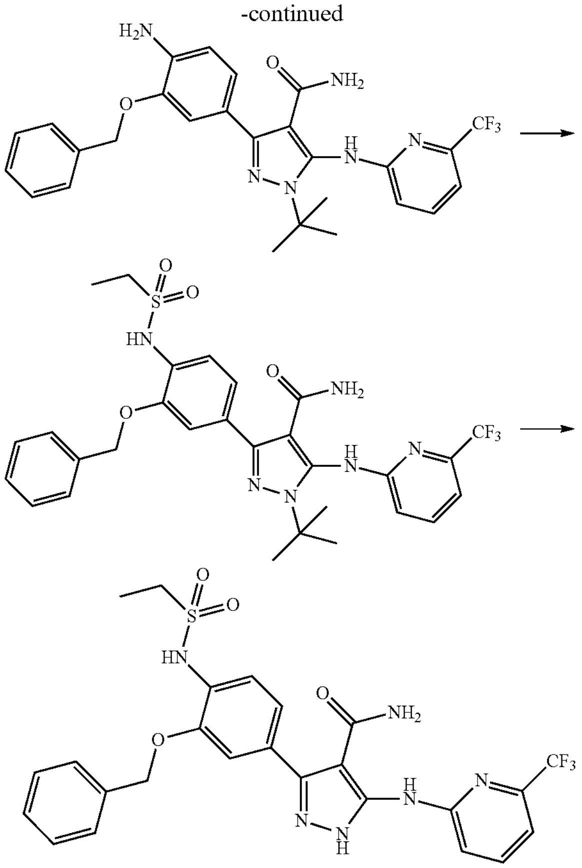

Step 1: 3-(benzyloxy)-4-nitrobenzaldehyde

A mixture of 3-hydroxy-4-nitrobenzaldehyde (10 g, 59.8 mmol), benzyl bromide (10.2 g, 59.8 mmol) and $K_2CO_3$ (16.4 g, 119 mmol) in MeCN (200 mL) was stirred at 70° C. under $N_2$ overnight. The mixture was diluted with $H_2O$ (100 mL) and extracted with DCM (3×100 mL). The combined organic layers were dried ($Na_2SO_4$), concentrated under reduced pressure and the crude residue purified by silica gel column chromatography (PE:EtOAc, 15:1) to afford the title product (3 g, 20%) as a yellow solid. $^1H$ NMR (400 MHz, DMSO-$d_6$): 10.70 (s, 1H), 8.10 (d, J=8.0 Hz, 1H), 7.93 (d, J=1.2 Hz, 1H), 7.69 (dd, J=8.0, 1.2 Hz, 1H), 7.48-7.34 (m, 5H), 5.42 (s, 2H).

Step 2: 5-amino-3-[3-(benzyloxy)-4-nitrophenyl]-1-tert-butyl-1H-pyrazole-4-carbonitrile A solution of 3-(benzyloxy)-4-nitrobenzaldehyde (3 g, 11.6 mmol) and t-BuNHNH$_2$·HCl (1.44 g, 11.6 mmol) in DMF (60 mL) was stirred at RT overnight. The mixture was neutralized to pH 7-8 with sat. aq. $Na_2CO_3$ and diluted with $H_2O$ (100 mL). The precipitated solids were collected by filtration and dried under reduced pressure to provide the hydrazone intermediate (3.5 g, 92%). LCMS (Method A): 4.61 min; m/z: 328.1 $[M+H]^+$.

The crude material was dissolved in DMF (60 mL) and NBS (2.06 g, 11.6 mmol) was added at RT. After 2 h, a pre-mixed solution of malononitrile (1.04 g, 15.7 mmol) and NaOEt (1.06 g, 15.7 mmol) in EtOH (40 mL) was added and the mixture stirred at RT for 16 h. The reaction mixture was concentrated under reduced pressure, diluted with $H_2O$ (70 mL) and extracted with DCM (3×60 mL). The combined organics were dried ($Na_2SO_4$), concentrated under reduced pressure and the crude residue purified by silica gel column chromatography (PE:EtOAc, 4:1) to afford the title product (1.6 g, 39%) as a yellow solid. LCMS (Method A): 4.49 min; m/z: 392.2 $[M+H]^+$.

Step 3: 3-[3-(benzyloxy)-4-nitrophenyl]-1-tert-butyl-5-{[6-(trifluoromethyl)pyridin-2-yl]amino}-1H-pyrazole-4-carbonitrile A mixture of 5-amino-3-[3-(benzyloxy)-4-nitrophenyl]-1-tert-butyl-1H-pyrazole-4-carbonitrile (1.5 g, 3.83 mmol), 2-chloro-6-(trifluoromethyl)pyridine (764 mg, 4.21 mmol), $Pd_2(dba)_3$ (350 mg, 383 μmol), Xantphos (221 mg, 383 μmol) and $Cs_2CO_3$ (2.49 g, 7.66 mmol) in degassed 1,4-dioxane (75 mL) was stirred at 100° C. under $N_2$ for 16 h. The reaction mixture was diluted with $H_2O$ (100 mL) and extracted with DCM (3×100 mL). The combined organic layers were dried ($Na_2SO_4$), concentrated under reduced pressure and the crude residue purified by silica gel column chromatography (PE:EtOAc, 4:1) to afford the title product (2 g, 98%) as a yellow solid. LCMS (Method A): 4.78 min; m/z: 537.3 $[M+H]^+$.

Step 4: 3-[3-(benzyloxy)-4-nitrophenyl]-1-tert-butyl-5-{[6-(trifluoromethyl)pyridin-2-yl]amino}-1H-pyrazole-4-carboxamide A mixture of 3-[3-(benzyloxy)-4-nitrophenyl]-1-tert-butyl-5-{[6-(trifluoromethyl)pyridin-2-yl]amino}-1H-pyrazole-4-carbonitrile (1.9 g, 3.54 mmol), 30% aq. $H_2O_2$ (100 mL) 5% aq. NaOH (10 mL) and DMSO (100 mL) in EtOH (200 mL) was stirred at 100° C. overnight. The reaction mixture was concentrated under reduced pressure, diluted with water (60 mL) to form a precipitate. The precipitated solids were collected by filtration and dried under reduced pressure to afford the title product (1.8 g, 92%) as a white solid. LCMS (Method A): 4.45 min; m/z: 555.2 $[M+H]^+$.

Step 5: 3-[4-amino-3-(benzyloxy)phenyl]-1-tert-butyl-5-{[6-(trifluoromethyl)pyridin-2-yl]amino}-1H-pyrazole-4-carboxamide A mixture of 3-[3-(benzyloxy)-4-nitrophenyl]-1-tert-butyl-5-{[6-(trifluoromethyl)pyridin-2-yl]amino}-1H-pyrazole-4-carboxamide (500 mg, 901 μmol), sat. aq. $NH_4Cl$ (2 mL) and Zn dust (294 mg, 4.50 mmol) in MeOH (8 mL) was stirred at 60° C. overnight. The reaction mixture was diluted with $H_2O$ (30 mL) and extracted with DCM (3×50 mL). The combined organic layers were dried ($Na_2SO_4$) and concentrated under reduced pressure to afford the title product (300 mg, 63%) as a yellow solid. LCMS (Method A): 3.27 min; m/z: 525.3 $[M+H]^+$.

Step 6: 3-[3-(benzyloxy)-4-ethanesulfonamidophenyl]-1-tert-butyl-5-{[6-(trifluoromethyl) pyridin-2-yl]amino}-1H-pyrazole-4-carboxamide A mixture of 3-[4-amino-3-(benzyloxy)phenyl]-1-tert-butyl-5-{[6-(trifluoromethyl)pyridin-2-yl]amino}-1H-pyrazole-4-carboxamide (200 mg, 0.38 mmol) and $EtSO_2Cl$ (73.4 mg, 0.57 mmol) in pyridine (5 mL) was stirred at 35° C. for 2 h. The reaction mixture was concentrated under reduced pressure and the crude residue was purified by prep-TLC (DCM:MeOH, 15:1) to afford the title product (140 mg, 60%) as a yellow solid. LCMS (Method A): 4.28 min; m/z: 617.2 $[M+H]^+$.

Step 7: 3-(3-(benzyloxy)-4-(ethylsulfonamido)phenyl)-5-((6-(trifluoromethyl)pyridin-2-yl) amino)-1H-pyrazole-4-carboxamide (compound 46)

A solution of 3-[3-(benzyloxy)-4-ethanesulfonamidophenyl]-1-tert-butyl-5-{[6-(trifluoromethyl)pyridin-2-yl]amino}-1H-pyrazole-4-carboxamide (120 mg, 194 μmol) in TFA (2 mL) and DCM (2 mL) was stirred at 30° C. for 1 h. The reaction mixture was concentrated under reduced pressure, neutralized to pH 7-8 with sat. aq. $Na_2CO_3$ and diluted with $H_2O$ (10 mL). The precipitated solids were collected by filtration and dried under reduced pressure to afford the title product (50 mg, 46%) as a white solid. LCMS (Method A): 4.13 min; m/z: 561.1 $[M+H]^+$. $^1H$ NMR (400 MHz, DMSO-$d_6$): 13.01 (s, 1H), 9.78 (s, 1H), 9.19 (s, 1H), 8.23 (d, J=8.0 Hz, 1H), 7.99 (t, J=7.6 Hz, 1H), 7.63-7.15 (m, 10H), 6.21 (br s, 1H), 5.21 (s, 2H), 3.06 (q, J=6.8 Hz, 2H), 1.17 (t, J=6.8 Hz, 3H).

Compound 229

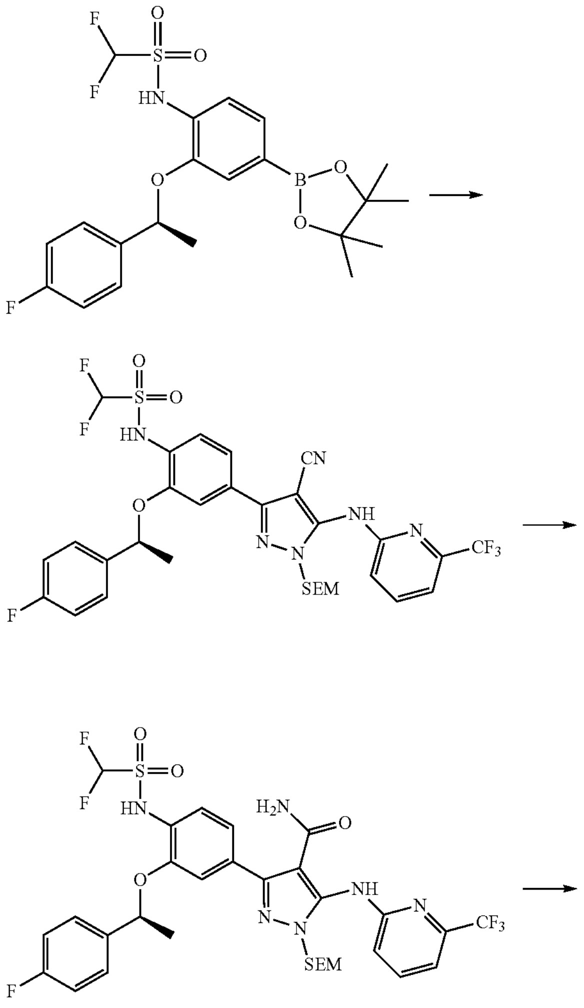

-continued

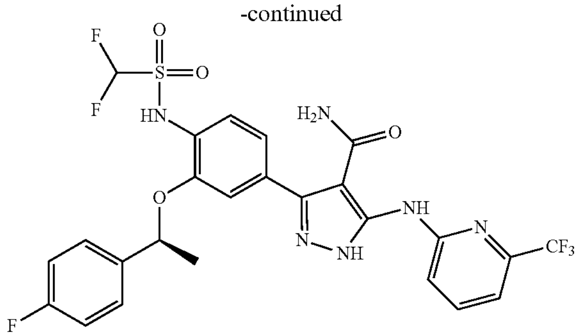

Step 1: N-[4-(4-cyano-5-{[6-(trifluoromethyl)pyridin-2-yl]amino}-1-{[2-(trimethylsilyl)ethoxy]methyl}-1H-pyrazol-3-yl)-2-[(1S)-1-(4-fluorophenyl)ethoxy]phenyl]-1,1-difluoromethanesulfonamide A mixture of 1,1-difluoro-N-{2-[(1S)-1-(4-fluorophenyl)ethoxy]-4-(4,4,5,5-tetramethyl-1,3,2-dioxaborolan-2-yl)phenyl}methanesulfonamide (Intermediate C11, 200 mg, 424 μmol), 3-bromo-5-{[6-(trifluoromethyl)pyridin-2-yl]amino}-1-{[2-(trimethylsilyl)ethoxy]methyl}-1H-pyrazole-4-carbonitrile (196 mg, 424 μmol), Pd(dppf)$Cl_2$·DCM (34.6 mg, 42.4 μmol), $Na_2CO_3$ (89.8 mg, 848 μmol) and 80% aq. 1,4-dioxane (15 mL) was stirred at 100° C. under $N_2$. After 1 h, the reaction mixture was diluted with $H_2O$ (50 mL) and then extracted with EtOAc (3x50 mL). The combined organic layers were washed (brine), dried ($Na_2SO_4$) and concentrated under reduced pressure. The crude residue was purified by prep-TLC (DCM:MeOH, 30:1) to afford the title product (190 mg, 61%) as a yellow solid. LCMS (Method A): 4.35 min; m/z: 725.2 $[M+H]^+$.

Step 2: 3-[4-(difluoromethanesulfonamido)-3-[(1S)-1-(4-fluorophenyl]ethoxy)phenyl]-5-{[6-(trifluoromethyl)pyridin-2-yl]amino}-1-{[2-(trimethylsilyl)ethoxy]methyl}-1H-pyrazole-4-carboxamide A solution of N[4-(4-cyano-5-{[6-(trifluoromethyl)pyridin-2-yl]amino}-1-{[2-(trimethylsilyl)ethoxy]methyl}-1H-pyrazol-3-yl)-2-[(1S)-1-(4-fluorophenyl)ethoxy]phenyl]-1,1-difluoromethanesulfonamide (160 mg, 220 μmol) and Ghaffar-Parkins catalyst (16 mg, 37.4 μmol) in 50% aq. 1,4-dioxane (4 mL) was stirred at 100° C. under $N_2$. After 16 h, the reaction mixture was diluted with $H_2O$ (20 mL) and then extracted with EtOAc (3x20 mL). The combined organic layers were washed (brine), dried ($Na_2SO_4$) and concentrated under reduced pressure. The crude residue was purified by prep-TLC (DCM:MeOH, 30:1) to afford the title product (70.0 mg, 43%) as a yellow solid. LCMS (Method D): 6.41 min; m/z: 745.0 $[M+H]^+$.

Step 3: 3-[4-(difluoromethanesulfonamido)-3-[(1S)-1-(4-fluorophenyl)ethoxy]phenyl]-5-{[6-(trifluoromethyl)pyridin-2-yl]amino}-1H-pyrazole-4-carboxamide (compound 229)

A solution of 3-[4-(difluoromethanesulfonamido)-3-[(1S)-1-(4-fluorophenyl)ethoxy]phenyl]-5-{[6-(trifluoromethyl)pyridin-2-yl]amino}-1-{[2-(trimethylsilyl)ethoxy]methyl}-1H-pyrazole-4-carboxamide (45 mg, 60.4 μmol) in DCM:TFA (4:1, 2.5 mL) was stirred at RT for 5 min. The reaction mixture was neutralized to pH 7-8 with $NH_4OH$ and then extracted with EtOAc (3x20 mL). The combined organic layers were dried ($Na_2SO_4$), concentrated and the crude residue purified sequentially four times by prep-TLC (DCM:MeOH, 60:1) to afford the title compound (19.2 mg, 52%) as a white solid. LCMS (Method A): 4.03 min; m/z: 615.1 $[M+H]^+$. $^1H$ NMR: (400 MHz, DMSO-$d_6$): 13.01 (s, 1H), 10.55 (s, 1H), 9.67 (s, 1H), 8.16 (d, J=8.4 Hz, 1H), 7.99-7.95 (m, 1H), 7.60-7.57 (m, 1H), 7.40 (d, J=8.0 Hz, 1H), 7.30 (d, J=7.2 Hz, 1H), 7.21-7.14 (m, 5H), 7.02 (t, J=52.8 Hz, 1H), 6.12 (br s 1H), 5.65 (m, 1H), 1.58 (d, J=6.0 Hz, 3H).

Compound 45

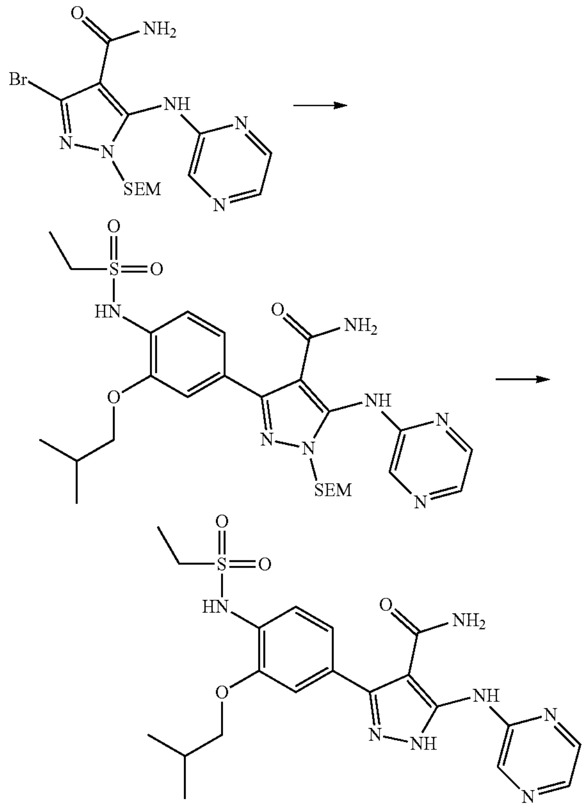

Step 1: 3-(4-(ethylsulfonamido)-3-isobutoxyphenyl)-5-(pyrazin-2-ylamino)-1-((2-(trimethylsilyl)ethoxy)methyl)-1H-pyrazole-4-carboxamide A mixture of 3-bromo-5-[(pyrazin-2-yl)amino]-1-{[2-(trimethylsilyl)ethoxy]methyl}-1H-pyrazole-4-carboxamide (Intermediate B4, 100 mg, 0.2419 mmol), N-(2-isobutoxy-4-(4,4,5,5-tetramethyl-1,3,2-dioxaborolan-2-yl)phenyl)ethanesulfonamide (Intermediate C9, 120 mg, 0.3130 mmol), Pd(dppf)$Cl_2$ (17.7 mg, 24.1 μmol) and $Na_2CO_3$ (76.9 mg, 0.7257 mmol) in degassed 70% aq. 1,4-dioxane (6.5 mL) was stirred at 100° C. for 2 h under microwave irradiation. The reaction mixture was concentrated under reduced pressure, diluted with $H_2O$ (50 mL) and extracted with EtOAc (3x50 mL). The combined organic layers were dried ($Na_2SO_4$), concentrated under reduced pressure and the crude residue purified by prep-TLC (DCM: MeOH, 18:1) to afford the title product (90 mg, 63%) as a yellow solid. LCMS (Method A): 4.16 min; m/z: 590.2 $[M+H]^+$.

Step 2: 3-(4-(ethylsulfonamido)-3-isobutoxyphenyl)-5-(pyrazin-2-ylamino)-1H-pyrazole-4-carboxamide (compound 45)

A solution of 3-(4-(ethylsulfonamido)-3-isobutoxyphenyl)-5-(pyrazin-2-ylamino)-1-((2-(trimethylsilyl)ethoxy)methyl)-1H-pyrazole-4-carboxamide (90 mg, 0.1525 mmol) in DCM (3 mL) and TFA (3 mL) was stirred at RT for 2 h. The reaction mixture was concentrated under reduced pressure, neutralized to pH 7-8 with sat. aq. $Na_2CO_3$ and then diluted with $H_2O$ (30 mL). The precipitated solids were collected by filtration and then purified by prep-TLC (DCM: MeOH, 15:1) to afford the title product (25 mg, 36%) as a white solid. LCMS (Method A): 3.45 min; m/z: 460.1 $[M+H]^+$. $^1H$ NMR (400 MHz, MeOD-$d_4$): 8.27 (s, 1H), 13.00 (s, 1H), 9.63 (s, 1H), 9.26 (s, 1H), 9.05 (s, 1H), 8.22 (s, 1H), 8.12 (s, 1H), 7.45 (d, J=8.0 Hz, 1H), 7.28 (s, 1H), 7.17 (d, J=8.0 Hz, 1H), 6.29 (s, 1H), 3.84 (d, J=6.4 Hz, 2H), 3.13 (q, J=7.2 Hz, 2H), 2.14 (s, 1H), 1.27 (t, J=7.6 Hz, 3H), 1.03 (d, J=6.4 Hz, 6H).

According to the method described for the synthesis of 3-(4-(ethylsulfonamido)-3-isobutoxyphenyl)-5-(pyrazin-2-ylamino)-1H-pyrazole-4-carboxamide, the following compounds (Table 19) were similarly prepared using the appropriate intermediate C in step 1:

TABLE 19

| Compound no | Name | Structure | LCMS data | $^1H$ NMR data | SM |
|---|---|---|---|---|---|
| 61 | 3-(4-(ethylsulfonamido)-3-methoxyphenyl)-5-(pyrazin-2-ylamino)-1H-pyrazole-4-carboxamide | 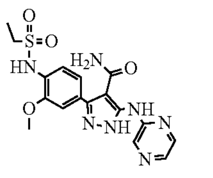 [SMILES: CCS(=O)(=O)Nc1ccc(-c2n[nH]c(Nc3cnccn3)c2C(N)=O)cc1OC] | LCMS (Method A): 2.86 min; m/z: 418.1 $[M + H]^+$. | $^1H$ NMR (400 MHz, $CDCl_3$): 10.34 (s, 1H), 8.40 (s, 1H), 8.24-8.21 (m, 1H), 8.17 (d, J = 2.8 Hz, 1H), 7.66 (d, J = 8.0 Hz, 1H), 7.20 (d, J = 8.4 Hz, 1H), 7.16 (d, J = 1.2 Hz, 1H), 6.96 (s, 1H), 5.53 (s, 2H), 3.94 (s, 3H), 3.14 (q, J = 7.2 Hz, 2H), 1.37 (t, J = 7.2 Hz, 3H). | Intermediate C10 |
| 47 | 3-(3-(cyclohexylmethoxy)-4-(ethylsulfonamido)pheny)-5-(pyrazin-2-ylamino)-1H-pyrazole-4-carboxamide | 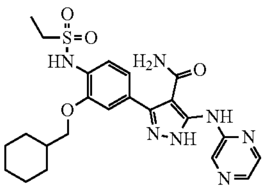 [SMILES: CCS(=O)(=O)Nc1ccc(-c2n[nH]c(Nc3cnccn3)c2C(N)=O)cc1OCC1CCCCC1] | LCMS (Method A): 3.82 min; m/z: 500.2 $[M + H]^+$. | $^1H$ NMR (400 MHz, DMSO-$d_6$): 12.99 (s, 1H), 9.64 (s, 1H), 9.26 (s, 1H), 9.03 (br s, 1H), 8.22 (s, 1H), 8.11 (s, 1H), 7.43 (d, J = 7.6 Hz, 1H), 7.62 (s, 1H), 7.15 (d, J = 8.4 Hz, 1H), 3.86 (d, J = 5.6 Hz, 2H), 3.11 (q, J = 7.2 Hz, 2H), 1.91-1.68 (m, 7H), 1.28-1.25 (m, 5H), 1.07-1.04 (m, 2H). | Intermediate C3 |

TABLE 19-continued

| Compound no | Name | Structure | LCMS data | $^1H$ NMR data | SM |
|---|---|---|---|---|---|
| 40 | 3-(3-(cyclopentylmethoxy)-4-(ethylsulfonamido)phenyl)-5-(pyrazin-2-ylamino)-1H-pyrazole-4-carboxamide | 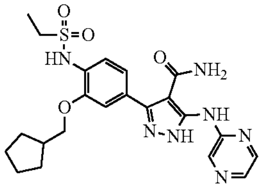 [SMILES: CCS(=O)(=O)Nc1ccc(-c2n[nH]c(Nc3cnccn3)c2C(N)=O)cc1OCC1CCCC1] | LCMS (Method A): 3.63 min; m/z: 486.2 $[M + H]^+$. | $^1H$ NMR (400 MHz, MeOD-$d_4$): 12.98 (s, 1H), 9.64 (s, 1H), 9.26 (s, 1H), 9.00 (s, 1H), 8.22 (s, 1H), 8.11 (d, J = 2.4 Hz, 1H), 7.43 (d, J = 8.0 Hz, 1H), 7.29 (s, 1H), 7.16 (d, J = 8.0 Hz, 1H), 6.24 (s, 1H), 3.94 (d, J = 6.8 Hz, 2H), 3.12 (q, J = 6.8 Hz, 2H), 2.41 (m, 1H), 1.83 (m, 2H), 1.58 (m, 4H), 1.37 (m, 2H), 1.27 (t, J = 7.2 Hz, 3H). | Intermediate C8 |

Compound 1

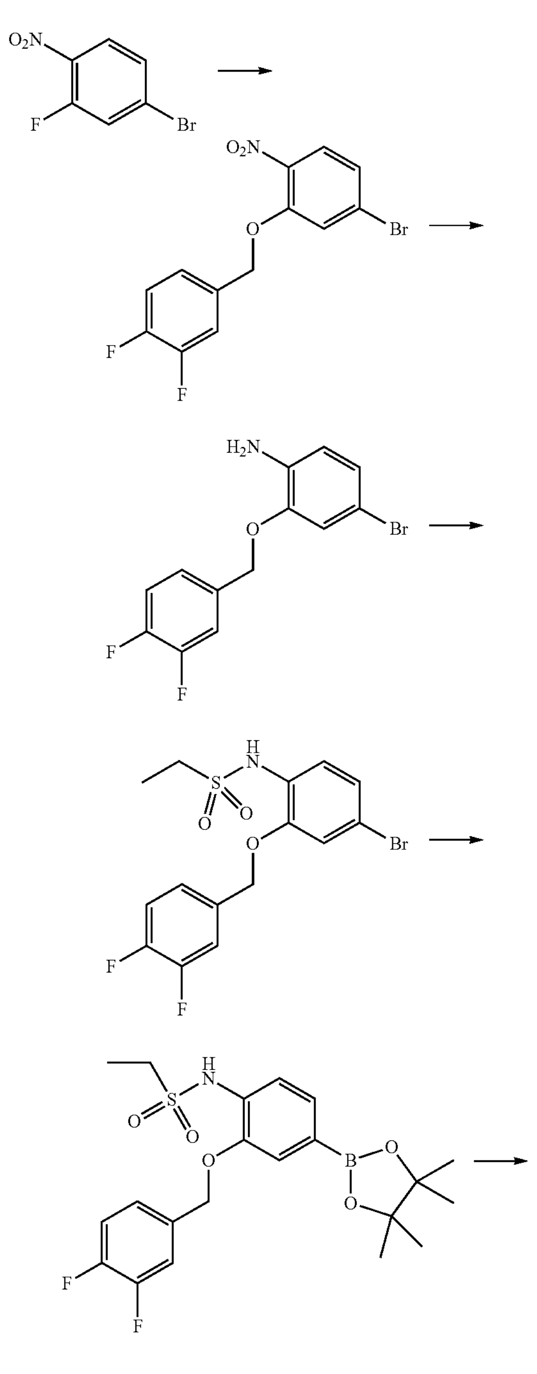

-continued

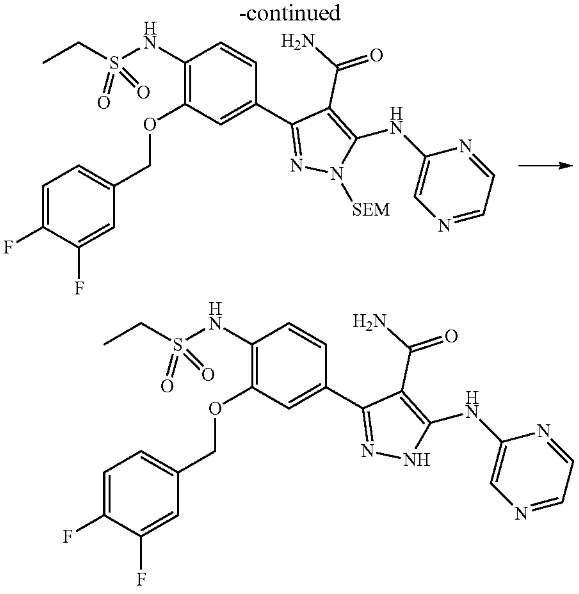

Step 1: 4-bromo-2-[(3,4-difluorophenyl)methoxy]-1-nitrobenzene

To a solution of (3,4-difluorophenyl)methanol (981 mg, 6.81 mmol) in THF (15 mL) at 0° C., was added NaH (489 mg, 20.4 mmol). After 10 min, 4-bromo-2-fluoro-1-nitrobenzene (1.5 g, 6.81 mmol) was added, and the resulting mixture was stirred at RT for 2 h. The reaction mixture was diluted with $H_2O$ (30 mL) and then extracted with EtOAc (3×50 mL). The combined organic layers were washed with brine, dried ($Na_2SO_4$) and concentrated under reduced pressure. The crude residue was purified by silica gel column chromatography (PE:EtOAc, 30:1) to afford the title product (1.8 g, 77%) as a white solid.

Step 2: 4-bromo-2-[(3,4-difluorophenyl)methoxy]aniline

A mixture of 4-bromo-2-[(3,4-difluorophenyl)methoxy]-1-nitrobenzene (1 g, 2.90 mmol), sat. aq. $NH_4Cl$ (5 mL) and Zn dust (941 mg, 14.4 mmol) in MeOH (10 mL) was stirred at 60° C. for 3 h. The reaction mixture was diluted with $H_2O$ (200 mL) and then extracted with EtOAc (3×150 mL). The combined organic layers were washed with brine, dried ($Na_2SO_4$) and concentrated under reduced pressure. The crude residue was purified by silica gel column chromatography (PE:EtOAc, 3:1) to afford the title product (810 mg, 89%) as a white solid. LCMS (Method A): 4.18 min; m/z: 314.0, 316.0 $[M+H]^+$.

Step 3: N-{4-bromo-2-[(3,4-difluorophenyl) methoxy]phenyl}ethane-1-sulfonamide

A mixture of 4-bromo-2-[(3,4-difluorophenyl)methoxy] aniline (800 mg, 2.54 mmol), $EtSO_2Cl$ (489 mg, 3.81 mmol) and pyridine (8 mL) in $CHCl_3$ (8 mL) was stirred at RT for 16 h. The reaction mixture was diluted with $H_2O$ (200 mL) and then extracted with DCM (3×150 mL). The combined organic layers were washed with brine, dried ($Na_2SO_4$) and concentrated under reduced pressure. The crude residue was purified by silica gel column chromatography (PE:EtOAc, 3:1) to afford the title product (720 mg, 70%) as a white solid. LCMS (Method A): 4.26 min; m/z: 427.9, 429.9 $[M+H]^+$.

Step 4: N-{2-[(3,4-difluorophenyl)methoxy]-4-(4,4,5,5-tetramethyl-1,3,2-dioxaborolan-2-yl) phenyl}ethane-1-sulfonamide A mixture of N-{4-bromo-2-[(3,4-difluorophenyl) methoxy]phenyl}ethane-1-sulfonamide (600 mg, 1.47 mmol), $Pd(dppf)Cl_2$ (1.07 g, 1.47 mmol), KOAc (432 mg, 4.41 mmol) and $B_2pin_2$ (558 mg, 2.20 mmol) in 1,4-dioxane (20 mL) was stirred at 110° C. for 16 h. The reaction mixture was diluted with $H_2O$ (200 mL) and then extracted with EtOAc (3×150 mL). The combined organic layers were washed with brine, dried ($Na_2SO_4$) and concentrated under reduced pressure. The crude residue was purified by silica gel column chromatography (PE:EtOAc, 2:1) to afford the title product (480 mg, 72%) as a white solid. LCMS (Method A): 4.46 min; m/z: 476.4 $[M+H]^+$.

Step 5: 3-{3-[(3,4-difluorophenyl)methoxy]-4-ethanesulfonamidophenyl}-5-[(pyrazin-2-yl)amino]-1-{[2-(trimethylsilyl)ethoxy]methyl}-1H-pyrazole-4-carboxamide To a mixture of N-{2-[(3,4-difluorophenyl)methoxy]-4-(4,4,5,5-tetramethyl-1,3,2-dioxaborolan-2-yl) phenyl}ethane-1-sulfonamide (200 mg, 441 μmol), 3-bromo-5-[(pyrazin-2-yl)amino]-1-{[2-(trimethylsilyl) ethoxy]methyl}-1H-pyrazole-4-carboxamide (Intermediate B4, 182 mg, 441 μmol), $Pd(dppf)Cl_2$ (32.2 mg, 44.1 μmol) and $Na_2CO_3$ (139 mg, 1.32 mmol) in 70% aq. 1,4-dioxane (15 mL) was stirred at 110° C. for 16 h. The reaction mixture was diluted with $H_2O$ (200 mL) and then extracted with EtOAc (3×150 mL). The combined organic layers were washed with brine, dried ($Na_2SO_4$) and concentrated under reduced pressure. The crude residue was purified by silica gel column chromatography (DCM:MeOH, 30:1) to afford the title product (180 mg, 62%) as a yellow oil. LCMS (Method A): 4.15 min; m/z: 660.2 $[M+H]^+$.

Step 6: 3-(3-((3,4-difluorobenzyl)oxy)-4-(ethylsulfonamido)phenyl)-5-(pyrazin-2-ylamino)-1H-pyrazole-4-carboxamide (compound 1)

A solution of 3-{3-[(3,4-difluorophenyl)methoxy]-4-ethanesulfonamidophenyl}-5-[(pyrazin-2-yl)amino]-1-{[2-(trimethylsilyl)ethoxy]methyl}-1H-pyrazole-4-carboxamide (150 mg, 227 μmol) in DCM (5 mL) and TFA (5 mL) was stirred at 25° C. for 3 h. The reaction mixture was neutralized to pH 7-8 with sat. aq. $NaHCO_3$ and then extracted with DCM (3×50 mL).

The combined organic layers were washed with brine, dried ($Na_2SO_4$) and concentrated under reduced pressure. The crude residue was purified by prep-TLC (DCM:MeOH, 30:1) to afford the title product (50 mg, 41%) as a white solid. LCMS (Method A): 3.59 min; m/z: 530.1 $[M+H]^+$. $^1H$ NMR (400 MHz, DMSO-$d_6$): 13.01 (s, 1H), 9.64 (s, 1H), 9.26 (s, 2H), 8.23 (s, 1H), 8.12 (s, 1H), 7.78-7.74 (m, 1H), 7.52-7.41 (m, 3H), 7.20 (d, J=8.4 Hz, 1H), 6.22 (s, 1H), 5.21 (s, 2H), 3.11-3.05 (m, 2H), 1.19 (t, J=7.2 Hz, 3H).

According to the method described for the synthesis of 3-(3-((3,4-difluorobenzyl)oxy)-4-(ethylsulfonamido)phenyl)-5-(pyrazin-2-yl amino)-1H-pyrazole-4-carboxamide, the following compounds (Table 20) were similarly prepared using the appropriate alcohol in step 1:

TABLE 20

| Compound No | Name | Structure | LCMS data | $^1H$ NMR data | SM |
|---|---|---|---|---|---|
| 25 | 3-(3-(benzyloxy)-4-(ethylsulfonamido) phenyl)-5-(pyrazin-2-ylamino)-1H-pyrazole-4-carboxamide | 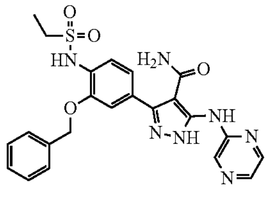 [SMILES: CCS(=O)(=O)Nc1ccc(-c2n[nH]c(Nc3cnccn3)c2C(N)=O)cc1OCc1ccccc1] | LCMS (Method A): 3.32 min; m/z: 494.1 $[M + H]^+$. | $^1H$ NMR (400 MHz, MeOD-$d_4$): 13.05 (s, 1H), 9.61 (s, 1H), 9.24 (s, 1H), 8.22 (s, 1H), 8.11 (s, 1H), 7.55 (d, J = 7.2 Hz, 2H), 7.40 (m, 5H), 7.19 (d, J = 7.6 Hz, 1H), 6.23 (s, 1H), 5.20 (s, 2H), 3.05 (q, J = 6.8 Hz, 2H), 1.16 (t, J = 7.2 Hz, 3H). | phenylmethanol |
| 42 | 3-(3-((4-chlorobenzyl) oxy)-4-(ethylsulfonamido) phenyl)-5-(pyrazin-2-ylamino)-1H-pyrazole-4-carboxamide | 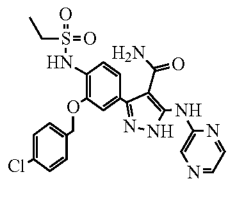 [SMILES: CCS(=O)(=O)Nc1ccc(-c2n[nH]c(Nc3cnccn3)c2C(N)=O)cc1OCc1ccc(Cl)cc1] | LCMS (Method A): 3.65 min; m/z: 528.1 $[M + H]^+$. | $^1H$ NMR (400 MHz, DMSO-$d_6$): 13.02 (s, 1H), 9.63 (s, 1H), 9.23 (d, J = 9.2 Hz, 2H), 8.22 (q, J = 1.6 Hz, 1H), 8.11 (d, J = 2.8 Hz, 2H), 7.60 (d, J = 8.8 Hz, 2H), 7.45 (q, J = 8.4 Hz, 4H),7.20 (q, J = 1.6 Hz, 1H), 5.75 (s, 1H), 5.20 (s, 1H), 3.05 (q, J = 7.2 Hz, 2H), 1.16 (t, J = 7.2 Hz, 3H). | (4-chlorophenyl) methanol |

TABLE 20-continued

| Compound No | Name | Structure | LCMS data | $^1$H NMR data | SM |
|---|---|---|---|---|---|
| 41 | 3-(3-((3-chlorobenzyl)oxy)-4-(ethylsulfonamido)phenyl)-5-(pyrazin-2-ylamino)-1H-pyrazole-4-carboxamide | 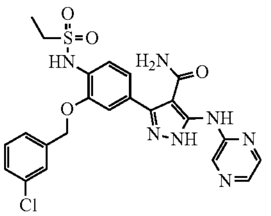 [SMILES: CCS(=O)(=O)Nc1ccc(-c2n[nH]c(Nc3cnccn3)c2C(N)=O)cc1OCc1cccc(Cl)c1] | LCMS (Method A): 3.65 min; m/z: 528.1 [M + H]$^+$. | $^1$H NMR (400 MHz, MeOD-$d_4$): 8.87 (s, 1H), 8.27 (s, 1H), 8.08 (d, J = 2.4 Hz, 2H), 7.60 (t, J = 8.0 Hz, 2H), 7.46-7.32 (m, 4H), 7.21 (d, J = 7.6 Hz, 2H), 5.26 (s, 2H), 3.12 (q, J = 7.6 Hz, 4H), 1.29 (s, 1H). | (3-chlorophenyl) methanol |
| 28 | 3-(4-(ethylsulfonamido)-3-(194yridine-4-ylmethoxy)phenyl)-5-(pyrazin-2-ylamino)-1H-pyrazole-4-carboxamide | 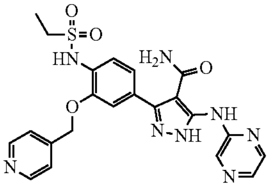 [SMILES: CCS(=O)(=O)Nc1ccc(-c2n[nH]c(Nc3cnccn3)c2C(N)=O)cc1OCc1ccncc1] | LCMS (Method A): 2.44 min; m/z: 495.1 [M + H]$^+$. | $^1$H NMR (400 MHz, DMSO-$d_6$): 9.65 (s, 1H), 9.25 (s, 1H), 8.66 (s, 2H), 8.22 (s, 1H), 8.12 (s, 1H), 7.61 (d, J = 3.6 Hz, 2H), 7.47 (d, J = 8.0 Hz, 1H), 7.38 (s, 1H), 7.22 (d, J = 8.0 Hz, 1H), 6.26 (s, 1H), 5.28 (s, 2H), 3.10 (q, J = 7.2 Hz, 2H), 1.21 (t, J = 7.2 Hz, 3H). | pyridin-4-ylmethanol |
| 32 | 3-(4-(ethylsulfonamido)-3-(194yridine-3-ylmethoxy)phenyl)-5-(pyrazin-2-ylamino)-1H-pyrazole-4-carboxamide | 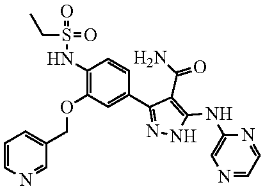 [SMILES: CCS(=O)(=O)Nc1ccc(-c2n[nH]c(Nc3cnccn3)c2C(N)=O)cc1OCc1cccnc1] | LCMS (Method A): 2.41 min; m/z: 495.1 [M + H]$^+$. | $^1$H NMR (400 MHz, DMSO-$d_6$): 13.12 (s, 1H), 9.64 (s, 1H), 9.27 (s, 1H), 8.83 (s, 1H), 8.60 (s, 1H), 8.22 (s, 1H), 8.12 (s, 1H), 8.00 (d, J = 7.6 Hz, 1H), 7.47 (s, 3H), 7.21 (d, J = 8.0 Hz, 1H), 6.20 (s, 1H), 5.26 (s, 2H), 3.05 (q, J = 7.2 Hz, 2H), 1.15 (t, J = 7.2 Hz, 3H). | pyridin-3-ylmethanol |
| 2 | 3-(4-(ethylsulfonamido)-3-((2-fluorobenzyl)oxy)phenyl)-5-(pyrazin-2-ylamino)-1H-pyrazole-4-carboxamide | 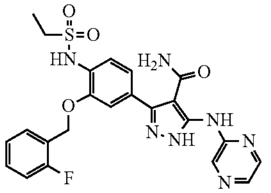 [SMILES: CCS(=O)(=O)Nc1ccc(-c2n[nH]c(Nc3cnccn3)c2C(N)=O)cc1OCc1ccccc1F] | LCMS (Method A): 3.34 min; m/z: 512.1 [M + H]$^+$. | $^1$H NMR (400 MHz, DMSO-$d_6$): 9.74 (s, 1H), 9.30 (s, 1H), 8.22 (t, J = 2.4 Hz, 1H), 8.11 (d, J = 2.8 Hz, 1H), 7.40-7.34 (m, 3H), 7.22-7.14 (m, 3H), 7.09 (s, 1H), 6.96 (q, J = 1.6 Hz, 1H), 5.17 (s, 2H), 4.09 (d, J = 4.4 Hz, 2H), 1.23 (s, 3H). | (2-fluorophenyl) methanol |
| 24 | 3-(4-(ethylsulfonamido)-3-(4-fluorophenethoxy)phenyl)-5-(pyrazin-2-ylamino)-1-((2-(trimethylsilyl)ethoxy)methyl)-1H-pyrazole-4-carboxamide | 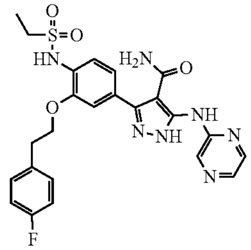 [SMILES: CCS(=O)(=O)Nc1ccc(-c2n[nH]c(Nc3cnccn3)c2C(N)=O)cc1OCCc1ccc(F)cc1] | LCMS (Method A): 3.58 min; m/z: 526.1 [M + H]$^+$. | $^1$H NMR (400 MHz, DMSO-$d_6$): 12.97 (s, 1H), 9.62 (s, 1H), 9.24 (s, 1H), 8.95 (s, 1H), 8.21 (q, J = 1.6 Hz, 1H), 8.10 (d, J = 2.8 Hz, 1H), 7.44-7.40 (m, 3H), 7.32 (s, 1H), 7.17-7.11 (m, 3H), 4.28 (t, J = 6.8 Hz, 2H), 3.13 (t, J = 6.8 Hz, 2H), 2.96 (q, J = 7.2 Hz, 2H), 1.13 (t, J = 7.6 Hz, 3H). | 2-(4-fluorophenyl) ethan-1-ol |
| 224 | 3-{4-ethanesulfonamido-3-[(6-fluoro-1,2,3,4-tetrahydronaphthalen-1-yl)oxy]phenyl}-5-[(pyrazin-2-yl)amino]-1H-pyrazole-4-carboxamide | 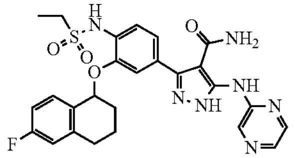 | LCMS (Method A): 5.40 min; m/z: 456.1 [M + H]$^+$. | $^1$H NMR (400 MHz, DMSO-$d_6$): 13.03 (s, 1H), 9.65 (s, 1H), 9.27 (s, 1H), 8.93 (s, 1H), 8.23 (t, J = 1.2 Hz, 1H), 8.11 (d, J = 2.4 Hz, 1H), 7.54 (s, 1H), 7.44-7.38 (m, 3H), 7.18 (dd, J = 8.4, 1.6 Hz, 1H), 7.05-7.02 (m, 2H), 8.23 (t, J = 1.2 Hz, 1H), 2.96 (t, J = 5.2 Hz, 2H), 2.85-2.75 (m, 2H), 2.13-1.95 (m, 3H), 1.75-1.72 (m, 1H), 1.04 (d, J = 8.4 Hz, 3H). | 6-fluoro-1,2,3,4-tetrahydronaphthalen-1-ol |
| 228 | 3-(4-ethanesulfonamido-3-{[2-(4-fluorophenyl)propan-2-yl]oxy}phenyl)-5-[(pyrazin-2-yl)amino]-1H-pyrazole-4-carboxamide | 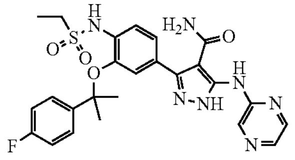 [SMILES: CCS(=O)(=O)Nc1ccc(-c2n[nH]c(Nc3cnccn3)c2C(N)=O)cc1OC(C)(C)c1ccc(F)cc1] | LCMS (Method A): 3.44 min m/z: 540.2 [M + H]$^+$. | $^1$H NMR (400 MHz, DMSO-d): 12.85 (s, 1H), 9.40 (s, 1H), 9.13 (s, 2H), 8.19 (s, 1H), 8.08 (d, J = 2.0 Hz, 1H), 7.49 (q, J = 4.8 Hz, 3H), 7.17-7.06 (m, 3H), 6.44 (s, 1H), 3.17 (q, J = 7.2 Hz, 2H), 1.77 (s, 6H), 1.36 (t, J = 8.4 Hz, 3H). | 2-(4-Fluorophenyl)-2-propanol |

TABLE 20-continued

| Compound No | Name | Structure | LCMS data | $^1$H NMR data | SM |
|---|---|---|---|---|---|
| 232 | 3-[4-ethanesulfonamido-3-(1,2,3,4-tetrahydronaphthalen-1-yloxy)phenyl]-5-[(pyrazin-2-yl)amino]-1H-pyrazole-4-carboxamide | 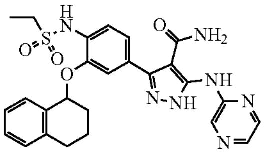 [SMILES: CCS(=O)(=O)Nc1ccc(-c2n[nH]c(Nc3cnccn3)c2C(N)=O)cc1OC1CCCc2ccccc21] | LCMS (Method A): 3.51 min m/z: 534.2 $[M + H]^+$. | $^1$H NMR (400 MHz, DMSO-$d_6$): 13.04 (s, 1H), 9.65 (s, 1H), 9.27 (s, 1H), 8.22-8.19 (m, 1H), 8.02-8.00 (m, 1H), 7.54 (s, 1H), 7.44-7.42 (m, 1H), 7.35 (d, J = 7.2 Hz, 2H), 7.28-7.25 (m, 1H), 7.21-7.26 (m, 3H), 5.67 (s, 1H), 2.97-2.93 (m, 2H), 2.89-2.84 (m, 1H), 2.78-2.71 (m, 1H), 2.16-2.10 (m, 1H), 2.05-1.98 (m, 2H), 1.76-1.72 (m, 1H), 1.03 (t, J = 7.2 Hz, 3H). | 1,2,3,4-tetrahydronaphthalen-1-ol |
| 7 | 3-(3-((1-acetylpiperidin-4-yl)methoxy)-4-(ethylsulfonamido)phenyl)-5-(pyrazin-2-ylamino)-1H-pyrazole-4-carboxamide | 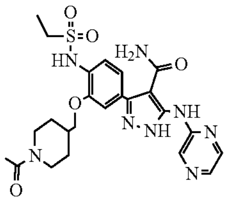 [SMILES: CCS(=O)(=O)Nc1ccc(-c2n[nH]c(Nc3cnccn3)c2C(N)=O)cc1OCC1CCN(C(C)=O)CC1] | LCMS (Method A): 3.02 min m/z: 543.2 $[M + H]^+$. | $^1$H NMR (400 MHz, DMSO-$d_6$): 13.03 (s, 1H), 9.63 (s, 1H), 9.26 (s, 1H), 9.08 (s, 1H), 8.24 (s, 1H), 8.11 (s, 1H), 7.44 (d, J = 7.6 Hz, 1H), 7.28 (s, 1H), 7.16 (m, J = 8.4 Hz, 1H), 3.93 (d, J = 6.4 Hz, 2H), 3.10 (m, 4H), 2.58 (m, 2H), 2.10 (brs, 1H), 2.00 (s, 3H), 1.99 (s, 1H), 1.87 (t, J= 17.2 Hz, 3H), 1.26 (t, J = 7.2 Hz, 3H). | 1-[4-(hydroxymethyl) piperidin-1-yl] ethan-1-one |

Compound 248

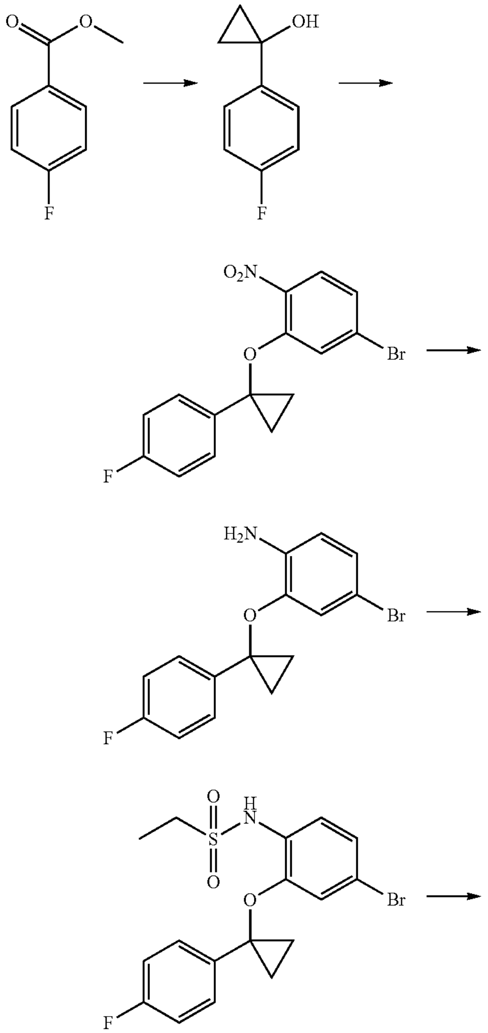

-continued

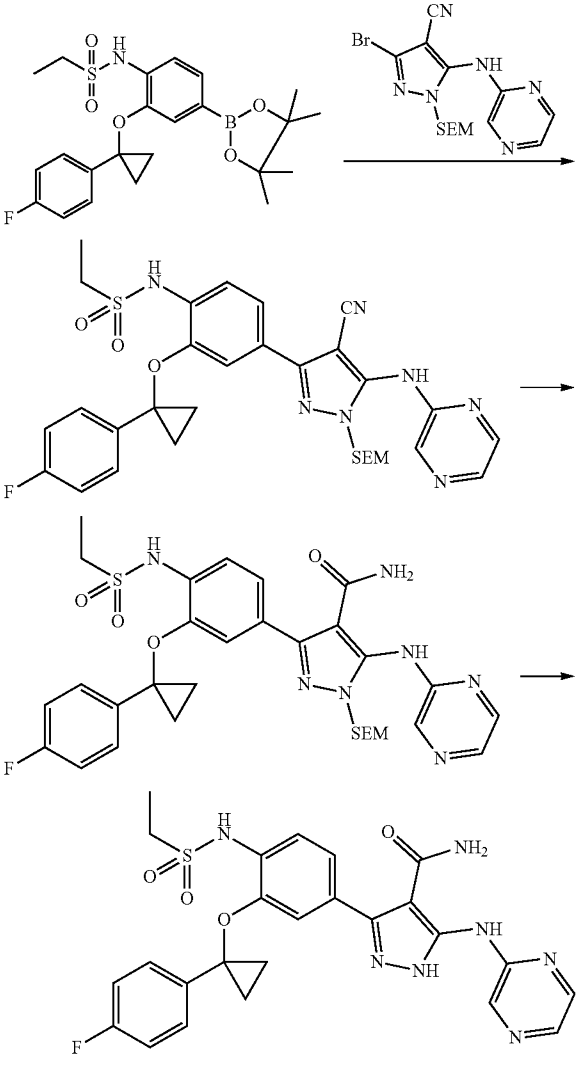

Step 1: 1-(4-fluorophenyl)cyclopropan-1-ol

To a solution of methyl 4-fluorobenzoate (9.0 g, 58.3 mmol) and $Ti(Oi-Pr)_4$ (29.5 g, 104 mmol) in THF (180 mL) at 0° C., was added EtMgBr (23.1 g, 174 mmol), and the mixture was stirred at RT for 16 h. The reaction mixture was quenched with sat. $NH_4Cl$ (100 mL) and then extracted with EtOAc (3×150 mL). The combined organic layers were dried ($Na_2SO_4$), concentrated and the crude residue purified by silica gel column chromatography (PE:EtOAc, 20:1) to afford the title product (7.5 g, 85%) as a yellow oil.

Step 2: 4-bromo-2-[1-(4-fluorophenyl)cyclopropoxy]-1-nitrobenzene

To a solution of 1-(4-fluorophenyl)cyclopropan-1-ol (4.5 g, 29.5 mmol) in THF (90 mL) at 0° C., was added NaH (3.20 g, 80.4 mmol). After 15 min, 4-bromo-2-fluoro-1-nitrobenzene (5.89 g, 26.8 mmol) was added, and the mixture was stirred at RT for 16 h. The mixture was quenched with $H_2O$ (50 mL) and then extracted with EtOAc (3×50 mL). The combined organic layers were washed (brine), dried ($Na_2SO_4$) and concentrated under reduced pressure to afford the crude product (10.0 g, >100%) as a brown oil.

Step 3: 4-bromo-2-[1-(4-fluorophenyl)cyclopropoxy]aniline

A mixture of 4-bromo-2-[1-(4-fluorophenyl)cyclopropoxy]-1-nitrobenzene (13.0 g, 36.9 mmol), Zn powder (12.0 g, 184 mmol), sat. $NH_4Cl$ (35 mL) and MeOH (105 mL) was stirred at 60° C. for 2 h. The reaction mixture was filtered, and the filtrate was concentrated. The residue was diluted with $H_2O$ (50 mL) and then extracted with EtOAc (3×50 mL). The combined organic layers were washed (brine), dried ($Na_2SO_4$) and concentrated to afford the crude product (10.0 g, 42%) as a brown oil. LCMS (Method D): 5.20 min; m/z: 322.0, 324.0 $[M+H]^+$.

Step 4: N-{4-bromo-2-[1-(4-fluorophenyl)cyclopropoxy]phenyl}ethane-1-sulfonamide A mixture of 4-bromo-2-[1-(4-fluorophenyl)cyclopropoxy]aniline (2.0 g, 6.20 mmol) and $EtSO_2Cl$ (956 mg, 7.44 mmol) in $CHCl_3$:pyridine (4:1, 25 mL) was stirred at RT for 16 h. The reaction mixture was concentrated and the crude residue was purified by silica gel column chromatography (PE:EtOAc, 30:1) to afford the title product (1.0 g, 39%) as a yellow solid. LCMS (Method D): 4.05 min; m/z: 322.0, 324.0 $[M+H]^+$.

Step 5: N-{2-[1-(4-fluorophenyl)cyclopropoxy]-4-(4,4,5,5-tetramethyl-1,3,2-dioxaborolan-2-yl)phenyl}ethane-1-sulfonamide A mixture of N-{4-bromo-2-[1-(4-fluorophenyl)cyclopropoxy]phenyl}ethane-1-sulfonamide (500 mg, 1.20 mmol), $B_2pin_2$ (454 mg, 1.79 mmol), $Pd(dppf)Cl_2$ (87.7 mg, 0.12 mmol), KOAc (235 mg, 2.40 mmol) and 1,4-dioxane (10 mL) was stirred at 100° C. under $N_2$ for 16 h. The mixture was concentrated, and the residue was diluted with $H_2O$ (50 mL) and then extracted with EtOAc (3×50 mL). The combined organic layers were washed (brine), dried ($Na_2SO_4$) and concentrated under reduced pressure. The crude residue was purified by prep-TLC (PE:EtOAc, 20:1) to afford the title product (240 mg, 43%) as a yellow solid. LCMS (Method D): 5.48 min; 462.2 $[M+H]^+$.

Step 6: N-(4-{4-cyano-5-[(pyrazin-2-yl)amino]-1-{[2-(trimethylsilyl)ethoxy]methyl}-1H-pyrazol-3-yl}-2-[1-(4-fluorophenyl)cyclopropoxy]phenyl)ethane-1-sulfonamide A mixture of N-{2-[1-(4-fluorophenyl)cyclopropoxy]-4-(4,4,5,5-tetramethyl-1,3,2-dioxaborolan-2-yl)phenyl} ethane-1-sulfonamide (250 mg, 0.54 mmol), 3-bromo-5-[(pyrazin-2-yl)amino]-1-{[2-(trimethylsilyl)ethoxy]methyl}-1H-pyrazole-4-carbonitrile (Intermediate B3, 214 mg, 0.54 mmol), $Pd(dppf)Cl_2$·DCM (44.2 mg, 0.05 mmol), $Na_2CO_3$ (114 mg, 1.08 mmol) and 80% aq. 1,4-dioxane (10 mL) was heated at 100° C. with microwave irradiation for 2 h. The reaction mixture was concentrated, diluted with $H_2O$ (100 mL) and then extracted with EtOAc (2×50 mL). The combined organic layers were dried ($Na_2SO_4$) and concentrated under reduced pressure. The crude residue was purified by prep-TLC (DCM:MeOH, 20:1) to afford the title product (50 mg, 14%) as a yellow solid. LCMS (Method D): 5.48 min; 650.2 $[M+H]^+$.

Step 7: 3-{4-ethanesulfonamido-3-[1-(4-fluorophenyl)cyclopropoxy]phenyl}-5-[(pyrazin-2-yl)amino]-1-{[2-(trimethylsilyl)ethoxy]methyl}-1Hpyrazole-4-carboxamide A mixture of N-(4-{4-cyano-5-[(pyrazin-2-yl)amino]-1-{[2-(trimethylsilyl)ethoxy]methyl}-1H-pyrazol-3-yl}-2-[1-(4-fluorophenyl)cyclopropoxy]phenyl)ethane-1-sulfonamide (50 mg, 76.9 μmol), Ghaffar-Parkins catalyst (20 mg, 46.8 μmol) and 65% aq. 1,4-dioxane (4.5 mL) was stirred at 100° C. for 16 h. The mixture was concentrated, and the residue diluted with $H_2O$ (50 mL) and then extracted with EtOAc (3×50 mL). The combined organic layers were washed (brine), dried ($Na_2SO_4$) and concentrated under reduced pressure. The crude residue was purified by prep-TLC (DCM:MeOH, 20:1) to afford the title product (30 mg, 59%) as a yellow solid. LCMS (Method D): 4.82 min; m/z: 668.2 $[M+H]^+$.

Step 8: 3-{4-ethanesulfonamido-3-[1-(4-fluorophenyl)cyclopropoxy]phenyl}-5-[(pyrazin yl)amino]-1H-pyrazole-4-carboxamide (compound 248)

A mixture of 3-{4-ethanesulfonamido-3-[1-(4-fluorophenyl)cyclopropoxy]phenyl}-5-[(pyrazin-2-yl)amino]-1-{[2-(trimethylsilyl)ethoxy]methyl}-1Hpyrazole-4-carboxamide (30 mg, 44.9 μmol) in DCM:TFA (1:1, 3 mL) was stirred at RT for 2 h. The mixture was concentrated and the residue was neutralized to pH 7-8 with sat. $Na_2CO_3$. The resulting precipitate was collected by filtration and then washed with MeOH to afford the title compound (10 mg, 41%) as a yellow solid. LCMS (Method A): 3.87 min; m/z: 538.2 $[M+H]^+$. $^1H$ NMR (400 MHz, MeOD-$d_4$): 12.93 (s, 1H), 9.59 (s, 1H), 9.22 (s, 1H), 8.20 (s, 1H), 8.10 (s, 1H), 7.46 (d, J=7.6 Hz, 1H), 7.31 (t, J=8.8 Hz, 2H), 7.13 (t, J=8.8 Hz, 3H), 7.05 (s, 1H), 6.21 (s, 1H), 3.16 (q, J=6.8 Hz, 2H), 1.47 (s, 2H), 1.41 (s, 2H), 1.31 (t, J=7.2 Hz, 3H).

The compounds below (Table 21) were similarly prepared following the synthesis of Compound 248, using the appropriate sulfonyl chloride in step 4 and appropriate Intermediate B in step 6:

TABLE 21

| Compound No | Name | Structure | LCMS data | $^1$H NMR data | Sulfonyl chloride | Intermediate B |
|---|---|---|---|---|---|---|
| 307 | 3-(4-((difluoromethyl) sulfonamido)-3-(1-(4-fluorophenyl) cyclopropoxy) phenyl)-5-(pyrazin-2-ylamino)-1H-pyrazole-4-carboxamide | 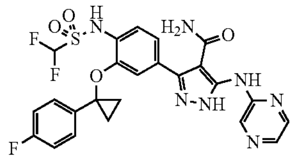 [SMILES: NC(=O)c1c(-c2ccc(NS(=O)(=O)C(F)F)c(OC3(c4ccc(F)cc4)CC3)c2)n[nH]c1Nc1cnccn1] | LCMS (Method A): 3.48 min m/z: 560.1 [M + H]$^+$. | $^1$H NMR (400 MHz, DMSO-$d_6$): 13.00 (s, 1H), 9.50 (s, 1H), 8.19 (s, 1H), 8.08 (s, 1H), 7.40-6.99 (m, 9H), 6.19 (s, 1H), 1.41 (s, 4H). | difluoromethanesulfonyl chloride | Intermediate B3 |
| 290 | 3-(4-((difluoromethyl) sulfonamido)-3-(1-(4-fluorophenyl) cyclopropoxy) phenyl)-5-((5-methylpyrazin-2-yl)amino)-1H-pyrazole-4-carboxamide | 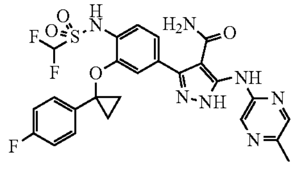 [SMILES: Cc1cnc(Nc2[nH]nc(-c3ccc(NS(=O)(=O)C(F)F)c(OC4(c5ccc(F)cc5)CC4)c3)c2C(N)=O)cn1] | LCMS (Method A): 3.59 min; m/z 574.1 [M + H]$^+$. | $^1$H NMR (400 MHz, DMSO-$d_6$): 12.93 (s, 1H), 9.42 (s, 1H), 9.11 (s, 1H), 8.09 (s, 1H), 7.40-7.00 (m, 9H), 2.38 (s, 3H), 1.42 (d, J = 6.8 Hz, 4H). | difluoromethanesulfonyl chloride | Intermediate B5 |

Compound 269

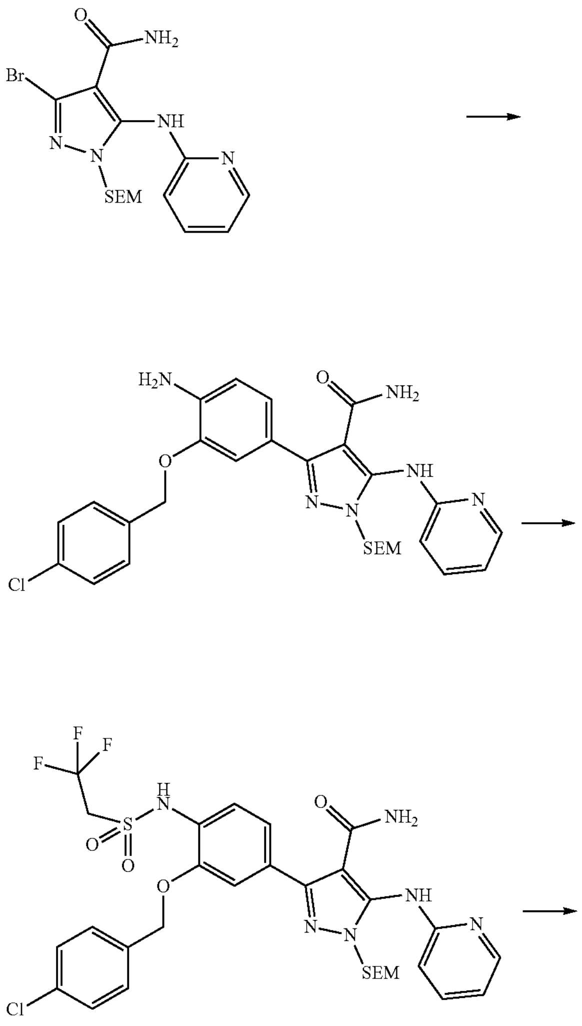

-continued

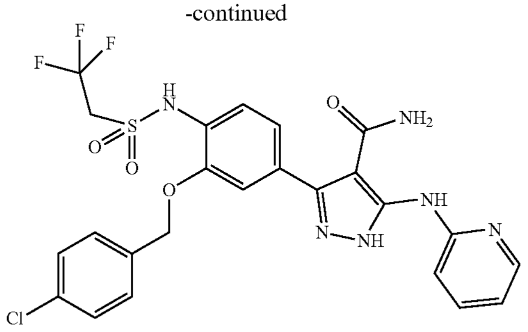

Step 1: 3-{4-amino-3-[(4-chlorophenyl)methoxy] phenyl}-5-[(pyridin-2-yl)amino]-1-{[2-(trimethylsilyl)ethoxy]methyl}-1H-pyrazole-4-carboxamide A mixture of 3-bromo-5-[(pyridin-2-yl)amino]-1-{[2-(trimethylsilyl)ethoxy]methyl}-1H-pyrazole-4-carboxamide (Intermediate B2, 500 mg, 1.21 mmol), 2-[(4-chlorophenyl)methoxy]-4-(4,4,5,5-tetramethyl-1,3,2-dioxaborolan-2-yl)aniline (435 mg, 1.21 mmol), Pd(dppf)$Cl_2$ (98.8 mg, 121 μmol) and $Na_2CO_3$ (256 mg, 2.42 mmol) in 80% aq. 1,4-dioxane (12.5 mL) was irradiated at 100° C. in a microwave reactor. After 1 h, the reaction mixture was concentrated and the crude residue was purified by silica gel column chromatography (PE:EtOAc, 20:1) to afford the title product (680 mg, 95%) as a yellow solid. LCMS (Method A): 4.43 min; m/z: 595.1 [M+H]$^+$.

Step 2: 3-{3-[(4-chlorophenyl)methoxy]-4-(2,2,2-trifluoroethanesulfonamido)phenyl}-5-[(pyridin-2-yl)amino]-1-{[2-(trimethylsilyl)ethoxy]methyl}-1H-pyrazole-4-carboxamide To a solution of 3-{4-amino-3-[(4-chlorophenyl) methoxy]phenyl}-5-[(pyridin-2-yl)amino]-1-{[2-(trimethylsilyl)ethoxy]methyl}-1H-pyrazole-4-carboxamide (300 mg, 530 μmol) in $CHCl_3$:pyridine (1:1, 6 mL), was added 2,2,2-trifluoroethane-1-sulfonyl chloride (145 mg, 795

μmol). The mixture was stirred at RT for 16 h and then concentrated under reduced pressure. The residue was diluted with $H_2O$ (50 mL) and then extracted with EtOAc (3×20 mL). The combined organic layers were washed (brine), dried ($Na_2SO_4$) and then concentrated. The residue was purified by prep-TLC (DCM:MeOH, 15:1) to afford the title product (100 mg, 33%) as a yellow solid. LCMS (Method A): 3.56 min; m/z: 710.5 $[M+H]^+$.

Step 3: 3-{3-[(4-chlorophenyl)methoxy]-4-(2,2,2-trifluoroethanesulfonamido)phenyl}-5-[(pyridin-2-yl)amino]-1H-pyrazole-4-carboxamide (compound 269)

A solution of 3-{3-[(4-chlorophenyl)methoxy]-4-(2,2,2-trifluoroethanesulfonamido)phenyl}-5-[(pyridin-2-yl) amino]-1-{[2-(trimethylsilyl)ethoxy]methyl}-1H-pyrazole-4-carboxamide (100 mg, 28.1 μmol) in DCM:TFA (1:1, 6 mL) was stirred at RT for 16 h. The reaction mixture was concentrated and the residue was neutralized to pH 7-8 with sat. $Na_2CO_3$. The resulting precipitate was collected by filtration and then purified by prep-TLC (DCM:MeOH, 15:1) to afford the title product (30 mg, 26%) as a yellow solid. LCMS (Method A): 3.41 min; m/z: 580.6 $[M+H]^+$. $^1H$ NMR (400 MHz, DMSO-$d_6$): 12.56 (s, 1H), 9.67 (s, 1H), 8.17 (s, 1H), 8.03 (s, 1H), 7.69 (t, J=6.8 Hz, 1H), 7.52-7.32 (m, 8H), 6.96 (d, J=11.2 Hz, 2H), 6.84 (d, J=6.4 Hz, 1H), 5.07 (s, 1H), 3.67-3.58 (m, 2H).

Compound 266

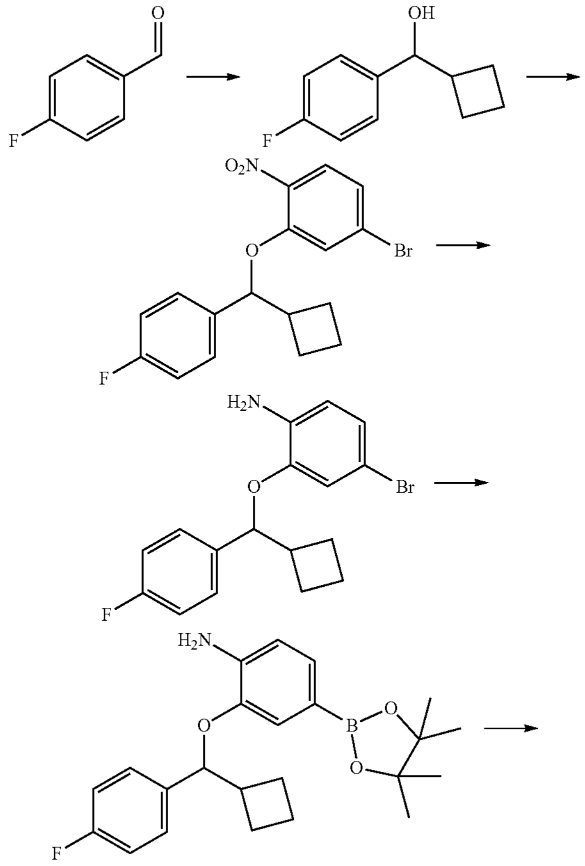

-continued

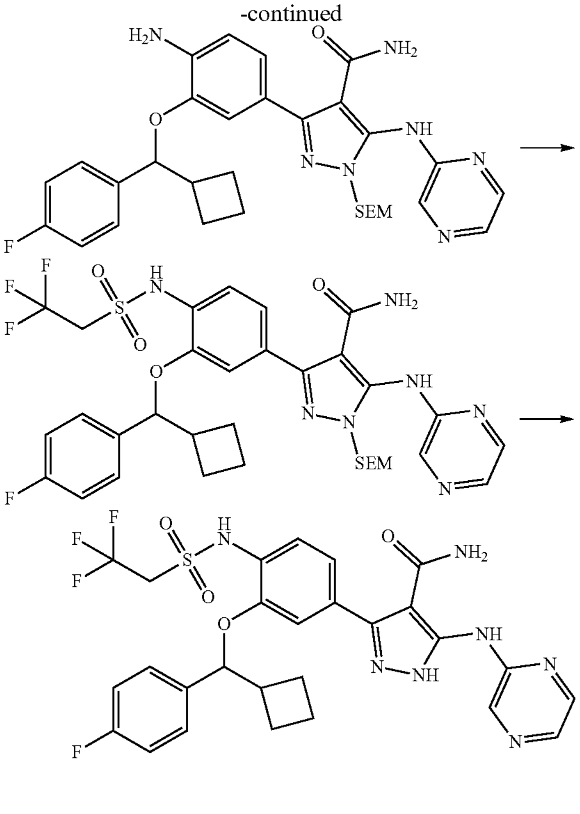

Step 1: cyclobutyl(4-fluorophenyl)methanol

To a solution of 4-fluorobenzaldehyde (3.10 g, 25.0 mmol) in THF (10 mL) at 0° C., was added c-BuMgBr (21.40 g, 161 mmol) and the mixture was stirred at RT for 16 h. The reaction mixture was quenched with sat. $NH_4Cl$ (100 mL) and then extracted with EtOAc (3×150 mL). The combined organic layers were washed (brine), dried ($Na_2SO_4$) and concentrated. The crude residue was purified by silica gel column chromatography (PE:EtOAc, 20:1 to 5:1) to afford the title product (4.30 g, 95%) as a colorless oil. $^1H$ NMR (400 MHz, DMSO-$d_6$): 7.38-7.29 (m, 2H), 7.15-7.05 (m, 2H), 5.17 (d, J=4.4 Hz, 2H), 4.48 (d, J=5.6 Hz, 1H), 2.46-2.38 (m, 1H), 1.94-1.61 (m, 5H).

Step 2: 4-bromo-2-[cyclobutyl(4-fluorophenyl) methoxy]-1-nitrobenzene

To a mixture of cyclobutyl(4-fluorophenyl)methanol (4.30 g, 23.8 mmol) in THF (100 mL) at 0° C., was added NaH (2.85 g, 71.4 mmol). After 30 min, 4-bromo-2-fluoro-1-nitrobenzene (5.23 g, 23.8 mmol) was added, and the mixture was stirred at RT for 16 h. The reaction mixture was concentrated, and the residue diluted with $H_2O$ (200 mL) and extracted with EtOAc (2×80 mL). The combined organic layers were washed (brine), dried ($Na_2SO_4$) and concentrated to afford the title product (6.50 g, 72%) as a brown solid. $^1H$ NMR (400 MHz, DMSO-$d_6$): 7.80 (d, J=8.8 Hz, 1H), 7.43-7.42 (m, 3H), 7.26-7.24 (m, 1H), 7.22-7.17 (m, 2H), 5.70 (d, J=7.2 Hz, 1H), 2.73-2.68 (m, 1H), 2.05-1.74 (m, 6H).

Step 3: 4-bromo-2-[cyclobutyl(4-fluorophenyl) methoxy]aniline

A mixture of 4-bromo-2-[cyclobutyl(4-fluorophenyl) methoxy]-1-nitrobenzene (6.50 g, 17.0 mmol), Zn powder (5.55 g, 85.0 mmol), sat. $NH_4Cl$ (30 mL) and MeOH (100 mL) was stirred at 60° C. for 3 h. The reaction mixture was filtered, and the filtrate concentrated, diluted with $H_2O$ (50 mL) and extracted with DCM (3×50 mL). The combined organic layers were washed (brine), dried ($Na_2SO_4$) and concentrated to afford the title product (6.00 g, 17.1 mmol) as a brown oil.

Step 4: 2-[cyclobutyl(4-fluorophenyl)methoxy]-4-(4,4,5,5-tetramethyl-1,3,2-dioxaborolan-2-yl)aniline A mixture of 4-bromo-2-[cyclobutyl(4-fluorophenyl)methoxy]aniline (1.0 g, 2.85 mmol), $B_2pin_2$ (723 mg, 2.85 mmol), Pd(dppf)$Cl_2$ (260 mg, 285 μmol), KOAc (559 mg, 5.70 mmol) and 1,4-dioxane (150 mL) was stirred at 100° C. for 16 h. The reaction mixture was concentrated, and the residue diluted with $H_2O$ (100 mL) and extracted with EtOAc (3×50 mL). The combined organic layers were washed (brine), dried ($Na_2SO_4$) and concentrated under reduced pressure. The crude residue was purified by silica gel column chromatography (PE:EtOAc, 10:1) to afford the title product (660 mg, 58%) as a black oil. LCMS (Method A): 4.67 min; m/z: 398.2 $[M+H]^+$.

Step 5: 3-{4-amino-3-[cyclobutyl(4-fluorophenyl)methoxy]phenyl}-5-[(pyrazin-2-yl)amino]-1-{[2-(trimethylsilyl)ethoxy]methyl}-1H-pyrazole-4-carboxamide A mixture of 2-[cyclobutyl(4-fluorophenyl)methoxy]-4-(4,4,5,5-tetramethyl-1,3,2-dioxaborolan-2-yl)aniline (600 mg, 1.51 mmol), 3-bromo-5-[(pyrazin-2-yl)amino]-1-{[2-(trimethylsilyl)ethoxy]methyl}-1H-pyrazole-4-carboxamide (624 mg, 1.51 mmol), Pd(dppf)$Cl_2$·DCM (123 mg, 151 μmol), $Na_2CO_3$ (320 mg, 3.02 mmol) and 80% aq. 1,4-dioxane (100 mL) was stirred at 100° C. under $N_2$. After 16 h the reaction mixture was concentrated, and the residue diluted with $H_2O$ (100 mL) and extracted with EtOAc (3×50 mL). The combined organic layers were washed (brine), dried ($Na_2SO_4$) and concentrated under reduced pressure. The crude residue was purified by silica gel column chromatography (DCM:MeOH, 60:1) to afford the title product (400 mg, 43%) as a brown solid. LCMS (Method A): 4.18 min; m/z: 604.3 $[M+H]^+$.

Step 6: 3-{3-[cyclobutyl(4-fluorophenyl)methoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide A mixture of 3-{4-amino-3-[cyclobutyl(4-fluorophenyl)methoxy]phenyl}-5-[(pyrazin-2-yl)amino]-1-{[2-(trimethylsilyl)ethoxy]methyl}-1H-pyrazole-4-carboxamide (400 mg, 662 μmol), 2,2,2-trifluoroethanesulfonyl chloride (181 mg, 993 μmol) and DCM:pyridine (1:1, 30 mL) was stirred at RT for 16 h. The reaction mixture was concentrated, and the residue diluted with $H_2O$ (50 mL) and extracted with EtOAc (3×30 mL). The combined organic layers were washed (brine), dried ($Na_2SO_4$) and concentrated under reduced pressure. The crude residue was purified by silica gel column chromatography (DCM:MeOH, 50:1) to afford the title product (350 mg, 70%) as a brown solid. LCMS (Method A): 4.32 min; m/z: 750.3 $[M+H]^+$.

Step 7: 3-{3-[cyclobutyl(4-fluorophenyl)methoxy]-4-(2,2,2-trifluoroethanesulfonamido)phenyl}-5-[(pyrazin-2-yl)amino]-1H-pyrazole-4-carboxamide (compound 266)

A solution of 3-{3-[cyclobutyl(4-fluorophenyl)methoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide (200 mg, 266 μmol) in DCM:TFA (10:1, 11 mL) was stirred at RT for 5 min. The reaction mixture was concentrated, and the residue was neutralized to pH 7-8 with sat. $Na_2CO_3$. The resulting precipitate was collected by filtration and then purified by prep-TLC (DCM:MeOH, 20:1) to afford the title compound (20.0 mg, 12%) as a white solid. LCMS (Method A): 3.85 min; m/z: 620.2 $[M+H]^+$. $^1H$ NMR (400 MHz, DMSO-$d_6$): 13.01 (s, 1H), 9.94 (s, 1H), 9.58 (s, 1H), 9.21 (s, 1H), 8.21-8.20 (m, 1H), 8.10 (d, J=2.8 Hz, 1H), 7.59-7.56 (m, 2H), 7.40 (d, J=7.6 Hz, 1H), 7.22 (s, 1H), 7.15-7.09 (m, 3H), 5.46-5.44 (m, 1H), 4.55-4.42 (m, 2H), 2.85-2.78 (m, 1H), 2.07-1.99 (m, 2H), 1.83 (s, 3H), 1.73-1.68 (m, 1H).

Compound 236

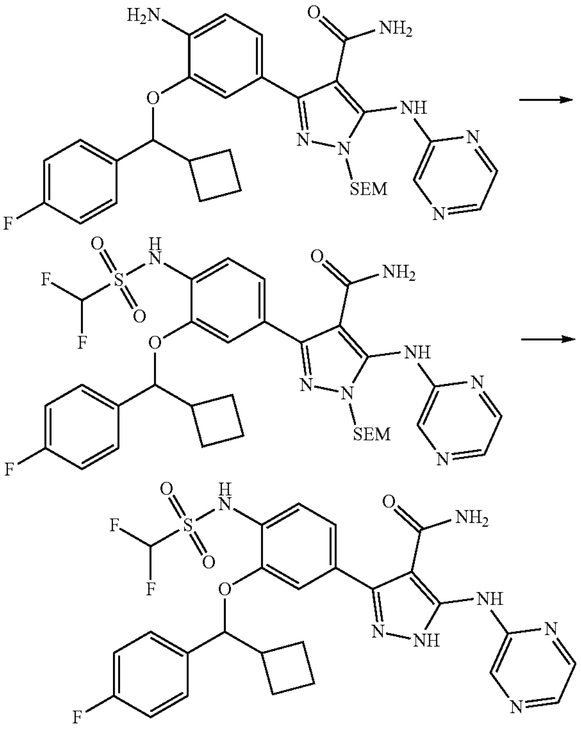

Step 1: 3-{3-[cyclobutyl(4-fluorophenyl)methoxy]-4-(difluoromethanesulfonamido)phenyl}-5-[(pyrazin-2-yl)amino]-1-{[2-(trimethylsilyl)ethoxy]methyl}-1H-pyrazole-4-carboxamide A solution of 3-{4-amino-3-[cyclobutyl(4-fluorophenyl)methoxy]phenyl}-5-[(pyrazin-2-yl)amino]-1-{[2-(trimethylsilyl)ethoxy]methyl}-1H-pyrazole-4-carboxamide (700 mg, 1.15 mmol) and $F_2CHSO_2Cl$ (258 mg, 1.72 mmol) in DCM:pyridine (1:1, 10 mL) was stirred at RT for 16 h. The reaction mixture was concentrated, and the residue was diluted with $H_2O$ (80 mL) and extracted with EtOAc (3×40 mL). The combined organic layers were washed (brine), dried ($Na_2SO_4$) and concentrated under reduced pressure. The crude residue was purified by silica gel column chromatography (DCM:MeOH, 55:1) to afford the title product (400 mg, 48%) as a yellow solid. LCMS (Method A): 4.37 min; 718.3 $[M+H]^+$.

Step 2: 3-{3-[cyclobutyl(4-fluorophenyl)methoxy]-4-(difluoromethanesulfonamido)phenyl}-5-[(pyrazin-2-yl)amino]-1H-pyrazole-4-carboxamide (compound 236)

A solution of 3-{3-[cyclobutyl(4-fluorophenyl)methoxy]-4-(difluoromethanesulfonamido)phenyl}-5-[(pyrazin-2-yl)amino]-1-{[2-(trimethylsilyl)ethoxy]methyl}-1H-pyrazole-4-carboxamide (180 mg, 250 µmol) in DCM:TFA (8:1, 9 mL) was stirred at RT for 5 min. The reaction mixture was concentrated, and the residue was neutralized to pH 7-8 with sat. $Na_2CO_3$. The resulting precipitate was collected by filtration and then purified by prep-HPLC to afford the title compound (20 mg, 13%) as a white solid. LCMS (Method A): 3.74 min; m/z: 588.2 $[M+H]^+$. $^1H$ NMR (400 MHz, DMSO-$d_6$): 12.92 (s, 1H), 10.51 (s, 1H), 9.56 (s, 1H), 9.20 (s, 1H), 8.20 (s, 1H), 8.10-8.09 (m, 1H), 7.54-7.51 (m, 2H), 7.37 (d, J=7.6 Hz, 1H), 7.15-7.07 (m, 5H), 6.05 (s, 1H), 5.39 (d, J=6.4 Hz, 1H), 2.80-2.74 (m, 1H), 2.17-2.09 (m, 1H), 2.03-1.90 (m, 2H), 1.84-1.72 (m, 3H).

The following compounds (Table 22) were similarly prepared from the appropriate benzyl alcohol 1-(4-fluorophenyl)-2-methoxyethan-1-ol following step 2 of Compound 266 synthesis according to the method described for the synthesis of compound 23.

TABLE 22

| Compound no | Name | Structure | LCMS data | $^1H$ NMR data |
|---|---|---|---|---|
| 319 | 3-(4-((difluoromethyl)sulfonamido)-3-(1-(4-fluorophenyl)-2-methoxyethoxy)phenyl)-5-(pyrazin-2-ylamino)-1H-pyrazole-4-carboxamide | 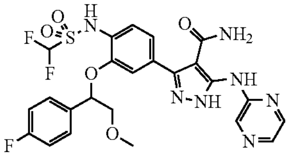 [SMILES: COCC(Oc1cc(-c2n[nH]c(Nc3cnccn3)c2C(N)=O)ccc1NS(=O)(=O)C(F)F)c1ccc(F)cc1] | LCMS (Method A): 3.34 min, m/z: 578.2 $[M + H]^+$. | $^1H$ NMR (400 MHz, $CDCl_3$): 12.31 (s, 1H), 10.26 (s, 1H), 8.35 (d, J = 1.5 Hz, 1H), 8.19 (dd, J = 2.9, 1.4 Hz, 1H), 8.15 (d, J = 2.9 Hz, 1H), 7.72 (d, J = 8.4 Hz, 1H), 7.44-7.36 (m, 2H), 7.31 (s, 1H), 7.10 (t, J = 8.6 Hz, 2H), 6.92 (d, J = 1.9 Hz, 1H), 6.37 (t, J = 53.6 Hz, 1H), 4.98 (dd, J = 9.4, 2.8 Hz, 1H), 3.81 (dd, J = 10.4, 9.4 Hz, 1H), 3.57 (dd, J = 10.5, 2.9 Hz, 1H), 3.54 (s, 3H). |
| 298 | 3-(4-((difluoromethyl)sulfonamido)-3-(1-(4-fluorophenyl)-2-methoxyethoxy)phenyl)-5-((5-methylisoxazol-3-yl)amino)-1H-pyrazole-4-carboxamide | 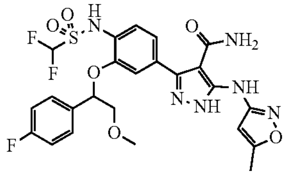 [SMILES: COCC(Oc1cc(-c2n[nH]c(Nc3cc(C)on3)c2C(N)=O)ccc1NS(=O)(=O)C(F)F)c1ccc(F)cc1] | LCMS (Method A): 3.54 min, m/z: 581.2 $[M + H]^+$. | $^1H$ NMR (400 MHz, DMSO-$d_6$): 12.77 (s, 1H), 10.61 (s, 1H), 9.08 (s, 1H), 7.58 (dd, J = 8.6, 5.6 Hz, 2H), 7.38 (d, J = 8.1 Hz, 1H), 7.18 (t, J = 8.8 Hz, 2H), 7.16-6.89 (m, 3H), 3.55 (s, 1H), 6.03 (brs, 1H), 5.67 (dd, J = 7.2, 4.0 Hz, 1H), 3.81 (dd, J = 10.8, 7.1 Hz, 1H), 3.60 (dd, J = 10.8, 3.9 Hz, 1H), 3.32 (s, 3H), 2.35 (s, 3H). |

-continued

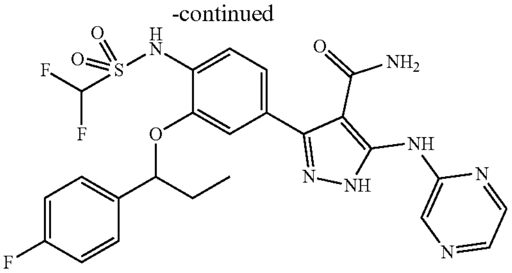

3-(3-(1-(4-fluorophenyl)propoxy)-4-(2,2,2-trifluoroethylsulfonamido)phenyl)-5-(pyrazin-2-ylamino)-1H-pyrazole-4-carboxamide A solution of 3-{3-[1-(4-fluorophenyl)propoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide (90 mg, 124 µmol) in $CHCl_3$:TFA (1:1, 5 mL) was stirred at RT for 2 min. The reaction mixture was neutralized to pH 7-8 with $NH_4OH$ and then concentrated under reduced pressure. The crude residue was purified by prep-HPLC to afford the title compound (22.0 mg, 29%) as a white solid. LCMS (Method A): 3.67 min; m/z: 594.2 $[M+H]^+$. $^1H$ NMR (400 MHz, DMSO-$d_6$): 13.06 (s, 1H), 9.77 (s, 1H), 9.31 (br s, 1H), 8.36-8.29 (m, 1H), 8.21 (d, J=2.8 Hz, 1H), 7.68-7.62 (m, 2H), 7.51 (d, J=8.4 Hz, 1H), 7.30-7.24 (m, 3H), 7.20 (dd, J=8.0, 1.6 Hz, 1H), 6.17 (br s, 1H), 5.54-5.44 (m, 1H), 4.50 (t, J=7.2 Hz, 2H), 2.21-2.09 (m, 1H), 2.08-1.86 (m, 1H), 1.00 (t, J=7.6 Hz, 3H).

Compounds 250 and 251

The following compounds were similarly prepared from the appropriate benzyl alcohol following step 1 according to the method described for the synthesis of 3-{3-[cyclobutyl(4-fluorophenyl)methoxy]-4-(2,2,2-trifluoroethanesulfonamido)phenyl}-5-[(pyrazin-2-yl)amino]-1H-pyrazole-4-carboxamide:

Compound 263

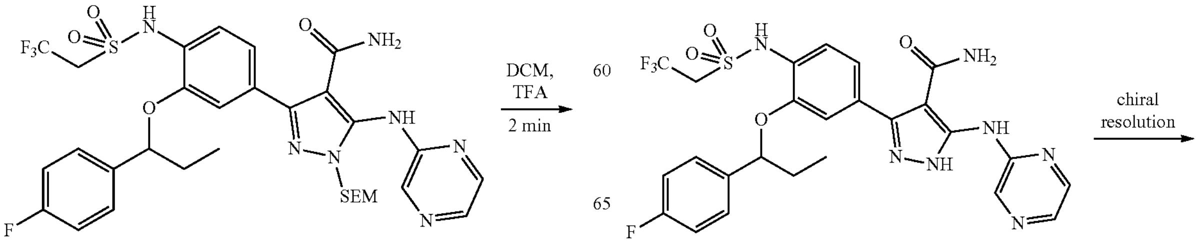

-continued

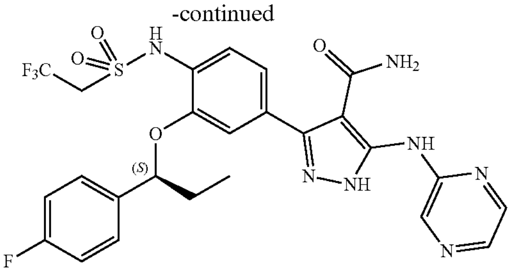

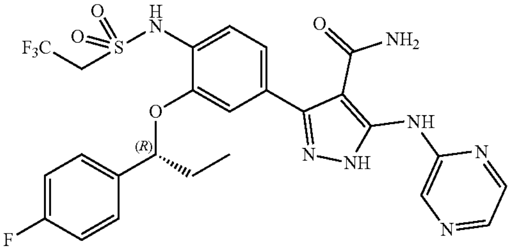

The racemic 3-(3-(1-(4-fluorophenyl)propoxy)-4-(2,2,2-trifluoroethylsulfonamido)phenyl)-5-(pyrazin-2-ylamino)-1H-pyrazole-4-carboxamide was subjected to purification by chiral HPLC on a AD-H column using heptane:EtOH, 60:40 with 0.1% $Et_2NH$ as the mobile phase.

Peak 1: (S)-3-(3-(1-(4-fluorophenyl)propoxy)-4-((2,2,2-trifluoroethyl)sulfonamido)phenyl)-5-(pyrazin-2-ylamino)-1H-pyrazole-4-carboxamide. Product retention time=2.72 min. LCMS (Method A): 2.13 min; m/z: 594.2 $[M+H]^+$. $^1H$ NMR (400 MHz, DMSO-$d_6$): 12.95 (s, 1H), 9.93 (s, 1H), 9.60 (s, 1H), 9.22 (s, 1H), 8.21 (s, 1H), 8.10 (d, J=2.4 Hz, 1H), 7.56 (q, J=4.8 Hz, 3H), 7.43 (d, J=7.2 Hz, 1H), 7.18-7.10 (m, 5H), 5.40 (s, 1H), 4.48 (q, J=6.4 Hz, 2H), 2.08-2.02 (m, 1H), 1.88-1.81 (m, 1H), 0.90 (t, J=7.2 Hz, 3H).

Peak 2: (R)-3-(3-(1-(4-fluorophenyl)propoxy)-4-((2,2,2-trifluoroethyl)sulfonamido)phenyl)-5-(pyrazin-2-ylamino)-1H-pyrazole-4-carboxamide. Product retention time=7.29 min. LCMS (Method A): 2.13 min; m/z: 594.2 $[M+H]^+$. $^1H$ NMR (400 MHz, DMSO-$d_6$): 12.93 (s, 1H), 9.91 (s, 1H), 9.60 (s, 1H), 9.22 (s, 1H), 8.21 (s, 1H), 8.10 (d, J=2.8 Hz, 1H), 7.57 (q, J=4.8 Hz, 3H), 7.41 (d, J=8.0 Hz, 1H), 7.18-7.09 (m, 5H), 5.38 (s, 1H), 4.46 (q, J=5.6 Hz, 2H), 2.07-2.02 (m, 1H), 1.87-1.80 (m, 1H), 0.90 (t, J=7.2 Hz, 3H).

Compound 233

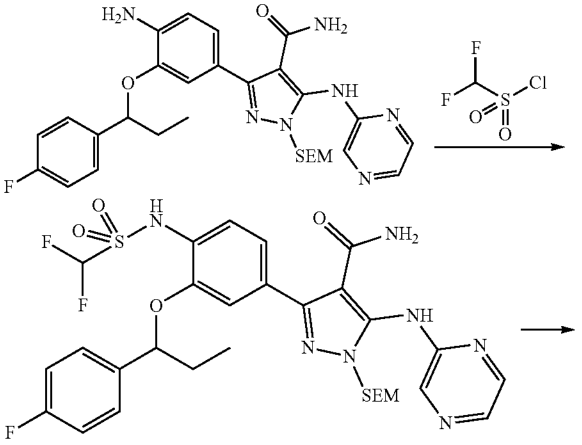

-continued

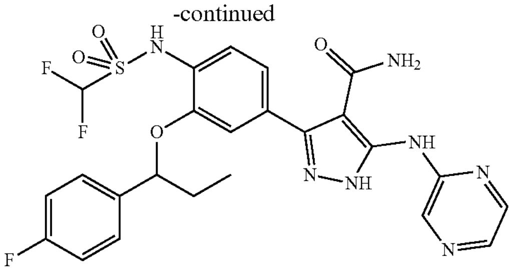

Step 1: 3-[4-(difluoromethanesulfonamido)-3-[1-(4-fluorophenyl)propoxy]phenyl]-5-[(pyrazin-2-yl)amino]-1-{[2-(trimethylsilyl)ethoxy]methyl}-1H-pyrazole-4-carboxamide A solution of 3-{4-amino-3-[1-(4-fluorophenyl)propoxy]phenyl}-5-[(pyrazin-2-yl)amino]-1-{[2-(trimethylsilyl)ethoxy]methyl}-1H-pyrazole-4-carboxamide (420 mg, 726 μmol) and $F_2CHSO_2Cl$ (141 mg, 943 μmol) in $CHCl_3$: pyridine (2:1, 15 mL) was stirred at RT for 5 min. The reaction mixture was concentrated and the crude residue was purified by silica gel column chromatography (PE:EtOAc, 5:1 to 0:1) to afford the title product (190 mg, 37%) as a brown solid. LCMS (Method A): 4.10 min; m/z: 692.2 $[M+H]^+$.

Step 2: 3-[4-(difluoromethanesulfonamido)-3-[1-(4-fluorophenyl)propoxy]phenyl]-5-[(pyrazin-2-yl)amino]-1H-pyrazole-4-carboxamide A solution of 3-[4-(difluoromethanesulfonamido)-3-[1-(4-fluorophenyl)propoxy]phenyl]-5-[(pyrazin-2-yl)amino]-1-{[2-(trimethylsilyl)ethoxy]methyl}-1H-pyrazole-4-carboxamide (190 mg, 274 μmol) in DCM:TFA (1:1, 6 mL) was stirred at RT for 5 min. The reaction mixture was neutralized to pH 7-8 with $NH_4OH$ and then concentrated under reduced pressure. The crude residue was purified by prep-HPLC to afford the title compound (7.9 mg, 5%) as a white solid. LCMS (Method A): 3.57 min; m/z: 562.2 $[M+H]^+$. $^1H$ NMR (400 MHz, DMSO-$d_6$): 12.96 (s, 1H), 10.52 (br s, 1H), 9.53 (s, 1H), 9.19 (s, 1H), 8.20 (s, 1H), 8.10 (s, 1H), 7.58-7.46 (m, 2H), 7.38 (d, J=7.2 Hz, 1H), 7.22-7.06 (m, 4H), 6.10 (br s, 1H), 5.39 (s, 1H), 2.10-1.94 (m, 1H), 1.93-1.76 (m, 1H), 0.90 (t, J=7.2 Hz, 3H).

Compounds 272 and 273

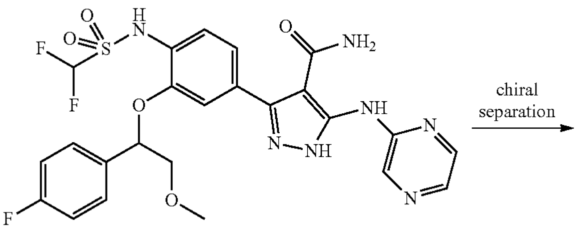

-continued

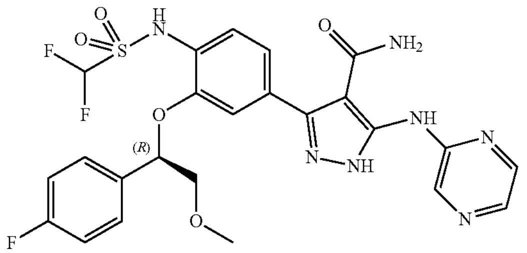

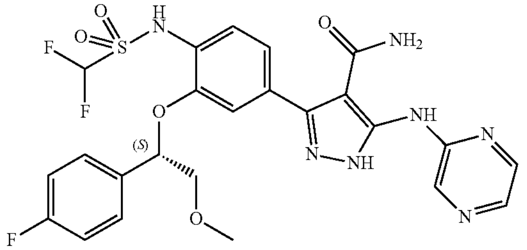

The racemic Compound 233 (232 mg) was subjected to purification by chiral HPLC. The separation was performed on a UniChiral CMD-5H column, (Column size 21.2 mm I.D×250 mm L. Mobile phase 100% Ethanol, flow rate 12 mL/min, temperature 25° C.). The enantiomeric excess was calculated on UniChiral CMD-5H, 4.6*250 mm (100% MeOH, flow rate 1 mL/min, injection 10 μL, temperature 25° C.).

Peak 1: (R)-3-(4-((difluoromethyl)sulfonamido)-3-(2-(4-fluorophenyl)-3-methoxypropyl)phenyl)-5-(pyrazin-2-ylamino)-1H-pyrazole-4-carboxamide (91 mg, retention time 5.89 min, ee >99%).

Peak 2: (S)-3-(4-((difluoromethyl)sulfonamido)-3-(2-(4-fluorophenyl)-3-methoxypropyl)phenyl)-5-(pyrazin-2-ylamino)-1H-pyrazole-4-carboxamide (114 mg, retention time 11.92 min, ee >99%).

Compounds 299 and 300

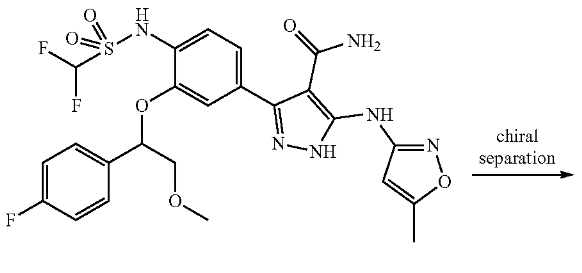

-continued

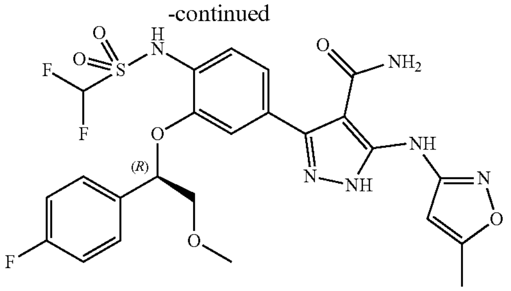

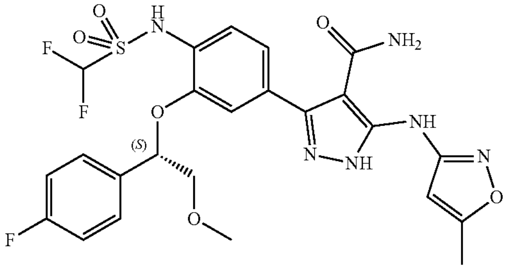

The racemic Compound 298 was subjected to purification by chiral SFC separation (CHIRALPAK IG 4.6*100 mm 3 μm, $CO_2$:Methanol 55:45, 130 bars, flow rate 2.5 mL/min).

Peak 1: (R)-3-(4-((difluoromethyl)sulfonamido)-3-(1-(4-fluoro phenyl)-2-methoxyethoxy)phenyl)-5-((5-methylisoxazol-3-yl)amino)-1H-pyrazole-4-carboxamide.

Peak 2: (S)-3-(4-((difluoromethyl)sulfonamido)-3-(1-(4-fluorophenyl)-2-methoxyethoxy)phenyl)-5-((5-methylisoxazol-3-yl)amino)-1H-pyrazole-4-carboxamide.

Compound 264

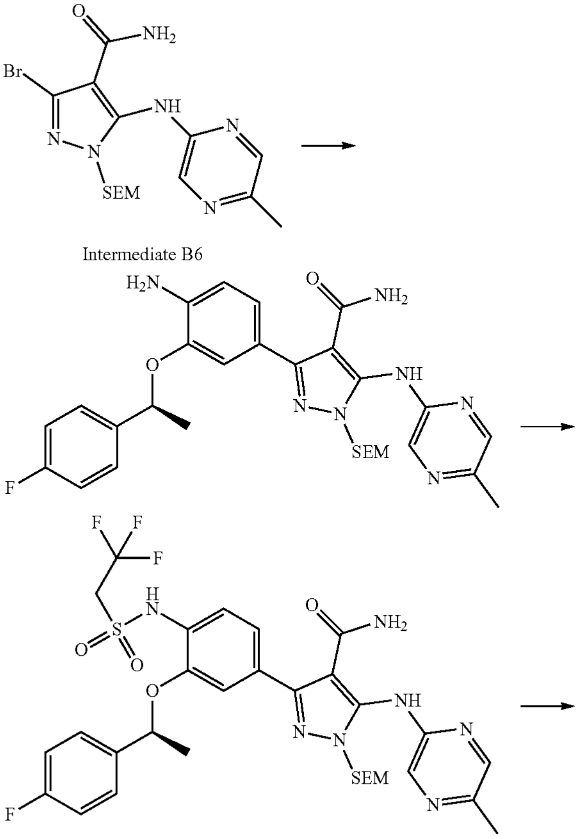

-continued

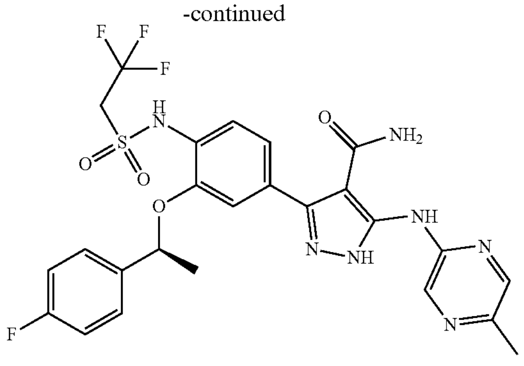

Step 1: 3-{4-amino-3-[(1S)-1-(4-fluorophenyl) ethoxy]phenyl}-5-[(5-methylpyrazin-2-yl)amino]-1-{[2-(trimethylsilyl)ethoxy]methyl}-1H-pyrazole-4-carboxamide A mixture of 3-bromo-5-[(5-methylpyrazin-2-yl)amino]-1-{[2-(trimethylsilyl)ethoxy]methyl}-1H-pyrazole-4-carboxamide (Intermediate B6, 300 mg, 0.70 mmol), 2-[(1S)-1-(4-fluorophenyl)ethoxy]-4-(4,4,5,5-tetramethyl-1,3,2-dioxaborolan-2-yl)aniline (250 mg, 0.70 mmol), Pd(dppf) $Cl_2$ (57.3 mg, 0.07 mmol), $Na_2CO_3$ (222 mg, 2.10 mmol) and 80% aq. 1,4-dioxane (25 mL) was stirred at 100° C. under $N_2$ for 16 h. The reaction mixture was concentrated, and the residue was diluted with $H_2O$ (50 mL) and then extracted with EtOAc (3x50 mL). The combined organic layers were washed (brine), dried ($Na_2SO_4$) and concentrated. The crude residue was purified by prep-TLC (DCM: MeOH, 20:1) to afford the title product (220 mg, 54%) as a yellow solid. LCMS (Method A): 2.86 min; m/z: 578.3 $[M+H]^+$.

Step 2: 3-{3-[(1S)-1-(4-fluorophenyl)ethoxy]-4-(2,2,2-trifluoroethanesulfonamido)phenyl}-5-[(5-methylpyrazin-2-yl)amino]-1-{[2-(trimethylsilyl)ethoxy] methyl}-1H-pyrazole-4-carboxamide A solution of 3-{4-amino-3-[(1S)-1-(4-fluorophenyl) ethoxy]phenyl}-5-[(5-methylpyrazin-2-yl)amino]-1-{[2-(trimethylsilyl)ethoxy]methyl}-1H-pyrazole4-carboxamide (210 mg, 0.36 mmol) and 2,2,2-trifluoroethane-1-sulfonyl chloride (99 mg, 0.54 mmol) in DCM:pyridine (3:1, 20 mL) was stirred at RT for 16 h. The reaction mixture was concentrated and the crude residue purified by prep-TLC (DCM:MeOH, 20:1) to afford the title product (150 mg, 57%) as a yellow solid. LCMS (Method A): 3.37 min; m/z: 724.2 $[M+H]^+$.

Step 3: 3-{3-[(1S)-1-(4-fluorophenyl)ethoxy]-4-(2,2,2-trifluoroethanesulfonamido)phenyl}-5-[(5-methylpyrazin-2-yl)amino]-1H-pyrazole-4-carboxamide (compound 264)

A solution of 3-{3-[(1S)-1-(4-fluorophenyl)ethoxy]-4-(2,2,2-trifluoroethanesulfonamido)phenyl}-5-[(5-methylpyrazin-2-yl)amino]-1-{[2-(trimethylsilyl)ethoxy] methyl}-1H-pyrazole-4-carboxamide (190 mg, 0.26 mmol) in DCM:TFA (10:1, 21 mL) was stirred at RT for 16 h. The reaction mixture was concentrated and then neutralized to pH 7-8 with sat. $Na_2CO_3$. The mixture was concentrated, and the residue was triturated with MeOH to afford the title compound (40 mg, 26%) as a white solid. LCMS (Method A): 1.95 min; m/z: 594.1 $[M+H]^+$. $^1H$ NMR (400 MHz, MeOD-$d_4$): 12.91 (s, 1H), 9.96 (s, 1H), 9.48 (s, 1H), 9.14 (s, 1H), 8.11 (s, 1H), 7.59 (t, J=8.0 Hz, 2H), 7.43 (d, J=8.0 Hz, 1H), 7.20-7.11 (m, 5H), 5.65 (d, J=6.0 Hz, 1H), 4.49-4.43 (m, 2H), 2.40 (s, 3H), 1.60 (t, J=6.4 Hz, 3H).

Compound 265

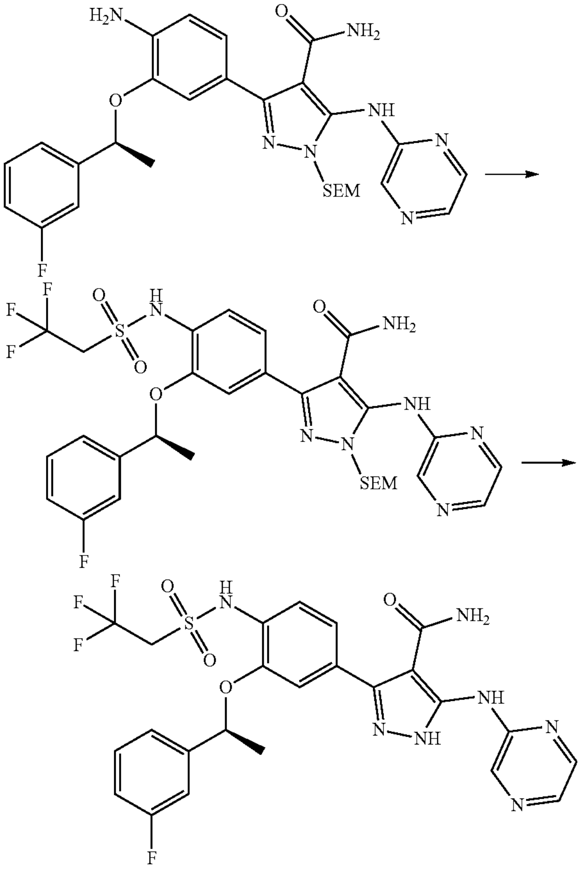

Step 1: 3-{3-[(1S)-1-(3-fluoro phenyl)ethoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide A solution of 3-{4-amino-3-[(1S)-1-(3-fluorophenyl) ethoxy]phenyl}-5-[(pyrazin-2-yl)amino]-1-{[2-(trimethylsilyl)ethoxy]methyl}-1H-pyrazole-4-carboxamide (200 mg, 0.35 mmol) and 2,2,2-trifluoroethane-1-sulfonyl chloride (77.6 mg, 0.42 mmol) in DCM:pyridine (3:1, 4 mL) was stirred at RT for 16 h. The reaction mixture was concentrated and the crude residue was purified by silica gel column chromatography (PE:EtOAc, 2:1) to afford the title product (130 mg, 51%) as a white solid. LCMS (Method A): 3.30 min; m/z: 710.2 $[M+H]^+$.

Step 2: 3-{3-[(1S)-1-(3-fluorophenyl)ethoxy]-4-(2,2,2-trifluoroethanesulfonamido)phenyl}-5-[(pyrazin-2-yl)amino]-1H-pyrazole carboxamide (compound 265)

A solution of 3-{3-[(1S)-1-(3-fluorophenyl)ethoxy]-4-(2,2,2-trifluoroethanesulfonamido)phenyl}-5-[(pyrazin-2-yl) amino]-1-{[2-(trimethylsilyl)ethoxy]methyl}-1H-pyrazole- 4-carboxamide (130 mg, 0.18 mmol) in DCM:TFA (10:1, 13 mL) was stirred at RT for 16 h. The reaction mixture was neutralized with sat. $Na_2CO_3$ and then concentrated under reduced pressure. The crude residue was purified by silica gel column chromatography (DCM:MeOH, 20:1) to afford the title compound (54 mg, 47%) as a white solid. LCMS (Method A): 3.52 min; m/z: 580.2 $[M+H]^+$. $^1H$ NMR (400 MHz, DMSO-$d_6$): 12.98 (s, 1H), 10.01 (s, 1H), 9.58 (s, 1H), 9.21 (s, 1H), 8.21 (s, 1H), 8.10 (d, J=2.0 Hz, 1H), 7.46-7.35 (m, 4H), 7.21-7.07 (m, 4H), 6.15 (s, 1H), 5.66 (q, J=6.4 Hz, 1H), 4.48 (q, J=4.4 Hz, 2H), 1.60 (d, J=6.0 Hz, 3H).

Compound 259

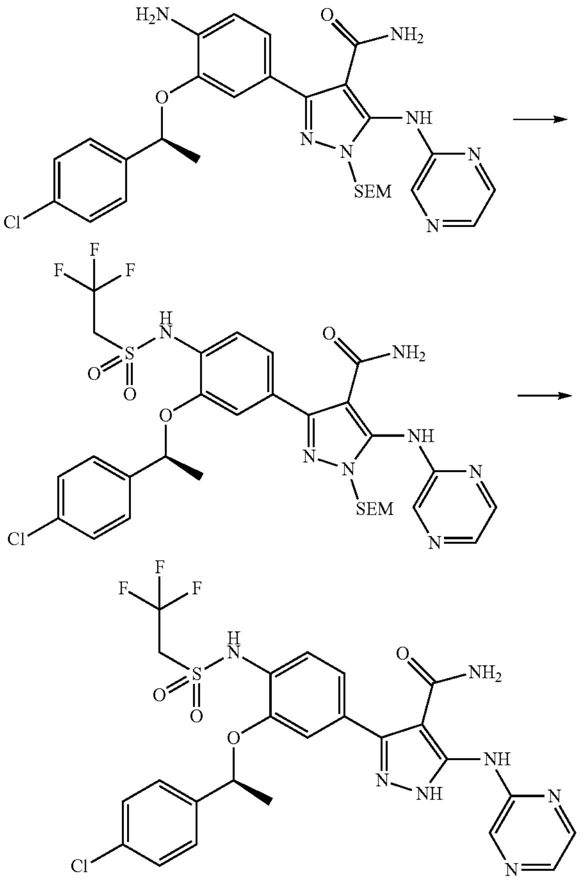

Step 1: 3-{3-[(1S)-1-(4-chlorophenyl)ethoxy]-4-(2,2,2-trifluoroethane-sulfonamido)phenyl}-5-[(pyrazin-2-yl)amino]-1-{[2-(trimethylsilyl)ethoxy]methyl}-1H-pyrazole-4-carboxamide A solution of 3-{4-amino-3-[(1S)-1-(4-chlorophenyl)ethoxy]phenyl}-5-[(pyrazin-2-yl)amino]-1-{[2-(trimethylsilyl)ethoxy]methyl}-1H-pyrazole-4-carboxamide (240 mg, 413 μmol) and 2,2,2-trifluoroethane-1-sulfonyl chloride (112 mg, 619 μmol) in DCM:pyridine (3:1, 4 mL) was stirred at RT for 16 h. The reaction mixture was concentrated and the residue was purified by prep-TLC (DCM:MeOH, 15:1) to afford the title product (210 mg, 70%) as a white solid. LCMS (Method D): 5.27 min; m/z:

Step 2: 3-{3-[(1S)-1-(4-chlorophenyl)ethoxy]-4-(2,2,2-trifluoroethane-sulfonamido)phenyl}-5-[(pyrazin-2-yl)amino]-1H-pyrazole-4-carboxamide (compound 259)

A solution of 3-{3-[(1S)-1-(4-chlorophenyl)ethoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide (210 mg, 289 μmol) in DCM:TFA (10:1, 11 mL) was stirred at RT for 16 h. The reaction mixture was neutralized with sat. $Na_2CO_3$ and then concentrated under reduced pressure. The crude residue was purified by prep-TLC (DCM:MeOH, 15:1) and then by prep-HPLC to afford the title compound (9.0 mg, 22%) as a white solid. LCMS (Method A): 2.17 min; m/z: 596.1 $[M+H]^+$. $^1H$ NMR (400 MHz, DMSO-$d_6$): 12.95 (s, 1H), 9.96 (s, 1H), 9.60 (s, 1H), 9.21 (s, 1H), 8.21 (s, 1H), 8.10 (d, J=2.4 Hz, 1H), 7.57 (d, J=8.4 Hz, 2H), 7.42-7.40 (m, 3H), 7.20 (s, 1H), 7.14-7.12 (m, 1H), 6.16 (br s, 1H), 5.65-5.64 (m, 1H), 4.44-4.42 (m, 2H), 1.59 (d, J=6.4 Hz, 3H).

Compound 239

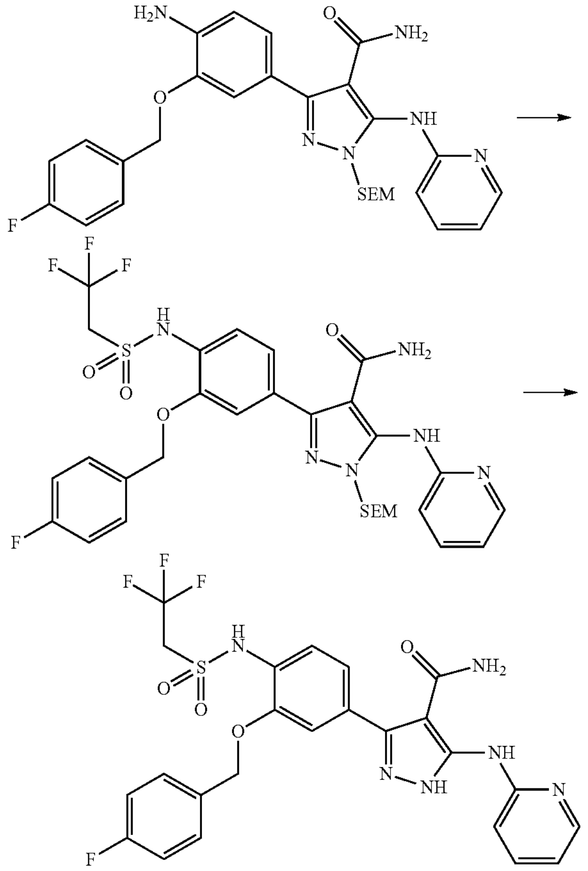

Step 1: 3-{3-[(4-fluorophenyl)methoxy]-4-(2,2,2-trifluoroethanesulfonamido)phenyl}-5-[(pyridin-2-yl)amino]-1-{[2-(trimethylsilyl)ethoxy]methyl}-1H-pyrazole-4-carboxamide A solution of 3-{4-amino-3-[(4-fluorophenyl)methoxy]phenyl}-5-[(pyridin-2-yl)amino]-1-{[2-(trimethylsilyl)ethoxy]methyl}-1H-pyrazole-4-carboxamide (400 mg, 729 μmol), 2,2,2-trifluoroethane-1-sulfonyl chloride (145 mg, 795 μmol) and pyridine (209 mg, 2.65 mmol) in $CHCl_3$ (3 mL) was stirred at RT for 16 h. The reaction mixture was concentrated, and the residue diluted with $H_2O$ (50 mL) and extracted with EtOAc (3×20 mL). The combined organic layers were washed (brine), dried ($Na_2SO_4$) and then concentrated under reduced pressure. The crude residue was purified by prep-TLC (DCM:MeOH, 15:1) to afford the title product (100 mg, 24%) as a yellow solid. LCMS (Method A): 4.13 min; m/z: 694.6 $[M+H]^+$.

Step 2: 3-{3-[(4-fluorophenyl)methoxy]-4-(2,2,2-trifluoroethanesulfonamido)phenyl}-5-[pyridin-2-yl)amino]-1H-pyrazole-4-carboxamide (compound 239)

A solution of 3-{3-[(4-fluorophenyl)methoxy]-4-(2,2,2-trifluoroethanesulfonamido)phenyl}-5-[(pyridin-2-yl)amino]-1-{[2-(trimethylsilyl)ethoxy]methyl}-1H-pyrazole-4-carboxamide (200 mg, 287 μmol) in DCM:TFA (1:1, 6 mL) was stirred at RT for 1 h. The reaction mixture was concentrated, and the residue was neutralized to pH 7-8 with sat. $Na_2CO_3$. The resulting precipitate was purified by prep-TLC (DCM:MeOH, 15:1) to afford the title compound (100 mg, 62%) as a yellow solid. LCMS (Method A): 3.27 min; m/z: 565.1 $[M+H]^+$. $^1H$ NMR (400 MHz, DMSO-$d_6$): 12.90 (s, 1H), 9.95 (s, 1H), 9.52 (s, 1H), 8.19 (s, 1H), 7.98 (s, 1H), 7.72-7.58 (m, 3H), 7.39-7.16 (m, 6H), 6.85 (s, 1H), 6.09 (s, 1H), 5.18 (s, 2H), 4.24 (s, 2H).

Compound 256

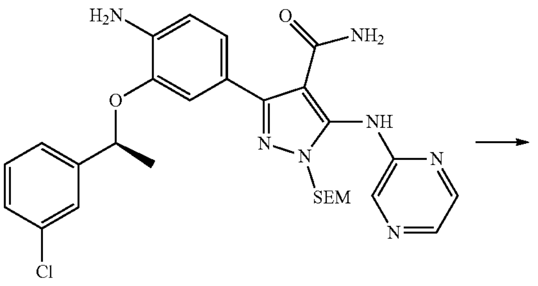

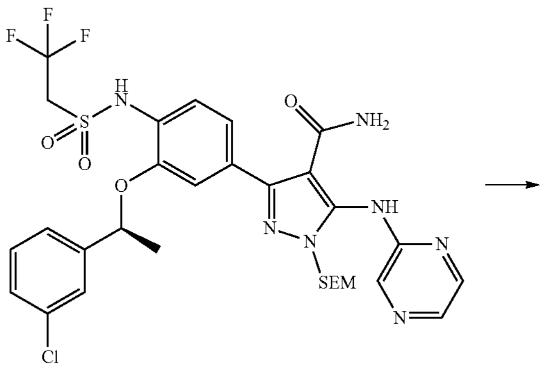

-continued

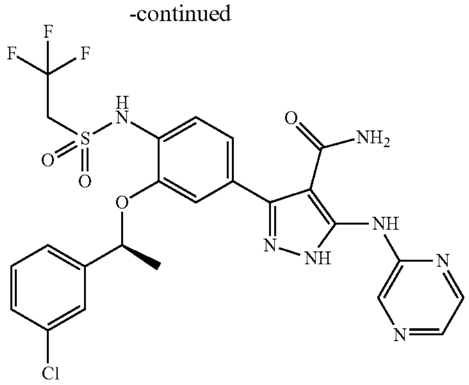

Step 1: 3-{3-[(1S)-1-(3-chlorophenyl)ethoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide A solution of 3-{4-amino-3-[(1S)-1-(3-chlorophenyl)ethoxy]phenyl]-5-[(pyrazin-2-yl)amino]-1-{[2-(trimethylsilyl)ethoxy]methyl}-1H-pyrazole-4-carboxamide (180 mg, 310 μmol) and 2,2,2-trifluoroethane-1-sulfonyl chloride (84.5 mg, 465 μmol) in DCM:pyridine (1:1, 6 mL) was stirred at RT for 16 h. The reaction mixture was concentrated, and the residue was diluted with $H_2O$ (30 mL) and then extracted with EtOAc (3×30 mL). The combined organic layers were washed (brine), dried ($Na_2SO_4$) and concentrated under reduced pressure. The crude residue was purified by silica gel column chromatography (DCM:MeOH, 20:1) to afford the title product (150 mg, 66%) as a yellow solid. LCMS (Method A): 4.19 min; m/z: 726.2 $[M+H]^+$.

Step 2: 3-{3-[(1S)-1-(3-chlorophenyl)ethoxy]-4-(2,2,2-trifluoroethane-sulfonamido)phenyl}-5-[(pyrazin-2-yl)amino]-1H-pyrazole-4-carboxamide (compounds 256)

A solution of 3-{3-[(1S)-1-(3-chlorophenyl)ethoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide (150 mg, 206 μmol) in DCM:TFA (10:1, 16 mL) was stirred at RT for 16 h. The reaction mixture was neutralized to pH 7-8 with $NH_4OH$, diluted with $H_2O$ (20 mL) and extracted with DCM (3×30 mL). The combined organic layers were washed (brine), dried over ($Na_2SO_4$) and concentrated to afford the title compound (60 mg, 50%) as a yellow solid. LCMS (Method A): 1.99 min; m/z: 596.1 $[M+H]^+$. $^1H$ NMR (400 MHz, DMSO-$d_6$): 12.98 (s, 1H), 10.02 (s, 1H), 9.60 (s, 1H), 9.22 (s, 1H), 8.21 (s, 1H), 8.10 (s, 1H), 7.70 (d, J=7.2 Hz, 1H), 7.45 (d, J=8.0 Hz, 1H), 7.40-7.32 (m, 3H), 7.21 (s, 1H), 7.15 (d, J=8.0 Hz, 2H), 6.15 (br s, 3H), 5.65 (d, J=6.0 Hz, 1H), 4.49-4.45 (m, 3H), 1.60 (d, J=6.0 Hz, 3H).

Compound 225

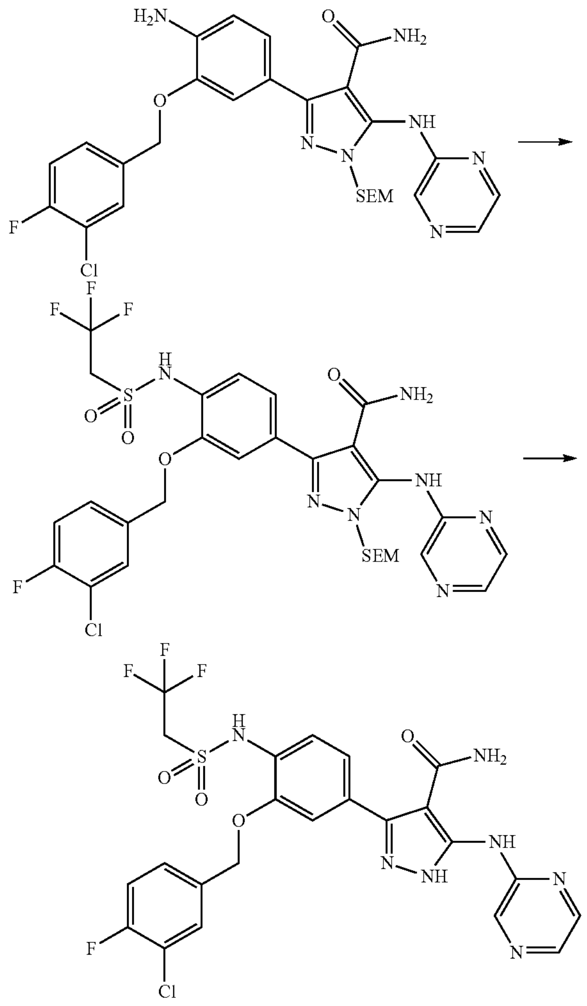

Step 1: 3-{3-[(3-chloro-4-fluorophenyl)methoxy]-4-(2,2,2-trifluoroethane-sulfonamido)phenyl}-5-[(pyrazin-2-yl)amino]-1-{[2-(trimethylsilyl)ethoxy]methyl}-1H-pyrazole-4-carboxamide A mixture of 3-{4-amino-3-[(3-chloro-4-fluorophenyl)methoxy]phenyl}-5-[(pyrazin-2-yl)amino]-1-{[2-(trimethylsilyl)ethoxy]methyl]-1H-pyrazole-4-carboxamide (320 mg, 0.54 mmol), 2,2,2-trifluoroethane-1-sulfonyl chloride (149 mg, 0.82 mmol), pyridine (131 μL, 1.64 mmol) and $CHCl_3$ (10 mL) was stirred at RT for 16 h. The reaction mixture was concentrated and the crude residue purified by silica gel column chromatography (DCM:MeOH, 50:1) to afford the title product (100 mg, 25%) as a yellow solid. LCMS (Method A): 4.10 min; m/z: 730.2, 732.2 $[M+H]^+$.

Step 2: 3-{3-[(3-chloro-4-fluorophenyl)methoxy]-4-(2,2,2-trifluoroethane-sulfonamido)phenyl}-5-[(pyrazin-2-yl)amino]-1H-pyrazole-4-carboxamide (compound 225)

A solution of 3-{3-[(3-chloro-4-fluorophenyl)methoxy]-4-(2,2,2-trifluoroethane-sulfonamido)phenyl}-5-[(pyrazin-2-yl)amino]-1-{[2-(trimethylsilyl)ethoxy]methyl}-1H-pyrazole-4-carboxamide (100 mg, 136 μmol) in DCM:TFA (1:1, 8 mL) was stirred at RT for 10 min. The reaction mixture was concentrated, and the residue neutralized to pH 7-8 with sat. $Na_2CO_3$. The resulting precipitate was collected by filtration and then triturated with $Et_2O$ to afford the title compound (33.0 mg, 40%). LCMS (Method A): 3.60 min; m/z: 600.1 $[M+H]^+$. $^1H$ NMR (400 MHz, DMSO-$d_6$): 9.81 (br s, 1H), 9.28 (br s, 1H), 8.21 (s, 1H), 8.10 (s, 1H), 7.35 (dd, J=7.8, 1.2 Hz, 1H), 7.51-7.32 (m, 4H), 7.01-6.98 (m, 2H), 5.07 (s, 2H), 3.65 (q, J=10.8 Hz, 2H).

Compound 249

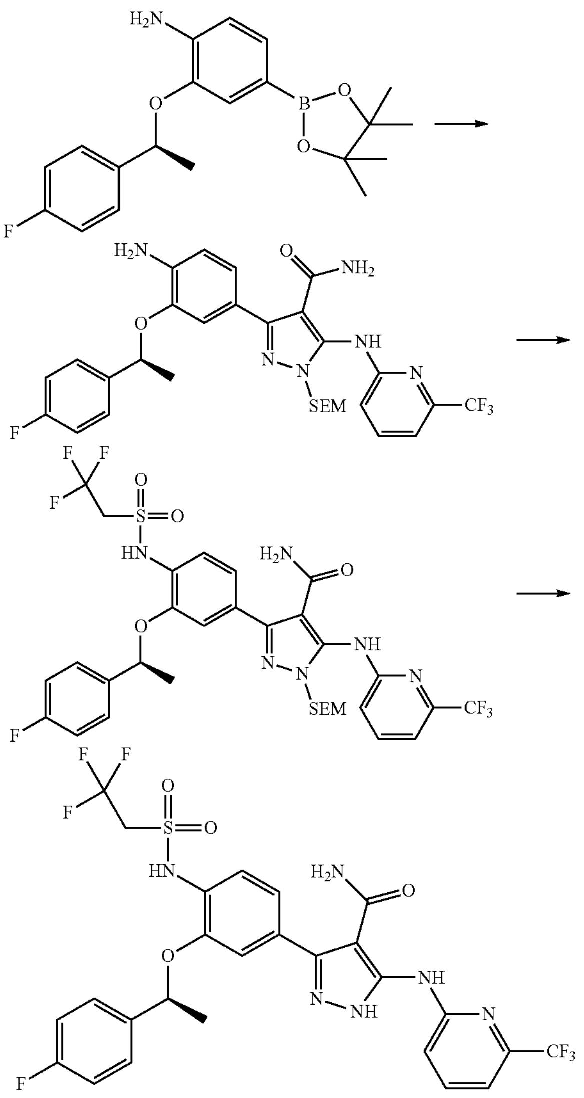

Step 1: 3-{4-amino-3-[(1S)-1-(4-fluorophenyl)ethoxy]phenyl}-5-{[6-(trifluoromethyl) pyridin-2-yl]amino}-1-{[2-(trimethylsilyl)ethoxy]methyl}-1H-pyrazole-4-carboxamide A mixture of 2-[(1S)-1-(4-fluorophenyl)ethoxy]-4-(4,4,5,5-tetramethyl-1,3,2-dioxaborolan-2-yl)aniline (360 mg, 1.00 mmol), 3-bromo-5-{[6-(trifluoromethyl)pyridin-2-yl]amino}-1-{[2-(trimethylsilyl)ethoxy]methyl}-1H-pyrazole-4-carboxamide (480 mg, 1 mmol), Pd(dppf)$Cl_2$ (81.6 mg, 100 μmol), $Na_2CO_3$ (211 mg, 2.00 mmol) and 80% aq. 1,4-dioxane (5 mL) was irradiated at 100° C. in a microwave reactor. After 1 h, the mixture was diluted with $H_2O$ (100 mL) and extracted with EtOAc (2×50 mL). The combined organic layers were dried ($Na_2SO_4$), concentrated and the crude residue purified by silica gel column chromatography (DCM:MeOH, 80:1) to afford the title product (330 mg, 56%) as a brown solid. LCMS (Method A): 3.71 min; m/z: 631.3 $[M+H]^+$.

Step 2: 3-{3-[(1S)-1-(4-fluorophenyl)ethoxy]-4-(2,2,2-trifluoroethane-sulfonamido)phenyl}-5-{[6-(trifluoromethyl)pyridin-2-yl]amino}-1-{[2-(trimethylsilyl)ethoxy]methyl}-1H-pyrazole-4-carboxamide A solution of 3-{4-amino-3-[(1S)-1-(4-fluorophenyl)ethoxy]phenyl}-5-{[6-(trifluoromethyl)pyridin-2-yl]amino}-1-{[2-(trimethylsilyl)ethoxy]methyl}-1H-pyrazole-4-carboxamide (330 mg, 523 μmol) and 2,2,2-trifluoroethanesulfonyl chloride (143 mg, 784 μmol) in $CHCl_3$:pyridine (1:1, 20 mL) was stirred at RT. After 16 h, the mixture was concentrated and the residue diluted with $H_2O$ (80 mL) and then extracted with EtOAc (2×50 mL). The combined organic layers were dried ($Na_2SO_4$), concentrated and the crude residue purified by silica gel column chromatography (DCM:MeOH, 70:1) to afford the title product (400 mg, 98%). LCMS (Method A): 3.84 min; m/z: 777.2 $[M+H]^+$.

Step 3: 3-{3-[(1S)-1-(4-fluorophenyl)ethoxy]-4-(2,2,2-trifluoroethane-sulfonamido)phenyl}-5-{[6-(trifluoromethyl)pyridin-2-yl]amino}-1H-pyrazole-4-carboxamide (compound 249)

A solution of 3-{3-[(1S)-1-(4-fluorophenyl)ethoxy]-4-(2,2,2-trifluoroethane-sulfonamido)phenyl}-5-{[6-(trifluoromethyl)pyridin-2-yl]amino}-1-{[2-(trimethylsilyl)ethoxy]methyl}-1H-pyrazole-4-carboxamide (150 mg, 193 μmol) in DCM:TFA (5:1, 12 mL) was stirred at RT for 5 min. The reaction mixture was concentrated and the residue was neutralized to pH 7-8 with sat. $Na_2CO_3$. The resulting precipitate was collected by filtration and then purified by prep-TLC (DCM:MeOH, 20:1) afford the title compound (84 mg, 67%) as a yellow solid. LCMS (Method A): 4.08 min; m/z: 647.2 $[M+H]^+$. $^1H$ NMR (400 MHz, DMSO-$d_6$): 12.97 (s, 1H), 9.96 (s, 1H), 9.74 (s, 1H), 8.18 (d, J=8.4 Hz, 1H), 7.97 (t, J=7.6 Hz, 1H), 7.62-7.59 (m, 2H), 7.44 (d, J=8.0 Hz, 2H), 7.30 (d, J=7.2 Hz, 1H), 7.23 (s, 1H), 7.20-7.13 (m, 3H), 5.66 (q, J=6.0 Hz, 1H), 4.52-4.43 (m, 2H), 1.60 (d, J=6.0 Hz, 3H).

Compound 311

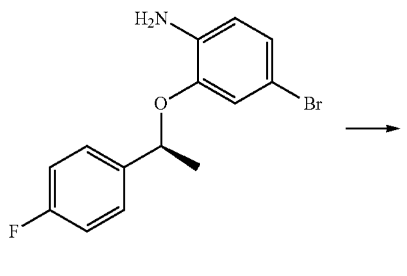

-continued

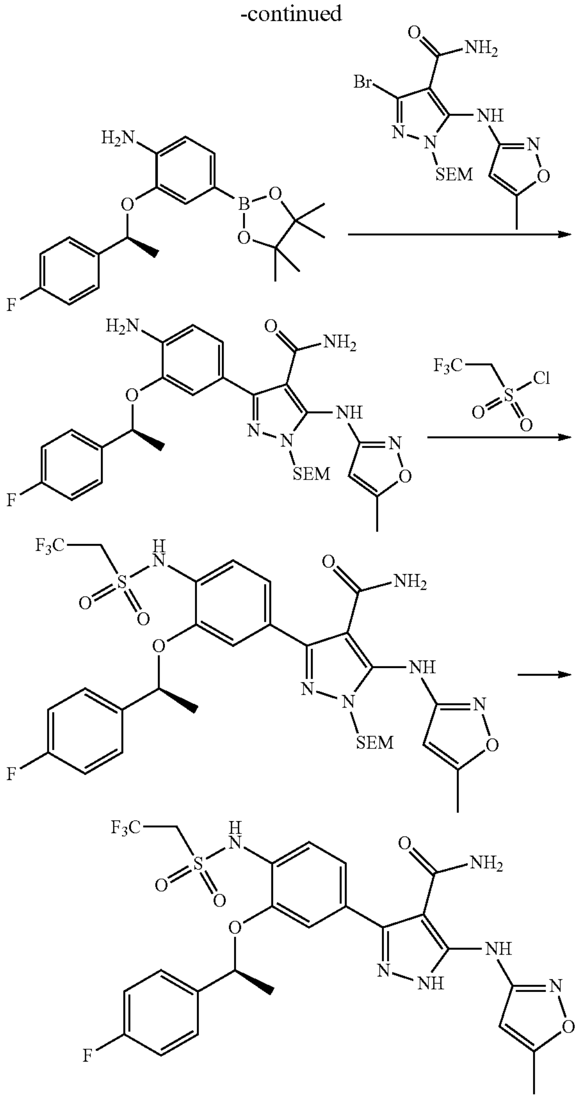

Step 1: (S)-2-(1-(4-fluorophenyl)ethoxy)-4-(4,4,5,5-tetramethyl-1,3,2-dioxaborolan-2-yl)aniline A mixture of 4-bromo-2-[(1S)-1-(4-fluorophenyl)ethoxy]aniline (3 g, 9.67 mmol), Pd(dppf)$Cl_2$ (789 mg, 967 μmol), AcOK (2.84 g, 29.0 mmol) and $B_2pin_2$ (2.94 g, 11.6 mmol) in 1,4-dioxane (20 mL) was stirred at 100° C. overnight. The mixture was filtered and the filtrate was concentrated under reduced pressure. The residue was purified by silica gel column chromatography (PE:EtOAc, 10:1) to give the title product (1.55 g, 45%) as a yellow oil. LCMS (Method A): 4.25 min; m/z: 358.2 $[M+H]^+$.

Step 2: (S)-3-(4-amino-3-(1-(4-fluorophenyl)ethoxy)phenyl)-5-((5-methylisoxazol-3-yl)amino)-1-((2-(trimethylsilyl)ethoxy)methyl)-1H-pyrazole-4-carboxamide A mixture of (S)-2-(1-(4-fluorophenyl)ethoxy)-4-(4,4,5,5-tetramethyl-1,3,2-dioxaborolan-2-yl) aniline (1.5 g, 4.19 mmol), $Na_2CO_3$ (1.32 g, 12.5 mmol), Pd(dppf)$Cl_2$ (343 mg, 419 μmol) and 3-bromo-5-[(5-methyl-1,2-oxazol-3-yl)amino]-1-{[2-(trimethylsilyl)ethoxy]methyl}-1H-pyrazole- 4-carboxamide (1.91 g, 4.60 mmol) in degassed 1,4-dioxane (80 mL) and $H_2O$ (20 mL) was stirred at 100° C. overnight. The mixture was filtered and the organic phase was concentrated under reduced pressure. The residue was purified by silica gel column chromatography (PE:EtOAc, 1:1) to give the title product (900 mg, 38%) as a brown solid. LCMS (Method A): 3.10 min; m/z: 567.3 $[M+H]^+$.

Step 3: (S)-3-(3-(1-(4-fluorophenyl)ethoxy)-4-((2,2,2-trifluoroethyl)sulfonamido)phenyl)-5-((5-methylisoxazol-3-yl)amino)-1-((2-(trimethylsilyl)ethoxy)methyl)-1H-pyrazole-4-carboxamide A mixture of (S)-3-(4-amino-3-(1-(4-fluorophenyl)ethoxy)phenyl)-5-((5-methylisoxazol-3-yl)amino)-1-((2-(trimethylsilyl)ethoxy)methyl)-1H-pyrazole-4-carboxamide (400 mg, 705 μmol), 2,2,2-trifluoroethanesulfonyl chloride (154 mg, 846 μmol) and pyridine (278 mg, 3.52 mmol) in DCM (20 mL) was stirred at RT overnight. The reaction mixture was concentrated under reduced pressure and the residue was purified by silica gel column chromatography (PE:EtOAc, 7:3 to 2:8) to give the title product (340 mg, 68%) as a brown solid. LCMS (Method B): 5.43 min; m/z: 713.1 $[M+H]^+$.

Step 4: (S)-3-(3-(1-(4-fluorophenyl)ethoxy)-4-((2,2,2-trifluoroethyl)sulfonamido)phenyl)-5-((5-methylisoxazol-3-yl)amino)-1H-pyrazole-4-carboxamide (compound 311)

A mixture of (S)-3-(3-(1-(4-fluorophenyl)ethoxy)-4-((2,2,2-trifluoroethyl)sulfonamido)phenyl)-5-((5-methylisoxazol-3-yl)amino)-1-((2-(trimethylsilyl)ethoxy)methyl)-1H-pyrazole-4-carboxamide (300 mg, 420 μmol) in HCOOH (2 mL) was stirred at RT for 3 h. The mixture was basified to pH=8 with sat. aq. $NaHCO_3$ and the organics were extracted with DCM (3×20 mL). The combined organics were washed with water, dried ($Na_2SO_4$) and concentrated under reduced pressure. The residue was purified by silica gel column chromatography (PE:EtOAc, 95:5 to 5:95) to give the title product (103.3 mg, 42%) as a white solid. LCMS (Method A): 3.68 min; m/z: 583.2 $[M+H]^+$. $^1H$ NMR (400 MHz, DMSO-$d_6$): 12.76 (s, 1H), 9.96 (s, 1H), 9.16 (s, 1H), 7.58 (dd, J=8.6, 5.6 Hz, 2H), 7.40 (d, J=7.7 Hz, 1H), 7.21-7.13 (m, 3H), 7.09 (dd, J=8.2, 1.6 Hz, 1H), 6.58 (s, 1H), 5.63 (q, J=5.5 Hz, 1H), 4.51-4.34 (m, 2H), 2.35 (s, 3H), 1.58 (d, J=6.3 Hz, 3H).

The following compound was prepared similarly, employing $EtO_2Cl$ in the place of 2,2,2-trifluoroethanesulfonyl chloride in step 1:

Compound 317

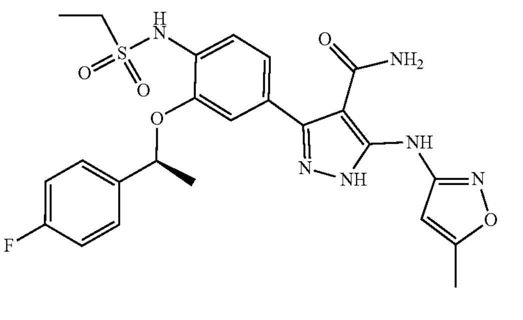 [SMILES: CCS(=O)(=O)Nc1ccc(-c2n[nH]c(Nc3cc(C)on3)c2C(N)=O)cc1O[C@@H](C)c1ccc(F)cc1]

(S)-3-(4-(ethylsulfonamido)-3-(1-(4-fluorophenyl)ethoxy)phenyl)-5-((5-methylisoxazol-3-yl)amino)-1H-pyrazole-4-carboxamide LCMS (Method A): 3.50 min; [M+H]+529.2. $^1H$ NMR (400 MHz, DMSO-$d_6$): 12.71 (s, 1H), 9.16 (d, J=19.4 Hz, 2H), 7.70-7.54 (m, 2H), 7.49-7.33 (m, 1H), 7.21-7.12 (m, 3H), 7.07 (dd, J=8.2, 1.8 Hz, 1H), 6.58 (s, 1H), 5.75 (s, 1H), 5.63 (d, J=6.5 Hz, 1H), 3.11 (q, J=7.3 Hz, 2H), 2.35 (d, J=0.9 Hz, 3H), 1.60 (d, J=6.2 Hz, 3H), 1.26 (t, J=7.3 Hz, 3H).

Compound 240

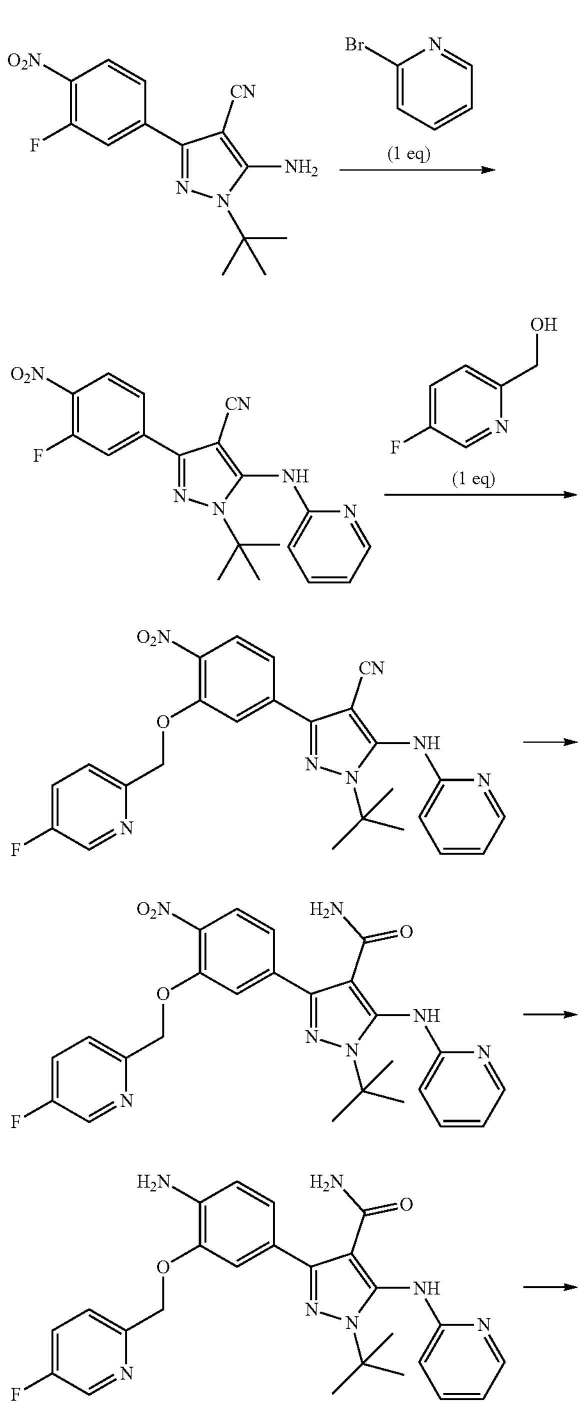

-continued

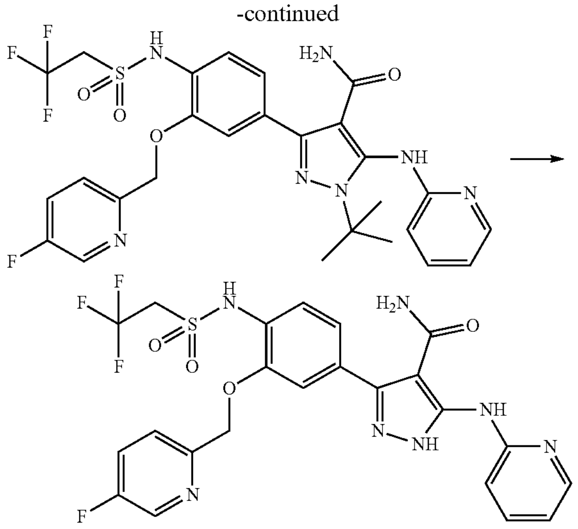

Step 1: 1-tert-butyl-3-(3-fluoro-4-nitrophenyl)-5-[(pyridin-2-yl)amino]-1H-pyrazole-4-carbonitrile A mixture of 5-amino-1-tert-butyl-3-(3-fluoro-4-nitrophenyl)-1H-pyrazole-4-carbonitrile (5.0 g, 16.4 mmol), 2-bromopyridine (2.59 g, 16.4 mmol), $Pd_2(dba)_3$ (1.50 g, 1.64 mmol), Xantphos (1.89 g, 3.28 mmol), $Cs_2CO_3$ (15.9 g, 49.1 mmol) and 1,4-dioxane (40 mL) was stirred at 100° C. for 16 h. The reaction mixture was concentrated and the residue diluted with $H_2O$ (60 mL) and then extracted with EtOAc (3x30 mL). The combined organic layers were washed (brine), dried ($Na_2SO_4$) and concentrated under reduced pressure. The crude residue was purified by silica gel column chromatography (PE:EtOAc, 10:1) to afford the title product (760 mg, 12%) as a yellow solid. LCMS (Method D): 3.70 min; m/z: 381.0 $[M+H]^+$.

Step 2: 1-tert-butyl-3-{3-[(5-fluoropyridin-2-yl)methoxy]-4-nitrophenyl}-5-[(pyridin-2-yl)amino]-1H-pyrazole-4-carbonitrile To a mixture of (5-fluoropyridin-2-yl)methanol (183 mg, 1.44 mmol) and THF (20 mL) at 0° C., was added NaH (172 mg, 7.19 mmol). After 15 min, 1-tert-butyl-3-(3-fluoro-4-nitrophenyl)-5-[(pyridin-2-yl)amino]-1H-pyrazole-4-carbonitrile (550 mg, 1.44 mmol) was added and the mixture was stirred at RT for 16 h. The mixture was concentrated and the residue diluted with $H_2O$ (30 mL) and then extracted with EtOAc (3x30 mL). The combined organic layers were washed (brine), dried ($Na_2SO_4$) and concentrated under reduced pressure. The crude residue was purified by silica gel column chromatography (DCM:MeOH, 10:1) to afford the title product (600 mg, 85%) as a yellow solid. LCMS (Method D): 3.90 min; m/z: 488.2 $[M+H]^+$.

Step 3: 1-tert-butyl-3-{3-[(5-fluoropyridin-2-yl)methoxy]-4-nitrophenyl}-5-[(pyridin-2-yl)amino]-1H-pyrazole-4-carboxamide A mixture of 1-tert-butyl-3-{3-[(5-fluoropyridin-2-yl)methoxy]-4-nitrophenyl}-5-[(pyridin-2-yl)amino]-1H-pyrazole-4-carbonitrile (600 mg, 1.23 mmol), Ghaffar-Parkins catalyst (52.5 mg, 123 μmol) and 80% aq. 1,4-dioxane (16 mL) was stirred at 100° C. for 16 h. The reaction mixture was concentrated and the residue diluted with $H_2O$ (30 mL) and then extracted with EtOAc (3x30 mL). The combined organic layers were washed (brine), dried ($Na_2SO_4$) and concentrated under reduced pressure. The crude residue was purified by silica gel column chromatography (DCM:MeOH, 20:1) to afford the title product (550 mg, 72%) as a yellow solid. LCMS (Method D): 3.90 min; m/z: 506.3 $[M+H]^+$.

Step 4: 3-{4-amino-3-[(5-fluoropyridin-2-yl)methoxy]phenyl}-1-tert-butyl-5-[(pyridin-2-yl)amino]-1H-pyrazole-4-carboxamide A mixture of 1-tert-butyl-3-{3-[(5-fluoropyridin-2-yl)methoxy]-4-nitrophenyl}-5-[(pyridin-2-yl)amino]-1H-pyrazole-4-carboxamide (280 mg, 553 μmol), Zn powder (180 mg, 2.76 mmol), sat. $NH_4Cl$ (2 mL) and MeOH (10 mL) was stirred at 60° C. for 1 h. The reaction mixture was filtered and the filtrate concentrated under reduced pressure. The residue was diluted with $H_2O$ (30 mL) and then extracted with EtOAc (3x30 mL). The combined organic layers were washed (brine), dried ($Na_2SO_4$), and concentrated. The residue was purified by silica gel column chromatography (DCM:MeOH, 20:1) to afford the title product (178 mg, 67%) as a yellow solid. $^1H$ NMR (400 MHz, DMSO-$d_6$): 8.56 (d, J=2.2 Hz, 1H), 8.21 (s, 1H), 8.05-8.03 (m, 1H), 7.78-7.75 (m, 2H), 7.53 (m, 1H), 7.33 (d, J=1.7 Hz, 1H), 7.14 (dd, J=8.1, 2.7 Hz, 1H), 7.09 (br s, 1H), 6.82 (br s, 1H), 6.72-6.69 (m, 1H), 6.66 (d, J=8.1 Hz, 1H), 6.50 (d, J=8.3 Hz, 1H), 5.12 (s, 2H), 4.96 (br s, 2H), 1.52 (s, 9H).

Step 5: 1-tert-butyl-3-{3-[(5-fluoropyridin-2-yl)methoxy]-4-(2,2,2-trifluoroethane-sulfonamido)phenyl}-5-[(pyridin-2-yl)amino]-1H-pyrazole-4-carboxamide A solution of 3-{4-amino-3-[(5-fluoropyridin-2-yl)methoxy]phenyl}-1-tert-butyl-5-[(pyridin-2-yl)amino]-1H-pyrazole-4-carboxamide (200 mg, 420 μmol) and 2,2,2-trifluoroethane-1-sulfonyl chloride (115 mg, 630 μmol) in DCM:pyridine (1:1, 8 mL) was stirred at RT for 16 h. The reaction mixture was concentrated and the residue diluted with $H_2O$ (30 mL) and then extracted with EtOAc (3x30 mL). The combined organic layers were washed (brine), dried ($Na_2SO_4$), concentrated and the crude residue purified by silica gel column chromatography (DCM:MeOH, 20:1) to afford the title product (39 mg, 14%) as a yellow solid. LCMS (Method D): 4.77 min; m/z: 622.1 $[M+H]^+$.

Step 6: 3-{3-[(5-fluoropyridin-2-yl)methoxy]-4-(2,2,2-trifluoroethanesulfonamido)phenyl}-5-[(pyridin-2-yl)amino]-1H-pyrazole-4-carboxamide (compound 240)

A solution of 1-tert-butyl-3-{3-[(5-fluoropyridin-2-yl)methoxy]-4-(2,2,2-trifluoroethanesulfonamido)phenyl}-5-[(pyridin-2-yl)amino]-1H-pyrazole-4-carboxamide (100 mg, 160 μmol) in DCM:TFA (1:1 4 mL) was stirred at RT for 16 h and then concentrated under reduced pressure. The residue was neutralized to pH 7-8 with $NH_4OH$ then diluted with $H_2O$ (20 mL) and extracted with DCM (3x30 mL). The combined organic layers were washed (brine), dried ($Na_2SO_4$) and then concentrated to afford the title compound (45 mg, 49%) as a yellow solid. LCMS (Method A): 3.00 min; m/z: 566.1 $[M+H]^+$. $^1H$ NMR (400 MHz, DMSO-$d_6$): 12.84 (s, 1H), 10.10 (s, 1H), 9.77 (s, 1H), 9.52 (s, 1H), 8.56 (s, 1H), 8.16 (s, 1H), 7.97 (d, J=6.4 Hz, 1H), 7.84-7.78 (m, 2H), 7.70 (t, J=7.6 Hz, 1H), 7.45-7.37 (m, 2H), 7.19 (d, J=8.0 Hz, 2H), 6.84 (s, 1H), 6.10 (s, 1H), 5.28 (s, 1H), 4.42 (s, 1H).

Compound 241

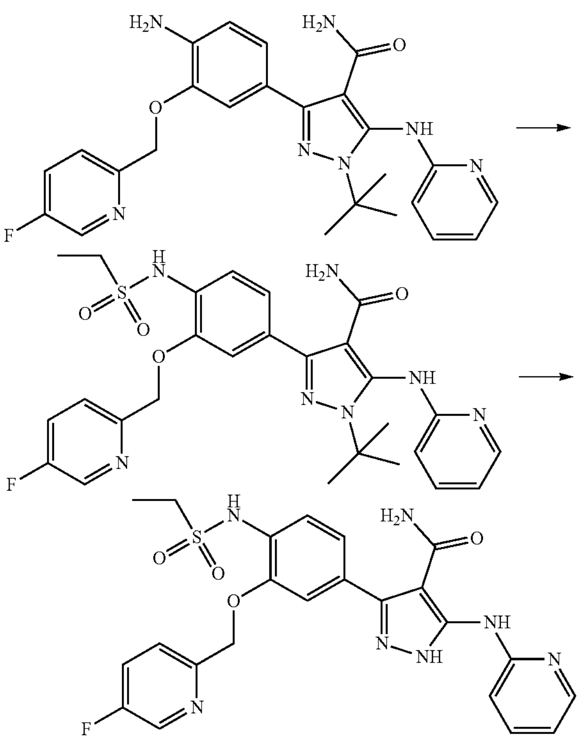

Step 1: 1-tert-butyl-3-{4-ethanesulfonamido-3-[(5-fluoropyridin-2-yl)methoxy]phenyl}-5-[(pyridin-2-yl)amino]-1H-pyrazole-4-carboxamide A solution of 3-{4-amino-3-[(5-fluoropyridin-2-yl)methoxy]phenyl}-1-tert-butyl-5-[(pyridin-2-yl)amino]-1H-pyrazole-4-carboxamide (170 mg, 357 μmol) and $EtSO_2Cl$ (68.7 mg, 535 μmol) in DCM:pyridine (1:1 10 mL) was stirred at RT for 16 h. The reaction mixture was diluted with $H_2O$ (100 mL) and extracted with EtOAc (3×50 mL). The combined organic layers were dried ($Na_2SO_4$), concentrated and the crude residue purified by prep-TLC (DCM:MeOH, 10:1) to afford the title product (70 mg, 34%) as a yellow solid. LCMS (Method D): 4.05 min; m/z: 568.1 $[M+H]^+$.

Step 2: 3-{4-ethanesulfonamido-3-[(5-fluoropyridin-2-yl)methoxy]phenyl}-5-[(pyridin-2-yl)amino]-1H-pyrazole-4-carboxamide (compound 241)

A solution of 1-tert-butyl-3-{4-ethanesulfonamido-3-[(5-fluoropyridin-2-yl)methoxy]phenyl}-5-[(pyridin-2-yl)amino]-1H-pyrazole-4-carboxamide (70 mg, 123 μmol) in DCM:TFA (1:1, 10 mL) was stirred at RT for 16 h. The reaction mixture was neutralized to pH 7-8 with sat. $Na_2CO_3$ and then extracted with DCM (2×50 mL). The combined organic layers were dried ($Na_2SO_4$), concentrated and the crude residue purified by prep-TLC (DCM:MeOH, 20:1) to afford the title compound (17.9 mg, 28%) as a white solid. LCMS (Method A): 2.71 min; m/z: 512.2 $[M+H]^+$. $^1H$ NMR (400 MHz, DMSO-$d_6$): 12.83 (s, 1H), 9.49 (s, 1H), 9.23 (s, 1H), 8.57 (s, 1H), 8.07 (m, 2H), 7.83 (d, J=6.8 Hz, 2H), 7.72 (t, J=16.0 Hz, 1H), 7.40 (m, 2H), 7.18 (m, 2H), 6.83 (m, 1H), 6.13 (s, 1H), 5.30 (s, 2H), 3.08 (q, J=22.0 Hz, 2H), 1.18 (t, J=14.8 Hz, 3H).

Compound 262

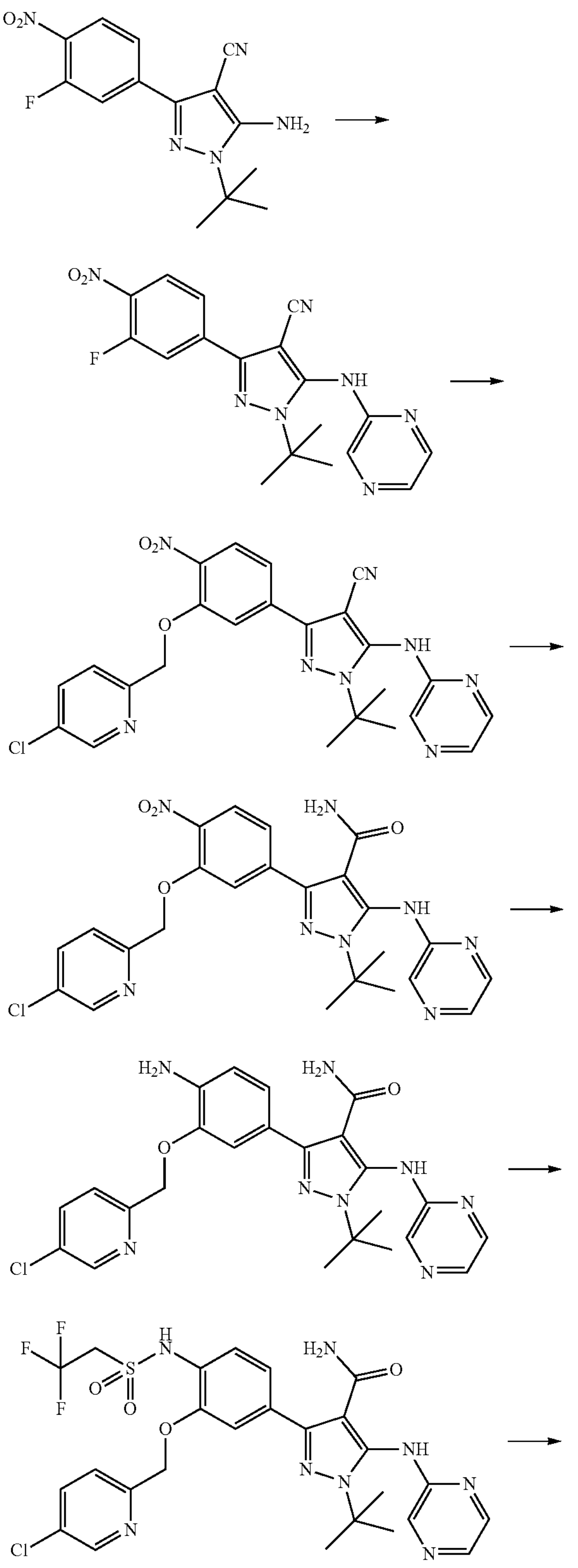

-continued

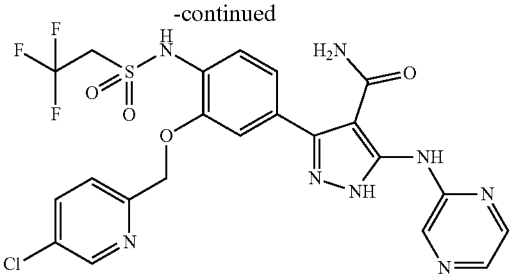

Step 1: 1-tert-butyl-3-(3-fluoro-4-nitrophenyl)-5-[(pyrazin-2-yl)amino]-1H-pyrazole-4-carbonitrile A mixture of 5-amino-1-(tert-butyl)-3-(3-fluoro-4-nitrophenyl)-1H-pyrazole-4-carbonitrile (10.0 g, 23.4 mmol), 2-bromopyrazine (3.72 g, 23.4 mmol), $Pd_2(dba)_3$ (1.07 g, 1.17 mmol), Xantphos (1.35 g, 2.34 mmol), $Cs_2CO_3$ (22.8 g, 70.2 mmol) and 1,4-dioxane (500 mL) was stirred at 100° C. After 16 h, the reaction mixture was concentrated and the crude residue was purified by silica gel column chromatography (PE:EtOAc, 10:1) to afford the title product (5.10 g, 43%) as a yellow solid. LCMS (Method D): 5.60 min; m/z: 382.0 $[M+H]^+$.

Step 2: 1-tert-butyl-3-{3-[(5-chloropyridin-2-yl)methoxy]-4-nitrophenyl}-5-[(pyrazin-2-yl)amino]-1H-pyrazole-4-carbonitrile To a solution of (5-chloropyridin-2-yl)methanol (383 mg, 2.67 mmol) in THF (20 mL) at 0° C., was added NaH (313 mg, 7.86 mmol). After 1 h, 1-tert-butyl-3-(3-fluoro-4-nitrophenyl)-5-[(pyrazin-2-yl)amino]-1H-pyrazole-4-carbonitrile (1.0 g, 2.62 mmol) was added and the mixture was stirred at RT for 16 h. The reaction mixture was concentrated and the residue diluted with $H_2O$ (50 mL) and then extracted with EtOAc (3×30 mL). The combined organic layers were washed (brine), dried ($Na_2SO_4$) and then concentrated under reduced pressure. The crude residue was purified by silica gel column chromatography (PE:EtOAc, 4:1) to afford the title product (720 mg, 54%) as a yellow solid. LCMS (Method D): 5.79 min; m/z: 505.0 $[M+H]^+$.

Step 3: 1-tert-butyl-3-{3-[(5-chloropyridin-2-yl)methoxy]-4-nitrophenyl}-5-[(pyrazin-2-yl)amino]-1H-pyrazole-4-carboxamide A solution of 1-tert-butyl-3-{3-[(5-chloropyridin-2-yl)methoxy]-4-nitrophenyl}-5-[(pyrazin-2-yl)amino]-1H-pyrazole-4-carbonitrile (720 mg, 1.42 mmol) and Ghaffar-Parkins catalyst (72 mg, 168 μmol) in 50% aq. 1,4-dioxane (10 mL) was stirred at 100° C. under $N_2$ for 16 h. The reaction mixture was concentrated, diluted with $H_2O$ (20 mL) and then extracted with EtOAc (3×20 mL). The combined organic layers were washed (brine), dried ($Na_2SO_4$) and concentrated to afford the title product (680 mg, 91%) as a red solid. LCMS (Method D): 4.75 min; m/z: 523.0 $[M+H]^+$.

Step 4: 3-(4-amino-3-((5-chloropyridin-2-yl)methoxy)phenyl)-1-(tert-butyl)-5-(pyrazin-2-ylamino)-1H-pyrazole-4-carboxamide A mixture of 1-tert-butyl-3-{3-[(5-chloropyridin-2-yl)methoxy]-4-nitrophenyl}-5-[(pyrazin-2-yl)amino]-1H-pyrazole-4-carboxamide (680 mg, 1.30 mmol), Zn powder (424 mg, 6.50 mmol), sat. $NH_4Cl$ (3 mL) and MeOH (12 mL) was stirred at 60° C. for 30 min. The reaction mixture was filtered and the filtrate concentrated and then purified by prep-TLC (PE:EtOAc, 3:1) to afford the title product (70.0 mg, 11%) as a yellow solid. LCMS (Method D): 3.77 min; m/z: 493.7 $[M+H]^+$.

Step 5: 1-tert-butyl-3-{3-[(5-chloropyridin-2-yl)methoxy]-4-(2,2,2-trifluoroethane-sulfonamido)phenyl}-5-[(pyrazin-2-yl)amino]-1H-pyrazole-4-carboxamide A mixture of 3-(4-amino-3-((5-chloropyridin-2-yl)methoxy)phenyl)-1-(tert-butyl)-5-(pyrazin-2-ylamino)-1H-pyrazole-4-carboxamide (70 mg, 141 μmol), 2,2,2-trifluoroethane-1-sulfonyl chloride (51.4 mg, 282 μmol) and DCM:pyridine (1:1, 2 mL) was stirred at RT. After 16 h, the mixture was concentrated and the crude residue purified by prep-TLC (DCM:MeOH, 15:1) to afford the title product (53.0 mg, 59%) as a white solid. LCMS (Method D): 4.64 min; m/z: 639.0 $[M+H]^+$.

Step 6: 3-{3-[(5-chloropyridin-2-yl)methoxy]-4-(2,2,2-trifluoroethane-sulfonamido)phenyl}-5-[(pyrazin-2-yl)amino]-1H-pyrazole-4-carboxamide (compound 262)

A solution of 1-tert-butyl-3-{3-[(5-chloropyridin-2-yl)methoxy]-4-(2,2,2-trifluoroethanesulfonamido)phenyl}-5-[(pyrazin-2-yl)amino]-1H-pyrazole carboxamide (50 mg, 78.2 μmol) in DCM:TFA (1:1, 2 mL) was stirred at RT. After 16 h, the reaction mixture was concentrated and the residue neutralized to pH 7-8 with sat. $Na_2CO_3$. The resulting precipitate was collected by filtration and then purified by prep-TLC (DCM:MeOH, 10:1) to afford the title compound (11.2 mg, 24%) as a white solid. LCMS (Method A): 3.37 min; m/z: 583.1 $[M+H]^+$. $^1H$ NMR (400 MHz, DMSO-$d_6$): 13.04 (s, 1H), 10.07 (br s, 1H), 9.65 (s, 1H), 9.25 (s, 1H), 8.62 (d, J=2.4 Hz, 1H), 8.23-8.22 (m, 1H), 8.11 (d, J=2.8 Hz, 1H), 8.03 (dd, J=8.4, 2.4 Hz, 1H), 7.77 (d, J=8.4 Hz, 1H), 7.47-7.42 (m, 2H), 7.23 (dd, J=8.0, 1.6 Hz, 1H), 6.28 (br s, 1H), 5.30 (s, 2H), 4.46 (q, J=9.6 Hz, 2H).

Compound 242

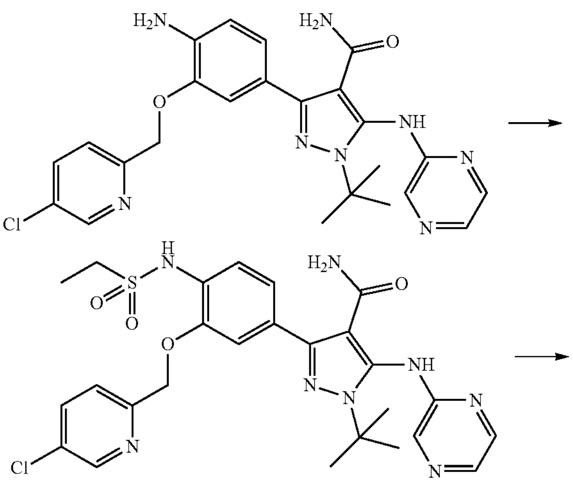

-continued

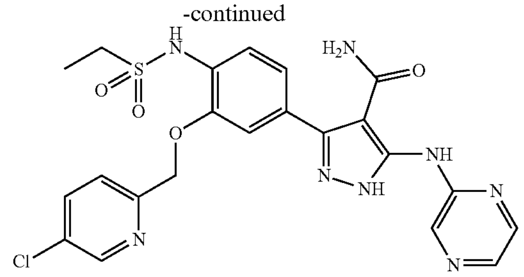

Step 1: 1-tert-butyl-3-{3-[(5-chloropyridin-2-yl) methoxy]-4-ethanesulfonamidophenyl}-5-[(pyrazin-2-yl)amino]-1H-pyrazole-4-carboxamide A mixture of 3-(4-amino-3-((5-chloropyridin-2-yl) methoxy)phenyl)-1-(tert-butyl)-5-(pyrazin-2-ylamino)-1H-pyrazole-4-carboxamide (42.9 mg, 87 μmol) and $EtSO_2Cl$ (14.3 mg, 112 μmol) in DCM:pyridine (2:1, 3 mL) was stirred at RT. After 16 h, the reaction mixture was concentrated and the crude residue purified by prep-TLC (DCM: MeOH, 20:1) to afford the title product (30.0 mg, 59%) as a white solid. LCMS (Method D): 4.18 min; m/z: 585.0 $[M+H]^+$.

Step 2: 3-{3-[(5-chloropyridin-2-yl)methoxy]-4-ethanesulfonamidophenyl}-5-[(pyrazin-2-yl)amino]-1H-pyrazole-4-carboxamide (compound 242)

A solution of 1-tert-butyl-3-{3-[(5-chloropyridin-2-yl) methoxy]-4-ethanesulfonamidophenyl}-5-[(pyrazin-2-yl) amino]-1H-pyrazole-4-carboxamide (30 mg, 51.2 μmol) in DCM:TFA (1:1, 2 mL) was stirred at RT for 16 h. The reaction mixture was concentrated and the residue was neutralized to pH 7-8 with sat. $Na_2CO_3$. The resulting precipitate was collected by filtration and then purified by prep-TLC (DCM:MeOH, 15:1) to afford the title compound (6.90 mg, 25%) as a white solid. LCMS (Method A): 3.14 min; m/z: 529.1 $[M+H]^+$. $^1H$ NMR (400 MHz, DMSO-$d_6$): 13.01 (s, 1H), 9.64 (s, 1H), 9.36 (s, 1H), 9.25 (s, 1H), 8.64 (d, J=2.4 Hz, 1H), 8.22-8.21 (m, 1H), 8.11 (d, J=2.4 Hz, 1H), 8.04 (dd, J=8.4, 2.4 Hz, 1H), 7.83 (d, J=8.4 Hz, 1H), 7.48 (d, J=8.0 Hz, 1H), 7.42 (d, J=0.8 Hz, 1H), 7.22 (dd, J=8.4, 2.0 Hz, 1H), 6.27 (br. s, 1H), 5.30 (s, 2H), 3.10 (q, J=7.2 Hz, 2H), 1.20 (t, J=7.6 Hz, 3H).

Compound 227

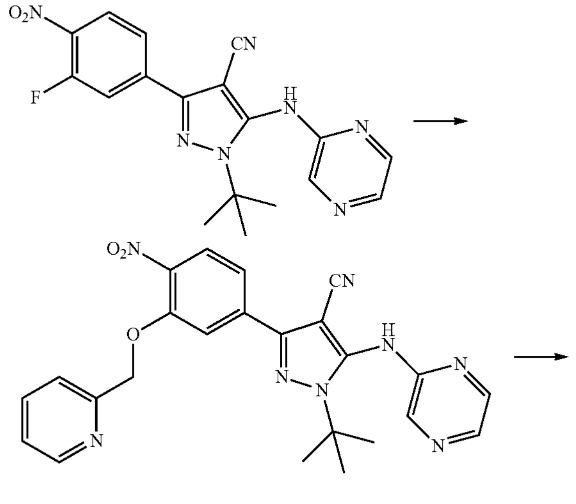

-continued

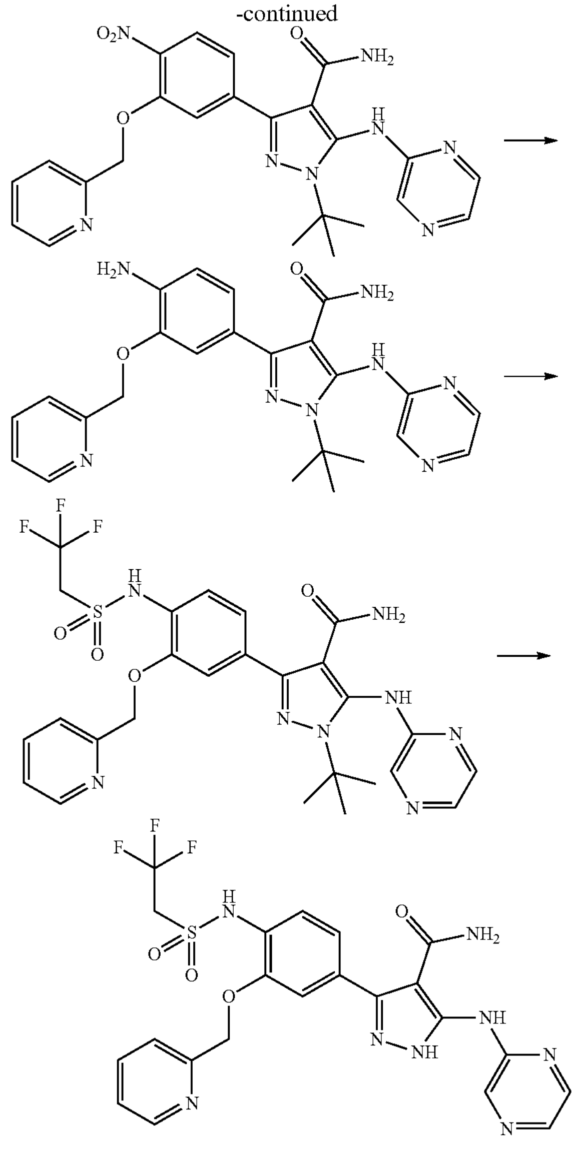

Step 1: 1-tert-butyl-3-{4-nitro-3-[(pyridin-2-yl) methoxy]phenyl}-5-[(pyrazin-2-yl)amino]-1H-pyrazole-4-carbonitrile To a solution of (pyridin-2-yl)methanol (285 mg, 2.62 mmol) in THF (30 mL) at 0° C., was added NaH (314 mg, 13.1 mmol). After 15 min, 1-tert-butyl-3-(3-fluoro-4-nitrophenyl)-5-[(pyrazin-2-yl)amino]-1H-pyrazole-4-carbonitrile (1.0 g, 2.62 mmol) was added and the mixture was stirred at RT for 16 h. The reaction mixture was concentrated and the residue diluted with $H_2O$ (200 mL) and then extracted with EtOAc (3×80 mL). The combined organic layers were dried ($Na_2SO_4$) and concentrated under reduced pressure to afford the title product (1.0 g, 81%) as a brown solid. LCMS (Method D): 4.53 min; m/z: 471.1 $[M+H]^+$.

Step 2: 1-tert-butyl-3-{4-nitro-3-[(pyridin-2-yl) methoxy]phenyl}-5-[(pyrazin yl)amino]-1H-pyrazole-4-carboxamide A mixture of 1-tert-butyl-3-{4-nitro-3-[(pyridin-2-yl) methoxy]phenyl}-5-[(pyrazin-2-yl)amino]-1H-pyrazole-4- carbonitrile (1.5 g, 3.18 mmol), Ghaffar-Parkins catalyst (400 mg, 0.93 mmol) and 80% aq. 1,4-dioxane (50 mL) was stirred at 100° C. under $N_2$ for 16 h. The reaction mixture was concentrated and the residue diluted with $H_2O$ (50 mL) and then extracted with EtOAc (3×50 mL). The combined organic layers were washed (brine), dried ($Na_2SO_4$) and concentrated under reduced pressure to afford the title product (1.0 g, 65%) as a brown solid. LCMS (Method A): 3.28 min; m/z: 489.2 $[M+H]^+$.

Step 3: 3-{4-amino-3-[(pyridin-2-yl)methoxy]phenyl}-1-tert-butyl-5-[(pyrazin-2-yl)amino]-1H-pyrazole-4-carboxamide A mixture of 1-tert-butyl-3-{4-nitro-3-[(pyridin-2-yl)methoxy]phenyl}-5-[(pyrazin-2-yl)amino]-1H-pyrazole-4-carboxamide (1.3 g, 2.66 mmol), Zn powder (863 mg, 13.2 mmol), sat. $NH_4Cl$ (5 mL) and MeOH (15 mL) was stirred at 60° C. After 2 h, the reaction mixture was filtered and the filtrate concentrated under reduced pressure. The residue was diluted with $H_2O$ (50 mL) and then extracted with EtOAc (3×50 mL). The combined organic layers were washed (brine), dried ($Na_2SO_4$), concentrated and then purified by silica gel column chromatography (DCM:MeOH, 10:1) to afford the title product (480 mg, 40%) as a brown solid. LCMS (Method A): 2.49 min; m/z: 459.2 $[M+H]^+$.

Step 4: 1-tert-butyl-5-[(pyrazin-2-yl)amino]-3-{3-[(pyridin-2-yl)methoxy]-4-(2,2,2-trifluoroethanesulfonamido)phenyl}-1H-pyrazole-4-carboxamide To a solution of 3-{4-amino-3-[(pyridin-2-yl)methoxy]phenyl}-1-tert-butyl-5-[(pyrazin-2-yl)amino]-1H-pyrazole-4-carboxamide (150 mg, 327 μmol) in DCM:pyridine (3:1, 8 mL) was added 2,2,2-trifluoroethane-1-sulfonyl chloride (89.5 mg, 0.49 mmol). After stirring at RT for 16 h, the reaction mixture was concentrated under reduced pressure. The crude residue was purified by prep-TLC (DCM:MeOH, 10:1) to afford the title product (40 mg, 20%) as a yellow solid. LCMS (Method A): 3.26 min; m/z: 605.2 $[M+H]^+$.

Step 5: 5-[(pyrazin-2-yl)amino]-3-{3-[(pyridin-2-yl)methoxy]-4-(2,2,2-trifluoroethanesulfonamido)phenyl}-1H-pyrazole-4-carboxamide (compound 227)

A solution of 1-tert-butyl-5-[(pyrazin-2-yl)amino]-3-{3-[(pyridin-2-yl)methoxy]-4-(2,2,2-trifluoroethanesulfonamido)phenyl}-1H-pyrazole-4-carboxamide (28 mg, 46.3 μmol) in DCM:TFA (1:1, 2 mL) was stirred at RT for 16 h. The reaction mixture was concentrated and the residue was neutralized to pH 7-8 with sat. $Na_2CO_3$ and then concentrated under reduced pressure. The residue was slurried in MeOH (20 mL), filtered and the filtrate concentrated then purified by prep-TLC (DCM:MeOH, 15:1) to afford the title product (20 mg, 78%) as a yellow solid. LCMS (Method A): 3.03 min; m/z: 549.1 $[M+H]^+$. $^1H$ NMR (400 MHz, MeOD-$d_4$): 13.06 (s, 1H), 9.64 (s, 1H), 9.24 (s, 1H), 8.56 (s, 1H), 8.22 (s, 1H), 8.11 (s, 1H), 7.87 (t, J=8.4 Hz, 1H), 7.68 (d, J=8.0 Hz, 1H), 7.41-7.21 (m, 7H), 5.30 (s, 2H), 4.47 (q, J=9.6 Hz, 2H), 1.15 (t, J=7.6 Hz, 3H).

Compound 261

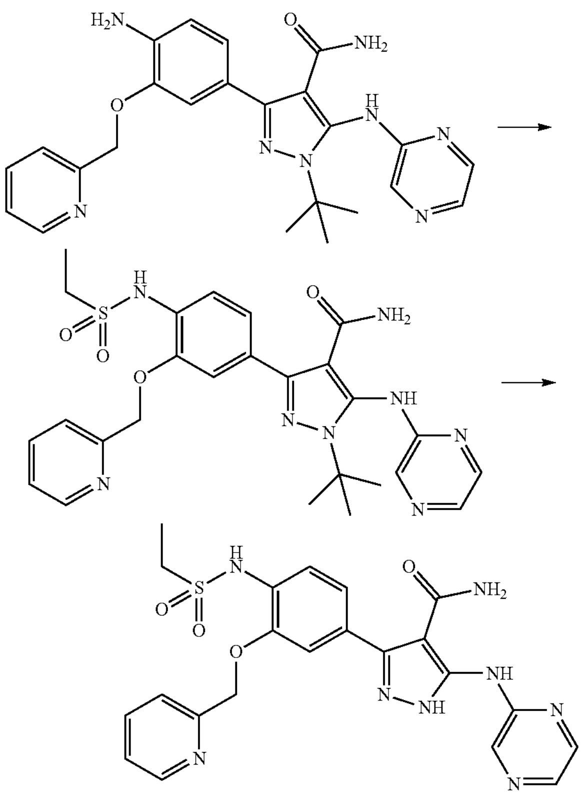

Step 1: 1-tert-butyl-3-{4-ethanesulfonamido-3-[(pyridin-2-yl)methoxy]phenyl}-5-[(pyrazin-2-yl)amino]-1H-pyrazole-4-carboxamide To a solution of 3-{4-amino-3-[(pyridin-2-yl)methoxy]phenyl}-1-tert-butyl-5-[(pyrazin-2-yl)amino]-1H-pyrazole-4-carboxamide (100 mg, 0.21 mmol) in DCM:pyridine (1:1, 2 mL), was added $EtSO_2Cl$ (33.6 mg, 0.26 mmol). The reaction mixture was stirred at RT for 16 h then concentrated under reduced pressure. The crude residue was purified by prep-TLC (DCM:MeOH, 10:1) to afford the title product (30 mg, 25%) as a yellow solid. LCMS (Method A): 2.97 min; m/z: 551.2 $[M+H]^+$.

Step 2: 3-{4-ethanesulfonamido-3-[(pyridin-2-yl)methoxy]phenyl}-5-[(pyrazin-2-yl)amino]-1H-pyrazole-4-carboxamide (Compound 261)

A solution of 1-tert-butyl-3-{4-ethanesulfonamido-3-[(pyridin-2-yl)methoxy]phenyl}-5-[(pyrazin-2-yl)amino]-1H-pyrazole-4-carboxamide (30 mg, 54.4 μmol) in DCM:TFA (1:1, 2 mL) was stirred at RT. After 16 h, the mixture was concentrated and the residue neutralized to pH 7-8 with aq. $Na_2CO_3$. The mixture was diluted with $H_2O$ (30 mL), and the resulting precipitate was collected by filtration and purified by prep-TLC (DCM:MeOH, 10:1) to afford the title product (10 mg, 37%) as a yellow solid. LCMS (Method A): 2.66 min; m/z: 495.1 $[M+H]^+$. $^1H$ NMR (400 MHz, MeOD-$d_4$): 13.06 (s, 1H), 9.64 (s, 1H), 9.25 (s, 1H), 8.59 (d, J=4.0 Hz, 1H), 8.22 (s, 1H), 8.11 (s, 1H), 7.88 (t, J=6.8 Hz, 1H), 7.72 (d, J=8.0 Hz, 1H), 7.48-7.37 (m, 3H), 7.22 (d, J=8.0 Hz, 1H), 6.28 (s, 1H), 5.29 (s, 2H), 3.10 (q, J=7.2 Hz, 2H), 1.19 (t, J=7.2 Hz, 3H).

Compound 267

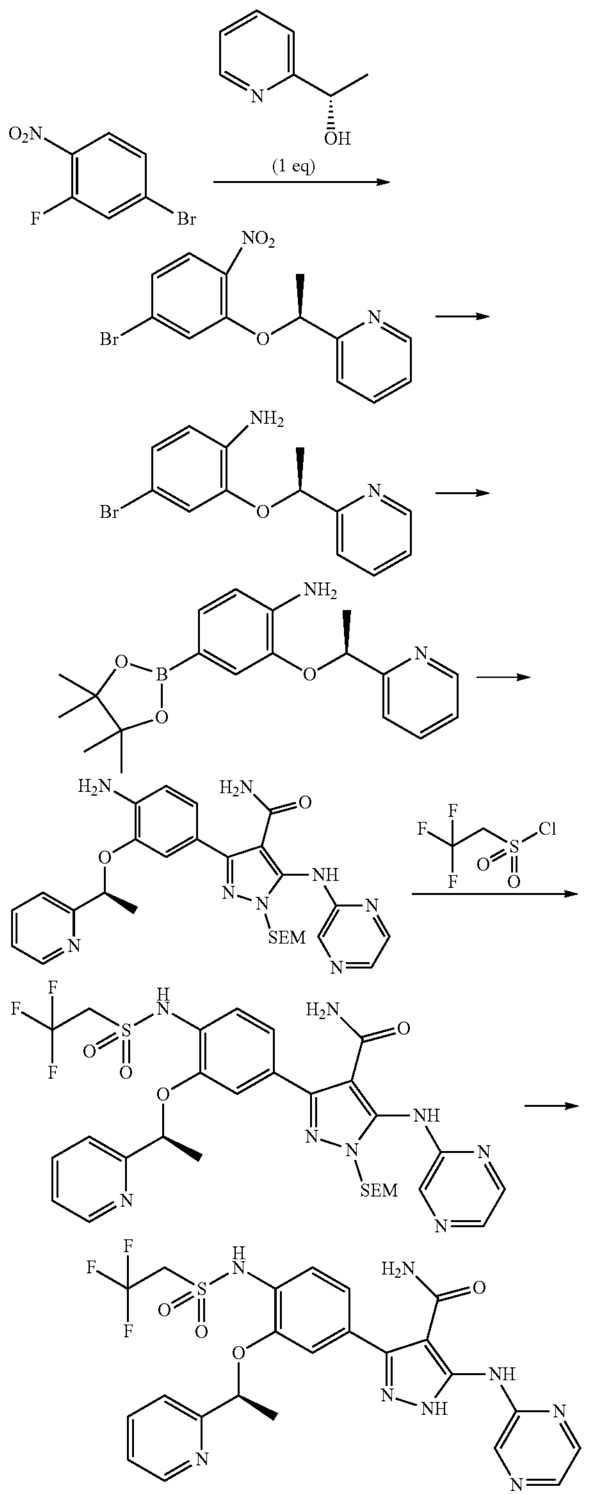

Step 1: 2-[(1S)-1-(5-bromo-2-nitrophenoxy)ethyl] pyridine

To mixture of (1S)-1-(pyridin-2-yl)ethan-1-ol (1.0 g, 8.18 mmol) in THF (20 mL) at 0° C., was added NaH (981 mg, 40.9 mmol). After 15 min, 4-bromo-2-fluoro nitrobenzene (1.8 g, 8.18 mmol) was added and the mixture was stirred at RT. After 16 h, the reaction mixture was diluted with $H_2O$ (30 mL) and extracted with EtOAc (3×30 mL). The combined organic layers were washed (brine), dried ($Na_2SO_4$) and then concentrated under reduced pressure. The crude residue was purified by silica gel column chromatography (PE:EtOAc, 20:1) to afford the title product (1.25 g, 50%) as a yellow liquid. LCMS (Method D): 5.01 min; m/z: 322.8 $[M+H]^+$.

Step 2: 4-bromo-2-[(1S)-1-(pyridin-2-yl)ethoxy] aniline

A mixture of 2-[(1S)-1-(5-bromo-2-nitrophenoxy)ethyl] pyridine (2.20 g, 6.80 mmol), Zn powder (2.21 g, 33.9 mmol), sat. $NH_4Cl$ (10 mL) and MeOH (30 mL) was stirred at 60° C. for 1 h. The reaction mixture was filtered and the filtrate was concentrated, diluted with $H_2O$ (30 mL) and then extracted with EtOAc (3×30 mL). The combined organic layers were washed (brine), dried ($Na_2SO_4$) and concentrated under reduced pressure. The crude residue was purified by silica gel column chromatography (PE:EtOAc, 3:1) to afford the title product (880 mg, 75%) as a yellow solid. LCMS (Method D): 3.90 min; m/z: 294.9 $[M+H]^+$.

Step 3: 2-[(1S)-1-(pyridin-2-yl)ethoxy]-4-(4,4,5,5-tetramethyl-1,3,2-dioxaborolan-2-yl)aniline A mixture of 4-bromo-2-[(1S)-1-(pyridin-2-yl)ethoxy] aniline (1.17 g, 3.99 mmol), $B_2pin_2$ (1.21 g, 4.78 mmol), $Pd(dppf)Cl_2$ (325 mg, 399 μmol), KOAc (1.16 g, 11.9 mmol) and 1,4-dioxane (16 mL) was stirred at 100° C. After 16 h, the mixture was concentrated and the residue diluted with $H_2O$ (30 mL) and extracted with EtOAc (3×30 mL). The combined organics were washed (brine), dried ($Na_2SO_4$) and concentrated under reduced pressure. The crude residue was purified by silica gel column chromatography (PE: EtOAc, 2:1) to afford the title product (600 mg, 74%) as a yellow liquid. LCMS (Method A): 3.50 min; m/z: 341.2 $[M+H]^+$.

Step 4: 3-{4-amino-3-[(1S)-1-(pyridin-2-yl)ethoxy] phenyl}-5-[(pyrazin-2-yl)amino]-1-{[2-(trimethylsilyl)ethoxy]methyl}-1H-pyrazole-4-carboxamide A mixture of 2-[(1S)-1-(pyridin-2-yl)ethoxy]-4-(4,4,5,5-tetramethyl-1,3,2-dioxaborolan-2-yl)aniline (680 mg, 1.99 mmol), 3-bromo-5-[(pyrazin-2-yl)amino]-1-{[2-(trimethylsilyl)ethoxy]methyl}-1H-pyrazole-4-carboxamide (822 mg, 1.99 mmol), $Pd(dppf)Cl_2$ (162 mg, 199 μmol), $Na_2CO_3$ (740 mg, 5.97 mmol) and 80% aq. 1,4-dioxane (10 mL) was stirred at 100° C. After 16 h, the reaction mixture was concentrated, diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (DCM:MeOH, 20:1) to afford the title product (330 mg, 30%) as a yellow solid. LCMS (Method A): 3.18 min; m/z: 547.3 $[M+H]^+$.

Step 5: 5-[(pyrazin-2-yl)amino]-3-{3-[(1S)-1-(pyridin-2-yl)ethoxy]-4-(2,2,2-trifluoroethanesulfonamido)phenyl}-1-{[2-(trimethylsilyl)ethoxy]methyl}-1H-pyrazole-4-carboxamide A solution of 3-{4-amino-3-[(1S)-1-(pyridin-2-yl)ethoxy]phenyl}-5-[(pyrazin-2-yl)amino]-1-{[2-(trimethylsilyl)ethoxy]methyl}-1H-pyrazole-4-carboxamide (330 mg, 603 μmol) and 2,2,2-trifluoroethane-1-sulfonyl chloride (165 mg, 904 μmol) in DCM:pyridine (1:1, 8 mL) was stirred at RT for 16 h. The reaction mixture was concentrated, diluted with $H_2O$ (30 mL) and extracted with EtOAc (3×30 mL). The combined organic layers were washed (brine), dried ($Na_2SO_4$), and concentrated under reduced pressure. The crude residue was purified by silica gel column chromatography (DCM:MeOH, 20:1) to afford the title product (180 mg, 43%) as a yellow solid. LCMS (Method A): 3.79 min; m/z: $[M+H]^+$.

Step 6: 5-[(pyrazin-2-yl)amino]-3-{3-[(1S)-1-(pyridin-2-yl)ethoxy]-4-(2,2,2-trifluoroethanesulfonamido)phenyl]-1H-pyrazole-4-carboxamide (Compound 267)

A solution of 5-[(pyrazin-2-yl)amino]-3-{3-[(1S)-1-(pyridin-2-yl)ethoxy]-4-(2,2,2-trifluoroethanesulfonamido)phenyl}-1-{[2-(trimethylsilyl)ethoxy]methyl}-1H-pyrazole-4-carboxamide (180 mg, 259 μmol) in DCM:TFA (4:1, 20 mL) was stirred for 5 min. The reaction mixture was neutralized to pH 7-8 with $NH_4OH$ and then extracted with DCM (3×30 mL). The combined organic layers were washed (brine), dried ($Na_2SO_4$) and concentrated to afford the title compound (50 mg 34%) as a yellow solid. LCMS (Method A): 3.20 min; m/z: 563.2 $[M+H]^+$. $^1H$ NMR (400 MHz, DMSO-$d_6$): 12.98 (s, 1H), 10.16 (br s, 1H), 9.60 (s, 1H), 9.34 (s, 1H), 9.22 (s, 1H), 8.53 (s, 1H), 8.21 (s, 1H), 8.11 (d, J=2.8 Hz, 1H), 7.82 (t, J=8.0 Hz, 1H), 7.61 (d, J=7.6 Hz, 1H), 7.44 (d, J=8.0 Hz, 1H), 7.36-7.31 (m, 1H), 7.20-7.13 (m, 2H), 6.12 (br s, 1H), 5.62 (q, J=6.4 Hz, 1H), 4.63 (q, J=10.0 Hz, 2H), 4.63 (d, J=6.4 Hz, 3H).

Compound 230

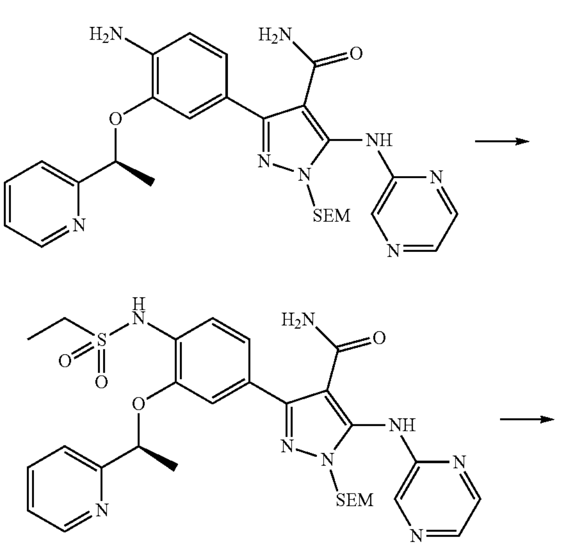

-continued

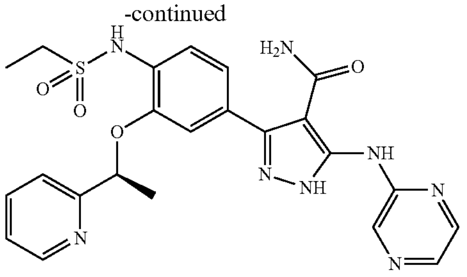

Step 1: 3-{4-ethanesulfonamido-3-[(1S)-1-(pyridin-2-yl)ethoxy]phenyl}-5-[(pyrazin-2-yl)amino]-1-{[2-(trimethylsilyl)ethoxy]methyl}-1H-pyrazole-4-carboxamide A solution of 3-{4-amino-3-[(1S)-1-(pyridin-2-yl)ethoxy]phenyl}-5-[(pyrazin-2-yl)amino]-1-{[2-(trimethylsilyl)ethoxy]methyl}-1H-pyrazole-4-carboxamide (100 mg, 182 μmol) and $EtO_2Cl$ (35.0 mg, 273 μmol) in DCM:pyridine (1:1, 10 mL) was stirred at RT for 16 h. The reaction mixture was concentrated, diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (DCM:MeOH, 20:1) to afford the title product (65 mg, 56%) as a yellow solid. LCMS (Method A): 3.57 min; m/z: 639.3 $[M+H]^+$.

Step 2: 3-{4-ethanesulfonamido-3-[(1S)-1-(pyridin-2-yl)ethoxy]phenyl}-5-[(pyrazin-2-yl)amino]-1H-pyrazole-4-carboxamide (Compound 230)

A solution of 3-{4-ethanesulfonamido-3-[(1S)-1-(pyridin-2-yl)ethoxy]phenyl}[(pyrazin-2-yl)amino]-1-{[2-(trimethylsilyl)ethoxy]methyl}-1H-pyrazole-4-carboxamide (100 mg, 156 μmol) in DCM:TFA (10:1, 10 mL) was stirred at RT. After 16 h, the reaction mixture was neutralized to pH 7-8 with sat. $Na_2CO_3$. The resulting precipitate was collected by filtration and then purified by prep-TLC (DCM:MeOH, 12:1) to afford the title compound (50 mg, 63%) as a yellow solid. LCMS (Method A): 2.85 min; m/z: 509.2 $[M+H]^+$. $^1H$ NMR (400 MHz, DMSO-$d_6$): 12.96 (s, 1H), 9.59 (s, 1H), 9.22 (s, 1H), 8.53 (d, J=4.4 Hz, 1H), 8.21 (s, 1H), 8.10 (s, 2H), 7.81 (t, J=8.4 Hz, 1H), 7.62 (d, J=7.6 Hz, 1H), 7.46 (d, J=8.4 Hz, 1H), 7.32 (t, J=4.8 Hz, 1H), 7.14 (d, J=8.4 Hz, 2H), 6.11 (s, 1H), 5.56 (s, 1H), 3.18-3.12 (m, 2H), 1.66 (d, J=6.4 Hz, 3H).

Compound 231

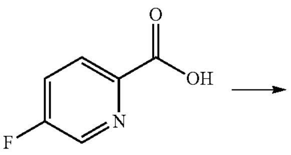

-continued

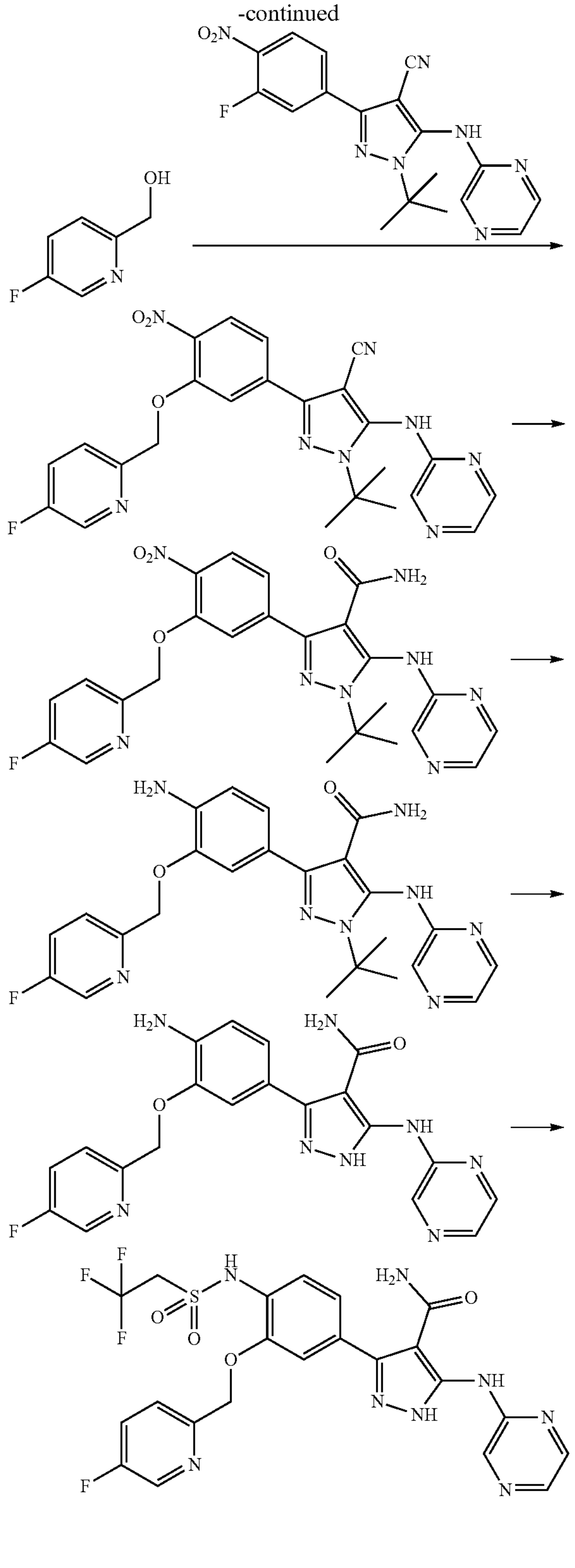

Step 1: (5-fluoropyridin-2-yl)methanol

To a solution of 5-fluoropyridine-2-carboxylic acid (5.0 g, 35.4 mmol) in THF (200 mL) at 0° C., was added $BH_3$·DMS (10.7 g, 141 mmol) and the resulting solution was stirred at 60° C. After 3 h, the solution was cooled to 0° C., quenched with MeOH (10 mL) and then heated to reflux for 1 h. The reaction mixture was concentrated and the residue diluted with $H_2O$ (200 mL) and then extracted with EtOAc (3×100 mL). The combined organic layers were dried ($Na_2SO_4$), concentrated and the crude residue purified by silica gel column chromatography (DCM:MeOH, 10:1) to afford the title product (2.6 g, 58%) as a yellow oil. $^1$H NMR (400 MHz, DMSO-$d_6$): 8.46 (d, J=2.9 Hz, 1H), 7.71 (td, J=8.8, 2.9 Hz, 1H), 7.52 (ddd, J=8.7, 4.6, 0.5 Hz, 1H), 4.54 (s, 2H).

Step 2: 1-tert-butyl-3-{3-[(5-fluoropyridin-2-yl) methoxy]-4-nitrophenyl}-5-[(pyrazin yl)amino]-1H-pyrazole-4-carbonitrile To a mixture of (5-fluoropyridin-2-yl)methanol (200 mg, 1.57 mmol) in THF (15 mL) at 0° C., was added NaH (37.6 mg, 1.57 mmol). After 15 min, 1-tert-butyl-3-(3-fluoro-4-nitrophenyl)-5-[(pyrazin-2-yl)amino]-1H-pyrazole-4-carbonitrile (598 mg, 1.57 mmol) was added and the mixture stirred at RT for 16 h. The reaction mixture was quenched with $H_2O$ (100 mL) and then extracted with EtOAc (2×50 mL). The combined organic layers were dried ($Na_2SO_4$), concentrated and the crude residue purified by silica gel column chromatography (PE/EtOAc, 3:1) to afford the title product (300 mg, 39%) as a yellow solid. LCMS (Method D): 4.31 min; m/z: 489.1 $[M+H]^+$.

Step 3: 1-tert-butyl-3-{3-[(5-fluoropyridin-2-yl) methoxy]-4-nitrophenyl}-5-[(pyrazin-2-yl)amino]-1H-pyrazole-4-carboxamide A mixture of 1-tert-butyl-3-{3-[(5-fluoropyridin-2-yl) methoxy]-4-nitrophenyl}-5-[(pyrazin-2-yl)amino]-1H-pyrazole-4-carbonitrile (800 mg, 1.63 mmol), Ghaffar-Parkins catalyst (696 mg, 1.63 mmol) and 80% aq. 1,4-dioxane (25 mL) was stirred at 100° C. After 16 h, the reaction mixture was diluted with $H_2O$ (100 mL) and then extracted with EtOAc (2×50 mL). The combined organic layers were dried ($Na_2SO_4$), concentrated and the residue purified by silica gel column chromatography (DCM:MeOH, 60:1) to afford the title product (630 mg, 76%) as a yellow solid. LCMS (Method D): 4.06 min; m/z: 507.3 $[M+H]^+$.

Step 4: 3-{4-amino-3-[(5-fluoropyridin-2-yl) methoxy]phenyl}-1-tert-butyl-5-[(pyrazin-2-yl) amino]-1H-pyrazole-4-carboxamide A mixture of 1-tert-butyl-3-{3-[(5-fluoropyridin-2-yl) methoxy]-4-nitrophenyl}-5-[(pyrazin-2-yl)amino]-1H-pyrazole-4-carboxamide (620 mg, 1.22 mmol), Zn powder (398 mg, 6.10 mmol), sat. $NH_4Cl$ (1 mL) and MeOH (10 mL) was stirred at 60° C. for 16 h. The mixture was filtered and the filtrate diluted with $H_2O$ (30 mL) and then extracted with EtOAc (3×30 mL). The combined organic layers were washed (brine), dried ($Na_2SO_4$) and then concentrated under reduced pressure. The crude residue was purified by silica gel column chromatography (DCM:MeOH, 10:1) to afford the title product (200 mg, 34%) as a red solid. LCMS (Method D): 3.01 min; m/z: 477.2 $M+H]^+$.

Step 5: 3-{4-amino-3-[(5-fluoropyridin-2-yl) methoxy]phenyl}-5-[(pyrazin-2-yl)amino]-1H-pyrazole-4-carboxamide A solution of 3-{4-amino-3-[(5-fluoropyridin-2-yl) methoxy]phenyl}-1-tert-butyl-5-[(pyrazin-2-yl)amino]-1H-pyrazole-4-carboxamide (100 mg, 209 µmol) in DCM:TFA (1:1, 6 mL) was stirred at RT. After 16 h, the reaction mixture was neutralized to pH 7-8 and then extracted with DCM (2×50 mL). The crude residue was purified by prep-TLC (DCM:MeOH, 20:1) to afford the title product (30 mg, 34%) as a white solid. LCMS (Method A): 2.68 min; m/z: 421.2 $[M+H]^+$.

Step 6: 3-(3-((5-fluoropyridin-2-yl)methoxy)-4-((2,2,2-trifluoroethyl)sulfonamido) phenyl)-5-(pyrazin-2-ylamino)-1H-pyrazole-4-carboxamide (Compound 231)

A mixture of 3-{4-amino-3-[(5-fluoropyridin-2-yl)methoxy]phenyl}-5-[(pyrazin-2-yl)amino]-1H-pyrazole-4-carboxamide (30 mg, 71.3 μmol), 2,2,2-trifluoroethane-1-sulfonyl chloride (19.3 mg, 106 μmol) and DCM:pyridine (1:1, 10 mL) was stirred at RT. After 16 h, the reaction mixture was diluted with $H_2O$ (100 mL) and extracted with EtOAc (2×50 mL). The combined organic layers were dried ($Na_2SO_4$), concentrated and the crude residue purified by silica gel column chromatography (DCM:MeOH, 10:1) to afford the title compound (10 mg, 25%) as a white solid. LCMS (Method A): 3.23 min; m/z: 567.1 $[M+H]^+$. $^1$H NMR (400 MHz, DMSO-$d_6$): 13.06 (s, 1H), 10.05 (s, 1H), 9.64 (s, 1H), 9.24 (s, 1H), 8.56 (d, J=2.8 Hz, 1H), 8.21 (t, J=4.0 Hz, 1H), 8.11 (d, J=2.4 Hz, 1H), 7.81 (m, 2H), 7.21 (m, 1H), 7.45 (d, J=8.0 Hz, 2H), 7.23 (m, 2H), 6.26 (s, 1H), 5.29 (s, 2H), 4.45 (q, J=29.6 Hz, 2H).

Compound 21

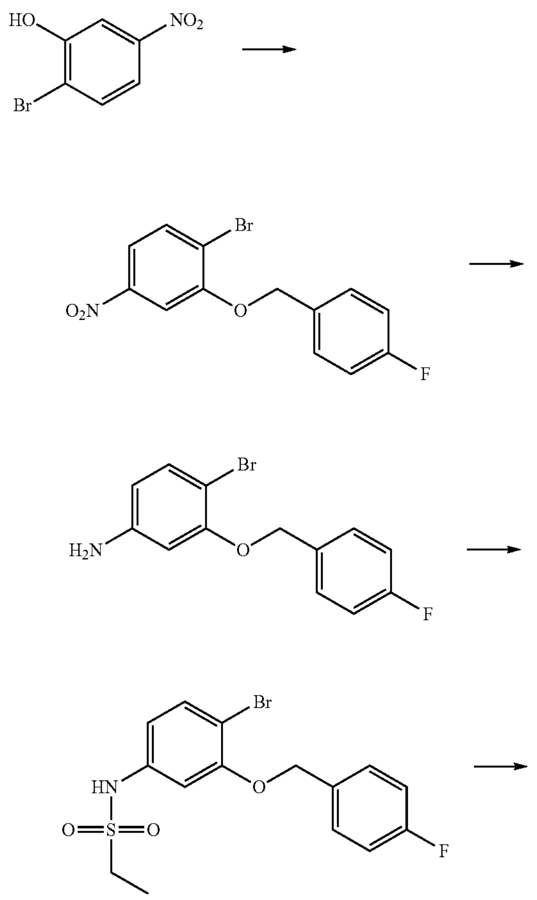

-continued

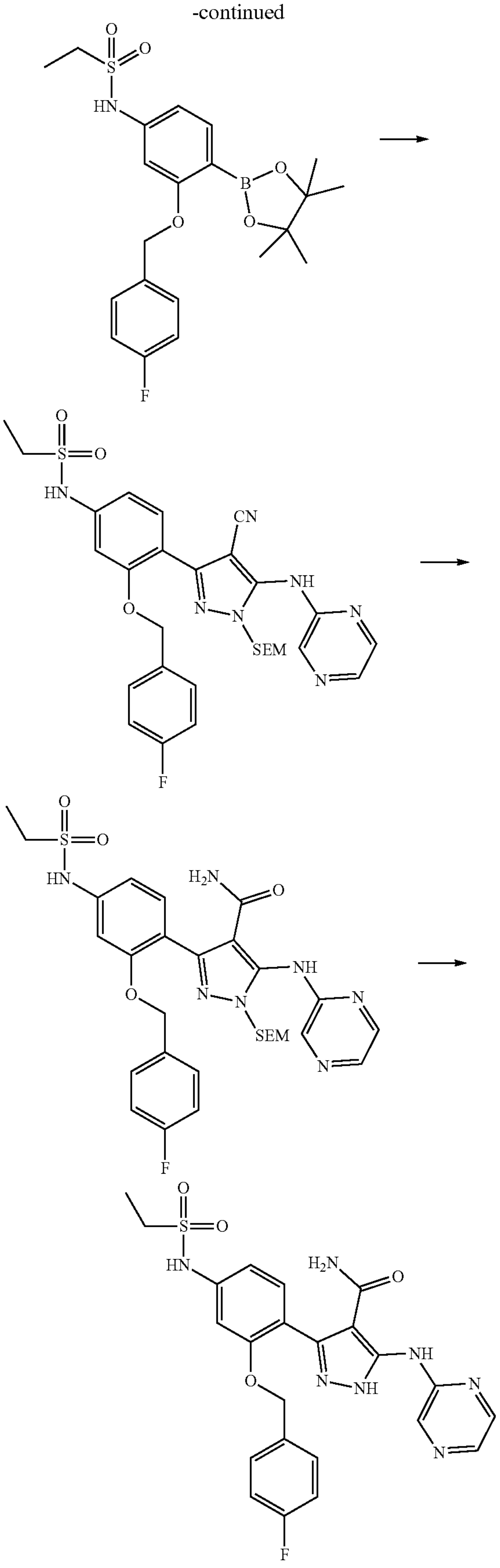

Step 1: 1-bromo-2-((4-fluorobenzyl)oxy)-4-nitrobenzene

A mixture of 2-bromo-5-nitrophenol (10 g, 45.8 mmol), 1-(bromomethyl)-4-fluorobenzene (8.65 g, 45.8 mmol) and $K_2CO_3$ (12.6 g, 91.6 mmol) in MeCN (100 mL) was stirred at 70° C. under $N_2$ overnight. The mixture was diluted with $H_2O$ (100 mL) and then extracted with EtOAc (3×200 mL). The combined organics were dried ($Na_2SO_4$) and concentrated under reduced pressure to afford the title compound (15.0 g, 100%) as a white solid.

Step 2: 4-bromo-3-((4-fluorobenzyl)oxy)aniline

A mixture of 1-bromo-2-((4-fluorobenzyl)oxy)-4-nitrobenzene (15 g, 45.9 mmol), sat. aq. $NH_4Cl$ (100 mL) and Zn dust (14.9 g, 229 mmol) in MeOH (300 mL) was stirred at 60° C. for 4 h. The reaction mixture was filtered, diluted with $H_2O$ (250 mL) and then extracted with EtOAc (3×300 mL). The combined organics were dried ($Na_2SO_4$) and concentrated under reduced pressure to afford the title product (13.0 g, 96%) as a black oil. LCMS (Method A): 4.24 min; m/z: 296.0 $[M+H]^+$.

Step 3: N-(4-bromo-3-((4-fluorobenzyl)oxy)phenyl) ethanesulfonamide

A mixture of 4-bromo-3-((4-fluorobenzyl)oxy)aniline (13 g, 43.8 mmol), $EtSO_2Cl$ (8.43 g, 65.6 mmol) and pyridine (50 mL) in $CHCl_3$ (50 mL) was stirred at RT under $N_2$ for 3 h. The mixture was concentrated under reduced pressure and the crude residue was purified by silica gel column chromatography (PE:EtOAc, 1:1) to afford the title product (12.5 g, 73%) as a yellow solid. LCMS (Method A): 4.24 min; m/z: 410.0 $[M+H]^+$.

Step 4: N-(3-((4-fluorobenzyl)oxy)-4-(4,4,5,5-tetramethyl-1,3,2-dioxaborolan-2-yl)phenyl)ethanesulfonamide A mixture of N-(4-bromo-3-((4-fluorobenzyl)oxy)phenyl)ethanesulfonamide (12.5 g, 32.1 mmol), $Pd(dppf)Cl_2$ (1.46 g, 1.60 mmol), KOAc (6.29 g, 64.2 mmol) and $B_2pin_2$ (8.96 g, 35.2 mmol) in degassed 1,4-dioxane (200 mL) was stirred at 100° C. under $N_2$ overnight. The mixture was concentrated under reduced pressure and the crude residue was purified by silica gel column chromatography (PE: EtOAc, 2:1) to afford the title product (14.8 g, >100%) as a brown solid. LCMS (Method A): 4.51 min; m/z: 453.2 $[M+H]^+$. $^1H$ NMR (400 MHz, DMSO-$d_6$): 8.99 (s, 1H), 7.63-7.60 (m, 2H), 7.38-7.32 (m, 2H), 7.28-7.21 (m, 3H), 5.15 (s, 2H), 3.03 (q, J=14.8, 7.2 Hz, 2H), 1.29 (s, 12H), 1.11 (t, J=7.2 Hz, 3H).

Step 5: N-(4-(4-cyano-5-(pyrazin-2-ylamino)-14(2-(trimethylsilyl)ethoxy)methyl)-1H-pyrazol-3-yl)-3-[(4-fluorobenzyl)oxy)phenyl)ethanesulfonamide A mixture of N-{3-[(4-fluorophenyl)methoxy]-4-(4,4,5,5-tetramethyl-1,3,2-dioxaborolan-2-yl)phenyl}ethane-1-sulfonamide (500 mg, 1.14 mmol), 3-bromo-5-[(pyrazin-2-yl)amino]-1-{[2-(trimethylsilyl)ethoxy]methyl}-1H-pyrazole-4-carbonitrile (450 mg, 1.14 mmol), $Pd(dppf)Cl_2$ (104 mg, 0.114 mmol) and $Na_2CO_3$ (241 mg, 2.28 mmol) in degassed 80% aq. 1,4-dioxane (15 mL) was stirred at 100° C. overnight. The mixture was concentrated under reduced pressure and the crude residue was purified by silica gel column chromatography (PE:EtOAc, 1:1) to afford the title product (420 mg, 59%) as a yellow solid. LCMS (Method A): 4.09 min; m/z: 624.2 $[M+H]^+$.

Step 6: 3-(4-(ethylsulfonamido)-2-((4-fluorobenzyl)oxy)phenyl)-5-(pyrazin-2-ylamino)-1-((2-(trimethylsilyl)ethoxy)methyl)-1H-pyrazole-4-carboxamide A mixture of N-(4-{4-cyano-5-[(pyrazin-2-yl)amino]-1-{[2-(trimethylsilyl)ethoxy]methyl}-1H-pyrazol-3-yl}-3-[(4-fluorophenyl)methoxy]phenyl)ethane-1-sulfonamide (420 mg, 0.673 mmol) and Ghaffar-Parkins catalyst (4 mg, 9.30 μmol) in 60% aq. 1,4-dioxane (14 mL) was stirred at 110° C. under $N_2$ overnight. The reaction mixture was diluted with $H_2O$ (50 mL) and then extracted with EtOAc (3×50 mL). The combined organic layers were washed with brine, dried over ($Na_2SO_4$) and concentrated under reduced pressure. The crude residue was purified by silica gel column chromatography (PE:EtOAc, 50:1) to afford the title product (108 mg, 25%) as a brown solid. LCMS (Method A): 3.76 min; m/z: 642.2 $[M+H]^+$.

Step 7: 3-(4-(ethylsulfonamido)-2-((4-fluorobenzyl)oxy)phenyl)-5-(pyrazin-2-ylamino)-1H-pyrazole-4-carboxamide (Compound 21)

A solution of 3-{4-ethanesulfonamido-2-[(4-fluorophenyl)methoxy]phenyl}-5-[(pyrazin-2-yl)amino]-1-{[2-(trimethylsilyl)ethoxy]methyl}-1H-pyrazole-4-carboxamide (108 mg, 0.1682 mmol) in DCM (2 mL) and TFA (2 mL) was stirred at 30° C. for 1 h then concentrated under reduced pressure. The residue was neutralized to pH 7-8 with $NH_4OH$, diluted with $H_2O$ (50 mL) and then extracted with EtOAc (3×50 mL). The combined organics were dried ($Na_2SO_4$), concentrated under reduced pressure and the crude residue was purified by silica gel column chromatography (DCM:MeOH, 1:0 to 9:1) to afford the title product (60.6 mg, 68%) as a yellow solid. LCMS (Method A): 3.19 min; m/z: 512.1 $[M+H]^+$. $^1H$ NMR (400 MHz, DMSO-$d_6$): 12.84 (s, 1H), 10.15 (br s, 1H), 9.74 (s, 1H), 9.30 (s, 1H), 8.24-8.22 (m, 1H), 8.12 (d, J=2.4 Hz, 1H), 7.45-7.41 (m. 2H), 7.35 (d, J=8.0 Hz, 2H), 7.17 (t, J=8.8 Hz, 2H), 7.07 (s, 1H), 6.94 (dd, J=8.8, 1.6 Hz, 1H), 5.68 (br s, 1H), 5.10 (s, 2H), 3.15 (q, J=7.2 Hz, 2H), 1.20 (t, J=7.2 Hz, 3H).

Compound 254

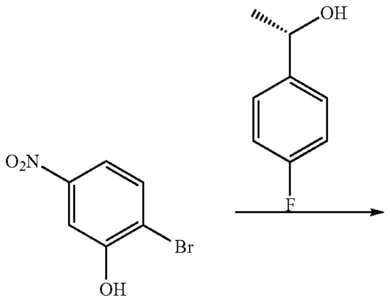

-continued

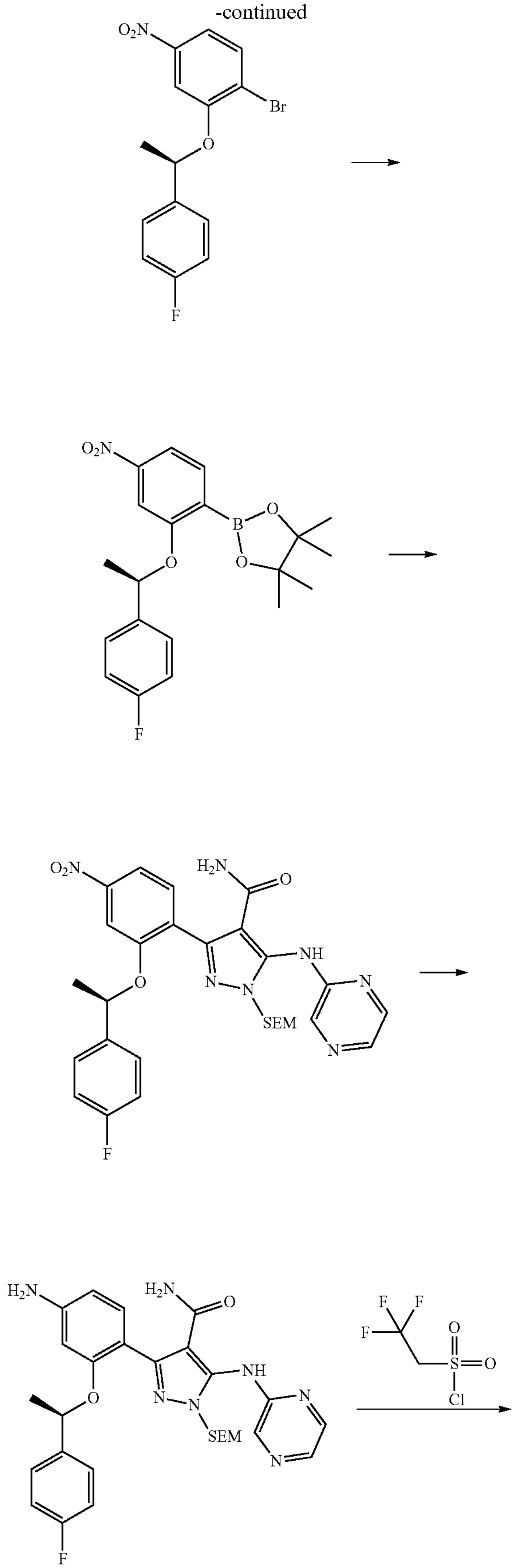

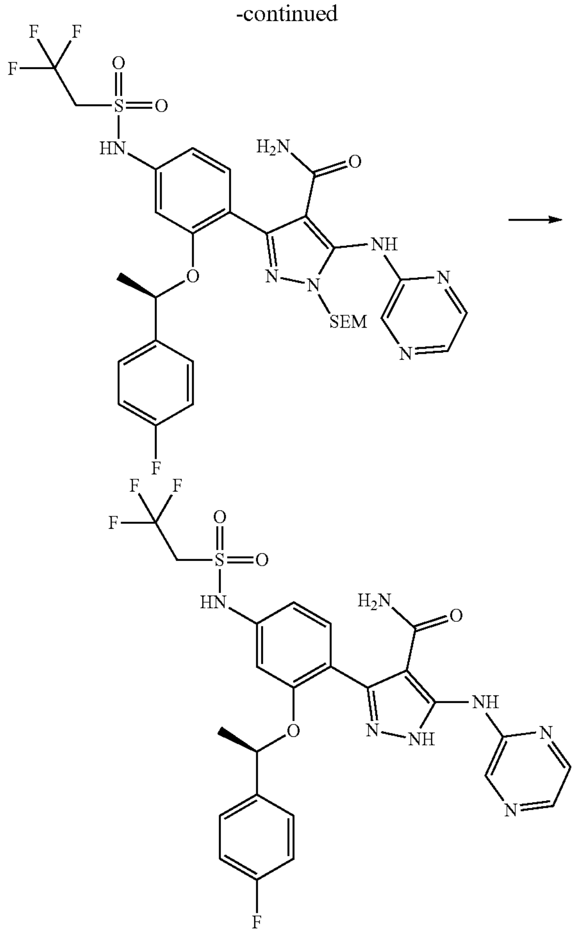

Step 1: 1-bromo-2-[(1R)-1-(4-fluorophenyl)ethoxy]-4-nitrobenzene

A mixture of 2-bromo-5-nitrophenol (2.40 g, 11.0 mmol), (1S)-1-(4-fluorophenyl)ethan-1-ol (1.54 g, 11.0 mmol), $PPh_3$ (4.32 g, 16.5 mmol), DIAD (3.33 g, 16.5 mmol) and THF (20 mL) was stirred at 70° C. for 16 h. The reaction mixture was concentrated and then diluted with $H_2O$ (60 mL) and extracted with EtOAc (3×30 mL). The combined organic layers were washed (brine), dried ($Na_2SO_4$) and concentrated under reduced pressure. The crude residue was purified by silica gel column chromatography (PE:EtOAc, 50:1) to afford the title product (2.5 g, 73%) as a yellow liquid. $^1H$ NMR (400 MHz, DMSO-$d_6$): 7.86 (d, J=8.7 Hz, 1H), 7.78 (d, J=2.5 Hz, 1H), 7.68 (dd, J=8.7, 2.5 Hz, 1H), 7.53-7.48 (m, 2H), 7.23-7.17 (m, 2H), 5.89 (q, J=6.3 Hz, 1H), 1.59 (d, J=6.3 Hz, 3H).

Step 2: 2-{2-[(1R)-1-(4-fluorophenyl)ethoxy]-4-nitrophenyl}-4,4,5,5-tetramethyl-1,3,2-dioxaborolane A mixture of 1-bromo-2-[(1R)-1-(4-fluorophenyl)ethoxy]-4-nitrobenzene (2.50 g, 7.34 mmol), $B_2pin_2$ (2.14 g, 8.44 mmol), Pd(dppf)$Cl_2$ (599 mg, 734 μmol), KOAc (2.15 g, 22.0 mmol) and 1,4-dioxane (10 mL) was stirred at 100° C. for 16 h. The reaction mixture was concentrated and then diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (PE:EtOAc, 3:1) to afford the title product (2.20 g, 77%) as a yellow solid.

Step 3: 3-{2-[(1R)-1-(4-fluorophenyl)ethoxy]-4-nitrophenyl}-5-[(pyrazin-2-yl)amino]-1-{[2-(trimethylsilyl)ethoxy]methyl}-1H-pyrazole-4-carboxamide A mixture of 2-{2-[(1R)-1-(4-fluorophenyl)ethoxy]-4-nitrophenyl}-4,4,5,5-tetramethyl-1,3,2-dioxaborolane (1 g, 2.58 mmol), 3-bromo-5-[(pyrazin-2-yl)amino]-1-{[2-(trimethylsilyl)ethoxy]methyl}-1H-pyrazole-4-carboxamide (1.06 g, 2.58 mmol), Pd(dppf)$Cl_2$ (210 mg, 258 μmol), $Na_2CO_3$ (820 mg, 7.74 mmol) and 80% aq. 1,4-dioxane (15 mL) was stirred at 100° C. for 1 h. The reaction mixture was concentrated, diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (EtOAc) to afford the title product (1.20 g, 66%) as a yellow solid. LCMS (Method A): 4.15 min; m/z: 594.2 $[M+H]^+$.

Step 4: 3-{4-amino-2-[(1R)-1-(4-fluorophenyl)ethoxy]phenyl}-5-[(pyrazin-2-yl)amino]-1-{[2-(trimethylsilyl)ethoxy]methyl}-1H-pyrazole-4-carboxamide A mixture of 3-{2-[(1R)-1-(4-fluorophenyl)ethoxy]-4-nitrophenyl}-5-[(pyrazin-2-yl)amino]-1-{[2-(trimethylsilyl)ethoxy]methyl}-1H-pyrazole-4-carboxamide (1.1 g, 1.85 mmol), Zn powder (604 mg, 9.25 mmol), sat. $NH_4Cl$ (5 mL) and MeOH (15 mL) was stirred at 60° C. for 1 h. The reaction mixture was filtered and the filtrate concentrated under reduced pressure. The residue was diluted with $H_2O$ (30 mL) and extracted with EtOAc (3×30 mL). The combined organic layers were washed (brine), dried ($Na_2SO_4$), concentrated and then purified by silica gel column chromatography (PE:EtOAc, 1:1) to afford product (540 mg, 48%) as a yellow solid. LCMS (Method A): 3.69 min; m/z: 564.3 $[M+H]^+$.

Step 5: 3-{2-[(1R)-1-(4-fluorophenyl)ethoxy]-4-(2,2,2-trifluoroethane-sulfonamido)phenyl}-5-[(pyrazin-2-yl)amino]-1-{[2-(trimethylsilyl)ethoxy]methyl}-1H-pyrazole-4-carboxamide A mixture of 3-{4-amino-2-[(1R)-1-(4-fluorophenyl)ethoxy]phenyl}-5-[(pyrazin-2-yl)amino]-1-{[2-(trimethylsilyl)ethoxy]methyl}-1H-pyrazole-4-carboxamide (250 mg, 421 μmol), 2,2,2-trifluoroethanesulfonyl chloride (115 mg, 631 μmol) and DCM:pyridine (1:1, 12 mL) was stirred at RT for 16 h. The reaction mixture was concentrated then diluted with $H_2O$ (30 mL) and extracted with EtOAc (3×30 mL). The combined organic layers were washed (brine), dried ($Na_2SO_4$) and concentrated under reduced pressure. The residue was purified by silica gel column chromatography (DCM:MeOH, 20:1) to afford the title product (120 mg, 40%) as a yellow solid. LCMS (Method A): 3.96 min; m/z: 710.3 $[M+H]^+$.

Step 6: 3-{2-[(1R)-1-(4-fluorophenyl)ethoxy]-4-(2,2,2-trifluoroethanesulfonamido)phenyl}-5-[(pyrazin-2-yl)amino]-1H-pyrazole-4-carboxamide (Compound 254)

A mixture of 3-{2-[(1R)-1-(4-fluorophenyl)ethoxy]-4-(2,2,2-trifluoroethanesulfonamido)phenyl}-5-[(pyrazin-2-yl)amino]-1-{[2-(trimethylsilyl)ethoxy]methyl}-1H-pyrazole-4-carboxamide (120 mg, 169 μmol) and DCM:TFA (10:1, 12 mL) was stirred at RT for 16 h. The reaction mixture was neutralized to pH 7-8 with $NH_4OH$ and then diluted with $H_2O$ (20 mL) and extracted with DCM (3×30 mL). The combined organic layers were washed (brine), dried ($Na_2SO_4$) and concentrated to afford the title compound (50 mg 51%) as a yellow solid. LCMS (Method A): 3.44 min; m/z: 580.2 $[M+H]^+$. $^1H$ NMR (400 MHz, DMSO-$d_6$): 12.85 (s, 1H), 10.74 (s, 1H), 9.77 (s, 1H), 9.34 (s, 1H), 8.24 (s, 1H), 8.13 (s, 1H), 7.36 (s, 3H), 7.14 (t, J=8.4 Hz, 2H), 6.88 (d, J=8.8 Hz, 2H), 5.69 (s, 1H), 5.42 (d, J=6.0 Hz, 1H), 4.48 (t, J=10.4 Hz, 2H), 1.45 (d, J=5.6 Hz, 3H).

Compound 255

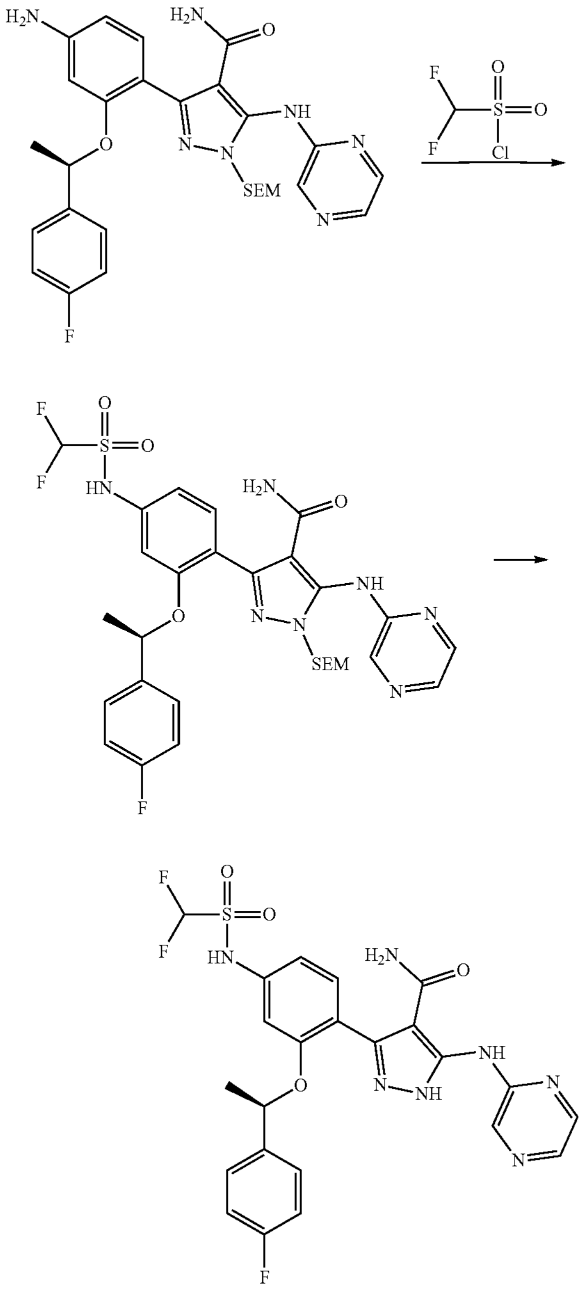

Step 1: 3-[4-(difluoromethanesulfonamido)-2-[(1R)-1-(4-fluorophenyl)ethoxy]phenyl]-5-[(pyrazin-2-yl)amino]-1-{[2-(trimethylsilyl)ethoxy]methyl}-1H-pyrazole-4-carboxamide A solution of 3-{2-[(1R)-1-(4-fluorophenyl)ethoxy]-4-nitrophenyl}-5-[(pyrazin-2-yl)amino]-1-{[2-(trimethylsilyl)ethoxy]methyl}-1H-pyrazole-4-carboxamide (280 mg, 471 μmol) and $F_2CHSO_2Cl$ (106 mg, 706 μmol) in DCM:pyridine (1:1, 4 mL) was stirred at RT for 16 h.

The reaction mixture was concentrated, diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (DCM:MeOH, 20:1) to afford the title product (180 mg, 56%) as a yellow solid. LCMS (Method A): 3.89 min; m/z: 678.2 $[M+H]^+$.

Step 2: 3-[4-(difluoromethanesulfonamido)-2-[(1R)-1-(4-fluorophenyl)ethoxy]phenyl]-5-[(pyrazin-2-yl)amino]-1H-pyrazole-4-carboxamide (Compound 255)

A solution of 3-[4-(difluoromethanesulfonamido)-2-[(1R)-1-(4-fluorophenyl)ethoxy]phenyl]-5-[(pyrazin-2-yl)amino]-1-{[2-(trimethylsilyl)ethoxy]methyl}-1H-pyrazole-4-carboxamide (180 mg, 265 μmol) in DCM:TFA (10:1, 20 mL) was stirred at RT for 16 h. The reaction mixture was concentrated under reduced pressure and the residue was neutralized to pH 7-8 with $NH_4OH$, then diluted with $H_2O$ (20 mL) and extracted with DCM (3×30 mL). The combined organic layers were washed (brine), dried ($Na_2SO_4$) and concentrated to afford the title compound (60 mg, 41%) as a yellow solid. LCMS (Method A): 3.35 min; m/z: 548.1 $[M+H]^+$. $^1H$ NMR (400 MHz, DMSO-$d_6$): 12.86 (s, 1H), 11.22 (s, 1H), 9.71 (s, 1H), 9.32 (s, 1H), 8.23 (s, 1H), 8.12 (d, J=2.4 Hz, 1H), 7.34 (t, J=5.6 Hz, 3H), 7.24-6.98 (m, 4H), 6.90 (t, J=8.4 Hz, 2H), 5.66 (s, 1H), 5.38 (d, J=6.4 Hz, 2H), 1.44 (d, J=6.0 Hz, 3H).

Compound 244

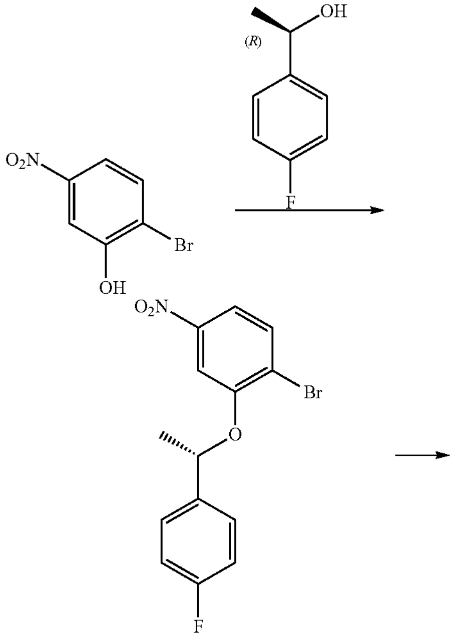

-continued

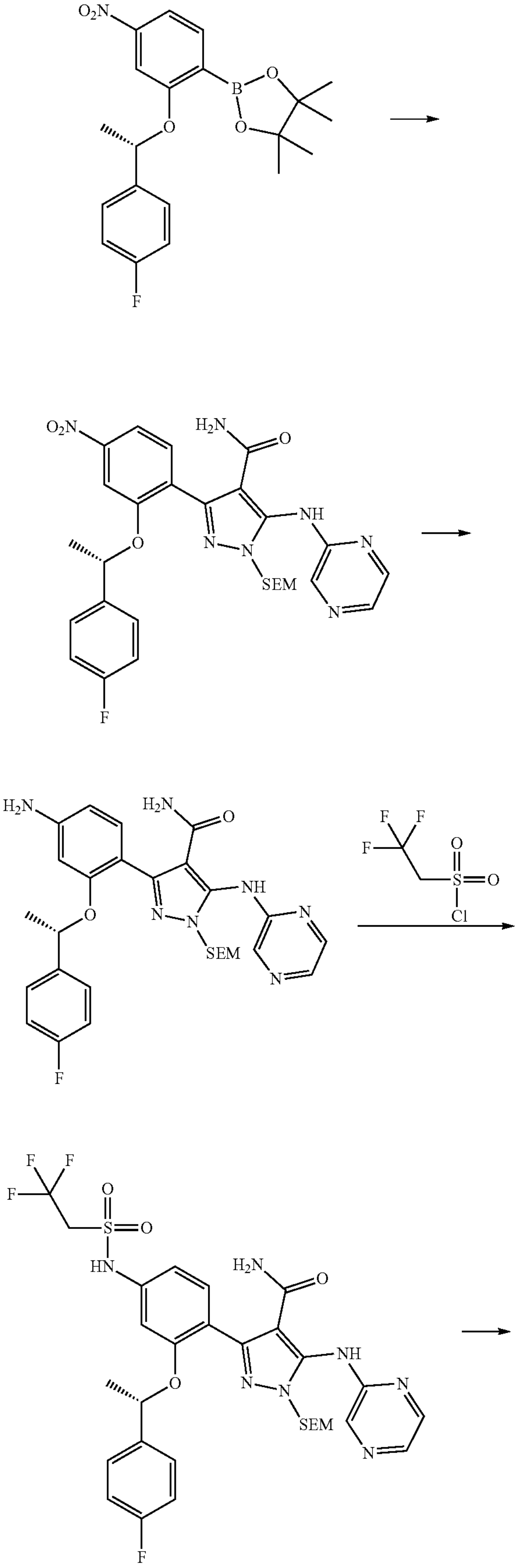

-continued

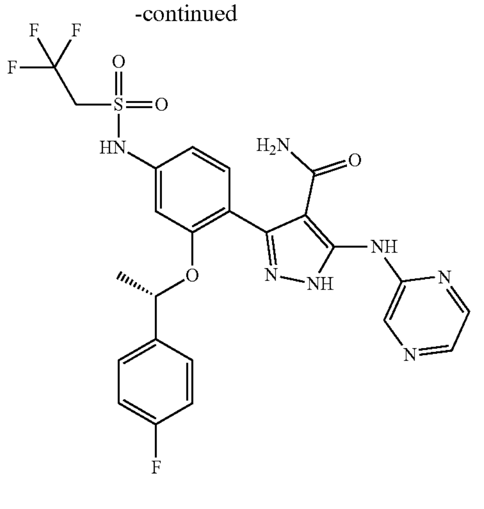

Step 1: 1-bromo-2-[(1S)-1-(4-fluorophenyl)ethoxy]-4-nitrobenzene

A mixture of 2-bromo-5-nitrophenol (3.00 g, 13.7 mmol), (1R)-1-(4-fluorophenyl)ethan-1-ol (1.92 g, 13.7 mmol), DIAD (4.14 g, 20.5 mmol), $PPh_3$ (5.37 g, 20.5 mmol) and THF (12 mL) was stirred at 70° C. After 16 h, the reaction mixture was concentrated then diluted with $H_2O$ (60 mL) and extracted with EtOAc (3×30 mL). The combined organic layers were washed (brine), dried ($Na_2SO_4$) and concentrated under reduced pressure. The crude residue was purified by silica gel column chromatography (PE:EtOAc, 3:1) to afford the title product (3.50 g, 75%) as a yellow liquid.

Step 2: 2-2-[(1S)-1-(4-fluorophenyl)ethoxy]-4-nitrophenyl}-4,4,5,5-tetramethyl-1,3,2-dioxaborolane A mixture of 1-bromo-2-[(1S)-1-(4-fluorophenyl) ethoxy]-4-nitrobenzene (3.63 g, 10.6 mmol), $B_2pin_2$ (2.94 g, 11.6 mmol), Pd(dppf)$Cl_2$ (857 mg, 1.05 mmol), KOAc (3.12 g, 31.8 mmol) and 1,4-dioxane (100 mL) was stirred at 100° C. After 16 h, the reaction mixture was concentrated and the residue diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (PE:EtOAc, 3:1) to afford the title product (2.60 g, 59%) as a yellow liquid.

Step 3: 3-{2-[(1S)-1-(4-fluorophenyl)ethoxy]-4-nitrophenyl}-5-[(pyrazin-2-yl)amino]-1-{[2-(trimethylsilyl)ethoxy]methyl}-1H-pyrazole-4-carboxamide A mixture of 2-{2-[(1S)-1-(4-fluorophenyl)ethoxy]-4-nitrophenyl}-4,4,5,5-tetramethyl-1,3,2-dioxaborolane (1.25 g, 3.22 mmol), 3-bromo-5-[(pyrazin-2-yl)amino]-1-{[2-(trimethylsilyl)ethoxy]methyl}-1H-pyrazole-4-carboxamide (1.33 g, 3.22 mmol), Pd(dppf)$Cl_2$ (262 mg, 0.32 mmol), $Na_2CO_3$ (1.02 g, 9.66 mmol) and 80% aq. 1,4-dioxane (15 mL) was stirred at 100° C. for 16 h. The reaction mixture was concentrated and then diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (EtOAc) to afford the title product (1.20 g, 66%) as a yellow solid. LCMS (Method A): 4.11 min; m/z: 594.3 $[M+H]^+$.

Step 4: 3-4-amino-2-[(1S)-1-(4-fluorophenyl) ethoxy]phenyl}-5-[(pyrazin-2-yl)amino]-1-{[2-(trimethylsilyl)ethoxy]methyl}-1H-pyrazole-4-carboxamide A mixture of 3-{2-[(1S)-1-(4-fluorophenyl)ethoxy]-4-nitrophenyl}-5-[(pyrazin-2-yl)amino]-1-{[2-(trimethylsilyl) ethoxy]methyl}-1H-pyrazole-4-carboxamide (1.25 g, 2.10 mmol), Zn powder (686 mg, 10.5 mmol), $NH_4Cl$ (5 mL) and MeOH (15 mL) was stirred at 60° C. After 1 h, the reaction mixture was filtered and the filtrate concentrated under reduced pressure. The residue was diluted with $H_2O$ (30 mL) and extracted with EtOAc (3×30 mL). The combined organic layers were washed (brine), dried ($Na_2SO_4$), concentrated and the residue purified by silica gel column chromatography (PE:EtOAc, 1:1) to afford the title product (1.10 g, 93%) as a yellow solid. LCMS (Method A): 3.71 min; m/z: 564.1 $[M+H]^+$.

Step 5: 3-2-[(1S)-1-(4-fluorophenyl)ethoxy]-4-(2,2,2-trifluoroethane-sulfonamido)phenyl}-5-[(pyrazin-2-yl)amino]-1-{[2-(trimethylsilyl)ethoxy]methyl}-1H-pyrazole-4-carboxamide A mixture of 3-{4-amino-2-[(1S)-1-(4-fluorophenyl) ethoxy]phenyl}-5-[(pyrazin-2-yl)amino]-1-{[2-(trimethylsilyl)ethoxy]methyl}-1H-pyrazole-4-carboxamide (450 mg, 0.79 mmol), 2,2,2-trifluoroethanesulfonyl chloride (206 mg, 1.13 mmol) and DCM:pyridine (1:1, 12 mL) was stirred at RT for 16 h. The reaction mixture was concentrated and then diluted with $H_2O$ (30 mL) and extracted with EtOAc (3×30 mL). The combined organic layers were washed (brine), dried ($Na_2SO_4$) and concentrated under reduced pressure. The crude residue was purified by silica gel column chromatography (DCM:MeOH, 20:1) to afford the title product (260 mg, 46%) as a yellow solid. LCMS (Method A): 3.96 min; m/z: 710.3 $[M+H]^+$.

Step 6: 3-{2-[(1S)-1-(4-fluorophenyl)ethoxy]-4-(2,2,2-trifluoroethanesulfonamido) phenyl}-5-[(pyrazin-2-yl)amino]-1H-pyrazole-4-carboxamide (Compound 244)

A mixture of 3-{2-[(1S)-1-(4-fluorophenyl)ethoxy]-4-(2,2,2-trifluoroethane-sulfonamido)phenyl}-5-[(pyrazin-2-yl) amino]-1-{[2-(trimethylsilyl)ethoxy]methyl}-1H-pyrazole-4-carboxamide (100 mg, 140 μmol) in DCM:TFA (10:1, 11 mL) was stirred at RT for 16 h. The reaction mixture was neutralized with $NH_4OH$ and then diluted with $H_2O$ (20 mL) and extracted with DCM (3×30 mL). The combined organic layers were washed (brine), dried ($Na_2SO_4$) and concentrated to afford the title compound (45 mg, 55%) as a yellow solid. LCMS (Method A): 3.44 min; m/z: 580.1 $[M+H]^+$. $^1H$ NMR (400 MHz, DMSO-$d_6$): 12.84 (s, 1H), 10.72 (s, 1H), 9.77 (s, 1H), 9.34 (s, 1H), 8.24 (t, J=0.8 Hz, 1H), 8.13 (d, J=2.8 Hz, 1H), 7.36 (m, 4H), 7.14 (t, J=8.8 Hz, 2H), 6.87 (d, J=10.4 Hz, 2H), 5.69 (s, 1H), 5.41 (s, 1H), 4.47 (s, 2H), 1.45 (s, 3H).

Compound 243

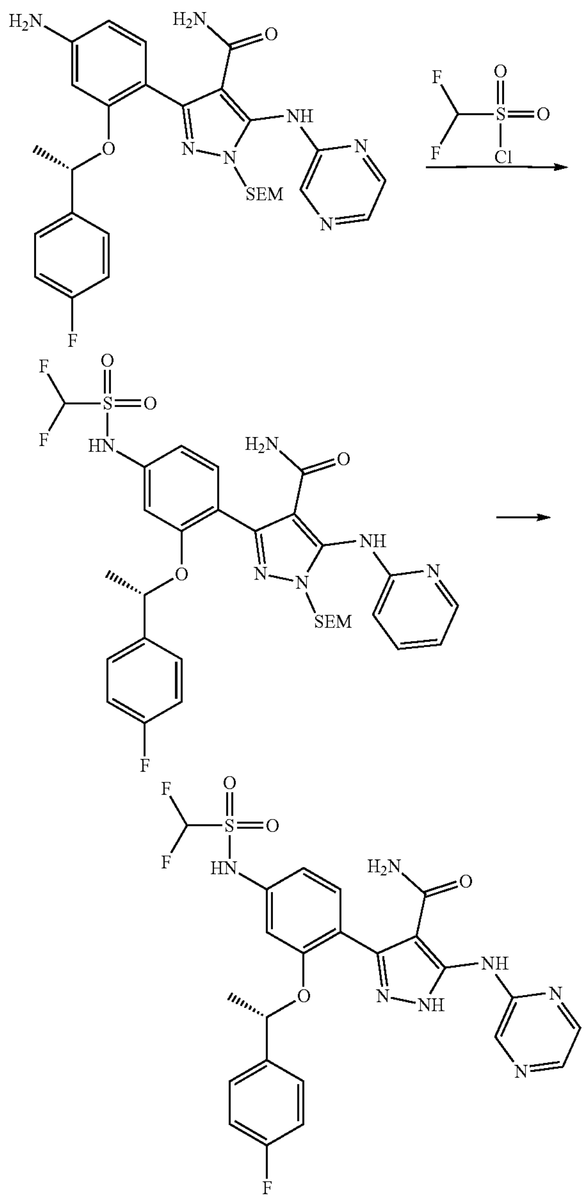

Step 1: 3-[4-(difluoromethanesulfonamido)-2-[(1S)-1-(4-fluorophenyl)ethoxy]phenyl]-5-[(pyridin-2-yl)amino]-1-{[2-(trimethylsilyl)ethoxy]methyl}-1H-pyrazole-4-carboxamide A mixture of 3-{2-[(1S)-1-(4-fluorophenyl)ethoxy]-4-nitrophenyl}-5-[(pyrazin-2-yl)amino]-1-{[2-(trimethylsilyl)ethoxy]methyl}-1H-pyrazole-4-carboxamide (530 mg, 892 μmol), $F_2CHSO_2Cl$ (200 mg, 1.33 mmol) and DCM:pyridine (1:1, 8 mL) was stirred at RT. After 16 h, the reaction mixture was diluted with $H_2O$ (30 mL) and extracted with EtOAc (3x30 mL). The combined organic layers were washed (brine), dried ($Na_2SO_4$) and concentrated under reduced pressure. The crude residue was purified by silica gel column chromatography (DCM:MeOH, 20:1) to afford the title product (150 mg, 25%) as a yellow solid. LCMS (Method A): 3.91 min; m/z: 678.2 $[M+H]^+$.

Step 2: 3-[4-(difluoromethanesulfonamido)-2-[(1S)-1-(4-fluorophenyl)ethoxy]phenyl]-5-[(pyrazin-2-yl)amino]-1H-pyrazole-4-carboxamide (Compound 243)

A mixture of 3-[4-(difluoromethanesulfonamido)-2-[(1S)-1-(4-fluorophenyl)ethoxy]phenyl]-5-[(pyridin-2-yl)amino]-1-{[2-(trimethylsilyl)ethoxy]methyl}-1H-pyrazole-4-carboxamide (90 mg, 132 μmol) in DCM:TFA (9:1, 10 mL) was stirred at RT for 16 h. The reaction mixture was neutralized to pH 7-8 with $NH_4OH$ then diluted with $H_2O$ (20 mL) and extracted with DCM (3x30 mL). The combined organic layers were washed (brine), dried ($Na_2SO_4$), and then concentrated to afford the title product (30 mg, 42%) as a yellow solid. LCMS (Method A): 3.39 min; m/z: 548.2 $[M+H]^+$. $^1H$ NMR (400 MHz, DMSO-$d_6$): 12.86 (s, 1H), 11.21 (s, 1H), 9.72 (s, 1H), 9.32 (s, 1H), 8.23 (s, 1H), 8.12 (d, J=2.8 Hz, 1H), 7.35 (t, J=6.0 Hz, 3H), 7.14 (t, J=9.2 Hz, 3H), 6.91 (t, J=8.0 Hz, 2H), 5.66 (br s, 1H), 5.38 (q, J=6.0 Hz, 1H), 1.44 (s, 3H).

Compound 19

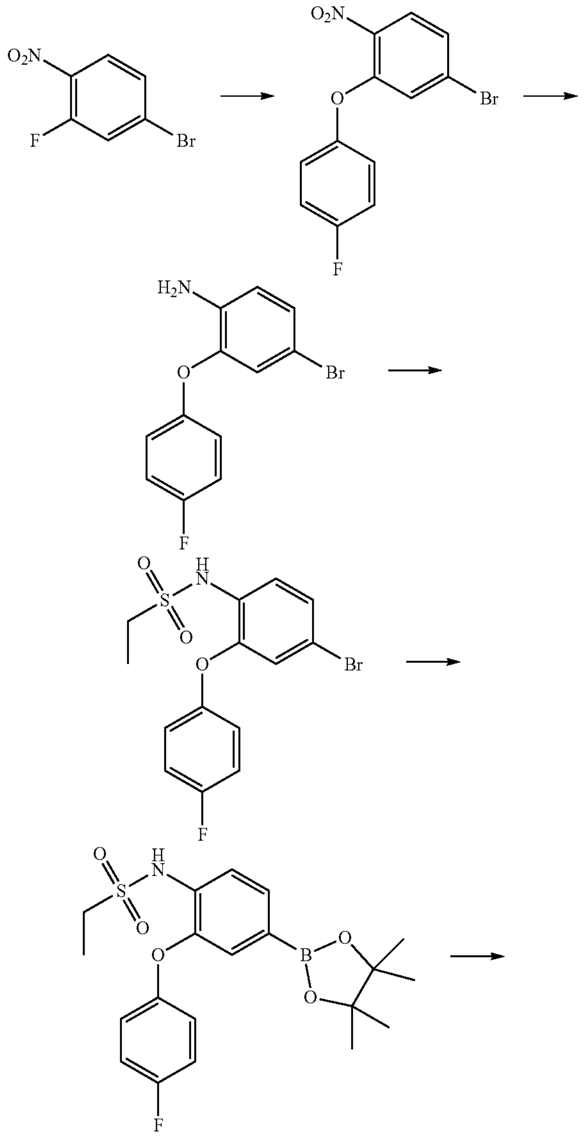

-continued

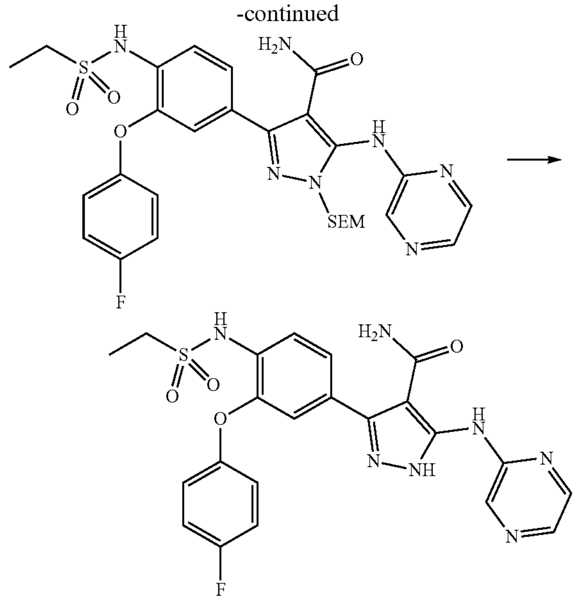

Step 1: 4-bromo-2-(4-fluorophenoxy)-1-nitrobenzene

A mixture of 4-bromo-2-fluoro-1-nitrobenzene (10 g, 45.4 mmol), 4-fluorophenol (6.09 g, 54.4 mmol), and $K_2CO_3$ (18.7 g, 136 mmol) in acetone (100 mL) was stirred at 80° C. overnight. The mixture was filtered, concentrated under reduced pressure and the crude residue was purified by silica gel column chromatography (PE:EtOAc, 10:1) to afford the title product (12 g, 99%) as a yellow oil.

Step 2: 4-bromo-2-(4-fluorophenoxy)aniline

A mixture of 4-bromo-2-(4-fluorophenoxy)-1-nitrobenzene (14 g, 44.8 mmol), sat. aq. $NH_4Cl$ (50 mL) and Zn dust (14.6 g, 224 mmol) in MeOH (50 mL) was stirred at 60° C. overnight. The mixture was filtered, and the filtrate concentrated under reduced pressure to afford the title product (13 g, >100%) as a yellow oil. LCMS (Method A): 4.13 min; m/z:

282.0 $[M+H]^+$.

Step 3: N-(4-bromo-2-(4-fluorophenoxy)phenyl) ethanesulfonamide

A mixture of 4-bromo-2-(4-fluorophenoxy)aniline (13 g, 46.0 mmol), $EtSO_2Cl$ (8.87 g, 69.0 mmol) and pyridine (10.9 g, 138 mmol) in $CHCl_3$ (20 mL) was stirred at RT overnight. The mixture was concentrated under reduced pressure and the crude residue was purified by silica gel column chromatography (PE:EtOAc, 10:1) to afford the title product (8 g, 46%) as a yellow solid.

Step 4: N-(2-(4-fluorophenoxy)-4-(4,4,5,5-tetramethyl-1,3,2-dioxaborolan-2-yl)phenyl) ethanesulfonamide A mixture of N-(4-bromo-2-(4-fluorophenoxy)phenyl) ethanesulfonamide (1 g, 2.67 mmol), $B_2pin_2$ (744 mg, 2.93 mmol), $Pd(dppf)Cl_2$ (217 mg, 267 μmol) and KOAc (524 mg, 5.34 mmol) in degassed 1,4-dioxane (10 mL) was stirred at 100° C. overnight. The mixture was concentrated under reduced pressure and the crude residue was purified by silica gel column chromatography (PE:EtOAc, 10:1) to afford the title product (500 mg, 44%) as a white solid. LCMS (Method A): 4.50 min; m/z: 422.1 $[M+H]^+$.

Step 5: 3-(4-(ethylsulfonamido)-3-(4-fluorophenoxy)phenyl)-5-(pyrazin-2-ylamino)-1-((2-(trimethylsilyl)ethoxy)methyl)-1H-pyrazole-4-carboxamide A mixture of 3-bromo-5-[(pyrazin-2-yl)amino]-1-{[2-(trimethylsilyl)ethoxy]methyl}-1H-pyrazole-4-carboxamide (150 mg, 362 μmol), N-(2-(4-fluorophenoxy)-4-(4,4,5,5-tetramethyl-1,3,2-dioxaborolan-2-yl)phenyl) ethanesulfonamide (228 mg, 543 μmol), $Pd(dppf)Cl_2$ (29.5 mg, 36.2 μmol) and $Na_2CO_3$ (114 mg, 1.08 mmol) in degassed 80% aq. 1,4-dioxane (5 mL) was stirred at 100° C. overnight. The mixture was concentrated under reduced pressure and the crude residue was purified by prep-TLC (DCM:MeOH, 10:1) to afford the title product (500 mg, 44%) as a white solid. LCMS (Method A): 3.95 min; m/z: 628.2 $[M+H]^+$.

Step 6: 3-(4-(ethylsulfonamido)-3-(4-fluorophenoxy)phenyl)-5-(pyrazin-2-ylamino)-1H-pyrazole-4-carboxamide (Compound 19)

A solution of 3-(4-(ethylsulfonamido)-3-(4-fluorophenoxy)phenyl)-5-(pyrazin-2-ylamino) ((2-(trimethylsilyl) ethoxy)methyl)-1H-pyrazole-4-carboxamide (30 mg, 47.7 μmol) in TFA (3 mL) and DCM (3 mL) was stirred at 30° C. for 2 h. The mixture was neutralized to pH 7-8 with sat. aq. $Na_2CO_3$ solution and then extracted with EtOAc (3×50 mL). The combined organic layers were washed with brine, dried ($Na_2SO_4$) and concentrated under reduced pressure. The crude residue was purified by prep-TLC (DCM:MeOH, 1:1) to afford the title product (8.4 mg, 35%) as a yellow solid. LCMS (Method A): 3.25 min; m/z: 498.1 $[M+H]^+$. $^1H$ NMR (400 MHz, DMSO-$d_6$): 9.64 (s, 1H), 9.25 (s, 1H), 8.30 (s, 1H), 8.19 (d, J=2.8 Hz, 1H), 7.68 (d, J=4.8 Hz, 1H), 7.46 (d, J=7.2 Hz, 1H), 7.37 (t, J=2.4 Hz, 2H), 7.26 (br s, 2H), 7.17 (d, J=2.0 1H), 3.25 (br s, 2H), 1.31 (br s, 3H).

Compound 13

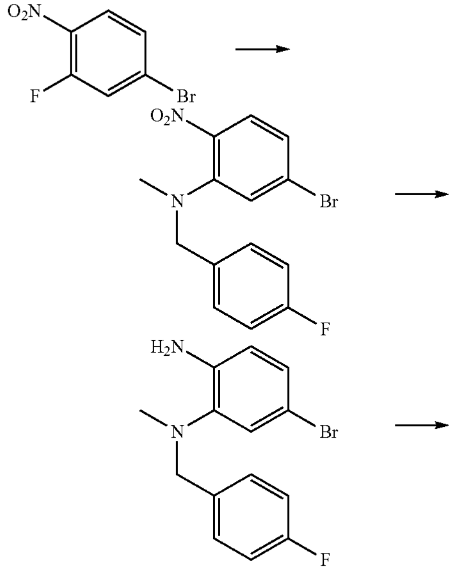

-continued

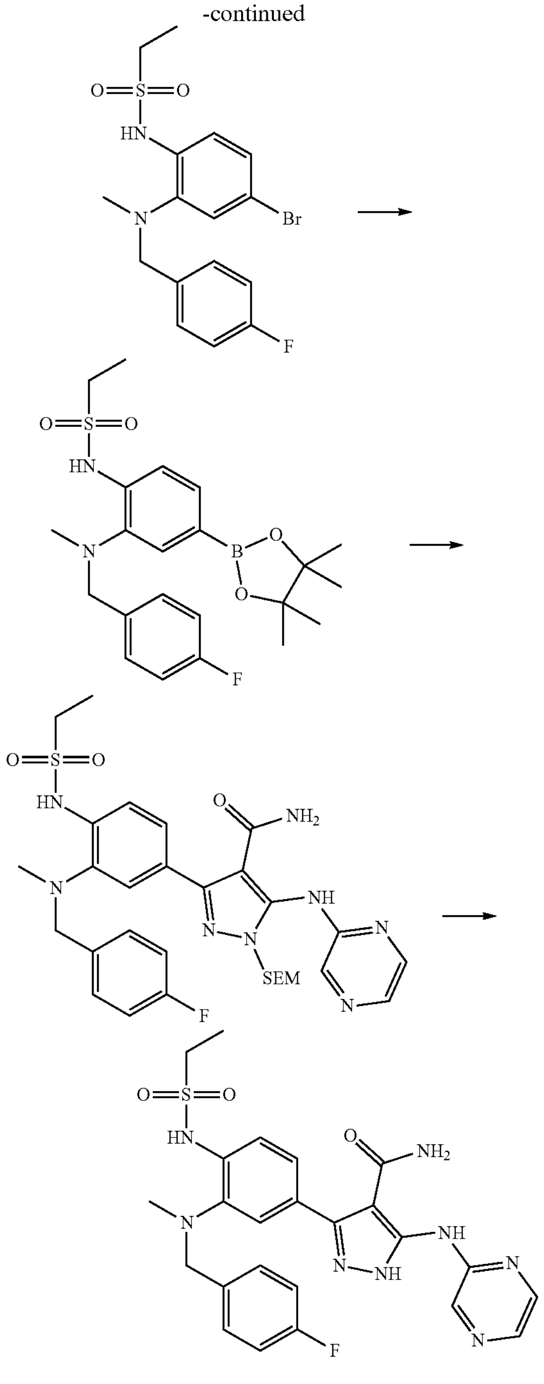

Step 1: 5-bromo-N-[(4-fluorophenyl)methyl]-N-methyl-2-nitroaniline

A mixture of 4-bromo-2-fluoro-1-nitrobenzene (100 mg, 0.4545 mmol), [(4-fluorophenyl)methyl](methyl)amine (69.5 mg, 0.499 mmol) and $K_2CO_3$ (125 mg, 0.909 mmol) in 60% aq. EtOAc (2.5 mL) was stirred at 85° C. for 16 hours. The mixture was acidified to pH 5-6 with 1.2 M aq. HCl and then extracted with EtOAc (3×20 mL). The combined organics were washed with brine, dried ($Na_2SO_4$) and concentrated under reduced pressure to afford the title product (100 mg, 65%) as a yellow solid. $^1$H NMR (400 MHz, DMSO-$d_6$): 7.73 (d, J=8.8 Hz, 1H), 7.39 (d, J=2.0 Hz, 1H), 7.29 (m, 2H), 7.18 (m, 2H), 7.11 (m, 1H), 4.41 (s, 2H), 2.71 (s, 3H).

Step 2: 5-bromo-N1-(4-fluorobenzyl)-N1-methylbenzene-1,2-diamine

A mixture of 5-bromo-N-[(4-fluorophenyl)methyl]-N-methyl-2-nitroaniline (4.3 g, 12.6 mmol), sat. aq. $NH_4Cl$ (2 mL) and Zn dust (4.09 g, 63.0 mmol) in MeOH (20 mL) was stirred at 60° C. overnight. The mixture was filtered, and the filtrate concentrated under reduced pressure. The residue was dissolved in EtOAc (50 mL), washed with $H_2O$ (2×20 mL) and dried over $Na_2SO_4$. The organic layer was concentrated under reduced pressure to afford the title product (3.67 g, 94%) as a black oil. $^1$H NMR (400 MHz, DMSO-$d_6$): 7.34 (m, 2H), 7.12 (m, 2H), 6.97 (d, J=2.4 Hz, 1H), 6.92 (m, 1H), 6.64 (d, J=8.4 Hz, 1H), 5.02 (s, 2H), 3.96 (s, 2H), 2.45 (s, 3H).

Step 3: N-(4-bromo-2-{[(4-fluorophenyl)methyl](methyl)amino}phenyl)ethane-1-sulfonamide A mixture of 5-bromo-N1-[(4-fluorophenyl)methyl]-N1-methylbenzene-1,2-diamine (3.67 g, 11.8 mmol), $EtO_2Cl$ (2.27 g, 17.7 mmol) and pyridine (10 mL) in $CHCl_3$ (10 mL) was stirred at RT overnight. The reaction mixture was concentrated under reduced pressure and the crude residue was purified by silica gel column chromatography (PE:EtOAc, 3:1) to afford the title product (4 g, 85%) as a black oil. LCMS (Method A): 3.35 min; m/z: 402.8 $[M+H]^+$. $^1$H NMR (400 MHz, DMSO-$d_6$): 8.62 (s, 1H), 7.36 (m, 2H), 7.30 (d, J=2.0 Hz, 1H), 7.25 (m, 2H), 7.12 (t, J=17.6 Hz, 2H), 4.08 (s, 2H), 3.22 (m, 2H), 2.55 (s, 3H), 1.22 (t, J=14.8 Hz, 3H).

Step 4: N-(2-((4-fluorobenzyl)(methyl)amino)-4-(4,4,5,5-tetramethyl-1,3,2-dioxaborolan-2-yl)phenyl)ethanesulfonamide A mixture of N-(4-bromo-2-{[(4-fluorophenyl)methyl](methyl)amino}phenyl)ethane-1-sulfonamide (800 mg, 1.99 mmol), $B_2pin_2$ (756 mg, 2.98 mmol), Pd(dppf)$Cl_2$ (145 mg, 199 µmol) and KOAc (585 mg, 5.97 mmol) in degassed 1,4-dioxane (10 mL) was heated at 100° C. overnight. The mixture was filtered concentrated under reduced pressure and the crude residue purified by silica gel column chromatography (PE:EtOAc, 10:1) to afford the title product (800 mg, 89%) as a yellow liquid. LCMS (Method A): 4.69 min; m/z: 449.2 $[M+H]^+$. $^1$H NMR (400 MHz, DMSO-$d_6$): 7.50 (s, 1H), 7.39 (m, 4H), 7.13 (t, J=18.0 Hz, 2H), 3.99 (s, 2H), 3.24 (m, 2H), 3.16 (s, 3H), 1.28 (s, 12H), 1.19 (m, 3H).

Step 5: 3-(4-(ethylsulfonamido)-3-((4-fluorobenzyl)(methyl)amino)phenyl)-5-(pyrazin-2-ylamino)-14(2-(trimethylsilyl)ethoxy)methyl)-1H-pyrazole-4-carboxamide A mixture of N-(2-{[(4-fluorophenyl)methyl](methyl)amino}-4-(4,4,5,5-tetramethyl-1,3,2-dioxaborolan-2-yl)phenyl)ethane-1-sulfonamide (300 mg, 0.67 mmol), 3-bromo-5-[(pyrazin-2-yl)amino]-1-{[2-(trimethylsilyl)ethoxy]methyl}-1H-pyrazole-4-carboxamide (276 mg, 669 µmol), Pd(dppf)$Cl_2$ (48.9 mg, 66.9 µmol) and $Na_2CO_3$ (211 mg, 2.00 mmol) in degassed 80% aq. 1,4-dioxane (12.5 mL) was stirred at 100° C. overnight. The reaction mixture was diluted with $H_2O$ (20 mL) and then extracted with EtOAc (3×30 mL). The combined organics were washed with brine, dried ($Na_2SO_4$) and concentrated under reduced pressure. The crude residue was purified by silica gel column chromatography (PE:EtOAc, 3:1) to afford the title product (450 mg, >100%) as a brown liquid. LCMS (Method A): 4.16 min; m/z: 655.2 $[M+H]^+$.

Step 6: 3-(4-(ethylsulfonamido)-3-((4-fluorobenzyl)(methyl)amino)phenyl)-5-(pyrazin-2-ylamino)-1H-pyrazole-4-carboxamide (Compound 13)

A solution of 3-(4-ethanesulfonamido-3-{[(4-fluorophenyl)methyl](methyl)amino}phenyl)-5-[(pyrazin-2-yl)amino]-1-{[2-(trimethylsilyl)ethoxy]methyl}-1H-pyrazole-4-carboxamide (200 mg, 305 μmol) in TFA (3 mL) and DCM (3 mL) was stirred at RT for 2 h. The reaction mixture was neutralized to pH 7-8 with sat. aq. $Na_2CO_3$ solution and then extracted with DCM (3×50 mL). The combined organics were dried ($Na_2SO_4$), concentrated under reduced pressure and the crude residue purified by prep-TLC (DCM:MeOH, 20:1) to afford the title product (40 mg, 25%) as a yellow solid. LCMS (Method A): 3.62 min; m/z: 525.1 $[M+H]^+$. $^1H$ NMR (400 MHz, DMSO-$d_6$): 12.98 (s, 1H), 9.68 (s, 1H), 9.20 (s, 1H), 8.67 (s, 1H), 8.22-8.21 (m, 1H), 8.13 (d, J=4.0 Hz, 1H), 7.50-7.46 (m, 2H), 7.42-7.38 (m, 2H), 7.33-7.31 (m, 1H), 7.13 (t, J=17.6 Hz, 2H), 4.09 (s, 2H), 3.3-3.28 (m, 1H), 2.58 (s, 3H), 1.26-1.24 (m, 3H).

Compound 238

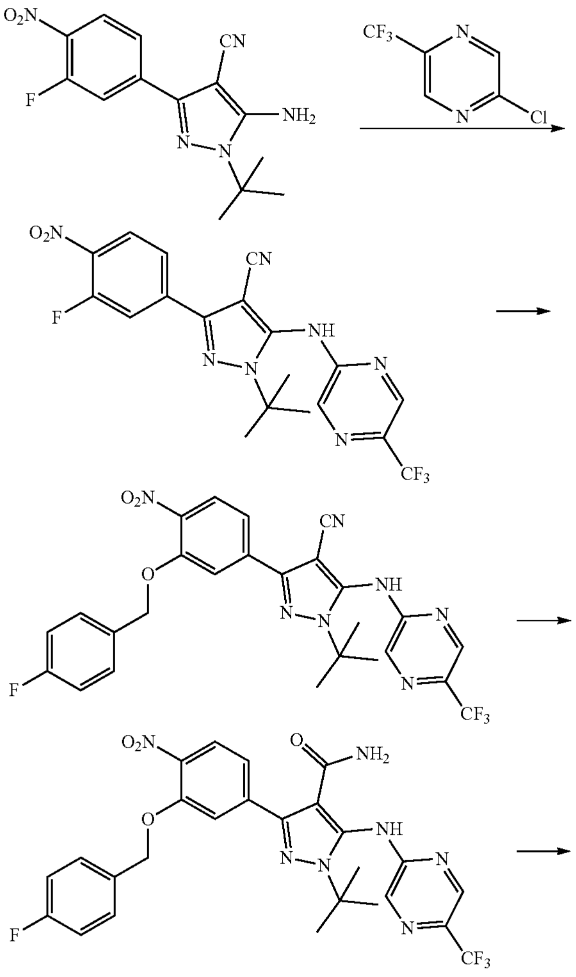

-continued

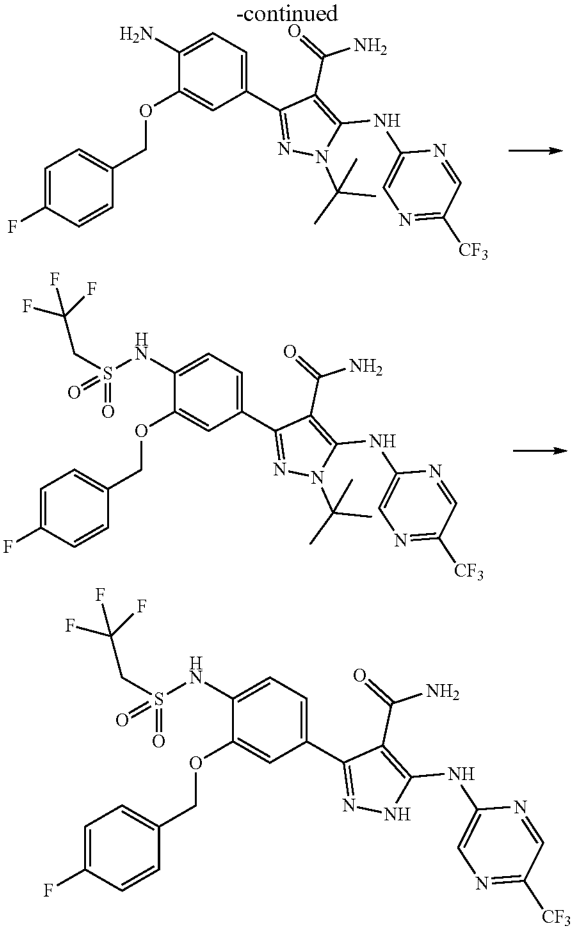

Step 1: 1-tert-butyl-3-(3-fluoro-4-nitrophenyl)-5-{[5-(trifluoromethyl)pyrazin-2-yl]amino}-1H-pyrazole-4-carbonitrile A mixture of 5-amino-1-tert-butyl-3-(3-fluoro-4-nitrophenyl)-1H-pyrazole-4-carbonitrile (2.20 g, 7.25 mmol), 2-chloro-5-(trifluoromethyl)pyrazine (1.10 g, 6.02 mmol), $Pd_2(dba)_3$ (551 mg, 602 μmol), Xantphos (692 mg, 1.20 mmol) and $Cs_2CO_3$ (5.86 g, 18.0 mmol) in 1,4-dioxane (120 mL) was stirred at 100° C. under $N_2$. After 16 h, the solvent was concentrated and the residue was purified by silica gel column chromatography (PE:EtOAc, 5:1) to afford the title product (1.70 g, 63%) as a yellow solid. LCMS (Method A): 4.32 min; m/z: 450.1 $[M+H]^+$.

Step 2: 1-tert-butyl-3-{3-[(4-fluorophenyl)methoxy]-4-nitrophenyl}-5-{[5-(trifluoromethyl)pyrazin-2-yl]amino}-1H-pyrazole-4-carbonitrile To a solution of (4-fluorophenyl)methanol (238 mg, 1.89 mmol) in THF (30 mL) at 0° C., was added NaH (136 mg, 5.67 mmol). After 10 min, 1-tert-butyl-3-(3-fluoro-4-nitrophenyl)-5-{[5-(trifluoromethyl)pyrazin-2-yl]amino}-1H-pyrazole-4-carbonitrile (850 mg, 1.89 mmol) was added and the resulting mixture was stirred at RT for 16 h. The solvent was removed by concentration and the residue was diluted with EtOAc (100 mL). The organic layer was washed with $H_2O$ (3×100 mL), dried ($Na_2SO_4$) and then concentrated under reduced pressure to afford the title product (1.30 g, >100%) as a yellow solid. LCMS (Method A): 4.52 min; m/z: 556.2 $[M+H]^+$.

Step 3: 1-tert-butyl-3-{3-[(4-fluorophenyl) methoxy]-4-nitrophenyl}-5-{[5-(trifluoromethyl) pyrazin-2-yl]amino}-1H-pyrazole-4-carboxamide A mixture of 1-tert-butyl-3-{3-[(4-fluorophenyl) methoxy]-4-nitrophenyl}-5-{[5-(trifluoromethyl)pyrazin-2-yl]amino}-1H-pyrazole-4-carbonitrile (1.2 g, 2.16 mmol) and Ghaffar-Parkins catalyst (92.2 mg, 216 μmol) in 50% aq. 1,4-dioxane (40 mL) was stirred at 100° C. After 16 h, the reaction mixture was diluted with $H_2O$ (50 mL) and then extracted with EtOAc (3×50 mL). The combined organic layer was washed (brine), dried ($Na_2SO_4$) and then concentrated under reduced pressure. The crude residue was purified by silica gel column chromatography (PE:EtOAc, 1:1) to afford the title product (450 mg, 36%) as a yellow solid. LCMS (Method A): 4.15 min; m/z: 574.1 $[M+H]^+$.

Step 4: 3-{4-amino-3-[(4-fluorophenyl)methoxy] phenyl}-1-tert-butyl-5-{[5-(trifluoromethyl)pyrazin-2-yl]amino}-1H-pyrazole-4-carboxamide A mixture of 1-tert-butyl-3-{3-[(4-fluorophenyl) methoxy]-4-nitrophenyl}-5-{[5-(trifluoromethyl)pyrazin-2-yl]amino}-1H-pyrazole-4-carboxamide (380 mg, 662 μmol), Zn powder (215 mg, 3.30 mmol), sat. $NH_4Cl$ (6 mL) and MeOH (30 mL) was stirred at 60° C. After 16 h, the mixture was filtered and the filtrate concentrated. The residue was diluted with $H_2O$ (100 mL) and then extracted with EtOAc (200 mL). The organic layer was washed (brine), dried ($Na_2SO_4$) and concentrated under reduced pressure. The crude residue was purified by silica gel column chromatography (PE:EtOAc, 1:1) to afford the title product (200 mg, 55%) as a yellow solid. LCMS (Method A): 3.83 min; m/z: 544.2 $[M+H]^+$.

Step 5: 1-tert-butyl-3-{3-[(4-fluorophenyl) methoxy]-4-(2,2,2-trifluoroethanesulfonamido)phenyl}-5-{[5-(trifluoromethyl)pyrazin-2-yl]amino}-1H-pyrazole-4-carboxamide To a solution of 3-{4-amino-3-[(4-fluorophenyl)methoxy] phenyl}-1-tert-butyl-5-{[5-(trifluoromethyl)pyrazin-2-yl] amino}-1H-pyrazole-4-carboxamide (100 mg, 183 μmol) and pyridine (43.4 mg, 549 μmol) in $CHCl_3$ (20 mL) was added 2,2,2-trifluoroethane-1-sulfonyl chloride (50.0 mg, 274 μmol). The mixture was stirred at RT for 16 h and then concentrated under reduced pressure. The crude residue was purified by prep-TLC (DCM:MeOH, 20:1) to afford the title product (40 mg, 31%) as a yellow solid. LCMS (Method A): 4.02 min; 690.1 $[M+H]^+$.

Step 6: 3-{3-[(4-fluorophenyl)methoxy]-4-(2,2,2-trifluoroethanesulfonamido)phenyl}-5-{[5-(trifluoromethyl)pyrazin-2-yl]amino}-1H-pyrazole-4-carboxamide (Compound 238)

A mixture of 1-tert-butyl-3-{3-[(4-fluorophenyl) methoxy]-4-(2,2,2-trifluoroethanesulfonamido)phenyl}-5-{[5-(trifluoromethyl)pyrazin-2-yl]amino}-1H-pyrazole-4-carboxamide (60 mg, 87.0 μmol) in DCM:TFA (1:1, 4 mL) was stirred at RT. After 16 h, the mixture was concentrated and the residue neutralized to pH 7-8 with sat. $Na_2CO_3$. The residue was purified by prep-TLC (DCM:MeOH, 20:1) to afford the title compound (10 mg, 18%) as a white solid. LCMS (Method A): 3.85 min; 634.1 $[M+H]^+$. $^1$H NMR (400 MHz, DMSO-$d_6$): 13.24 (s, 1H), 10.13 (s, 1H), 9.93 (s, 1H), 9.18 (s, 1H), 8.65 (s, 1H), 7.60 (s, 2H), 7.49-7.42 (m, 2H), 7.25-7.21 (m, 3H), 5.19 (s, 2H), 4.33 (t, J=8.8 Hz, 2H).

Compound 246

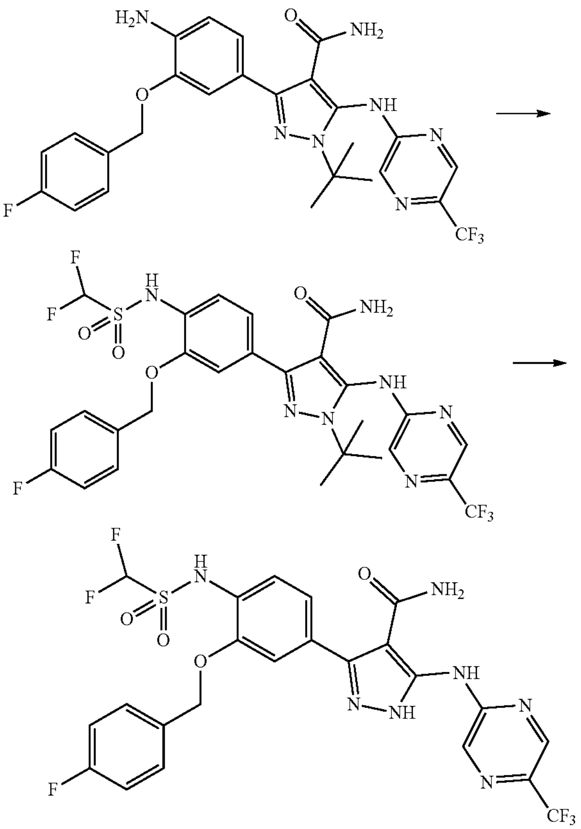

Step 1: 1-tert-butyl-3-[4-(difluoromethanesulfonamido)-3-[(4-fluorophenyl)methoxy]phenyl]-5-{[5-(trifluoromethyl)pyrazin-2-yl]amino}-1H-pyrazole-4-carboxamide To a solution of 3-{4-amino-3-[(4-fluorophenyl)methoxy] phenyl}-1-tert-butyl-5-{[5-(trifluoromethyl)pyrazin-2-yl] amino}-1H-pyrazole-4-carboxamide (100 mg, 183 μmol) and pyridine (43.4 mg, 549 μmol) in $CHCl_3$ (20 mL) was added $CF_2HSO_2Cl$ (41.2 mg, 274 μmol). The mixture was stirred at RT for 16 h, and then concentrated reduced pressure. The crude residue was purified by prep-TLC (DCM:MeOH, 20:1) to afford the title product (30 mg, 25%) as a yellow solid. LCMS (Method A): 3.97 min; 658.1 $[M+H]^+$.

Step 2: 3-[4-(difluoromethanesulfonamido)-3-[(4-fluorophenyl)methoxy]phenyl]-5-{[5-(trifluoromethyl)pyrazin-2-yl]amino}-1H-pyrazole-4-carboxamide (Compound 246)

A mixture of 1-tert-butyl-3-[4-(difluoromethanesulfonamido)-3-[(4-fluorophenyl)methoxy]phenyl]-5-{[5-(trifluoromethyl)pyrazin-2-yl]amino}-1H-pyrazole-4-carboxamide (40 mg, 60.8 μmol) in DCM:TFA (1:1, 4 mL) was stirred at RT. After 16 h, the mixture was concentrated and the residue neutralized to pH 7-8 with sat. $Na_2CO_3$. The crude residue was purified by prep-TLC (DCM:MeOH, 20:1) to afford the title compound (6.0 mg, 16%) as a white solid. LCMS (Method A): 3.79 min; 602.1 $[M+H]^+$. $^1H$ NMR (400 MHz, DMSO-$d_6$) 13.45 (s, 1H), 10.56 (s, 1H), 10.12 (s, 1H), 9.06 (s, 1H), 8.63 (s, 1H), 7.61 (q, J=4.8 Hz, 2H), 7.53 (s, 2H), 7.38 (d, J=8.0 Hz, 1H), 7.26-7.22 (m, 3H), 6.94 (t, J=52.8 Hz, 1H), 5.22 (s, 2H).

Compound 234

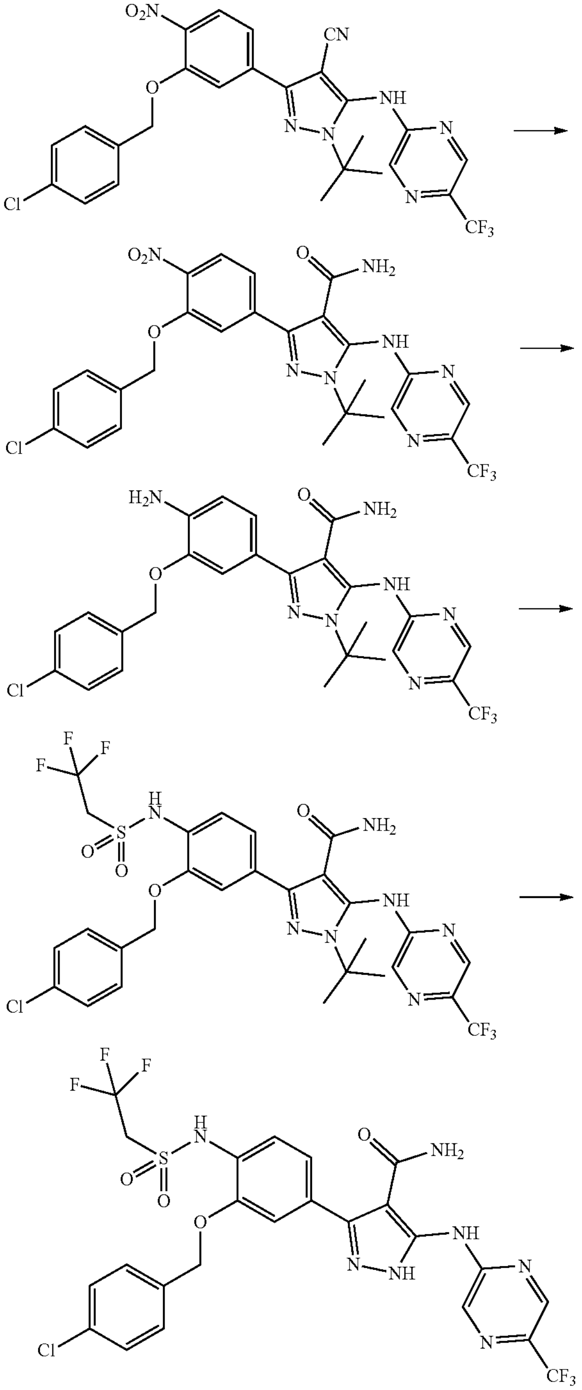

Step 1: 1-tert-butyl-3-{3-[(4-chlorophenyl)methoxy]-4-nitrophenyl}-5-{[5-(trifluoromethyl)pyrazin-2-yl]amino}-1H-pyrazole-4-carboxamide A mixture of 1-tert-butyl-3-{3-[(4-chlorophenyl)methoxy]-4-nitrophenyl}-5-{[5-(trifluoromethyl)pyrazin-2-yl]amino}-1H-pyrazole-4-carbonitrile (400 mg, 21.9 mmol) and Ghaffar-Parkins catalyst (150 mg, 351 μmol) in 50% aq. 1,4-dioxane (100 mL) was stirred at 100° C. After 16 h, the mixture was concentrated and the residue diluted with $H_2O$ (50 mL) and then extracted with EtOAc (3×50 mL). The combined organic layers were dried ($Na_2SO_4$) and then concentrated under reduced pressure to afford the title product (400 mg, 100%). LCMS (Method A): 4.28 min; m/z: 590.2 $[M+H]^+$.

Step 2: 3-{4-amino-3-[(4-chlorophenyl)methoxy]phenyl}-1-tert-butyl-5-{[5-(trifluoromethyl)pyrazin-2-yl]amino}-1H-pyrazole-4-carboxamide A mixture of 1-tert-butyl-3-{3-[(4-chlorophenyl)methoxy]-4-nitrophenyl}-5-{[5-(trifluoromethyl)pyrazin-2-yl]amino}-1H-pyrazole-4-carboxamide (300 mg, 508 μmol), Zn powder (165 mg, 2.53 mmol), sat. $NH_4Cl$ (5 mL) and MeOH (15 mL) was stirred at 60° C. under $N_2$. After 16 h, the reaction mixture was filtered and the filtrate was concentrated under reduced pressure. The crude residue was purified by silica gel column chromatography (DCM: MeOH, 30:1) to afford to the title product (200 mg, 70%) as a yellow solid. LCMS (Method A): 3.99 min; m/z: 560.1 $[M+H]^+$.

Step 3: 1-(tert-butyl)-3-(3-((4-chlorobenzyl)oxy)-4-((2,2,2-trifluoroethyl)sulfonamido)phenyl)-5-((5-(trifluoromethyl)pyrazin-2-yl)amino)-1H-pyrazole-4-carboxamide A solution of 3-{4-amino-3-[(4-chlorophenyl)methoxy]phenyl}-1-tert-butyl-5-{[5-(trifluoromethyl)pyrazin-2-yl]amino}-1H-pyrazole-4-carboxamide (50 mg, 89.2 μmol) and 2,2,2-trifluoroethane-1-sulfonyl chloride (16.2 mg, 89.2 μmol) in $CHCl_3$:pyridine (1:1, 6 mL) was stirred at RT. After 16 h, the reaction mixture was concentrated and the residue diluted with $H_2O$ (30 mL) and then extracted with EtOAc (2×20 mL). The combined organic layers were dried ($Na_2SO_4$) and then concentrated under reduced pressure. The crude residue was purified by prep-TLC (DCM:MeOH, 15:1) to afford the title product (25 mg, 50%) as a yellow solid. LCMS (Method A): 4.14 min; m/z: 706.1 $[M+H]^+$.

Step 4: 3-{3-[(4-chlorophenyl)methoxy]-4-(2,2,2-trifluoroethanesulfonamido) phenyl}-5-{[5-(trifluoromethyl)pyrazin-2-yl]amino}-1H-pyrazole-4-carboxamide (Compound 234)

A solution of 1-(tert-butyl)-3-(3-((4-chlorobenzyl)wry)-4-((2,2,2-trifluoroethyl)sulfonamido)phenyl)-5-((5-(trifluoromethyl)pyrazin-2-yl)amino)-1H-pyrazole-4-carboxamide (124 mg, 190 μmol) in DCM:TFA (1:1, 10 mL) was stirred at RT. After 16 h, the reaction mixture was concentrated and the residue was neutralized to pH 7-8 with sat. $Na_2CO_3$. The resulting precipitate was collected by filtration and then purified by prep-TLC (DCM:MeOH, 15:1) to afford the title product (10 mg, 20%) as a yellow solid. LCMS (Method A): 3.07 min; m/z: 650.1 $[M+H]^+$. $^1H$ NMR (400 MHz, DMSO-$d_6$): 13.20 (s, 1H), 10.17 (s, 1H), 9.18 (s, 1H), 8.65 (s, 1H), 7.57 (d, J=8.0 Hz, 2H), 7.46 (d, J=8.0 Hz, 2H), 7.40 (d, J=8.4 Hz, 2H), 7.20 (d, J=7.2 Hz, 1H), 5.18 (s, 1H), 4.22 (t, J=9.2 Hz, 2H).

Compound 235

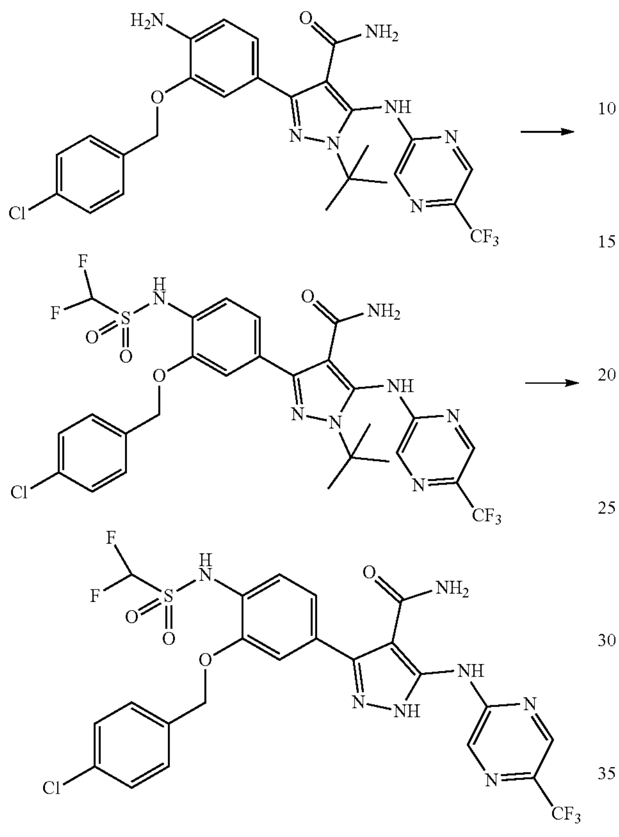

Step 1: 1-(tert-butyl)-3-(3-((4-chlorobenzyl)oxy)-4-((difluoromethyl) sulfonamido)phenyl)-5-((5-(trifluoromethyl)pyrazin-2-yl)amino)-1H-pyrazole-4-carboxamide A solution of 3-{4-amino-3-[(4-chlorophenyl)methoxy]phenyl}-1-tert-butyl-5-{[5-(trifluoromethyl)pyrazin-2-yl]amino}-1H-pyrazole-4-carboxamide (50 mg, 89.2 μmol) and $F_2CHSO_2Cl$ (20.0 mg, 133 μmop in $CHCl_3$:pyridine (1:1, 6 mL) was stirred at RT. After 16 h, the reaction mixture was concentrated and the residue diluted with $H_2O$ (30 mL) and then extracted with EtOAc (2×20 mL). The combined organic layers were dried ($Na_2SO_4$) and concentrated under reduced pressure. The crude residue was purified by prep-TLC (DCM:MeOH, 15:1) to afford the title product (20 mg, 33%) as a yellow solid. LCMS (Method A): 4.05 min; m/z: 674.2 $[M+H]^+$.

Step 2: 3-(3-((4-chlorobenzyl)oxy)-4-((difluoromethyl)sulfonamido)phenyl)-5-((5-(trifluoromethyl)pyrazin-2-yl)amino)-1H-pyrazole-4-carboxamide (Compound 235)

A solution of 1-tert-butyl-3-{3-[(4-chlorophenyl)methoxy]-4-(difluoromethanesulfonamido)phenyl}-5-{[5-(trifluoromethyl)pyrazin-2-yl]amino}-1H-pyrazole-4-carboxamide (20.0 mg, 29.6 μmol) in DCM:TFA (1:1, 10 mL) was stirred at RT. After 16 h, the reaction mixture was concentrated under reduced pressure and the residue neutralized to pH 7-8 with sat. $Na_2CO_3$. The resulting precipitate was collected by filtration and then purified by prep-TLC (DCM:MeOH, 15:1) to afford the title product (6.0 mg, 33%) as a yellow solid. LCMS (Method A): 3.99 min; m/z: 618.1 $[M+H]^+$. $^1H$ NMR (400 MHz, DMSO-$d_6$): 13.38 (s, 1H), 10.60 (s, 1H), 10.11 (s, 1H), 9.09 (s, 1H), 8.65 (s, 2H), 7.69 (d, J=8.4 Hz, 2H), 7.48 (d, J=7.4 Hz, 3H), 7.40 (m, 2H), 7.25 (d, J=8.8 Hz, 2H), 6.65 (s, 1H), 5.23 (s, 2H).

Compound 282

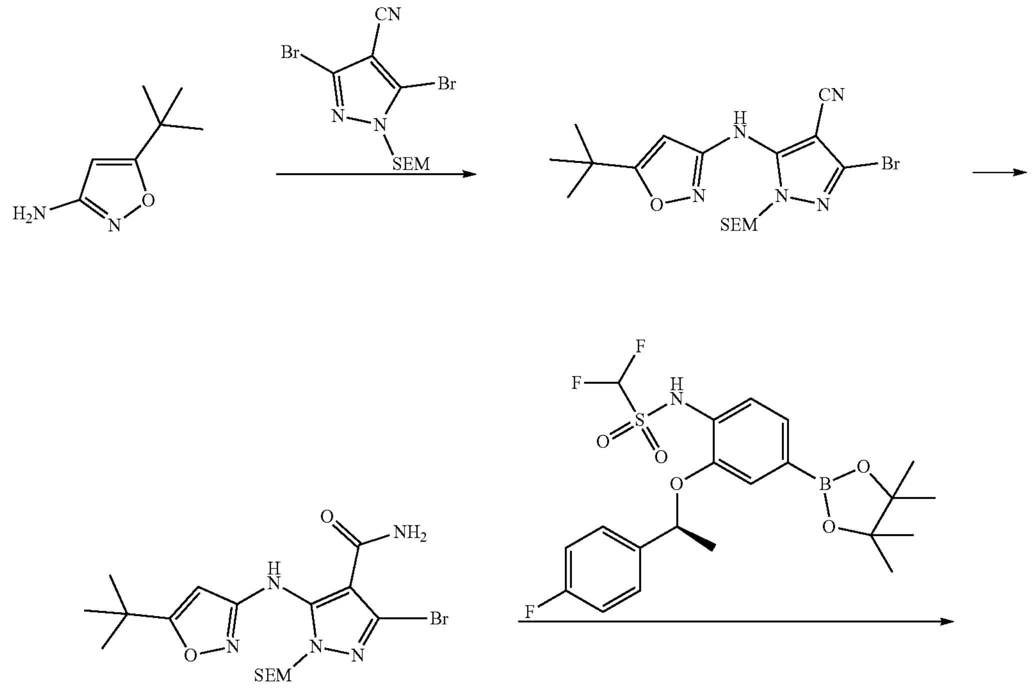

-continued

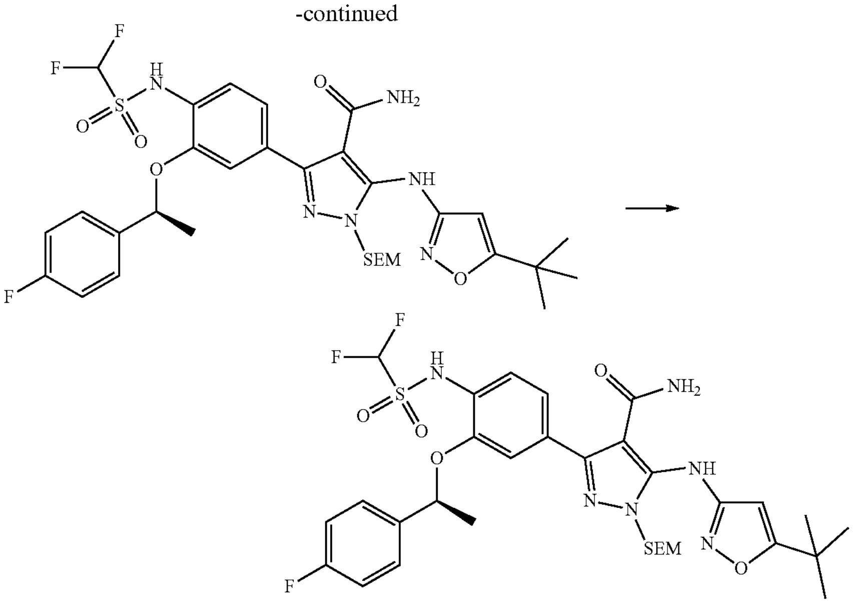

Step 1: 3-bromo-5-[(5-tert-butyl-1,2-oxazol-3-yl) amino]-1-{[2-(trimethylsilyl)ethoxy]methyl}-1H-pyrazole-4-carbonitrile A mixture of 5-tert-butyl-1,2-oxazol-3-amine (500 mg, 3.56 mmol), 3,5-dibromo-1-{[2-(trimethylsilyl)ethoxy] methyl}-1H-pyrazole-4-carbonitrile (1.35 g, 3.56 mmol), $Pd_2(dba)_3$ (325 mg, 356 μmol), Xantphos (411 mg, 712 μmol) and $Cs_2CO_3$ (3.45 g, 10.6 mmol) in degassed 1,4-dioxane (30 mL) was heated at 100° C. under $N_2$ for 14h. The reaction was filtered through a pad of celite and the filtrate was concentrated under reduced pressure. The residue was purified by column chromatography on silica gel (PE:EtOAc, 3:1) to give the title compound (600 mg, 39%) as a yellow solid. $^1H$ NMR (400 MHz, DMSO-$d_6$): 9.99 (s, 1H), 6.04 (d, J=2.3 Hz, 1H), 5.42 (d, J=2.4 Hz, 2H), 3.51 (t, J=7.7 Hz, 2H), 1.28 (d, J=2.3 Hz, 9H), 0.81 (t, J=7.6 Hz, 2H), −0.09 (d, J=2.3 Hz, 10H).

Step 2: 3-bromo-5-((5-(tert-butyl)isoxazol-3-yl) amino)-1-((2-(trimethylsilyl)ethoxy)methyl)-1H-pyrazole-4-carboxamide A mixture of 3-bromo-5-[(5-tert-butyl-1,2-oxazol-3-yl) amino]-1-{[2-(trimethylsilyl)ethoxy]methyl}-1H-pyrazole-4-carbonitrile (1274 mg, 2.88 mmol) and Ghaffar-Parkins catalyst (121 mg, 0.288 mmol) in in 50% aq. 1,4-dioxane (80 mL) was stirred at 100° C. under $N_2$ overnight. The mixture was concentrated under reduced pressure and the residue was purified by column chromatography on silica gel (PE: EtOAc, 4:1 to 1:4) to give the title product (700 mg, 1.52 mmol, 53%) as a yellow solid. $^1H$ NMR (400 MHz, DMSO-$d_6$): 8.93 (s, 1H), 7.41 (s, 1H), 7.07 (s, 1H), 5.80 (d, J=1.5 Hz, 1H), 5.32 (d, J=1.5 Hz, 2H), 3.46 (t, J=8.2 Hz, 2H), 1.23 (d, J=1.6 Hz, 9H), 0.78 (t, J=8.2 Hz, 2H), −0.09 (d, J=1.5 Hz, 9H).

Step 3: 5-[(5-tert-butyl-1,2-oxazol-3-yl)amino]-3-[4-(difluoromethanesulfonamido)-3-[(1S)-1-(4-fluorophenyl)ethoxy]phenyl]-1-{[2-(trimethylsilyl)ethoxy] methyl}-1H-pyrazole-4-carboxamide A mixture of 3-bromo-5-[(5-tert-butyl-1,2-oxazol-3-yl) amino]-1-{[2-(trimethylsilyl)ethoxy]methyl}-1H-pyrazole-4-carboxamide (500 mg, 1090 μmol), 1,1-difluoro-N-{2-[(1S)-1-(4-fluorophenyl)ethoxy]-4-(4,4,5,5-tetramethyl-1,3,2-dioxaborolan-2-yl)phenyl}methanesulfonamide (537 mg, 1140 μmol), Pd(dppf) $Cl_2$ (89 mg, 109 μmol) and $Na_2CO_3$ (231 mg, 2180 μmol) in water (5 mL) and degassed 1,4-dioxane (20 mL) was stirred at 100° C. under microwave for 1 h. The mixture was concentrated under reduced pressure and the residue was purified by column chromatography on silica gel (PE:EtOAc, 4:1 to 1:4) to give the title product (300 mg, 38%) as a yellow solid. LCMS (Method A): 4.47 min; m/z: 723.4 $[M+H]^+$.

Step 4: (S)-5-((5-(tert-butyl)isoxazol-3-yl)amino)-3-(4-((difluoromethyl)sulfonamido)-3-(1-(4-fluorophenyl)ethoxy)phenyl)-1H-pyrazole-4-carboxamide (Compound 282)

A mixture of 5-[(5-tert-butyl-1,2-oxazol-3-yl)amino]-3-[4-(difluoromethanesulfonamido)-3-[(1S)-1-(4-fluorophenyl)ethoxy]phenyl]-1-{[2-(trimethylsilyl)ethoxy]methyl}-1H-pyrazole-4-carboxamide (300 mg, 415 μmol) in TFA (0.5 mL) and dichloromethane (20 mL) was stirred at RT under $N_2$ for 1 h. The reaction mixture was adjusted to pH=8 with sat. aq. $Na_2CO_3$. The mixture was poured into water (5 mL) and the organics were extracted with EtOAc (2×10 mL). The combined organic phases were dried ($Na_2SO_4$) and concentrated under reduced pressure. The residue was purified by prep-TLC (DCM:MeOH, 15:1) to give the title product (58.8 mg, 24%) as a white solid. LCMS (Method A): 4.88 min, m/z 593.2 $[M+H]^+$. $^1H$ NMR (400 MHz, DMSO-$d_6$): 12.72 (s, 1H), 10.53 (s, 1H), 9.14 (s, 1H), 7.58-7.52 (m, 2H), 7.37 (d, J=8.1 Hz, 1H), 7.20-7.13 (m, 2H), 7.06 (d, J=12.5 Hz, 2H), 6.54 (s, 1H), 5.62 (d, J=6.5 Hz, 1H), 1.55 (d, J=6.3 Hz, 3H), 1.29 (s, 9H).

The examples below (Table 23) were synthesized according to procedures described in the previous examples. These compounds and their tautomers, enantiomers, stereoisomers and salts are further preferred embodiments of the present invention.

Further exemplary compounds prepared by the methods similar to those described herein are detailed in Table 24 below.

TABLE 23

| Compound No | Name | Structure | LCMS data | NMR data | SM |
|---|---|---|---|---|---|
| 270 | (S)-3-(4-((difluoromethyl)sulfonamido)-3-(1-(4-fluorophenyl)ethoxy)phenyl)-5-((1,3-dimethyl-1H-pyrazol-4-yl)amino)-1H-pyrazole-4-carboxamide | 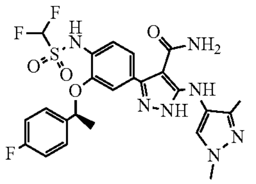 [SMILES: Cc1nn(C)cc1Nc1[nH]nc(-c2ccc(NS(=O)(=O)C(F)F)c(O[C@@H](C)c3ccc(F)cc3)c2)c1C(N)=O] | LCMS (Method A): 3.36 min; m/z 564.1 [M + H]$^+$. | $^1$H NMR (400 MHz, DMSO-$d_6$): 12.44 (s, 1H), 10.52 (s, 1H), 8.09 (s, 1H), 7.71 (d, J = 9.1 Hz, 1H), 7.57 (dd, J = 8.6, 5.6 Hz, 2H), 7.38 (d, J = 7.4 Hz, 1H), 7.18 (t, J = 8.9 Hz, 2H), 7.13-6.86 (m, 3H), 5.67-5.59 (m, 1H), 3.71 (s, 3H), 2.09 (s, 3H), 1.57 (d, J = 6.3 Hz, 3H). | 1,3-dimethyl-1H-pyrazol-4-amine |
| 285 | (S)-3-(4-((difluoromethyl)sulfonamido)-3-(1-(4-fluorophenyl)ethoxy)phenyl)-5-((1,5-dimethyl-1H-pyrazol-4-yl)amino)-1H-pyrazole-4-carboxamide | 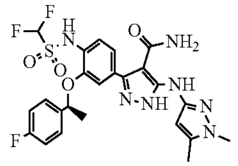 [SMILES: Cc1cc(Nc2[nH]nc(-c3ccc(NS(=O)(=O)C(F)F)c(O[C@@H](C)c4ccc(F)cc4)c3)c2C(N)=O)nn1C] | LCMS (Method A): 3.31 min; m/z 564.1 [M + H]$^+$. | $^1$H NMR (400 MHz, MeOD-$d_4$): 7.50-7.47 (m, 3H), 7.06 (dd, J = 8.0, 4.0 Hz, 4H), 6.80-6.53 (t, J = 5.2 Hz,1H), 5.53 (d, J = 8 Hz, 1H), 3.75 (s, 2H), 2.27 (s, 3H), 1.67 (d, J = 4.0 Hz, 3H). | 1,5-dimethyl-1H-pyrazol-3-amine |
| 286 | (S)-3-(4-((difluoromethyl)sulfonamido)-3-(1-(4-fluorophenyl)ethoxy)phenyl)-5-((1,4-dimethyl-1H-pyrazol-4-yl)amino)-1H-pyrazole-4-carboxamide | 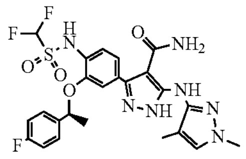 [SMILES: Cc1cn(C)nc1Nc1[nH]nc(-c2ccc(NS(=O)(=O)C(F)F)c(O[C@@H](C)c3ccc(F)cc3)c2)c1C(N)=O] | LCMS (Method A): 4.36 min, m/z 564.2 [M + H]$^+$. | $^1$H NMR (400 MHz, DMSO-$d_6$): 12.24 (s, 1H), 10.49 (s, 1H), 9.21 (s, 1H), 7.59-7.50 (m, 2H), 7.40 (s, 1H), 7.33 (d, J = 8.0 Hz, 1H), 7.16 (t, J = 8.9 Hz, 2H), 7.09-7.01 (m, 2H), 7.00-6.82 (m, 1H), 5.58 (q, J = 6.3 Hz, 1H), 3.72 (s, 3H), 1.92 (s, 3H), 1.56 (d, J = 6.3 Hz, 3H). | 1,4-dimethyl-1H-pyrazol-3-amine |
| 283 | (S)-3-(4-((difluoromethyl)sulfonamido)-3-(1-(4-fluorophenyl)ethoxy)phenyl)-5-((1-methyl-1H-1,2,4-triazol-3-yl)amino)-1H-pyrazole-4-carboxamide | 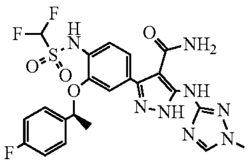 [SMILES: C[C@H](Oc1cc(-c2n[nH]c(Nc3ncn(C)n3)c2C(N)=O)ccc1NS(=O)(=O)C(F)F)c1ccc(F)cc1] | LCMS (Method A): 3.32 min, m/z: 551.1 [M + H]$^+$. | $^1$H NMR (400 MHz, MeOD-$d_4$): 8.18 (s, 1H), 7.51 (m, 3H), 7.09 (m, 4H), 6.77 (t, J = 53.4 Hz, 1H), 5.56 (q, J = 18.8 Hz, 1H), 3.88 (s, 3H), 1.68 (d, J = 6.4 Hz, 3H). | 1-methyl-1H-1,2,4-triazol-3-amine |
| 308 | (S)-3-(4-((difluoromethyl)sulfonamido)-3-(1-(4-fluorophenyl)ethoxy)phenyl)-5-((6,7-dihydro-4H-pyrazolo[5,1-c][1,4]oxazin-2-yl)amino)-1H-pyrazole-4-carboxamide | 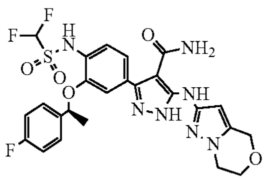 [SMILES: C[C@H](Oc1cc(-c2n[nH]c(Nc3cc4n(n3)CCOC4)c2C(N)=O)ccc1NS(=O)(=O)C(F)F)c1ccc(F)cc1] | LCMS (Method A): 3.55 min, m/z: 592.2 [M + H]$^+$. | $^1$H NMR (400 MHz, DMSO-$d_6$): 12.54 (s, 1H), 10.50 (s, 1H), 8.82 (s, 1H), 7.55 (dd, J = 8.8, 5.6 Hz, 2H), 7.36 (d, J = 4.2 Hz, 1H), 7.16 (t, J = 8.8 Hz, 2H), 7.11-7.06 (m, 2H), 6.98 (t, J = 52.4 Hz, 1H), 6.24 (s, 1H), 5.60 (q, J = 5.6 Hz, 1H), 4.73 (s, 2H), 4.04-3.93 (m, 4H), 1.56 (d, 6 Hz, 3H). | 6,7-dihydro-4H-pyrazolo [5,1 c][1,4] oxazin-2-amine |
| 277 | (S)-3-(4-((difluoromethyl)sulfonamido)-3-(1-(4-fluorophenyl)ethoxy)phenyl)-5-((1-methyl-5-(trifluoromethyl)-1H-pyrazol-3-yl)amino)-1H-pyrazole-4-carboxamide | 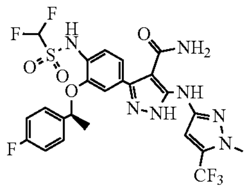 [SMILES: C[C@H](Oc1cc(-c2n[nH]c(Nc3cc(C(F)(F)F)n(C)n3)c2C(N)=O)ccc1NS(=O)(=O)C(F)F)c1ccc(F)cc1] | LCMS (Method A): 2.79 min, m/z 618.2 [M + H]$^+$. | $^1$H NMR (400 MHz, DMSO-$d_6$): 12.67(s, 1H), 10.54 (s, 1H), 9.04 (s, 1H), 7.58 (dd, J = 8.8, 5.6 Hz, 2H), 7.39 (d, J = 8.0 Hz, 1H), 7.20-7.15 (m, 3H), 7.09 (dd, J = 8.0, 2.0 Hz, 1H), 7.02 (t, J = 52.4 Hz, 1H), 6.92 (s, 1H), 5.64 (q, J = 6.0 Hz, 1H), 3.83 (s, 3H), 1.58 (d, J = 6.4 Hz, 3H). | 1-methyl-5-(trifluoromethyl)-1H-pyrazol-3-amine |

TABLE 23-continued

| Compound No | Name | Structure | LCMS data | NMR data | SM |
|---|---|---|---|---|---|
| 274 | (S)-3-(4-((difluoromethyl)sulfonamido)-3-(1-(4-fluorophenyl)ethoxy)phenyl)-5-((5-ethylisoxazol-3-yl)amino)-1H-pyrazole-4-carboxamide | 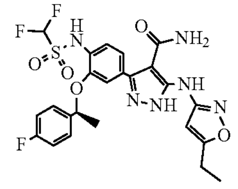 | LCMS (Method A): 3.68 min; m/z: 565.2 [M + H]$^+$. | $^1$H NMR (400 MHz, $CDCl_3$): 9.82 (s, 7.68 (d, J = 8.2 Hz, 1H), 7.30 (dd, J = 8.7, 5.2 Hz, 2H), 7.07 (q, J = 8.3 Hz, 3H), 6.92 (S, 1H), 6.38 (t, J = 53.5 Hz, 2H), 5.80 (s, 1H), 5.42 (q, J = 6.3 Hz, 1H), 5.17 (s, 2H), 2.64 (q, J = 7.6 Hz, 2H), 1.70 (d, J = 6.4 Hz, 3H), 1.26 (s, 3H). | 5-ethylisoxazol-3-amine |
| 284 | (S)-3-(4-((difluoromethyl)sulfonamido)-3-(1-(4-fluorophenyl)ethoxy)phenyl)-5-((4,5-dimethylthiazol-2-yl)amino)-1H-pyrazole-4-carboxamide | 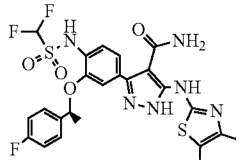 [SMILES: Cc1nc(Nc2[nH]nc(-c3ccc(NS(=O)(=O)C(F)F)c(O[C@@H](C)c4ccc(F)cc4)c3)c2C(N)=O)sc1C] | LCMS (Method A): 3.41 min; m/z: 581.2 [M + H]$^+$. | $^1$H NMR (400 MHz, MeOD-$d_4$): 7.56 (d, J = 8.3 Hz, 1H), 7.53-7.48 (m, 2H), 7.15 (d, J = 6.2 Hz, 2H), 7.07 (t, J = 8.8 Hz, 2H), 6.68 (t, J = 53.2 Hz, 1H), 5.56 (q, J = 6.3 Hz, 1H), 2.28 (s, 6H), 1.69 (d, J = 6.4 Hz, 3H). | 4,5-dimethylthiazol-2-amine |
| 294 | (S)-3-(4-((difluoromethyl)sulfonamido)-3-(1-(4-fluorophenyl)ethoxy)phenyl)-5-((5-methoxy-1-methyl-1H-pyrazol-3-yl)amino)-1H-pyrazole-4-carboxamide | 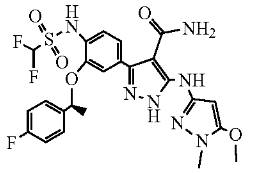 [SMILES: COc1cc(Nc2[nH]nc(-c3ccc(NS(=O)(=O)C(F)F)c(O[C@@H](C)c4ccc(F)cc4)c3)c2C(N)=O)nn1C] | LCMS (Method A): 3.09 min; m/z: 580.2 [M + H]$^+$. | $^1$H NMR (400 MHz, DMSO-$d_6$): 13.08 (s, 1H), 10.58 (s, 1H), 9.53 (s, 1H), 7.58 (t, J = 5.6 Hz, 2H), 7.37 (d, J = 8.0 Hz, 2H), 7.20-7.03 (m, 5H), 7.02 (t, J = 52.4 Hz, 1H), 6.37 (s, 0.5H), 6.63 (s, 1H), 5.27 (s, 1H), 3.07 (s, 3H), 3.00 (s, 3H), 1.58 (d, J = 5.6 Hz, 3H). | 5-methoxy-1-methyl-1H-pyrazol-3-amine |
| 295 | (S)-5-((3-(tert-butyl)isoxazol-5-yl)amino)-3-(4-((difluoromethyl)sulfonamido)-3-(1-(4-fluorophenyl)ethoxy)phenyl)-1H-pyrazole-4-carboxamide | 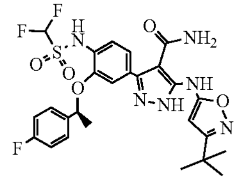 [SMILES: C[C@H](Oc1cc(-c2n[nH]c(Nc3cc(C(C)(C)C)no3)c2C(N)=O)ccc1NS(=O)(=O)C(F)F)c1ccc(F)cc1] | LCMS (Method A): 3.80 min; m/z: 593.2 [M + H]$^+$. | $^1$H NMR (400 MHz, DMSO-$d_6$): 12.96 (s, 1H), 10.59 (s, 1H), 9.72 (s, 1H), 7.57 (t, J = 5.6 Hz, 2H), 7.37 (d, J = 8.0 Hz, 1H), 7.17 (t, J = 8.8 Hz, 3H), 7.08 (d, J = 8.4 Hz, 1H), 6.93-6.68 (m, 1H), 6.25 (s, 0.5H), 5.91 (s, 1H), 5.63 (q, J = 6.4 Hz, 1H), 1.56 (d, J = 6.4 Hz, 3H), 1.25 (s, 9H). | 3-(tert-butyl)isoxazol-5-amine |
| 302 | (S)-3-(4-((difluoromethyl)sulfonamido)-3-(1-(4-fluorophenyl)ethoxy)phenyl)-5-((3-methylisoxazol-5-yl)amino)-1H-pyrazole-4-carboxamide | 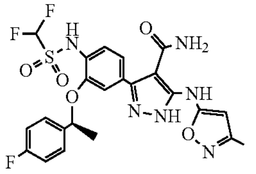 [SMILES: Cc1cc(Nc2[nH]nc(-c3ccc(NS(=O)(=O)C(F)F)c(O[C@@H](C)c4ccc(F)cc4)c3)c2C(N)=O)on1] | LCMS (Method A): 3.49 min, m/z: 551.2 [M + H]$^+$. | $^1$H NMR (400 MHz, DMSO-$d_6$): 12.94 (s, 1H), 10.55 (s, 1H), 9.73 (s, 1H), 7.58 (dd, J = 8.7, 5.5 Hz, 2H), 7.39 (d, J = 8.1 Hz, 1H), 7.21-7.17 (m, 2H), 7.17-6.88 (m, 3H), 5.85 (s, 1H), 5.62 (q, J = 6.2 Hz, 1H), 2.15 (s, 3H), 1.58 (d, J = 6.3 Hz, 3H). | 3-methylisoxazol-5-amine |
| 303 | (S)-3-(4-((difluoromethyl)sulfonamido)-3-(1-(4-fluorophenyl)ethoxy)phenyl)-5-((5-(tetrahydro-2H-pyran-4-yl)isoxazol-3-yl)amino)-1H-pyrazole-4-carboxamide | 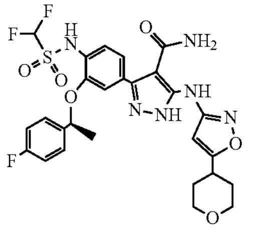 [SMILES: C[C@H](Oc1cc(-c2n[nH]c(Nc3cc(C4CCOCC4)on3)c2C(N)=O)ccc1NS(=O)(=O)C(F)F)c1ccc(F)cc1] | LCMS (Method A): 3.52 min, m/z: 621.2 [M + H]$^+$. | $^1$H NMR (400 MHz, MeOD-$d_4$): 7.55 (d, J = 8.2 Hz, 1H), 7.51 (dd, J = 8.7, 5.3 Hz, 2H), 7.13-7.05 (m, 4H), 6.05 (s, 1H), 5.56 (q, J = 6.4 Hz, 1H), 4.01 (ddd, J = 11.6, 4.3, 2.2 Hz, 2H), 3.56 (td, J = 11.6, 2.5 Hz, 2H), 2.95 (tt, J = 11.4, 4.1 Hz, 1H), 1.92-1.78 (m, 4H), 1.69 (d, J = 6.4 Hz, 3H). | 5-(tetrahydropyran-4-yl)isoxazol-3-amine |

TABLE 23-continued

| Compound No | Name | Structure | LCMS data | NMR data | SM |
|---|---|---|---|---|---|
| 306 | (S)-3-(4-((difluoromethyl) sulfonamido)-3-(1-(4-fluorophenyl) ethoxy)phenyl)-5-((1-(tetrahydro-2H-pyran-4-yl)-1H-pyrazol-4-yl) amino)-1H-pyrazole-4-carboxamide | 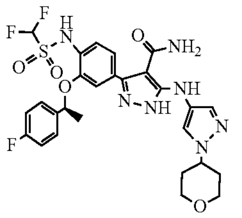 [SMILES: C[C@H](Oc1cc(-c2n[nH]c(Nc3cnn(C4CCOCC4)c3)c2C(N)=O)ccc1NS(=O)(=O)C(F)F)c1ccc(F)cc1] | LCMS (Method A): 3.39 min; m/z: 620.2 [M + H]+. | $^1$H NMR (400 MHz, DMSO-d$_6$): 12.45 (s, 1H), 10.51 (s, 1H), 8.24 (s, 1H), 7.84 (s, 1H), 7.56 (t, J = 8.4 Hz, 2H), 7.51 (s, 1H), 7.37 (d, J = 8.0 Hz, 1H), 7.19 (t, J = 8.8 Hz, 2H), 7.11 (d, J = 12 Hz, 2H), 7.07 (s, 0.3H), 7.02 (s, 0.4H), 6.89 (s, 0.2H), 5.62 (q, J = 5.6 Hz, 1H), 4.35-4.27 (m, 1H), 3.95 (d, J = 10.4 Hz, 2H), 3.46 (t, J = 9.6 Hz, 3H), 1.97-1.84 (m, 4H), 1.59 (d, J = 6.4 Hz, 3H). | 1-(tetrahydro-2H-pyran-4-yl)-1H-pyrazol-4-amine |
| 281 | (S)-5-((5-cyclobutylisoxazol-3-yl)amino)-3-(4-((difluoromethyl) sulfonamido)-3-(1-(4-fluorophenyl) ethoxy)phenyl)-1H-pyrazole-4-carboxamide | 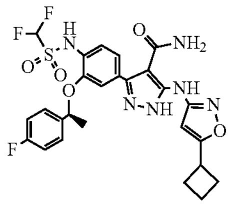 [SMILES: C[C@H](Oc1cc(-c2n[nH]c(Nc3cc(C4CCC4)on3)c2C(N)=O)ccc1NS(=O)(=O)C(F)F)c1ccc(F)cc1] | LCMS (Method A): 3.80 min; m/z: 591.2 [M + H]+. | 1H NMR (400 MHz, MeOD-d$_4$): 7.58-7.44 (m, 3H), 7.14-7.05 (m, 3H), 6.65 (t, J = 53.3 Hz, 1H), 6.06 (s, 1H), 5.63-5.30 (m, 2H), 3.53 (p, J = 8.8 Hz, 1H), 2.42-2.31 (m, 2H), 2.29-2.22 (m, 1H), 2.10 (q, J = 9.3, 8.8 Hz, 1H), 1.99 (ddd, J = 24.3, 16.0, 8.5 Hz, 2H), 1.68 (d, J = 6.4 Hz, 3H), 1.31 (d, J = 10.9 Hz, 6H). | 5-cyclo-butylisoxazol-3-amine |
| 289 | (S)-3-(4-((difluoromethyl) sulfonamido)-3-(1-(4-fluorophenyl) ethoxy)phenyl)-5-((5-(1-(trifluoromethyl) cyclopropyl) isoxazol-3-yl) amino)-1H-pyrazole-4-carboxamide | 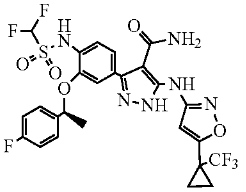 [SMILES: C[C@H](Oc1cc(-c2n[nH]c(Nc3cc(C4(C(F)(F)F)CC4)on3)c2C(N)=O)ccc1NS(=O)(=O)C(F)F)c1ccc(F)cc1] | LCMS (Method A): 3.86 min, m/z: 645.2 [M + H]+. | $^1$H NMR (400 MHz, DMSO-d$_6$): 12.79 (s, 1H), 10.08 (s, 1H), 9.27 (s, 1H), 7.55 (dd, J = 8.5, 5.7 Hz, 2H), 7.36 (d, J = 8.0 Hz, 1H), 7.16 (t, J = 8.9 Hz, 3H), 7.10-7.01 (m, 2H), 6.90 (s, 1H), 6.62 (d, J = 48.0 Hz, 1H), 6.06 (s, 1H), 5.60 (q, J = 6.1 Hz, 1H), 1.55 (d, J = 6.3 Hz, 3H), 1.54-1.46 (m, 4H). | 5-(1-(trifluoromethyl) cyclopropyl) isoxazol-3-amine |
| 276 | (S)-3-(4-((difluoromethyl) sulfonamido)-3-(1-(4-fluorophenyl) ethoxy)phenyl)-5-((5-(1-methylcyclopropyl) isoxazol-3-yl) amino)-1H-pyrazole-4-carboxamide | 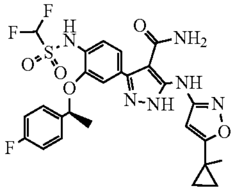 [SMILES: C[C@H](Oc1cc(-c2n[nH]c(Nc3cc(C4(C)CC4)on3)c2C(N)=O)ccc1NS(=O)(=O)C(F)F)c1ccc(F)cc1] | LCMS (Method A): 3.80 min; m/z: 591.2 [M + H]+. | $^1$H NMR (400 MHz, DMSO-d$_6$): 12.52 (s, 1H), 9.23 (s, 1H), 7.48 (t, J = 5.6 Hz, 2H), 7.35 (d, J = 8.0 Hz, 1H), 7.12 (t, J = 8.8 Hz, 2H), 6.83 (t, J = 8.4 Hz, 2H), 6.57 (s, 1H), 6.41-6.14 (m, 1H), 5.63-5.58 (m, 1H), 1.48 (d, J = 6.4 Hz, 3H), 1.41 (s, 3H), 1.08 (q, J = 4.4 Hz, 2H), 0.88 (q, J = 4.0 Hz, 2H), 6.21 (s, 1H), 5.30 (s, 2H), 3.05 (q, J = 7.2 Hz, 2H), 1.15 (t, J = 7.6 Hz, 3H). | 5-(1-methylcyclopropyl) isoxazol-3-amine |
| 288 | (S)-3-(4-((difluoromethyl) sulfonamido)-3-(1-(4-fluorophenyl) ethoxy)phenyl)-5-((5-(1-methoxy-2-methylpropan-2-yl)isoxazol-3-yl)amino)-1H-pyrazole-4-carboxamide | 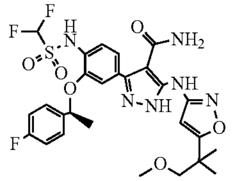 [SMILES: COCC(C)(C)c1cc(Nc2[nH]nc(-c3ccc(NS(=O)(=O)C(F)F)c(O[C@@H](C)c4ccc(F)cc4)c3)c2C(N)=O)no1] | LCMS (Method A): 3.83 min; m/z: 623.2 [M + H]+. | $^1$H NMR (400 MHz, DMSO-d$_6$): 12.79 (s, 1H), 10.57 (s, 1H), 9.10 (s, 1H), 7.57 (dd, J = 8.6, 5.6 Hz, 2H), 7.38 (d, J = 8.1 Hz, 1H), 7.21-7.09 (m, 4H), 7.08-6.86 (m, 1H), 6.56 (s, 1H), 5.62 (q, J = 6.3 Hz, 1H), 3.39 (s, 2H), 3.24 (s, 3H), 1.57 (d, J = 6.3 Hz, 3H), 1.25 (s, 6H). | 5-(1-methoxy-2-methylpropan-2-yl)isoxazol-3-amine |
| 301 | (S)-3-(4-((difluoromethyl) sulfonamido)-3-(1-(4-fluorophenyl) ethoxy)phenyl)-5-((5-(4-methyltetrahydro-2H-pyran-4-yl) isoxazol-3-yl)amino)-1H- | 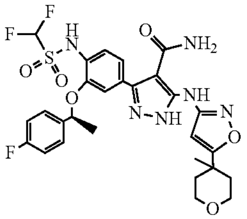 [SMILES: C[C@H](Oc1cc(-c2n[nH]c(Nc3cc(C4(C)CCOCC4)on3)c2C(N)=O)ccc1NS(=O)(=O)C(F)F)c1ccc(F)cc1] | LCMS (Method A): 4.31 min; m/z: 634.0 [M + H]+. | $^1$H NMR (400 MHz, DMSO-d$_6$): 12.93 (s, 1H), 10.58 (s, 1H), 9.78 (s, 1H), 7.64-7.51 (m, 2H), 7.38 (d, J = 8.1 Hz, 1H), 7.24-7.15 (m, 3H), 7.10 (d, J = 8.3 Hz, 1H), 6.95 (d, J = 52.6 Hz, 1H), 6.28 (s, 1H), 5.89 (s, 1H), 5.61 (q, J = 6.3 Hz, 1H), 3.69 (dt, J = 11.6, 4.6 Hz, 2H), 3.46 (ddd, J = 11.8, 9.1, 2.8 Hz, 3H), 2.01-1.92 (m, 2H), 1.63-1.53 (m, 4H), 1.25 (s, 3H). | 5-(4-methyltetrahydro-2H-pyran-4-yl)isoxazol-3-amine |

TABLE 23-continued

| Compound No | Name | Structure | LCMS data | NMR data | SM |
|---|---|---|---|---|---|
| | pyrazole-4-carboxamide | | | | |
| 297 | (S)-3-(4-((difluoromethyl) sulfonamido)-3-(1-(4-fluorophenyl) ethoxy)phenyl)-5-((5-(4-methyltetrahydro-2H-pyran-4-yl) isoxazol-3-yl)amino)-1H-pyrazole-4-carboxamide | 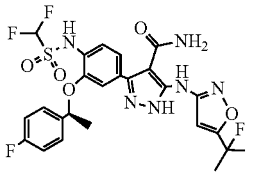 [SMILES: C[C@H](Oc1cc(-c2n[nH]c(Nc3cc(C(C)(C)F)on3)c2C(N)=O)ccc1NS(=O)(=O)C(F)F)c1ccc(F)cc1] | LCMS (Method A): 3.71 min; m/z: 597.2 [M + H]$^+$. | $^1$H NMR (400 MHz, DMSO-$d_6$): 13.02 (s, 1H), 10.59 (s, 1H), 9.90 (s, 1H), 7.59 (d, J = 6.8 Hz, 2H), 7.38 (d, J = 7.9 Hz, 1H), 7.25-6.64 (m, 6H), 6.36 (s, 1H), 6.02 (s, 1H), 5.63 (t, J = 6.6 Hz, 1H), 1.67 (d, J = 21.9 Hz, 6H), 1.57 (d, J = 5.8 Hz, 3H). | 5-(2-fluoropropan 2-yl)isoxazol-3-amine |
| 292 | (S)-3-(4-((difluoromethyl) sulfonamido)-3-(1-(4-fluorophenyl) ethoxy)phenyl)-5-((5-(3-methyloxetan-3-yl)isoxazol-3-yl)amino)-1H-pyrazole-4-carboxamide | 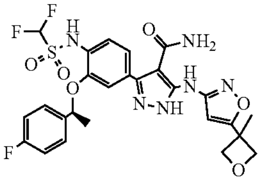 [SMILES: C[C@H](Oc1cc(-c2n[nH]c(Nc3cc(C4(C)COC4)on3)c2C(N)=O)ccc1NS(=O)(=O)C(F)F)c1ccc(F)cc1] | LCMS (Method A): 3.57 min; m/z: 607.2 [M + H]$^+$. | $^1$H NMR (400 MHz, DMSO-$d_6$): 12.94 (s, 1H), 10.57 (s, 1H), 9.85 (s, 1H), 7.57 (dd, J = 8.6, 5.6 Hz, 2H), 7.39 (d, J = 8.1 Hz, 1H), 7.18 (t, J = 8.9 Hz, 3H), 7.13-6.86 (m, 2H), 6.04 (s, 1H), 5.61 (q, J = 6.2 Hz, 1H), 4.76 (d, J = 5.7 Hz, 2H), 4.51 (d, J = 5.8 Hz, 2H), 1.62 (s, 3H), 1.57 (d, J = 6.3 Hz, 3H). | 5-(3-methyloxetan-3-yl)isoxazol-3-amine |
| 304 | (S)-5-((5-(adamantan-1-yl)isoxazol-3-yl)amino)-3-(4-((difluoromethyl) sulfonamido)-3-(1-(4-fluorophenyl) ethoxy)phenyl)-1H-pyrazole-4-carboxamide | 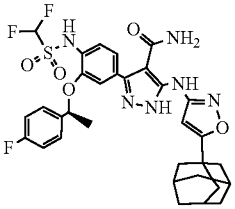 [SMILES: C[C@H](Oc1cc(-c2n[nH]c(Nc3cc(C45CC6CC7CC(C4)C5(C7)C6)on3)c2C(N)=O)ccc1NS(=O)(=O)C(F)F)c1ccc(F)cc1] | LCMS (Method A): 4.27 min, m/z: [M + H]$^+$. | $^1$H NMR (400 MHz, MeOD-$d_4$): 7.54 (d, J = 8.1 Hz, 1H), 7.53-7.48 (m, 2H), 7.13-7.04 (m, 4H), 6.67 (s, 1H), 6.04 (s, 1H), 5.56 (q, J = 6.4 Hz, 1H), 2.06 (d, J = 5.6 Hz, 3H), 1.98 (d, J = 2.8 Hz, 5H), 1.85-1.81 (m, 4H), 1.69 (d, J = 6.4 Hz, 3H). | 5-(adamantan-1-yl)isoxazol-3-amine |
| 305 | 3-(4-((difluoromethyl) sulfonamido)-3-((S)-1-(4-fluorophenyl) ethoxy)phenyl)-5-((5-(tetrahydrofuran-3-yl)isoxazol-3-yl)amino)-1H-pyrazole-4-carboxamide | 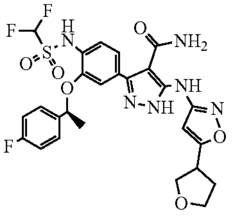 | LCMS (Method A): 3.46 min; m/z: 607.2 [M + H]$^+$. | $^1$H NMR (400 MHz, DMSO-$d_6$): 12.97 (s, 1H), 10.56 (s, 1H), 9.78 (s, 1H), 7.58 (t, J = 5.6 Hz, 2H), 7.39 (d, J = 8.0 Hz, 1H), 7.18 (t, J = 8.4 Hz, 3H), 7.12 (d, J = 8.0 Hz, 2H), 7.03 (s, 0.4H), 6.89 (s, 0.2H), 6.30 (s, 0.6H), 5.62 (q, J = 5.6 Hz, 1H), 3.97 (t, J = 8.0 Hz, 1H), 3.88-3.83 (m, 1H), 3.76 (q, J = 7.2 Hz, 1H), 3.67 (t, J = 6.4 Hz, 1H), 3.44 (s, 1H), 2.31-2.22 (m, 1H), 2.02-1.93 (m, 1H), 1.58 (d, J = 6.0 Hz, 3H). | 5-(tetrahydrofuran-3-yl) isoxazol-3-amine |
| 314 | (S)-5-((5-(difluoromethyl) isoxazol-3-yl)amino)-3-(4-((difluoromethyl) sulfonamido)-3-(1-(4-fluorophenyl) ethoxy) phenyl)-1H-pyrazole-4-carboxamide | 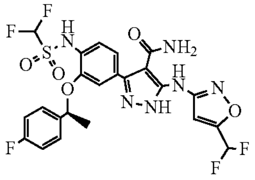 [SMILES: C[C@H](Oc1cc(-c2n[nH]c(Nc3cc(C(F)F)on3)c2C(N)=O)ccc1NS(=O)(=O)C(F)F)c1ccc(F)cc1] | LCMS (Method A): 3.73 min; m/z: 587.1 [M + H]$^+$. | $^1$H NMR (400 MHz, DMSO-$d_6$): 13.05 (s, 1H), 10.56 (s, 1H), 10.16 (s, 1H), 7.58 (dd, J = 8.5, 5.4 Hz, 2H), 7.38 (d, J = 8.1 Hz, 2H), 7.29-6.87 (m, 7H), 6.14 (s, 1H), 5.61 (q, J = 5.9 Hz, 1H), 1.58 (d, J = 6.1 Hz, 3H). | 5-(difluoro-methylisoxazol-3-amine |
| 310 | (S)-5-((5-cyclopropyl-isoxazol-3-yl)amino)-3-(4-((difluoromethyl) sulfonamido)-3-(1-(4-fluorophenyl) ethoxy) | 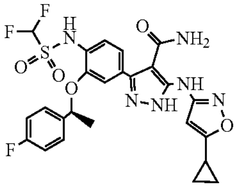 | LCMS (Method A): 3.73 min; m/z: 587.1 [M + H]$^+$. | $^1$H NMR (400 MHz, DMSO-$d_6$): 12.88 (s, 1H), 10.56 (s, 1H), 9.73 (s, 1H), 7.63-7.52 (m, 2H), 7.38 (dd, J = 8.1, 1.5 Hz, 1H), 7.18 (td, J = 8.9, 1.7 Hz, 3H), 7.08 (d, J = 8.1 Hz, 1H), 5.62 (d, J = 6.4 Hz, 1H), 1.90 (tt, J = 8.8, 5.1 Hz, 1H), 1.57 (d, J = 6.2 Hz, 2H), 1.01-0.94 (m, 2H), 0.75-0.69 (m, 2H). | 5-cyclopropyl-1,2-oxazol-3-amine |

TABLE 23-continued

| Compound No | Name | Structure | LCMS data | NMR data | SM |
|---|---|---|---|---|---|
| | phenyl)-1H-pyrazole-4-carboxamide | | | | |
| 312 | (S)-5-((5-(tert-butyl)pyrazin-2-yl)amino)-3-(4-((difluoromethyl)sulfonamido)-3-(1-(4-fluorophenyl)ethoxy)phenyl)-1H-pyrazole-4-carboxamide | 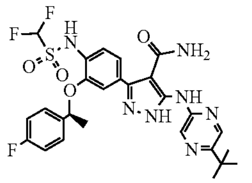 [SMILES: C[C@H](Oc1cc(-c2n[nH]c(Nc3cnc(C(C)(C)C)cn3)c2C(N)=O)ccc1NS(=O)(=O)C(F)F)c1ccc(F)cc1] | LCMS (Method A): 4.03 min; m/z: 604.2 [M + H]+. | $^1$H NMR (400 MHz, DMSO-$d_6$): 12.94 (s, 1H), 10.52 (s, 1H), 9.41 (s, 1H), 9.13 (s, 1H), 8.26 (s, 1H), 7.58 (dd, J = 8.0, 5.8 Hz, 2H), 7.40 (d, J = 8.2 Hz, 1H), 7.23-7.11 (m, 4H), 5.75-5.56 (m, 1H), 1.58 (d, J = 6.3 Hz, 3H), 1.32 (s, 9H). | 5-(tert-butyl) pyrazin-2-amine |
| 296 | (S)-3-(4-((difluoromethyl)sulfonamido)-3-(1-(4-fluorophenyl)ethoxy)phenyl)-5-((5-(tetrahydro-2H-pyran-4-yl)pyrazin-2-yl)amino)-1H-pyrazole-4-carboxamide | 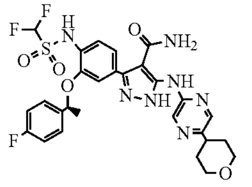 [SMILES: C[C@H](Oc1cc(-c2n[nH]c(Nc3cnc(C4CCOCC4)cn3)c2C(N)=O)ccc1NS(=O)(=O)C(F)F)c1ccc(F)cc1] | LCMS (Method A): 3.54 min; m/z: 632.2 M + H]+. | $^1$H NMR (400 MHz, MeOD-$d_4$): 9.23 (s, 1H), 8.35 (s, 1H), 8.16 (s, 1H), 7.49 (dd, J = 8.6, 5.5 Hz, 3H), 7.13-7.03 (m, 4H), 6.66 (t, J = 53.3 Hz, 1H), 5.54 (q, J = 6.3 Hz, 1H), 4.08-4.01 (m, 2H), 3.57 (td, J = 11.6, 2.5 Hz, 2H), 2.96 (td, J = 11.7, 9.5, 5.7 Hz, 1H), 1.95-1.78 (m, 4H), 1.68 (d, J = 6.3 Hz, 3H). | 5-(tetrahydro-2H-pyran-4-yl)pyrazin-2-amine |
| 278 | (S)-3-(4-((difluoromethyl)sulfonamido)-3-(1-(4-fluorophenyl)ethoxy)phenyl)-5-((5-(tetrahydro-2H-pyran-4-yl)pyridin-2-yl)amino)-1H-pyrazole-4-carboxamide | 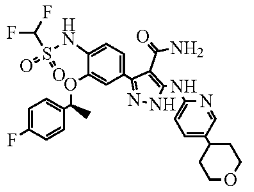 [SMILES: C[C@H](Oc1cc(-c2n[nH]c(Nc3ccc(C4CCOCC4)cn3)c2C(N)=O)ccc1NS(=O)(=O)C(F)F)c1ccc(F)cc1] | LCMS (Method A): 3.31 min; m/z: 631.2 [M + H]+. | $^1$H NMR (400 MHz, $CDCl_3$): 12.78 (s, 1H), 9.86 (s, 1H), 8.14 (s, 1H), 7.60 (d, J = 8.2 Hz, 1H), 7.56-7.44 (m, 2H), 7.38-7.29 (m, 2H), 7.13 (d, J = 8.0 Hz, 1H), 7.03 (dd, J = 16.0, 7.4 Hz, 3H), 6.82 (d, J = 8.5 Hz, 1H), 6.34 (t, J = 53.6 Hz, 1H), 5.42 (d, J = 5.8 Hz, 1H), 5.12 (s, 2H), 4.11 (t, J = 7.2 Hz, 2H), 3.60-3.50 (m, 2H), 2.86-2.67 (m, 1H), 1.83-1.72 (m, 4H), 1.67 (d, J = 6.4 Hz, 3H). | 5-(tetrahydro-2H-pyran-4-yl)pyridin-2-amine |
| 287 | (S)-3-(4-((difluoromethyl)sulfonamido)-3-(1-(4-fluorophenyl)ethoxy)phenyl)-5 ((4-(tetrahyd ro-2H-pyran-4-yl)pyridin-2-yl)amino)-1H-pyrazole-4-carboxamide | 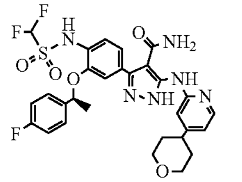 [SMILES: C[C@H](Oc1cc(-c2n[nH]c(Nc3cc(C4CCOCC4)ccn3)c2C(N)=O)ccc1NS(=O)(=O)C(F)F)c1ccc(F)cc1] | LCMS (Method A): 3.19 min; m/z: 631.2 [M + H]+. | $^1$H NMR (400 MHz, DMSO-$d_6$): 12.83 (s, 1H), 10.56 (s, 1H), 9.81 (s, 1H), 9.41 (s, 1H), 8.19-8.04 (m, 1H), 7.91 (s, 1H), 7.57 (dd, J = 8.3, 5.7 Hz, 2H), 7.39 (d, J = 8.3 Hz, 1H), 7.18 (t, J = 8.8 Hz, 3H), 7.14-7.05 (m, 2H), 7.04-6.71 (m, 3H), 5.68-5.55 (m, 1H), 3.99-3.91 (m, 2H), 3.48 (t, J = 6.4 Hz, 2H), 2.76 (s, 1H), 1.77-1.61 (m, 4H), 1.57 (d, J = 6.2 Hz, 3H). | 4-(tetrahydro-2H-pyran-4-yl)pyridin-2-amine |
| 316 | (S)-5-((5-cyclopropylpyrazin-2-yl)amino)-3-(4-((difluoromethyl)sulfonamido)-3-(1-(4-fluorophenyl)ethoxy)phenyl)-1H-pyrazole-4-carboxamide | 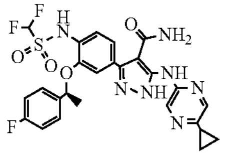 [SMILES: C[C@H](Oc1cc(-c2n[nH]c(Nc3cnc(C4CC4)cn3)c2C(N)=O)ccc1NS(=O)(=O)C(F)F)c1ccc(F)cc1] | LCMS (Method A): 3.88 min; m/z: 588.2 [M + H]+. | $^1$H NMR (400 MHz, $CDCl_3$): 12.39 (s, 1H), 10.07 (s, 1H), 8.18 (d, J = 1.5 Hz, 1H), 8.10 (d, J = 1.4 Hz, 1H), 7.78 (s, 1H), 7.59 (d, J = 8.3 Hz, 1H), 7.34-7.28 (m, 2H), 7.12 (dd, J = 8.2, 1.7 Hz, 1H), 7.04 (t, J = 8.6 Hz, 2H), 6.97 (d, J = 1.7 Hz, 1H), 6.36 (t, J = 53.6 Hz, 1H), 5.39 (q, J = 7.3, 6.5 Hz, 1H), 5.21 (s, 2H), 2.03 (tt, J = 7.7, 5.1 Hz, 1H), 1.66 (d, J = 6.4 Hz, 3H), 1.00 (dd, J = 7.6, 5.3 Hz, 3H). | 5-cyclopropyl-pyrazin-2-amine |
| 318 | (S)-3-(4-((difluoromethyl)sulfonamido)-3-(1-(4-fluorophenyl)ethoxy)phenyl)-5-((5-methyl-5,6,7,8-tetrahydro-4H-pyrazolo[1,5-a][1,4]diazepin- | 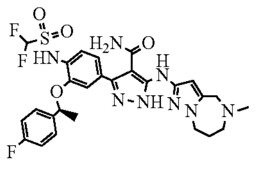 [SMILES: C[C@H](Oc1cc(-c2n[nH]c(Nc3cc4n(n3)CCCN(C)C4)c2C(N)=O)ccc1NS(=O)(=O)C(F)F)c1ccc(F)cc1] | LCMS (Method D): 1.42 min; m/z: 619.8 [M + H]+. | $^1$H NMR (300 MHz, DMSO-$d_6$): 12.46 (s, 1H), 8.85 (s, 1H), 7.54 (dd, J = 8.4, 5.4 Hz, 2H), 7.36 (d, J = 8.1 Hz, 1H), 7.16 (t, J = 8.7 Hz, 2H), 7.01 (d, J = 6.5 Hz, 2H), 6.79 (dd, J = 55.4 Hz, 1H), 6.38 (s, 1H), 5.61 (q, J = 5.8 Hz, 1H), 4.18 (s, 2H), 3.86 (s, 2H), 3.03 (s, 2H), 2.34 (s, 3H), 1.80 (s, 2H), 1.55 (d, J = 6.2 Hz, 3H). | |

TABLE 23-continued

| Compound No | Name | Structure | LCMS data | NMR data | SM |
|---|---|---|---|---|---|
| | 2-yl)amino)-1H-pyrazole-4-carboxamide | | | | |

TABLE 24

| Compound No. | Name | Structure | LCMS data | NMR data |
| --- | --- | --- | --- | --- |
| 137 | 5-(pyrazin-2-ylamino)-3-(4-((2,2,2-trifluoroethyl)sulfonamido)phenyl)-1H-pyrazole-4-carboxamide | 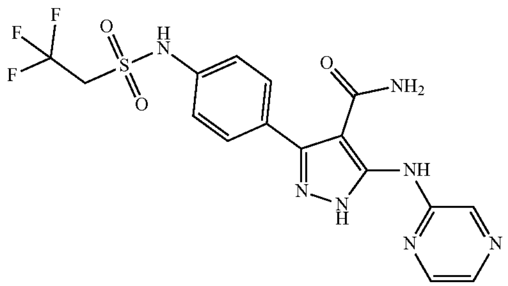 [SMILES: NC(=O)c1c(-c2ccc(NS(=O)(=O)CC(F)(F)F)cc2)n[nH]c1Nc1cnccn1] | LCMS (Method A): 3.08 min; m/z: 442.0 $[M+H]^+$. | $^1H$ NMR (400 MHz, MeOD-$d_4$): 12.99 (s, 1H), 9.71 (s, 1H), 9.23 (s, 1H), 8.22 (s, 1H), 8.11 (d, J = 2.4 Hz, 1H), 7.55 (d, J = 8.4 Hz, 2H), 7.33 (d, J = 8.8 Hz, 2H), 6.10 (s, 1H), 4.50 (q, J = 9.6 Hz, 2H). |
| 138 | 5-((7-chloroquinolin-2-yl)amino)-3-(4-(ethylsulfonamido)-3-((4-fluorobenzyl)oxy)phenyl)-1H-pyrazole-4-carboxamide | 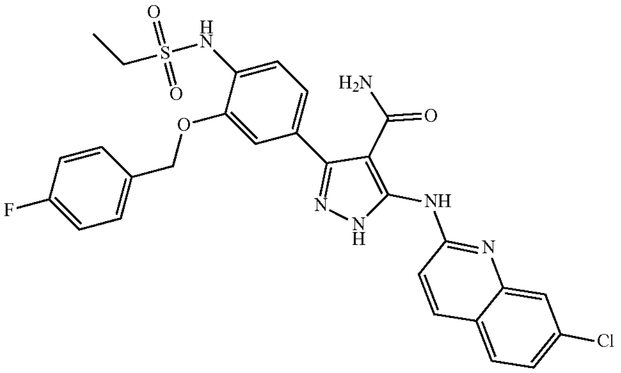 [SMILES: CCS(=O)(=O)Nc1ccc(-c2n[nH]c(Nc3ccc4ccc(Cl)cc4n3)c2C(N)=O)cc1OCc1ccc(F)cc1] | LCMS (Method A): 4.83 min; m/z: 595.1 $[M+H]^+$. | $^1H$ NMR (400 MHz, DMSO-$d_6$): 13.56 (s, 1H), 10.40 (s, 1H), 9.10 (s, 1H), 8.48 (s, 1H), 8.25 (q, J = 8.0 Hz, 1H), 7.85 (d, J = 8.4 Hz, 1H), 7.63 (q, J = 5.6 Hz, 2H), 7.46-7.37 (m, 4H), 7.27-7.21 (m, 3H), 6.35 (s, 1H), 5.20 (s, 2H), 3.05 (q, J = 7.2 Hz, 2H), 1.16 (t, J = 7.2 Hz, 3H). |

TABLE 24-continued

| Compound No. | Name | Structure | LCMS data | NMR data |
|---|---|---|---|---|
| 139 | 3-(2-((4-fluorobenzyl)oxy)-4-((2,2,2-trifluoroethyl)sulfonamido)phenyl)-5-(pyrazin-2-ylamino)-1H-pyrazole-4-carboxamide | 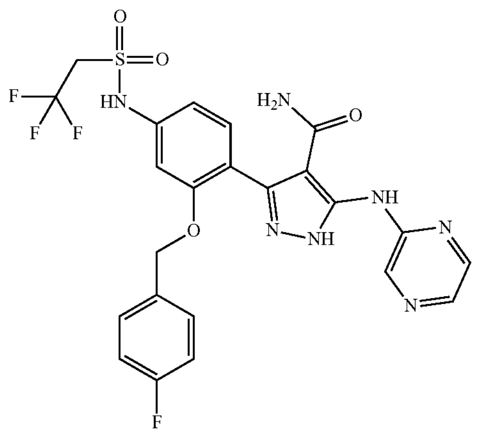 [SMILES: NC(=O)c1c(-c2ccc(NS(=O)(=O)CC(F)(F)F)cc2OCc2ccc(F)cc2)n[nH]c1Nc1cnccn1] | LCMS (Method A): 3.92 min; m/z: 566.1 $[M + H]^+$. | $^1H$ NMR (400 MHz, DMSO-$d_6$): 12.83 (s, 1H), 9.79 (s, 1H), 9.32 (s, 1H), 8.22 (m, 1H), 8.10 (d, J = 3.2 Hz, 1H), 7.41 (m, 2H), 7.22 (d, J = 8.4 Hz, 1H), 7.15 (t, J = 8.8 Hz, 2H), 6.97 (s, 1H), 6.84 (d, J = 14.4 Hz, 1H), 5.07 (s, 2H), 4.20 (s, 2H). |
| 140 | 3-(2-((4-fluorobenzyl)oxy)-4-((2,2,2-trifluoroethyl)sulfonamido)phenyl)-5-((6-(trifluoromethyl)pyridine-2-yl)amino)-1H-pyrazole-4-carboxamide | 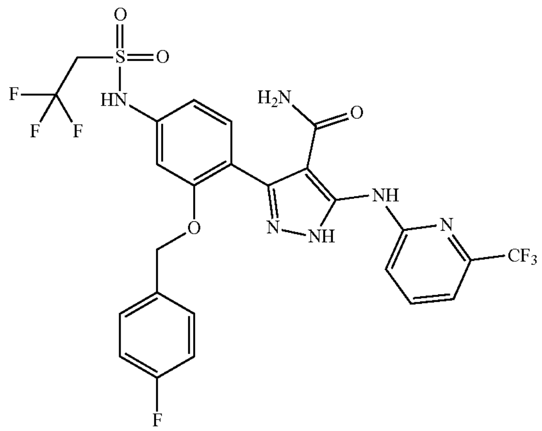 [SMILES: NC(=O)c1c(-c2ccc(NS(=O)(=O)CC(F)(F)F)cc2OCc2ccc(F)cc2)n[nH]c1Nc1cccc(C(F)(F)F)n1] | LCMS (Method A): 4.92 min; m/z: 633.1 $[M + H]^+$. | $^1H$ NMR (400 MHz, DMSO-$d_6$): 12.85 (s, 1H), 10.83 (s, 1H), 9.89 (s, 1H), 8.28 (d, J = 8.4 Hz, 1H), 7.98 (t, J = 7.6 Hz, 1H), 7.44-7.39 (m, 3H), 7.30 (d, J = 7.2 Hz, 1H), 7.17 (t, J = 8.8 Hz, 2H), 7.10-7.09 (m, 1H), 6.97-6.95 (m, 1H), 5.11 (s, 2H), 4.64 (q, J = 10.4 Hz, 2H). |

TABLE 24-continued

| Compound No. | Name | Structure | LCMS data | NMR data |
|---|---|---|---|---|
| 141 | 3-(4-(ethylsulfonamido)-2-((4-fluorobenzyl)oxy)phenyl)-5-((6-(trifluoromethyl)pyridine-2-yl)amino)-1H-pyrazole-4-carboxamide | 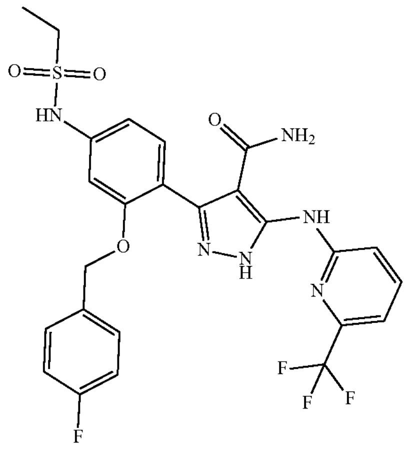 [SMILES: CCS(=O)(=O)Nc1ccc(-c2n[nH]c(Nc3cccc(C(F)(F)F)n3)c2C(N)=O)c(OCc2ccc(F)cc2)c1] | LCMS (Method A): 4.58 min; m/z: 579.1 [M + H]+. | $^1$H NMR (400 MHz, DMSO-$d_6$): 12.82 (s, 1H), 10.16 (s, 1H), 9.87 (s, 1H), 8.27 (d, J = 8.4 Hz, 1H), 7.98 (t, J = 8.0 Hz, 1H), 7.44-7.41 (m, 2H), 7.37 (d, J = 8.4 Hz, 1H), 7.30 (d, J = 7.2 Hz, 1H), 7.19-7.15 (m, 2H), 7.09-7.08 (m, 1H), 6.96-6.93 (m, 1H), 5.69 (s, 1H), 5.09 (s, 1H), 3.17-3.15 (m, 2H), 1.20 (t, J = 7.2 Hz, 1H). |
| 142 | 3-(4-(ethylsulfonamido)-3-((4-fluoro-2,6-dimethylbenzyl)oxy)phenyl)-5-(pyrazin-2-ylamino)-1H-pyrazole-4-carboxamide | 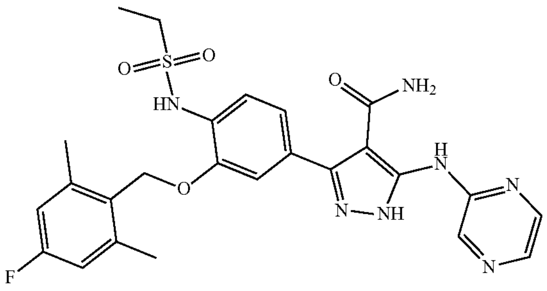 [SMILES: CCS(=O)(=O)Nc1ccc(-c2n[nH]c(Nc3cnccn3)c2C(N)=O)cc1OCc1c(C)cc(F)cc1C] | LCMS (Method A): 4.13 min; m/z: 540.1 [M + H]+. | $^1$H NMR (400 MHz, DMSO-$d_6$): 13.05 (s, 1H), 9.66 (s, 1H), 9.27 (s, 1H), 8.23-8.22 (m, 1H), 8.12 (d, J = 2.4 Hz, 1H), 7.55 (br s, 1H), 7.40 (d, J = 8.4 Hz, 1H), 7.21 (dd, J = 8.0, 1.6 Hz, 1H), 6.98 (d, J = 9.6 Hz, 2H), 5.11 (s, 2H), 2.96 (q, J = 14.0, 6.8 Hz, 2H), 2.37 (s, 6H), 1.07 (t, J = 7.2 Hz, 3H). |

TABLE 24-continued

| Compound No. | Name | Structure | LCMS data | NMR data |
| --- | --- | --- | --- | --- |
| 143 | 3-(3-((4-fluorobenzyl)oxy)-4-((2,2,2-trifluoroethyl)sulfonamido)phenyl)-5-((5-methoxypyrazin-2-yl)amino)-1H-pyrazole-4-carboxamide | 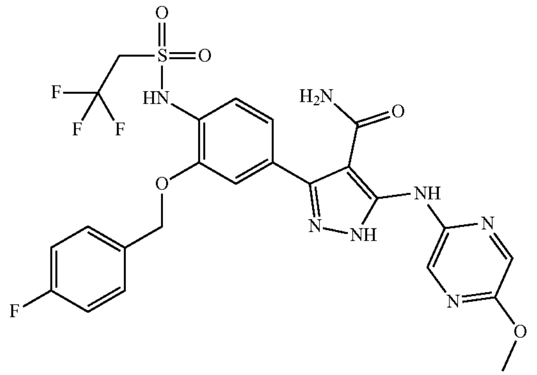 [SMILES: COc1cnc(Nc2[nH]nc(-c3ccc(NS(=O)(=O)CC(F)(F)F)c(OCc4ccc(F)cc4)c3)c2C(N)=O)cn1] | LCMS (Method A): 4.55 min; m/z: 596.2 [M + H]+. | $^1$H NMR (400 MHz, DMSO-$d_6$): 12.92 (s, 1H), 9.94 (s, 1H), 9.41 (s, 1H), 8.84 (s, 1H), 7.98 (s, 1H), 7.59 (q, J = 5.6 Hz, 2H), 7.43-7.40 (m, 1H), 7.26-7.17 (m, 4H), 5.18 (s, 2H), 4.30 (d, J = 10.8 Hz, 2H), 3.86 (s, 3H). |
| 144 | 3-(3-(1-(4-fluorophenyl)cyclopropoxy)-4-((2,2,2-trifluoroethyl)sulfonamido)phenyl)-5-(pyrazin-2-ylamino)-1H-pyrazole-4-carboxamide | 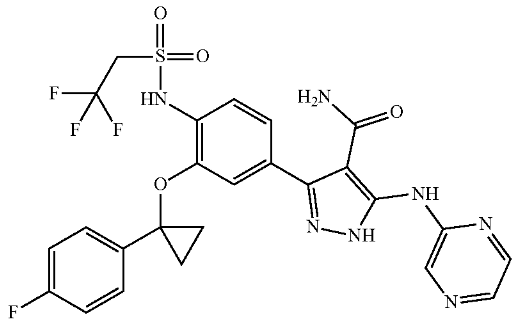 [SMILES: NC(=O)c1c(-c2ccc(NS(=O)(=O)CC(F)(F)F)c(OC3(c4ccc(F)cc4)CC3)c2)n[nH]c1Nc1cnccn1] | LCMS (Method A): 4.27 min; m/z: 592.1 [M + H]+. | $^1$H NMR (400 MHz, MeOD-$d_4$): 12.97 (s, 1H), 10.06 (s, 1H), 9.62 (s, 1H), 9.21 (s, 1H), 8.20 (s, 1H), 8.09 (s, 1H), 7.45 (d, J = 7.6 Hz, 1H), 7.31 (t, J = 8.8 Hz, 3H), 7.17-7.04 (m, 4H), 6.21 (s, 1H), 4.47 (d, J = 8.8 Hz, 2H), 1.47 (s, 2H), 1.40 (s, 2H). |
| 145 | 3-(4-((difluoromethyl)sulfonamido)phenyl)-5-((5-(trifluoromethyl)pyridine-2-yl)amino)-1H-pyrazole-4-carboxamide | 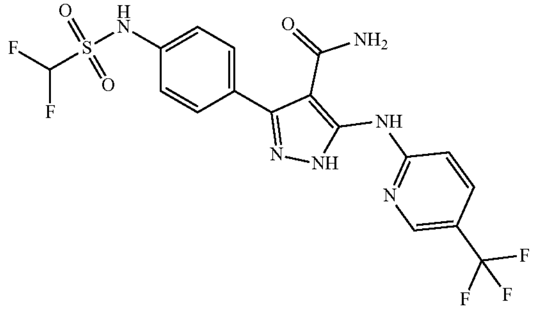 [SMILES: NC(=O)c1c(-c2ccc(NS(=O)(=O)C(F)F)cc2)n[nH]c1Nc1ccc(C(F)(F)F)cn1] | LCMS (Method B): 1.63 min; m/z: 477.2 [M + H]+. | $^1$H NMR (400 MHz, DMSO-$d_6$): 13.02 (s, 1H), 11.27 (s, 1H), 9.89 (s, 1H), 8.53 (s, 1H), 8.06 (t, J = 9.2 Hz, 2H), 7.60 (d, J = 8.4 Hz, 2H), 7.39 (d, J = 8.4 Hz, 2H), 7.22 (s, 1H), 6.17 (s, 1H). |

TABLE 24-continued

| Compound No. | Name | Structure | LCMS data | NMR data |
| --- | --- | --- | --- | --- |
| 146 | 3-(3-((4-chloro-3-fluorobenzyl)oxy)-4-((2,2,2-trifluoroethyl)sulfonamido)phenyl)-5-((5-methylpyrazin-2-yl)amino)-1H-pyrazole-4-carboxamide | 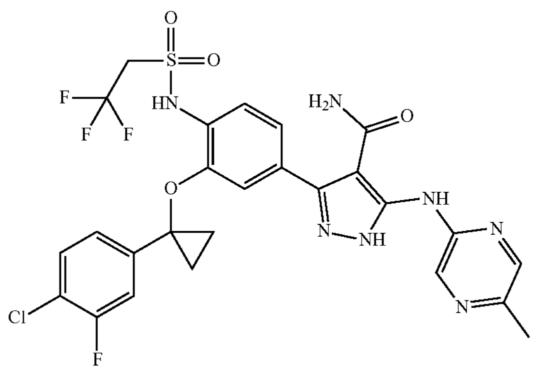 | LCMS (Method A): 3.46 min; m/z: 613.9 $[M + H]^+$. | $^1H$ NMR (400 MHz, DMSO-$d_6$): 12.98 (s, 1H), 10.00 (s, 1H), 9.52 (s, 1H), 9.16 (s, 1H), 8.11 (s, 1H), 7.70-7.61 (m, 2H), 7.46-7.40 (m, 4H), 7.22-7.19 (m, 1H), 6.22 (s, 1H), 5.21 (s, 2H), 3.11-3.05 (m, 2H), 1.19 (t, J = 7.2 Hz, 3H). |
| 147 | 3-(4-((difluoromethyl)sulfonamido)-3-(4-fluorophenoxy)phenyl)-5-((6-(trifluoromethyl)pyridine-2-yl)amino)-1H-pyrazole-4-carboxamide | 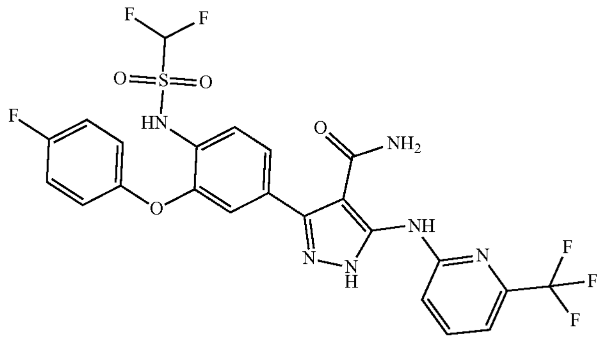 [SMILES: NC(=O)c1c(-c2ccc(NS(=O)(=O)C(F)F)c(Oc3ccc(F)cc3)c2)n[nH]c1Nc1cccc(C(F)(F)F)n1] | LCMS (Method A): 3.90 min; m/z: 587.1 $[M + H]^+$. | $^1H$ NMR (400 MHz, DMSO-$d_6$): 13.02 (s, 1H), 10.91 (s, 1H), 9.61 (s, 1H), 8.13 (d, J = 8.4 Hz, 1H), 7.95 (t, J = 8.0 Hz, 1H), 7.54 (d, J = 8.4 Hz, 1H), 7.37 (m, 1H), 7.27 (m, 3H), 7.18 (m, 2H), 7.07 (m, 2H). |

TABLE 24-continued

| Compound No. | Name | Structure | LCMS data | NMR data |
|---|---|---|---|---|
| 148 | 3-(3-(4-fluorophenoxy)-4-((2,2,2-trifluoroethyl)sulfonamido)phenyl)-5-((6-(trifluoromethyl)pyridine-2-yl)amino)-1H-pyrazole-4-carboxamide | 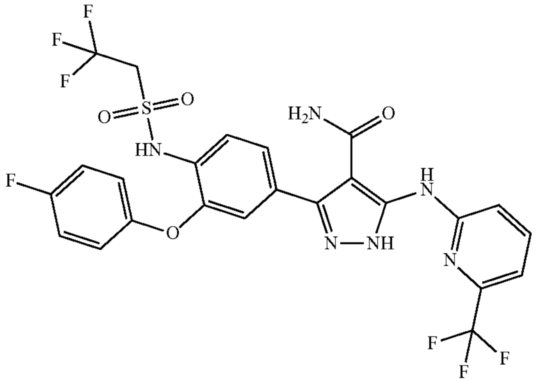 [SMILES: NC(=O)c1c(-c2ccc(NS(=O)(=O)CC(F)(F)F)c(Oc3ccc(F)cc3)c2)n[nH]c1Nc1cccc(C(F)(F)F)n1] | LCMS (Method A): 4.01 min; m/z: 619.1 $[M + H]^+$. | $^1H$ NMR (400 MHz, DMSO-$d_6$): 13.13 (s, 1H), 10.38 (s, 1H), 9.68 (s, 1H), 8.16 (d, J = 8.4 Hz, 1H), 7.97 (t, J = 8.0 Hz, 1H), 7.60 (d, J = 8.4 Hz, 1H), 7.38 (m, 1H), 7.29 (m, 3H), 7.19 (m, 2H), 7.07 (s, 1H), 4.52 (m, 2H), |
| 149 | 3-(4-(ethylsulfonamido)-3-(4-fluorophenoxy)phenyl)-5-((6-(trifluoromethyl)pyridine-2-yl)amino)-1H-pyrazole-4-carboxamide | 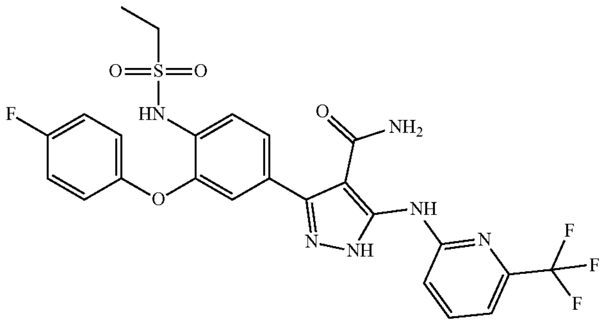 [SMILES: CCS(=O)(=O)Nc1ccc(-c2n[nH]c(Nc3cccc(C(F)(F)F)n3)c2C(N)=O)cc1Oc1ccc(F)cc1] | LCMS (Method A): 3.82 min; m/z: 565.1 $[M + H]^+$. | $^1H$ NMR (400 MHz, DMSO-$d_6$): 12.96 (s, 1H), 9.70 (s, 1H), 8.17 (s, 1H), 7.96 (t, J = 8.0 Hz, 1H), 7.59 (d, J = 8.4 Hz, 1H), 7.36 (m, 1H), 7.27 (m, 3H), 7.15 (m, 2H), 7.07 (d, J = 2.0 Hz, 1H), 3.13 (q, J = 7.2 Hz, 2H), 1.23 (t, J = 7.2 Hz, 2H). |

TABLE 24-continued

| Compound No. | Name | Structure | LCMS data | NMR data |
| --- | --- | --- | --- | --- |
| 150 | 3-(3-((3-chloro-4-fluorobenzyl)oxy)-4-(ethylsulfonamido)phenyl)-5-((5-methylpyrazin-2-yl)amino)-1H-pyrazole-4-carboxamide | 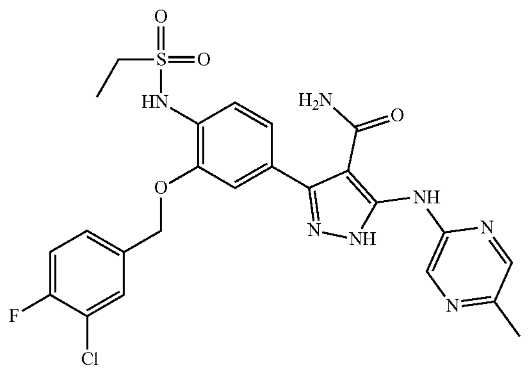 [SMILES: CCS(=O)(=O)Nc1ccc(-c2n[nH]c(Nc3cnc(C)cn3)c2C(N)=O)cc1OCc1ccc(F)c(Cl)c1] | LCMS (Method A): 3.38 min; m/z: 560.1 [M + H]+. | $^1$H NMR (400 MHz, DMSO-d$_6$): 12.97 (br s, 1H), 9.35 (br s, 1H), 9.16 (br s, 1H), 8.11 (s, 1H), 7.88 (dd, J = 7.2, 2.0 Hz, 1H), 7.59-7.37 (m, 5H), 7.18 (dd, J = 8.4, 2.0 Hz, 1H), 5.19 (s, 2H), 3.05 (q, J = 7.2 Hz, 2H), 2.40 (s, 3H), 1.17 (t, J = 7.2 Hz, 3H). |
| 151 | 3-(3-((3,4-difluorobenzyl)oxy)-4-((difluoromethyl)sulfonamido)phenyl)-5-((6-(trifluoromethyl)pyridine-2-yl)amino)-1H-pyrazole-4-carboxamide | 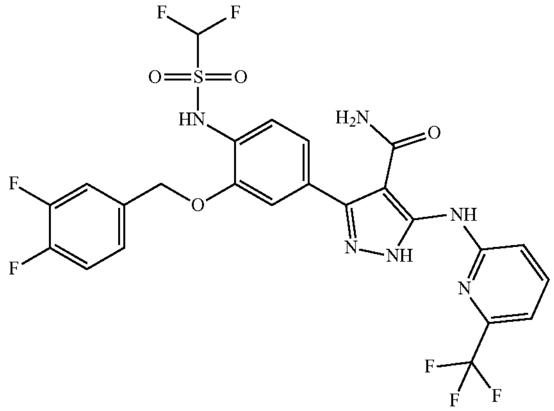 [SMILES: NC(=O)c1c(-c2ccc(NS(=O)(=O)C(F)F)c(OCc3ccc(F)c(F)c3)c2)n[nH]c1Nc1cccc(C(F)(F)F)n1] | LCMS (Method A): 2.23 min; m/z: 619.1 [M + H]+. | $^1$H NMR (400 MHz, DMSO-d$_6$): 13.06 (s, 1H), 10.61 (s, 1H), 9.72 (s, 1H), 8.18 (d, J = 8.4 Hz, 1H), 7.97 (t, J = 8.0 Hz, 1H), 7.71-7.66 (m, 1H), 7.51-7.39 (m, 4H), 7.30 (d, J = 7.2 Hz, 1H), 7.22 (d, J = 8.0 Hz, 1H), 6.98 (t, J = 52.8 Hz, 1H), 6.22 (s, 1H), 5.21 (s, 1H). |

TABLE 24-continued

| Compound No. | Name | Structure | LCMS data | NMR data |
| --- | --- | --- | --- | --- |
| 152 | 3-(4-(ethylsulfonamido)-3-(1-phenylcyclopropoxy)phenyl)-5-(pyrazin-2-ylamino)-1H-pyrazole-4-carboxamide | 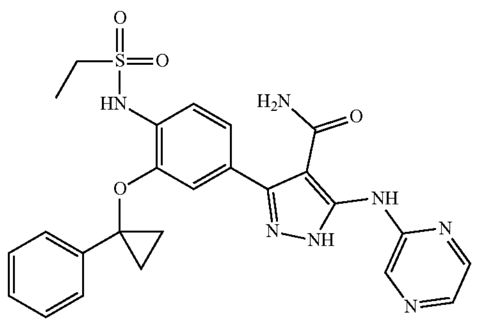 [SMILES: CCS(=O)(=O)Nc1ccc(-c2n[nH]c(Nc3cnccn3)c2C(N)=O)cc1OC1(c2ccccc2)CC1] | LCMS (Method B): 1.29 min; m/z: 520.1 $[M + H]^+$. | $^1H$ NMR (400 MHz, DMSO-$d_6$): 12.92 (br s, 1H), 9.60 (s, 1H), 9.31 (br s, 1H), 9.21 (s, 1H), 8.19 (s, 1H), 8.09 (d, J = 2.4 Hz, 1H), 7.44 (br s, 1H), 7.38-7.22 (m, 5H), 7.21-7.12 (m, 2H), 7.03 (br s, 1H), 6.18 (br s, 1H) 3.17 (q, J = 7.2 Hz, 2H), 1.49 (m, 2H), 1.42 (m, 2H) 1.32 (t, J = 7.6 Hz, 3H). |
| 153 | 3-(4-((2,2,2-trifluoroethyl)sulfonamido)phenyl)-5-((5-(trifluoromethyl)pyridine-2-yl)amino)-1H-pyrazole-4-carboxamide | 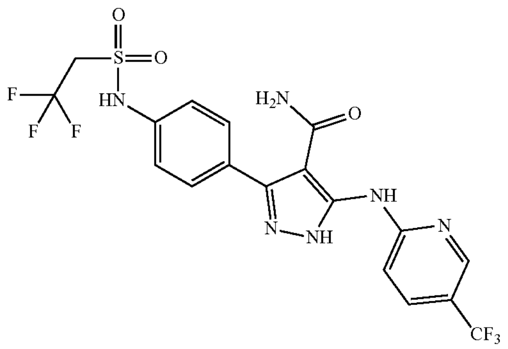 [SMILES: NC(=O)c1c(-c2ccc(NS(=O)(=O)CC(F)(F)F)cc2)n[nH]c1Nc1ccc(C(F)(F)F)cn1] | LCMS (Method A): 3.60 min; m/z: 509.1 $[M + H]^+$. | $^1H$ NMR (400 MHz, DMSO-$d_6$): 12.86 (s, 1H), 10.08 (s, 1H), 8.53 (s, 1H), 8.08 (s, 2H), 7.37 (d, J = 8.4 Hz, 3H), 7.14 (d, J = 8.4 Hz, 2H), 5.96 (s, 1H), 4.01 (t, J = 4.8 Hz, 2H). |
| 154 | (S)-3-(3-(1-(4-fluorophenyl)ethoxy)-4-((2,2,2-trifluoroethyl)sulfonamido)phenyl)-5-(pyridine-2-ylamino)-1H-pyrazole-4-carboxamide | 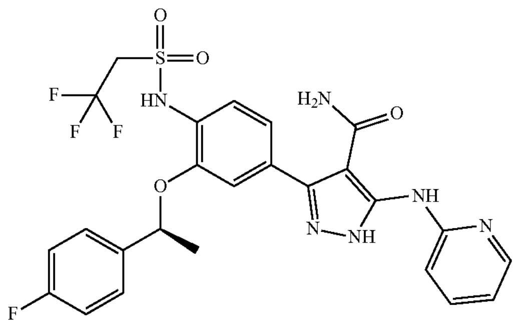 [SMILES: C[C@H](Oc1cc(-c2n[nH]c(Nc3ccccn3)c2C(N)=O)ccc1NS(=O)(=O)CC(F)(F)F)c1ccc(F)cc1] | LCMS (Method A): 2.00 min; m/z: 578.9 $[M + H]^+$. | $^1H$ NMR (400 MHz, MeOD-$d_4$): 8.28 (s, 1H), 7.71 (t, J = 8.0 Hz, 1H), 7.54-7.48 (m, 3H), 7.14-7.05 (m, 5H), 6.93 (t, J = 4.8 Hz, 1H), 5.58 (q, J = 6.0 Hz, 1H), 4.24 (q, J = 9.2 Hz, 2H), 1.69 (d, J = 6.4 Hz, 2H). |

TABLE 24-continued

| Compound No. | Name | Structure | LCMS data | NMR data |
|---|---|---|---|---|
| 155 | 3-(3-((3-chloro-4-fluorobenzyl)oxy)-4-((2,2,2-trifluoroethyl)sulfonamido)phenyl)-5-((5-methylpyrazin-2-yl)amino)-1H-pyrazole-4-carboxamide | 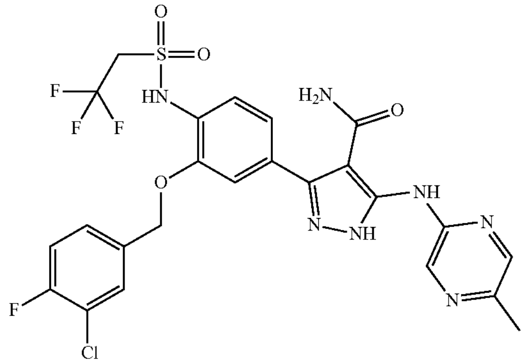 [SMILES: Cc1cnc(Nc2[nH]nc(-c3ccc(NS(=O)(=O)CC(F)(F)F)c(OCc4ccc(F)c(Cl)c4)c3)c2C(N)=O)cn1] | LCMS (Method A): 4.58 min; m/z: 614.1, 616.1 $[M + H]^+$. | $^1H$ NMR (400 MHz, DMSO-$d_6$): 13.00 (br s, 1H), 12.02 (br s, 1H), 9.51 (br s, 1H), 9.16 (br s, 1H), 8.11 (s, 1H), 7.83 (dd, J = 7.2, 2.0 Hz, 1H), 7.58-7.38 (m, 5H), 7.20 (dd, J = 7.6, 2.0 Hz, 1H), 5.19 (s, 2H), 4.34 (q, J = 10.0, Hz, 2H), 2.40 (s, 3H). |
| 156 | 3-(4-(ethylsulfonamido)-3-((5-fluoropyridin-2-yl)methoxy)phenyl)-5-(pyrazin-2-ylamino)-1H-pyrazole-4-carboxamide | 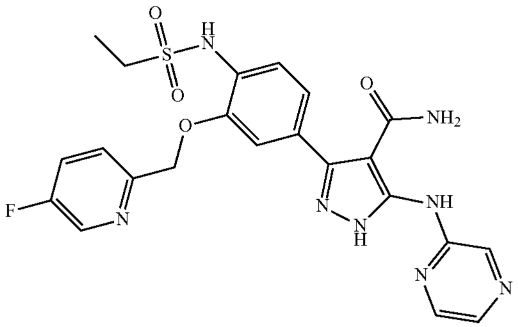 [SMILES: CCS(=O)(=O)Nc1ccc(-c2n[nH]c(Nc3cnccn3)c2C(N)=O)cc1OCc1ccc(F)cn1] | LCMS (Method A): 3.03 min; m/z: 513.1 $[M + H]^+$. | $^1H$ NMR (400 MHz, DMSO-$d_6$): 13.01 (s, 1H), 9.63 (s, 1H), 9.24 (s, 1H), 8.58 (s, 1H), 8.22 (s, 1H), 8.10 (d, J = 2.4 Hz, 1H), 7.84 (t, J = 6.8 Hz, 2H), 7.48 (m, 4H), 7.21 (m, 1H), 6.25 (s, 1H), 5.28 (s, 2H), 3.09 (m, 2H), 1.18 (t, J = 14.8 Hz, 3 H). |
| 157 | 3-(3-((4-chlorobenzyl)oxy)-4-((2,2,2-trifluoroethyl)sulfonamido)phenyl)-5-((5-methoxypyrazin-2-yl)amino)-1H-pyrazole-4-carboxamide | 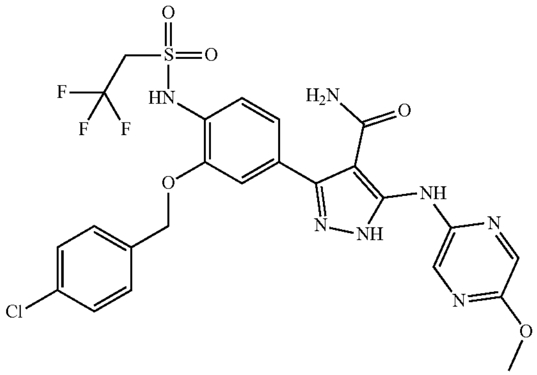 [SMILES: COc1cnc(Nc2[nH]nc(-c3ccc(NS(=O)(=O)CC(F)(F)F)c(OCc4ccc(Cl)cc4)c3)c2C(N)=O)cn1] | LCMS (Method A): 3.85 min; m/z: 612.1 $[M + H]^+$. | $^1H$ NMR (400 MHz, DMSO-$d_6$): 12.83 (s, 1H), 9.45 (s, 1H), 8.84 (s, 1H), 7.97 (s, 1H), 7.54 (m, 2H), 7.44 (m, 2H), 7.36 (m, 1H), 7.06 (s, 1H), 5.14 (s, 2H), 3.86 (m, 3H), 3.35 (m, 2H). |

TABLE 24-continued

| Compound No. | Name | Structure | LCMS data | NMR data |
|---|---|---|---|---|
| 158 | 5-((5-cyclopropylpyrazin-2-yl)amino)-3-(4-(ethylsulfonamido)phenyl)-1H-pyrazole-4-carboxamide | 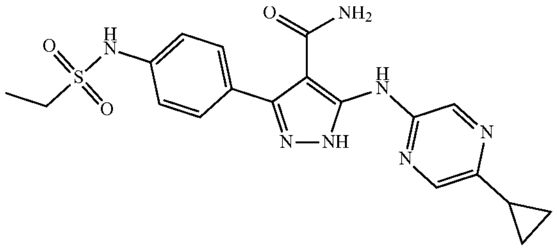 [SMILES: CCS(=O)(=O)Nc1ccc(-c2n[nH]c(Nc3cnc(C4CC4)cn3)c2C(N)=O)cc1] | LCMS (Method A): 3.14 min; m/z: 428.1 $[M + H]^+$. | $^1H$ NMR (400 MHz, DMSO-$d_6$): 12.88 (s, 1H), 9.55 (s, 1H), 9.05 (s, 1H), 8.30 (s, 1H), 8.18 (S, 1H), 7.53 (d, J = 8.4 Hz, 2H), 7.33 (d, J = 8.4 Hz, 2H), 3.17 (q, J = 14.8 Hz, 2H), 2.11 (m, 1H), 1.22 (m, 3H), 0.93 (m, 2H), 0.85 (m, 2H). |
| 159 | 3-(3-((4-fluorobenzyl)oxy)-4-((2,2,2-trifluoroethyl)sulfonamido)phenyl)-5-((6-methoxypyridin-3-yl)amino)-1H-pyrazole-4-carboxamide | 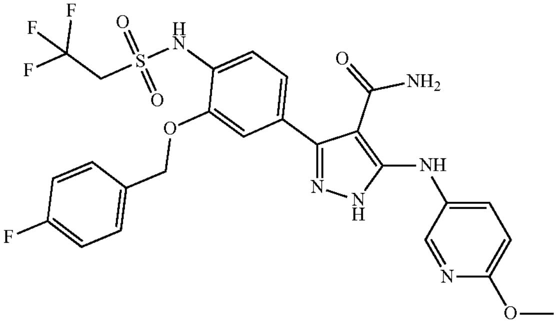 [SMILES: COc1ccc(Nc2[nH]nc(-c3ccc(NS(=O)(=O)CC(F)(F)F)c(OCc4ccc(F)cc4)c3)c2C(N)=O)cn1] | LCMS (Method A): 3.63 min; m/z: 595.1 $[M + H]^+$. | $^1H$ NMR (400 MHz, DMSO-$d_6$): 12.71 (s, 1H), 9.96 (s, 1H), 8.75 (s, 1H), 8.39 (s, 1H), 9.96 (d, J = 11.2 Hz, 1H), 7.62-7.58 (m, 2H), 7.43-7.40 (m, 2H), 7.26-7.22 (m, 2H), 7.19-7.17 (m, 1H), 6.75 (d, J = 8.8 Hz, 1H), 5.18 (s, 2H), 4.31 (q, J = 10.0 Hz, 2H), 3.80 (s, 3H). |
| 160 | 3-(3-((3,4-difluorobenzyl)oxy)-4-((2,2,2-trifluoroethyl)sulfonamido)phenyl)-5-(pyridine-2-ylamino)-1H-pyrazole-4-carboxamide | 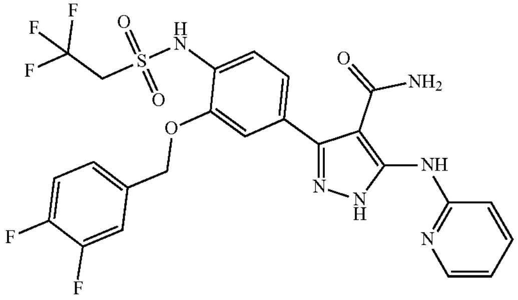 [SMILES: NC(=O)c1c(-c2ccc(NS(=O)(=O)CC(F)(F)F)c(OCc3ccc(F)c(F)c3)c2)n[nH]c1Nc1ccccn1] | LCMS (Method A): 3.35 min; m/z: 583.1 $[M + H]^+$. | $^1H$ NMR (400 MHz, DMSO-$d_6$): 12.89 (s, 1H), 9.94 (s, 1H), 9.50 (s, 1H), 8.18 (s, 1H), 7.96 (d, J = 8.0 Hz, 1H), 7.72-7.69 (m, 2H), 7.51-7.40 (m, 4H), 7.21 (d, J = 7.6 Hz, 1H), 6.92-6.86 (m, 1H), 6.13 (s, 1H), 5.20 (s, 2H), 4.38 (q, J = 9.2 Hz, 2H). |

TABLE 24-continued

| Compound No. | Name | Structure | LCMS data | NMR data |
|---|---|---|---|---|
| 161 | 3-(3-(1-phenylcyclopropoxy)-4-((2,2,2-trifluoroethyl)sulfonamido)phenyl)-5-(pyrazin-2-ylamino)-1H-pyrazole-4-carboxamide | 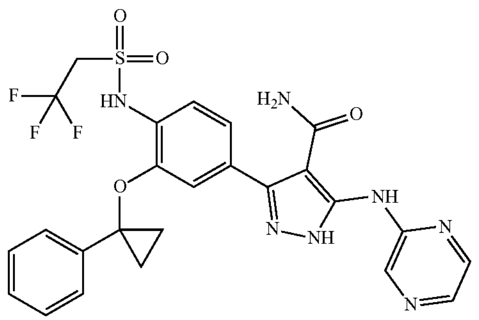 [SMILES: NC(=O)c1c(-c2ccc(NS(=O)(=O)CC(F)(F)F)c(OC3(c4ccccc4)CC3)c2)n[nH]c1Nc1cnccn1] | LCMS (Method A): 1.62 min; m/z: 574.3 $[M + H]^+$. | $^1H$ NMR (400 MHz, DMSO-$d_6$): 12.95 (s, 1H), 10.05 (br s, 1H), 9.63 (s, 1H), 9.22 (s, 1H), 8.19 (s, 1H), 8.09 (d, J = 2.4 Hz, 1H), 7.50-7.38 (m. 1H), 7.32-7.22 (m, 5H), 7.21-7.10 (m, 2H), 7.03 (s, 1H), 6.20 (br s, 1H), 4.44 (d, J = 6.8 Hz, 2H), 1.52-1.45 (m, 2H), 1.51-1.38 (m, 2H). |
| 162 | 3-(3-((4-chlorobenzyl)oxy)-4-((2,2,2-trifluoroethyl)sulfonamido)phenyl)-5-((5-methylpyrazin-2-yl)amino)-1H-pyrazole-4-carboxamide | 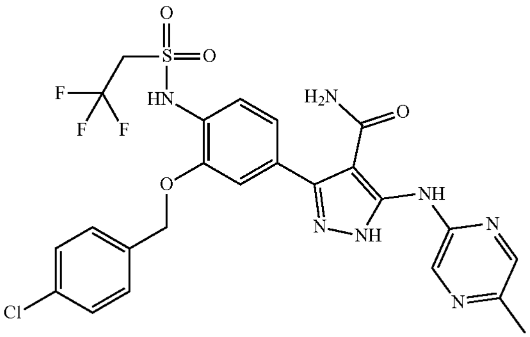 [SMILES: Cc1cnc(Nc2[nH]nc(-c3ccc(NS(=O)(=O)CC(F)(F)F)c(OCc4ccc(Cl)cc4)c3)c2C(N)=O)cn1] | LCMS (Method A): 3.68 min; m/z: 596.1, 598.1 $[M + H]^+$. | $^1H$ NMR (400 MHz, DMSO-$d_6$): 13.04 (br s, 1H), 9.98 (br s, 1H), 9.51 (br s, 1H), 9.16 (br s, 1H), 8.11 (s, 1H), 7.58 (d, J = 8.4 Hz, 2H), 7.47 (d, J = 8.4 Hz, 2H), 7.44-7.34 (m, 3H), 7.20 (dd, J = 8.0, 2.0 Hz, 1H), 5.21 (s, 2H), 4.33 (q, J = 9.6 Hz, 2H), 2.40 (s, 3H). |
| 163 | 3-(3-((4-fluorobenzyl)oxy)-4-((2,2,2-trifluoroethyl)sulfonamido)phenyl)-5-((5-methylpyrazin-2-yl)amino)-1H-pyrazole-4-carboxamide | 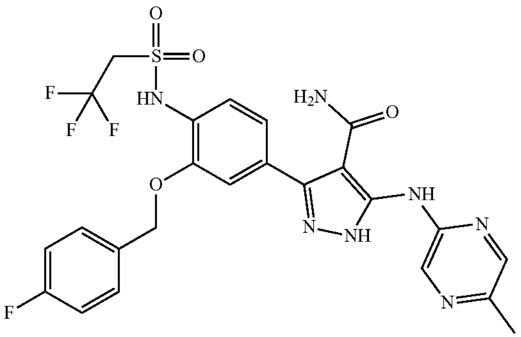 | LCMS (Method A): 3.55 min; m/z: 560.1 $[M + H]^+$. | $^1H$ NMR (400 MHz, DMSO-$d_6$): 13.06 (br s, 1H), 10.02 (br s, 1H), 9.49 (br s, 1H), 9.15 (br s, 1H), 8.12 (s, 1H), 7.61-7.57 (m, 2H), 7.47-7.38 (m, 3H), 7.26-7.18 (m, 3H), 5.19 (s, 2H), 4.31 (q, J = 9.6 Hz, 2H), 2.39 (s, 3H). |

TABLE 24-continued

| Compound No. | Name | Structure | LCMS data | NMR data |
|---|---|---|---|---|
| 164 | (S)-3-(3-(1-(4-fluorophenyl)ethoxy)-4-((2,2,2-trifluoroethyl)sulfonamido)phenyl)-5-(pyrazin-2-ylamino)-1H-pyrazole-4-carboxamide | 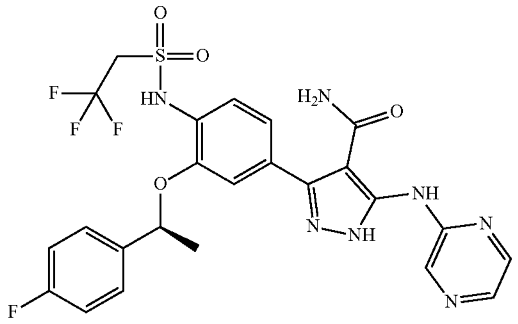 | LCMS (Method A): 3.55 min; m/z: 580.1 $[M + H]^+$. | $^1H$ NMR (400 MHz, DMSO-$d_6$): 13.01 (s, 1H), 9.96 (s, 1H), 9.60 (s, 1H), 9.21 (s, 1H), 8.21 (s, 1H), 8.10 (d, J = 2.4 Hz, 1H), 7.59 (d, J = 5.6 Hz, 2H), 7.43 (d, J = 8.0 Hz, 1H), 7.24 (s, 1H), 7.20-7.13 (m, 3H), 6.15 (s, 1H), 5.66 (q, J = 5.6 Hz, 1H), 4.52-4.41 (m, 2H), 1.59 (d, J = 6.4 Hz, 3H). |
| 165 | 3-(3-((4-chloro-3-fluorobenzyl)oxy)-4-((2,2,2-trifluoroethyl)sulfonamido)phenyl)-5-(pyrazin-2-ylamino)-1H-pyrazole-4-carboxamide | 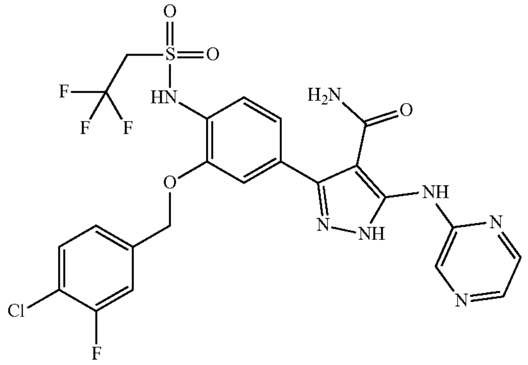 [SMILES: NC(=O)c1c(-c2ccc(NS(=O)(=O)CC(F)(F)F)c(OCc3ccc(Cl)c(F)c3)c2)n[nH]c1Nc1cnccn1] | LCMS (Method A): 3.62 min; m/z: 600.1 $[M + H]^+$. | $^1H$ NMR (400 MHz, DMSO-$d_6$): 13.02 (s, 1H), 10.01 (s, 1H), 9.66 (s, 1H), 9.26 (s, 1H), 8.23 (s, 1H), 8.12 (s, 1H), 7.69-7.61 (m, 2H), 7.45-7.36 (m, 4H), 7.20 (d, J = 8.4 Hz, 1H), 6.22 (s, 1H), 5.21 (s, 2H), 4.29 (s, 2H). |
| 166 | 3-(3-((4-chloro-3-fluorobenzyl)oxy)-4-(ethylsulfonamido)phenyl)-5-(pyrazin-2-ylamino)-1H-pyrazole-4-carboxamide | 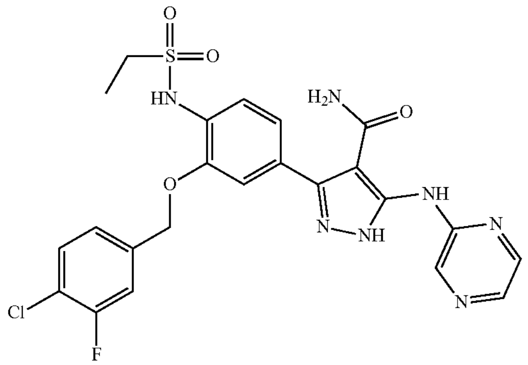 [SMILES: CCS(=O)(=O)Nc1ccc(-c2n[nH]c(Nc3cnccn3)c2C(N)=O)cc1OCc1ccc(Cl)c(F)c1] | LCMS (Method A): 3.46 min; m/z: 546.1 $[M + H]^+$. | $^1H$ NMR (400 MHz, DMSO-$d_6$): 13.01 (s, 1H), 9.64 (s, 1H), 9.31 (s, 1H), 9.25 (s, 1H), 8.23 (s, 1H), 8.11 (s, 1H), 7.76-7.73 (m, 1H), 7.73-7.76 (m, 1H), 7.48-7.38 (m, 4H), 7.22-7.19 (m, 1H), 6.22 (s, 1H), 5.21 (s, 2H), 3.11-3.05 (m, 2H), 1.19 (t, J = 7.2 Hz, 3H). |

TABLE 24-continued

| Compound No. | Name | Structure | LCMS data | NMR data |
| --- | --- | --- | --- | --- |
| 167 | 3-(3-(3-fluorophenoxy)-4-((2,2,2-trifluoroethyl)sulfonamido)phenyl)-5-(pyrazin-2-ylamino)-1H-pyrazole-4-carboxamide | 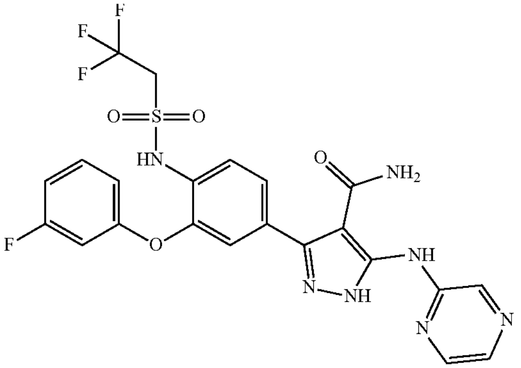 [SMILES: NC(=O)c1c(-c2ccc(NS(=O)(=O)CC(F)(F)F)c(Oc3cccc(F)c3)c2)n[nH]c1Nc1cnccn1] | LCMS (Method A): 1.53 min; m/z: 552.2 $[M + H]^+$. | $^1H$ NMR (400 MHz, DMSO-$d_6$): 13.03 (s, 1H), 10.36 (s, 1H), 9.55 (s, 1H), 9.20 (s, 1H), 8.20 (s, 1H), 8.09 (d, J = 2.8 Hz, 1H), 7.62 (d, J = 8.4 Hz, 1H), 7.46-7.41 (m, 2H), 7.21-7.19 (m, 1H), 6.99-6.94 (m, 2H), 4.50-4.48 (m, 2H). |
| 168 | 3-(3-(4-chlorophenoxy)-4-((2,2,2-trifluoroethyl)sulfonamido)phenyl)-5-(pyrazin-2-ylamino)-1H-pyrazole-4-carboxamide | 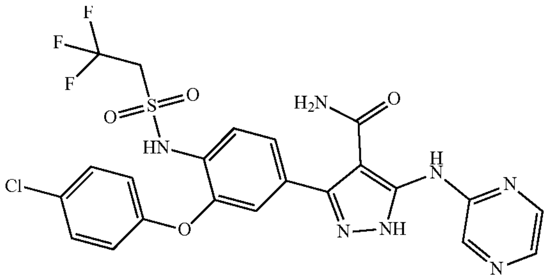 [SMILES: NC(=O)c1c(-c2ccc(NS(=O)(=O)CC(F)(F)F)c(Oc3ccc(Cl)cc3)c2)n[nH]c1Nc1cnccn1] | LCMS (Method A): 3.53 min; m/z: 568.1, 570.1 $[M + H]^+$. | $^1H$ NMR (400 MHz, DMSO-$d_6$): 13.11 (br s, 1H), 9.55 (br s, 1H), 9.19 (br s, 1H), 8.19 (s, 1H), 8.08 (d, J = 2.0 Hz, 1H), 7.59-7.56 (m, 1H), 7.44-7.35 (m, 4H), 7.14-7.06 (m, 3H), 4.42 (q, J = 9.6 Hz, 2H). |
| 169 | 3-(4-(cyclopropanesulfonamido)-3-((4-fluorobenzyl)oxy)phenyl)-5-(pyrazin-2-ylamino)-1H-pyrazole-4-carboxamide | 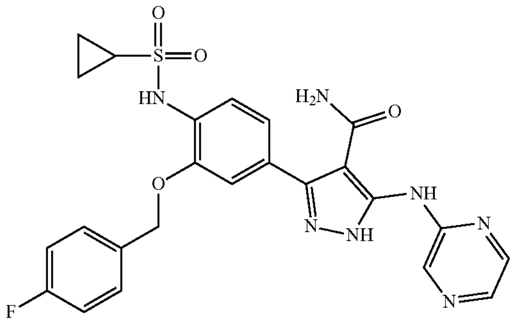 [SMILES: NC(=O)c1c(-c2ccc(NS(=O)(=O)C3CC3)c(OCc3ccc(F)cc3)c2)n[nH]c1Nc1cnccn1] | LCMS (Method A): 3.36 min; m/z: 524.1 $[M + H]^+$. | $^1H$ NMR (400 MHz, DMSO-$d_6$): 9.31 (s, 1H), 8.44 (s, 1H), 8.32-8.23 (m, 1H), 8.08 (s, 1H), 7.61-7.54 (m, 3H), 7.34 (m, 1H), 7.20 (d, J = 9.2 Hz, 1H), 7.13 (t, J = 8.4 Hz, 2H), 5.24 (s, 1H), 2.60-2.54 (m, 1H), 1.12-0.98 (m, 2H), 0.90-0.85 (m, 2H). |

TABLE 24-continued

| Compound No. | Name | Structure | LCMS data | NMR data |
|---|---|---|---|---|
| 170 | 3-(3-((4-fluorobenzyl)oxy)-4-((2,2,2-trifluoroethyl)sulfonamido)phenyl)-5-(pyrazin-2-ylamino)-1H-pyrazole-4-carboxamide | 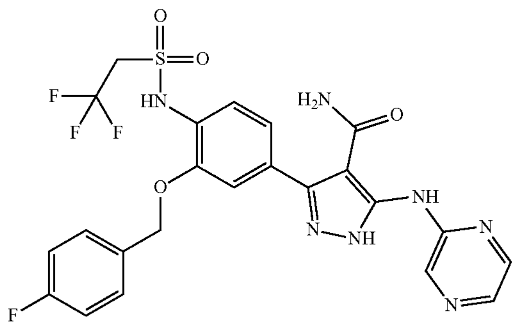 [SMILES: NC(=O)c1c(-c2ccc(NS(=O)(=O)CC(F)(F)F)c(OCc3ccc(F)cc3)c2)n[nH]c1Nc1cnccn1] | LCMS (Method A): 3.49 min; m/z: 566.1 $[M + H]^+$. | $^1H$ NMR (400 MHz, DMSO-$d_6$): 13.07 (s, 1H), 9.95 (s, 1H), 9.64 (s, 1H), 9.25 (s, 1H), 8.23-8.22 (m, 1H), 8.11 (d, J = 2.4 Hz, 1H), 7.62-7.59 (m, 2H), 7.45-7.43 (m, 1H), 7.27-7.21 (m, 3H), 5.19 (s, 2H), 4.34 (q, J = 9.6 Hz, 2H). |
| 171 | 3-(4-(ethylsulfonamido)-3-((4-fluoro-2-methylbenzyl)oxy)phenyl)-5-(pyrazin-2-ylamino)-1H-pyrazole-4-carboxamide | 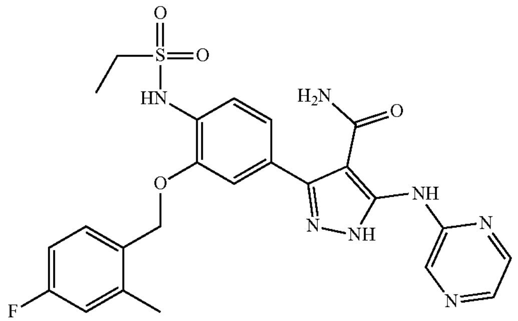 [SMILES: CCS(=O)(=O)Nc1ccc(-c2n[nH]c(Nc3cnccn3)c2C(N)=O)cc1OCc1ccc(F)cc1C] | LCMS (Method A: 3.42 min; m/z: 526.1 $[M + H]^+$. | $^1H$ NMR (400 MHz, DMSO-$d_6$): 13.03 (s, 1H), 9.63 (s, 1H), 9.25 (s, 1H), 9.13 (s, 1H), 8.22 (q, J = 1.6 Hz, 1H), 8.11 (d, J = 2.4 Hz, 1H), 7.55 (q, J = 6.4 Hz, 1H), 7.45 (t, J = 5.2 Hz, 2H), 7.20 (q, J = 1.6 Hz, 1H), 7.12 (q, J = 2.4 Hz, 1H), 7.08-7.03 (m, 1H), 5.14 (s, 2H), 3.03 (q, J = 7.2 Hz, 2H), 2.37 (s, 3H), 1.11 (t, J = 7.6 Hz, 3H). |
| 172 | 3-(4-(ethylsulfonamido)-3-((4-fluorobenzyl)oxy)phenyl)-5-((6-(trifluoromethoxy)pyridine-2-yl)amino)-1H-pyrazole-4-carboxamide | 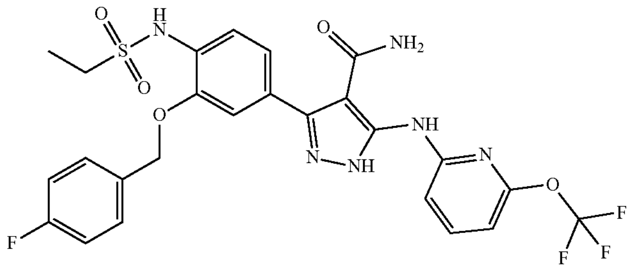 [SMILES: CCS(=O)(=O)Nc1ccc(-c2n[nH]c(Nc3cccc(OC(F)(F)F)n3)c2C(N)=O)cc1OCc1ccc(F)cc1] | LCMS (Method A): 3.99 min; m/z: 595.1 $[M + H]^+$. | $^1H$ NMR (400 MHz, DMSO-$d_6$): 12.98 (s, 1H), 9.60 (s, 1H), 9.19 (s, 1H), 7.95-7.88 (m, 2H), 7.61 (q, J = 6.0 Hz, 2H), 7.45 (d, J = 8.0 Hz, 1H), 7.40 (d, J = 1.6 Hz, 1H), 7.27-7.17 (m, 3H), 6.68 (q, J = 1.6 Hz, 1H), 5.18 (s, 2H), 3.04 (q, J = 7.2 Hz, 2H), 1.15 (t, J = 7.2 Hz, 3H). |

TABLE 24-continued

| Compound No. | Name | Structure | LCMS data | NMR data |
|---|---|---|---|---|
| 173 | 5-((6-(difluoromethyl)pyridine-2-yl)amino)-3-(3-((4-fluorobenzyl)oxy)-4-((2,2,2-trifluoroethyl)sulfonamido)phenyl)-1H-pyrazole-4-carboxamide | 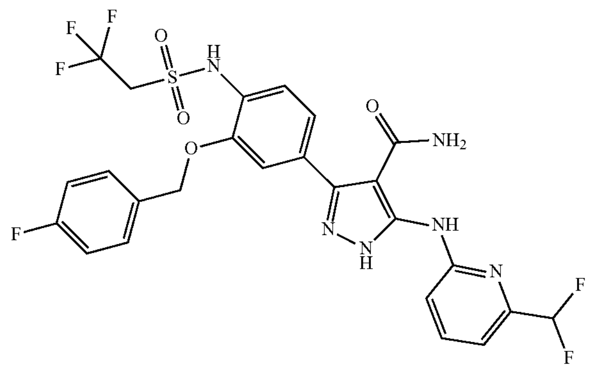 [SMILES: NC(=O)c1c(-c2ccc(NS(=O)(=O)CC(F)(F)F)c(OCc3ccc(F)cc3)c2)n[nH]c1Nc1cccc(C(F)F)n1] | LCMS (Method A): 3.89 min; m/z: 615.1 $[M + H]^+$. | $^1H$ NMR (400 MHz, DMSO-$d_6$): 12.98 (s, 1H), 9.96 (s, 1H), 9.68 (s, 1H), 8.10 (d, J = 8.4 Hz, 1H), 7.90 (t, J = 7.6 Hz, 1H), 7.60 (q, J = 3.2 Hz, 2H), 8.13 (d, J = 7.6 Hz, 1H), 7.45 (s, 1H), 7.35 (m, 2H), 7.22 (m, 1H), 7.13 (d, J = 7.2 Hz, 1H), 6.82 (t, J = 5.2 Hz, 1H), 6.17 (s, 1H), 5.19 (s, 2H), 4.35 (q, J = 9.6 Hz, 2H). |
| 174 | 3-(4-(ethylsulfonamido)-3-((4-fluorobenzyl)oxy)phenyl)-5-((6-(2-methoxyethoxy)pyridine-2-yl)amino)-1H-pyrazole-4-carboxamide | 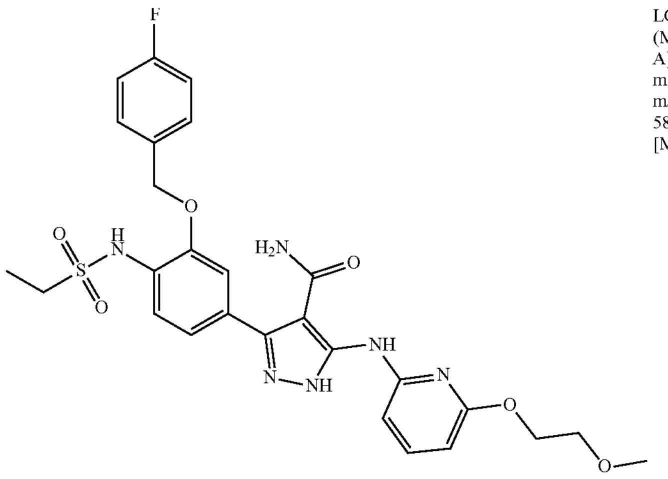 | LCMS (Method A): 3.78 min; m/z: 585.2 $[M + H]^+$. | $^1H$ NMR (400 MHz, DMSO-$d_6$): 12.79 (s, 1H), 9.38 (s, 1H), 7.63 (m, 4H), 7.42 (d, J = 8.4 Hz, 1H), 7.30 (s, 1H), 7.26 (t, J = 2.4 Hz, 3H), 7.12 (d, 1H), 6.27 (d, J = 8.0 Hz, 1H), 5.16 (s, 2H), 4.35 (s, 2H), 3.67 (t, J = 4.8 Hz, 2H), 3.31 (s, 3H), 3.02-2.66 (m, 2H), 1.17 (t, J = 7.2, 3H). |

TABLE 24-continued

| Compound No. | Name | Structure | LCMS data | NMR data |
|---|---|---|---|---|
| 175 | 3-(3-((3,4-difluorobenzyl)oxy)-4-((2,2,2-trifluoroethyl)sulfonamido)phenyl)-5-(pyrazin-2-ylamino)-1H-pyrazole-4-carboxamide | 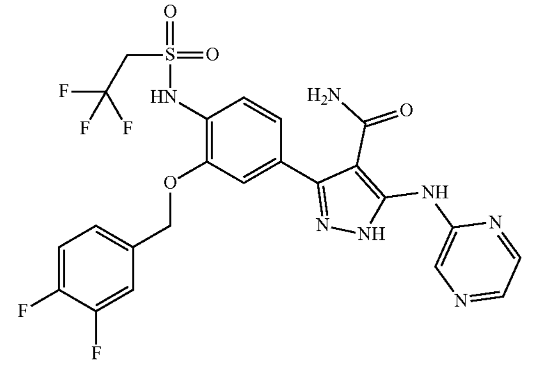 [SMILES: NC(=O)c1c(-c2ccc(NS(=O)(=O)CC(F)(F)F)c(OCc3ccc(F)c(F)c3)c2)n[nH]c1Nc1cnccn1] | LCMS (Method A): 1.69 min; m/z: 584.1 $[M + H]^+$. | $^1H$ NMR (400 MHz, DMSO-$d_6$): 13.06 (s, 1H), 9.99 (s, 1H), 9.63 (s, 1H), 9.24 (s, 1H), 8.23-8.22 (m, 1H), 8.11-8.09 (m, 1H), 7.72-7.67 (m, 1H), 7.55-7.39 (m, 5H), 7.24-7.21 (m, 1H), 6.25 (s, 1H), 5.19 (s, 2H), 4.42-4.35 (m, 2H). |
| 176 | 3-(3-((4-fluorobenzyl)oxy)-4-((2,2,2-trifluoroethyl)sulfonamido)phenyl)-5-((6-(trifluoromethyl)pyridine-3-yl)amino)-1H-pyrazole-4-carboxamide | 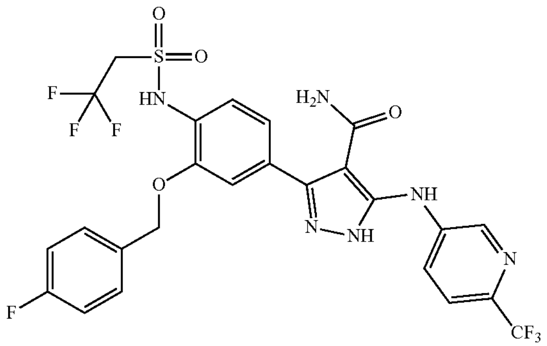 [SMILES: NC(=O)c1c(-c2ccc(NS(=O)(=O)CC(F)(F)F)c(OCc3ccc(F)cc3)c2)n[nH]c1Nc1ccc(C(F)(F)F)nc1] | LCMS (Method A): 3.91 min; m/z: 633.1 $[M + H]^+$. | $^1H$ NMR (400 MHz, DMSO-$d_6$): 13.01 (s, 1H), 9.96 (s, 1H), 9.43 (s, 1H), 8.82 (d, J = 2.4 Hz, 1H), 8.27 (dd, J = 8.4, 2.4 Hz, 1H), 7.77 (d, J = 8.4 Hz, 1H), 7.62-7.59 (m, 2H), 7.46 (d, J = 1.6 Hz, 1H), 7.43 (d, J = 8.4 Hz, 1H), 7.27-7.22 (m, 3H), 5.19 (s, 2H), 4.35 (q, J = 9.6 Hz, 2H). |
| 177 | 3-(4-((difluoromethyl)sulfonamido)-3-(4-fluorophenoxy)phenyl)-5-(pyrazin-2-ylamino)-1H-pyrazole-4-carboxamide | 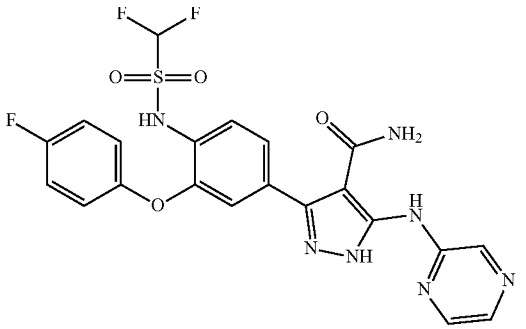 [SMILES: NC(=O)c1c(-c2ccc(NS(=O)(=O)C(F)F)c(Oc3ccc(F)cc3)c2)n[nH]c1Nc1cnccn1] | LCMS (Method A): 3.30 min; m/z: 520.1 $[M + H]^+$. | $^1H$ NMR (400 MHz, DMSO-$d_6$): 13.0 (br s, 1H), 9.53 (br s, 1H), 9.19 (br s, 1H), 8.19 (s, 1H), 8.08 (s, 1H), 7.53 (d, J = 8.0 Hz, 1H), 7.40-7.14 (m, 5H), 7.10-7.02 (m, 3H). |

TABLE 24-continued

| Compound No. | Name | Structure | LCMS data | NMR data |
|---|---|---|---|---|
| 178 | 3-(4-((2,2-difluoroethyl)sulfonamido)-3-((4-fluorobenzyl)oxy)phenyl)-5-((6-(trifluoromethyl)pyridine-2-yl)amino)-1H-pyrazole-4-carboxamide | 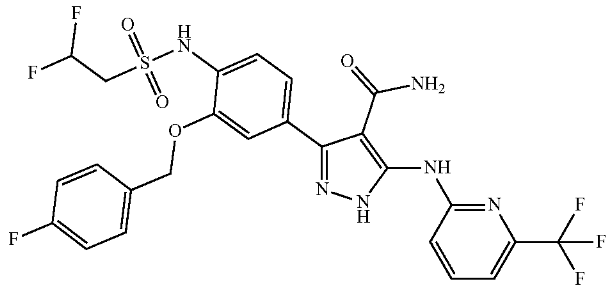 [SMILES: NC(=O)c1c(-c2ccc(NS(=O)(=O)CC(F)F)c(OCc3ccc(F)cc3)c2)n[nH]c1Nc1cccc(C(F)(F)F)n1] | LCMS (Method A): 3.07 min; m/z: 615.1 $[M + H]^+$. | $^1H$ NMR (400 MHz, DMSO-$d_6$): 13.03 (s, 1H), 9.78 (s, 1H), 8.21 (d, J = 8.4 Hz, 1H), 7.98 (t, J = 7.6 Hz, 1H), 7.61 (q, J = 5.6 Hz, 2H), 7.44 (t, J = 3.6 Hz, 2H), 7.31-7.20 (m, 5H), 7.47-6.17 (m, 1H), 5.19 (s, 2H), 3.85-3.77 (m, 2H). |
| 179 | 5-((6-(difluoromethyl)pyridine-2-yl)amino)-3-(4-(ethylsulfonamido)-3-((4-fluorobenzyl)oxy)phenyl)-1H-pyrazole-4-carboxamide | 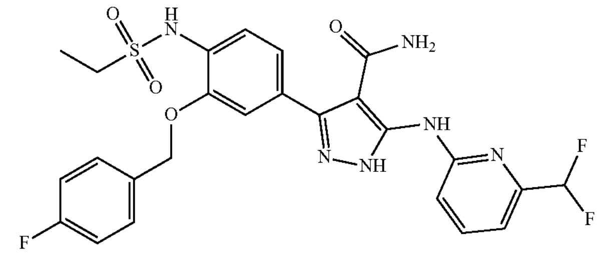 [SMILES: CCS(=O)(=O)Nc1ccc(-c2n[nH]c(Nc3cccc(C(F)F)n3)c2C(N)=O)cc1OCc1ccc(F)cc1] | LCMS (Method A): 2.47 min; m/z: 561.1 $[M + H]^+$. | $^1H$ NMR (400 MHz, DMSO-$d_6$): 12.94 (s, 1H), 9.68 (s, 1H), 9.19 (s, 1H), 8.11 (d, J = 8.4 Hz, 1H), 7.90 (t, J = 8.0 Hz, 1H), 7.62 (q, J = 5.6 Hz, 2H), 7.44 (t, J = 8.0 Hz, 2H), 7.26-7.12 (m, 4H), 6.82 (t, J = 5.2 Hz, 1H), 5.18 (s, 2H), 3.04 (q, J = 7.2 Hz, 2H), 1.15 (t, J = 7.2 Hz, 1H). |
| 180 | 3-(4-((2,2-difluoroethyl)sulfonamido)-3-((4-fluorobenzyl)oxy)phenyl)-5-(pyrazin-2-ylamino)-1H-pyrazole-4-carboxamide | 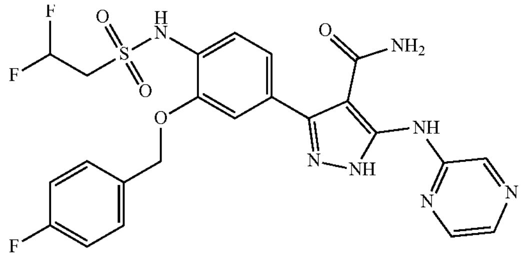 [SMILES: NC(=O)c1c(-c2ccc(NS(=O)(=O)CC(F)F)c(OCc3ccc(F)cc3)c2)n[nH]c1Nc1cnccn1] | LCMS (Method A): 3.37 min; m/z: 548.1 $[M + H]^+$. | $^1H$ NMR (400 MHz, DMSO-$d_6$): 13.06 (s, 1H), 9.79 (s, 1H), 9.65 (s, 1H), 9.25 (s, 1H), 8.23-8.22 (m, 1H), 8.11 (d, J = 2.4 Hz, 1H), 7.63-7.60 (m, 2H), 7.45-7.43 (m, 2H), 7.27-7.21 (m, 3H), 6.37-6.17 (m, 2H), 5.19 (s, 2H), 3.81 (td, J = 14.1, 4.0 Hz, 2H). |

TABLE 24-continued

| Compound No. | Name | Structure | LCMS data | NMR data |
|---|---|---|---|---|
| 181 | 5-((5-(tert-butyl)pyrazin-2-yl)amino)-3-(4-(ethylsulfonamido)phenyl)-1H-pyrazole-4-carboxamide | 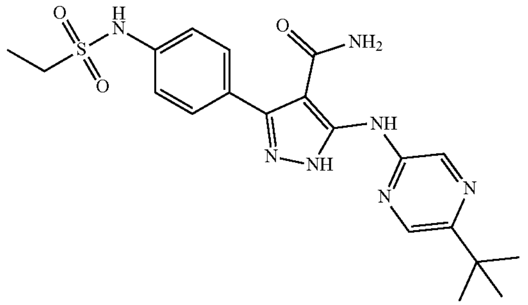 [SMILES: CCS(=O)(=O)Nc1ccc(-c2n[nH]c(Nc3cnc(C(C)(C)C)cn3)c2C(N)=O)cc1] | LCMS (Method A): 3.38 min; m/z: 444.2 $[M + H]^+$. | $^1$H NMR (400 MHz, DMSO-$d_6$): 12.89 (s, 1H), 10.08 (s, 1H), 9.49 (s, 1H), 9.18 (s, 1H), 8.26 (s, 1H), 7.55 (d, J = 8.8 Hz, 2H), 7.34 (d, J = 8.0 Hz, 3H), 6.11 (s, 1H), 3.20-3.15 (m, 2H), 1.32 (s, 9H), 1.22 (t, J = 7.2 Hz, 3H). |
| 182 | 3-(3-((4-fluorobenzyl)oxy)-4-((3,3,3-trifluoropropyl)sulfonamido)phenyl)-5-((6-(trifluoromethyl)pyridine-2-yl)amino)-1H-pyrazole-4-carboxamide | 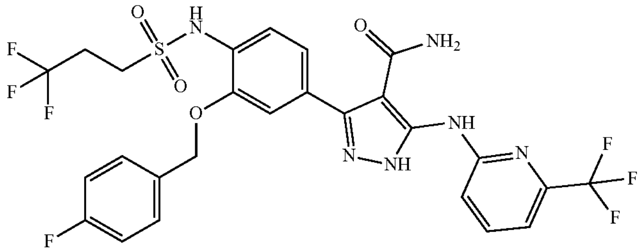 [SMILES: NC(=O)c1c(-c2ccc(NS(=O)(=O)CCC(F)(F)F)c(OCc3ccc(F)cc3)c2)n[nH]c1Nc1cccc(C(F)(F)F)n1] | LCMS (Method A): 4.08 min; m/z: 647.1 $[M + H]^+$. | $^1$H NMR (400 MHz, DMSO-$d_6$): 13.17 (s, 1H), 9.77 (s, 1H), 8.22 (s, 1H), 7.98 (t, J = 8.0 Hz, 1H), 7.64 (m, 2H), 7.43 (t, J = 8.4 Hz, 2H), 7.31 (d, J = 7.2 Hz, 1H), 7.23 (m, 3H), 6.30 (s, 1H), 5.19 (m, 2H), 3.20 (m, 2H), 2.67 (m, 2H). |
| 183 | 3-(3-((4-fluorobenzyl)oxy)-4-((3,3,3-trifluoropropyl)sulfonamido)phenyl)-5-((5-methylpyrazin-2-yl)amino)-1H-pyrazole-4-carboxamide | 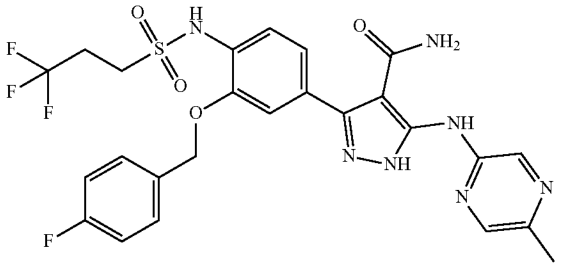 [SMILES: Cc1cnc(Nc2[nH]nc(-c3ccc(NS(=O)(=O)CCC(F)(F)F)c(OCc4ccc(F)cc4)c3)c2C(N)=O)cn1] | LCMS (Method A): 3.59 min; m/z: 594.1 $[M + H]^+$. | $^1$H NMR (400 MHz, DMSO-$d_6$): 13.03 (s, 1H), 9.54 (s, 1H), 9.17 (s, 1H), 8.11 (s, 1H), 7.61 (m, 2H), 7.39 (m, 2H), 7.22 (t, J = 8.8 Hz, 2H), 7.15 (d, J = 8.0 Hz, 1H), 5.16 (s, 2H), 3.15 (m, 2H), 2.65 (m, 2H), 2.40 (s, 3H). |

TABLE 24-continued

| Compound No. | Name | Structure | LCMS data | NMR data |
| --- | --- | --- | --- | --- |
| 184 | 3-(3-((4-fluorobenzyl)oxy)-4-((3,3,3-trifluoropropyl)sulfonamido)phenyl)-5-(pyrazin-2-ylamino)-1H-pyrazole-4-carboxamide | 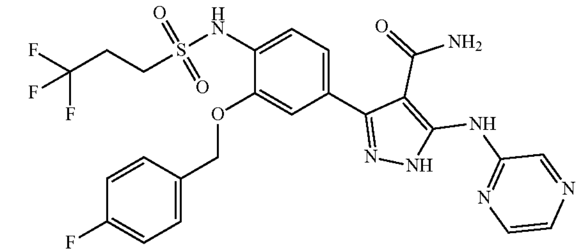 [SMILES: NC(=O)c1c(-c2ccc(NS(=O)(=O)CCC(F)(F)F)c(OCc3ccc(F)cc3)c2)n[nH]c1Nc1cnccn1] | LCMS (Method A): 3.52 min; m/z: 580.1 $[M + H]^+$. | $^1$H NMR (400 MHz, DMSO-$d_6$): 13.19 (s, 1H), 9.72 (s, 1H), 9.63 (s, 1H), 9.24 (s, 1H), 8.20 (s, 1H), 8.10 (d, J = 2.4 Hz, 1H), 7.63 (m, 2H), 7.43 (m, 2H), 7.23 (t, J = 8.8 Hz, 3H), 5.19 (s, 2H), 3.22 (m, 2 H), 2.66 (m, 2H). |
| 185 | 3-(3-(4-chlorophenoxy)-4-(ethylsulfonamido)phenyl)-5-(pyrazin-2-ylamino)-1H-pyrazole-4-carboxamide | 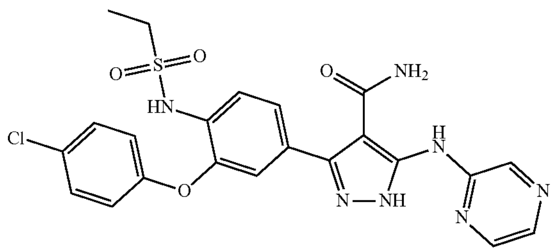 [SMILES: CCS(=O)(=O)Nc1ccc(-c2n[nH]c(Nc3cnccn3)c2C(N)=O)cc1Oc1ccc(Cl)cc1] | LCMS (Method A): 3.33 min; m/z: 514.1, 516.1 $[M + H]^+$. | $^1$H NMR (400 MHz, DMSO-$d_6$): 13.15 (br s, 1H), 9.55 (br s, 1H), 9.20 (br s, 1H), 9.19 (d, J = 0.8 Hz, 1H), 8.09 (d, J = 0.8 Hz, 1H), 7.62-7.60 (m, 1H), 7.47-7.40 (m, 4H), 7.16-7.14 (m, 3H), 3.15 (q, J = 7.2 Hz, 2H), 1.20 (t, J = 7.2 Hz, 3H). |
| 186 | 3-(3-((4-fluorobenzyl)oxy)-4-((2,2,2-trifluoroethyl)sulfonamido)phenyl)-5-((2-(trifluoromethyl)pyrimidin-4-yl)amino)-1H-pyrazole-4-carboxamide | 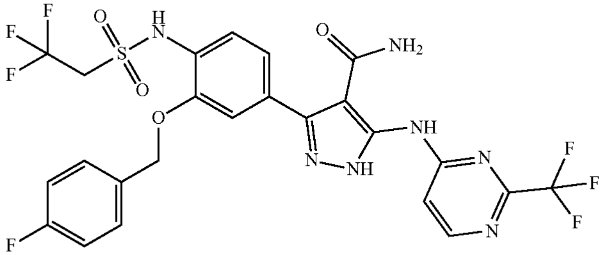 [SMILES: NC(=O)c1c(-c2ccc(NS(=O)(=O)CC(F)(F)F)c(OCc3ccc(F)cc3)c2)n[nH]c1Nc1ccnc(C(F)(F)F)n1] | LCMS (Method A): 3.83 min; m/z: 634.1 $[M + H]^+$. | $^1$H NMR (400 MHz, MeOD-$d_4$): 13.32 (s, 1H), 10.21 (s, 1H), 9.96 (s, 1H), 8.66 (d, J = 6.0 Hz, 1H), 7.91 (d, J = 6.0 Hz, 1H), 7.61 (t, J = 5.6 Hz, 2H), 7.49 (s, 1H), 7.43 (d, J = 8.0 Hz, 1H), 7.25 (t, J = 8.8 Hz, 3H), 6.54 (s, 1H), 5.19 (s, 2H), 4.35 (q, J = 10.0 Hz, 2H). |
| 187 | 3-(4-(ethylsulfonamido)-3-((1-methylpiperidin-3-yl)methoxy)phenyl)-5-(pyrazin-2-ylamino)-1H-pyrazole-4-carboxamide | 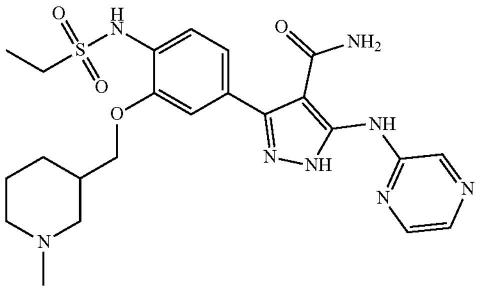 [SMILES: CCS(=O)(=O)Nc1ccc(-c2n[nH]c(Nc3cnccn3)c2C(N)=O)cc1OCC1CCCN(C)C1] | LCMS (Method A): 2.35 min; m/z: 515.2 $[M + H]^+$. | $^1$H NMR (400 MHz, MeOD-$d_4$): 13.05 (s, 1H), 10.54 (s, 1H), 9.64 (s, 1H), 9.25 (s, 1H), 9.16 (s, 1H), 8.22 (s, 1H), 8.11 (s, 1H), 7.48 (s, 1H), 7.31 (s, 1H), 7.19 (d, J = 8.4 Hz, 1H), 4.03 (s, 1H), 3.92 (s, 1H), 3.69 (s, 1H), 3.41 (s, 1H), 3.12 (q, J = 6.8 Hz, 2H), 2.82 (m, 4H), 1.89 (s, 3H). |

TABLE 24-continued

| Compound No. | Name | Structure | LCMS data | NMR data |
|---|---|---|---|---|
| 188 | 3-(4-((difluoromethyl)sulfonamido)-3-((4-fluorobenzyl)oxy)phenyl)-5-((6-(trifluoromethyl)pyridine-3-yl)amino)-1H-pyrazole-4-carboxamide | 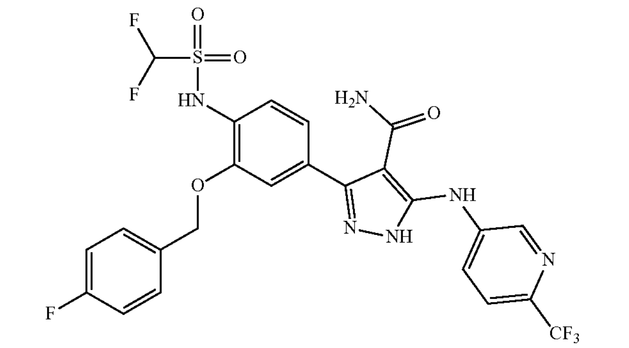 [SMILES: NC(=O)c1c(-c2ccc(NS(=O)(=O)C(F)F)c(OCc3ccc(F)cc3)c2)n[nH]c1Nc1ccc(C(F)(F)F)nc1] | LCMS (Method A): 3.84 min; m/z: 601.2 $[M + H]^+$. | $^1H$ NMR (400 MHz, DMSO-$d_6$): 13.00 (s, 1H), 10.56 (br s, 1H), 9.38 (s, 1H), 8.81 (d, J = 2.4 Hz, 1H), 8.26 (dd, J = 8.8, 2.4 Hz, 1H), 7.76 (d, J = 8.8 Hz, 1H), 7.61-7.58 (m, 2H), 7.40 (d, J = 8.0 Hz, 2H), 7.27-7.18 (m, 3H), 6.87 (t, J = 49.6 Hz, 1H), 5.18 (s, 2H). |
| 189 | 5-((6-(trifluoromethyl)pyridine-2-yl)amino)-3-(4-((3,3,3-trifluoropropyl)sulfonamido)phenyl)-1H-pyrazole-4-carboxamide | 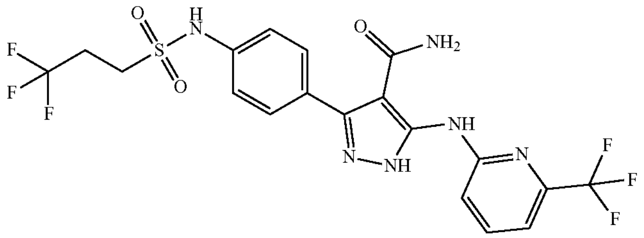 [SMILES: NC(=O)c1c(-c2ccc(NS(=O)(=O)CCC(F)(F)F)cc2)n[nH]c1Nc1cccc(C(F)(F)F)n1] | LCMS (Method A): 3.71 min; m/z: 523.1 $[M + H]^+$. | $^1H$ NMR (400 MHz, DMSO-$d_6$): 12.95 (s, 1H), 10.40 (s, 1H), 9.77 (s, 1H), 8.21 (s, 1H), 7.98 (t, J = 8.0 Hz, 1H), 7.58 (d, J = 8.4 Hz, 2H), 7.26 (d, J = 8.4 Hz, 2H), 7.31 (d, J = 7.6 Hz, 1H), 3.44 (m, 2H), 2.77 (m, 2H). |
| 190 | 3-(3-((4-chlorobenzyl)oxy)-4-((difluoromethyl)sulfonamido)phenyl)-5-((5-methoxypyrazin-2-yl)amino)-1H-pyrazole-4-carboxamide | 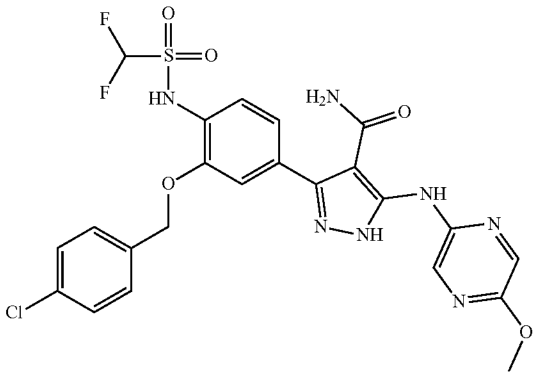 [SMILES: COc1cnc(Nc2[nH]nc(-c3ccc(NS(=O)(=O)C(F)F)c(OCc4ccc(Cl)cc4)c3)c2C(N)=O)cn1] | LCMS (Method A): 3.36 min; m/z: 580.1 $[M + H]^+$. | $^1H$ NMR (400 MHz, DMSO-$d_6$): 9.53 (s, 1H), 8.84 (s, 1H), 7.97 (d, J = 1.2 Hz, 1H), 7.52 (d, J = 8.4 Hz, 2H), 7.42 (d, J = 8.4 Hz, 2H), 7.37 (d, J = 8.0 Hz, 1H), 6.98 (d, J = 1.2 Hz, 1H), 6.93 (dd, J = 8.0, 2.0 Hz, 1H), 6.22 (t, J = 55.2 Hz, 1H), 5.07 (s, 2H), 3.86 (s, 3H). |

TABLE 24-continued

| Compound No. | Name | Structure | LCMS data | NMR data |
|---|---|---|---|---|
| 191 | 3-(4-((difluoromethyl)sulfonamido)-3-((4-fluorobenzyl)oxy)phenyl)-5-((5-methoxypyrazin-2-yl)amino)-1H-pyrazole-4-carboxamide | 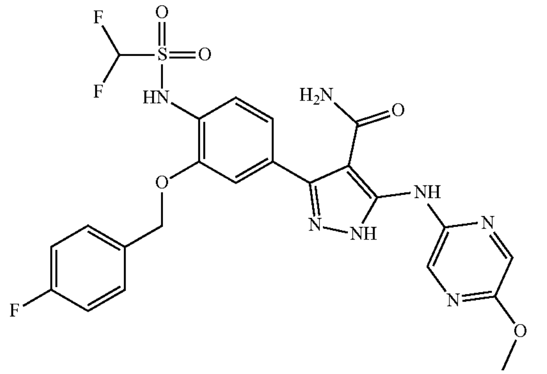 [SMILES: COc1cnc(Nc2[nH]nc(-c3ccc(NS(=O)(=O)C(F)F)c(OCc4ccc(F)cc4)c3)c2C(N)=O)cn1] | LCMS (Method A): 2.75 min; m/z: 564.3 [M + H]+. | $^1H$ NMR (400 MHz, DMSO-$d_6$): 12.70 (s, 1H), 9.53 (s, 1H), 8.84 (s, 1H), 7.97 (d, J = 1.2 Hz, 1H), 7.54-7.51 (m, 2H), 7.37 (d, J = 8.4 Hz, 1H), 7.19 (t, J = 6.8 Hz, 2H), 6.98 (d, J = 2.0 Hz, 1H), 6.92 (dd, J = 8.0, 2.0 Hz, 1H), 6.21 (t, J = 55.2 Hz, 1H), 5.05 (s, 2H), 3.86 (s, 3H). |
| 192 | 3-(4-(ethylsulfonamido)-3-((4-fluorobenzyl)oxy)phenyl)-5-((2-(trifluoromethyl)pyridine-3-yl)amino)-1H-pyrazole-4-carboxamide | 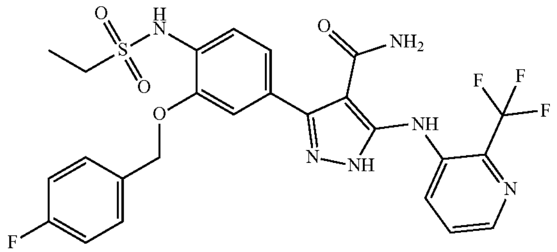 [SMILES: CCS(=O)(=O)Nc1ccc(-c2n[nH]c(Nc3cccnc3C(F)(F)F)c2C(N)=O)cc1OCc1ccc(F)cc1] | LCMS (Method A): 2.77 min; m/z: 579.3 [M + H]+. | $^1H$ NMR (400 MHz, DMSO-$d_6$): 12.98 (s, 1H), 10.09 (s, 1H), 9.00 (d, J = 8.8 Hz, 1H), 8.16 (d, J = 4.4 Hz, 1H), 7.67-7.60 (m, 3H), 7.47 (d, J = 8.0 Hz, 1H), 7.40 (d, J = 1.6 Hz, 1H), 7.27-7.23 (m, 2H), 7.18 (dd, J = 8.0, 1.6 Hz, 1H), 5.19 (s, 2H), 3.06 (q, J = 7.2 Hz, 2H), 1.16 (t, J = 7.2 Hz, 3H). |
| 193 | (R)-3-(4-(ethylsulfonamido)-3-(1-(4-fluorophenyl)ethoxy)phenyl)-5-(pyrazin-2-ylamino)-1H-pyrazole-4-carboxamide | 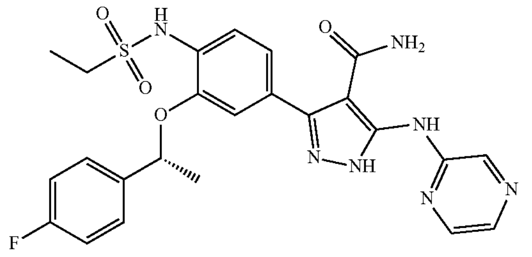 [SMILES: CCS(=O)(=O)Nc1ccc(-c2n[nH]c(Nc3cnccn3)c2C(N)=O)cc1O[C@H](C)c1ccc(F)cc1] | LCMS (Method A): 3.93 min; m/z: 526.2 [M + H]+. | $^1H$ NMR (400 MHz, DMSO-$d_6$): 12.93 (s, 1H), 9.59 (s, 1H), 9.22 (s, 2H), 8.21-8.20 (m, 1H), 8.11-8.09 (m, 1H), 7.63-7.59 (m, 2H), 7.44 (d, J = 8.0 Hz, 1H), 7.29-7.15 (m, 4H), 7.12-7.09 (m, 1H), 6.09 (s, 1H), 5.63 (s, 1H), 3.14-3.08 (m, 2H), 1.60 (d, J = 6.4 Hz, 3H), 1.26 (t, J = 7.2 Hz, 3H). |

TABLE 24-continued

| Compound No. | Name | Structure | LCMS data | NMR data |
|---|---|---|---|---|
| 194 | 3-(4-(ethylsulfonamido)-3-((4-fluorobenzyl)oxy)phenyl)-5-((6-(trifluoromethpyridinedin-3-yl)amino)-1H-pyrazole-4-carboxamide | 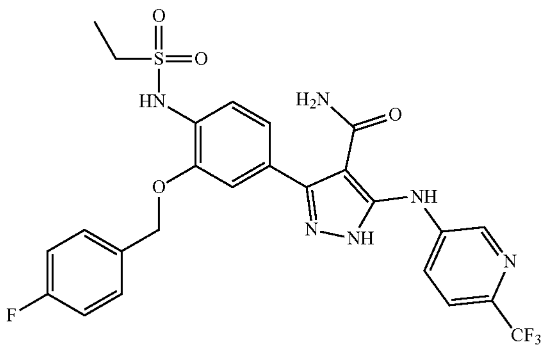 [SMILES: CCS(=O)(=O)Nc1ccc(-c2n[nH]c(Nc3ccc(C(F)(F)F)nc3)c2C(N)=O)cc1OCc1ccc(F)cc1] | LCMS (Method A): 3.93 min; m/z: 579.1 $[M + H]^+$. | $^1H$ NMR (400 MHz, DMSO-$d_6$): 12.98 (s, 1H), 9.41 (s, 1H), 9.17 (br s, 1H), 8.81 (s, 1H), 8.26 (d, J = 8.0 Hz, 1H), 7.76 (d, J = 8.8 Hz, 1H), 7.63-7.60 (m, 2H), 7.45-7.41 (m, 2H), 7.24 (t, J = 8.8 Hz, 2H), 7.19 (dd, J = 8.0, 1.6 Hz, 1H), 5.18 (s, 1H), 3.04 (q, J = 7.2 Hz, 2H), 1.15 (t, J = 7.2 Hz, 3H). |
| 195 | 3-(4-(ethylsulfonamido)-3-((4-fluorobenzyl)oxy)phenyl)-5-((2-(trifluoromethyl)pyrimidin-4-yl)amino)-1H-pyrazole-4-carboxamide | 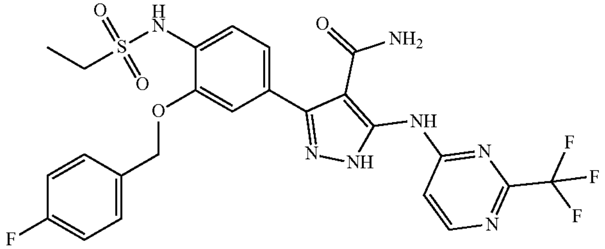 [SMILES: CCS(=O)(=O)Nc1ccc(-c2n[nH]c(Nc3ccnc(C(F)(F)F)n3)c2C(N)=O)cc1OCc1ccc(F)cc1] | LCMS (Method A): 2.82 min; m/z: 580.1 $[M + H]^+$. | $^1H$ NMR (400 MHz, MeOD-$d_4$): 13.26 (s, 1H), 10.21 (s, 1H), 9.19 (s, 1H), 8.65 (s, 1H), 7.93 (s, 1H), 7.62 (t, J = 5.6 Hz, 2H), 7.45 (s, 2H), 7.25 (t, J = 8.8 Hz, 3H), 6.45 (s, 1H), 5.75 (s, 1H), 5.18 (s, 2H), 3.04 (q, J = 7.2 Hz, 2H), 1.15 (t, J = 7.6 Hz, 3H). |
| 196 | 3-(4-((difluoromethyl)sulfonamido)-3-((4-fluorobenzyl)oxy)phenyl)-5-((6-methoxypyridin-3-yl)amino)-1H-pyrazole-4-carboxamide | 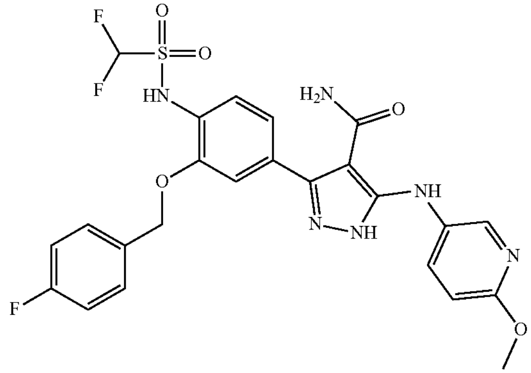 | LCMS (Method A): 3.63 min; m/z: 563.1 $[M + H]^+$. | $^1H$ NMR (400 MHz, DMSO-$d_6$): 12.73 (s, 1H), 10.56 (s, 1H), 8.69 (s, 1H), 8.39 (d, J = 2.4 Hz, 1H), 7.95 (dd, J = 8.8, 2.8 Hz, 1H), 7.62-7.59 (m, 2H), 7.42-7.39 (m, 2H), 7.27-7.18 (m, 3H), 7.06-6.80 (m, 1H), 6.75 (d, J = 8.8 Hz, 1H), 5.20 (s, 2H), 3.80 (s, 3H). |

TABLE 24-continued

| Compound No. | Name | Structure | LCMS data | NMR data |
|---|---|---|---|---|
| 197 | 3-(4-(ethylsulfonamido)-3-((4-fluorobenzyl)oxy)phenyl)-5-((6-methoxypyridin-3-yl)amino)-1H-pyrazole-4-carboxamide | 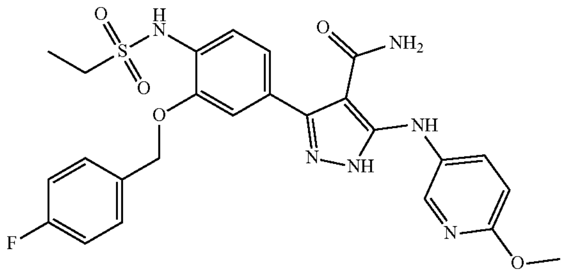 [SMILES: CCS(=O)(=O)Nc1ccc(-c2n[nH]c(Nc3ccc(OC)nc3)c2C(N)=O)cc1OCc1ccc(F)cc1] | LCMS (Method A): 3.48 min; m/z: 541.1 [M + H]+. | $^1$H NMR (400 MHz, DMSO-d$_6$): 12.66 (s, 1H), 9.18 (s, 1H), 8.75 (s, 1H), 8.40-8.39 (m, 1H), 7.97-7.94 (m, 1H), 7.64-7.60 (m, 1H), 7.44 (d, J = 8.4 Hz, 1H), 7.39-7.38 (m, 1H), 7.27-7.22 (m, 1H), 7.17 (dd, J = 8.0, 1.6 Hz, 1H), 6.75 (d, J = 8.8 Hz, 1H), 5.18 (s, 2H), 3.80 (s, 3H), 3.04 (q, J = 7.2 Hz, 2H), 1.15 (t, J = 7.2 Hz, 3H). |
| 198 | 3-(2-((4-chlorobenzyl)oxy)-4-(ethylsulfonamido)phenyl)-5-(pyrazin-2-ylamino)-1H-pyrazole-4-carboxamide | 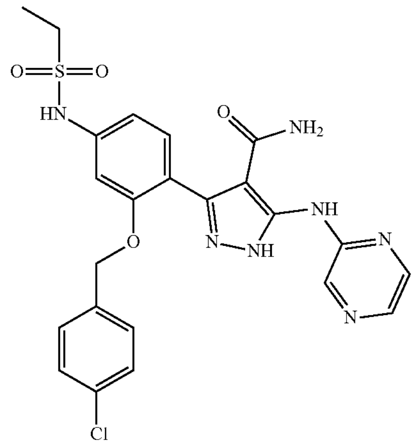 [SMILES: CCS(=O)(=O)Nc1ccc(-c2n[nH]c(Nc3cnccn3)c2C(N)=O)c(OCc2ccc(Cl)cc2)c1] | LCMS (Method A): 3.33 min; m/z: 528.1 [M + H]+. | $^1$H NMR (400 MHz, DMSO-d$_6$): 12.84 (s, 1H), 10.11 (br s, 1H), 9.73 (s, 1H), 9.30 (s, 1H), 8.23-8.22 (m, 1H), 8.11 (d, J = 2.8 Hz, 1H), 7.40 (s, 4H), 7.37 (t, J = 7.6 Hz, 1H), 7.04 (s, 1H), 6.94 (dd, J = 8.4, 1.6 Hz, 1H), 5.11 (s, 2H), 3.14 (q, J = 7.6 Hz, 2H), 1.19 (t, J = 7.2 Hz, 3H). |
| 199 | (S)-3-(4-(ethylsulfonamido)-3-(1-(4-fluorophenyl)ethoxy)phenyl)-5-(pyrazin-2-ylamino)-1H-pyrazole-4-carboxamide | 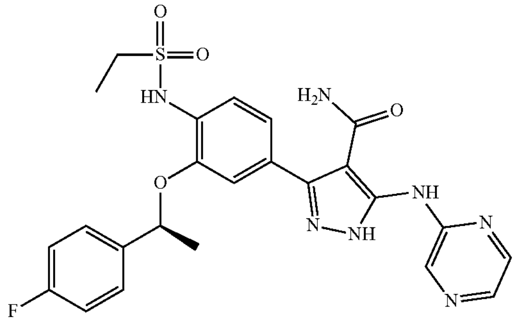 [SMILES: CCS(=O)(=O)Nc1ccc(-c2n[nH]c(Nc3cnccn3)c2C(N)=O)cc1O[C@@H](C)c1ccc(F)cc1] | LCMS (Method A): 3.93 min; m/z: 526.2 [M + H]+. | $^1$H NMR (400 MHz, DMSO-d$_6$): 12.93 (s, 1H), 9.59 (s, 1H), 9.22 (s, 2H), 8.21-8.20 (m, 1H), 8.11-8.09 (m, 1H), 7.63-7.59 (m, 2H), 7.44 (d, J = 8.0 Hz, 1H), 7.29-7.15 (m, 4H), 7.12-7.09 (m, 1H), 6.09 (s, 1H), 5.63 (s, 1H), 3.14-3.08 (m, 2H), 1.60 (d, J = 6.4 Hz, 3H), 1.26 (t, J = 7.2 Hz, 3H). |

TABLE 24-continued

| Compound No. | Name | Structure | LCMS data | NMR data |
|---|---|---|---|---|
| 200 | 3-(3-(cyclohexylmethoxy)-4-(ethylsulfonamido)phenyl)-5-((6-(trifluoromethpyridinedin-2-yl)amino)-1H-pyrazole-4-carboxamide | 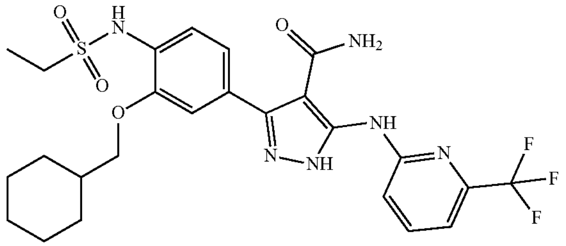 [SMILES: CCS(=O)(=O)Nc1ccc(-c2n[nH]c(Nc3cccc(C(F)(F)F)n3)c2C(N)=O)cc1OCC1CCCCC1] | LCMS (Method A): 4.64 min; m/z: 567.2 $[M + H]^+$. | $^1H$ NMR (400 MHz, DMSO-$d_6$): 12.97 (s, 1H), 9.77 (s, 1H), 9.03 (s, 1H), 8.21 (d, J = 8.4 Hz, 1H), 7.98 (t, J = 16.0 Hz, 1H), 7.44 (d, J = 8 Hz, 1H), 7.38-7.26 (m, 3H), 7.16-7.13 (m, 1H), 6.23 (s, 1H), 3.86 (d, J = 6.0 Hz, 2H), 3.11 (q, J = 22.0 Hz, 2H), 1.9 (s, 1H), 1.74-1.64 (m, 3H), 1.32-1.16 (m, 10H). |
| 201 | 3-(4-(ethylsulfonamido)-2-((4-fluorobenzyl)oxy)phenyl)-292yridinedin-2-ylamino)-1H-pyrazole-4-carboxamide | 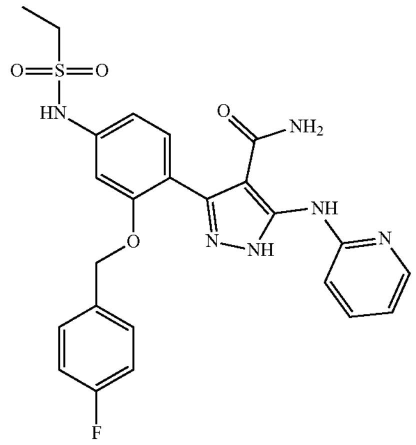 [SMILES: CCS(=O)(=O)Nc1ccc(-c2n[nH]c(Nc3ccccn3)c2C(N)=O)c(OCc2ccc(F)cc2)c1] | LCMS (Method A): 2.86 min; m/z: 511.1 $[M + H]^+$. | $^1H$ NMR (400 MHz, MeOD-$d_4$): 12.66 (s, 1H), 10.14 (s, 1H), 9.61 (s, 1H), 8.18 (s, 1H), 8.01 (d, J = 8.4 Hz, 1H), 7.70 (t, J = 6.8 Hz, 1H), 7.42 (t, J = 8.0 Hz, 2H), 7.35 (d, J = 8.0 Hz, 1H), 7.17 (t, J = 8.8 Hz, 3H), 7.08 (s, 1H), 6.94 (d, J = 7.6 Hz, 1H), 6.84 (t, J = 5.6 Hz, 1H), 5.09 (s, 2H), 3.15 (q, J = 7.2 Hz, 2H), 1.20 (t, J = 7.2 Hz, 3H). |
| 202 | 3-(4-((difluoromethyl)sulfonamido)-3-((4-fluorobenzyl)oxy)phenyl)-5-(pyrazin-2-ylamino)-1H-pyrazole-4-carboxamide | 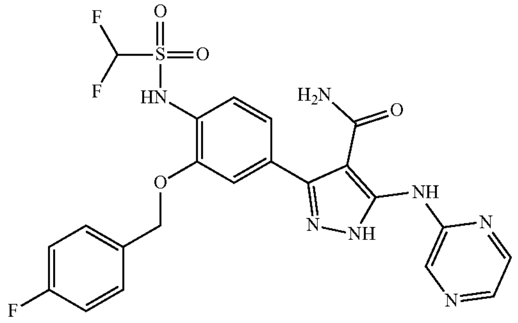 [SMILES: NC(=O)c1c(-c2ccc(NS(=O)(=O)C(F)F)c(OCc3ccc(F)cc3)c2)n[nH]c1Nc1cnccn1] | LCMS (Method A): 4.21 min; m/z: 534.1 $[M + H]^+$. | $^1H$ NMR (400 MHz, DMSO-$d_6$): 13.14 (br s, 1H), 10.57 (br s, 1H), 9.60 (br s, 1H), 9.22 (br s, 1H), 8.21 (s, 1H), 8.10 (d, J = 2.4 Hz, 1H), 7.61-7.58 (m, 2H), 7.40 (d, J = 8.0 Hz, 2H), 7.26-7.13 (m, 4H), 6.99-6.54 (m, 1H), 5.19 (s, 2H). |

TABLE 24-continued

| Compound No. | Name | Structure | LCMS data | NMR data |
|---|---|---|---|---|
| 203 | 3-(4-(ethylsulfonamido)-3-((1-methylpiperidin-4-yl)methoxy)phenyl)-5-(pyrazin-2-ylamino)-1H-pyrazole-4-carboxamide | 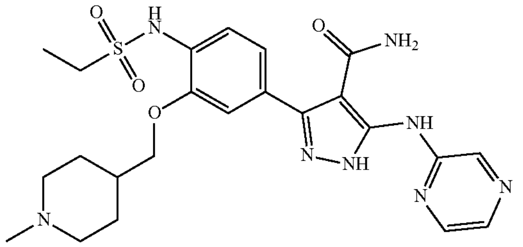 [SMILES: CCS(=O)(=O)Nc1ccc(-c2n[nH]c(Nc3cnccn3)c2C(N)=O)cc1OCC1CCN(C)CC1] | LCMS (Method A): 0.40 min; m/z: 515.2 [M + H]+. | $^1$H NMR (400 MHz, DMSO-$d_6$): 13.10 (s, 1H), 9.66 (s, 1H), 9.24 (s, 1H), 9.08 (s, 1H), 8.22 (q, J = 1.6 Hz, 1H), 8.11 (d, J = 2.4 Hz, 1H), 7.44 (d, J = 8.0 Hz, 1H), 7.31 (s, 1H), 7.17 (d, J = 1.6 Hz, 1H), 3.94 (m, 2H), 3.12 (q, J = 7.6 Hz, 2H), 2.46 (br s, 4H), 1.97 (m, 3H), 1.50 (br s, 2H), 1.24 (m, 3H). |
| 204 | 3-(4-(ethylsulfonamido)-3-(3-fluorophenoxy)phenyl)-5-(pyrazin-2-ylamino)-1H-pyrazole-4-carboxamide | 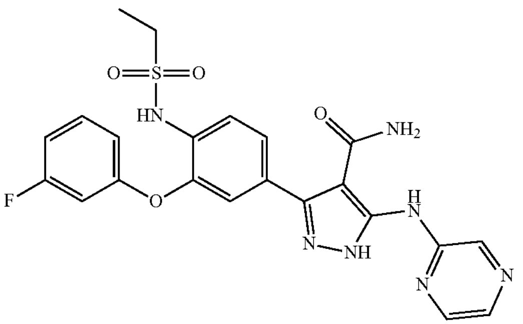 [SMILES: CCS(=O)(=O)Nc1ccc(-c2n[nH]c(Nc3cnccn3)c2C(N)=O)cc1Oc1cccc(F)c1] | LCMS (Method A): 3.26 min; m/z: 498.1 [M + H]+. | $^1$H NMR (400 MHz, DMSO-$d_6$): 12.99 (s, 1H), 9.64 (s, 1H), 9.66 (s, 1H), 9.55 (s, 1H), 9.21 (s, 1H), 8.20 (s, 1H), 8.09 (d, J = 2.4 Hz, 1H), 7.62 (d, J = 8.4 Hz, 1H), 7.46-7.40 (m, 2H), 7.21 (s, 1H), 7.01-6.93 (m, 3H), 3.13 (q, J = 7.2 Hz, 2H), 1.20 (t, J = 7.2 Hz, 3H). |
| 205 | 5-((6-(trifluoromethpyridinedin-2-yl)amino)-3-(4-((trifluoromethyl)sulfonamido)phenyl)-1H-pyrazole-4-carboxamide | 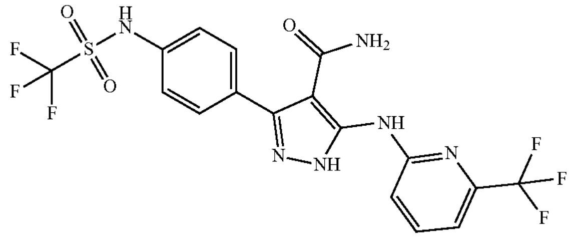 [SMILES: NC(=O)c1c(-c2ccc(NS(=O)(=O)C(F)(F)F)cc2)n[nH]c1Nc1cccc(C(F)(F)F)n1] | LCMS (Method A): 3.94 min; m/z: 495.0 [M + H]+. | $^1$H NMR (400 MHz, DMSO-$d_6$): 9.90 (s, 1H), 8.52 (s, 1H), 8.04-7.94 (m, 2H), 7.59 (d, J = 7.6 Hz, 2H), 7.36 (d, J = 8.4 Hz, 2H), 7.21-6.95 (m, 2H). |

TABLE 24-continued

| Compound No. | Name | Structure | LCMS data | NMR data |
| --- | --- | --- | --- | --- |
| 206 | 3-(3-(2-chlorophenethoxy)-4-(ethylsulfonamido)phenyl)-5-(pyrazin-2-ylamino)-1H-pyrazole-4-carboxamide | 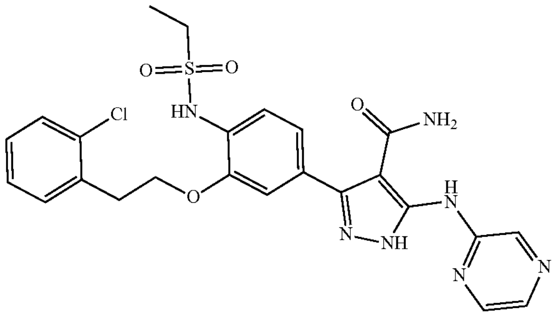 [SMILES: CCS(=O)(=O)Nc1ccc(-c2n[nH]c(Nc3cnccn3)c2C(N)=O)cc1OCCc1ccccc1Cl] | LCMS (Method A): 2.67 min; m/z: 542.1 $[M + H]^+$. | $^1H$ NMR (400 MHz, MeOD-$d_4$): 12.97 (s, 1H), 9.63 (s, 1H), 9.25 (s, 1H), 8.94 (s, 1H), 8.22 (m, 1H), 8.11 (d, J = 2.4 Hz, 1H), 7.57 (dd, J = 2.6, 2.0 Hz, 1H), 7.46 (m, 2H), 7.34 (m, 3H), 7.18 (dd, J = 2.0, 1.6 Hz, 1H), 4.32 (t, J = 6.8 Hz, 2H), 3.28 (d, J = 6.8 Hz, 2H), 3.01 (q, J = 7.6 Hz, 2H), 1.16 (d, J = 7.2 Hz, 3H). |
| 207 | 3-(4-(ethylsulfonamido)-3-((4-fluorobenzyl)oxy)phenyl)-5-((5-(trifluoromethpyridinedin-2-yl)amino)-1H-pyrazole-4-carboxamide | 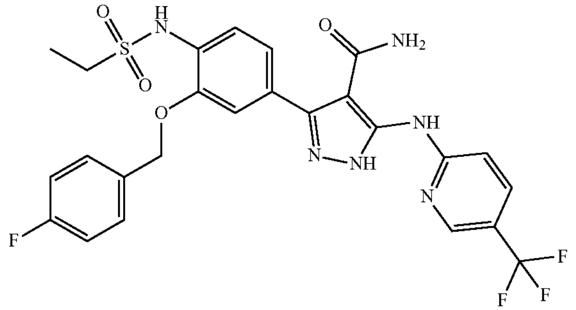 [SMILES: CCS(=O)(=O)Nc1ccc(-c2n[nH]c(Nc3ccc(C(F)(F)F)cn3)c2C(N)=O)cc1OCc1ccc(F)cc1] | LCMS (Method A): 3.01 min; m/z: 579.2 $[M + H]^+$. | $^1H$ NMR (400 MHz, DMSO-$d_6$): 13.04 (s, 1H), 9.95 (s, 1H), 9.26 (s, 1H), 9.19 (s, 1H), 8.53 (s, 1H), 8.07 (s, 1H), 7.64-7.60 (m, 2H), 7.46-7.42 (m, 2H), 7.27-7.19 (m, 3H), 5.18 (s, 2H), 3.05 (q, J = 7.6 Hz, 2H), 1.16 (t, J = 7.2 Hz, 3H). |
| 208 | 3-(4-(ethylsulfonamido)-2-((3-fluorobenzyl)oxy)phenyl)-5-(pyrazin-2-ylamino)-1H-pyrazole-4-carboxamide | 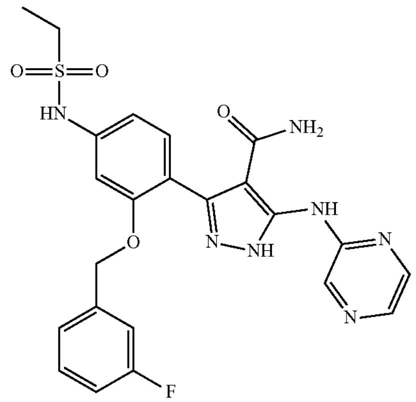 [SMILES: CCS(=O)(=O)Nc1ccc(-c2n[nH]c(Nc3cnccn3)c2C(N)=O)c(OCc2cccc(F)c2)c1] | LCMS (Method A): 0.60 min; m/z: 512.2 $[M + H]^+$. | $^1H$ NMR (400 MHz, DMSO-$d_6$): 12.86 (s, 1H), 10.16 (s, 1H), 9.76 (s, 1H), 9.32 (s, 1H), 8.23 (s, 1H), 8.12 (d, J = 2.4 Hz, 1H), 7.42-7.30 (m, 3H), 7.22-7.18(m, 2H), 7.12 (t, J = 8.8 Hz, 1H), 7.05 (s, 1H), 6.95 (d, J = 8.0 Hz, 1H) 5.71 (br s, 1H), 5.14 (s, 2H), 3.15 (q, J = 7.2 Hz, 2H), 1.19 (t, J = 7.2 Hz, 3H). |

TABLE 24-continued

| Compound No. | Name | Structure | LCMS data | NMR data |
|---|---|---|---|---|
| 209 | 3-(4-(ethylsulfonamido)-2-methoxyphenyl)-5-(pyrazin-2-ylamino)-1H-pyrazole-4-carboxamide | 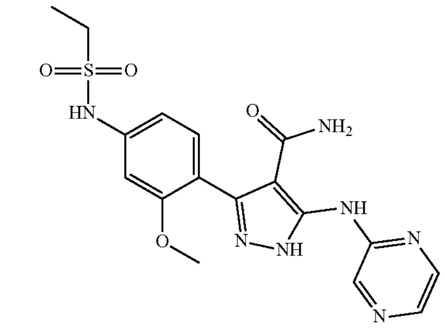 [SMILES: CCS(=O)(=O)Nc1ccc(-c2n[nH]c(Nc3cnccn3)c2C(N)=O)c(OC)c1] | LCMS (Method A): 0.70 min; m/z: 418.2 [M + H]$^+$. | $^1$H NMR (400 MHz, DMSO-$d_6$): 12.79 (s, 1H), 10.14 (br s, 1H), 9.74 (s, 1H), 9.33 (s, 1H), 8.23 (s, 1H), 8.13 (s, 1H), 7.33 (d, J = 8.0 Hz, 1H), 7.27 (br s, 1H), 7.02 (s, 1H), 6.94 (d, J = 8.0 Hz, 1H), 5.65 (br s, 1H), 3.76 (s, 3H), 3.2 (q, J = 7.6 Hz, 2H), 1.24 (t, J = 7.2 Hz, 3H). |
| 210 | 3-(4-(ethylsulfonamido)-3-phenethoxyphenyl)-5-(pyrazin-2-ylamino)-1H-pyrazole-4-carboxamide | 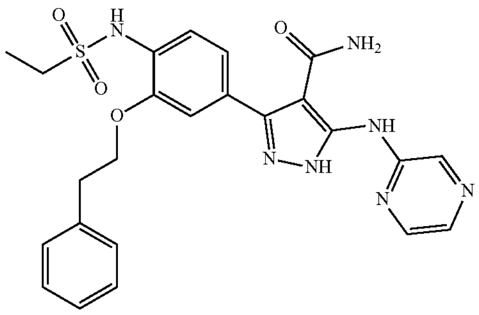 [SMILES: CCS(=O)(=O)Nc1ccc(-c2n[nH]c(Nc3cnccn3)c2C(N)=O)cc1OCCc1ccccc1] | LCMS (Method A): 3.49 min; m/z: 508.1 [M + H]$^+$. | $^1$H NMR (400 MHz, DMSO-$d_6$): 12.98 (s, 1H), 9.63 (s, 1H), 9.25 (s, 1H), 8.95 (s, 1H), 8.22-8.21 (m, 1H), 8.11 (d, J = 2.4 Hz, 1H), 7.44 (d, J = 8.0 Hz, 2H), 7.40-7.38 (m, 2H), 7.34-7.30 (m, 3H), 7.25-7.21 (m, 1H), 7.18-7.15 (m, 1H), 4.31 (t, J = 6.8 Hz, 2H), 3.15 (t, J = 6.8 Hz, 2H), 2.95 (q, J = 7.6 Hz, 2H), 1.13 (t, J = 7.2 Hz, 3H). |
| 211 | 3-(4-(ethylsulfonamido)-3-(2-fluorophenethoxy)phenyl)-5-(pyrazin-2-ylamino)-1H-pyrazole-4-carboxamide | 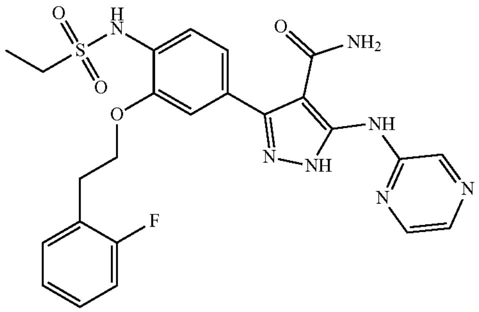 [SMILES: CCS(=O)(=O)Nc1ccc(-c2n[nH]c(Nc3cnccn3)c2C(N)=O)cc1OCCc1ccccc1F] | LCMS (Method A): 3.61 min; m/z: 526.1 [M + H]$^+$. | $^1$H NMR (400 MHz, DMSO-$d_6$): 12.98 (s, 1H), 9.62 (s, 1H), 9.24 (s, 1H), 8.88 (br s, 1H), 8.22-8.21 (m, 1H), 8.10 (d, J = 2.4 Hz, 1H), 7.52-7.50 (m, 1H), 7.44 (d, J = 8.0 Hz, 1H), 7.34 (s, 1H), 7.31-7.28 (m, 1H), 7.20-7.14 (m, 3H), 4.30 (t, J = 6.8 Hz, 2H), 3.19 (t, J = 6.8 Hz, 2H), 2.99 (q, J = 14.8, 7.2 Hz, 2H), 1.14 (t, J = 7.2 Hz, 3H). |

TABLE 24-continued

| Compound No. | Name | Structure | LCMS data | NMR data |
|---|---|---|---|---|
| 212 | 3-(3-(3-chlorophenethoxy)-4-(ethylsulfonamido)phenyl)-5-(pyrazin-2-ylamino)-1H-pyrazole-4-carboxamide | 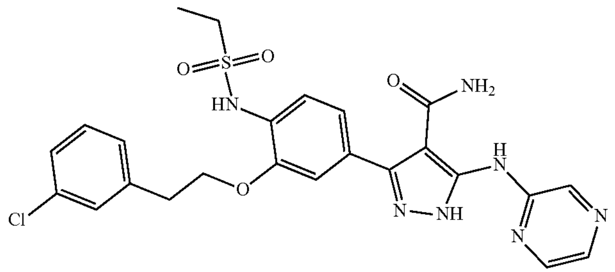 | LCMS (Method A): 3.61 min; m/z: 526.2 [M + H]$^+$. | $^1$H NMR (400 MHz, DMSO-$d_6$): 12.98 (s, 1H), 9.64 (s, 1H), 9.25 (s, 1H), 9.03 (s, 1H), 8.22-8.21 (m, 1H), 8.11 (d, J = 2.4 Hz, 1H), 7.51 (s, 1H), 7.44 (d, J = 8.0 Hz, 1H), 7.33 (s, 4H), 7.16 (d, J = 1.6 Hz, 1H), 4.31 (t, J = 6.4 Hz, 2H), 3.14 (br s, 2H), 2.95 (q, J = 7.2 Hz, 2H), 1.11 (t, J = 7.2 Hz, 3H). |
| 213 | 3-(4-(ethylsulfonamido)-3-((4-fluorobenzyl)oxy)phenyl)-5-((4-(trifluoromethpyridinedin-2-yl)amino)-1H-pyrazole-4-carboxamide | 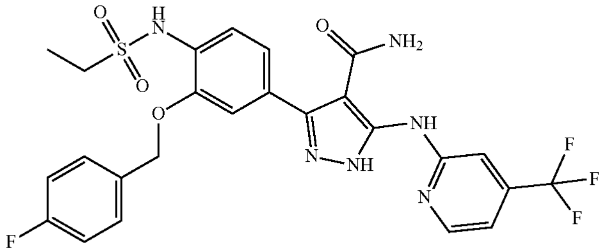 [SMILES: CCS(=O)(=O)Nc1ccc(-c2n[nH]c(Nc3cc(C(F)(F)F)ccn3)c2C(N)=O)cc1OCc1ccc(F)cc1] | LCMS (Method A): 0.79 min; m/z: 580.1 [M + H]$^+$. | $^1$H NMR (400 MHz, DMSO-$d_6$): 13.04 (s, 1H), 9.90 (s, 1H), 9.14 (s, 1H), 8.45 (d, J = 5.2 Hz, 1H), 8.33 (s, 1H), 7.64-7.60 (m, 2H), 7.50 (d, J = 8.0 Hz, 1H), 7.40 (s, 1H), 7.24 (t, J = 8.8 Hz, 2H), 7.19 (d, J = 6.4 Hz, 2H), 6.25 (s, 1H), 5.18 (s, 2H), 3.05 (q, J = 7.2 Hz, 2H), 1.16 (t, J = 7.2 Hz, 3H). |
| 214 | 3-(4-(ethylsulfonamido)-3-((3-(trifluoromethoxy)benzyl)oxy)phenyl)-5-(pyrazin-2-ylamino)-1H-pyrazole-4-carboxamide | 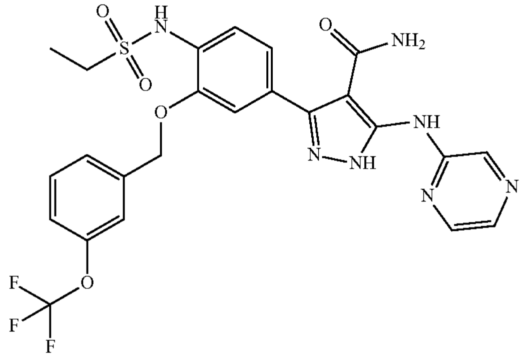 [SMILES: CCS(=O)(=O)Nc1ccc(-c2n[nH]c(Nc3cnccn3)c2C(N)=O)cc1OCc1cccc(OC(F)(F)F)c1] | LCMS (Method A): 3.67 min; m/z: 578.1 [M + H]$^+$. | $^1$H NMR (400 MHz, DMSO-$d_6$): 13.03 (s, 1H), 9.62 (s, 1H), 9.25 (s, 1H), 8.22 (s, 1H), 8.11 (s, 1H), 7.66-7.33 (m, 8H), 6.23 (br s, 1H), 5.26 (s, 1H), 3.04 (s, 2H), 1.18-1.84 (m, 3H). |

TABLE 24-continued

| Compound No. | Name | Structure | LCMS data | NMR data |
|---|---|---|---|---|
| 215 | 3-(4-(ethylsulfonamido)-3-((4-(trifluoromethoxy)benzyl)oxy)phenyl)-5-(pyrazin-2-ylamino)-1H-pyrazole-4-carboxamide | 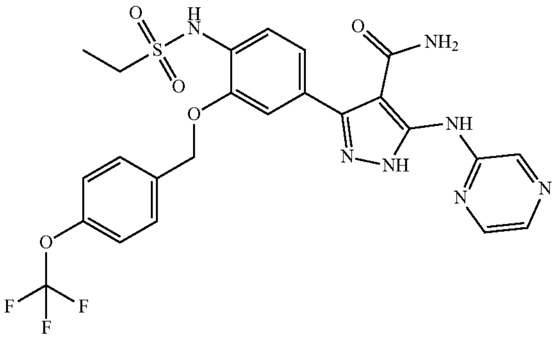 [SMILES: CCS(=O)(=O)Nc1ccc(-c2n[nH]c(Nc3cnccn3)c2C(N)=O)cc1OCc1ccc(OC(F)(F)F)cc1] | LCMS (Method A): 3.88 min; m/z: 578.1 [M + H]$^+$. | $^1$H NMR (400 MHz, DMSO-$d_6$): 13.01 (s, 1H), 9.62 (s, 1H), 9.23 (d, J = 14.4 Hz, 2H), 8.21 (s, 1H), 8.11 (s, 1H), 7.71 (d, J = 8.0 Hz, 3H), 7.47-7.41 (m, 5H), 7.21 (d, J = 8.4 Hz, 1H), 5.23 (s, 2H), 3.10-3.03 (m, 2H), 1.16 (t, J = 14.4 Hz, 3H). |
| 216 | 3-(4-(ethylsulfonamido)-3-((4-(trifluoromethyl)benzyl)oxy)phenyl)-5-(pyrazin-2-ylamino)-1H-pyrazole-4-carboxamide | 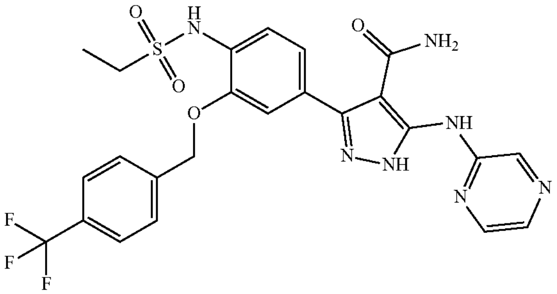 [SMILES: CCS(=O)(=O)Nc1ccc(-c2n[nH]c(Nc3cnccn3)c2C(N)=O)cc1OCc1ccc(C(F)(F)F)cc1] | LCMS (Method A): 3.67 min; m/z: 562.1 [M + H]$^+$. | $^1$H NMR (400 MHz, DMSO-$d_6$): 13.04 (s, 1H), 10.12 (s, 1H), 9.61 (s, 1H), 9.23 (s, 1H), 8.21 (s, 1H), 8.10 (d, J = 2.4 Hz, 1H), 7.81-7.77 (m, 5H), 7.48-7.42 (m, 3H), 7.21 (d, J = 8.0 Hz, 1H), 5.31 (s, 1H), 3.07 (d, J = 7.2 Hz, 2H), 1.17 (t, J = 14.8 Hz, 3H). |
| 217 | 3-(4-((difluoromethyl)sulfonamido)-3-((4-fluorobenzyl)oxy)phenyl)-5-((6-(trifluoromethpyridinedin-2-yl)amino)-1H-pyrazole-4-carboxamide | 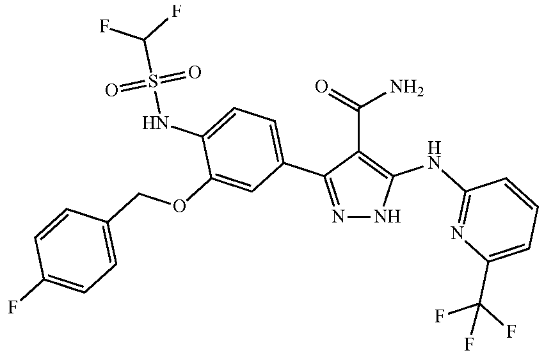 [SMILES: NC(=O)c1c(-c2ccc(NS(=O)(=O)C(F)F)c(OCc3ccc(F)cc3)c2)n[nH]c1Nc1cccc(C(F)(F)F)n1] | LCMS (Method A): 1.82 min; m/z: 601.1 [M + H]$^+$. | $^1$H NMR (400 MHz, DMSO-$d_6$): 13.15 (br s, 1H), 10.64 (br s, 1H), 9.72 (br s, 1H) 8.20 (br s, 1H), 7.98 (s, 1H), 7.62-7.57 (m, 2H), 7.39-7.14 (m, 7H), 6.72-6.58 (m, 1H), 5.18 (s, 2H). |

TABLE 24-continued

| Compound No. | Name | Structure | LCMS data | NMR data |
|---|---|---|---|---|
| 218 | 3-(4-(ethylsulfonamido)-3-((3-(trifluoromethyl)benzyl)oxy)phenyl)-5-(pyrazin-2-ylamino)-1H-pyrazole-4-carboxamide | 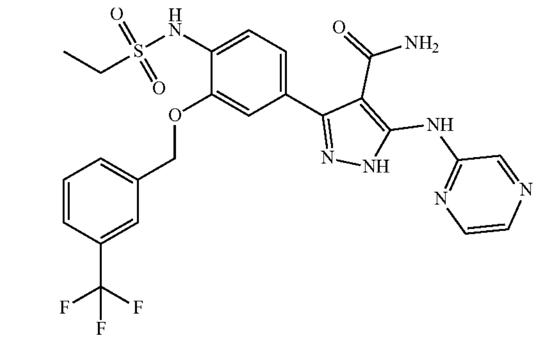 [SMILES: CCS(=O)(=O)Nc1ccc(-c2n[nH]c(Nc3cnccn3)c2C(N)=O)cc1OCc1cccc(C(F)(F)F)c1] | LCMS (Method A): 3.72 min; m/z: 562.1 $[M + H]^+$. | $^1$H NMR (400 MHz, MeOD-$d_4$): 13.02 (s, 1H), 9.61 (s, 1H), 9.24 (s, 1H), 8.22 (s, 1H), 8.11 (s, 1H), 7.98 (s, 1H), 7.87 (d, J = 7.2 Hz, 1H), 7.67 (m, 2H), 7.46 (d, J = 7.2 Hz, 2H), 7.20 (d, J = 8.0 Hz, 1H), 6.21 (s, 1H), 5.30 (s, 2H), 3.05 (q, J = 7.2 Hz, 2H), 1.15 (t, J = 7.6 Hz, 3H). |
| 219 | 3-(4-(ethylsulfonamido)-3-(3-fluorophenethoxy)phenyl)-5-(pyrazin-2-ylamino)-1H-pyrazole-4-carboxamide | 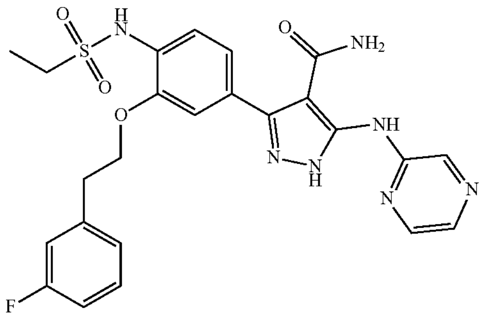 [SMILES: CCS(=O)(=O)Nc1ccc(-c2n[nH]c(Nc3cnccn3)c2C(N)=O)cc1OCCc1cccc(F)c1] | LCMS (Method A): 0.54 min; m/z: 526.1 $[M + H]^+$. | $^1$H NMR (400 MHz, DMSO-$d_6$): 12.98 (s, 1H), 9.62 (s, 1H), 9.25 (s, 1H), 9.00 (br s, 1H), 8.22-8.21 (m, 1H), 8.11 (d, J = 2.4 Hz, 1H), 7.44 (d, J = 8.4 Hz, 1H), 7.38-7.33 (m, 2H), 7.29-7.25 (m, 1H), 7.23 (d, J = 7.6 Hz, 1H), 7.16 (dd, J = 8.0, 1.6 Hz, 1H), 7.08-7.03 (m, 1H), 4.31 (t, J = 6.8 Hz, 2H), 3.18-3.15 (m, 2H), 2.95 (q, J = 14.8, 7.6 Hz, 2H), 1.12 (t, J = 7.2 Hz, 3H). |
| 220 | 5-((6-chloroquinolin-2-yl)amino)-3-(4-(ethylsulfonamido)-3-((4-fluorobenzyl)oxy)phenyl)-1H-pyrazole-4-carboxamide | 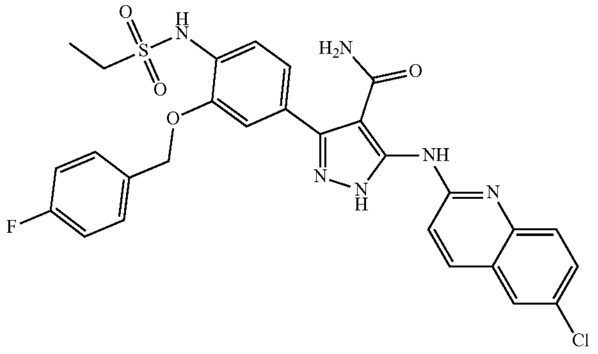 [SMILES: CCS(=O)(=O)Nc1ccc(-c2n[nH]c(Nc3ccc4cc(Cl)ccc4n3)c2C(N)=O)cc1OCc1ccc(F)cc1] | LCMS (Method A): 4.10 min; m/z: 595.1 $[M + H]^+$. | $^1$H NMR (400 MHz, DMSO-$d_6$): 13.53 (s, 1H), 10.36 (s, 1H), 9.06 (s, 1H), 8.32-8.18 (m, 2H), 7.94 (s, 1H), 7.68-7.61 (m, 3H), 7.46-7.39 (m, 3H), 7.27-7.20 (m, 3H), 5.19 (s, 2H), 3.05 (q, J = 7.2 Hz, 2H), 1.16 (t, J = 7.2 Hz, 3H). |

TABLE 24-continued

| Compound No. | Name | Structure | LCMS data | NMR data |
|---|---|---|---|---|
| 26 | 3-(4-(ethylsulfonamido)-3-((3-fluorobenzyl)oxy)phenyl)-5-(pyrazin-2-ylamino)-1H-pyrazole-4-carboxamide | 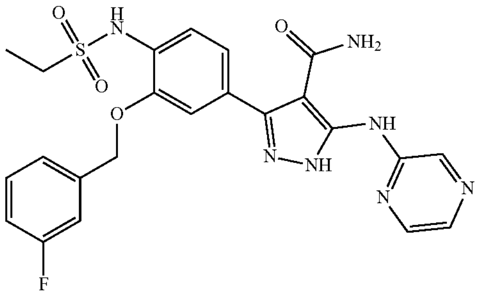 [SMILES: CCS(=O)(=O)Nc1ccc(-c2n[nH]c(Nc3cnccn3)c2C(N)=O)cc1OCc1cccc(F)c1] | LCMS (Method A): 3.52 min; m/z: 512.1 $[M + H]^+$. | $^1H$ NMR (400 MHz, MeOD-$d_4$): 13.02 (s, 1H), 9.62 (s, 1H), 9.25 (s, 1H), 8.22 (s, 1H), 8.11 (d, J = 2.8 Hz, 1H), 7.48 (m, 3H), 7.37 (d, J = 8.0 Hz, 2H), 7.19 (m, 2H), 5.74 (s, 1H), 5.23 (s, 2H), 3.07 (q, J = 7.2 Hz, 2H), 1.78 (t, J = 7.2 Hz, 3H). |
| 309 | (S)-3-(4-((difluoromethyl)sulfonamido)-3-(1-(4-fluorophenyl)ethoxy)phenyl)-5-((2-methylpyrimidin-4-yl)amino)-1H-pyrazole-4-carboxamide | 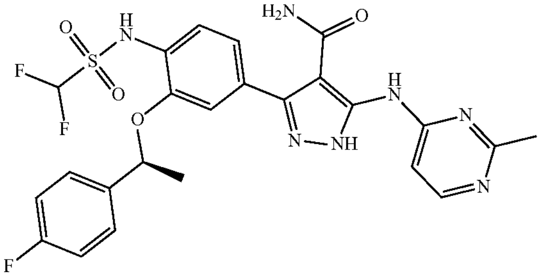 [SMILES: Cc1nccc(Nc2[nH]nc(-c3ccc(NS(=O)(=O)C(F)F)c(O[C@@H](C)c4ccc(F)cc4)c3)c2C(N)=O)n1] | LCMS (Method A): 3.30 min; m/z: 563.8 $[M + H]^+$. | $^1H$ NMR (400 MHz, DMSO-$d_6$): 13.09 (s, 1H), 9.78 (s, 1H), 8.41 (d, J = 5.9 Hz, 1H), 7.78-7.67 (m, 1H), 7.61 (dd, J = 8.5, 5.5 Hz, 2H), 7.42 (d, J = 8.2 Hz, 2H), 7.20 (t, J = 8.7 Hz, 2H), 7.16-6.98 (m, 2H), 6.70 (t, J = 53.9 Hz, 1H), 6.06 (d, J = 20.9 Hz, 1H), 5.71 (d, J = 6.5 Hz, 1H), 2.56 (s, 3H), 1.59 (d, J = 6.3 Hz, 3H). |
| 313 | 3-(4-((difluoromethyl)sulfonamido)-3-(oxazol-2-ylmethoxy)phenyl)-5-(pyrazin-2-ylamino)-1H-pyrazole-4-carboxamide | 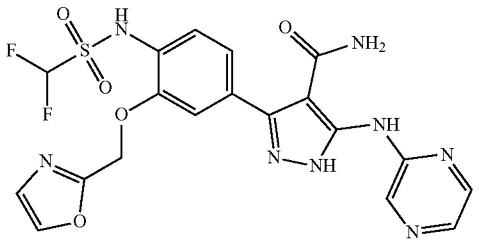 [SMILES: NC(=O)c1c(-c2ccc(NS(=O)(=O)C(F)F)c(OCc3ncco3)c2)n[nH]c1Nc1cnccn1] | LCMS (Method A): 2.93 min; m/z: 507.1 $[M + H]^+$. | $^1H$ NMR (400 MHz, DMSO-$d_6$): 13.13 (s, 1H), 10.63 (s, 1H), 9.63 (s, 1H), 9.24 (s, 1H), 8.22 (t, J = 1.8 Hz, 2H), 8.11 (d, J = 2.7 Hz, 1H), 7.56 (s, 1H), 7.42 (d, J = 8.2 Hz, 1H), 7.32 (s, 1H), 7.25 (dd, J = 8.1, 1.8 Hz, 1H), 7.02 (t, J = 52.7 Hz, 1H), 5.36 (s, 2H). |

TABLE 24-continued
| Compound No. | Name | Structure | LCMS data | NMR data |
|---|---|---|---|---|
| 315 | (S)-6-((4-carbamoyl-3-(4-(ethylsulfonamido)-3-(1-(4-fluorophenyl)ethoxy)phenyl)-1H-pyrazol-5-yl)amino)nicotinic acid | 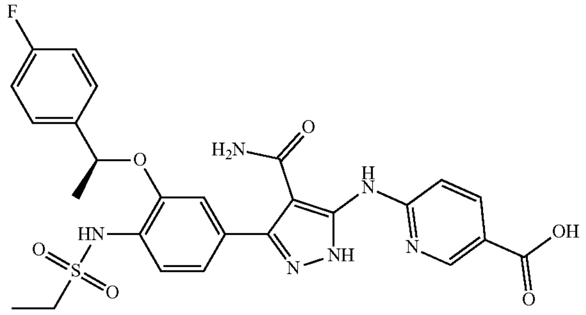 [SMILES: CCS(=O)(=O)Nc1ccc(-c2n[nH]c(Nc3ccc(C(=O)O)cn3)c2C(N)=O)cc1O[C@@H](C)c1ccc(F)cc1] | LCMS (Method A): 3.22 min; m/z: 569.2 $[M + H]^+$. | $^1H$ NMR (400 MHz, DMSO-$d_6$): 13.01 (s, 1H), 9.83 (s, 1H), 8.71 (s, 1H), 8.14 (s, 1H), 7.84 (d, J = 19.7 Hz, 1H), 7.70 (s, 1H), 7.62 (d, J = 13.7 Hz, 2H), 7.42 (s, 1H), 7.29 (d, J = 7.2 Hz, 1H), 7.17 (d, J = 18.0 Hz, 3H), 7.09 (s, 1H), 5.65 (s, 1H), 3.11 (d, J = 7.3 Hz, 2H), 1.60 (d, J = 6.1 Hz, 3H), 1.26 (s, 3H). |

Compound 222

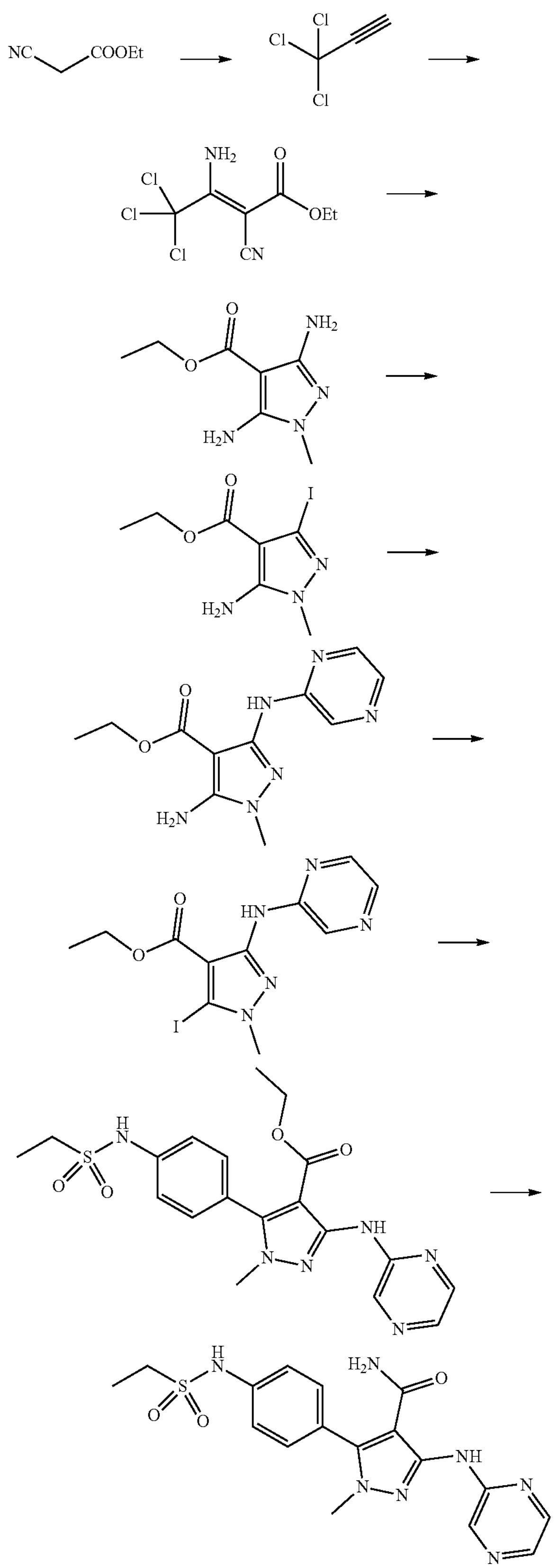

Step 1: ethyl (2Z)-3-amino-4,4,4-trichloro-2-cyanobut-2-enoate

To a solution of ethyl 2-cyanoacetate (20 mL, 196 mmol) and trichloroacetonitrile (54 g, 374 mmol) in EtOH (70 mL) at 0° C., was added $Et_3N$ (1.97 g, 19.6 mmol) and the reaction mixture was stirred for 2 h under $N_2$. The mixture was concentrated under reduced pressure and the residue was purified by silica gel column chromatography (PE:EtOAc, 5:1) to afford the title product (37 g, 79%) as a white solid. LCMS (Method A): 2.04 min; m/z: 257.1, 259.2 $[M+H]^+$.

Step 2: ethyl 3,5-diamino-1-methyl-1H-pyrazole-4-carboxylate

A solution of ethyl (2Z)-3-amino-4,4,4-trichloro-2-cyanobut-2-enoate (1 g, 3.88 mmol) and $MeNHNH_2$ (450 mg, 9.76 mmol) in DMF (10 mL) was stirred at 100° C. for 3 h and then concentrated under reduced pressure. The residue was purified by silica gel column chromatography (PE:EtOAc, 5:1 then DCM:MeOH, 20:1) to afford the title product (660 mg, 92%) as a brown solid. LCMS (Method A): 1.01 min; m/z: 185.1 $[M+H]^+$.

Step 3: 5-amino-3-iodo-1-methyl-1H-pyrazole-4-carboxylate

A solution of ethyl 3,5-diamino-1-methyl-1H-pyrazole-4-carboxylate (100 mg, 0.54 mmol), $CH_2I_2$ (145 mg, 0.542 mmol) and isoamyl nitrite (160 mg, 0.542 mmol) in MeCN (3 mL) was stirred at 60° C. for 3 h under $N_2$. The reaction mixture was concentrated under reduced pressure and the residue was purified by prep-TLC (PE:EtOAc, 3:1) to afford the title product (30 mg, 19%) as a yellow solid. The structure was confirmed by HMBC experiment. LCMS (Method A): 3.04 min; m/z: 295.9 $[M+H]^+$.

Step 4: ethyl 5-amino-1-methyl-3-[(pyrazin-2-yl)amino]-1H-pyrazole-4-carboxylate A mixture of ethyl 5-amino-3-iodo-1-methyl-1H-pyrazole-4-carboxylate (1.4 g, 4.74 mmol), pyrazin-2-amine (450 mg, 4.74 mmol), $Pd_2(dba)_3$ (434 mg, 0.47 mmol), Xantphos (411 mg, 0.7110 mmol) and $Cs_2CO_3$ (4.62 g, 14.2 mmol) in degassed 1,4-dioxane (30 mL) was stirred at 100° C. overnight under $N_2$. The reaction mixture was concentrated under reduced pressure and the residue was purified by silica gel column chromatography (PE:EtOAc, 5:1 to 1:1) to afford the title product (600 mg, 48%) as a yellow solid. LCMS (Method A): 2.78 min; m/z: 263.0 $[M+H]^+$.

Step 5: ethyl 5-iodo-1-methyl-3-(pyrazin-2-ylamino)-1H-pyrazole-4-carboxylate

A mixture of ethyl 5-amino-1-methyl-3-[(pyrazin-2-yl)amino]-1H-pyrazole-4-carboxylate (1 g, 3.81 mmol), isoamyl nitrite (891 mg, 7.62 mmol) and $CH_2I_2$ (2.03 g, 7.62 mmol) in MeCN (20 mL) was stirred at 100° C. for 3 h under $N_2$. The reaction mixture was concentrated under reduced pressure and the residue was purified by silica gel column chromatography (PE:EtOAc, 10:1 to 3:1) to afford the title product (700 mg, 49%) as a yellow solid. LCMS (Method A): 1.28 min; m/z: 373.9 $[M+H]^+$.

Step 6: ethyl 5-(4-(ethylsulfonamido)phenyl)-1-methyl-3-(pyrazin-2-ylamino)-1H-pyrazole-4-carboxylate A mixture of ethyl 5-iodo-1-methyl-3-[(pyrazin-2-yl)amino]-1H-pyrazole-4-carboxylate (150 mg, 0.401 mmol), N-[4-(4,4,5,5-tetramethyl-1,3,2-dioxaborolan-2-yl)phenyl]ethane-1-sulfonamide (125 mg, 0.402 mmol), Pd(dppf)$Cl_2$ (32.8 mg, 0.04 mmol), $K_2CO_3$ (165 mg, 1.20 mmol) and 70% aq. 1,4-dioxane (7 mL) was stirred at 100° C. overnight under $N_2$. The reaction mixture was concentrated under reduced pressure and the residue was purified by silica gel column chromatography (PE:EtOAc, 5:1 to 1:5) to afford the title product (95 mg, 49%) as a yellow solid. LCMS (Method A): 3.87 min; m/z: 431.1 $[M+H]^+$.

Step 7: 5-(4-(ethylsulfonamido)phenyl)-1-methyl-3-(pyrazin-2-ylamino)-1H-pyrazole-4-carboxamide (Compound 222)

A solution of ethyl 5-(4-ethanesulfonamidophenyl)-1-methyl-3-[(pyrazin-2-yl)amino]-1H-pyrazole-4-carboxylate (140 mg, 0.32 mmol) in MeOH:$NH_4OH$ (1:1, 28 mL) was divided equally between 7 sealed tubes. The seal tubes were successively heated at 115° C. for 2 h under MW irradiation. The reaction mixtures were combined, concentrated under reduced pressure and the residue was purified by prep-TLC (DCM:MeOH, 20:1) to provide the title product (11.4 mg, 8%) as a grey solid. LCMS (Method A): 3.37 min; m/z: 402.1 $[M+H]^+$. $^1$H NMR (400 MHz, $CDCl_3$): 9.74 (s, 1H), 9.43 (s, 1H), 8.20 (s, 1H), 8.11 (d, J=1.6 Hz, 1H), 7.51 (d, J=8.4 Hz, 2H), 7.42 (d, J=8.4 Hz, 2H), 3.64 (s, 3H), 3.27 (q, J=7.2 Hz, 2H), 1.45 (t, J=7.2 Hz, 3H).

Compound 253

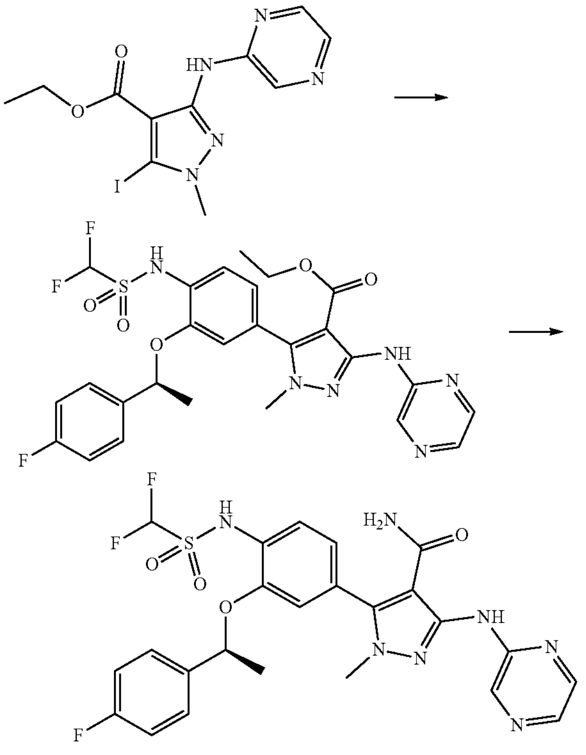

Step 1: ethyl 5-[4-(difluoromethanesulfonamido)-3-[(1S)-1-(4-fluorophenyl)ethoxy]phenyl]-1-methyl-3-[(pyrazin-2-yl)amino]-1H-pyrazole-4-carboxylate A mixture of ethyl 5-iodo-1-methyl-3-[(pyrazin-2-yl)amino]-1H-pyrazole-4-carboxylate (134 mg, 360 μmol), 1,1-difluoro-N-{2-[(1S)-1-(4-fluorophenyl)ethoxy]-4-(4,4,5,5-tetramethyl-1,3,2-dioxaborolan-2-yl)phenyl}methanesulfonamide (170 mg, 360 μmol), Pd(dppf)$Cl_2$ (29.3 mg, 36.0 μmol), $K_2CO_3$ (295 mg, 900 μmol) and 90% aq. 1,4-dioxane (5 mL) was stirred at 100° C. under $N_2$. After 16 h, the reaction mixture was concentrated and the residue was purified by silica gel column chromatography (PE:EtOAc, 5:1 to 1:1) to afford the title product (150 mg, 70%) as a yellow solid. LCMS (Method A): 4.13 min; m/z: 591.2 $[M+H]^+$.

Step 2: 5-[4-(difluoromethanesulfonamido)-3-[(1S)-1-(4-fluorophenyl)ethoxy]phenyl]-1-methyl-3-[(pyrazin-2-yl)amino]-1H-pyrazole-4-carboxamide (Compound 253)

A solution of ethyl 5-[4-(difluoromethanesulfonamido)-3-[(1S)-1-(4-fluorophenyl)ethoxy]phenyl]-1-methyl-3-[(pyrazin-2-yl)amino]-1H-pyrazole-4-carboxylate (40 mg, 67.7 μmol) in $NH_4OH$ (2 mL) was stirred at 50° C. for 2 h. The reaction mixture was concentrated and the residue was diluted with $H_2O$ (20 mL) and extracted with DCM (3×30 mL). The combined organic layers were washed (brine), dried ($Na_2SO_4$) and concentrated under reduced pressure. The crude residue was purified by prep-HPLC to afford the title compound (6.0 mg, 15%) as a white solid. LCMS (Method D): 4.23 min; m/z: 561.9 $[M+H]^+$. $^1$H NMR (400 MHz, DMSO-$d_6$): 9.89 (s, 1H), 9.35 (s, 1H), 8.27 (br s, 3H), 7.48 (q, J=8.4, 6.0 Hz, 2H), 7.41 (d, J=8.4 Hz, 1H), 7.12 (t, J=8.8 Hz, 2H), 6.77 (dd, J=8.0, 2.0 Hz, 1H), 6.66 (d, J=1.6 Hz, 1H), 6.30 (t, J=54.4 Hz, 1H), 5.65-5.61 (m, 1H), 3.36 (s, 3H), 1.51 (d, J=6.4 Hz, 3H).

Compound 320

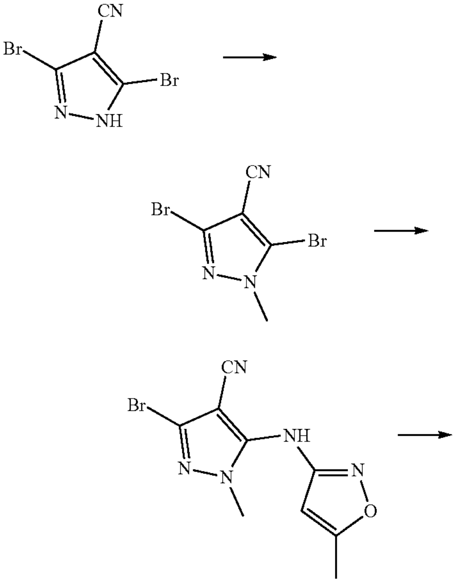

-continued

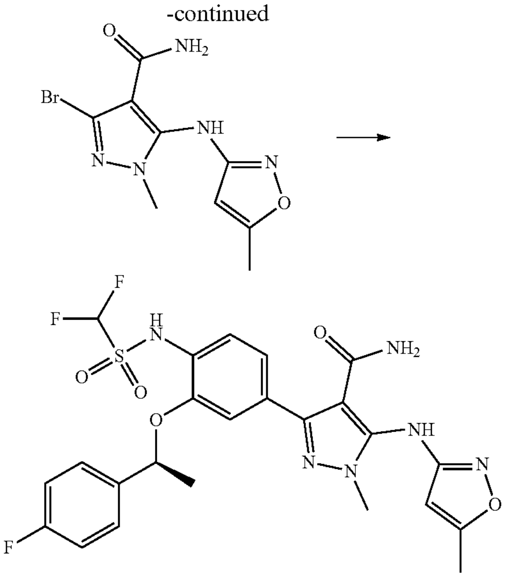

Step 1: 3,5-dibromo-1-methyl-1H-pyrazole-4-carbonitrile

To a solution of 3,5-dibromo-1H-pyrazole-4-carbonitrile (1.0 g, 3.98 mmol) in dry DMF (20 mL) was added NaH (475 mg, 11.9 mmol) at 0° C., and the solution was stirred for 30 min at 0° C. MeI (1.68 g, 11.9 mmol) was slowly added and the reaction mixture was stirred at RT for 1 h. Water (200 mL) was added and the organics were extracted with EtOAc (3×200 mL). The combined organics were dried ($Na_2SO_4$) and concentrated under reduced pressure. The residue was purified by column chromatography on silica gel (PE:EtOAc, 10:1 to 5:1) to give the title product (750 mg, 71%) as a white solid. LCMS (Method A): 3.51 min, m/z 263.9/265.9/267.9 [M+H]+.

Step 2: 3-bromo-1-methyl-5-[(5-methyl-1,2-oxazol-3-yl)amino]-1H-pyrazole-4-carbonitrile A mixture of 3,5-dibromo-1-methyl-1H-pyrazole-4-carbonitrile (200 mg, 0.7549 mmol), 5-methyl-1,2-oxazol-3-amine (59.1 mg, 603 μmol), $Cs_2CO_3$ (736 mg, 2.26 mmol), Xantphos (86.7 mg, 150 μmol), $Pd_2(dba)_3$ (69.0 mg, 75.4 μmol) in degassed 1,4-dioxane (5 mL) was stirred under $N_2$ at 100° C. overnight. The reaction mixture was concentrated under reduced pressure and the residue was purified by Prep-TLC (PE:EA, 2:1) to give the title product (70 mg, 28%) as a yellow solid. LCMS (Method A): 3.17 min, m/z 282.0/284.0 $[M+H]^+$.

Step 4: 3-bromo-1-methyl-5-[(5-methyl-1,2-oxazol-3-yl)amino]-1H-pyrazole-4-carboxamide A mixture of 3-bromo-1-methyl-5-[(5-methyl-1,2-oxazol-3-yl)amino]-1H-pyrazole-4-carbonitrile (40 mg, 0.1417 mmol) and Ghaffar-Parkins catalyst (30 mg, 0.07022 mmol) in dioxane (10 mL) and $H_2O$ (2 mL) was stirred overnight at 100° C. under $N_2$. The reaction mixture was concentrated under reduced pressure and the residue was purified by Prep-TLC (PE:EtOAc, 1:1) to give the title product (20 mg, 47%) as a yellow solid. LCMS (Method A): 2.36 min; 300.0/302.0 [M+H]+

Step 5: (S)-3-(4-((difluoromethyl)sulfonamido)-3-(1-(4-fluorophenyl)ethoxy)phenyl)-1-methyl-5-((5-methylisoxazol-3-yl)amino)-1H-pyrazole-4-carboxamide (Compound 320)

A mixture of 3-bromo-1-methyl-5-[(5-methyl-1,2-oxazol-3-yl)amino]-1H-pyrazole-4-carboxamide (15 mg, 0.050 mmol), 1,1-difluoro-N-{2-[(1S)-1-(4-fluorophenyl)ethoxy]-4-(4,4,5,5-tetramethyl-1,3,2-dioxaborolan-2-yl) phenyl}methanesulfonamide (35.3 mg, 0.749 mmol), $Na_2CO_3$ (10.5 mg, 99.9 μmol) and $Pd(PPh_3)_4$ (5.76 mg, 4.99 μmol) in degassed 1,4-dioxane (4 mL) and $H_2O$ (1 mL) was stirred at 100° C. under microwave for 30 min. The reaction mixture was concentrated under reduced pressure and the residue was purified by Prep-TLC (DCM:MeOH, 20:1) to give the title product (30 mg, 32%) as a white solid. LCMS (Method A): 3.56 min; 565.2 $[M+H]^+$. $^1H$ NMR (400 MHz, DMSO-$d_6$): 10.36 (s, 1H), 8.53 (s, 1H), 7.58 (dd, J=8.6, 5.7 Hz, 2H), 7.37-7.28 (m, 2H), 7.25-7.13 (m, 4H), 7.13-6.84 (m, 2H), 5.86 (d, J=1.1 Hz, 1H), 5.50 (q, J=6.3 Hz, 1H), 3.62 (s, 3H), 2.28 (s, 3H), 1.57 (d, J=6.3 Hz, 3H).

Biology

In Vitro Assay

Binding affinity of the test compounds for MLKL (full length), RIP1 and RIP3 was determined using the KINOMEscan™ technology developed by DiscoverX (USA; http://www.discoverx.com). The assay was conducted according to manufacturer instructions.

Protocol Description

Kinase assays. For most assays, kinase-tagged T7 phage strains were grown in parallel in 24-well blocks in an *E. coli* host derived from the BL21 strain. *E. coli* were grown to log-phase and infected with T7 phage from a frozen stock (multiplicity of infection=0.4) and incubated with shaking at 32° C. until lysis (90-150 minutes). The lysates were centrifuged (6,000×g) and filtered (0.2 μm) to remove cell debris. The remaining kinases were produced in HEK293 cells and subsequently tagged with DNA for qPCR detection. Streptavidin-coated magnetic beads were treated with biotinylated small molecule ligands for 30 minutes at room temperature to generate affinity resins for kinase assays. The liganded beads were blocked with excess biotin and washed with blocking buffer (SeaBlock (Pierce), 1% BSA, 0.05% Tween 20, 1 mM DTT) to remove unbound ligand and to reduce non-specific phage binding. Binding reactions to screen test compounds for kinase binding activity were assembled by combining kinases, liganded affinity beads, and test compounds in 1× binding buffer (20% SeaBlock, 0.17×PBS, 0.05% Tween 20, 6 mM DTT). All reactions were performed in polypropylene 384-well plates in a final volume of 20 μL. The assay plates were incubated at room temperature with shaking for 1 hour and the affinity beads were washed with wash buffer (1×PBS, 0.05% Tween 20). The beads were then re-suspended in elution buffer (1×PBS, 0.05% Tween 20, 0.5 μM non-biotinylated affinity ligand) and incubated at room temperature with shaking for 30 minutes. The kinase concentration in the eluates was measured by qPCR.

Compound Handling

An 11-point 3-fold serial dilution of each test compound was prepared in 100% DMSO at 100× final test concentration and subsequently diluted to 1x in the assay (final DMSO concentration=1%). Most $K_D$s were determined using a compound top concentration=30,000 nM. If the initial $K_D$ determined was <0.5 nM (the lowest concentration tested in the initial serial dilution), the measurement was repeated with a further 11 point 3-fold serial dilution starting at 3,000 nM.

Binding Constants ($K_D$s)

$K_D$ for each test compound was calculated with a standard dose-response curve using the Hill equation (equation (1)):

$$\text{Response} = \text{Background} + \frac{\text{Signal} - \text{Background}}{1 + (K_D^{\text{Hill Slope}} / \text{Dose}^{\text{Hill Slope}})} \quad (1)$$

The Hill Slope was set to −1.

Curves were fitted using a non-linear least square fit with the Levenberg-Marquardt algorithm.

REFS

Fabian, M. A. et al. A small molecule-kinase interaction map for clinical kinase inhibitors. Nat. Biotechnol. 23, 329-336 (2005).

Karaman, M. W. et al. A quantitative analysis of kinase inhibitor selectivity. Nat. Biotechnol. 26, 127-132 (2008).

Hill, A. V. The possible effects of the aggregation of the molecules of hemoglobin on its dissociation curves. J. Physiol. (Lond.). 40, iv-vii (1910).

Levenberg, K. A method for the solution of certain non-linear problems in least squares. Q. Appl. Math. 2, 164-168 (1944).

Table 25: Results of binding assay for compounds of the invention against MLKL, RIPK1 and RIPK3. Binding affinity is measured by the equilibrium dissociation constant ($K_D$). The smaller the $K_D$ value, the greater the binding affinity of the ligand for its target. Activity is provided as follows:

++++=$K_D$<10 nM

+++=10 nM<$K_D$<1000 nM

++=1,000 nM<$K_D$<30,000 nM

+=$K_D$>30,000 nM

| Compound No | MLKL ($K_D$) | RIP1 ($K_D$) | RIP3 ($K_D$) |
|---|---|---|---|
| 1 | ++++ | + | + |
| 2 | +++ | + | + |
| 3 | ++ | + | + |
| 4 | +++ | + | + |
| 5 | +++ | + | + |
| 6 | +++ | + | + |
| 7 | ++ | + | + |
| 8 | +++ | + | + |
| 9 | ++++ | + | + |
| 10 | +++ | + | + |
| 11 | ++++ | + | + |
| 12 | +++ | + | + |
| 13 | +++ | + | + |
| 14 | ++++ | + | + |
| 15 | ++++ | + | + |
| 16 | +++ | + | + |
| 17 | ++++ | + | + |
| 18 | ++++ | + | ++ |
| 19 | ++++ | + | + |
| 20 | ++++ | + | + |
| 21 | ++++ | + | + |
| 22 | ++++ | + | + |
| 23 | ++++ | + | + |
| 24 | ++++ | + | + |
| 25 | ++++ | + | + |
| 26 | ++++ | + | + |
| 27 | ++++ | + | + |
| 28 | ++++ | + | + |

-continued

| Compound No | MLKL ($K_D$) | RIP1 ($K_D$) | RIP3 ($K_D$) |
|---|---|---|---|
| 29 | ++++ | + | + |
| 30 | ++++ | + | + |
| 31 | ++++ | + | + |
| 32 | ++++ | + | + |
| 33 | +++ | + | ++ |
| 34 | ++++ | + | + |
| 35 | +++ | + | + |
| 36 | +++ | ++ | + |
| 37 | +++ | + | + |
| 38 | ++++ | ++ | + |
| 39 | ++++ | ++ | + |
| 40 | ++++ | + | + |
| 41 | ++++ | + | + |
| 42 | ++++ | + | + |
| 43 | ++++ | + | ++ |
| 44 | +++ | + | + |
| 45 | +++ | ++ | + |
| 46 | +++ | + | + |
| 47 | ++++ | + | + |
| 48 | ++++ | + | + |
| 49 | ++++ | + | ++ |
| 50 | +++ | + | + |
| 51 | +++ | + | + |
| 52 | ++++ | + | ++ |
| 53 | ++++ | + | ++ |
| 54 | ++++ | + | ++ |
| 55 | +++ | + | ++ |
| 56 | +++ | + | ++ |
| 57 | +++ | ++ | + |
| 58 | +++ | + | ++ |
| 59 | +++ | + | ++ |
| 60 | +++ | + | + |
| 61 | +++ | + | ++ |
| 62 | ++++ | + | + |
| 63 | ++++ | + | + |
| 64 | +++ | + | + |
| 65 | +++ | + | + |
| 66 | ++++ | + | ++ |
| 67 | ++++ | + | + |
| 68 | ++++ | + | + |
| 69 | +++ | + | + |
| 70 | ++++ | + | + |
| 71 | ++++ | + | ++ |
| 72 | ++++ | + | + |
| 73 | +++ | + | + |
| 74 | +++ | + | ++ |
| 75 | ++++ | + | + |
| 76 | +++ | + | + |
| 77 | +++ | + | ++ |
| 78 | +++ | + | + |
| 79 | +++ | + | + |
| 80 | +++ | + | + |
| 81 | +++ | + | + |
| 82 | +++ | + | + |
| 83 | +++ | + | + |
| 84 | ++++ | + | ++ |
| 85 | +++ | + | ++ |
| 86 | ++++ | + | ++ |
| 87 | ++++ | + | + |
| 88 | ++++ | ++ | ++ |
| 89 | ++++ | ++ | ++ |
| 90 | ++++ | + | + |
| 91 | ++++ | + | + |
| 92 | ++++ | + | ++ |
| 93 | ++++ | + | + |
| 94 | +++ | + | ++ |
| 95 | +++ | + | ++ |
| 96 | +++ | + | ++ |
| 97 | +++ | + | + |
| 98 | ++++ | + | + |
| 99 | ++++ | + | + |
| 100 | ++++ | + | + |
| 101 | ++++ | + | + |
| 102 | ++++ | + | + |
| 103 | ++++ | + | ++ |
| 104 | ++++ | + | + |

-continued

| Compound No | MLKL ($K_D$) | RIP1 ($K_D$) | RIP3 ($K_D$) |
|---|---|---|---|
| 105 | ++++ | + | + |
| 106 | ++++ | + | + |
| 107 | ++++ | + | ++ |
| 108 | ++++ | + | + |
| 109 | ++++ | + | ++ |
| 110 | ++++ | + | + |
| 111 | +++ | + | + |
| 112 | ++++ | + | + |
| 113 | ++++ | + | + |
| 114 | ++++ | + | ++ |
| 115 | ++++ | ++ | + |
| 116 | +++ | + | + |
| 117 | +++ | ++ | + |
| 118 | +++ | + | + |
| 119 | +++ | ++ | + |
| 120 | ++++ | + | + |
| 121 | ++++ | ++ | ++ |
| 122 | ++++ | + | ++ |
| 123 | ++++ | + | + |
| 124 | ++++ | + | + |
| 125 | ++ | + | + |
| 126 | ++++ | + | + |
| 127 | ++++ | + | ++ |
| 128 | ++ | + | ++ |
| 129 | ++ | + | ++ |
| 130 | ++ | + | ++ |
| 131 | ++++ | + | ++ |
| 132 | +++ | + | + |
| 133 | ++ | + | ++ |
| 134 | ++ | + | ++ |
| 135 | ++ | | |
| 136 | ++ | | |
| 137 | ++++ | + | + |
| 138 | ++ | + | + |
| 139 | ++++ | + | + |
| 140 | ++++ | + | + |
| 141 | ++ | + | + |
| 142 | ++ | ++ | + |
| 143 | ++++ | + | + |
| 144 | ++++ | + | + |
| 145 | ++++ | + | + |
| 146 | ++++ | + | + |
| 147 | ++++ | + | + |
| 148 | ++++ | + | + |
| 149 | ++++ | + | + |
| 150 | ++++ | + | ++ |
| 151 | ++++ | + | + |
| 152 | ++++ | + | + |
| 153 | ++++ | + | + |
| 154 | ++++ | + | + |
| 155 | ++++ | + | + |
| 156 | ++++ | + | + |
| 157 | ++++ | + | + |
| 158 | ++++ | + | + |
| 159 | ++++ | + | + |
| 160 | ++++ | + | + |
| 161 | ++++ | + | + |
| 162 | ++++ | + | + |
| 163 | ++++ | + | + |
| 164 | ++++ | + | + |
| 165 | ++++ | + | + |
| 166 | ++++ | + | + |
| 167 | ++++ | + | + |
| 168 | ++++ | + | + |
| 169 | ++++ | + | + |
| 170 | ++++ | + | + |
| 171 | ++++ | + | + |
| 172 | ++++ | + | + |
| 173 | ++++ | + | + |
| 174 | +++ | + | ++ |
| 175 | ++++ | + | + |
| 176 | ++++ | + | + |
| 177 | ++++ | + | + |
| 178 | ++++ | + | + |
| 179 | ++++ | + | + |
| 180 | ++++ | + | + |

-continued

| Compound No | MLKL ($K_D$) | RIP1 ($K_D$) | RIP3 ($K_D$) |
|---|---|---|---|
| 181 | ++++ | + | ++ |
| 182 | +++ | + | + |
| 183 | ++++ | + | + |
| 184 | ++++ | + | + |
| 185 | ++++ | + | + |
| 186 | ++++ | + | + |
| 187 | +++ | + | + |
| 188 | ++++ | + | + |
| 189 | ++++ | + | ++ |
| 190 | ++++ | + | + |
| 191 | ++++ | + | + |
| 192 | +++ | + | + |
| 193 | ++++ | + | + |
| 194 | ++++ | + | + |
| 195 | ++++ | + | + |
| 196 | ++++ | + | + |
| 197 | ++++ | + | ++ |
| 198 | ++++ | + | + |
| 199 | ++++ | + | + |
| 200 | +++ | + | + |
| 201 | ++++ | + | + |
| 202 | ++++ | + | + |
| 203 | +++ | + | + |
| 204 | ++++ | + | + |
| 205 | ++++ | + | + |
| 206 | ++++ | + | + |
| 207 | +++ | + | + |
| 208 | +++ | + | + |
| 209 | +++ | + | + |
| 210 | ++++ | + | + |
| 211 | ++++ | + | + |
| 212 | +++ | ++ | + |
| 213 | +++ | + | + |
| 214 | +++ | + | + |
| 215 | +++ | + | + |
| 216 | +++ | + | + |
| 217 | ++++ | + | + |
| 218 | +++ | + | + |
| 219 | ++++ | + | + |
| 220 | +++ | + | + |
| 221 | ++++ | + | + |
| 222 | ++++ | + | + |
| 223 | ++++ | + | + |
| 224 | ++++ | + | + |
| 225 | ++++ | + | + |
| 226 | ++++ | + | + |
| 227 | ++++ | + | + |
| 228 | ++++ | + | + |
| 229 | ++++ | + | + |
| 230 | ++++ | + | + |
| 231 | ++++ | + | + |
| 232 | ++++ | + | + |
| 233 | ++++ | + | + |
| 234 | ++++ | + | + |
| 235 | ++++ | + | + |
| 236 | ++++ | + | + |
| 237 | ++++ | + | + |
| 238 | ++++ | + | + |
| 239 | ++++ | + | + |
| 240 | ++++ | + | + |
| 241 | ++++ | + | + |
| 242 | ++++ | + | + |
| 243 | +++ | + | + |
| 244 | +++ | + | + |
| 245 | ++++ | + | + |
| 246 | ++++ | + | + |
| 247 | ++++ | + | + |
| 248 | ++++ | + | + |
| 249 | ++++ | + | + |
| 250 | +++ | n.d. | n.d. |
| 251 | ++++ | n.d. | n.d. |
| 252 | ++++ | + | + |
| 253 | ++++ | + | + |
| 254 | +++ | + | + |
| 255 | +++ | + | + |
| 256 | ++++ | + | + |

-continued

| Compound No | MLKL ($K_D$) | RIP1 ($K_D$) | RIP3 ($K_D$) |
|---|---|---|---|
| 257 | ++++ | + | + |
| 258 | ++++ | + | + |
| 259 | ++++ | + | + |
| 260 | ++++ | + | + |
| 261 | ++++ | + | + |
| 262 | ++++ | + | + |
| 263 | ++++ | + | + |
| 264 | ++++ | + | + |
| 265 | ++++ | + | + |
| 266 | ++++ | + | + |
| 267 | ++++ | + | + |
| 268 | ++++ | + | + |
| 269 | ++++ | + | + |
| 270 | ++++ | + | + |
| 271 | ++++ | + | + |
| 272 | ++++ | + | + |
| 273 | ++++ | + | + |
| 274 | ++++ | + | + |
| 275 | ++++ | + | + |
| 276 | ++++ | + | + |
| 277 | ++++ | + | + |
| 278 | ++++ | + | + |
| 279 | ++++ | + | + |
| 280 | ++++ | + | + |
| 281 | ++++ | + | + |
| 282 | ++++ | + | + |
| 283 | ++++ | + | + |
| 284 | ++++ | + | + |
| 285 | ++++ | + | + |
| 286 | ++++ | + | + |
| 287 | ++++ | + | + |
| 288 | ++++ | + | + |
| 289 | ++++ | + | + |
| 290 | ++++ | + | + |
| 291 | ++++ | + | + |
| 292 | ++++ | + | + |
| 293 | ++++ | + | + |
| 294 | ++++ | + | + |
| 295 | ++++ | + | + |
| 296 | ++++ | + | + |
| 297 | ++++ | + | + |
| 298 | ++++ | + | + |
| 299 | ++++ | + | + |
| 300 | ++++ | + | + |
| 301 | ++++ | + | + |
| 302 | ++++ | + | + |
| 303 | ++++ | + | + |
| 304 | +++ | + | + |
| 305 | ++++ | + | + |
| 306 | ++++ | + | + |
| 307 | ++++ | + | + |
| 308 | ++++ | + | + |
| 309 | ++++ | + | + |
| 310 | ++++ | + | + |
| 311 | ++++ | + | + |
| 312 | ++++ | + | + |
| 313 | ++++ | + | + |
| 314 | ++++ | + | + |
| 315 | ++++ | + | + |
| 316 | ++++ | + | + |
| 317 | ++++ | + | + |
| 318 | ++++ | + | + |
| 319 | ++++ | + | + |
| 320 | ++++ | + | + |

CELLULAR ASSAY: Screening compounds for inhibition of TSQ induced necroptosis, 384 well plate format.

Cell Line ID: U937 human histiocytic leukemia cell line.

Cell Concentration (cells/well): Final cell density is 20000 cells per well.

Cell growth medium: HT-RPMI medium+7.4% Fetal Bovine Serum (FBS). Cells are cultured in Corning 150 $cm^2$ tissue culture flasks with vented caps at 37° C./5% $CO_2$.

Incubation: Plates were incubated at 37° C./5% $CO_2$ in a humidified incubator for 48 hours following addition of compounds and death stimuli (TSQ cocktail).

Compound concentration: 36 μM starting concentration, 1:3 dilution, 10 point

DMSO final concentration (% v/v): 0.3%.

Compounds in TSQ cocktail (T: TNF; S: Smac mimetic; Q: Q-VD-OPh) and their final concentrations:

hTNF-Fc (100 ng/ml)—produced by standard procedures as shown in Bossen et al., *J Biol Chem,* 2006, 281(20), 13964-13971.

Compound A (500 nM)—Smac mimetic, Tetralogic and SYNthesis med chem

Q-VD-OPh (10 μM)—MP Biomedicals

Assay Experimental Outline

The cellular assay was carried out according to the following steps:

1. Each well was prepared by sequential addition of:
   a. DMSO (control; columns 1-2 and 23-24) or compound in DMSO—addition was performed using acoustic transfer of nl volumes of stock compound to give final test concentrations of 36, 12, 4, 1.3, 0.44, 0.148, 0.049, 0.016, 0.005 and 0.002 μM. All wells were backfilled with DMSO to a final total volume in the well of 100 nl.
   b. Following compound/DMSO addition in step (a), 40 μL of cell suspension ($5\times10^5$ cells/mL) was added to provide a final cell concentration of 20,000 cells per well, and
   c. Following cell addition in step (b), 10 μL of 5×TSQ cocktail (except to positive controls; columns 1 and 23) was added to each well.
2. After 48 hours, plate was removed from the 37° C. incubator and equilibrated to room temperature for 45 minutes.
3. 15 μL of room temperature CellTitre-Glo2™ (Promega™) was added to each well.
4. Shook plates for 2 minutes (~600 rpm) and incubated at room temperature for 15 minutes to allow signal to stabilise.
5. Read luminescence readout on a plate reader.

Analysis:

Percent viability was calculated for each compound according to equation (2):

$$\%\ \text{viability} = 100 \times \frac{(RawData - NSA)}{(TA - NSA)} \quad (2)$$

wherein

RawData is the readout of any cell containing a compound of the invention

TA is the total activity provided by the luminescence readout from DMSO only wells (columns 2 and 24)=100% viability NSA is the non-specific activity provided by DMSO+TSQ wells (columns 1 and 23)=0% viability Curve fitting: 10-point titration curves are fitted with the 4-parameter logistic nonlinear regression model and the $IC_{50}$ reported is the inflection point of the curve.

Analysis: Data was loaded into Dotmatics™ and visualised using the Tibco® Spotfire™ software. 10 points titration curves were fitted with the 4-parameter logistic nonlinear regression model and the $IC_{50}$ reported reflect the inflection point of the curve for curve fitting.

Interpretation of Results:

Assay involving the TSQ cocktail (T: TNF; S: Smac mimetic; Q: Q-VD-OPh): TSQ treatment ensures that cells specifically undergo necroptotic cell death. TNF activates the TNF receptor, Smac mimetic directs the signal away from proinflammatory signaling and toward the RIP1/RIP3-mediated cell death pathways, and Q-VD-OPh ensures that the apoptotic response is blocked leaving only the programmed necrosis response. The compounds' activity (solution in DMSO) tested in this TSQ-induced assay was evaluated by determining the number of viable cells in culture by measuring the amount of ATP present as measured by CelltiterGlo.

Counter screen: In parallel, all compounds were tested for their ability to affect cell viability. The same U937 cells were treated with compound in DMSO without the TSQ cocktail. This counter screen enabled evaluation of off-target effects. In this case, cell viability was measured by CelltiterGlo.

The results of the screening of the compounds described above are shown below in the Table 26.

Table 26: Table showing the results of cell-based assays performed, analysed as the half maximal inhibitory concentration ($IC_{50}$), being the concentration of the test compound needed to inhibit TSQ induced necroptosis by 50%. The lower the $IC_{50}$, the more potent the compound. Activity is provided as follows:

++++=$IC_{50}$<10 nM

+++=10 nM<$IC_{50}$<1000 nM

++=1,000 nM<$IC_{50}$<30,000 nM

+=$IC_{50}$>30,000 nM

| Compound No | Inhibition of TSQ-induced necroptosis ($IC_{50}$ cell-based assay) | Off-target effect ($IC_{50}$ cell-based assay) |
|---|---|---|
| 9 | +++ | + |
| 14 | +++ | + |
| 21 | ++ | + |
| 22 | +++ | + |
| 24 | ++ | + |
| 25 | +++ | + |
| 34 | +++ | + |
| 39 | ++ | + |
| 41 | ++ | + |
| 42 | +++ | + |
| 43 | +++ | + |
| 53 | +++ | + |
| 62 | +++ | + |
| 63 | ++ | + |
| 66 | +++ | + |
| 68 | ++ | + |
| 71 | ++ | + |
| 84 | ++ | + |
| 88 | ++ | + |
| 90 | ++ | + |
| 92 | ++ | + |
| 93 | ++ | + |
| 101 | ++ | + |
| 102 | ++ | + |
| 108 | ++ | + |
| 113 | ++ | + |
| 115 | ++ | + |
| 123 | ++ | + |
| 124 | ++ | + |
| 127 | ++ | + |
| 128 | ++ | + |
| 139 | +++ | + |
| 140 | +++ | ++ |
| 143 | +++ | + |
| 144 | +++ | + |
| 146 | ++++ | + |
| 150 | +++ | + |
| 152 | +++ | + |
| 153 | +++ | + |
| 154 | +++ | ++ |
| 155 | +++ | ++ |
| 156 | ++ | + |
| 157 | +++ | + |
| 158 | ++ | + |
| 160 | ++ | + |
| 161 | +++ | ++ |
| 162 | +++ | + |
| 163 | +++ | + |
| 164 | ++++ | + |
| 165 | ++++ | + |
| 166 | +++ | + |
| 169 | +++ | + |
| 170 | +++ | + |
| 171 | +++ | + |
| 175 | ++++ | + |
| 176 | +++ | ++ |
| 181 | ++ | + |
| 188 | +++ | + |
| 190 | +++ | + |
| 191 | +++ | + |
| 194 | +++ | ++ |
| 196 | +++ | + |
| 198 | ++ | + |
| 199 | +++ | + |
| 202 | +++ | + |
| 208 | ++ | + |
| 222 | ++ | + |
| 223 | ++++ | + |
| 229 | +++ | + |
| 233 | +++ | + |
| 234 | +++ | ++ |
| 235 | +++ | + |
| 238 | +++ | + |
| 242 | +++ | + |
| 245 | ++++ | + |
| 246 | +++ | + |
| 248 | +++ | + |
| 249 | ++ | + |
| 251 | ++ | + |
| 252 | ++ | + |
| 253 | ++ | + |
| 256 | + | + |
| 259 | + | + |
| 260 | ++++ | + |
| 262 | +++ | + |
| 264 | ++++ | + |
| 265 | ++ | + |
| 266 | ++ | + |
| 271 | +++ | + |
| 273 | +++ | + |
| 274 | +++ | + |
| 275 | ++ | + |
| 276 | ++++ | ++ |
| 277 | ++++ | + |
| 278 | ++++ | + |
| 279 | +++ | + |
| 281 | +++ | + |
| 282 | ++++ | ++ |
| 283 | +++ | + |
| 284 | +++ | + |
| 285 | ++++ | + |
| 286 | ++ | + |
| 288 | ++++ | + |
| 289 | ++++ | + |
| 290 | +++ | + |
| 291 | ++++ | ++ |
| 292 | +++ | + |
| 293 | +++ | + |
| 294 | ++ | + |
| 295 | +++ | + |
| 296 | ++++ | + |
| 297 | +++ | + |
| 298 | ++++ | + |

-continued

| Compound No | Inhibition of TSQ-induced necroptosis ($IC_{50}$ cell-based assay) | Off-target effect ($IC_{50}$ cell-based assay) |
|---|---|---|
| 299 | ++++ | + |
| 301 | +++ | + |
| 302 | +++ | + |
| 303 | +++ | + |
| 304 | +++ | ++ |
| 305 | +++ | + |
| 306 | +++ | + |
| 307 | +++ | + |
| 308 | ++++ | + |
| 309 | +++ | + |
| 310 | +++ | + |
| 311 | ++ | + |
| 312 | ++++ | + |
| 314 | +++ | + |
| 316 | ++++ | + |
| 317 | +++ | ++ |
| 318 | ++++ | + |
| 319 | +++ | + |
| 320 | ++++ | + |

It will be appreciated by persons skilled in the art that numerous variations and/or modifications may be made to the above-described embodiments, without departing from the broad general spirit and scope of the present disclosure. The present embodiments are, therefore, to be considered in all respects as illustrative and not restrictive.

The invention claimed is:

1. A compound of formula (I)

(I)

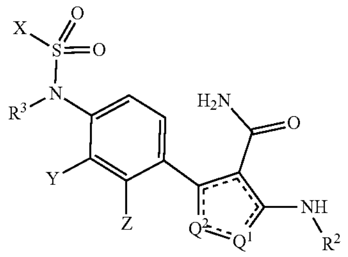

wherein $Q^1$ and $Q^2$ are selected from N and $NR^1$, wherein when $Q^1$ is N, $Q^2$ is $NR^1$ and when $Q^2$ is N, $Q^1$ is $NR^1$;

$R^1$ and $R^3$ are independently selected from H and an optionally substituted $C_{1-6}$-alkyl;

$R^2$ is an optionally substituted $C_{1-6}$-alkyl, an optionally substituted aryl or an optionally substituted heterocyclyl;

X is selected from optionally substituted $C_{1-6}$alkyl, optionally substituted halo$C_{1-6}$alkyl, optionally substituted $C_{2-6}$alkynyl, optionally substituted cycloalkyl, optionally substituted halocycloalkyl, optionally substituted aryl, optionally substituted alkylaryl, optionally substituted $C_{1-6}$alkylcycloalkyl and optionally substituted amino;

Y and Z are independently selected from H, $R^4$, $—OR^4$, $—NR^4R^5$, wherein at least one of Y and Z is H;

$R^4$ is selected from optionally substituted $C_{1-6}$alkyl, optionally substituted aryl, optionally substituted $C_{1-6}$alkylaryl, optionally substituted heterocyclyl, optionally substituted $C_{1-6}$alkylheterocyclyl, optionally substituted cycloalkyl, optionally substituted $C_{1-6}$alkyl$C_{3-10}$cycloalkyl, optionally substituted $C_{3-10}$cycloalkylaryl, optionally substituted $C_{3-10}$cycloalkylheterocyclyl, optionally substituted $C_{3-10}$cycloalkyl$C_{3-10}$cycloalkyl, optionally substituted 3-6 membered non-aromatic heterocyclyl-aryl, optionally substituted 3-6 membered non-aromatic heterocyclyl$C_{3-10}$cycloalkyl and optionally substituted 3-6 membered non-aromatic heterocyclyl-3-10 membered heterocyclyl; and $R^5$ is H or optionally substituted $C_{1-6}$alkyl, or a pharmaceutically acceptable salt, solvate, tautomer, N-oxide, stereoisomer and/or prodrug thereof.

2. The compound of claim 1, or pharmaceutically acceptable salt, solvate, tautomer, stereoisomer and/or prodrug thereof, wherein X is selected from $C_{1-6}$alkyl, $C_{2-6}$alkynyl, $C_{3-6}$cycloalkyl, aryl, $—(CH_2)_n$aryl, $—(CH_2)_n$cycloalkyl, and $—N(R^7)R^8$ n is 1 or 2, wherein each alkyl and alkynyl is optionally substituted with one or more groups selected from halo, nitrile, $—OR^6$, $—N(R^7)R^8$;

$R^6$, $R^7$ and $R^8$ are independently selected from H, $C_{1-6}$alkyl and halo$C_{1-6}$alkyl, and wherein each aryl and cycloalkyl is optionally substituted with one or more groups that are independently selected from halo, nitrile, $C_{1-4}$alkyl, $C_{1-4}$alkoxy, halo$C_{1-4}$alkyl and halo$C_{1-4}$alkoxy.

3. The compound of claim 1, or a pharmaceutically acceptable salt, solvate, tautomer, N-oxide, stereoisomer and/or prodrug thereof, wherein $R^4$ is selected from $C_{1-6}$alkyl, aryl, cycloalkyl, heterocyclyl, $C_{1-6}$alkyl$C_{3-10}$cycloalkyl, $C_{1-6}$alkylaryl and $C_{1-6}$alkylheterocyclyl, wherein each alkyl is optionally substituted with one or more groups independently selected from halo, $C_{1-4}$alkoxy, hydroxy, nitrile, amino, $C_{1-4}$alkylamino, $(C_{1-4}alkyl)_2$amino, aryl, cycloalkyl and heterocyclyl;

wherein each aryl is optionally substituted with one or more groups independently selected from halo, hydroxy, nitrile, amino, $C_{1-4}$alkylamino and $(C_{1-4}alkyl)_2$ amino, $C_{1-4}$alkyl, $C_{1-4}$alkoxy, halo$C_{1-4}$alkyl, halo$C_{1-4}$alkoxy, aryl, cycloalkyl and heterocyclyl;

wherein each cycloalkyl is optionally substituted with one or more groups independently selected from halo, hydroxy, nitrile, amino, $C_{1-4}$alkylamino and $(C_{1-4}alkyl)_2$amino, $C_{1-4}$alkyl, $C_{1-4}$alkoxy, halo$C_{1-4}$alkyl, halo$C_{1-4}$alkoxy, aryl, cycloalkyl and heterocyclyl; and wherein each heterocyclyl is optionally substituted with one or more groups independently selected from halo, hydroxy, nitrile, amino, $C_{1-4}$alkylamino and $(C_{1-4}alkyl)_2$ amino, $C_{1-4}$alkyl, $C_{1-4}$alkoxy, halo$C_{1-4}$alkyl, halo$C_{1-4}$alkoxy, cycloalkyl, heterocyclyl and aryl.

4. The compound of claim 1, or a pharmaceutically acceptable salt, solvate, tautomer, N-oxide, stereoisomer and/or prodrug thereof, wherein Z is H.

5. The compound of claim 4, or a pharmaceutically acceptable salt, solvate, tautomer, N-oxide, stereoisomer and/or prodrug thereof, wherein Y is selected from $—OR^4$, $—NR^4R^5$.

6. The compound of claim 5, or a pharmaceutically acceptable salt, solvate, tautomer, N-oxide, stereoisomer and/or prodrug thereof, wherein $R^4$ has partial structure (A):

(A)

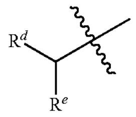

wherein $R^d$ is selected from H, optionally substituted $C_{1-4}$alkyl, optionally substituted $C_{1-4}$alkoxy, optionally substituted $C_{1-4}$alkoxy$C_{1-4}$alkyl, optionally substituted $C_{1-4}$alkylhydroxy, optionally substituted $C_{1-4}$alkylnitrile, optionally substituted $C_{1-4}$alkylamino and optionally substituted $(C_{1-4}alkyl)_2$amino, optionally substituted cycloalkyl and optionally substituted $C_{1-4}$alkylcycloalkyl; and $R^e$ is selected from optionally substituted aryl, optionally substituted $C_{1-5}$alkylaryl, optionally substituted heterocyclyl, optionally substituted $C_{1-5}$alkylheterocyclyl, optionally substituted cycloalkyl, and optionally substituted $C_{1-5}$alkyl$C_{3-10}$cycloalkyl.

7. The compound of claim 6, or a pharmaceutically acceptable salt, solvate, tautomer, N-oxide, stereoisomer and/or prodrug thereof, wherein $R^d$ is optionally substituted $C_{1-4}$alkyl, and the carbon atom to which $R^d$ and $R^e$ are attached is enriched in the(S) stereoisomer.

8. The compound of claim 1, or a pharmaceutically acceptable salt, solvate, tautomer, N-oxide, stereoisomer and/or prodrug thereof, wherein Y and Z are H.

9. The compound of claim 1, or a pharmaceutically acceptable salt, solvate, tautomer, N-oxide, stereoisomer and/or prodrug thereof, wherein $R^2$ is selected from an optionally substituted phenyl, an optionally substituted 5-membered monocyclic heteroaryl, an optionally substituted 6-membered monocyclic heteroaryl or an optionally substituted 10-membered bicyclic heteroaryl.

10. The compound of claim 1, or a pharmaceutically acceptable salt, solvate, tautomer, N-oxide, stereoisomer and/or prodrug thereof, wherein $R^2$ is represented by any one of partial formulas Ar1-Ar3:

Ar1

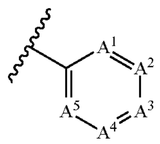

Ar2

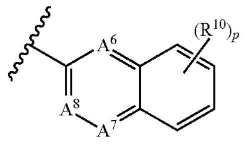

Ar3

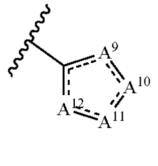

wherein $A^1$, $A^2$, $A^3$, $A^4$, $A^5$, $A^6$, $A^7$, and $A^8$ are independently selected from $CR^{11}$ and N $A^9$, $A^{10}$, $A^{11}$ and $A^{12}$ are independently selected from $C(R^{11})_q$, O, S, N and $NR^{12}$;

wherein not more than 2 of $A^1$, $A^2$, $A^3$, $A^4$ and $A^5$ are N;

wherein not more than 2 of $A^6$, $A^7$ and $A^8$ are N;

wherein at least 1 of $A^9$, $A^{10}$, $A^{11}$ and $A^{12}$ is selected from $C(R^{11})_q$, O, S and $NR^{12}$;

each $R^{11}$ is independently selected from H and $R^{10}$;

each $R^{10}$ is independently selected from halo, $C_{1-6}$alkyl, $C_{1-6}$alkoxy, $C_{3-6}$cycloalkyl, —O$C_{1-6}$alkyl$C_{1-6}$alkoxy, halo$C_{1-6}$alkyl, halo$C_{1-6}$alkoxy, nitrile, amido, $C_{1-6}$alkylamido, $(C_{1-6}alkyl)_2$amido, halo$C_{1-6}$alkylamido, $(haloC_{1-6}alkyl)_2$amido, acyl, $C_{1-6}$alkylacyl, halo$C_{1-6}$alkylacyl, arylacyl, heterocyclylacyl, cycloalkylacyl, heterocyclyl, halo$C_{1-6}$alkoxy, $C_{3-10}$cycloalkyl, $C_{1-6}$alkyl$C_{3-10}$cycloalkyl, $C_{1-6}$alkoxy$C_{3-10}$cycloalkyl, halo$C_{1-6}$alkyl$C_{3-10}$cycloalkyl, halo$C_{1-6}$alkoxy$C_{3-10}$cycloalkyl, $C_{1-6}$alkylheterocyclyl, $C_{1-6}$alkoxyheterocyclyl, halo$C_1$-6alkylheterocyclyl, halo$C_{1-6}$alkoxyheterocyclyl, $C_{1-6}$alkyl$C_{1-6}$alkoxy, and —COOH;

each $R^{12}$ is independently selected from H, $C_{1-6}$alkyl, halo$C_{1-4}$alkyl, $C_{1-6}$alkylacyl and halo$C_{1-6}$alkylacyl;

or when two adjacent groups selected from $A^1$, $A^2$, $A^3$, $A^4$, $A^5$, $A^7$, $A^8$ $A^9$, $A^{10}$, $A^{11}$ and $A^{12}$ are selected from $CR^{11}$ and $NR^{12}$, two $R^{11}$, two $R^{12}$ or one $R^{11}$ and one $R^{12}$ may together form an optionally substituted 5-10 membered ring selected from cycloalkyl, aryl and heterocyclyl;

p is an integer from 0 to 4; and q is 1 or 2.

11. The compound of claim 10, or a pharmaceutically acceptable salt, solvate, tautomer, N-oxide, stereoisomer and/or prodrug thereof, wherein $R^2$ is represented by partial formula Ar1.

12. The compound of claim 10, or a pharmaceutically acceptable salt, solvate, tautomer, N-oxide, stereoisomer and/or prodrug thereof, wherein $A^1$ is N.

13. The compound of claim 10, or a pharmaceutically acceptable salt, solvate, tautomer, N-oxide, stereoisomer and/or prodrug thereof, wherein $A^4$ is N.

14. The compound of claim 10, or a pharmaceutically acceptable salt, solvate, tautomer, N-oxide, stereoisomer and/or prodrug thereof, wherein $A^2$ is $CR^{10}$.

15. The compound of claim 1, or a pharmaceutically acceptable salt, solvate, tautomer, N-oxide, stereoisomer and/or prodrug thereof, wherein $R^1$ and $R^3$ are H.

16. The compound of claim 1, or a pharmaceutically acceptable salt, solvate, tautomer, N-oxide, stereoisomer and/or prodrug thereof, wherein the compound of formula (I) is a compound of formula (1A):

(1A)

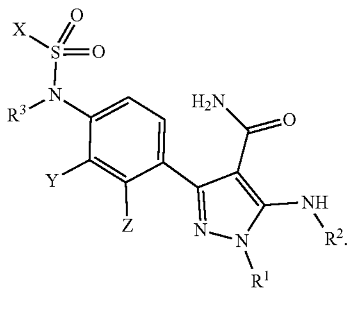

17. The compound of claim 1, or a pharmaceutically acceptable salt, solvate, tautomer, N-oxide, stereoisomer and/or prodrug thereof, wherein the compound of formula (I) is a compound of formula (1B):

(1B)

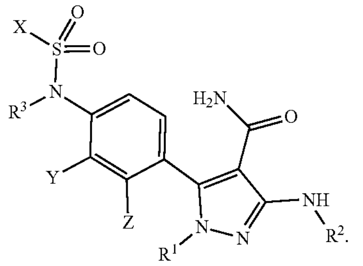

18. The compound of claim 1, or a pharmaceutically acceptable salt, solvate, tautomer, N-oxide, stereoisomer and/or prodrug thereof, wherein the compound is selected from:

3-(3-((3,4-difluorobenzyl)oxy)-4-(ethylsulfonamido)phenyl)-5-(pyrazin-2-ylamino)-1H-pyrazole-4-carboxamide
3-(4-(ethylsulfonamido)-3-((2-fluorobenzyl)oxy)phenyl)-5-(pyrazin-2-ylamino)-1H-pyrazole-4-carboxamide
3-(3-((3-chlorobenzyl)oxy)-4-(ethylsulfonamido)phenyl)-5-((6-(trifluoromethyl)pyridin-2-yl)amino)-1H-pyrazole-4-carboxamide
3-(3-((4-chlorobenzyl)oxy)-4-(ethylsulfonamido)phenyl)-5-((6-(trifluoromethyl)pyridin-2-yl)amino)-1H-pyrazole-4-carboxamide
3-(3-((4-fluorobenzyl)oxy)-4-((2,2,2-trifluoroethyl)sulfonamido)phenyl)-5-((6-(trifluoromethyl)pyridin-2-yl)amino)-1H-pyrazole-4-carboxamide
3-(4-(ethylsulfonamido)-3-((4-fluorobenzyl)oxy)phenyl)-5-(pyridin-3-ylamino)-1H-pyrazole-4-carboxamide
3-(3-((1-acetylpiperidin-4-yl)methoxy)-4-(ethylsulfonamido)phenyl)-5-(pyrazin-2-ylamino)-1H-pyrazole-4-carboxamide
3-(4-(ethylsulfonamido)-3-((4-fluorobenzyl)oxy)phenyl)-5-((6-(trifluoromethyl)pyridin-2-yl)amino)-1H-pyrazole-4-carboxamide
3-(4-(ethylsulfonamido)-3-((4-fluorobenzyl)oxy)phenyl)-5-((5-(trifluoromethyl)pyrazin-2-yl)amino)-1H-pyrazole-4-carboxamide
3-(3-(cyclopentylmethoxy)-4-(ethylsulfonamido)phenyl)-5-((6-(trifluoromethyl)pyridin-2-yl)amino)-1H-pyrazole-4-carboxamide
3-(4-(ethylsulfonamido)-3-((4-fluorobenzyl)oxy)phenyl)-5-((6-methoxypyridin-2-yl)amino)-1H-pyrazole-4-carboxamide
3-(4-(ethylsulfonamido)-3-isobutoxyphenyl)-5-((6-(trifluoromethyl)pyridin-2-yl)amino)-1H-pyrazole-4-carboxamide
3-(4-(ethylsulfonamido)-3-((4-fluorobenzyl)(methyl)amino)phenyl)-5-(pyrazin-2-ylamino)-1H-pyrazole-4-carboxamide
3-(4-(ethylsulfonamido)-3-((4-fluorobenzyl)oxy)phenyl)-5-((5-methoxypyrazin-2-yl)amino)-1H-pyrazole-4-carboxamide
3-(4-(ethylsulfonamido)-3-((4-fluorobenzyl)oxy)phenyl)-5-((6-methoxypyrazin-2-yl)amino)-1H-pyrazole-4-carboxamide
3-(4-(ethylsulfonamido)-3-(pyridin-4-ylmethoxy)phenyl)-5-((6-(trifluoromethyl)pyridin-2-yl)amino)-1H-pyrazole-4-carboxamide
3-(4-(ethylsulfonamido)-3-((4-fluorobenzyl)oxy)phenyl)-5-((6-(trifluoromethyl)pyrazin-2-yl)amino)-1H-pyrazole-4-carboxamide
3-(4-(ethylsulfonamido)-3-((4-fluorobenzyl)oxy)phenyl)-5-((2-methoxypyridin-4-yl)amino)-1H-pyrazole-4-carboxamide
3-(4-(ethylsulfonamido)-3-(4-fluorophenoxy)phenyl)-5-(pyrazin-2-ylamino)-1H-pyrazole-4-carboxamide
3-(3-(benzyloxy)-4-(ethylsulfonamido)phenyl)-5-(pyridin-2-ylamino)-1H-pyrazole-4-carboxamide
3-(4-(ethylsulfonamido)-2-((4-fluorobenzyl)oxy)phenyl)-5-(pyrazin-2-ylamino)-1H-pyrazole-4-carboxamide
3-(4-(ethylsulfonamido)-3-((4-fluorobenzyl)oxy)phenyl)-5-((5-methylpyrazin-2-yl)amino)-1H-pyrazole-4-carboxamide
3-(4-((3,3-difluoropropyl)sulfonamido)phenyl)-5-(pyrazin-2-ylamino)-1H-pyrazole-4-carboxamide
3-(4-(ethylsulfonamido)-3-(4-fluorophenethoxy)phenyl)-5-(pyrazin-2-ylamino)-1H-pyrazole-4-carboxamide
3-(3-(benzyloxy)-4-(ethylsulfonamido)phenyl)-5-(pyrazin-2-ylamino)-1H-pyrazole-4-carboxamide
3-(4-(ethylsulfonamido)-3-((3-fluorobenzyl)oxy)phenyl)-5-(pyrazin-2-ylamino)-1H-pyrazole-4-carboxamide
3-(4-(ethylsulfonamido)-3-(pyridin-4-ylmethoxy)phenyl)-5-(pyridin-2-ylamino)-1H-pyrazole-4-carboxamide
3-(4-(ethylsulfonamido)-3-(pyridin-4-ylmethoxy)phenyl)-5-(pyrazin-2-ylamino)-1H-pyrazole-4-carboxamide
3-(4-((cyanomethyl)sulfonamido)phenyl)-5-((6-(trifluoromethyl)pyridin-2-yl)amino)-1H-pyrazole-4-carboxamide
3-(4-(ethylsulfonamido)-3-((4-fluorobenzyl)oxy)phenyl)-5-(pyridin-2-ylamino)-1H-pyrazole-4-carboxamide
3-(4-(ethylsulfonamido)-3-(pyridin-3-ylmethoxy)phenyl)-5-(pyridin-2-ylamino)-1H-pyrazole-4-carboxamide
3-(4-(ethylsulfonamido)-3-(pyridin-3-ylmethoxy)phenyl)-5-(pyrazin-2-ylamino)-1H-pyrazole-4-carboxamide
3-(4-(ethylsulfonamido)-3-(pyridin-3-ylmethoxy)phenyl)-5-((6-(trifluoromethyl)pyridin-2-yl)amino)-1H-pyrazole-4-carboxamide
3-(4-(ethylsulfonamido)-3-((4-fluorobenzyl)oxy)phenyl)-5-((5-isopropylpyrazin-2-yl)amino)-1H-pyrazole-4-carboxamide
3-(3-(cyclohexylmethoxy)-4-(ethylsulfonamido)phenyl)-5-(pyridin-2-ylamino)-1H-pyrazole-4-carboxamide
3-(3-(cyclopentylmethoxy)-4-(ethylsulfonamido)phenyl)-5-(pyridin-2-ylamino)-1H-pyrazole-4-carboxamide
3-(4-(ethylsulfonamido)-3-isobutoxyphenyl)-5-(pyridin-2-ylamino)-1H-pyrazole-4-carboxamide
3-(3-((3-chlorobenzyl)oxy)-4-(ethylsulfonamido)phenyl)-5-(pyridin-2-ylamino)-1H-pyrazole-4-carboxamide
3-(3-((4-chlorobenzyl)oxy)-4-(ethylsulfonamido)phenyl)-5-(pyridin-2-ylamino)-1H-pyrazole-4-carboxamide
3-(3-(cyclopentylmethoxy)-4-(ethylsulfonamido)phenyl)-5-(pyrazin-2-ylamino)-1H-pyrazole-4-carboxamide
3-(3-((3-chlorobenzyl)oxy)-4-(ethylsulfonamido)phenyl)-5-(pyrazin-2-ylamino)-1H-pyrazole-4-carboxamide
3-(3-((4-chlorobenzyl)oxy)-4-(ethylsulfonamido)phenyl)-5-(pyrazin-2-ylamino)-1H-pyrazole-4-carboxamide 3-(4-((2,2,2-trifluoroethyl)sulfonamido)phenyl)-5-((6-(trifluoromethyl)pyridin-2-yl)amino)-1H-pyrazole-4-carboxamide 3-(4-(ethylsulfonamido)phenyl)-5-((6-(trifluoromethyl)pyrazin-2-yl)amino)-1H-pyrazole-4-carboxamide 3-(4-(ethylsulfonamido)-3-isobutoxyphenyl)-5-(pyrazin-2-ylamino)-1H-pyrazole-4-carboxamide 3-(3-(benzyloxy)-4-(ethylsulfonamido)phenyl)-5-((6-(trifluoromethyl)pyridin-2-yl)amino)-1H-pyrazole-4-carboxamide 3-(3-(cyclohexylmethoxy)-4-(ethylsulfonamido)phenyl)-5-(pyrazin-2-ylamino)-1H-pyrazole-4-carboxamide 3-(4-((difluoromethyl)sulfonamido)phenyl)-5-(pyridin-2-ylamino)-1H-pyrazole-4-carboxamide 3-(4-((2,2-difluoroethyl)sulfonamido)phenyl)-5-((6-(trifluoromethyl)pyridin-2-yl)amino)-1H-pyrazole-4-carboxamide 3-(4-((2-methoxyethyl)sulfonamido)phenyl)-5-((6-(trifluoromethyl)pyridin-2-yl)amino)-1H-pyrazole-4-carboxamide 3-(4-((2-(dimethylamino) ethyl)sulfonamido)phenyl)-5-((6-(trifluoromethyl)pyridin-2-yl)amino)-1H-pyrazole-4-carboxamide 3-(4-(cyclopropanesulfonamido)phenyl)-5-((6-(trifluoromethyl)pyridin-2-yl)amino)-1H-pyrazole-4-carboxamide 3-(4-((difluoromethyl)sulfonamido)phenyl)-5-((6-(trifluoromethyl)pyridin-2-yl)amino)-1H-pyrazole-4-carboxamide 3-(4-((1-methylethyl)sulfonamido)phenyl)-5-((6-(trifluoromethyl)pyridin-2-yl)amino)-1H-pyrazole-4-carboxamide 3-(4-(((4-fluorophenyl)methyl)sulfonamido)phenyl)-5-((6-(trifluoromethyl)pyridin-2-yl)amino)-1H-pyrazole-4-carboxamide 3-(4-(((3,4-dichlorophenyl)methyl)sulfonamido)phenyl)-5-((6-(trifluoromethyl)pyridin-2-yl)amino)-1H-pyrazole-4-carboxamide 3-(4-((p-tolylmethyl)sulfonamido)phenyl)-5-((6-(trifluoromethyl)pyridin-2-yl)amino)-1H-pyrazole-4-carboxamide 3-(4-(((2-chlorophenyl)methyl)sulfonamido)phenyl)-5-((6-(trifluoromethyl)pyridin-2-yl)amino)-1H-pyrazole-4-carboxamide 3-(4-(((3-chlorophenyl)methyl)sulfonamido)phenyl)-5-((6-(trifluoromethyl)pyridin-2-yl)amino)-1H-pyrazole-4-carboxamide 3-(4-(((4-chlorophenyl)methyl)sulfonamido)phenyl)-5-((6-(trifluoromethyl)pyridin-2-yl)amino)-1H-pyrazole-4-carboxamide 3-(4-(ethylsulfonamido)-3-methoxyphenyl)-5-(pyrazin-2-ylamino)-1H-pyrazole-4-carboxamide 3-(4-(ethylsulfonamido)-3-((4-fluorobenzyl)oxy)phenyl)-5-(pyrazin-2-ylamino)-1H-pyrazole-4-carboxamide 3-(4-((difluoromethyl)sulfonamido)phenyl)-5-(pyrazin-2-ylamino)-1H-pyrazole-4-carboxamide 3-(4-(ethylsulfonamido)phenyl)-5-(pyridazin-3-ylamino)-1H-pyrazole-4-carboxamide 5-((6-chloroquinoxalin-2-yl)amino)-3-(4-(ethylsulfonamido)phenyl)-1H-pyrazole-4-carboxamide 3-(4-(ethylsulfonamido)phenyl)-5-((5-isopropylpyrazin-2-yl)amino)-1H-pyrazole-4-carboxamide 3-(4-(ethylsulfonamido)phenyl)-5-(quinoxalin-2-ylamino)-1H-pyrazole-4-carboxamide 3-(4-(cyclopropanesulfonamido)phenyl)-5-(pyrazin-2-ylamino)-1H-pyrazole-4-carboxamide 3-(4-((1,1-dimethylethyl)sulfonamido)phenyl)-5-(pyrazin-2-ylamino)-1H-pyrazole-4-carboxamide 3-(4-(((4-chlorophenyl)methyl)sulfonamido)phenyl)-5-(pyrazin-2-ylamino)-1H-pyrazole-4-carboxamide 3-(4-((1-methylethyl)sulfonamido)phenyl)-5-(pyrazin-2-ylamino)-1H-pyrazole-4-carboxamide 5-(pyrazin-2-ylamino)-3-(4-((3,3,3-trifluoropropyl)sulfonamido)phenyl)-1H-pyrazole-4-carboxamide 5-(pyrazin-2-ylamino)-3-(4-((3-(trifluoromethyl)phenyl)sulfonamido)phenyl)-1H-pyrazole-4-carboxamide 3-(4-(cyclohexanesulfonamido)phenyl)-5-(pyrazin-2-ylamino)-1H-pyrazole-4-carboxamide 3-(4-(ethylsulfonamido)phenyl)-5-((5-(trifluoromethyl)pyrazin-2-yl)amino)-1H-pyrazole-4-carboxamide 5-(pyrazin-2-ylamino)-3-(4-(((4-(trifluoromethyl)phenyl)methyl)sulfonamido)phenyl)-1H-pyrazole-4-carboxamide 3-(4-((phenylmethyl)sulfonamido)phenyl)-5-(pyrazin-2-ylamino)-1H-pyrazole-4-carboxamide 5-(pyrazin-2-ylamino)-3-(4-((4-(trifluoromethoxy)phenyl)sulfonamido)phenyl)-1H-pyrazole-4-carboxamide 5-(pyrazin-2-ylamino)-3-(4-((4-(trifluoromethyl)phenyl)sulfonamido)phenyl)-1H-pyrazole-4-carboxamide 5-(pyrazin-2-ylamino)-3-(4-(((4-(trifluoromethoxy)phenyl)methyl)sulfonamido)phenyl)-1H-pyrazole-4-carboxamide 3-(4-((cyclobutylmethyl)sulfonamido)phenyl)-5-(pyrazin-2-ylamino)-1H-pyrazole-4-carboxamide 3-(4-((4-methoxyphenyl)sulfonamido)phenyl)-5-(pyrazin-2-ylamino)-1H-pyrazole-4-carboxamide 5-(pyrazin-2-ylamino)-3-(4-(((3-(trifluoromethyl)phenyl)methyl)sulfonamido)phenyl)-1H-pyrazole-4-carboxamide 3-(4-(ethylsulfonamido)phenyl)-5-((6-methylpyrazin-2-yl)amino)-1H-pyrazole-4-carboxamide 3-(4-(ethylsulfonamido)phenyl)-5-((4-(trifluoromethyl)pyridin-2-yl)amino)-1H-pyrazole-4-carboxamide 3-(4-(ethylsulfonamido)phenyl)-5-(naphthalen-2-ylamino)-1H-pyrazole-4-carboxamide 3-(4-(ethylsulfonamido)phenyl)-5-(isoquinolin-3-ylamino)-1H-pyrazole-4-carboxamide 3-(4-(ethylsulfonamido)phenyl)-5-((5-methoxypyridin-2-yl)amino)-1H-pyrazole-4-carboxamide 3-(4-(ethylsulfonamido)phenyl)-5-(quinolin-2-ylamino)-1H-pyrazole-4-carboxamide 3-(4-(ethylsulfonamido)phenyl)-5-((5-methoxypyrazin-2-yl)amino)-1H-pyrazole-4-carboxamide 3-(4-(ethylsulfonamido)phenyl)-5-((1-methyl-1H-pyrazol-3-yl)amino)-1H-pyrazole-4-carboxamide 5-((6-(difluoromethyl)pyridin-2-yl)amino)-3-(4-(ethylsulfonamido)phenyl)-1H-pyrazole-4-carboxamide 3-(4-(ethylsulfonamido)phenyl)-5-((5-(trifluoromethyl)pyridin-2-yl)amino)-1H-pyrazole-4-carboxamide 3-(4-(ethylsulfonamido)phenyl)-5-((6-methylpyridin-2-yl)amino)-1H-pyrazole-4-carboxamide 3-(4-(ethylsulfonamido)phenyl)-5-((4-methoxypyridin-2-yl)amino)-1H-pyrazole-4-carboxamide 5-((6-ethoxypyridin-2-yl)amino)-3-(4-(ethylsulfonamido)phenyl)-1H-pyrazole-4-carboxamide 3-(4-(propylsulfonamido)phenyl)-5-(pyrazin-2-ylamino)-1H-pyrazole-4-carboxamide 5-((2-ethoxypyrimidin-4-yl)amino)-3-(4-(ethylsulfonamido)phenyl)-1H-pyrazole-4-carboxamide 3-(4-(ethylsulfonamido)phenyl)-5-((6-methoxypyrazin-2-yl)amino)-1H-pyrazole-4-carboxamide 3-(4-(ethylsulfonamido)phenyl)-5-((1-methyl-1H-pyrazol-4-yl)amino)-1H-pyrazole-4-carboxamide 3-(4-(ethylsulfonamido)phenyl)-5-((5-methylpyrazin-2-yl)amino)-1H-pyrazole-4-carboxamide 5-((4-cyanophenyl)amino)-3-(4-(ethylsulfonamido)phenyl)-1H-pyrazole-4-carboxamide 3-(4-(ethylsulfonamido)phenyl)-5-((6-(trifluoromethoxy)pyridin-2-yl)amino)-1H-pyrazole-4-carboxamide 3-(4-(ethylsulfonamido)phenyl)-5-((2-(trifluoromethyl)pyridin-4-yl)amino)-1H-pyrazole-4-carboxamide 5-((2-ethoxypyridin-4-yl)amino)-3-(4-(ethylsulfonamido)phenyl)-1H-pyrazole-4-carboxamide 5-((2-(2,2-difluoroethoxy)pyridin-4-yl)amino)-3-(4-(ethylsulfonamido)phenyl)-1H-pyrazole-4-carboxamide 3-(4-(ethylsulfonamido)phenyl)-5-((6-methoxypyridin-2-yl)amino)-1H-pyrazole-4-carboxamide 3-(4-(ethylsulfonamido)phenyl)-5-(pyrazin-2-ylamino)-1H-pyrazole-4-carboxamide 5-((2-(2-methoxyethoxy)pyridin-4-yl)amino)-3-(4-(prop-2-yn-1-ylsulfonamido)phenyl)-1H-pyrazole-4-carboxamide 3-(4-((cyanomethyl)sulfonamido)phenyl)-5-((2-(2-methoxyethoxy)pyridin-4-yl)amino)-1H-pyrazole-4-carboxamide 3-(4-(ethylsulfonamido)phenyl)-5-((5-fluoro-2-methylpyridin-4-yl)amino)-1H-pyrazole-4-carboxamide 5-((2,6-dimethylpyridin-4-yl)amino)-3-(4-(ethylsulfonamido)phenyl)-1H-pyrazole-4-carboxamide 3-(4-(ethylsulfonamido)phenyl)-5-((2-methylpyridin-4-yl)amino)-1H-pyrazole-4-carboxamide 5-((2-(2-methoxyethoxy)pyridin-4-yl)amino)-3-(4-((trifluoromethyl)sulfonamido)phenyl)-1H-pyrazole-4-carboxamide 3-(4-(ethylsulfonamido)phenyl)-5-((6-methoxypyridin-3-yl)amino)-1H-pyrazole-4-carboxamide 3-(4-((2-(dimethylamino) ethyl)sulfonamido)phenyl)-5-((2-(2-methoxyethoxy)pyridin-4-yl)amino)-1H-pyrazole-4-carboxamide 5-((2-(2-methoxyethoxy)pyridin-4-yl)amino)-3-(4-(N-methylethylsulfonamido)phenyl)-1H-pyrazole-4-carboxamide 3-(4-(ethylsulfonamido)phenyl)-5-((2-methoxy-5-methylpyridin-4-yl)amino)-1H-pyrazole-4-carboxamide 3-(4-(ethylsulfonamido)phenyl)-5-(methylamino)-1H-pyrazole-4-carboxamide 5-((2-(2-methoxyethoxy)pyridin-4-yl)amino)-3-(4-((2-methoxyethyl)sulfonamido)phenyl)-1H-pyrazole-4-carboxamide 3-(4-(ethylsulfonamido)phenyl)-5-((2-methoxypyridin-4-yl)amino)-1H-pyrazole-4-carboxamide 5-((2-(2-methoxyethoxy)pyridin-4-yl)amino)-3-(4-(methylsulfonamido)phenyl)-1H-pyrazole-4-carboxamide 3-(4-(ethylsulfonamido)phenyl)-5-((2-methoxypyrimidin-4-yl)amino)-1H-pyrazole-4-carboxamide 3-(4-(ethylsulfonamido)phenyl)-5-(phenylamino)-1H-pyrazole-4-carboxamide 3-(4-(ethylsulfonamido)phenyl)-5-((2-methylpyrimidin-4-yl)amino)-1H-pyrazole-4-carboxamide 3-(4-(ethylsulfonamido)phenyl)-5-((6-(trifluoromethyl)pyridin-2-yl)amino)-1H-pyrazole-4-carboxamide 3-(4-(ethylsulfonamido)phenyl)-5-((2-(2-methoxyethoxy)pyridin-4-yl)amino)-1H-pyrazole-4-carboxamide 3-(4-(ethylsulfonamido)phenyl)-5-((6-(2-methoxyethoxy)pyridin-2-yl)amino)-1H-pyrazole-4-carboxamide 3-(4-(((3-chlorophenyl)methyl)sulfonamido)phenyl)-5-(pyridin-2-ylamino)-1H-pyrazole-4-carboxamide 3-(4-(ethylsulfonamido)phenyl)-5-((5-(2-methoxyethoxy)pyridin-2-yl)amino)-1H-pyrazole-4-carboxamide 3-(4-((2-phenylethyl)sulfonamido)phenyl)-5-(pyridin-2-ylamino)-1H-pyrazole-4-carboxamide 3-(4-(ethylsulfonamido)phenyl)-5-(pyridin-2-ylamino)-1H-pyrazole-4-carboxamide 5-(pyridin-2-ylamino)-3-(4-((p-tolylmethyl)sulfonamido)phenyl)-1H-pyrazole-4-carboxamide 3-(4-(phenylsulfonamido)phenyl)-5-(pyridin-2-ylamino)-1H-pyrazole-4-carboxamide 3-(4-((cyclobutylmethyl)sulfonamido)phenyl)-5-(pyridin-2-ylamino)-1H-pyrazole-4-carboxamide 5-(pyridin-2-ylamino)-3-(4-(((4-(trifluoromethoxy)phenyl)methyl)sulfonamido)phenyl)-1H-pyrazole-4-carboxamide 3-(4-((phenylmethyl)sulfonamido)phenyl)-5-(pyridin-2-ylamino)-1H-pyrazole-4-carboxamide 5-(pyrazin-2-ylamino)-3-(4-((2,2,2-trifluoroethyl)sulfonamido)phenyl)-1H-pyrazole-4-carboxamide 5-((7-chloroquinolin-2-yl)amino)-3-(4-(ethylsulfonamido)-3-((4-fluorobenzyl)oxy)phenyl)-1H-pyrazole-4-carboxamide 3-(2-((4-fluorobenzyl)oxy)-4-((2,2,2-trifluoroethyl)sulfonamido)phenyl)-5-(pyrazin-2-ylamino)-1H-pyrazole-4-carboxamide 3-(2-((4-fluorobenzyl)oxy)-4-((2,2,2-trifluoroethyl)sulfonamido)phenyl)-5-((6-(trifluoromethyl)pyridin-2-yl)amino)-1H-pyrazole-4-carboxamide 3-(4-(ethylsulfonamido)-2-((4-fluorobenzyl)oxy)phenyl)-5-((6-(trifluoromethyl)pyridin-2-yl)amino)-1H-pyrazole-4-carboxamide 3-(4-(ethylsulfonamido)-3-((4-fluoro-2,6-dimethylbenzyl)oxy)phenyl)-5-(pyrazin-2-ylamino)-1H-pyrazole-4-carboxamide 3-(3-((4-fluorobenzyl)oxy)-4-((2,2,2-trifluoroethyl)sulfonamido)phenyl)-5-((5-methoxypyrazin-2-yl)amino)-1H-pyrazole-4-carboxamide 3-(3-(1-(4-fluorophenyl) cyclopropoxy)-4-((2,2,2-trifluoroethyl)sulfonamido)phenyl)-5-(pyrazin-2-ylamino)-1H-pyrazole-4-carboxamide 3-(4-((difluoromethyl)sulfonamido)phenyl)-5-((5-(trifluoromethyl)pyridin-2-yl)amino)-1H-pyrazole-4-carboxamide 3-(3-((4-chloro-3-fluorobenzyl)oxy)-4-((2,2,2-trifluoroethyl)sulfonamido)phenyl)-5-((5-methylpyrazin-2-yl)amino)-1H-pyrazole-4-carboxamide 3-(4-((difluoromethyl)sulfonamido)-3-(4-fluorophenoxy)phenyl)-5-((6-(trifluoromethyl)pyridin-2-yl)amino)-1H-pyrazole-4-carboxamide 3-(3-(4-fluorophenoxy)-4-((2,2,2-trifluoroethyl)sulfonamido)phenyl)-5-((6-(trifluoromethyl)pyridin-2-yl)amino)-1H-pyrazole-4-carboxamide 3-(4-(ethylsulfonamido)-3-(4-fluorophenoxy)phenyl)-5-((6-(trifluoromethyl)pyridin-2-yl)amino)-1H-pyrazole-4-carboxamide 3-(3-((3-chloro-4-fluorobenzyl)oxy)-4-(ethylsulfonamido)phenyl)-5-((5-methylpyrazin-2-yl)amino)-1H-pyrazole-4-carboxamide 3-(3-((3,4-difluorobenzyl)oxy)-4-((difluoromethyl)sulfonamido)phenyl)-5-((6-(trifluoromethyl)pyridin-2-yl)amino)-1H-pyrazole-4-carboxamide 3-(4-(ethylsulfonamido)-3-(1-phenylcyclopropoxy)phenyl)-5-(pyrazin-2-ylamino)-1H-pyrazole-4-carboxamide 3-(4-((2,2,2-trifluoroethyl)sulfonamido)phenyl)-5-((5-(trifluoromethyl)pyridin-2-yl)amino)-1H-pyrazole-4-carboxamide (S)-3-(3-(1-(4-fluorophenyl) ethoxy)-4-((2,2,2-trifluoroethyl)sulfonamido)phenyl)-5-(pyridin-2-ylamino)-1H-pyrazole-4-carboxamide 3-(3-((3-chloro-4-fluorobenzyl)oxy)-4-((2,2,2-trifluoroethyl)sulfonamido)phenyl)-5-((5-methylpyrazin-2-yl)amino)-1H-pyrazole-4-carboxamide 3-(4-(ethylsulfonamido)-3-((5-fluoropyridin-2-yl)methoxy)phenyl)-5-(pyrazin-2-ylamino)-1H-pyrazole-4-carboxamide 3-(3-((4-chlorobenzyl)oxy)-4-((2,2,2-trifluoroethyl)sulfonamido)phenyl)-5-((5-methoxypyrazin-2-yl)amino)-1H-pyrazole-4-carboxamide 5-((5-cyclopropylpyrazin-2-yl)amino)-3-(4-(ethylsulfonamido)phenyl)-1H-pyrazole-4-carboxamide 3-(3-((4-fluorobenzyl)oxy)-4-((2,2,2-trifluoroethyl)sulfonamido)phenyl)-5-((6-methoxypyridin-3-yl)amino)-1H-pyrazole-4-carboxamide 3-(3-((3,4-difluorobenzyl)oxy)-4-((2,2,2-trifluoroethyl)sulfonamido)phenyl)-5-(pyridin-2-ylamino)-1H-pyrazole-4-carboxamide 3-(3-(1-phenylcyclopropoxy)-4-((2,2,2-trifluoroethyl)sulfonamido)phenyl)-5-(pyrazin-2-ylamino)-1H-pyrazole-4-carboxamide 3-(3-((4-chlorobenzyl)oxy)-4-((2,2,2-trifluoroethyl)sulfonamido)phenyl)-5-((5-methylpyrazin-2-yl)amino)-1H-pyrazole-4-carboxamide 3-(3-((4-fluorobenzyl)oxy)-4-((2,2,2-trifluoroethyl)sulfonamido)phenyl)-5-((5-methylpyrazin-2-yl)amino)-1H-pyrazole-4-carboxamide (S)-3-(3-(1-(4-fluorophenyl) ethoxy)-4-((2,2,2-trifluoroethyl)sulfonamido)phenyl)-5-(pyrazin-2-ylamino)-1H-pyrazole-4-carboxamide 3-(3-((4-chloro-3-fluorobenzyl)oxy)-4-((2,2,2-trifluoroethyl)sulfonamido)phenyl)-5-(pyrazin-2-ylamino)-1H-pyrazole-4-carboxamide 3-(3-((4-chloro-3-fluorobenzyl)oxy)-4-(ethylsulfonamido)phenyl)-5-(pyrazin-2-ylamino)-1H-pyrazole-4-carboxamide 3-(3-(3-fluorophenoxy)-4-((2,2,2-trifluoroethyl)sulfonamido)phenyl)-5-(pyrazin-2-ylamino)-1H-pyrazole-4-carboxamide 3-(3-(4-chlorophenoxy)-4-((2,2,2-trifluoroethyl)sulfonamido)phenyl)-5-(pyrazin-2-ylamino)-1H-pyrazole-4-carboxamide 3-(4-(cyclopropanesulfonamido)-3-((4-fluorobenzyl)oxy)phenyl)-5-(pyrazin-2-ylamino)-1H-pyrazole-4-carboxamide 3-(3-((4-fluorobenzyl)oxy)-4-((2,2,2-trifluoroethyl)sulfonamido)phenyl)-5-(pyrazin-2-ylamino)-1H-pyrazole-4-carboxamide 3-(4-(ethylsulfonamido)-3-((4-fluoro-2-methylbenzyl)oxy)phenyl)-5-(pyrazin-2-ylamino)-1H-pyrazole-4-carboxamide 3-(4-(ethylsulfonamido)-3-((4-fluorobenzyl)oxy)phenyl)-5-((6-(trifluoromethoxy)pyridin-2-yl)amino)-1H-pyrazole-4-carboxamide 5-((6-(difluoromethyl)pyridin-2-yl)amino)-3-(3-((4-fluorobenzyl)oxy)-4-((2,2,2-trifluoroethyl)sulfonamido)phenyl)-1H-pyrazole-4-carboxamide 3-(4-(ethylsulfonamido)-3-((4-fluorobenzyl)oxy)phenyl)-5-((6-(2-methoxyethoxy)pyridin-2-yl)amino)-1H-pyrazole-4-carboxamide 3-(3-((3,4-difluorobenzyl)oxy)-4-((2,2,2-trifluoroethyl)sulfonamido)phenyl)-5-(pyrazin-2-ylamino)-1H-pyrazole-4-carboxamide 3-(3-((4-fluorobenzyl)oxy)-4-((2,2,2-trifluoroethyl)sulfonamido)phenyl)-5-((6-(trifluoromethyl)pyridin-3-yl)amino)-1H-pyrazole-4-carboxamide 3-(4-((difluoromethyl)sulfonamido)-3-(4-fluorophenoxy)phenyl)-5-(pyrazin-2-ylamino)-1H-pyrazole-4-carboxamide 3-(4-((2,2-difluoroethyl)sulfonamido)-3-((4-fluorobenzyl)oxy)phenyl)-5-((6-(trifluoromethyl)pyridin-2-yl)amino)-1H-pyrazole-4-carboxamide 5-((6-(difluoromethyl)pyridin-2-yl)amino)-3-(4-(ethylsulfonamido)-3-((4-fluorobenzyl)oxy)phenyl)-1H-pyrazole-4-carboxamide 3-(4-((2,2-difluoroethyl)sulfonamido)-3-((4-fluorobenzyl)oxy)phenyl)-5-(pyrazin-2-ylamino)-1H-pyrazole-4-carboxamide 5-((5-(tert-butyl)pyrazin-2-yl)amino)-3-(4-(ethylsulfonamido)phenyl)-1H-pyrazole-4-carboxamide 3-(3-((4-fluorobenzyl)oxy)-4-((3,3,3-trifluoropropyl)sulfonamido)phenyl)-5-((6-(trifluoromethyl)pyridin-2-yl)amino)-1H-pyrazole-4-carboxamide 3-(3-((4-fluorobenzyl)oxy)-4-((3,3,3-trifluoropropyl)sulfonamido)phenyl)-5-((5-methylpyrazin-2-yl)amino)-1H-pyrazole-4-carboxamide 3-(3-((4-fluorobenzyl)oxy)-4-((3,3,3-trifluoropropyl)sulfonamido)phenyl)-5-(pyrazin-2-ylamino)-1H-pyrazole-4-carboxamide 3-(3-(4-chlorophenoxy)-4-(ethylsulfonamido)phenyl)-5-(pyrazin-2-ylamino)-1H-pyrazole-4-carboxamide 3-(3-((4-fluorobenzyl)oxy)-4-((2,2,2-trifluoroethyl)sulfonamido)phenyl)-5-((2-(trifluoromethyl) pyrimidin-4-yl)amino)-1H-pyrazole-4-carboxamide 3-(4-(ethylsulfonamido)-3-((1-methylpiperidin-3-yl)methoxy)phenyl)-5-(pyrazin-2-ylamino)-1H-pyrazole-4-carboxamide 3-(4-((difluoromethyl)sulfonamido)-3-((4-fluorobenzyl)oxy)phenyl)-5-((6-(trifluoromethyl)pyridin-3-yl)amino)-1H-pyrazole-4-carboxamide 5-((6-(trifluoromethyl)pyridin-2-yl)amino)-3-(4-((3,3,3-trifluoropropyl)sulfonamido)phenyl)-1H-pyrazole-4-carboxamide 3-(3-((4-chlorobenzyl)oxy)-4-((difluoromethyl)sulfonamido)phenyl)-5-((5-methoxypyrazin-2-yl)amino)-1H-pyrazole-4-carboxamide 3-(4-((difluoromethyl)sulfonamido)-3-((4-fluorobenzyl)oxy)phenyl)-5-((5-methoxypyrazin-2-yl)amino)-1H-pyrazole-4-carboxamide 3-(4-(ethylsulfonamido)-3-((4-fluorobenzyl)oxy)phenyl)-5-((2-(trifluoromethyl)pyridin-3-yl)amino)-1H-pyrazole-4-carboxamide (R)-3-(4-(ethylsulfonamido)-3-(1-(4-fluorophenyl)ethoxy)phenyl)-5-(pyrazin-2-ylamino)-1H-pyrazole-4-carboxamide 3-(4-(ethylsulfonamido)-3-((4-fluorobenzyl)oxy)phenyl)-5-((6-(trifluoromethyl)pyridin-3-yl)amino)-1H-pyrazole-4-carboxamide 3-(4-(ethylsulfonamido)-3-((4-fluorobenzyl)oxy)phenyl)-5-((2-(trifluoromethyl) pyrimidin-4-yl)amino)-1H-pyrazole-4-carboxamide 3-(4-((difluoromethyl)sulfonamido)-3-((4-fluorobenzyl)oxy)phenyl)-5-((6-methoxypyridin-3-yl)amino)-1H-pyrazole-4-carboxamide 3-(4-(ethylsulfonamido)-3-((4-fluorobenzyl)oxy)phenyl)-5-((6-methoxypyridin-3-yl)amino)-1H-pyrazole-4-carboxamide 3-(2-((4-chlorobenzyl)oxy)-4-(ethylsulfonamido)phenyl)-5-(pyrazin-2-ylamino)-1H-pyrazole-4-carboxamide
(S)-3-(4-(ethylsulfonamido)-3-(1-(4-fluorophenyl)ethoxy)phenyl)-5-(pyrazin-2-ylamino)-1H-pyrazole-4-carboxamide
3-(3-(cyclohexylmethoxy)-4-(ethylsulfonamido)phenyl)-5-((6-(trifluoromethyl)pyridin-2-yl)amino)-1H-pyrazole-4-carboxamide
3-(4-(ethylsulfonamido)-2-((4-fluorobenzyl)oxy)phenyl)-5-(pyridin-2-ylamino)-1H-pyrazole-4-carboxamide
3-(4-((difluoromethyl)sulfonamido)-3-((4-fluorobenzyl)oxy)phenyl)-5-(pyrazin-2-ylamino)-1H-pyrazole-4-carboxamide
3-(4-(ethylsulfonamido)-3-((1-methylpiperidin-4-yl)methoxy)phenyl)-5-(pyrazin-2-ylamino)-1H-pyrazole-4-carboxamide
3-(4-(ethylsulfonamido)-3-(3-fluorophenoxy)phenyl)-5-(pyrazin-2-ylamino)-1H-pyrazole-4-carboxamide
5-((6-(trifluoromethyl)pyridin-2-yl)amino)-3-(4-((trifluoromethyl)sulfonamido)phenyl)-1H-pyrazole-4-carboxamide
3-(3-(2-chlorophenethoxy)-4-(ethylsulfonamido)phenyl)-5-(pyrazin-2-ylamino)-1H-pyrazole-4-carboxamide
3-(4-(ethylsulfonamido)-3-((4-fluorobenzyl)oxy)phenyl)-5-((5-(trifluoromethyl)pyridin-2-yl)amino)-1H-pyrazole-4-carboxamide
3-(4-(ethylsulfonamido)-2-((3-fluorobenzyl)oxy)phenyl)-5-(pyrazin-2-ylamino)-1H-pyrazole-4-carboxamide
3-(4-(ethylsulfonamido)-2-methoxyphenyl)-5-(pyrazin-2-ylamino)-1H-pyrazole-4-carboxamide
3-(4-(ethylsulfonamido)-3-phenethoxyphenyl)-5-(pyrazin-2-ylamino)-1H-pyrazole-4-carboxamide
3-(4-(ethylsulfonamido)-3-(2-fluorophenethoxy)phenyl)-5-(pyrazin-2-ylamino)-1H-pyrazole-4-carboxamide
3-(3-(3-chlorophenethoxy)-4-(ethylsulfonamido)phenyl)-5-(pyrazin-2-ylamino)-1H-pyrazole-4-carboxamide
3-(4-(ethylsulfonamido)-3-((4-fluorobenzyl)oxy)phenyl)-5-((4-(trifluoromethyl)pyridin-2-yl)amino)-1H-pyrazole-4-carboxamide
3-(4-(ethylsulfonamido)-3-((3-(trifluoromethoxy) benzyl)oxy)phenyl)-5-(pyrazin-2-ylamino)-1H-pyrazole-4-carboxamide
3-(4-(ethylsulfonamido)-3-((4-(trifluoromethoxy) benzyl)oxy)phenyl)-5-(pyrazin-2-ylamino)-1H-pyrazole-4-carboxamide
3-(4-(ethylsulfonamido)-3-((4-(trifluoromethyl) benzyl)oxy)phenyl)-5-(pyrazin-2-ylamino)-1H-pyrazole-4-carboxamide
3-(4-((difluoromethyl)sulfonamido)-3-((4-fluorobenzyl)oxy)phenyl)-5-((6-(trifluoromethyl)pyridin-2-yl)amino)-1H-pyrazole-4-carboxamide
3-(4-(ethylsulfonamido)-3-((3-(trifluoromethyl) benzyl)oxy)phenyl)-5-(pyrazin-2-ylamino)-1H-pyrazole-4-carboxamide
3-(4-(ethylsulfonamido)-3-(3-fluorophenethoxy)phenyl)-5-(pyrazin-2-ylamino)-1H-pyrazole-4-carboxamide
5-((6-chloroquinolin-2-yl)amino)-3-(4-(ethylsulfonamido)-3-((4-fluorobenzyl)oxy)phenyl)-1H-pyrazole-4-carboxamide
3-(4-((N,N-dimethylsulfamoyl)amino)phenyl)-5-((2-(2-methoxyethoxy)pyridin-4-yl)amino)-1H-pyrazole-4-carboxamide
5-(4-(ethylsulfonamido)phenyl)-1-methyl-3-(pyrazin-2-ylamino)-1H-pyrazole-4-carboxamide (S)-3-(4-((difluoromethyl)sulfonamido)-3-(1-(4-fluorophenyl)ethoxy)phenyl)-5-(pyrazin-2-ylamino)-1H-pyrazole-4-carboxamide
3-(4-(ethylsulfonamido)-3-((6-fluoro-1,2,3,4-tetrahydronaphthalen-1-yl)oxy)phenyl)-5-(pyrazin-2-ylamino)-1H-pyrazole-4-carboxamide
3-(3-((3-chloro-4-fluorobenzyl)oxy)-4-((2,2,2-trifluoroethyl)sulfonamido)phenyl)-5-(pyrazin-2-ylamino)-1H-pyrazole-4-carboxamide
3-(3-((3,4-difluorobenzyl)oxy)-4-((difluoromethyl)sulfonamido)phenyl)-5-(pyridin-2-ylamino)-1H-pyrazole-4-carboxamide
5-(pyrazin-2-ylamino)-3-(3-(pyridin-2-ylmethoxy)-4-((2,2,2-trifluoroethyl)sulfonamido)phenyl)-1H-pyrazole-4-carboxamide
3-(4-(ethylsulfonamido)-3-((2-(4-fluorophenyl) propan-2-yl)oxy)phenyl)-5-(pyrazin-2-ylamino)-1H-pyrazole-4-carboxamide
(S)-3-(4-((difluoromethyl)sulfonamido)-3-(1-(4-fluorophenyl) ethoxy)phenyl)-5-((6-(trifluoromethyl)pyridin-2-yl)amino)-1H-pyrazole-4-carboxamide
(S)-3-(4-(ethylsulfonamido)-3-(1-(pyridin-2-yl) ethoxy)phenyl)-5-(pyrazin-2-ylamino)-1H-pyrazole-4-carboxamide
3-(3-((5-fluoropyridin-2-yl)methoxy)-4-((2,2,2-trifluoroethyl)sulfonamido)phenyl)-5-(pyrazin-2-ylamino)-1H-pyrazole-4-carboxamide
3-(4-(ethylsulfonamido)-3-((1,2,3,4-tetrahydronaphthalen-1-yl)oxy)phenyl)-5-(pyrazin-2-ylamino)-1H-pyrazole-4-carboxamide
3-(4-((difluoromethyl)sulfonamido)-3-(1-(4-fluorophenyl) propoxy)phenyl)-5-(pyrazin-2-ylamino)-1H-pyrazole-4-carboxamide
3-(3-((4-chlorobenzyl)oxy)-4-((2,2,2-trifluoroethyl)sulfonamido)phenyl)-5-((5-(trifluoromethyl)pyrazin-2-yl)amino)-1H-pyrazole-4-carboxamide
3-(3-((4-chlorobenzyl)oxy)-4-((difluoromethyl)sulfonamido)phenyl)-5-((5-(trifluoromethyl)pyrazin-2-yl)amino)-1H-pyrazole-4-carboxamide
3-(3-(cyclobutyl (4-fluorophenyl)methoxy)-4-((difluoromethyl)sulfonamido)phenyl)-5-(pyrazin-2-ylamino)-1H-pyrazole-4-carboxamide
5-((6-cyanopyridin-2-yl)amino)-3-(4-((2,2,2-trifluoroethyl)sulfonamido)phenyl)-1H-pyrazole-4-carboxamide
3-(3-((4-fluorobenzyl)oxy)-4-((2,2,2-trifluoroethyl)sulfonamido)phenyl)-5-((5-(trifluoromethyl)pyrazin-2-yl)amino)-1H-pyrazole-4-carboxamide
3-(3-((4-fluorobenzyl)oxy)-4-((2,2,2-trifluoroethyl)sulfonamido)phenyl)-5-(pyridin-2-ylamino)-1H-pyrazole-4-carboxamide
3-(3-((5-fluoropyridin-2-yl)methoxy)-4-((2,2,2-trifluoroethyl)sulfonamido)phenyl)-5-(pyridin-2-ylamino)-1H-pyrazole-4-carboxamide
3-(4-(ethylsulfonamido)-3-((5-fluoropyridin-2-yl)methoxy)phenyl)-5-(pyridin-2-ylamino)-1H-pyrazole-4-carboxamide
3-(3-((5-chloropyridin-2-yl)methoxy)-4-(ethylsulfonamido)phenyl)-5-(pyrazin-2-ylamino)-1H-pyrazole-4-carboxamide
(S)-3-(4-((difluoromethyl)sulfonamido)-2-(1-(4-fluorophenyl) ethoxy)phenyl)-5-(pyrazin-2-ylamino)-1H-pyrazole-4-carboxamide
(S)-3-(2-(1-(4-fluorophenyl) ethoxy)-4-((2,2,2-trifluoroethyl)sulfonamido)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-5-((5-methylpyrazin-2-yl) amino)-1H-pyrazole-4-carboxamide 3-(4-((difluoromethyl)sulfonamido)-3-((4-fluorobenzyl) oxy)phenyl)-5-((5-(trifluoromethyl)pyrazin-2-yl) amino)-1H-pyrazole-4-carboxamide 3-(3-((4-chlorobenzyl)oxy)-4-((difluoromethyl)sulfonamido)phenyl)-5-(pyridin-2-ylamino)-1H-pyrazole-4-carboxamide 3-(4-(ethylsulfonamido)-3-(1-(4-fluorophenyl) cyclopropoxy)phenyl)-5-(pyrazin-2-ylamino)-1H-pyrazole-4-carboxamide (S)-3-(3-(1-(4-fluorophenyl) ethoxy)-4-((2,2,2-trifluoroethyl)sulfonamido)phenyl)-5-((6-(trifluoromethyl) pyridin-2-yl)amino)-1H-pyrazole-4-carboxamide (S)-3-(3-(1-(4-fluorophenyl) propoxy)-4-((2,2,2-trifluoroethyl)sulfonamido)phenyl)-5-(pyrazin-2-ylamino)-1H-pyrazole-4-carboxamide (R)-3-(3-(1-(4-fluorophenyl) propoxy)-4-((2,2,2-trifluoroethyl)sulfonamido)phenyl)-5-(pyrazin-2-ylamino)-1H-pyrazole-4-carboxamide (S)-3-(3-(1-(4-chlorophenyl) ethoxy)-4-((difluoromethyl) sulfonamido)phenyl)-5-(pyrazin-2-ylamino)-1H-pyrazole-4-carboxamide (S)-5-(4-((difluoromethyl)sulfonamido)-3-(1-(4-fluorophenyl) ethoxy)phenyl)-1-methyl-3-(pyrazin-2-ylamino)-1H-pyrazole-4-carboxamide (R)-3-(2-(1-(4-fluorophenyl) ethoxy)-4-((2,2,2-trifluoroethyl)sulfonamido)phenyl)-5-(pyrazin-2-ylamino)-1H-pyrazole-4-carboxamide (R)-3-(4-((difluoromethyl)sulfonamido)-2-(1-(4-fluorophenyl) ethoxy)phenyl)-5-(pyrazin-2-ylamino)-1H-pyrazole-4-carboxamide (S)-3-(3-(1-(3-chlorophenyl) ethoxy)-4-((2,2,2-trifluoroethyl)sulfonamido)phenyl)-5-(pyrazin-2-ylamino)-1H-pyrazole-4-carboxamide 6-((4-carbamoyl-3-(4-((difluoromethyl)sulfonamido)phenyl)-1H-pyrazol-5-yl)amino) picolinamide 5-((6-cyanopyridin-2-yl)amino)-3-(4-((difluoromethyl) sulfonamido)phenyl)-1H-pyrazole-4-carboxamide (S)-3-(3-(1-(4-chlorophenyl) ethoxy)-4-((2,2,2-trifluoroethyl)sulfonamido)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-5-(pyridin-2-ylamino)-1H-pyrazole-4-carboxamide 3-(4-(ethylsulfonamido)-3-(pyridin-2-ylmethoxy)phenyl)-5-(pyrazin-2-ylamino)-1H-pyrazole-4-carboxamide 3-(3-((5-chloropyridin-2-yl)methoxy)-4-((2,2,2-trifluoroethyl)sulfonamido)phenyl)-5-(pyrazin-2-ylamino)-1H-pyrazole-4-carboxamide 3-(3-(1-(4-fluorophenyl) propoxy)-4-((2,2,2-trifluoroethyl)sulfonamido)phenyl)-5-(pyrazin-2-ylamino)-1H-pyrazole-4-carboxamide (S)-3-(3-(1-(4-fluorophenyl) ethoxy)-4-((2,2,2-trifluoroethyl)sulfonamido)phenyl)-5-((5-methylpyrazin-2-yl) amino)-1H-pyrazole-4-carboxamide (S)-3-(3-(1-(3-fluorophenyl) ethoxy)-4-((2,2,2-trifluoroethyl)sulfonamido)phenyl)-5-(pyrazin-2-ylamino)-1H-pyrazole-4-carboxamide 3-(3-(cyclobutyl (4-fluorophenyl)methoxy)-4-((2,2,2-trifluoroethyl)sulfonamido)phenyl)-5-(pyrazin-2-ylamino)-1H-pyrazole-4-carboxamide (S)-5-(pyrazin-2-ylamino)-3-(3-(1-(pyridin-2-yl) ethoxy)-4-((2,2,2-trifluoroethyl)sulfonamido)phenyl)-1H-pyrazole-4-carboxamide 5-(pyridin-2-ylamino)-3-(4-((2,2,2-trifluoroethyl)sulfonamido)phenyl)-1H-pyrazole-4-carboxamide 3-(3-((4-chlorobenzyl)oxy)-4-((2,2,2-trifluoroethyl) sulfonamido)phenyl)-5-(pyridin-2-ylamino)-1H-pyrazole-4-carboxamide (S)-3-(4-((difluoromethyl)sulfonamido)-3-(1-(4-fluorophenyl) ethoxy)phenyl)-5-((1,3-dimethyl-1H-pyrazol-4-yl)amino)-1H-pyrazole-4-carboxamide (R)-3-(4-((difluoromethyl)sulfonamido)-3-(1-(4-fluorophenyl) ethoxy)phenyl)-5-(pyrazin-2-ylamino)-1H-pyrazole-4-carboxamide (S)-3-(4-((difluoromethyl)sulfonamido)-3-(1-(4-fluorophenyl)-2-methoxyethoxy)phenyl)-5-(pyrazin-2-ylamino)-1H-pyrazole-4-carboxamide (R)-3-(4-((difluoromethyl)sulfonamido)-3-(1-(4-fluorophenyl)-2-methoxyethoxy)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-5-((5-ethylisoxazol-3-yl) amino)-1H-pyrazole-4-carboxamide 3-(4-((difluoromethyl)sulfonamido)-3-(thiazol-2-ylmethoxy)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-5-((5-(1-methylcyclopropyl) isoxazol-3-yl)amino)-1H-pyrazole-4-carboxamide (S)-3-(4-((difluoromethyl)sulfonamido)-3-(1-(4-fluorophenyl) ethoxy)phenyl)-5-((1-methyl-5-(trifluoromethyl)-1H-pyrazol-3-yl)amino)-1H-pyrazole-4-carboxamide (S)-3-(4-((difluoromethyl)sulfonamido)-3-(1-(4-fluorophenyl) ethoxy)phenyl)-5-((5-(tetrahydro-2H-pyran-4-yl)pyridin-2-yl)amino)-1H-pyrazole-4-carboxamide (S)-3-(4-((difluoromethyl)sulfonamido)-3-(1-(oxazol-2-yl) ethoxy)phenyl)-5-(pyrazin-2-ylamino)-1H-pyrazole-4-carboxamide (R)-3-(4-((difluoromethyl)sulfonamido)-3-(1-(oxazol-2-yl) ethoxy)phenyl)-5-(pyrazin-2-ylamino)-1H-pyrazole-4-carboxamide (S)-5-((5-cyclobutylisoxazol-3-yl)amino)-3-(4-((difluoromethyl)sulfonamido)-3-(1-(4-fluorophenyl) ethoxy) phenyl)-1H-pyrazole-4-carboxamide (S)-5-((5-(tert-butyl) isoxazol-3-yl)amino)-3-(4-((difluoromethyl)sulfonamido)-3-(1-(4-fluorophenyl) ethoxy) phenyl)-1H-pyrazole-4-carboxamide (S)-3-(4-((difluoromethyl)sulfonamido)-3-(1-(4-fluorophenyl) ethoxy)phenyl)-5-((1-methyl-1H-1,2,4-triazol-3-yl)amino)-1H-pyrazole-4-carboxamide (S)-3-(4-((difluoromethyl)sulfonamido)-3-(1-(4-fluorophenyl) ethoxy)phenyl)-5-((4,5-dimethylthiazol-2-yl) amino)-1H-pyrazole-4-carboxamide (S)-3-(4-((difluoromethyl)sulfonamido)-3-(1-(4-fluorophenyl) ethoxy)phenyl)-5-((1,5-dimethyl-1H-pyrazol-3-yl)amino)-1H-pyrazole-4-carboxamide (S)-3-(4-((difluoromethyl)sulfonamido)-3-(1-(4-fluorophenyl) ethoxy)phenyl)-5-((1,4-dimethyl-1H-pyrazol-3-yl)amino)-1H-pyrazole-4-carboxamide (S)-3-(4-((difluoromethyl)sulfonamido)-3-(1-(4-fluorophenyl) ethoxy)phenyl)-5-((4-(tetrahydro-2H-pyran-4-yl)pyridin-2-yl)amino)-1H-pyrazole-4-carboxamide (S)-3-(4-((difluoromethyl)sulfonamido)-3-(1-(4-fluorophenyl) ethoxy)phenyl)-5-((5-(1-methoxy-2-methylpropan-2-yl) isoxazol-3-yl)amino)-1H-pyrazole-4-carboxamide (S)-3-(4-((difluoromethyl)sulfonamido)-3-(1-(4-fluorophenyl) ethoxy)phenyl)-5-((5-(1-(trifluoromethyl) cyclopropyl) isoxazol-3-yl)amino)-1H-pyrazole-4-carboxamide 3-(4-((difluoromethyl)sulfonamido)-3-(1-(4-fluorophenyl) cyclopropoxy)phenyl)-5-((5-methylpyrazin-2-yl) amino)-1H-pyrazole-4-carboxamide 3-(3-((3,4-difluorobenzyl)oxy)-4-((difluoromethyl)sulfonamido)phenyl)-5-((5-methylpyrazin-2-yl)amino)-1H-pyrazole-4-carboxamide (S)-3-(4-((difluoromethyl)sulfonamido)-3-(1-(4-fluorophenyl) ethoxy)phenyl)-5-((5-(3-methyloxetan-3-yl) isoxazol-3-yl)amino)-1H-pyrazole-4-carboxamide 3-(4-((difluoromethyl)sulfonamido)-3-(1-(oxazol-2-yl) ethoxy)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-5-((5-methoxy-1-methyl-1H-pyrazol-3-yl)amino)-1H-pyrazole-4-carboxamide (S)-5-((3-(tert-butyl) isoxazol-5-yl)amino)-3-(4-((difluoromethyl)sulfonamido)-3-(1-(4-fluorophenyl) ethoxy) phenyl)-1H-pyrazole-4-carboxamide (S)-3-(4-((difluoromethyl)sulfonamido)-3-(1-(4-fluorophenyl) ethoxy)phenyl)-5-((5-(tetrahydro-2H-pyran-4-yl)pyrazin-2-yl)amino)-1H-pyrazole-4-carboxamide (S)-3-(4-((difluoromethyl)sulfonamido)-3-(1-(4-fluorophenyl) ethoxy)phenyl)-5-((5-(2-fluoropropan-2-yl) isoxazol-3-yl)amino)-1H-pyrazole-4-carboxamide 3-(4-((difluoromethyl)sulfonamido)-3-(1-(4-fluorophenyl)-2-methoxyethoxy)phenyl)-5-((5-methylisoxazol-3-yl)amino)-1H-pyrazole-4-carboxamide (R)-3-(4-((difluoromethyl)sulfonamido)-3-(1-(4-fluorophenyl)-2-methoxyethoxy)phenyl)-5-((5-methylisoxazol-3-yl)amino)-1H-pyrazole-4-carboxamide (S)-3-(4-((difluoromethyl)sulfonamido)-3-(1-(4-fluorophenyl)-2-methoxyethoxy)phenyl)-5-((5-methylisoxazol-3-yl)amino)-1H-pyrazole-4-carboxamide (S)-3-(4-((difluoromethyl)sulfonamido)-3-(1-(4-fluorophenyl) ethoxy)phenyl)-5-((5-(4-methyltetrahydro-2H-pyran-4-yl) isoxazol-3-yl)amino)-1H-pyrazole-4-carboxamide (S)-3-(4-((difluoromethyl)sulfonamido)-3-(1-(4-fluorophenyl) ethoxy)phenyl)-5-((3-methylisoxazol-5-yl) amino)-1H-pyrazole-4-carboxamide (S)-3-(4-((difluoromethyl)sulfonamido)-3-(1-(4-fluorophenyl) ethoxy)phenyl)-5-((5-(tetrahydro-2H-pyran-4-yl) isoxazol-3-yl)amino)-1H-pyrazole-4-carboxamide (S)-5-((5-(adamantan-1-yl) isoxazol-3-yl)amino)-3-(4-((difluoromethyl)sulfonamido)-3-(1-(4-fluorophenyl) ethoxy)phenyl)-1H-pyrazole-4-carboxamide 3-(4-((difluoromethyl)sulfonamido)-3-((S)-1-(4-fluorophenyl) ethoxy)phenyl)-5-((5-(tetrahydrofuran-3-yl) isoxazol-3-yl)amino)-1H-pyrazole-4-carboxamide (S)-3-(4-((difluoromethyl)sulfonamido)-3-(1-(4-fluorophenyl) ethoxy)phenyl)-5-((1-(tetrahydro-2H-pyran-4-yl)-1H-pyrazol-4-yl)amino)-1H-pyrazole-4-carboxamide 3-(4-((difluoromethyl)sulfonamido)-3-(1-(4-fluorophenyl) cyclopropoxy)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-5-((6,7-dihydro-4H-pyrazolo [5,1-c][1,4]oxazin-2-yl)amino)-1H-pyrazole-4-carboxamide (S)-3-(4-((difluoromethyl)sulfonamido)-3-(1-(4-fluorophenyl) ethoxy)phenyl)-5-((2-methylpyrimidin-4-yl) amino)-1H-pyrazole-4-carboxamide (S)-5-((5-cyclopropylisoxazol-3-yl)amino)-3-(4-((difluoromethyl)sulfonamido)-3-(1-(4-fluorophenyl) ethoxy) phenyl)-1H-pyrazole-4-carboxamide (S)-3-(3-(1-(4-fluorophenyl) ethoxy)-4-((2,2,2-trifluoroethyl)sulfonamido)phenyl)-5-((5-methylisoxazol-3-yl) amino)-1H-pyrazole-4-carboxamide (S)-5-((5-(tert-butyl)pyrazin-2-yl)amino)-3-(4-((difluoromethyl)sulfonamido)-3-(1-(4-fluorophenyl) ethoxy) phenyl)-1H-pyrazole-4-carboxamide 3-(4-((difluoromethyl)sulfonamido)-3-(oxazol-2-ylmethoxy)phenyl)-5-(pyrazin-2-ylamino)-1H-pyrazole-4-carboxamide (S)-5-((5-(difluoromethyl) isoxazol-3-yl)amino)-3-(4-((difluoromethyl)sulfonamido)-3-(1-(4-fluorophenyl) ethoxy)phenyl)-1H-pyrazole-4-carboxamide (S)-6-((4-carbamoyl-3-(4-(ethylsulfonamido)-3-(1-(4-fluorophenyl) ethoxy)phenyl)-1H-pyrazol-5-yl)amino) nicotinic acid (S)-5-((5-cyclopropylpyrazin-2-yl)amino)-3-(4-((difluoromethyl)sulfonamido)-3-(1-(4-fluorophenyl) ethoxy) phenyl)-1H-pyrazole-4-carboxamide (S)-3-(4-(ethylsulfonamido)-3-(1-(4-fluorophenyl) ethoxy)phenyl)-5-((5-methylisoxazol-3-yl)amino)-1H-pyrazole-4-carboxamide 3-(4-(difluoromethanesulfonamido)-3-((1S)-1-(4-fluorophenyl) ethoxy)phenyl]-5-((5-methyl-4H,5H,6H,7H,8H-pyrazolo[1,5-a][1,4]diazepin-2-yl)amino)-1H-pyrazole-4-carboxamide 3-(4-((difluoromethyl)sulfonamido)-3-(1-(4-fluorophenyl)-2-methoxyethoxy)phenyl)-5-(pyrazin-2-ylamino)-1H-pyrazole-4-carboxamide (S)-3-(4-((difluoromethyl)sulfonamido)-3-(1-(4-fluorophenyl) ethoxy)phenyl)-1-methyl-5-((5-methylisoxazol-3-yl)amino)-1H-pyrazole-4-carboxamide.

19. A pharmaceutical composition comprising a compound of claim 1, or a pharmaceutically acceptable salt, solvate, tautomer, N-oxide, stereoisomer and/or prodrug thereof, and a pharmaceutically acceptable excipient.

20. A method of treating necroptosis, comprising administering to a subject in need thereof an effective amount of a compound of claim 1, or a pharmaceutically acceptable salt, solvate, tautomer, N-oxide, stereoisomer and/or prodrug thereof.

21. The method of claim 20, wherein the subject has a disease selected from the group consisting of diseases of the bones, joints, connective tissue and cartilage, muscular diseases, skin diseases, cardiovascular diseases, circulatory diseases, hematological and vascular diseases, diseases of the lung, diseases of the gastro-intestinal tract, diseases of the liver, diseases of the pancreas, metabolic diseases, diseases of the kidneys, viral and bacterial infections, severe intoxications, degenerative diseases associated with the Acquired Immune Deficiency Syndrome (AIDS), disorders associated with aging, inflammatory diseases, auto-immune diseases, dental disorders, ophthalmic diseases or disorders, diseases of the audition tracts, diseases associated with mitochondria, neuronal loss, ischemic reperfusion injury, diseases of the central nervous system, cancer and metastatic cancer.

22. A method of inhibiting mixed lineage kinase domain-like protein (MLKL), comprising contacting a cell with a compound of claim 1, or a pharmaceutically acceptable salt, solvate, tautomer, N-oxide, stereoisomer and/or prodrug thereof.

* * * * *